United States Patent
Beck et al.

(10) Patent No.: US 10,975,394 B2
(45) Date of Patent: *Apr. 13, 2021

(54) RECOMBINANT MICROORGANISMS FOR ENHANCED PRODUCTION OF MEVALONATE, ISOPRENE, AND ISOPRENOIDS

(71) Applicants: Danisco US Inc., Palo Alto, CA (US); The Goodyear Tire & Rubber Company, Akron, OH (US)

(72) Inventors: Zachary Q. Beck, Palo Alto, CA (US); Michael C. Miller, Palo Alto, CA (US); Caroline M. Peres, Palo Alto, CA (US); Yuliya A. Primak, Menlo Park, CA (US); Jeff P. Pucci, Pacifica, CA (US); Derek H. Wells, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/200,485

(22) Filed: Nov. 26, 2018

(65) Prior Publication Data

US 2019/0153479 A1 May 23, 2019

Related U.S. Application Data

(62) Division of application No. 14/806,343, filed on Jul. 22, 2015, now Pat. No. 10,138,498, which is a division of application No. 13/459,067, filed on Apr. 27, 2012, now Pat. No. 9,121,038.

(60) Provisional application No. 61/481,121, filed on Apr. 29, 2011.

(51) Int. Cl.

| | |
|---|---|
| *C12P 5/00* | (2006.01) |
| *C12N 9/04* | (2006.01) |
| *C12N 9/02* | (2006.01) |
| *C12N 9/10* | (2006.01) |
| *C12N 9/12* | (2006.01) |
| *C12N 9/18* | (2006.01) |
| *C12N 9/88* | (2006.01) |
| *C12P 7/02* | (2006.01) |
| *C12P 7/04* | (2006.01) |
| *C12P 7/42* | (2006.01) |
| *C12N 15/70* | (2006.01) |
| *C12P 5/02* | (2006.01) |

(52) U.S. Cl.
CPC ............ *C12P 5/007* (2013.01); *C12N 9/0006* (2013.01); *C12N 9/0008* (2013.01); *C12N 9/1025* (2013.01); *C12N 9/1029* (2013.01); *C12N 9/1217* (2013.01); *C12N 9/18* (2013.01); *C12N 9/88* (2013.01); *C12N 15/70* (2013.01); *C12P 5/002* (2013.01); *C12P 5/026* (2013.01); *C12P 7/02* (2013.01); *C12P 7/04* (2013.01); *C12P 7/42* (2013.01); *C12Y 101/01027* (2013.01); *C12Y 101/01034* (2013.01); *C12Y 101/01037* (2013.01); *C12Y 102/01051* (2013.01); *C12Y 102/04001* (2013.01); *C12Y 203/01008* (2013.01); *C12Y 203/01016* (2013.01); *C12Y 203/03001* (2013.01); *C12Y 203/0301* (2013.01); *C12Y 207/02001* (2013.01); *C12Y 301/01031* (2013.01); *C12Y 401/01031* (2013.01); *Y02E 50/30* (2013.01)

(58) Field of Classification Search
None
See application file for complete search history.

(56) References Cited

U.S. PATENT DOCUMENTS

| | | | |
|---|---|---|---|
| 7,371,558 B2 | 5/2008 | Cervin et al. | |
| 7,659,097 B2 | 2/2010 | Renninger et al. | |
| 7,745,184 B2 | 6/2010 | Cervin et al. | |
| 7,785,858 B2 | 8/2010 | Kozlov et al. | |
| 7,915,026 B2 | 3/2011 | Keasling et al. | |
| 8,420,360 B2 | 4/2013 | Calabria et al. | |
| 9,121,038 B2 * | 9/2015 | Beck ................ | C12N 9/0006 |

(Continued)

FOREIGN PATENT DOCUMENTS

| | | | |
|---|---|---|---|
| EP | 1 510 583 A1 | | 3/2005 |
| EP | 1510583 A1 | * | 3/2005 |

(Continued)

OTHER PUBLICATIONS

Martin et al Engineering a mevalonate pathway in *Escherichia coli* for production of terpenoids. Nature Biotechnology (2003), 21(7): 796-802.*

(Continued)

*Primary Examiner* — Iqbal H Chowdhury
(74) *Attorney, Agent, or Firm* — Mintz Levin Cohn Ferris Glovsky and Popeo PC; Terri Shieh-Newton; David Dang

(57) ABSTRACT

The invention features compositions and methods for the increased production of mevalonate, isoprene, isoprenoid precursor molecules, and/or isoprenoids in microorganisms by engineering a microorganism for increased carbon flux towards mevalonate production in the following enzymatic pathways: (a) citrate synthase, (b) phosphotransacetylase, (c) acetate kinase, (d) lactate dehydrogenase, (e) malic enzyme, and (f) pyruvate dehydrogenase such that one of more of the enzyme activity is modulated. In addition, production of mevalonate, isoprene, isoprenoid precursor molecules, and/or isoprenoids can be further enhanced by the heterologous expression of the mvaE and mvaS genes (such as, but not limited to, mvaE and mvaS genes from the organisms *Listeria grayi* DSM 20601, *Enterococcus faecium*, *Enterococcus gallinarum* EG2, and *Enterococcus casseliflavus*).

17 Claims, 69 Drawing Sheets

Specification includes a Sequence Listing.

(56) References Cited

U.S. PATENT DOCUMENTS

| | | |
|---|---|---|
| 10,138,498 B2 | 11/2018 | Beck et al. |
| 2005/0287655 A1 | 12/2005 | Tabata et al. |
| 2008/0038805 A1 | 2/2008 | Melis |
| 2009/0047719 A1* | 2/2009 | Burgard ............... B01D 3/002 435/158 |
| 2009/0203102 A1 | 8/2009 | Cervin et al. |
| 2009/0282545 A1 | 11/2009 | Eichelberger et al. |
| 2010/0003716 A1 | 1/2010 | Cervin et al. |
| 2010/0086978 A1 | 4/2010 | Beck et al. |
| 2010/0196977 A1 | 8/2010 | Chotani et al. |
| 2010/0285549 A1 | 11/2010 | Masayoshi et al. |
| 2010/0297749 A1 | 11/2010 | Aravanis et al. |
| 2011/0045563 A1 | 2/2011 | Melis |
| 2011/0053216 A1 | 3/2011 | Vermaas |
| 2011/0151531 A1 | 6/2011 | Green et al. |
| 2011/0159557 A1 | 6/2011 | Beck et al. |
| 2011/0178261 A1 | 7/2011 | Feher et al. |
| 2012/0045812 A1 | 2/2012 | Bergsma |
| 2012/0164711 A1 | 6/2012 | Muir et al. |
| 2013/0045891 A1 | 2/2013 | Beck et al. |

FOREIGN PATENT DOCUMENTS

| | | |
|---|---|---|
| JP | 2008/061506 A | 3/2008 |
| JP | 4168870 B2 | 10/2008 |
| WO | WO-1998/02550 A2 | 1/1998 |
| WO | WO-1998/02550 A3 | 1/1998 |
| WO | WO-2000/78935 A1 | 12/2000 |
| WO | WO-2007/140339 A2 | 12/2007 |
| WO | WO-2007/140339 A3 | 12/2007 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2009/143490 A1 | 11/2009 |
| WO | WO-2010/003007 A2 | 1/2010 |
| WO | WO-2010/003007 A3 | 1/2010 |
| WO | WO-2010/013077 A1 | 2/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/148150 A1 | 12/2010 |
| WO | WO-2010/148256 A1 | 12/2010 |
| WO | WO-2011/034863 A1 | 3/2011 |
| WO | WO-2011/079314 A2 | 6/2011 |
| WO | WO-2011/079314 A3 | 6/2011 |
| WO | WO-2012/019169 A1 | 2/2012 |
| WO | WO-2012/058494 A2 | 5/2012 |
| WO | WO-2012/058494 A3 | 5/2012 |
| WO | WO-2012/149491 A2 | 11/2012 |
| WO | WO-2012/149491 A3 | 11/2012 |

OTHER PUBLICATIONS

Causey et al. Engineering *Escherichia coli* for efficient conversion of glucose to pyruvate. PNAS (2004), 101(8): 2235-2240.*

Thomason et al. Identification of *Escherichia coli* K-12 ybhE gene as pgl, encoding 6-phosphogluconolactonase. J Bacteriol (2004), 184(24): 8248-8253.*

Altschul, et al., "Gapped BLAST and PSI-BLAST: a New Generation of Protein Database Search Programs," Nucl. Acids Res., 1997, 25 (17): 3389-3402.

Atsumi, et al., "Evolution, Genomic Analysis, and Reconstruction of Isobutanol Tolerance in *Escherichia coli*," Mol Sys Biol., 2010, 6:449, pp. 1-11.

Ausubel, F.M. et al., Current Protocols in Molecular Biology, eds, Chapter 9, 1987.

Baba, et al., "Construction of *Escherichia coli* K-12 In-Frame, Single-Gene Knockout Mutants: The Keio Collection," Mol. Syst. Biol., 2006.008, pp. 1-11.

Berka et al., "The Development of Gene Expression Systems for Filamentous Fungi," Biotechnology Advances, 1989, 7(2):127-154.

Bhayana, et al., "Amino Acid Sequence of *Escherichia coli* Citrate Synthase," Biochemistry, 1984, 23: 2900-2905 (Figure 5).

Bologna, et al., "*Escherichia coli* Malic Enzymes: Two Isoforms with Substantial Differences in Kinetic Properties, Metabolic Regulation, and Structure," Journal of Bacteriology, Aug. 2007, 189(16):5937-5946.

Bunch, et al., "The IdhA Gene Encoding the Fermentative Lactate Dehydrogenase of *Escherichia coli*," Microbiology, 1997, 143:187-195.

Burgard et al. (Dec. 20, 20030. "OptKnock: A bilevel programming framework for identifying gene knockout strategies for microbial strain optimization," *Biotechnology and Bioengineering* 84(6):647-657.

Campbell, et al., "Improved Transformation Efficiency of *Aspergillus niger* Using the Homologous niaD Gene for Nitrate Reductase," Current Genetics, 1989, 16:53-56.

Danner, et al., "Four Terpene Synthases Produce Major Compounds of the Gypsy Moth Feeding-induced Volatile blend of *Populus trichocarpa*," Phytochemistry, Jun. 2011, 72(9):897-908.

Datsenko, K.A. et al, "One-step inactivation of Chromosomal Genes in *Escherichia coli* K12 using PCR Products," PNAS, Jun. 6, 2000, 97(12):6640-6645.

Dawes, et al., "The Route of Ethanol Formation in *Zymomonas mobilis*," Biochem. J., 1966, 98:795-803.

Duckworth, et al., "Structural Basis for Regulation in Gram-Negative Bacterial Citrate Synthases," Biochem Soc Symp., 1987, 54:83-92.

Egan, et al., "Molecular Characterization of the Entner-Doudoroff Pathway in *Escherichia coli*: Sequence Analysis and Localization of Promoters for the Edd-eda Operon," J. Bact., Jul. 1992, 174(14):4638-4646.

Farmer, W.R. et al., "Precursor Balancing for Metabolic Engineering of Lycopene Production in *Escherichia coli*," Biotechnology Prog., Feb. 2, 2001, 17(1):57-61.

Fowler, et. al., "Increased Malonyl Coenzyme A Biosynthesis by Tuning the *Escherichia coli* Metabolic Network and Its Application to Flavanone Production," Applied and Environmental Microbiology, Sep. 2009, 75(18):5831-5839.

Garms, S. "A Multiproduct Terpene Synthase from *Medicago truncatula* Generates Cadalane Sesquiterpenes Via Two Different Mechanisms," J Org Chem., Aug. 20, 2010, 75(16):5590-5600.

Harada, H. et al., "Novel Approaches and Achievements in Biosynthesis of Functional Isoprenoids in *Echerichia coli*," Applied Microbiology and Biotechnology, Aug. 12, 2009, 84(6):1021-1031.

Hedl, et al. "*Enterococcus faecalis* Acetoacetyl-Coenzyme a Thiolase/3-Hydroxy-3-Methyglutaryl-Coenzyme a Reductase, a Dual-Function Protein of Isopentenyl Diphosphate Biosynthesis," Journal of Bacteriology, Apr. 2002, 184(8):2116-2122.

Hemmi H, et al., "Identification of Genes Affecting Lycopene Formation in *Escherichia coli* Transformed With Carotenoid Biosynthetic Genes: Candidates for Early Genes in Isoprenoid Biosynthesis," Journal of Biochemistry, Jun. 1, 1998, 123(6):1088-1096.

Hsieh, et al., "Structure and Mechanism of an *Arabidopsis* Medium/Long-Chain-Length Prenyl Pyrophosphate Synthase," Plant Physiology, Mar. 2011, 155(3):1079-1090.

Iwakura, et al., "Studies on Regulatory Functions of Malic Enzymes," Journal of Biochemistry, 1979, 85:1355-1365.

Jones et al., "Sandalwood Fragrance Biosynthesis Involves Sesquiterpene Synthases of Both the Terpene Synthase (TPS)-a and TPS-b Subfamilies, including Santalene Synthases," J Biol Chem., 2011, 286(20):17445-17454.

Kakuda, et al., "Identification and Characterization of the ackA (Acetate Kinase A)-pta (Phosphotransacetylase) Operon and Complementation Analysis of Acetate Utilization by an ackA-pta Deletion Mutant of *Escherichia coli*," J. Biochem., 1994, 116:916-922.

(56) References Cited

OTHER PUBLICATIONS

Keeling, et al., "Transcriptome Mining, Functional Characterization, and Phylogeny of a Large Terpene Synthase Gene Family in Spruce (*Picea* spp.)," BMC Plant Biol., Mar. 2011, 7, 11:43, pp. 1-14.
Kotlarz et al., "Regulation of the Amount and of the Activity of Phosphofructokinases and Pyruvate Kinases in *Escherichia coli*," Biochim. Biophys. Acta, 1975, 381:257-268.
Kumeta, Y. et al. "Characterization of S-Guaiene Synthases from Cultured Cells of Aquilaria, Responsible for the Formation of the Sesquiterpenes in Agarwood," Plant Physiol., Dec. 2010; 154(4):1998-2007.
Lacour, S. "$6^S$-Dependent Gene Expression at the Onset of Stationary Phase in *Escherichia coli*: Function of $\sigma^S$-Dependent Genes and Identification of Their Promoter Sequences," J. Bact., 2004, 186(21):7186-7195.
Lindberg, et al., "Engineering a Platform for Photosynthetic Isoprene Production in Cyanobacteria, Using Synechocystis as the Model Organism," Metab. Eng., 2010, 12(1):70-79.
Ma, S.M. et a., "Optimization of a Heterologous Mevalonate Pathway Through the Use of Variant HMG-CoA Reductases," Metabolic Engineering, Jul. 13, 2011, 13(5):588-597.
Martin, et al., "Functional Annotation, Genome Organization and Phylogeny of the Grapevine (*Vitis vinifera*) Terpene Synthase Gene Family Based on Genome Assembly, FLcDNA Cloning, and Enzyme Assays," BMC Plant Biol. Oct. 21, 2010;10:226, pp. 1-22.
Martin, et al., "Engineering a Mevalonate Pathway in *Escherichia coli* for Production of Terpenoids," Nature Biotechnology, Jul. 2003, 21(7):796-802.
Maurus, et al., "Insights into the Evolution of Allosteric Properties. The NADH Binding Site of Hexameric Type II Citrate Synthases," Biochemistry, 2003, 42:5555-5565.
Meile, et al., "Characterization of the D-Xylulose 5-Phosphate/D-Fructose 6-Phosphate Phosphoketolase Gene (xfP) from *Bifidobacterium lactis*," J. Bact., May 2001, 183(9):2929-2936.
Miller, et al., "First Isolation of an Isoprene Synthase Gene from Poplar and Successful Expression of the Gene in *Escherichia coli*," Planta, e-pub, May 10, 2001, 213:483-487.
Miziorko, et al., "Enzymes of the Mevalonate Pathway of Isoprenoid Biosynthesis," Archives of Biochemistry and Biophysics, Jan. 15, 2011, 505(2):131-143.
Ner, et al., "Complete Sequence of the glt A Gene Encoding Citrate Synthase in *Escherichia coli*," Biochemistry, Nov. 8, 1983, 22(23):5243-5249.
Newman, et al., (Nov. 5, 2006, e-pub. Jul. 28, 2006). "High-Level Production of Amorpha-4, 11-Diene in a Two-Phase Partitioning Bioreactor of Metabolically Engineered *Escherichia coli*," Biotechnol. Bioeng. 95(4):684-691.
Ogasawara, H. et al., "PdhR (Pyruvate Dehydrogenase Co Regulator) Controls the Respiratory Electron Transport System in *Escherichia coli*," J. Bact., Aug. 2007. 189(15):5534-5541.
Oh, et al., "Global Expression Profiling of Acetate-grown *Escherichia coli*," J. Biol. Chem., Apr. 12, 2002, 277(15):13175-13183.
Okamura, et al., "Unprecedented Acetoacetyl-coenzyme a Synthesizing Enzyme of the Thiolase Superfamily Involved in the Mevalonate Pathway," PNAS, Jun. 22, 2010, vol. 107, No. 25:11265-11270.
Peekhaus, N. et al., "What's for Dinner?: Entner-Doudoroff Metabolism in *Escherichia coli*," J. Bact., Jul. 1998 180(14):3495-3502.
Pitera, et al., "Balancing a Heterologous Mevalonate Pathway for Improved Isoprenoid Production in *Escherichia coli*," Metabolic Engineering, Feb. 16, 2007, 9(2):193-207.
Quant, et al., "Treatment of Rats With Glucagon or Mannoheptulose Increases Mitochondrial 3-Hydroxy-3-Methylglutaryl-Coa Synthase Activity Mitochondrial 3-Hydroxy-3-Methylglutaryl-Coa Synthase Activity," Biochem J., 1989, 262:159-164.
Rodriguez-Villalon, A. et al. (2008). "Carotenoid accumulation in bacteria with enhanced supply of isoprenoid precursors by upregulation of exogenous or endogenous pathways", *Journal of Biotechnology*, 135:78-84.

Romanos, et al., "Foreign Gene Expression in Yeast: a Review," Yeast, 1992, 8(6):423-488.
Salis, et al., "Automated Design of Synthetic Ribosome Binding Sites to Precisely Control Protein Expression," Nat Biotechnol. Oct. 2009; 27(10):946-950.
Sambrook, et al., "Molecular Cloning": A Laboratory Manual, 2nd ed., Cold Spring Harbor, 1989.
Sanchez, et al., "Novel Pathway Engineering Design of The Anaerobic Central Metabolic Pathway in *Escherichia coli* to Increase Succinate Yield and Productivity," Metab. Eng., 2005, 7:229-239.
Savadze, G.A. et al. (1977). Changes in the specific activity of carbon-14 dioxide and isoprene at the compensation point, CAPLUS Accession No. 1977:419164, 1 page.
Schenk, B. et al. (May 2001). "The ins(ide) and out(side) of dolichyl phosphate biosynthesis and recycling in the endoplasmic reticulum," Glycobiology 11(5):61R-70R.
Schoner et al., "Translation of a synthetic two-cistron mRNA in *Escherichia coli*," Proc. Natl. Acad. Sci. USA, Nov. 1986, 83:8506-8510.
Sharkey, et al., "Evolution of the Isoprene Biosynthetic Pathway in Kudzu," Plant Physiology, Feb. 2005, 137:700-712.
Shimizu, et al., "Phosphotransacetylase of *Escherichia coli* B, Purification and Properties," Biochim. Biophys. Acta, 1969, 191:550-558.
Silver, et al., "Characterization of Aspen Isoprene Synthase, an Enzyme Responsible for Leaf Isoprene Emission to the Atmosphere," J. Biol. Chem., Jun. 2, 1995, 270(22):13010-13016.
Sprenger, "*Escherichia coli* K-12," Arch. Microbiol., 1995. 164:324-330.
Stokell, D.J. et al. (Sep. 12, 2003). "Probing the Roles of Key Residues in the Unique Regulatory NADH Binding Site of Type II Citrate Synthase of *Escherichia coli*," The Journal of Biological Chemistry 278(37):35435-35443.
Studier, et al., "Understanding the Differences Between Genome Sequences of *Escherichia coli* B Strains REL606 and BL21(DE3) and Comparison of the *E. Coli* B and K12 Genomes," J. Mol. Biol., 2009. 394:653-680.
Stülke, J. et al. "Regulation of Carbon Catabolism in *Bacillus* Species," Annu. Rev. Microbiol. 200, 54, 849-880.
Sugden, P.H. et al., "Activities of Citrate Synthase, NADtLinked and $NADP^+$—Linked Isocitrate Dehydrogenases, Glutamate Dehydrogenase, Aspartate Aminotransferase and Alanine Aminotransferase in Nervous Tissues from Vertebrates and Invertebrates," Biochem. J., 1975, 150:105-111.
Tabata, K. et al., "Production of Mevalonate by a Metabolically-Engineered *Escherichia coli*," Biotechnology Letters, Oct. 1, 2004, 26(19):1487-1491.
Tao L., et al., "Isolation of Chromosomal Mutations that Affect Carotenoid Production in *Escherichia coli*: Mutations Alter Copy Number of Cole1-type Plasmids," Fems Microbiology Letters, Feb. 1, 2005, 243(1):227-233.
Underwood, et al. "Flux through Citrate Synthase Limits the Growth of Ethanologenic *Escherichia coli* KO11 during Xylose Fermentation," Appl. Environ. Microbiol., 2002, 68(3):1071-1081.
Vadali, R.V. et al., "Enhanced Lycopene Productivity by Manipulation of Carbon Flow to Isopentenyl Diphosphate in *Escherichia coli*," Biotechnology Prog., Oct. 7, 2005, 21(5):1558-1561.
Wiegand, G. et al., "Citrate Synthase: Structure, Control and Mechanism," Annual Rev. Biophysics Biophys. Chem., 1986, 15:97-117.
Wilde, et al., "Transcript Analysis of the Citrate Synthase and Succinate Dehydrogenase Genes of *Escherichia coli* K12," J. Gen. Microbiol., 1986, 132:3239-3251.
Wilding, E.I., et al., "Identification, Evolution, and Essentiality of the Mevalonate Pathway for Isopentenyl Diphosphate Biosynthesis in Gram-Positive Cocci," Journal of Bacteriology, Aug. 1, 2000, 182(15):4319-4327.
Wolfe, "The Acetate Switch," Microb. Mol. Biol. Rev., 2005, 69:12-50.
Yuanyuan, Z. (2010). "Construction and Regulation of *Escherichia coli* Mevalonate Pathway", Shandong University, a master's degree thesis, Publication date: Feb. 1, 2010, 69 pages.

(56) References Cited

OTHER PUBLICATIONS

International Search Report and Written Opinion of the International Searching Authority for International Application No. PCT/US12/35687, dated Nov. 7, 2012.

* cited by examiner

W-CmR-PL.6-pdh (aceE, aceF, lpd-Term) Operon
13066 bp

RECOMBINANT MICROORGANISMS FOR ENHANCED PRODUCTION OF MEVALONATE, ISOPRENE, AND ISOPRENOIDS

CROSS-REFERENCE TO RELATED APPLICATIONS

This application is a divisional of U.S. patent application Ser. No. 14/806,343, filed Jul. 22, 2015, which is a divisional of U.S. patent application Ser. No. 13/459,067, now U.S. Pat. No. 9,121,038, filed Apr. 27, 2012, which claims priority to U.S. Provisional Application No. 61/481,121, filed Apr. 29, 2011, the disclosures of which are incorporated by reference herein in their entireties.

INCORPORATION BY REFERENCE

This application contains a Sequence Listing in computer readable form (filename: 048768-514D02US_Sequence_Listing.txt; 169,809 bytes ASCII text file; created Oct. 11, 2018), which is incorporated herein by reference in its entirety and forms part of the disclosure.

FIELD OF THE INVENTION

This disclosure relates to compositions and methods for the increased production of mevalonate, isoprene, isoprenoids and isoprenoid precursor molecules in recombinant microorganisms, as well as methods for producing and using the same.

BACKGROUND OF THE INVENTION

R-Mevalonate is an intermediate of the mevalonate-dependent biosynthetic pathway that converts acetyl-CoA to isopentenyl diphosphate and dimethylallyl diphosphate. The conversion of acetyl-CoA to mevalonate can be catalyzed by the thiolase, HMG-CoA synthase and the HMG-CoA reductase activities of the upper mevalonate-dependent biosynthetic pathway (MVA pathway). Based on molar conversion of glucose to acetyl-CoA via glycolysis, the theoretical mass yield for the production of mevalonate using the upper MVA pathway enzymes thiolase, HMG-CoA synthase and the HMG-CoA reductase is 54.8%.

Commercially, mevalonate has been used as an additive in cosmetics, for the production of biodegradable polymers, and can have value as a chiral building block for the synthesis of other chemicals.

The products of the mevalonate-dependent pathway are isopentenyl pyrophosphate (IPP) and dimethylallyl diphosphate (DMAPP). IPP and DMAPP are precursors to isoprene as well as isoprenoids. Isoprene (2-methyl-1,3-butadiene) is the monomer of natural rubber and also a common structural motif to an immense variety of other naturally occurring compounds, collectively termed the isoprenoids. Isoprene is additionally the critical starting material for a variety of synthetic polymers, most notably synthetic rubbers.

Isoprenoids are compounds derived from the isoprenoid precursor molecules IPP and DMAPP. Over 29,000 isoprenoid compounds have been identified and new isoprenoids are being discovered each year. Isoprenoids can be isolated from natural products, such as microorganisms and species of plants that use isoprenoid precursor molecules as a basic building block to form the relatively complex structures of isoprenoids. Isoprenoids are vital to most living organisms and cells, providing a means to maintain cellular membrane fluidity and electron transport. In nature, isoprenoids function in roles as diverse as natural pesticides in plants to contributing to the scents associated with cinnamon, cloves, and ginger. Moreover, the pharmaceutical and chemical communities use isoprenoids as pharmaceuticals, nutraceuticals, flavoring agents, and agricultural pest control agents. Given their importance in biological systems and usefulness in a broad range of applications, isoprenoids have been the focus of much attention by scientists.

Conventional means for obtaining mevalonate and isoprenoids include extraction from biological materials (e.g., plants, microbes, and animals) and partial or total organic synthesis in the laboratory. Such means, however, have generally proven to be unsatisfactory. In particular for isoprenoids, given the often times complex nature of their molecular structure, organic synthesis is impractical given that several steps are usually required to obtain the desired product. Additionally, these chemical synthesis steps can involve the use of toxic solvents as can extraction of isoprenoids from biological materials. Moreover, these extraction and purification methods usually result in a relatively low yield of the desired isoprenoid, as biological materials typically contain only minute amounts of these molecules. Unfortunately, the difficulty involved in obtaining relatively large amounts of isoprenoids has limited their practical use.

Recent developments in the production of isoprene, isoprenoid precursor molecules, and isoprenoids disclose methods for the production of isoprene and isoprenoids at rates, titers, and purities that can be sufficient to meet the demands of robust commercial processes (see, for example, International Patent Application Publication No. WO 2009/076676 A2 and U.S. Pat. No. 7,915,026); however, improvements to increase the production of isoprene and isoprenoids and to increase yields of the same are still needed.

Such improvements are provided herein by the disclosure of compositions and methods to increase production of mevalonate as an intermediate of the mevalonate-dependent biosynthetic pathway as well as to increase production of molecules derived from mevalonate, such as isoprene, isoprenoid precursors, and/or isoprenoids.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, compositions and methods for the increased production of mevalonate, isoprene, isoprenoid precursor molecules, and/or isoprenoids in microorganisms by using specific gene manipulations in recombinant microorganisms which result in increased carbon flux towards mevalonate production.

Accordingly, in one aspect, provided herein are recombinant cells capable of increased production of isoprene wherein the cells are engineered for increased carbon flux towards isoprene production such that the activity of one or more enzymes from the group consisting of: citrate synthase, phosphotransacetylase, acetate kinase, lactate dehydrogenase, malate dehydrogenase, pyruvate dehydrogenase, phosphogluconolactonase (PGL), and phosphoenolpyruvate carboxylase is modulated, and wherein said cells further comprise one or more nucleic acids encoding one or more mevalonate (MVA) pathway polypeptides and one or more heterologous nucleic acids encoding an isoprene synthase polypeptide; and wherein said cells produce increased amounts of isoprene compared to isoprene-producing cells that have not been engineered for increased carbon flux towards isoprene. In some aspects, the one or more nucleic acids encoding MVA pathway polypeptides are from the upper MVA pathway, wherein the upper MVA pathway nucleic acids are selected from the group consisting of AA-CoA thiolase, HMG-CoA synthase, and HMG-CoA reductase nucleic acids. In some aspects, said one or more nucleic acids encoding an upper mevalonate (MVA) pathway polypeptide is an mvaE gene and an mvaS gene. In some aspects, the mvaE gene and the mvaS gene is selected from the group consisting of: (a) an mvaE gene and an mvaS gene from *L. grayi*; (b) an mvaE gene and an mvaS gene from *E. faecium*; (c) an mvaE gene and an mvaS gene from *E. gallinarum*; (d) an mvaE gene and an mvaS gene from *E. casseliflavus*; and (e) an mvaE gene and an mvaS gene from *E. faecalis*. In some aspects, the one or more nucleic acids encoding MVA pathway polypeptides are from the lower MVA pathway, wherein the lower MVA pathway nucleic acids are selected from the group consisting of MVK, PMK, and MVD nucleic acids. In some aspects, the MVK is selected from the group consisting of *M. mazei* mevalonate kinase, *M. burtonii* mevalonate kinase polypeptide, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In some aspects, the cells further comprise one or more heterologous nucleic acids encoding one or DXP pathway polypeptides. In some aspects, the isoprene synthase polypeptide is a polypeptide from *Pueraria* or *Populus* or a hybrid, *Populus alba* x *Populus tremula* or variant thereof. In some aspects, the cells are gram-positive bacterial cells, *Streptomyces* cells, gram-negative bacterial cells, *Escherichia* cells, *Pantoea* cells, fungal cells, filamentous fungal cells, *Trichoderma* cells, *Aspergillus* cells, or yeast cells. In some aspects, the activity of citrate synthase is modulated by decreasing the activity of an endogenous citrate synthase gene. In some aspects, the activity of citrate synthase is modulated by chromosomal replacement of an endogenous citrate synthase gene with a transgene encoding an NADH-insensitive citrate synthase. In some aspects, the transgene encoding an NADH-insensitive citrate synthase is derived from *Bacillus subtilis*. In some aspects, the activity of citrate synthase is modulated by replacing the endogenous citrate synthase gene promoter with a synthetic constitutively low expressing promoter. In some aspects of any of the aspects provided herein, decreasing the activity of citrate synthase results in more carbon flux into the mevalonate dependent biosynthetic pathway in comparison to microorganisms that do not have decreased expression of citrate synthase. In some aspects, carbon flux is directed towards mevalonate production by modulating the activity of phosphotransacetylase and/or acetate kinase. In some aspects, the activity of phosphotransacetylase and/or acetate kinase is modulated by attenuating the activity of an endogenous phosphotransacetylase gene and/or an endogenous acetate kinase gene. In some aspects, endogenous phosphotransacetylase and/or endogenous acetate kinase gene expression is attenuated by deletion of the endogenous phosphotransacetylase gene and/or the endogenous acetate kinase gene. In some aspects of any of the aspects provided herein, the cells produces decreased amounts of acetate in comparison to microorganisms that do not have attenuated endogenous phosphotransacetylase gene and/or endogenous acetate kinase gene expression. In some aspects of any of the aspects provided herein, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression. In some aspects, carbon flux is directed towards mevalonate production by modulating the activity of lactate dehydrogenase. In some aspects, the activity of lactate dehydrogenase is modulated by attenuating the activity of an endogenous lactate dehydrogenase gene. In some aspects, endogenous lactate dehydrogenase gene expression is attenuated by deletion of the endogenous lactate dehydrogenase gene. In some aspects of any of the aspects provided herein, the cells produces decreased amounts of lactate in comparison to microorganisms that do not have attenuated endogenous lactate dehydrogenase gene expression. In some aspects of any of the aspects provided herein, attenuating the activity of the endogenous lactate dehydrogenase gene results in more carbon flux into the mevalonate dependent biosynthetic pathway in comparison to microorganisms that do not have attenuated endogenous lactate dehydrogenase gene expression. In some aspects, carbon flux is directed towards mevalonate production by modulating the activity of NADP-dependent malate dehydrogenase. In some aspects, the activity of NADP-dependent malate dehydrogenase is modulated by increasing the activity of an NADP-dependent malate dehydrogenase gene. In some aspects, the NADP-dependent malate dehydrogenase gene is an endogenous gene. In some aspects, expression of the endogenous NADP-dependent malate dehydrogenase gene is increased by replacing the endogenous NADP-dependent malate dehydrogenase gene promoter with a synthetic constitutively expressing promoter. In some aspects of any of the aspects provided herein, the cells further comprise a heterologous nucleic acid encoding an NADP-dependent malate dehydrogenase polypeptide. In some aspects of any of the aspects provided herein, the cells produces increased amounts of pyruvate in comparison to microorganisms that do not have increased expression of an NADP-dependent malate dehydrogenase gene. In some aspects of any of the aspects provided herein, increasing the activity of an NADP-dependent malate dehydrogenase gene results in more carbon flux into the mevalonate dependent biosynthetic pathway in comparison to microorganisms that do not have increased NADP-dependent malate dehydrogenase gene expression. In some aspects, carbon flux is directed towards mevalonate production by modulating the activity of pyruvate dehydrogenase. In some aspects, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. In some aspects of any of the aspects provided herein, the activity of the pyruvate dehydrogenase complex is modulated by attenuating the activity of an endogenous pyruvate dehydrogenase complex repressor gene. In some aspects, the one or more genes of the pyruvate dehydrogenase complex are endogenous genes. In some aspects, expression of the one or more endogenous genes of the pyruvate dehydrogenase complex is increased by replacing one or more endogenous gene promoters with one or more synthetic constitutively expressing promoters. In some aspects of any of the aspects provided herein, the cells further comprise one or more heterologous nucleic acids encoding one or more polypeptides from the group consisting of (a) pyruvate dehydrogenase (E1), (b) dihydrolipoyl transacetylase, and (c) dihydrolipoyl dehydrogenase. In some aspects, the activity of an endogenous pyruvate dehydrogenase complex repressor is attenuated by deletion of the endogenous pyruvate dehydrogenase complex repressor gene. In some aspects of any of the aspects provided herein, the cells produce increased amounts of acetyl Co-A in comparison to microorganisms wherein the activity of pyruvate dehydrogenase is not modulated. In some aspects of any of the aspects provided herein, modulating the activity of pyruvate dehydrogenase results in more carbon flux into the mevalonate dependent biosynthetic pathway in comparison to microorganisms that do not have modulated pyruvate dehydrogenase expression. In some aspects, carbon flux is directed towards mevalonate production by modulating the activity of phosphogluconolactonase (PGL). In some aspects, the activity of PGL is modulated by attenuating the activity of an endogenous PGL gene. In some aspects, the activity of PGL is attenuated by replacing the endogenous PGL gene promoter with a synthetic constitutively low expressing promoter. In some aspects, the activity of an endogenous PGL is attenuated by deletion of the endogenous PGL gene. In some aspects, carbon flux is directed towards mevalonate production by modulating the activity of phosphoenolpyruvate carboxylase. In some aspects, the activity of phosphoenolpyruvate carboxylase is modulated by attenuating the activity of an endogenous phosphoenolpyruvate carboxylase gene. In some aspects, the activity of phosphoenolpyruvate carboxylase is attenuated by replacing the endogenous phosphoenolpyruvate carboxylase gene promoter with a synthetic constitutively low expressing promoter. In some aspects, the activity of an endogenous phosphoenolpyruvate carboxylase is attenuated by deletion of the endogenous phosphoenolpyruvate carboxylase gene. In some aspects, the cells further comprise one or more nucleic acids encoding an isopentenyl-diphosphate delta-isomerase (IDI) polypeptide.

In other aspects, provided herein are methods for producing isoprene, comprising: (a) culturing any of the cells provided by any of the aspects disclosed herein under suitable culture conditions for production of isoprene; and (b) producing the isoprene. In another embodiment, the method further comprises recovering the isoprene.

In another aspect, provided herein are recombinant cells capable of increased production of mevalonate wherein the cells are engineered for increased carbon flux towards mevalonate, production such that the activity of one or more enzymes from the group consisting of citrate synthase, phosphotransacetylase, acetate kinase, lactate dehydrogenase, malate dehydrogenase, pyruvate dehydrogenase, phosphogluconolactonase, and phosphoenolpyruvate carboxylase is modulated and wherein said cells further comprise one or more nucleic acids encoding one or more upper mevalonate (MVA) pathway polypeptides; and wherein the cells produce increased amounts of mevalonate compared to mevalonate-producing cells that have not been engineered for increased carbon flux towards mevalonate. In some aspects, said one or more nucleic acids encoding an upper mevalonate (MVA) pathway polypeptide is an mvaE gene and an mvaS gene. In some aspects, the mvaE gene and the mvaS gene is selected from the group consisting of: (a) an mvaE gene and an mvaS gene from *L. grayi*; (b) an mvaE gene and an mvaS gene from *E. faecium*; (c) an mvaE gene and an mvaS gene from *E. gallinarum*; (d) an mvaE gene and an mvaS gene from *E. casseliflavus*; and (e) an mvaE gene and an mvaS gene from *E. faecalis*. In some aspects, the activity of citrate synthase is modulated by decreasing the activity of an endogenous citrate synthase gene. In some aspects, the activity of citrate synthase is modulated by chromosomal replacement of an endogenous citrate synthase gene with a transgene encoding an NADH-insensitive citrate synthase. In some aspects, the transgene encoding an NADH-insensitive citrate synthase is derived from *Bacillus subtilis*. In some aspects, the activity of citrate synthase is modulated by replacing the endogenous citrate synthase gene promoter with a synthetic constitutively low expressing promoter. In some aspects of any of the aspects provided herein, decreasing the activity of citrate synthase results in more carbon flux into the mevalonate dependent biosynthetic pathway in comparison to microorganisms that do not have decreased expression of citrate synthase. In some aspects, carbon flux is directed towards mevalonate production by modulating the activity of phosphotransacetylase and/or acetate kinase. In some aspects, the activity of phosphotransacetylase and/or acetate kinase is modulated by attenuating the activity of an endogenous phosphotransacetylase gene and/or an endogenous acetate kinase gene. In some aspects, endogenous phosphotransacetylase and/or endogenous acetate kinase gene expression is attenuated by deletion of the endogenous phosphotransacetylase gene and/or the endogenous acetate kinase gene. In some aspects of any of the aspects provided herein, the cells produces decreased amounts of acetate in comparison to microorganisms that do not have attenuated endogenous phosphotransacetylase gene and/or endogenous acetate kinase gene expression. In some aspects of any of the aspects provided herein, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression. In some aspects, carbon flux is directed towards mevalonate production by modulating the activity of lactate dehydrogenase. In some aspects, the activity of lactate dehydrogenase is modulated by attenuating the activity of an endogenous lactate dehydrogenase gene. In some aspects, endogenous lactate dehydrogenase gene expression is attenuated by deletion of the endogenous lactate dehydrogenase gene. In some aspects of any of the aspects provided herein, the cells produces decreased amounts of lactate in comparison to microorganisms that do not have attenuated endogenous lactate dehydrogenase gene expression. In some aspects of any of the aspects provided herein, attenuating the activity of the endogenous lactate dehydrogenase gene results in more carbon flux into the mevalonate dependent biosynthetic pathway in comparison to microorganisms that do not have attenuated endogenous lactate dehydrogenase gene expression. In some aspects, carbon flux is directed towards mevalonate production by modulating the activity of NADP-dependent malate dehydrogenase. In some aspects, the activity of NADP-dependent malate dehydrogenase is modulated by increasing the activity of an NADP-dependent malate dehydrogenase gene. In some aspects, the NADP-dependent malate dehydrogenase gene is an endogenous gene. In some aspects, expression of the endogenous NADP-dependent malate dehydrogenase gene is increased by replacing the endogenous NADP-dependent malate dehydrogenase gene promoter with a synthetic constitutively expressing promoter. In some aspects of any of the aspects provided herein, the cells further comprises a heterologous nucleic acid encoding an NADP-dependent malate dehydrogenase polypeptide. In some aspects of any of the aspects provided herein, wherein the cells produces increased amounts of pyruvate in comparison to microorganisms that do not have increased expression of an NADP-dependent malate dehydrogenase gene. In some aspects of any of the aspects provided herein, wherein increasing the activity of an NADP-dependent malate dehydrogenase gene results in more carbon flux into the mevalonate dependent biosynthetic pathway in comparison to microorganisms that do not have increased NADP-dependent malate dehydrogenase gene expression. In some aspects, carbon flux is directed towards mevalonate production by modulating the activity of pyruvate dehydrogenase. In some aspects, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. In some aspects of any of the aspects provided herein, the activity of the pyruvate dehydrogenase complex is modulated by attenuating the activity of an endogenous pyruvate dehydrogenase complex repressor gene. In some aspects, the one or more genes of the pyruvate dehydrogenase complex are endogenous genes. In some aspects, expression of the one or more endogenous genes of the pyruvate dehydrogenase complex is increased by replacing one or more endogenous gene promoters with one or more synthetic constitutively expressing promoters. In some aspects of any of the aspects provided herein, the cells further comprises one or more heterologous nucleic acids encoding one or more polypeptides from the group consisting of (a) pyruvate dehydrogenase (E1), (b) dihydrolipoyl transacetylase, and (c) dihydrolipoyl dehydrogenase. In some aspects, the activity of an endogenous pyruvate dehydrogenase complex repressor is attenuated by deletion of the endogenous pyruvate dehydrogenase complex repressor gene. In some aspects of any of the aspects provided herein, the cells produce increased amounts of acetyl Co-A in comparison to microorganisms wherein the activity of pyruvate dehydrogenase is not modulated. In some aspects of any of the aspects provided herein, modulating the activity of pyruvate dehydrogenase results in more carbon flux into the mevalonate dependent biosynthetic pathway in comparison to microorganisms that do not have modulated pyruvate dehydrogenase expression. In some aspects, carbon flux is directed towards mevalonate production by modulating the activity of phosphogluconolactonase (PGL). In some aspects, the activity of PGL is modulated by attenuating the activity of an endogenous PGL gene. In some aspects, the activity of PGL is attenuated by replacing the endogenous PGL gene promoter with a synthetic constitutively low expressing promoter. In some aspects, the activity of an endogenous PGL is attenuated by deletion of the endogenous PGL gene. In some aspects, carbon flux is directed towards mevalonate production by modulating the activity of phosphoenolpyruvate carboxylase. In some aspects, the activity of phosphoenolpyruvate carboxylase is modulated by attenuating the activity of an endogenous phosphoenolpyruvate carboxylase gene. In some aspects, the activity of phosphoenolpyruvate carboxylase is attenuating by replacing the endogenous phosphoenolpyruvate carboxylase gene promoter with a synthetic constitutively low expressing promoter. In some aspects, the activity of an endogenous phosphoenolpyruvate carboxylase is attenuated by deletion of the endogenous phosphoenolpyruvate carboxylase gene. In some aspects of any of the aspects provided herein, mevalonate production is increased compared to microorganisms that are not grown under conditions of tri-carboxylic acid (TCA) cycle activity, wherein metabolic carbon flux in the cells is directed towards mevalonate production by modulating the activity of one or more enzymes from the group consisting of (a) citrate synthase, (b) phosphotransacetylase and/or acetate kinase, (c) lactate dehydrogenase, (d) malate dehydrogenase, and (e) pyruvate decarboxylase complex. In some aspects of any of the aspects provided herein, the activity of citrate synthase is modulated by replacing the endogenous citrate synthase gene promoter with a synthetic constitutively low expressing promoter, the activity of lactate dehydrogenase is modulated by attenuating the activity of an endogenous lactate dehydrogenase gene, and the activity of acetate kinase is modulated by attenuating the activity of an endogenous acetate kinase gene.

In some aspects, provided herein are methods for producing mevalonate, comprising: (a) culturing any of the cells provided by any of the aspects disclosed herein under suitable culture conditions for production of isoprene; and (b) producing the mevalonate. In one embodiment, the method further comprises recovering the mevalonate.

In yet other aspects, provided herein are recombinant cells capable of increased production of isoprenoids wherein the cells are engineered for increased carbon flux towards mevalonate, production such that the activity of one or more enzymes from the group consisting of: citrate synthase, phosphotransacetylase, acetate kinase, lactate dehydrogenase, malate dehydrogenase, pyruvate dehydrogenase, phosphogluconolactonase (PGL), and phosphoenolpyruvate carboxylase is modulated and wherein said cells further comprise (i) one or more nucleic acids encoding one or more mevalonate (MVA) pathway polypeptides and (ii) one or more nucleic acids encoding polyprenyl pyrophosphate synthases; and wherein the cells produce increased amounts of isoprenoids compared to isoprenoid-producing cells that have not been engineered for increased carbon flux towards mevalonate. In some aspects, the one or more nucleic acids encoding MVA pathway polypeptides are from the upper MVA pathway, wherein the upper MVA pathway nucleic acids are selected from the group consisting of AA-CoA thiolase, HMG-CoA synthase, and HMG-CoA reductase nucleic acids. In some aspects, said one or more nucleic acids encoding an upper mevalonate (MVA) pathway polypeptide is an mvaE gene and an mvaS gene. In some aspects, the mvaE gene and the mvaS gene is selected from the group consisting of: (a) an mvaE gene and an mvaS gene from *L. grayi*; (b) an mvaE gene and an mvaS gene from *E. faecium*; (c) an mvaE gene and an mvaS gene from *E. gallinarum*; (d) an mvaE gene and an mvaS gene from *E. casseliflavus*; and (e) an mvaE gene and an mvaS gene from *E. faecalis*. In some aspects, the one or more nucleic acids encoding MVA pathway polypeptides are from the lower MVA pathway, wherein the lower MVA pathway nucleic acids are selected from the group consisting of MVK, PMK, and, MVD nucleic acids. In some aspects, the MVK is selected from the group consisting of *M. mazei* mevalonate kinase, *M. burtonii* mevalonate kinase polypeptide, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In some aspects, the cells further comprise one or more heterologous nucleic acids encoding one or DXP pathway polypeptides. In some aspects, the cells are gram-positive bacterial cells, *Streptomyces* cells, gram-negative bacterial cells, *Escherichia* cells, Pantoea cells, fungal cells, filamentous fungal cells, *Trichoderma* cells, *Aspergillus* cells, or yeast cells. In some aspects, the activity of citrate synthase is modulated by decreasing the activity of an endogenous citrate synthase gene. In some aspects, the activity of citrate synthase is modulated by chromosomal replacement of an endogenous citrate synthase gene with a transgene encoding an NADH-insensitive citrate synthase. In some aspects, the transgene encoding an NADH-insensitive citrate synthase is derived from *Bacillus subtilis*. In some aspects, the activity of citrate synthase is modulated by replacing the endogenous citrate synthase gene promoter with a synthetic constitutively low expressing promoter. In some aspects of any of the aspects provided herein, decreasing the activity of citrate synthase results in more carbon flux into the mevalonate dependent biosynthetic pathway in comparison to microorganisms that do not have decreased expression of citrate synthase. In some aspects, carbon flux is directed towards mevalonate production by modulating the activity of phosphotransacetylase and/or acetate kinase. In some aspects, the activity of phosphotransacetylase and/or acetate kinase is modulated by attenuating the activity of an endogenous phosphotransacetylase gene and/or an endogenous acetate kinase gene. In some aspects, endogenous phosphotransacetylase and/or endogenous acetate kinase gene expression is attenuated by deletion of the endogenous phosphotransacetylase gene and/or the endogenous acetate kinase gene. In some aspects of any of the aspects provided herein, the cells produces decreased amounts of acetate in comparison to microorganisms that do not have attenuated endogenous phosphotransacetylase gene and/or endogenous acetate kinase gene expression. In some aspects of any of the aspects provided herein, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression. In some aspects, carbon flux is directed towards mevalonate production by modulating the activity of lactate dehydrogenase. In some aspects, the activity of lactate dehydrogenase is modulated by attenuating the activity of an endogenous lactate dehydrogenase gene. In some aspects, endogenous lactate dehydrogenase gene expression is attenuated by deletion of the endogenous lactate dehydrogenase gene. In some aspects of any of the aspects provided herein, the cells produces decreased amounts of lactate in comparison to microorganisms that do not have attenuated endogenous lactate dehydrogenase gene expression. In some aspects of any of the aspects provided herein, attenuating the activity of the endogenous lactate dehydrogenase gene results in more carbon flux into the mevalonate dependent biosynthetic pathway in comparison to microorganisms that do not have attenuated endogenous lactate dehydrogenase gene expression. In some aspects, carbon flux is directed towards mevalonate production by modulating the activity of NADP-dependent malate dehydrogenase. In some aspects, the activity of NADP-dependent malate dehydrogenase is modulated by increasing the activity of an NADP-dependent malate dehydrogenase gene. In some aspects, the NADP-dependent malate dehydrogenase gene is an endogenous gene. In some aspects, expression of the endogenous NADP-dependent malate dehydrogenase gene is increased by replacing the endogenous NADP-dependent malate dehydrogenase gene promoter with a synthetic constitutively expressing promoter. In some aspects of any of the aspects provided herein, the cells further comprise a heterologous nucleic acid encoding an NADP-dependent malate dehydrogenase polypeptide. In some aspects of any of the aspects provided herein, the cells produces increased amounts of pyruvate in comparison to microorganisms that do not have increased expression of an NADP-dependent malate dehydrogenase gene. In some aspects of any of the aspects provided herein, increasing the activity of an NADP-dependent malate dehydrogenase gene results in more carbon flux into the mevalonate dependent biosynthetic pathway in comparison to microorganisms that do not have increased NADP-dependent malate dehydrogenase gene expression. In some aspects, carbon flux is directed towards mevalonate production by modulating the activity of pyruvate dehydrogenase. In some aspects, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. In some aspects of any of the aspects provided herein, the activity of the pyruvate dehydrogenase complex is modulated by attenuating the activity of an endogenous pyruvate dehydrogenase complex repressor gene. In some aspects, the one or more genes of the pyruvate dehydrogenase complex are endogenous genes. In some aspects, expression of the one or more endogenous genes of the pyruvate dehydrogenase complex is increased by replacing one or more endogenous gene promoters with one or more synthetic constitutively expressing promoters. In some aspects of any of the aspects provided herein, the cells further comprises one or more heterologous nucleic acids encoding one or more polypeptides from the group consisting of (a) pyruvate dehydrogenase (E1), (b) dihydrolipoyl transacetylase, and (c) dihydrolipoyl dehydrogenase. In some aspects, the activity of an endogenous pyruvate dehydrogenase complex repressor is attenuated by deletion of the endogenous pyruvate dehydrogenase complex repressor gene. In some aspects of any of the aspects provided herein, the cell produces increased amounts of acetyl Co-A in comparison to microorganisms wherein the activity of pyruvate dehydrogenase is not modulated. In some aspects of any of the aspects provided herein, modulating the activity of pyruvate dehydrogenase results in more carbon flux into the mevalonate dependent biosynthetic pathway in comparison to microorganisms that do not have modulated pyruvate dehydrogenase expression. In some aspects, carbon flux is directed towards mevalonate production by modulating the activity of phosphogluconolactonase (PGL). In some aspects, the activity of PGL is modulated by attenuating the activity of an endogenous PGL gene. In some aspects, the activity of PGL is decreased by replacing the endogenous PGL gene promoter with a synthetic constitutively low expressing promoter. In some aspects, the activity of an endogenous PGL is attenuated by deletion of the endogenous PGL gene. In some aspects, carbon flux is directed towards mevalonate production by modulating the activity of phosphoenolpyruvate carboxylase. In some aspects, the activity of phosphoenolpyruvate carboxylase is modulated by attenuating the activity of an endogenous phosphoenolpyruvate carboxylase gene. In some aspects, the activity of phosphoenolpyruvate carboxylase is decreased by replacing the endogenous phosphoenolpyruvate carboxylase gene promoter with a synthetic constitutively low expressing promoter. In some aspects, the activity of an endogenous phosphoenolpyruvate carboxylase is attenuated by deletion of the endogenous phosphoenolpyruvate carboxylase gene. In some aspects of any of the aspects provided herein, wherein the isoprenoid is selected from group consisting of monoterpenes, diterpenes, triterpenes, tetraterpenes, sesquiterpenes, and polyterpenes. In some aspects, the isoprenoid is a sesquiterpene. In some aspects, the isoprenoid is selected from the group consisting of abietadiene, amorphadiene, carene, α-farnesene, β-farnesene, farnesol, geraniol, geranylgeraniol, linalool, limonene, myrcene, nerolidol, ocimene, patchoulo, β-pinene, sabinene, γ-terpinene, terpindene and valencene. In some aspects, the cells further comprise one or more nucleic acids encoding an isopentenyl-diphosphate delta-isomerase (IDI) polypeptide.

In other aspects, provided herein is a method for producing isoprenoids, comprising: (a) culturing any of the cells provided by any of the aspects disclosed herein under suitable culture conditions for production of isoprenoids; and (b) producing the isoprenoids. In one aspect, the method further comprises recovering the isoprenoids.

In one aspect, the invention provides a recombinant microorganism, or progeny thereof, comprising cells engineered for increased carbon flux towards mevalonate production wherein the activity of one or more enzymes from the group consisting of: (a) citrate synthase, (b) phosphotransacetylase; (c) acetate kinase; (d) lactate dehydrogenase; (e) NADP-dependent malic enzyme, and; (f) pyruvate dehydrogenase is modulated. In any of aspects herein, the cells can further comprise an mvaE gene and an mvaS gene (such as an mvaE gene and an mvaS gene selected from the group consisting of: (a) an mvaE gene and an mvaS gene from *L. grayi*; (b) an mvaE gene and an mvaS gene from *E. faecium*; (c) an mvaE gene and an mvaS gene from *E. gallinarum*; (d) an mvaE gene and an mvaS gene from *E. casseliflavus*; and (e) an mvaE gene and an mvaS gene from *E. faecalis*).

In any of the aspects herein, the invention provides a recombinant microorganism, or progeny thereof, wherein increased carbon flux is directed towards mevalonate production by modulating the activity of citrate synthase. In some aspects, the activity of citrate synthase is modulated by decreasing the activity of an endogenous citrate synthase gene. In some aspects, the activity of citrate synthase is modulated by chromosomal replacement of an endogenous citrate synthase gene with a transgene encoding an NADH-insensitive citrate synthase. In some aspects, the transgene encoding an NADH-insensitive citrate synthase is derived from *Bacillus subtilis*. In some aspects, the activity of citrate synthase is modulated by replacing the endogenous citrate synthase gene promoter with a synthetic constitutively low expressing promoter. In any of the aspects herein, decreasing the activity of citrate synthase results in more carbon flux into the mevalonate dependent biosynthetic pathway in comparison to microorganisms that do not have decreased expression of citrate synthase.

In any of the aspects herein, the invention provides a recombinant microorganism, or progeny thereof, wherein increased carbon flux is directed towards mevalonate production by modulating the activity of phosphotransacetylase and/or acetate kinase. In some aspects, the activity of phosphotransacetylase and/or acetate kinase is modulated by attenuating the activity of an endogenous phosphotransacetylase gene and/or an endogenous acetate kinase gene. In one aspect, endogenous phosphotransacetylase and/or endogenous acetate kinase gene expression is attenuated by deletion of the endogenous phosphotransacetylase gene and/or the endogenous acetate kinase gene. In any of the aspects herein, the recombinant microorganism produces decreased amounts of acetate in comparison to microorganisms that do not have attenuated endogenous phosphotransacetylase gene and/or endogenous acetate kinase gene expression. In any of the aspects herein, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression.

In any of the aspects herein, the invention provides a recombinant microorganism, or progeny thereof, wherein increased carbon flux is directed towards mevalonate production by modulating the activity of lactate dehydrogenase. In some aspects, the activity of lactate dehydrogenase is modulated by attenuating the activity of an endogenous lactate dehydrogenase gene. In some aspects, endogenous lactate dehydrogenase gene expression is attenuated by deletion of the endogenous lactate dehydrogenase gene. In any of the aspects herein, the recombinant microorganism produces decreased amounts of lactate in comparison to microorganisms that do not have attenuated endogenous lactate dehydrogenase gene expression. In any of the aspects herein, attenuating the activity of the endogenous lactate dehydrogenase gene results in more carbon flux into the mevalonate dependent biosynthetic pathway in comparison to microorganisms that do not have attenuated endogenous lactate dehydrogenase gene expression.

In any of the aspects herein, the invention provides a recombinant microorganism, or progeny thereof, wherein increased carbon flux is directed towards mevalonate production by modulating the activity of NADP-dependent malic enzyme. In some aspects, the activity of NADP-dependent malic enzyme is modulated by increasing the activity of an NADP-dependent malic enzyme gene. In some aspects, the NADP-dependent malic enzyme gene is an endogenous gene. In some aspects, expression of the endogenous NADP-dependent malic enzyme gene is increased by replacing the endogenous NADP-dependent malic enzyme gene promoter with a synthetic constitutively expressing promoter. In some aspects, the recombinant microorganism further comprises a heterologous nucleic acid encoding an NADP-dependent malic enzyme polypeptide. In any of the aspects herein, the recombinant microorganism produces increased amounts of pyruvate in comparison to microorganisms that do not have increased expression of an NADP-dependent malic enzyme gene. In any of the aspects herein, increasing the activity of an NADP-dependent malic enzyme gene results in more carbon flux into the mevalonate dependent biosynthetic pathway in comparison to microorganisms that do not have increased NADP-dependent malic enzyme gene expression.

In any of the aspects herein, the invention provides a recombinant microorganism, or progeny thereof, wherein increased carbon flux is directed towards mevalonate production by modulating the activity of pyruvate dehydrogenase. In some aspects, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. In any of the aspects herein, the activity of the pyruvate dehydrogenase complex is modulated by attenuating the activity of an endogenous pyruvate dehydrogenase complex repressor gene. In some aspects, the one or more genes of the pyruvate dehydrogenase complex are endogenous genes. In some aspects, expression of the one or more endogenous genes of the pyruvate dehydrogenase complex is increased by replacing one or more endogenous gene promoters with one or more synthetic constitutively expressing promoters. In some aspects, the recombinant microorganism further comprises one or more heterologous nucleic acids encoding one or more polypeptides from the group consisting of (a) pyruvate dehydrogenase (E1), (b) dihydrolipoyl transacetylase, and (c) dihydrolipoyl dehydrogenase. In some aspects, the activity of an endogenous pyruvate dehydrogenase complex repressor is attenuated by deletion of the endogenous pyruvate dehydrogenase complex repressor gene. In any of the aspects herein, the recombinant microorganism produces increased amounts of acetyl Co-A in comparison to microorganisms wherein the activity of pyruvate dehydrogenase is not modulated. In any of the aspect herein, modulating the activity of pyruvate dehydrogenase results in more carbon flux into the mevalonate dependent biosynthetic pathway in comparison to microorganisms that do not have modulated pyruvate dehydrogenase expression.

In any of the aspects herein, the invention provides a recombinant microorganism wherein mevalonate production is increased compared to microorganisms that have not been engineered in one or more enzymes from the group consisting of (a) citrate synthase, (b) phosphotransacetylase and/or acetate kinase, (c) lactate dehydrogenase, (d) NADP-dependent malic enzyme, and (e) pyruvate decarboxylase complex for increase of carbon flux toward mevalonate production.

In any of the aspects herein, the invention provides a recombinant microorganism wherein mevalonate production is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase and/or acetate kinase, (c) lactate dehydrogenase, (d) malic enzyme, and (e) pyruvate decarboxylase complex.

In any of the aspects herein, the invention provides a recombinant microorganism wherein the recombinant microorganism is selected from the group consisting of yeast, bacteria, filamentous fungi, algae, and cyanobacteria. In some aspects, the recombinant microorganism is *E. coli*. In some aspects, the recombinant microorganism is a yeast.

In any of the aspects herein, the invention provides a recombinant microorganism wherein the activity of citrate synthase is modulated by replacing the endogenous citrate synthase gene promoter with a synthetic constitutively low expressing promoter, the activity of lactate dehydrogenase is modulated by attenuating the activity of an endogenous lactate dehydrogenase gene, and the activity of acetate kinase is modulated by attenuating the activity of an endogenous acetate kinase gene.

In another aspect, the invention provides for methods of producing mevalonate using any of the recombinant microorganisms described herein.

In another aspect, the invention provides for methods of producing isoprene using any of the recombinant microorganisms described herein.

In another aspect, the invention provides for methods of producing isoprenoid precursors using any of the recombinant microorganisms described herein.

In another aspect, the invention provides for methods of producing isoprenoids using any of the recombinant microorganisms described herein.

DETAILED DESCRIPTION

Figure 1:
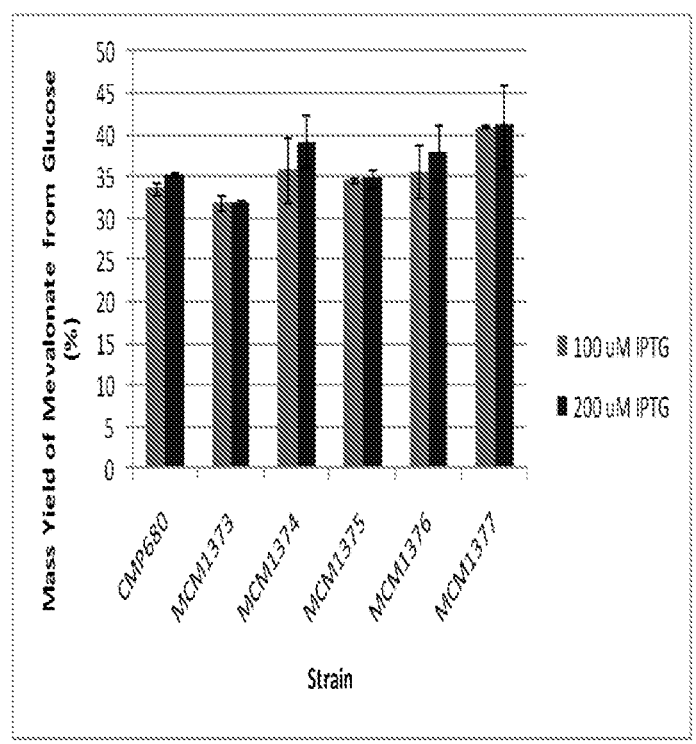
FIG. 1 depicts a graph showing mass yield of mevalonate from glucose. Error bars represent one standard deviation of two replicates.

The invention provides, inter alia, compositions and methods for the increased production of mevalonate, isoprene, isoprenoid precursor molecules, and/or isoprenoids in recombinant microorganisms that have been engineered for increased carbon flux towards mevalonate production. In one aspect, the invention provides, inter alia, recombinant microorganisms, or progeny thereof, comprising cells engineered for increased carbon flux towards mevalonate production wherein the activity of one or more enzymes or proteins from the group consisting of: (a) citrate synthase, (b) phosphotransacetylase; (c) acetate kinase; (d) lactate dehydrogenase; (e) NADP-dependent malic enzyme; (f) pyruvate dehydrogenase; (g) 6-phosphogluconolactonase; (h) phosphoenolpyruvate carboxylase; (i) the inhibitor of RssB activity during magnesium starvation protein; (j) the acrA component of the multidrug efflux pump acrAB-TolC; and (k) the fumarate and nitrate reduction sRNA (FNR) is modulated. In one aspect, the recombinant microorganisms disclosed herein are cells that have been engineered to heterologously express nucleic acids encoding one or more upper MVA pathway polypeptides. In another aspect, the recombinant microorganisms are cells (such as bacterial cells) that have been engineered to heterologously express polypeptides encoded by the mvaE and mvaS genes (such as mvaE and mvaS genes from the microorganisms *Listeria grayi, Enterococcus faecium, Enterococcus gallinarum, Enterococcus casseliflavus* and/or *Enterococcus faecalis*). Any progeny of the recombinant microorganism is contemplated to be within the scope of the invention as well.

The mevalonate-dependent biosynthetic pathway is particularly important for the production of the isoprenoid precursor molecules dimethylallyl diphosphate (DMAPP) and isopentenyl pyrophosphate (IPP). The enzymes of the upper mevalonate pathway convert acetyl CoA, produced from glucose, into mevalonate via three enzymatic reactions. Together, upper MVA pathway genes (for example, the mvaE and mvaS genes, such as the mvaE and mvaS from the above-mentioned bacterial species) encode polypeptides that possess the enzymatic activities of the upper mevalonate pathway. Without being bound to theory, it is believed that increasing the efficiency and productivity of these three enzymatic activities in the upper mevalonate-dependent biosynthetic pathway will substantially increase intracellular concentrations of mevalonate and, consequently, of downstream isoprenoid precursor molecules such as DMAPP and IPP. The increased yield of mevalonate production by these strains is therefore advantageous for commercial applications.

As detailed herein, the enzymatic pathways that include citrate synthase, phosphotransacetylase, acetate kinase, lactate dehydrogenase, malic enzyme and/or pyruvate dehydrogenase can be modulated to increase or decrease the activity of enzymes in these pathways such that more carbon flux is directed toward mevalonate production. Other factors, the modulation of which can increase carbon flux towards mevalonate in cells, can include 6-phosphogluconolactonase, phosphoenolpyruvate carboxylase, the inhibitor of RssB activity during magnesium starvation protein, the acrA component of the multidrug efflux pump acrAB-TolC, and the fumarate and nitrate reduction sRNA. This, in turn, can lead to more substrate for the production of isoprene, isoprenoid precursors, and isoprenoids. The compositions and methods of the present application, therefore, represent an improvement over what has previously been practiced in the art, both in the number of strains of microorganisms available for increased production of mevalonate, isoprene, isoprenoid precursor molecules, and isoprenoids as well as in the amount of these compounds (e.g., mevalonate) produced by those cells (such as bacterial cells).

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

Definitions

The terms "complete mevalonate (MVA) pathway" or "entire mevalonate (MVA) pathway" refer to the cellular metabolic pathway which converts acetyl Co-A into dimethylallyl pyrophosphate (DMAPP) and isopentenyl pyrophosphate (IPP) and which is catalyzed by the enzymes acetoacetyl-CoenzymeA synthase (e.g., thiolase), 3-hydroxy-3-methylglutaryl-Coenzyme A synthase, 3-hydroxy-3-methylglutaryl-Coenzyme A reductase, mevalonate kinase (MVK), phosphomevalonate kinase (PMK), diphosphomevalonate decarboxylase (MVD), and isopentenyl diphosphate isomerase (IDI).

As used herein, the terms "upper mevalonate pathway" or "upper MVA pathway" refer to the series of reactions in cells catalyzed by the enzymes acetoacetyl-CoenzymeA synthase (e.g., thiolase), 3-hydroxy-3-methylglutaryl-Coenzyme A synthase, and 3-hydroxy-3-methylglutaryl-Coenzyme A reductase.

The terms "lower mevalonate pathway" or "lower MVA pathway" refer to the series of reactions in cells catalyzed by the enzymes mevalonate kinase (MVK), phosphomevalonate kinase (PMK), diphosphomevalonate decarboxylase (MVD), and isopentenyl diphosphate isomerase (IDI).

The term "isoprene" refers to 2-methyl-1,3-butadiene (CAS #78-79-5). It can be the direct and final volatile C5 hydrocarbon product from the elimination of pyrophosphate from 3,3-dimethylallyl diphosphate (DMAPP). It may not involve the linking or polymerization of IPP molecules to DMAPP molecules. The term "isoprene" is not generally intended to be limited to its method of production unless indicated otherwise herein.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide encoded by a nucleic acid sequence derived from a different organism, species, or strain than the host cell. In some embodiments, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some embodiments, the heterologous nucleic acid is not identical to a wild-type nucleic acid that is found in the same host cell in nature. For example, a nucleic acid encoded by the mvaE and mvaS genes (such as, but not limited to, the mvaE and mvaS genes from *L. grayi*, *E. faecium*, *E. gallinarum*, and *E. casseliflavus*) transformed in or integrated into the chromosome of *E. coli* is a heterologous nucleic acid.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

As used herein, the terms "minimal medium" or "minimal media" refer to growth medium containing the minimum nutrients possible for cell growth, generally without the presence of amino acids. Minimal medium typically contains: (1) a carbon source for microorganism (e.g., bacterial) growth; (2) various salts, which can vary among microorganism (e.g., bacterial) species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

As used herein, the term "isoprenoid" refers to a large and diverse class of naturally-occurring class of organic compounds composed of two or more units of hydrocarbons, with each unit consisting of five carbon atoms arranged in a specific pattern. As used herein, "isoprene" is expressly excluded from the definition of "isoprenoid."

As used herein, the term "terpenoid" refers to a large and diverse class of organic molecules derived from five-carbon isoprenoid units assembled and modified in a variety of ways and classified in groups based on the number of isoprenoid units used in group members. Hemiterpenoids have one isoprenoid unit. Monoterpenoids have two isoprenoid units. Sesquiterpenoids have three isoprenoid units. Diterpenoids have four isoprene units. Sesterterpenoids have five isoprenoid units. Triterpenoids have six isoprenoid units. Tetraterpenoids have eight isoprenoid units. Polyterpenoids have more than eight isoprenoid units.

As used herein, "isoprenoid precursor" refers to any molecule that is used by organisms in the biosynthesis of terpenoids or isoprenoids. Non-limiting examples of isoprenoid precursor molecules include, e.g., isopentenyl pyrophosphate (IPP) and dimethylallyl diphosphate (DMAPP).

As used herein, the term "mass yield" refers to the mass of the product produced by the cells (such as bacterial cells) divided by the mass of the glucose consumed by the cells (such as bacterial cells) multiplied by 100.

By "specific productivity," it is meant the mass of the product produced by the cells (such as bacterial cells) divided by the product of the time for production, the cell density, and the volume of the culture.

By "titer," it is meant the mass of the product produced by the cells (such as bacterial cells) divided by the volume of the culture.

As used herein, the term "cell productivity index (CPI)" refers to the mass of the product produced by the cells (such as bacterial cells) divided by the mass of the cells (such as bacterial cells) produced in the culture.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Recombinant Cells (Such as Bacterial Cells) Capable of Increased Production of Mevalonate The mevalonate-dependent biosynthetic pathway (MVA pathway) is a key metabolic pathway present in all higher eukaryotes and certain bacteria. In addition to being important for the production of molecules used in processes as diverse as protein prenylation, cell membrane maintenance, protein anchoring, and N-glycosylation, the mevalonate pathway provides a major source of the isoprenoid precursor molecules DMAPP and IPP, which serve as the basis for the biosynthesis of terpenes, terpenoids, isoprenoids, and isoprene.

In the upper portion of the MVA pathway, acetyl Co-A produced during cellular metabolism is converted to mevalonate via the actions of polypeptides having thiolase, HMG-CoA reductase, and HMG-CoA synthase enzymatic activity. First, acetyl Co-A is converted to acetoacetyl CoA via the action of a thiolase. Next, acetoacetyl CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production. Mevalonate is then converted into mevalonate-5-phosphate via the action of mevalonate kinase which is subsequently transformed into mevalonate-5-pyrophosphate by the enzymatic activity of phosphomevalonate kinase. Finally, IPP is formed from mevalonate-5-pyrophosphate by the activity of the enzyme mevalonate-5-pyrophosphate decarboxylase.

In some aspects, modulation of the any of the enzymes referred to herein can affect the expression (e.g., transcription or translation), production, post-translational modification or any other function of the enzyme. In some embodiments, the function of the enzyme (e.g. catalytic ability) in recombinant cells is increased or decreased as compared to a cell that has not been engineered for such modulation. In one embodiment, the function of the enzyme (e.g. activity) is increased as compared to a cell that has not been engineered. In another embodiment, the function of the enzyme (e.g. activity) is decreased as compared to a cell that has not been engineered.

Citrate Synthase Pathway

Figure 5:
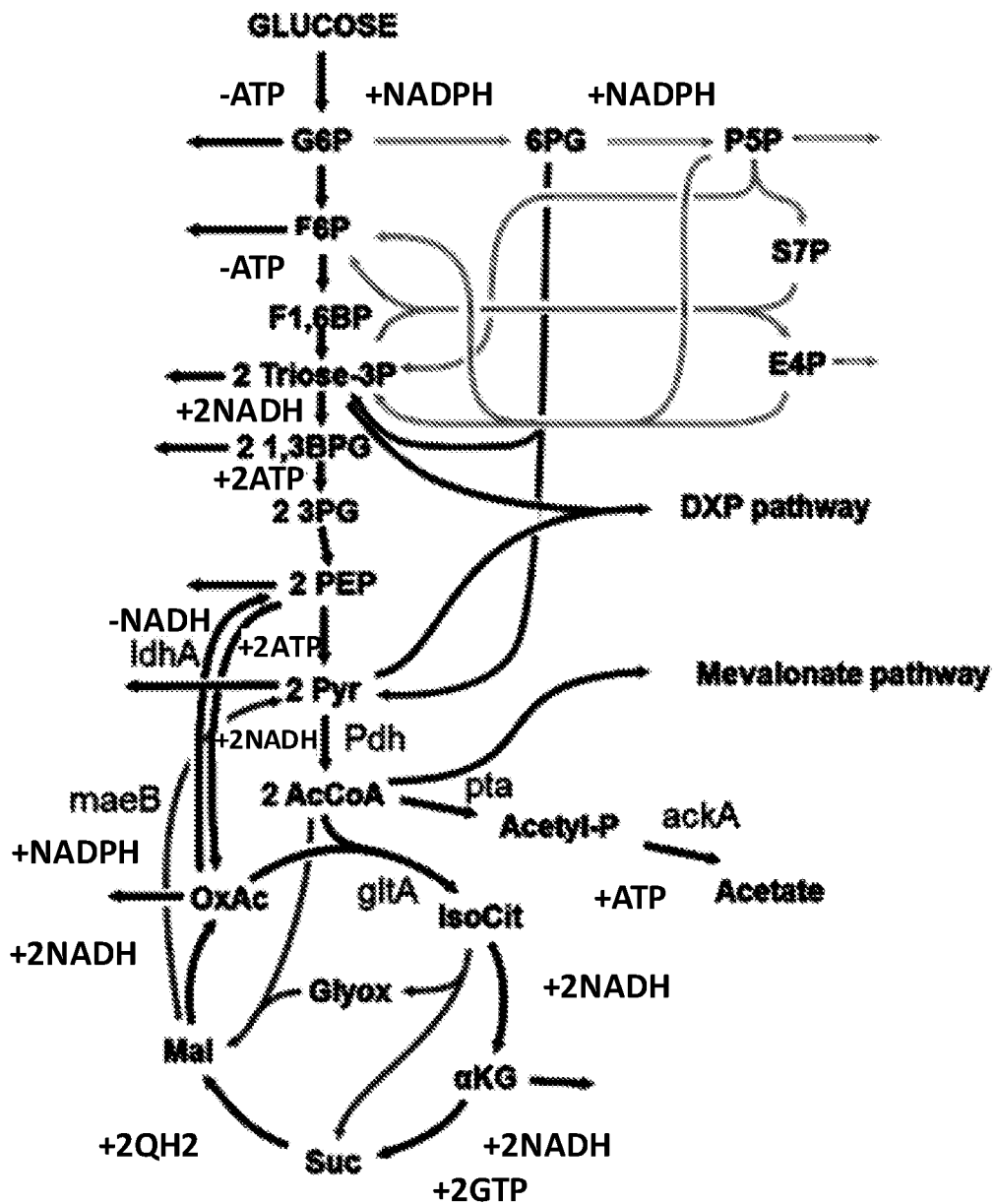
FIG. 5 depicts central metabolism of *E. coli*. The enzymes citrate synthase (OA), phosphotransacetylase (pta), acetate kinase (ackA), lactate dehydrogenase (ldhA), NADP+-dependent malic enzyme (maeB) and the pyruvate dehydrogenase complex (Pdh) are shown.

Citrate synthase catalyzes the condensation of oxaloacetate and acetyl-CoA to form citrate, a metabolite of the Tricarboxylic acid (TCA) cycle (Ner, S. et al. 1983. *Biochemistry,* 22: 5243-5249; Bhayana, V. and Duckworth, H. 1984. *Biochemistry* 23: 2900-2905) (FIG. 5). In *E. coli*, this enzyme, encoded by gltA, behaves like a trimer of dimeric subunits. The hexameric form allows the enzyme to be allosterically regulated by NADH. This enzyme has been widely studied (Wiegand, G., and Remington, S. 1986. Annual Rev. Biophysics *Biophys. Chem.* 15: 97-117; Duckworth et al. 1987. *Biochem Soc Symp.* 54:83-92; Stockell, D. et al. 2003. *J. Biol. Chem.* 278: 35435-43; Maurus, R. et al. 2003. *Biochemistry.* 42:5555-5565). To avoid allosteric inhibition by NADH, replacement by or supplementation with the *Bacillus subtilis* NADH-insensitive citrate synthase has been considered (Underwood et al. 2002. *Appl. Environ. Microbiol.* 68:1071-1081; Sanchez et al. 2005. *Met. Eng.* 7:229-239).

The reaction catalyzed by citrate synthase is directly competing with the thiolase catalyzing the first step of the mevalonate pathway, as they both have acetyl-CoA as a substrate (Hedl et al. 2002. *J. Bact.* 184:2116-2122). Therefore, one of skill in the art can modulate citrate synthase expression (e.g., decrease enzyme activity) to allow more carbon to flux into the mevalonate pathway, thereby increasing the eventual production of mevalonate, isoprene and isoprenoids. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis*. The activity of citrate synthase can also be modulated (e.g., decreased) by replacing the endogenous citrate synthase gene promoter with a synthetic constitutively low expressing promoter. The decrease of the activity of citrate synthase can result in more carbon flux into the mevalonate dependent biosynthetic pathway in comparison to microorganisms that do not have decreased expression of citrate synthase.

Pathways Involving Phosphotransacetylase and/or Acetate Kinase

Phosphotransacetylase (pta) (Shimizu et al. 1969. Biochim. Biophys. Acta 191: 550-558) catalyzes the reversible conversion between acetyl-CoA and acetylphosphate (acetyl-P), while acetate kinase (ackA) (Kakuda, H. et al. 1994. J. Biochem. 11:916-922) uses acetyl-P to form acetate. These genes can be transcribed as an operon in *E. coli*. Together, they catalyze the dissimilation of acetate, with the release of ATP. Thus, one of skill in the art can increase the amount of available acetyl Co-A by attenuating the activity of phosphotransacetylase gene (e.g., the endogenous phosphotransacetylase gene) and/or an acetate kinase gene (e.g., the endogenous acetate kinase gene). One way of achieving attenuation is by deleting phosphotransacetylase (pta) and/or acetate kinase (ackA). This can be accomplished by replacing one or both genes with a chloramphenicol cassette followed by looping out of the cassette. Acetate is produced by E. coli for a variety of reasons (Wolfe, A. 2005. Microb. Mol. Biol. Rev. 69:12-50). Without being bound by theory, since ackA-pta use acetyl-CoA, deleting those genes might allow carbon not to be diverted into acetate and to increase the yield of mevalonate, isoprene or isoprenoids.

In some aspects, the recombinant microorganism produces decreased amounts of acetate in comparison to microorganisms that do not have attenuated endogenous phosphotransacetylase gene and/or endogenous acetate kinase gene expression. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of phosphotransacetylase (pta) and/or acetate kinase (ackA) can also be decreased by other molecular manipulation of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression.

Pathways Involving Lactate Dehydrogenase

In E. coli, D-Lactate is produced from pyruvate through the enzyme lactate dehydrogenase (ldhA—FIG. 5) (Bunch, P. et al. 1997. Microbiol. 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevalonate production (and isoprene, isoprenoid precursor and isoprenoids production, if desired), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant microorganism produces decreased amounts of lactate in comparison to microorganisms that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to microorganisms that do not have attenuated endogenous lactate dehydrogenase gene expression.

Pathways Involving Malic Enzyme

Malic enzyme (in E. coli sfcA and maeB) is an anaplerotic enzyme that catalyzes the conversion of malate into pyruvate (using NAD+ or NADP+) by the equation below:

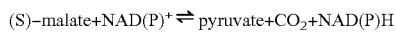

$$(S)\text{-malate} + NAD(P)^+ \rightleftharpoons \text{pyruvate} + CO_2 + NAD(P)H$$

Thus, the two substrates of this enzyme are (S)-malate and $NAD(P)^+$, whereas its 3 products are pyruvate, $CO_2$, and NADPH.

Expression of the NADP-dependent malic enzyme (maeB—FIG. 5) (Iwikura, M. et al. 1979. J. Biochem. 85: 1355-1365) can help increase mevalonate, isoprene, isoprenoid precursors and isoprenoids yield by 1) bringing carbon from the TCA cycle back to pyruvate, direct precursor of acetyl-CoA, itself direct precursor of the mevalonate pathway and 2) producing extra NADPH which could be used in the HMG-CoA reductase reaction (Oh, M K et al. (2002) J. Biol. Chem. 277: 13175-13183; Bologna, F. et al. (2007) J. Bact. 189:5937-5946).

As such, more starting substrate (pyruvate or acetyl-CoA) for the downstream production of mevalonate, isoprene, isoprenoid precursors and isoprenoids can be achieved by modulating, such as increasing, the activity and/or expression of malic enzyme. The NADP-dependent malic enzyme gene can be an endogenous gene. One non-limiting way to accomplish this is by replacing the endogenous NADP-dependent malic enzyme gene promoter with a synthetic constitutively expressing promoter. Another non-limiting way to increase enzyme activity is by using one or more heterologous nucleic acids encoding an NADP-dependent malic enzyme polypeptide. One of skill in the art can monitor the expression of maeB RNA during fermentation or culturing using readily available molecular biology techniques.

Accordingly, in some embodiments, the recombinant microorganism produces increased amounts of pyruvate in comparison to microorganisms that do not have increased expression of an NADP-dependent malic enzyme gene. In some aspects, increasing the activity of an NADP-dependent malic enzyme gene results in more carbon flux into the mevalonate dependent biosynthetic pathway in comparison to microorganisms that do not have increased NADP-dependent malic enzyme gene expression.

Increase in the amount of pyruvate produced can be measured by routine assays known to one of skill in the art. The amount of pyruvate increase can be at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of malic enzyme can also be increased by other molecular manipulations of the enzyme. The increase of enzyme activity can be any amount of increase of specific activity or total activity as compared to when no manipulation has been effectuated. In some instances, the increase of enzyme activity is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataaccatctgcggt-gataaattatctctggcggtgttgacataaataccactggcggtgatactgagca-catc agcaggacgcactgaccaccatgaaggtg-lambda promoter, GenBank NC_001416 (SEQ ID NO:117)), in front of the operon or using one or more synthetic constitutively expressing promoters.

Accordingly, in one aspect, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of these genes can be manipulated for increasing activity of pyruvate dehydrogenase. In another aspect, the activity of the pyruvate dehydrogenase complex can be modulated by attenuating the activity of an endogenous pyruvate dehydrogenase complex repressor gene, further detailed below. The activity of an endogenous pyruvate dehydrogenase complex repressor can be attenuated by deletion of the endogenous pyruvate dehydrogenase complex repressor gene.

In some cases, one or more genes of the pyruvate dehydrogenase complex are endogenous genes. Another way to increase the activity of the pyruvate dehydrogenase complex is by introducing into the microorganism one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant microorganism can produce increased amounts of acetyl Co-A in comparison to microorganisms wherein the activity of pyruvate dehydrogenase is not modulated. Modulating the activity of pyruvate dehydrogenase can result in more carbon flux into the mevalonate dependent biosynthetic pathway in comparison to microorganisms that do not have modulated pyruvate dehydrogenase expression.

Combinations of Mutations

It is understood that for any of the enzymes and/or enzyme pathways described herein, molecular manipulations that modulate any combination (two, three, four, five or six) of the enzymes and/or enzyme pathways described herein is expressly contemplated. For ease of the recitation of the combinations, citrate synthase (gltA) is designated as A, phosphotransacetylase (ptaB) is designated as B, acetate kinase (ackA) is designated as C, lactate dehydrogenase (ldhA) is designated as D, malic enzyme (sfcA or maeB) is designated as E, pyruvate decarboxylase (aceE, aceF, and/or lpdA) is designated as F, 6-phosphogluconolactonase (ybhE) is designated as G, and phosphoenolpyruvate carboxylase (ppl) is designated as H. As discussed above, aceE, aceF, and/or lpdA enzymes of the pyruvate decarboxylase complex can be used singly, or two of three enzymes, or three of three enzymes for increasing pyruvate decarboxylase activity.

Accordingly, for combinations of any two of the enzymes A-H, non-limiting combinations that can be used are: AB, AC, AD, AE, AF, AG, AH, BC, BD, BE, BF, BG, BH, CD, CE, CF, CG, CH, DE, DF, DG, DH, EF, EG, EH, and GH. For combinations of any three of the enzymes A-H, non-limiting combinations that can be used are: ABC, ABD, ABE, ABF, ABG, ABH, BCD, BCE, BCF, BCG, BCH, CDE, CDF, CDG, CDH, DEF, DEH, ACD, ACE, ACF, ACG, ACH, ADE, ADF, ADG, ADH, AEF, AEG, AEH, BDE, BDF, BDG, BDH, BEF, BEG, BEH, CEF, CEG, CEH, CFG, CFH, and CGH. For combinations of any four of the enzymes A-H, non-limiting combinations that can be used are: ABCD, ABCE, ABCF, ABCG, ABCH, ABDE, ABDF, ABDG, ABDH, ABEF, ABEG, ABEH, BCDE, BCDF, BCDG, BCDH, CDEF, CDEG, CDEH, ACDE, ACDF, ACDG, ACDH, ACEF, ACEG, ACEH, BCEF, BDEF, BGEF, BHEF, ADEF. For combinations of any five of the enzymes A-H, non-limiting combinations that can be used are: ABCDE, ABCDF, ABCDG, ABCDH, ABDEF, ABDEG, ABDEH, BCDEF, BCDEG, BCDEH, ACDEF, ACDEG, ACEDH, ABCEF, ABCEG, and ABCEH. For combinations of any six of the enzymes A-H, non-limiting combinations that can be used are: ABCDEF, ABCDEG, ABCDEH, BCDEFG, BCDEFH, and CDEFGH. For combinations of any seven of the enzymes A-H, non-limiting combinations that can be used are: ABCDEFG, ABCDEFH, BCDEFGH. In another aspect, all eight enzyme combinations are used ABCDEFGH.

Accordingly, the recombinant microorganism as described herein can achieve increased mevalonate production that is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase and/or acetate kinase, (c) lactate dehydrogenase, (d) malic enzyme, and (e) pyruvate decarboxylase complex.

Other Regulators and Factors for Increased Production

Other molecular manipulations can be used to increase the flow of carbon towards mevalonate production. One method is to reduce, decrease or eliminate the effects of negative regulators for pathways that feed into the mevalonate pathway. For example, in some cases, the genes aceEF-lpdA are in an operon, with a fourth gene upstream pdhR. pdhR is a negative regulator of the transcription of its operon. In the absence of pyruvate, it binds its target promoter and represses transcription. It also regulates ndh and cyoABCD in the same way (Ogasawara, H. et al. 2007. *J. Bact.* 189:5534-5541). In one aspect, deletion of pdhR regulator can improve the supply of pyruvate, and hence the production of mevalonate, isoprene, isoprenoid precursors, and isoprenoids.

In other aspects, the introduction of 6-phosphogluconolactonase (PGL) into microorganisms (such as various *E. coli* strains) which lack PGL can be used to improve production of mevalonate, isoprene, isoprenoid precursors, and isoprenoids. PGL may be introduced using chromosomal integration or extra-chromosomal vehicles, such as plasmids. In yet other aspects, PGL may be deleted from the genome of cells (for example, microorganisms, such as various E. coli strains) which express a PGL to improve production of mevalonate and/or isoprene. In another aspect, a heterologous nucleic acid encoding a PGL polypeptide can be expressed in a cell which does not endogenously express PGL. In some aspects, deletion of PGL results in any of about 10%, 20%, 30%, 40%, 50%, 60%, 70%, 80%, 90%, or 100%, inclusive, such as any values in between these percentages, higher percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher instantaneous percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher cell productivity index for isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher volumetric productivity of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher peak specific productivity of isoprene in comparison to microorganisms that express PGL. In some aspects the deletion of PGL results in peak specific productivity being maintained for a longer period of time in comparison to microorganisms that express PGL.

In another aspect, modulation of phosphoenolpyruvate carboxylase (ppc in E. coli) gene expression can be used to improve production of mevalonate, isoprene, isoprenoid precursors, and isoprenoids in any of the cells disclosed herein. In one aspect, the gene expression of phosphoenolpyruvate carboxylase can be decreased by replacing the promoter sequence of the ppc gene with another promoter that results in decreased ppc gene expression in comparison to wild type cells. In some aspects, ppc gene expression can be decreased by any of about 10%, 20%, 30%, 40%, 50%, 60%, 70%, 80%, 90%, or 100%, inclusive, including any values in between these percentages, in comparison to wild type cells. In some aspects, decreased expression of phosphoenolpyruvate carboxylase results in any of about 10%, 20%, 30%, 40%, 50%, 60%, 70%, 80%, 90%, or 100%, inclusive, such as any values in between these percentages, higher percent yield of isoprene in comparison to microorganisms that express phosphoenolpyruvate carboxylase at wild type levels. In other aspects, decreased expression of phosphoenolpyruvate carboxylase results in any of about 10%, 20%, 30%, 40%, 50%, 60%, 70%, 80%, 90%, or 100%, inclusive, including any values in between these percentages, higher instantaneous percent yield of isoprene in comparison to microorganisms that express phosphoenolpyruvate carboxylase at wild type levels. In other aspects, decreased expression of phosphoenolpyruvate carboxylase results in any of about 10%, 20%, 30%, 40%, 50%, 60%, 70%, 80%, 90%, or 100%, inclusive, including any values in between these percentages, higher cell productivity index for isoprene in comparison to microorganisms that express phosphoenolpyruvate carboxylase at wild type levels. In other aspects, decreased expression of phosphoenolpyruvate carboxylase results in any of about 10%, 20%, 30%, 40%, 50%, 60%, 70%, 80%, 90%, or 100%, inclusive, including any values in between these percentages, higher volumetric productivity of isoprene in comparison to microorganisms that express phosphoenolpyruvate carboxylase at wild type levels. In other aspects, decreased expression of phosphoenolpyruvate carboxylase results in any of about 10%, 20%, 30%, 40%, 50%, 60%, 70%, 80%, 90%, or 100%, inclusive, including any values in between these percentages, higher peak specific productivity of isoprene in comparison to microorganisms that express phosphoenolpyruvate carboxylase at wild type levels. In some aspects decreased expression of phosphoenolpyruvate carboxylase results in peak specific productivity being maintained for a longer period of time in comparison to microorganisms that express phosphoenolpyruvate carboxylase at wild type levels.

In another aspect, modulation of the inhibitor of RssB activity during magnesium starvation (iraM in E. coli) gene expression can be used to improve production of mevalonate, isoprene, isoprenoid precursors, and isoprenoids in any of the cells disclosed herein. In one aspect, the gene expression of iraM can be increased by replacing the promoter sequence of the iraM gene with another promoter that results in increased iraM gene expression in comparison to wild type cells. In some aspects, iraM gene expression can be increased by any of about 10%, 20%, 30%, 40%, 50%, 60%, 70%, 80%, 90%, or 100%, inclusive, including any values in between these percentages, in comparison to wild type cells. In some aspects, increased expression of the iraM gene results in any of about 10%, 20%, 30%, 40%, 50%, 60%, 70%, 80%, 90%, or 100%, inclusive, such as any values in between these percentages, higher percent yield of isoprene in comparison to microorganisms that express the iraM gene at wild type levels. In other aspects, increased expression of the iraM gene results in any of about 10%, 20%, 30%, 40%, 50%, 60%, 70%, 80%, 90%, or 100%, inclusive, including any values in between these percentages, higher instantaneous percent yield of isoprene in comparison to microorganisms that express the iraM gene at wild type levels. In other aspects, increased expression of the iraM gene results in any of about 10%, 20%, 30%, 40%, 50%, 60%, 70%, 80%, 90%, or 100%, inclusive, including any values in between these percentages, higher cell productivity index for isoprene in comparison to microorganisms that express the iraM gene at wild type levels. In other aspects, increased expression of the iraM gene results in any of about 10%, 20%, 30%, 40%, 50%, 60%, 70%, 80%, 90%, or 100%, inclusive, including any values in between these percentages, higher volumetric productivity of isoprene in comparison to microorganisms that express the iraM gene at wild type levels. In other aspects, increased expression of the iraM gene results in any of about 10%, 20%, 30%, 40%, 50%, 60%, 70%, 80%, 90%, or 100%, inclusive, including any values in between these percentages, higher peak specific productivity of isoprene in comparison to microorganisms that express the iraM gene at wild type levels. In some aspects increased expression of the iraM gene results in peak specific productivity being maintained for a longer period of time in comparison to microorganisms that express the iraM gene at wild type levels.

In another aspect, modulation of the acrA component of the multidrug efflux pump acrAB-TolC (acrA in E. coli) gene expression can be used to improve production of mevalonate, isoprene, isoprenoid precursors, and isoprenoids in any of the cells disclosed herein. In one aspect, the gene expression of acrA can be decreased by replacing the promoter sequence of the acrA gene with another promoter that results in decreased acrA gene expression in comparison to wild type cells. In some aspects, acrA gene expression can be decreased by any of about 10%, 20%, 30%, 40%, 50%, 60%, 70%, 80%, 90%, or 100%, inclusive, including any values in between these percentages, in comparison to wild type cells. In another aspect, expression of acrA can be completely abolished, such as by deleting, the acrA gene in the genome of the cell, so that it no longer produces a functional acrA protein. In some aspects, deletion or decreased expression of the acrA gene results in any of about 10%, 20%, 30%, 40%, 50%, 60%, 70%, 80%, 90%, or 100%, inclusive, such as any values in between these percentages, higher percent yield of isoprene in comparison to microorganisms that express the acrA gene at wild type levels. In other aspects, deletion or decreased expression of the acrA gene results in any of about 10%, 20%, 30%, 40%, 50%, 60%, 70%, 80%, 90%, or 100%, inclusive, including any values in between these percentages, higher instantaneous percent yield of isoprene in comparison to microorganisms that express the acrA gene at wild type levels. In other aspects, deletion or decreased expression of the acrA gene results in any of about 10%, 20%, 30%, 40%, 50%, 60%, 70%, 80%, 90%, or 100%, inclusive, including any values in between these percentages, higher cell productivity index for isoprene in comparison to microorganisms that express the acrA gene at wild type levels. In other aspects, deletion or decreased expression of the acrA gene results in any of about 10%, 20%, 30%, 40%, 50%, 60%, 70%, 80%, 90%, or 100%, inclusive, including any values in between these percentages, higher volumetric productivity of isoprene in comparison to microorganisms that express the acrA gene at wild type levels. In other aspects, deletion or decreased expression of the acrA gene results in any of about 10%, 20%, 30%, 40%, 50%, 60%, 70%, 80%, 90%, or 100%, inclusive, including any values in between these percentages, higher peak specific productivity of isoprene in comparison to microorganisms that express the acrA gene at wild type levels. In some aspects deletion or decreased expression of the acrA gene results in peak specific productivity being maintained for a longer period of time in comparison to microorganisms that express the acrA gene at wild type levels.

In another aspect, modulation of FNR DNA binding transcriptional regulator (FNR) gene expression can be used to improve production of mevalonate, isoprene, isoprenoid precursors, and isoprenoids in any of the cells disclosed herein. In one aspect, the gene expression of FNR can be increased by replacing the promoter sequence of the gene which encodes FNR with another promoter that results in increased FNR expression in comparison to wild type cells. In other aspects, a heterologous nucleic acid encoding FNR can be expressed in a cell that does not endogenously express FNR. In some aspects, FNR expression can be increased by any of about 10%, 20%, 30%, 40%, 50%, 60%, 70%, 80%, 90%, or 100%, inclusive, including any values in between these percentages, in comparison to wild type cells or cells that do not endogenously express FNR. In some aspects, increased FNR expression results in any of about 10%, 20%, 30%, 40%, 50%, 60%, 70%, 80%, 90%, or 100%, inclusive, such as any values in between these percentages, higher percent yield of isoprene in comparison to wild type cells or cells that do not endogenously express FNR. In other aspects, increased FNR expression results in any of about 10%, 20%, 30%, 40%, 50%, 60%, 70%, 80%, 90%, or 100%, inclusive, including any values in between these percentages, higher instantaneous percent yield of isoprene in comparison to in comparison to wild type cells or cells that do not endogenously express FNR. In other aspects, increased FNR expression results in any of about 10%, 20%, 30%, 40%, 50%, 60%, 70%, 80%, 90%, or 100%, inclusive, including any values in between these percentages, higher cell productivity index for isoprene in comparison to wild type cells or cells that do not endogenously express FNR. In other aspects, increased FNR expression results in any of about 10%, 20%, 30%, 40%, 50%, 60%, 70%, 80%, 90%, or 100%, inclusive, including any values in between these percentages, higher volumetric productivity of isoprene in comparison to wild type cells or cells that do not endogenously express FNR. In other aspects, increased FNR expression results in any of about 10%, 20%, 30%, 40%, 50%, 60%, 70%, 80%, 90%, or 100%, inclusive, including any values in between these percentages, higher peak specific productivity of isoprene in comparison to wild type cells or cells that do not endogenously express FNR. In some aspects increased FNR expression results in peak specific productivity being maintained for a longer period of time i in comparison to wild type cells or cells that do not endogenously express FNR.

In addition to the host cell (e.g., microorganism) mutations for modulating various enzymatic pathways described herein that increase carbon flux towards mevalonate production, host cells expressing one or more copies of a heterologous nucleic acid encoding upper MVA pathway polypeptides can be used in conjunction with the host cell mutations to increase the production of desired end products, such as mevalonate, isoprene, isoprenoid precursors, and isoprenoids. In another embodiment, genes encoding mvaE and mvaS from various species can be used in conjunction with the host cell mutations to increase the production of desired end products, such as mevalonate, isoprene, isoprenoid precursors, and isoprenoids.

In addition, other enzymes from the upper and lower MVA pathway may be used as well as the mvaE and mvaS gene products. Non-limiting examples of MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. MVA pathway polypeptides can include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein.

Non-limiting examples of MVA pathway polypeptides which can be used are described in International Patent Application Publication No. WO2009/076676; WO2010/003007 and WO2010/148150.

Genes Encoding mvaE and mvaS Polypeptides

In some microorganisms (such as, but not limited to, *L. grayi, E. faecium, E. gallinarum, E. casseliflavus*, and *E.*

*faecalis*), the mvaE gene encodes a polypeptide that possesses both thiolase and HMG-CoA reductase activities. In fact, the mvaE gene product represented the first bifunctional enzyme of IPP biosynthesis found in eubacteria and the first example of HMG-CoA reductase fused to another protein in nature (Hedl, et al., J Bacteriol. 2002 April; 184(8): 2116-2122). The mvaS gene, on the other hand, encodes a polypeptide having an HMG-CoA synthase activity. The mvaE and mvaS genes of a different bacterial species, *E. faecalis*, have been incorporated into *E. coli* strains previously to produce mevalonate (see US 2005/0287655 A1, the disclosure of which is incorporated by reference herein; Tabata, K. and Hashimoto, S.-I. *Biotechnology Letters* 26: 1487-1491, 2004).

Accordingly, cells (such as bacterial cells, e.g., *E. coli*) can be engineered to express one or more mvaE and mvaS genes (such as, but not limited to, mvaE and mvaS genes from *L. grayi, E. faecium, E. gallinarum, E. casseliflavus*, and/or *E. faecalis*), to increase production, peak titer, and cell productivity of mevalonate. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

Any genes encoding an upper MVA pathway polypeptide can be used in the present invention. In certain embodiments, various options of mvaE and mvaS genes (such as, but not limited to, mvaE and mvaS genes from *L. grayi, E. faecium, E. gallinarum, E. casseliflavus*, and/or *E. faecalis*) alone or in combination with one or more other mvaE and mvaS genes encoding proteins from the upper MVA pathway are contemplated within the scope of the invention. Thus, in certain aspects, any of the combinations of genes contemplated in Table 1 can be expressed in cells (such as bacterial cells) in any of the ways described above.

naturally-occurring polypeptides and nucleic acids from any of the source organisms described herein as well as mutant polypeptides and nucleic acids derived from any of the source organisms described herein that have at least one activity of a mvaE polypeptide.

Mutant mvaE polypeptides include those in which one or more amino acid residues have undergone an amino acid substitution while retaining mvaE polypeptide activity (i.e., the ability to convert acetyl Co-A to acetoacetyl CoA as well as the ability to convert 3-hydroxy-3-methylglutaryl-CoA to mevalonate). The amino acid substitutions can be conservative or non-conservative and such substituted amino acid residues can or can not be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the mvaE polypeptide can be introduced to improve the functionality of the molecule. For example, amino acid substitutions that increase the binding affinity of the mvaE polypeptide for its substrate, or that improve its ability to convert acetyl Co-A to acetoacetyl CoA and/or the ability to convert 3-hydroxy-3-methylglutaryl-CoA to mevalonate can be introduced into the mvaE polypeptide. In some aspects, the mutant mvaE polypeptides contain one or more conservative amino acid substitutions.

TABLE 1

Options for expression of mvaE and mvaS genes in host cells contemplated for the present invention.

|  | *L. grayi*, mvaE | *E. faecium*, mvaE | *E. gallinarum*, mvaE | *E. casseliflavus*, mvaE | *E. faecalis*, mvaE |
|---|---|---|---|---|---|
| *L. grayi*, mvaS | *L. grayi*, mvaE<br>*L. grayi*, mvaS | *E. faecium*, mvaE<br>*L. grayi*, mvaS | *E. gallinarum*, mvaE<br>*L. grayi*, mvaS | *E. casseliflavus*, mvaE<br>*L. grayi*, mvaS | *E. faecalis*, mvaE<br>*L. grayi*, mvaS |
| *E. faecium*, mvaS | *L. grayi*, mvaE<br>*E. faecium*, mvaS | *E. faecium*, mvaE<br>*E. faecium*, mvaS | *E. gallinarum*, mvaE<br>*E. faecium*, mvaS | *E. casseliflavus*, mvaE<br>*E. faecium*, mvaS | *E. faecalis*, mvaE<br>*E. faecium*, mvaS |
| *E. gallinarum*, mvaS | *L. grayi*, mvaE<br>*E. gallinarum*, mvaS | *E. faecium*, mvaE<br>*E. gallinarum*, mvaS | *E. gallinarum*, mvaE<br>*E. gallinarum*, mvaS | *E. casseliflavus*, mvaE<br>*E. gallinarum*, mvaS | *E. faecalis*, mvaE<br>*E. gallinarum*, mvaS |
| *E. casseliflavus*, mvaS | *L. grayi*, mvaE<br>*E. casseliflavus*, mvaS | *E. faecium*, mvaE<br>*E. casseliflavus*, mvaS | *E. gallinarum*, mvaE<br>*E. casseliflavus*, mvaS | *E. casseliflavus*, mvaE<br>*E. casseliflavus*, mvaS | *E. faecalis*, mvaE<br>*E. casseliflavus*, mvaS |
| *E. faecalis*, mvaS | *L. grayi*, mvaE<br>*E. faecalis*, mvaS | *E. faecium*, mvaE<br>*E. faecalis*, mvaS | *E. gallinarum*, mvaE<br>*E. faecalis*, mvaS | *E. casseliflavus*, mvaE<br>*E. faecalis*, mvaS | *E. faecalis*, mvaE<br>*E. faecalis*, mvaS |

Exemplary mvaE Polypeptides and Nucleic Acids

The mvaE gene encodes a polypeptide that possesses both thiolase and HMG-CoA reductase activities. The thiolase activity of the polypeptide encoded by the mvaE gene converts acetyl Co-A to acetoacetyl CoA whereas the HMG-CoA reductase enzymatic activity of the polypeptide converts 3-hydroxy-3-methylglutaryl-CoA to mevalonate. Exemplary mvaE polypeptides and nucleic acids include In one aspect, mvaE proteins that are not degraded or less prone to degradation can be used for the production of mevalonate, isoprene, isoprenoid precursors, and/or isoprenoids. Examples of gene products of mvaEs that are not degraded or less prone to degradation which can be used include, but are not limited to, those from the organisms *E. faecium, E. gallinarum, E. casseliflavus, E. faecalis*, and *L. grayi*. One of skill in the art can express mvaE protein in *E.*

*coli* BL21 (DE3) and look for absence of fragments by any standard molecular biology techniques. For example, absence of fragments can be identified on Safestain stained SDS-PAGE gels following His-tag mediated purification or when expressed in mevalonate, isoprene or isoprenoid producing *E. coli* BL21 using the methods of detection described herein.

Standard methods, such as those described in Hedl et al., (*J Bacteriol.* 2002, April; 184(8): 2116-2122) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA, are 1 mM acetyl-CoA, 10 mM $MgCl_2$, 50 mM Tris, pH 10.5 and the reaction is initiated by addition of enzyme. Assays can employ a final volume of 200 µl. For the assay, 1 enzyme unit (eu) represents the synthesis or thiolysis in 1 min of 1 µmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)-HMG-CoA, 100 mM KCl, and 100 mM $K_xPO_4$, pH 6.5. Assays employ a final volume of 200 µl. Reactions are initiated by adding the enzyme. For the assay, 1 eu represents the turnover, in 1 min, of 1 µmol of NADP(H). This corresponds to the turnover of 0.5 µmol of HMG-CoA or mevalonate.

Alternatively, production of mevalonate in cells (such as bacterial cells) can be measured by, without limitation, gas chromatography (see U.S. Patent Application Publication No.: US 2005/0287655 A1) or HPLC (See U.S. patent application Ser. No. 12/978,324). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 µM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevalonate containing solutions of known concentration.

Exemplary mvaE nucleic acids include nucleic acids that encode a polypeptide, fragment of a polypeptide, peptide, or fusion polypeptide that has at least one activity of a mvaE polypeptide. Exemplary mvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi* DSM 20601, *Enterococcus faecium*, *Enterococcus gallinarum* EG2, and/or *Enterococcus casseliflavus*. The mvaE nucleic acid encoded by the *Listeria grayi* DSM 20601 mvaE gene can have at least about 99%, 98%, 97%, 96%, 95%, 95%, 93%, 92%, 91%, 90%, 89%, 88%, 87%, 86%, 85% sequence identity to SEQ ID NO:1. In another aspect, the mvaE nucleic acid encoded by the *Listeria grayi* DSM 20601 mvaE gene can have at least about 84%, 83%, 82%, 81%, or 80% sequence identity to SEQ ID NO:1. The mvaE nucleic acid encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:3. In another aspect, the mvaE nucleic acid encoded by the *Enterococcus faecium* mvaE gene can have at least about 84%, 83%, 82%, 81%, or 80% sequence identity to SEQ ID NO:3. The mvaE nucleic acid encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:5. In another aspect, the mvaE nucleic acid encoded by the *Enterococcus gallinarum* EG2 mvaE gene can have at least about 84%, 83%, 82%, 81%, or 80% sequence identity to SEQ ID NO:5. The mvaE nucleic acid encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:7. In another aspect, the mvaE nucleic acid encoded by the *Enterococcus casseliflavus* mvaE gene can have at least about 84%, 83%, 82%, 81%, or 80% sequence identity to SEQ ID NO:7. In any of the aspects herein, the upper MVA pathway polypeptides may be encoded by a nucleic acid with at least about 99%, 98%, 97%, 96%, 95%, 95%, 93%, 92%, 91%, 90%, 89%, 88%, 87%, 86%, 85%, 84%, 83%, 82%, 81%, or 80% sequence identity to any one of SEQ ID NOs:1-8. In any of the aspects herein, the upper MVA pathway polypeptides may be encoded by a nucleic acid with of any one of SEQ ID NOs:1-8.

Exemplary mvaE polypeptides include fragments of a polypeptide, peptide, or fusion polypeptide that has at least one activity of an mvaE polypeptide. Exemplary mvaE polypeptides and include naturally-occurring polypeptides from any of the source organisms described herein as well as mutant polypeptides derived from any of the source organisms described herein. Exemplary mvaE polypeptides include, for example, mvaE polypeptides isolated from *Listeria grayi* DSM 20601, *Enterococcus faecium*, *Enterococcus gallinarum* EG2, and/or *Enterococcus casseliflavus*. The mvaE polypeptide encoded by the *Listeria grayi* DSM 20601 mvaE gene can have at least about 99%, 98%, 97%, 96%, 95%, 95%, 93%, 92%, 91%, 90%, 89%, 88%, 87%, 86%, 85% sequence identity to SEQ ID NO:13. In another aspect, the mvaE polypeptide encoded by the *Listeria grayi* DSM 20601 mvaE gene can have at least about 84%, 83%, 82%, 81%, or 80% sequence identity to SEQ ID NO:13. The mvaE polypeptide encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:15. In another aspect, the mvaE polypeptide encoded by the *Enterococcus faecium* mvaE gene can have at least about 84%, 83%, 82%, 81%, or 80% sequence identity to SEQ ID NO:15. The mvaE polypeptide encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:11. In another aspect, the mvaE polypeptide encoded by the *Enterococcus gallinarum*

EG2 mvaE gene can have at least about 84%, 83%, 82%, 81%, or 80% sequence identity to SEQ ID NO:11. The mvaE polypeptide encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:17. In another aspect, the mvaE polypeptide encoded by the *Enterococcus casseliflavus* mvaE gene can have at least about 84%, 83%, 82%, 81%, or 80% sequence identity to SEQ ID NO:17. In any of the aspects herein, the upper MVA pathway polypeptides may be encoded by a polypeptide with at least about 99%, 98%, 97%, 96%, 95%, 95%, 93%, 92%, 91%, 90%, 89%, 88%, 87%, 86%, 85%, 84%, 83%, 82%, 81%, or 80% sequence identity to any one of SEQ ID NOs:11-18. In any of the aspects herein, the upper MVA pathway polypeptides may be encoded by a polypeptide with any one of SEQ ID NOs:11-18.

The mvaE nucleic acid can be expressed in a cell (such as a bacterial cell) on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

Exemplary mvaS Polypeptides and Nucleic Acids

The mvaS gene encodes a polypeptide that possesses HMG-CoA synthase activity. This polypeptide can convert acetoacetyl CoA to 3-hydroxy-3-methylglutaryl-CoA (HMG-CoA). Exemplary mvaS polypeptides and nucleic acids include naturally-occurring polypeptides and nucleic acids from any of the source organisms described herein as well as mutant polypeptides and nucleic acids derived from any of the source organisms described herein that have at least one activity of a mvaS polypeptide.

Mutant mvaS polypeptides include those in which one or more amino acid residues have undergone an amino acid substitution while retaining mvaS polypeptide activity (i.e., the ability to convert acetoacetyl CoA to 3-hydroxy-3-methylglutaryl-CoA). Amino acid substitutions in the mvaS polypeptide can be introduced to improve the functionality of the molecule. For example, amino acid substitutions that increase the binding affinity of the mvaS polypeptide for its substrate, or that improve its ability to convert acetoacetyl CoA to 3-hydroxy-3-methylglutaryl-CoA can be introduced into the mvaS polypeptide. In some aspects, the mutant mvaS polypeptides contain one or more conservative amino acid substitutions.

Standard methods, such as those described in Quant et al. (*Biochem J.*, 1989, 262:159-164), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 ml assay system containing 50 mm-Tris/HCl, pH 8.0, 10 mM-MgCl2 and 0.2 mM-dithiothreitol at 30° C.; 5 mM-acetyl phosphate, 10, M-acetoacetyl-CoA and 5 ul samples of extracts can be added, followed by simultaneous addition of acetyl-CoA (100 uM) and 10 units of PTA. HMG-CoA synthase activity is then measured as the difference in the rate before and after acetyl-CoA addition. The absorption coefficient of acetoacetyl-CoA under the conditions used (pH 8.0, 10 mM-MgCl2), is $12.2 \times 10^3$ $M^{-1}$ $cm^{-1}$. By definition, 1 unit of enzyme activity causes 1 umol of acetoacetyl-CoA to be transformed per minute.

Alternatively, production of mevalonate in cells (such as bacterial cells) can be measured by, without limitation, gas chromatography (see U.S. Patent Application Publication No.: US 2005/0287655 A1) or HPLC (See U.S. patent application Ser. No. 12/978,324). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 μM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevonate containing solutions of known concentration.

Exemplary mvaS nucleic acids include nucleic acids that encode a polypeptide, fragment of a polypeptide, peptide, or fusion polypeptide that has at least one activity of a mvaS polypeptide. Exemplary mvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria grayi* DSM 20601, *Enterococcus faecium*, *Enterococcus gallinarum* EG2, and/or *Enterococcus casseliflavus*. The mvaS nucleic acid encoded by the *Listeria grayi* DSM 20601 mvaS gene can have at least about 99%, 98%, 97%, 96%, 95%, 95%, 93%, 92%, 91%, 90%, 89%, 88%, 87%, 86%, or 85% sequence identity to SEQ ID NO:2. The mvaS nucleic acid encoded by the *Listeria grayi* DSM 20601 mvaS gene can also have at least about 84%, 83%, 82%, 81%, or 80% sequence identity to SEQ ID NO:2. The mvaS nucleic acid encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:4. The mvaS nucleic acid encoded by the *Enterococcus faecium* mvaS gene can have at least about 84%, 83%, 82%, 81%, or 80% sequence identity to SEQ ID NO:4. The mvaS nucleic acid encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:6. The mvaS nucleic acid encoded by the *Enterococcus gallinarum* EG2 mvaS gene can have at least about 84%, 83%, 82%, 81%, or 80% sequence identity to SEQ ID NO:6. The mvaS nucleic acid encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:8. The mvaS nucleic acid encoded by the *Enterococcus casseliflavus* mvaS gene can have at least about 84%, 83%, 82%, 81%, or 80% sequence identity to SEQ ID NO:8.

Exemplary mvaS polypeptides include fragments of a polypeptide, peptide, or fusion polypeptide that has at least one activity of an mvaS polypeptide. Exemplary mvaS polypeptides include naturally-occurring polypeptides and polypeptides from any of the source organisms described herein as well as mutant polypeptides derived from any of the source organisms described herein. Exemplary mvaS polypeptides include, for example, mvaS polypeptides isolated from *Listeria grayi* DSM 20601, *Enterococcus faecium, Enterococcus gallinarum* EG2, and/or *Enterococcus casseliflavus*. The mvaS polypeptide encoded by the *Listeria grayi* DSM 20601 mvaS gene can have at least about 99%, 98%, 97%, 96%, 95%, 95%, 93%, 92%, 91%, 90%, 89%, 88%, 87%, 86%, or 85% sequence identity to SEQ ID NO:14. The mvaS polypeptide encoded by the *Listeria grayi* DSM 20601 mvaS gene can also have at least about 84%, 83%, 82%, 81%, or 80% sequence identity to SEQ ID NO:14. The mvaS polypeptide encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:16. The mvaS polypeptide encoded by the *Enterococcus faecium* mvaS gene can have at least about 84%, 83%, 82%, 81%, or 80% sequence identity to SEQ ID NO:16. The mvaS polypeptide encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:12. The mvaS polypeptide encoded by the *Enterococcus gallinarum* EG2 mvaS gene can have at least about 84%, 83%, 82%, 81%, or 80% sequence identity to SEQ ID NO:12. The mvaS polypeptide encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:18. The mvaS polypeptide encoded by the *Enterococcus casseliflavus* mvaS gene can have at least about 84%, 83%, 82%, 81%, or 80% sequence identity to SEQ ID NO:18.

The mvaS nucleic acid can be expressed in a cell (such as a bacterial cell) on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Nucleic Acids Encoding Acetoacetyl-CoA Synthase Polypeptides

In one aspect, any of the cells (such as bacterial cells) described herein can contain one or more heterologous nucleic acid(s) encoding an acetoacetyl-CoA synthase polypeptide. The acetoacetyl-CoA synthase gene (a.k.a. nphT7) is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., *PNAS* Vol 107, No. 25, pp. 11265-11270 (2010), the contents of which are expressly incorporated herein for teaching about nphT7. An acetoacetyl-CoA synthase gene from an actinomycete of the genus *Streptomyces* CL190 strain was described in Japanese Patent Publication (Kokai) No. 2008-61506 A and U.S. Patent Application Publication No. 2010/0285549, the disclosure of each of which are incorporated by reference herein. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In one aspect, acetoacetyl-CoA synthase of the present invention synthesizes acetoacetyl-CoA from malonyl-CoA and acetyl-CoA via an irreversible reaction. The use of acetoacetyl-CoA synthase to generate acetyl-CoA provides an additional advantage in that this reaction is irreversible while acetoacetyl-CoA thiolase enzyme's action of synthesizing acetoacetyl-CoA from two acetyl-CoA molecules is reversible. Consequently, the use of acetoacetyl-CoA synthase to synthesize acetoacetyl-CoA from malonyl-CoA and acetyl-CoA can result in significant improvement in productivity for isoprene compared with using thiolase to generate the end same product.

Furthermore, the use of acetoacetyl-CoA synthase to produce isoprene provides another advantage in that acetoacetyl-CoA synthase can convert malonyl CoA to acetyl CoA via decarboxylation of the malonyl CoA. Thus, stores of starting substrate are not limited by the starting amounts of acetyl CoA. The synthesis of acetoacetyl-CoA by acetoacetyl-CoA synthase can still occur when the starting substrate is only malonyl-CoA. In one aspect, the pool of starting malonyl-CoA is increased by using host strains that have more malonyl-CoA. Such increased pools can be naturally occurring or be engineered by molecular manipulation. See, for example Fowler, et al., *Applied and Environmental Microbiology*, Vol. 75, No. 18, pp. 5831-5839 (2009).

In any of the aspects or embodiments described herein, an enzyme that has the ability to synthesize acetoacetyl-CoA from malonyl-CoA and acetyl-CoA can be used. Non-limiting examples of such an enzyme are described herein. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used.

An example of such an acetoacetyl-CoA synthase gene is the gene encoding a protein having the amino acid sequence of SEQ ID NO:19. Such a protein having the amino acid sequence of SEQ ID NO:19 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules.

In one embodiment, the gene encoding a protein having the amino acid sequence of SEQ ID NO:19 can be obtained by a nucleic acid amplification method (e.g., PCR) with the use of genomic DNA obtained from an actinomycete of the *Streptomyces* sp. CL190 strain as a template and a pair of primers that can be designed with reference to Japanese Patent Publication (Kokai) No. 2008-61506 A.

As described herein, an acetoacetyl-CoA synthase gene for use in the present invention is not limited to a gene encoding a protein having the amino acid sequence of SEQ ID NO:19 from an actinomycete of the *Streptomyces* sp. CL190 strain. Any gene encoding a protein having the ability to synthesize acetoacetyl-CoA from malonyl-CoA and acetyl-CoA and which does not synthesize acetoacetyl-CoA from two acetyl-CoA molecules can be used in the presently described methods. In certain embodiments, the acetoacetyl-CoA synthase gene can be a gene encoding a protein having an amino acid sequence with high similarity or substantially identical to the amino acid sequence of SEQ ID NO:19 and having the function of synthesizing acetoacetyl-CoA from malonyl-CoA and acetyl-CoA. The expression "highly similar" or "substantially identical" refers to, for example, at least about 80% identity, at least about 85%, at least about 90%, at least about 91%, at least about 92%, at least about 93%, at least about 94%, at least about 95%, at least about 96%, at least about 97%, at least about 98%, and at least about 99% identity. As used above, the identity value corresponds to the percentage of identity between amino acid residues in a different amino acid sequence and the amino acid sequence of SEQ ID NO:19, which is calculated by performing alignment of the amino acid sequence of SEQ ID NO:19 and the different amino acid sequence with the use of a program for searching for a sequence similarity.

In other embodiments, the acetoacetyl-CoA synthase gene may be a gene encoding a protein having an amino acid sequence derived from the amino acid sequence of SEQ ID NO:19 by substitution, deletion, addition, or insertion of 1 or more amino acid(s) and having the function of synthesizing acetoacetyl-CoA from malonyl-CoA and acetyl-CoA. Herein, the expression "more amino acids" refers to, for example, 2 to 30 amino acids, preferably 2 to 20 amino acids, more preferably 2 to 10 amino acids, and most preferably 2 to 5 amino acids.

In still other embodiments, the acetoacetyl-CoA synthase gene may consist of a polynucleotide capable of hybridizing to a portion or the entirety of a polynucleotide having a nucleotide sequence complementary to the nucleotide sequence encoding the amino acid sequence of SEQ ID NO:19 under stringent conditions and capable of encoding a protein having the function of synthesizing acetoacetyl-CoA from malonyl-CoA and acetyl-CoA. Herein, hybridization under stringent conditions corresponds to maintenance of binding under conditions of washing at 60° C. 2×SSC. Hybridization can be carried out by conventionally known methods such as the method described in J. Sambrook et al. Molecular Cloning, A Laboratory Manual, 3rd Ed., Cold Spring Harbor Laboratory (2001).

As described herein, a gene encoding an acetoacetyl-CoA synthase having an amino acid sequence that differs from the amino acid sequence of SEQ ID NO:19 can be isolated from potentially any organism, for example, an actinomycete that is not obtained from the *Streptomyces* sp. CL 190 strain. In addition, acetoacetyl-CoA synthase genes for use herein can be obtained by modifying a polynucleotide encoding the amino acid sequence of SEQ ID NO:19 by a method known in the art. Mutagenesis of a nucleotide sequence can be carried out by a known method such as the Kunkel method or the gapped duplex method or by a method similar to either thereof. For instance, mutagenesis may be carried out with the use of a mutagenesis kit (e.g., product names; Mutant-K and Mutant-G (TAKARA Bio)) for site-specific mutagenesis, product name; an LA PCR in vitro Mutagenesis series kit (TAKARA Bio), and the like.

The activity of an acetoacetyl-CoA synthase having an amino acid sequence that differs from the amino acid sequence of SEQ ID NO:19 can be evaluated as described below. Specifically, a gene encoding a protein to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein being tested has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

Exemplary Host Cells

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any microorganism or progeny thereof that can be used to heterologously express genes can be used for modulation of any of the genes described herein for increased production of mevalonate, isoprene, isoprenoid precursor molecules, and/or isoprenoids (e.g., citrate synthase, phosphotransacetylase, acetate kinase, lactate dehydrogenase, malic enzyme, pyruvate dehydrogenase, 6-phosphogluconolactonase, phosphoenolpyruvate carboxylase, the inhibitor of RssB activity during magnesium starvation protein, the acrA component of the multidrug efflux pump acrAB-TolC, and/or FNR. Also, any microorganism or progeny thereof that can be used to heterologously express genes can be used to express one or more heterologous nucleic acids encoding upper MVA pathway polypeptides. In some aspects, any microorganism or progeny thereof that can be used to heterologously express genes can be used to express one or more mvaE and mvaS genes (such as, but not limited to, mvaE and mvaS genes from *L. grayi, E. faecium, E. gallinarum, E. casseliflavus*, and/or *E. faecalis*). Bacteria cells, including gram positive or gram negative bacteria can be used to express any of the upper MVA pathway genes (such as mvaE and mvaS genes) described above. In particular, upper MVA pathway gene (such as mvaE and mvaS genes) can be expressed in any one of *P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In some aspects, the host cell can be a *Lactobacilis* spp., such as *Lactobacillus lactis* or a *Lactobacillus plantarum*.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce mevalonate, isoprene, isoprenoid precursors, and/or isoprenoids can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce mevalonate, isoprene, isoprenoid precursors, and/or isoprenoids. Facultative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, *Biotechnology Advances*, (1989), 7(2):127-154). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A sojae, A. japonicus, A. nidulans,* or *A. awamori, Fusarium* sp., such as *F. roseum, F. graminum F. cerealis, F. oxysporuim,* or *F. venenatum, Neurospora* sp., such as *N. crassa,* Hypocrea sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum,* or *F. solani.* In certain embodiments, plasmids or plasmid components for use herein include those described in U.S. patent pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., *Yeast*, (1992), 8(6): 423-488). In certain embodiments, plasmids or plasmid components for use herein include those described in U.S. Pat. No. 7,659,097 and U.S. patent pub. No. US 2011/0045563.

The host cell can additionally be a species of algae, such as a green algae, red algae, glaucophytes, chlorarachniophytes, euglenids, chromista, or dinoflagellates. (See, e.g., Saunders & Warmbrodt, "*Gene Expression in Algae and Fungi, Including Yeast,*" (1993), National Agricultural Library, Beltsville, Md.). In certain embodiments, plasmids or plasmid components for use herein include those described in U.S. Patent Pub. No. US 2011/0045563. In some aspects, the host cell is a cyanobacterium, such as cyanobacterium classified into any of the following groups based on morphology: *Chlorococcales, Pleurocapsales, Oscillatoriales, Nostocales,* or *Stigonematales* (See, e.g., Lindberg et al., Metab. Eng., (2010) 12(1):70-79). In certain embodiments, plasmids or plasmid components for use herein include those described in U.S. patent pub. No. US 2010/0297749; US 2009/0282545 and Intl. Pat. Appl. No. WO 2011/034863.

*E. coli* host cells that have been engineered to increase carbon flux to mevalonate can be used to express one or more upper MVA pathway polypeptides, such as any of the upper MVA pathway polypeptides described herein. In some aspects, *E. coli* host cells can be used to express one or more mvaE and mvaS polypeptides (such as, but not limited to, mvaE and mvaS polypeptides from *L. grayi, E. faecium, E. gallinarum, E. casseliflavus,* and/or *E. faecalis*) in the compositions and methods described herein. In one aspect, the host cell is a recombinant cell of an *Escherichia coli* (*E. coli*) strain, or progeny thereof, capable of producing mevalonate that expresses one or more nucleic acids encoding upper MVA pathway polypeptides (e.g., mvaE and mvaS polypeptides, such as, but not limited to, mvaE and mvaS polypeptides from *L. grayi, E. faecium, E. gallinarum, E. casseliflavus,* and/or *E. faecalis*). The *E. coli* host cells (such as those cells that have been engineered to increase carbon flux to mevalonate as described herein) can produce mevalonate in amounts, peak titers, and cell productivities greater than that of the same cells lacking one or more heterologously expressed nucleic acids encoding upper MVA pathway polypeptides (e.g., mvaE and mvaS polypeptides, such as, but not limited to, mvaE and mvaS polypeptides from *L. grayi, E. faecium, E. gallinarum, E. casseliflavus,* and/or *E. faecalis*) and which have not been engineered to increase carbon flux to mevalonate. In addition, the one or more heterologously expressed nucleic acids encoding upper MVA pathway polypeptides in *E. coli* can be chromosomal copies (e.g., integrated into the *E. coli* chromosome). In another aspect, the one or more heterologously expressed nucleic acids encoding mvaE and mvaS polypeptides (such as, but not limited to, mvaE and mvaS polypeptides from *L. grayi, E. faecium, E. gallinarum, E. casseliflavus,* and/or *E. faecalis*) in *E. coli* can be chromosomal copies (e.g., integrated into the *E. coli* chromosome). In other aspects, the *E. coli* cells are in culture.

Exemplary Cell Culture Media

As used herein, the terms "minimal medium" or "minimal media" refer to growth medium containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for microorganism (e.g., bacterial cell) growth; (2) various salts, which can vary among microorganism (e.g., bacterial) species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4$-$7H_2O$, 15 g $KH_2PO_4$, 2.5 g NaCl, and 5.0 g $NH_4Cl$ per liter); (2) 2 ml of 1 M $MgSO_4$ (sterile); (3) 20 ml of 20% (w/v) glucose (or other carbon source); and (4) 100 µl of 1 M $CaCl_2$ (sterile). Each liter of TM3 minimal medium contains (1) 13.6 g $K_2HPO_4$; (2) 13.6 g $KH_2PO_4$; (3) 2 g $MgSO_4$*$7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4*H_2O$; (3) 10 g NaCl; (4) 1 g $FeSO_4*7H_2O$; (4) 1 g $CoCl_2*6H_2O$; (5) 1 g $ZnSO_4*7H_2O$; (6) 100 mg $CuSO_4*5H_2O$; (7) 100 mg $H_3BO_3$; and (8) 100 mg $NaMoO_4*2H_2O$; pH is adjusted to ~3.0.

An additional exemplary minimal media includes (1) potassium phosphate $K_2HPO_4$, (2) Magnesium Sulfate $MgSO_4*7H_2O$, (3) citric acid monohydrate $C_6H_8O_7*H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 ml All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

Any carbon source can be used to cultivate the host cells. The term "carbon source" refers to one or more carbon-containing compounds capable of being metabolized by a host cell or organism. For example, the cell medium used to cultivate the host cells can include any carbon source suitable for maintaining the viability or growing the host cells. In some aspects, the carbon source is a carbohydrate (such as monosaccharide, disaccharide, oligosaccharide, or polysaccharides), or invert sugar (e.g., enzymatically treated sucrose syrup).

In some aspects, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

Exemplary Cell Culture Conditions

Materials and methods suitable for the maintenance and growth of the recombinant cells of the invention are described infra, e.g., in the Examples section. Other materials and methods suitable for the maintenance and growth of cell (e.g. bacterial) cultures are well known in the art. Exemplary techniques can be found in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716, *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of one or more isoprene synthase, DXP pathway (e.g., DXS), IDI, MVA pathway (e.g., but not limited to, mvaE and/or mvaS), or PGL polypeptides encoded by a nucleic acid inserted into the host cells.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the host cells. In addition, more specific cell culture conditions can be used to culture the cells. For example, in some embodiments, the cells (e.g., bacterial cells, such as *E. coli* cells) express one or more heterologous nucleic acids encoding mvaE and mvaS polypeptides (such as, but not limited to, mvaE and mvaS polypeptides from *L. grayi*, *E. faecium*, *E. gallinarum*, *E. casseliflavus*, and/or *E. faecalis*) under the control of a strong promoter in a low to medium copy plasmid and are cultured at 34° C.

Standard culture conditions and modes of fermentation, such as batch, fed-batch, or continuous fermentation that can be used are described in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716. Batch and Fed-Batch fermentations are common and well known in the art and examples can be found in Brock, *Biotechnology: A Textbook of Industrial Microbiology*, Second Edition (1989) Sinauer Associates, Inc.

In some aspects, the cells are cultured under limited glucose conditions. By "limited glucose conditions" is meant that the amount of glucose that is added is less than or about 105% (such as about 100%, 90%, 80%, 70%, 60%, 50%, 40%, 30%, 20%, or 10%) of the amount of glucose that is consumed by the cells. In particular aspects, the amount of glucose that is added to the culture medium is approximately the same as the amount of glucose that is consumed by the cells during a specific period of time. In some aspects, the rate of cell growth is controlled by limiting the amount of added glucose such that the cells grow at the rate that can be supported by the amount of glucose in the cell medium. In some aspects, glucose does not accumulate during the time the cells are cultured. In various aspects, the cells are cultured under limited glucose conditions for greater than or about 1, 2, 3, 5, 10, 15, 20, 25, 30, 35, 40, 50, 60, or 70 hours. In various aspects, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions can allow more favorable regulation of the cells.

In some aspects, the cells (such as bacterial cells) are grown in batch culture. The cells (such as bacterial cells) can also be grown in fed-batch culture or in continuous culture. Additionally, the cells (such as bacterial cells) can be cultured in minimal medium, including, but not limited to, any of the minimal media described above. The minimal medium can be further supplemented with 1.0% (w/v) glucose, or any other six carbon sugar, or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract.

Recombinant Microorganisms Capable of Increased Production of Mevalonate

The recombinant microorganisms (e.g., recombinant bacterial cells) described herein have the ability to produce mevalonate at an amount and/or concentration greater than that of the same cells without any manipulation to the various enzymatic pathways described herein. The recombinant microorganisms (e.g., bacterial cells) that have been engineered for modulation in the various pathways described herein to increase carbon flux to mevalonate can be used to produce mevalonate. These engineered cells can also contain one or more copies of a heterologous nucleic acid encoding upper MVA pathway polypeptides. In some aspects, the cells can contain one or more copies of a heterologous nucleic acid encoding mvaE and mvaS polypeptides (such as, but not limited to, mvaE and mvaS polypeptides from *L. grayi, E. faecium, E. gallinarum, E. casseliflavus*, and/or *E. faecalis*). In one aspect, the recombinant cells (such as bacterial cells) described herein have the ability to produce mevalonate at a concentration greater than that of the same cells that have not been engineered to increase carbon flux towards mevalonate. In other aspects, the recombinant cells described herein have the ability to produce mevalonate at a concentration greater than that of the same cells lacking one or more copies of a heterologous nucleic acid encoding mvaE and mvaS polypeptides (such as, but not limited to, mvaE and mvaS polypeptides from *L. grayi, E. faecium, E. gallinarum, E. casseliflavus*, and/or *E. faecalis*). In one aspect, any of the cells disclosed herein can be cultured in minimal medium. In some cases, the one or more copies of a heterologous nucleic acid encoding an upper MVA pathway polypeptide (e.g., an mvaE and/or mvaS polypeptide such as, but not limited to, mvaE and mvaS polypeptides from *L. grayi, E. faecium, E. gallinarum, E. casseliflavus*, and/or *E. faecalis*) is a heterologous nucleic acid that is integrated into the host cell's chromosome. The cells (such as bacterial cells) can produce greater than about 85 mg/L/hr/OD of mevalonate. Alternatively, the cells (such as bacterial cells) can produce greater than about 30 mg/L/hr/OD, 40 mg/L/hr/OD, 50 mg/L/hr/OD, 60 mg/L/hr/OD, 70 mg/L/hr/OD, 80 mg/L/hr/OD, 90 mg/L/hr/OD, 100 mg/L/hr/OD, 110 mg/L/hr/OD, 120 mg/L/hr/OD, 130 mg/L/hr/OD, 140 mg/L/hr/OD, 150 mg/L/hr/OD, 160 mg/L/hr/OD, 170 mg/L/hr/OD, 180 mg/L/hr/OD, 190 mg/L/hr/OD, or 200 mg/L/hr/OD of mevalonate, inclusive, as well as any numerical value in between these numbers.

The host cells (such as bacterial cells) described herein are engineered to have one or more mutations which increase carbon flux towards the MVA pathway and can produce higher peak titers of mevalonate in comparison to cells which have not been similarly engineered. Additionally, the cells described herein produce mevalonate at a higher peak titer than that of the same cells lacking one or more copies of a heterologous nucleic acid encoding an upper MVA pathway polypeptide. In another aspect, the cells (such as bacterial cells) described herein produce mevalonate at a higher peak titer than that of the same cells lacking one or more copies of a heterologous nucleic acid encoding mvaE and mvaS polypeptides (such as, but not limited to, mvaE and mvaS polypeptides from *L. grayi, E. faecium, E. gallinarum, E. casseliflavus*, and/or *E. faecalis*) when cultured in minimal medium. The cells (such as bacterial cells) can produce greater than about 105 g/L peak titer of mevalonate after 48 hours of fermentation. Alternatively, the cells (such as bacterial cells) can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, 200 g/L, 210 g/L, 220 g/L, 230 g/L, 240 g/L, 250 g/L, 260 g/L, 270 g/L, 280 g/L, 290 g/L, 300 g/L peak titer of mevalonate after 48 hours of fermentation, inclusive, as well as any numerical value in between these numbers.

The host cells (such as bacterial cells) described herein are engineered to have one or more mutations which increase carbon flux towards the MVA pathway which results in a higher cell productivity index (CPI) for mevalonate in comparison to cells which have not been similarly engineered. Additionally, the cells described herein have a higher CPI than that of the same cells lacking one or more copies of a heterologous nucleic acid encoding an upper MVA pathway polypeptide. In some aspects, the cells (such as bacterial cells) described herein have a higher CPI than that of the same cells lacking one or more copies of a heterologous nucleic acid encoding an mvaE and mvaS polypeptides (such as, but not limited to, mvaE and mvaS polypeptides from *L. grayi, E. faecium, E. gallinarum, E. casseliflavus*, and/or *E. faecalis*). In one aspect, the cells can be cultured in minimal medium. The cells (such as bacterial cells) can have a CPI for mevalonate of at least about 4.5 (g/g). Alternatively, the cells (such as bacterial cells) can have a CPI for mevalonate of at least about 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers.

The host cells (such as bacterial cells) described herein are engineered to have one or more mutations which increase carbon flux towards the MVA pathway which results in a higher mass yield of mevalonate in comparison to cells which have not been similarly engineered. Additionally, the cells described herein have a higher mass yield of mevalonate from glucose than that of the same cells lacking one or more copies of a heterologous nucleic acid encoding an upper MVA pathway polypeptide. In some aspects, the cells (such as bacterial cells) described herein have a higher mass yield of mevalonate from glucose than that of the same cells lacking one or more copies of a heterologous nucleic acid encoding mvaE and mvaS polypeptides (such as, but not limited to, mvaE and mvaS polypeptides from *L. grayi, E. faecium, E. gallinarum, E. casseliflavus*, and/or *E. faecalis*). In one aspect, the cells can be cultured in minimal medium. The cells (such as bacterial cells) can produce a mass yield of mevalonate from glucose of at least about 38%. Alternatively, the cells (such as bacterial cells) can produce a mass yield of mevalonate from glucose of at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or 55%, inclusive, as well as any numerical value in between these numbers.

Methods of Using Recombinant Cells (e.g. Recombinant Bacterial Cells) to Produce High Amounts of Mevalonate Also provided herein are methods for the production of mevalonate. In some aspects, the method for producing mevalonate comprises: (a) culturing a composition comprising recombinant cells (such as bacterial cells) which have been engineered to increase carbon flux to mevalonate as described herein (including any of the cells, such as the bacterial cells described above), or progeny thereof, capable of producing mevalonate; and (b) producing mevalonate. In some aspects, the method of producing mevalonate comprises the steps of culturing any of the recombinant cells described herein under conditions suitable for the production of mevalonate and allowing the recombinant cells to produce mevalonate. In some aspects, the method of producing mevalonate further comprises a step of recovering the mevalonate.

The method of producing mevalonate can also comprise the steps of: (a) culturing cells heterologously expressing one or more copies of a gene encoding an upper MVA pathway polypeptide; and (b) producing mevalonate. In other aspects, the method of producing mevalonate can comprise the steps of: (a) culturing cells (such as bacterial cells, including, but not limited to, E. coli cells) that do not endogenously have an mvaE gene and an mvaS gene (such as, but not limited to, mvaE and mvaS genes from L. grayi, E. faecium, E. gallinarum, E. casseliflavus, and/or E. faecalis) in minimal medium, wherein the cells heterologously express one or more copies of a gene encoding a mvaE polypeptide and an mvaS polypeptide (such as, but not limited to, mvaE and mvaS polypeptides from L. grayi, E. faecium, E. gallinarum, E. casseliflavus, and/or E. faecalis); and (b) producing mevalonate. Additionally, the cells can produce mevalonate in concentrations greater than that of the same cells lacking one or more heterologous copies of a gene encoding an upper MVA pathway polypeptide and which have not been engineered for greater carbon flux towards mevalonate. In other aspects, the cells (such as bacterial cells) can produce mevalonate in concentrations greater than that of the same cells lacking one or more heterologous copies of a gene encoding an mvaE polypeptide and an mvaS polypeptide (such as, but not limited to, mvaE and mvaS polypeptides from L. grayi, E. faecium, E. gallinarum, E. casseliflavus, and/or E. faecalis), when the cells are cultured in minimal medium. In some cases, the one or more copies of a heterologous nucleic acid encoding an upper MVA pathway polypeptide is a heterologous nucleic acid that is integrated into the host cell's chromosome. In one aspect, the one or more copies of a heterologous nucleic acid encoding an mvaE and an mvaS polypeptide (such as, but not limited to, mvaE and mvaS polypeptides from L. grayi, E. faecium, E. gallinarum, E. casseliflavus, and/or E. faecalis) is a heterologous nucleic acid that is integrated into the host cell's chromosome The instant methods for the production of mevalonate can produce greater than about 85 mg/L/hr/OD of mevalonate. Alternatively, mevalonate can be produced in amounts greater than about 30 mg/L/hr/OD, 40 mg/L/hr/OD, 50 mg/L/hr/OD, 60 mg/L/hr/OD, 70 mg/L/hr/OD, 80 mg/L/hr/OD, 90 mg/L/hr/OD, 100 mg/L/hr/OD, 110 mg/L/hr/OD, 120 mg/L/hr/OD, 130 mg/L/hr/OD, 140 mg/L/hr/OD, 150 mg/L/hr/OD, 160 mg/L/hr/OD, 170 mg/L/hr/OD, 180 mg/L/hr/OD, 190 mg/L/hr/OD, or 200 mg/L/hr/OD of mevalonate, inclusive, as well as any numerical value in between these numbers. In some aspects, the method of producing mevalonate further comprises a step of recovering the mevalonate.

The method of producing mevalonate can similarly comprise the steps of: (a) culturing cells which have been engineered for increased carbon flux to mevalonate as described herein, wherein the cells heterologously express one or more copies of an upper MVA pathway gene encoding one or more upper MVA pathway polypeptides; and (b) producing mevalonate, wherein the cells produce mevalonate with a higher peak titer after 48 hours of fermentation than that of the same cells lacking one or more copies of an upper MVA pathway gene encoding one or more upper MVA pathway polypeptides, and which have not been engineered for increased carbon flux to mevalonate production. In other aspects, the method of producing mevalonate can similarly comprise the steps of: (a) culturing cells (such as bacterial cells) which have been engineered for increased carbon flux to mevalonate as described herein (including, but not limited to, E. coli cells) that do not endogenously have an mvaE gene and an mvaS gene from (such as, but not limited to, mvaE and mvaS genes from L. grayi, E. faecium, E. gallinarum, E. casseliflavus, and/or E. faecalis) in minimal medium, wherein the cells (such as bacterial cells) heterologously express one or more copies of a gene encoding a mvaE polypeptide and an mvaS polypeptide (such as, but not limited to, mvaE and mvaS polypeptides from L. grayi, E. faecium, E. gallinarum, E. casseliflavus, and/or E. faecalis); and (b) producing mevalonate, wherein the cells (such as bacterial cells) produce mevalonate with a higher peak titer after 48 hours of fermentation than that of the same cells lacking one or more heterologous copies of a gene encoding an mvaE polypeptide and an mvaS polypeptide (such as, but not limited to, mvaE and mvaS polypeptides from L. grayi, E. faecium, E. gallinarum, E. casseliflavus, and/or E. faecalis), and which have not been engineered for increased carbon flux to mevalonate production when the cells are cultured in minimal medium.

The instant methods for the production of mevalonate can produce greater than about 105 g/L peak titer of mevalonate after 48 hours of fermentation. Alternatively, the cells (such as bacterial cells) can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, or 200 g/L peak titer of mevalonate after 48 hours of fermentation, inclusive, as well as any numerical value in between these numbers. In some aspects, the method of producing mevalonate further comprises a step of recovering the mevalonate.

The method of producing mevalonate can similarly comprise the steps of: (a) culturing cells which have been engineered for increased carbon flux to mevalonate as described herein, wherein the cells heterologously express one or more copies of an upper MVA pathway gene encoding one or more upper MVA pathway polypeptides; and (b) producing mevalonate, wherein the cells have a CPI for mevalonate higher than that of the same cells lacking one or more copies of an upper MVA pathway gene encoding one or more upper MVA pathway polypeptides, and which have not been engineered for increased carbon flux to mevalonate production. In other aspects, the method of producing mevalonate can similarly comprise the steps of: (a) culturing cells (such as bacterial cells) which have been engineered for increased carbon flux as described herein (including, but not limited to, E. coli cells) that do not endogenously have an mvaE gene and an mvaS gene (such as, but not limited to, mvaE and mvaS genes from L. grayi, E. faecium, E. gallinarum, E. casseliflavus, and/or E. faecalis) in minimal medium, wherein the cells (such as bacterial cells) heterologously express one or more copies of a gene encoding a mvaE polypeptide and an mvaS polypeptide (such as, but not limited to, mvaE and mvaS polypeptides from L. grayi, E. faecium, E. gallinarum, E. casseliflavus, and/or E. faecalis); and (b) producing mevalonate, wherein the cells (such as bacterial cells) have a CPI for mevalonate higher than that of the same cells lacking one or more heterologous copies of a gene encoding an mvaE polypeptide and an mvaS polypeptide (such as, but not limited to, mvaE and mvaS polypeptides from *L. grayi, E. faecium, E. gallinarum, E. casseliflavus*, and/or *E. faecalis*), and which have not been engineered for increased carbon flux to mevalonate production when the cells are cultured in minimal medium.

The instant methods for the production of mevalonate can produce mevalonate using cells with a CPI for mevalonate of at least 4.5 (g/g). Alternatively, the cells (such as bacterial cells) can have a CPI of at least 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers. In some aspects, the method of producing mevalonate further comprises a step of recovering the mevalonate.

Provided herein are methods of using any of the cells described above for enhanced mevalonate production. The production of mevalonate by the cells can be enhanced by the expression of one or more heterologous nucleic acids encoding an upper MVA pathway polypeptide (e.g., mvaE and mvaS polypeptides, such as, but not limited to, mvaE and/or mvaS polypeptides from *L. grayi, E. faecium, E. gallinarum, E. casseliflavus*, and/or *E. faecalis*). The production of mevalonate can be enhanced by about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of mevalonate by cells without the expression of one or more heterologous nucleic acids encoding an upper MVA pathway polypeptide (e.g., an mvaE and/or mvaS polypeptide, such as, but not limited to, mvaE and mvaS polypeptides from *L. grayi, E. faecium, E. gallinarum, E. casseliflavus*, and/or *E. faecalis*) which have not been engineered for increased carbon flux to MVA production.

The production of mevalonate by cells according to any of the methods described herein can be enhanced (e.g., enhanced by the expression of one or more heterologous nucleic acids encoding an upper MVA pathway polypeptide. In some aspects, the production of mevalonate by the cells according to any of the methods described herein can be enhanced (e.g., enhanced by the expression of one or more heterologous nucleic acids encoding the mvaE and mvaS polypeptides (such as, but not limited to, mvaE and mvaS polypeptides from *L. grayi, E. faecium, E. gallinarum, E. casseliflavus*, and/or *E. faecalis*). The production of mevalonate can be enhanced by about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of mevalonate by naturally-occurring cells (e.g., cells not expressing one or more heterologous nucleic acids encoding an upper MVA pathway polypeptide, for example, an mvaE and/or mvaS polypeptide (such as, but not limited to, mvaE and mvaS polypeptides from *L. grayi, E. faecium, E. gallinarum, E. casseliflavus*, and/or *E. faecalis*)).

The production of mevalonate can also be enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of mevalonate by naturally-occurring cells or by cells without the expression of one or more heterologous nucleic acids encoding an upper MVA pathway polypeptide (e.g., mvaE and mvaS polypeptides, such as, but not limited to, mvaE and mvaS polypeptides from *L. grayi, E. faecium, E. gallinarum, E. casseliflavus*, and/or *E. faecalis*) which have not been engineered for increased carbon flux to MVA production.

In addition, more specific cell culture conditions can be used to culture the cells in the methods described herein. For example, the method for the production of mevalonate can comprise the steps of (a) culturing cells (such as any cell engineered for increased carbon flux to mevalonate as described herein) in minimal medium at 34° C., wherein the cells heterologously express one or more copies of a gene encoding an upper MVA pathway polypeptide on a low to medium copy plasmid under the control of a strong promoter; and (b) producing mevalonate. In some aspects, the method for the production of mevalonate comprises the steps of (a) culturing cells (such as bacterial cells, including, but not limited to, *E. coli* cells) that do not endogenously have an mvaE gene and an mvaS gene (such as, but not limited to, mvaE and mvaS genes from *L. grayi, E. faecium, E. gallinarum, E. casseliflavus*, and/or *E. faecalis*) in minimal medium at 34° C., wherein the cells (such as bacterial cells) heterologously express one or more copies of a gene encoding a mvaE polypeptide and an mvaS polypeptide (such as, but not limited to, mvaE and mvaS polypeptides from *L. grayi, E. faecium, E. gallinarum, E. casseliflavus*, and/or *E. faecalis*) on a low to medium copy plasmid and under the control of a strong promoter; and (b) producing mevalonate. In some aspects, the method of producing mevalonate further comprises a step of recovering the mevalonate.

Recombinant Cells (Such as Bacterial Cells) Capable of Increased Production of Isoprene Isoprene (2-methyl-1,3-butadiene) is an important organic compound used in a wide array of applications. For instance, isoprene is employed as an intermediate or a starting material in the synthesis of numerous chemical compositions and polymers, including in the production of synthetic rubber. Isoprene is also an important biological material that is synthesized naturally by many plants and animals.

Isoprene is produced from DMAPP by the enzymatic action of isoprene synthase. Therefore, without being bound to theory, it is thought that increasing the cellular production of mevalonate in cells (such as bacterial cells) by any of the compositions and methods described above will similarly result in the production of higher amounts of isoprene. Increasing the molar yield of mevalonate production from glucose translates into higher molar yields of isoprenoid precursors and isoprenoids, including isoprene, produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprene and isoprenoid production.

Production of isoprene can be made by using any of the recombinant host cells described here where one or more of the enzymatic pathways have been manipulated such that enzyme activity is modulated to increase carbon flow towards isoprene production. The recombinant microorganisms described herein that have various enzymatic pathways manipulated for increased carbon flow to mevalonate production can be used to produce isoprene. Any of the recombinant host cells expressing one or more copies of a heterologous nucleic acid encoding upper MVA pathway polypeptides including, but not limited to, an mvaE and an mvaS polypeptide (such as, but not limited to, mvaE and mvaS polypeptides from *L. grayi, E. faecium, E. gallinarum, E. casseliflavus*, and/or *E. faecalis*) capable of increased production of mevalonate described above can also be capable of increased production of isoprene. In some aspects, these cells further comprise one or more heterologous nucleic acids encoding polypeptides of the lower MVA pathway and a heterologous nucleic acid encoding an isoprene synthase polypeptide. As an alternative to using mvaE and mvaS genes (such as, but not limited to, mvaE and mvaS genes from *L. grayi, E. faecium, E. gallinarum, E. casseliflavus*, and/or *E. faecalis*) any known MVA pathway polypeptides (upper and lower MVA pathway) can be used as well. MVA pathway polypeptides are well known to one of skill in the art.

Nucleic Acids Encoding Polypeptides of the Lower MVA Pathway

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of *M. mazei* mevalonate kinase polypeptide, *Lactobacillus* mevalonate kinase polypeptide, *M. burtonii* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In another aspect, the enzyme that phosphorylates mevalonate to mevalonate 5-phosphate is *M. mazei* mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from *Saccharomyces cerevisiae, Enterococcus faecalis*, or *Methanosarcina mazei*.

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus *Methanosarcina* and, more specifically, the lower MVK polypeptide can be from *Methanosarcina mazei*. In other aspects, the lower MVK polypeptide can be from *M. burtonii*. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variants.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from *Saccharomyces cerevisiae, Enterococcus faecalis*, or *Methanosarcina mazei*. In some aspects, the MVK polypeptide is selected from the group consisting of *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, *M. burtonii* mevalonate kinase polypeptide, and *Methanosarcina mazei* mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

Nucleic Acids Encoding Isoprene Synthase Polypeptides

In some aspects of the invention, the cells described in any of the compositions or methods described herein (including host cells that have been engineered for increased carbon flux as described herein) further comprise one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In a particular aspect, the cells are engineered to over-express the endogenous isoprene synthase pathway polypeptide relative to wild-type cells. In some aspects, the endogenous nucleic acid encoding an isoprene synthase polypeptide is operably linked to a weak promoter. In some aspects, the isoprene synthase polypeptide is a polypeptide from *Pueraria* or *Populus* or a hybrid such as *Populus alba* x *Populus tremula*.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., *J. Biol. Chem.* 270:13010-13016, 1995. In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 μL of 1M $MgCl_2$, 1 mM (250 μg/ml) DMAPP, 65 μL of Plant Extract Buffer (PEB) (50 mM Tris-HCl, pH 8.0, 20 mM $MgCl_2$, 5% glycerol, and 2 mM DTT) can be added to 25 μL of cell extract in a 20 ml Headspace vial with a metal screw cap and teflon coated silicon septum (Agilent Technologies) and cultured at 370 C for 15 minutes with shaking. The reaction can be quenched by adding 200 μL of 250 mM EDTA and quantified by GC/MS.

In some aspects, the isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a polypeptide from *Pueraria* or *Populus* or a hybrid, *Populus alba* x *Populus tremula*, or a variant thereof.

In some aspects, the isoprene synthase polypeptide or nucleic acid is from the family Fabaceae, such as the Faboideae subfamily. In some aspects, the isoprene synthase polypeptide or nucleic acid is a polypeptide or nucleic acid from *Pueraria montana* (kudzu) (Sharkey et al., *Plant Physiology* 137: 700-712, 2005), *Pueraria lobata*, poplar (such as *Populus alba, Populus nigra, Populus trichocarpa*, or *Populus alba* x *tremula* (CAC35696) (Miller et al., *Planta* 213: 483-487, 2001), aspen (such as *Populus tremuloides*) (Silver et al., JBC 270(22): 13010-1316, 1995), English Oak (*Quercus robur*) (Zimmer et al., WO 98/02550), or a variant thereof. In some aspects, the isoprene synthase polypeptide is an isoprene synthase from *Pueraria montana, Pueraria lobata, Populus tremuloides, Populus alba, Populus nigra*, or *Populus trichocarpa* or a variant thereof. In some aspects, the isoprene synthase polypeptide is an isoprene synthase from *Populus alba* or a variant thereof. In some aspects, the nucleic acid encoding the isoprene synthase (e.g., isoprene synthase from *Populus alba* or a variant thereof) is codon optimized.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring isoprene synthase. The variant can share sequence similarity with a wild-type or naturally occurring isoprene synthase. In some aspects, a variant of a wild-type or naturally occurring isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring isoprene synthase. In some aspects, a variant of a wild-type or naturally occurring isoprene synthase has any of about 70% to about 99.9%, about 75% to about 99%, about 80% to about 98%, about 85% to about 97%, or about 90% to about 95% amino acid sequence identity as that of the wild-type or naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed). In other aspects, the variant of isoprene synthase from *Populus alba* has at least one amino acid substitution, at least one amino acid insertion, and/or at least one amino acid deletion at the amino acid residue shown in Table 2. In another aspect, the variant of isoprene synthase comprises at least one amino acid substitution, at least one amino acid deletion, and at least one amino acid insertion at any of the amino acid residues shown in Table 2, wherein the amino acid residue number corresponds to the amino acid residue number of *P. alba* isoprene synthase. In one aspect, the *P. alba* isoprene synthase is a truncated isoprene synthase, for example, MEA isoprene synthase which is 16 amino acid shorter than full-length isoprene synthase.

TABLE 2

| Isoprene Synthase Variants of *P. alba* (MEA) | | | | |
|---|---|---|---|---|
| A118E | E472R | S510C | D323Y | W392S |
| S22K | K463F | S510V | D323D | W392T |
| S21R | K463T | I342I | G99D | W392V |
| S22K | R71K | K348F | K161K | A118P |
| S22R | R71L | K348Y | W392A | A118Q |
| E58L | R71M | K348K | W392C | A118A |
| T481V | R71V | C437L | W392F | E41M |
| T481Y | R71R | T240C | S288Y | GUIS |
| T502F | K393L | M460M | M228Y | S74Q |
| T381L | F542L | R461A | A3T | S74S |
| T381M | P538K | H424P | W392Y | K36D |
| T381Y | P538R | H424H | W392W | S282H |
| T383H | P538P | A448L | F89D | S282I |
| T383L | A503A | A448Q | F89E | S282W |
| E480I | L436I | A448V | F89F | S282Y |
| E480R | L436Y | G389D | E41Y | S282S |
| K393V | L436F | S444E | E41E | K36S |
| K393I | E488L | S444S | R43E | K36T |
| E415H | E488M | H511Y | R43L | K36W |
| E415V | E488T | H511H | K36E | K36Y |
| E415Y | E488W | R071I | K36H | K36K |
| R71H | E488E | R071K | K36N | |
| R71I | I342Y | R071L | K36P | |
| E58Y | C437M | K374Y | K36Q | |
| E135G | C437W | K374K | A453I | |
| A363L | C437Y | L526E | A453V | |
| K374Y | C437C | L526Q | A453A | |
| T381I | M460A | L526L | V409I | |
| L436L | I447T | R242G | V409T | |
| H254R | I447V | R242R | K161C | |
| H254C | I447Y | A443G | K161E | |
| E488C | S444D | A443Q | K161N | |

TABLE 2-continued

Isoprene Synthase Variants of *P. alba* (MEA)

| E488F | G389E | A443R | K161Q |
|-------|-------|-------|-------|
| T383Y | L376I | A443S | G99E |
| K414I | L376M | S13S | G99G |
| K414R | L376L | V268I | S288A |
| K414S | I504F | V268V | S288C |
| K414W | I504I | K161A | S288T |
| E472C | E467H | V409V | W392I |
| E472L | E467W | D323F | W392M |

*In one embodiment, the MEA *P. alba* isoprene synthase is truncated so that it is 16 amino acids shorter than full length *P. alba* isoprene synthase.

The isoprene synthase polypeptide provided herein can be any of the isoprene synthases or isoprene synthase variants described in WO 2009/132220, WO 2010/124146, and U.S. Patent Application Publication No.: 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making microorganisms encoding isoprene synthase described herein are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/124146, WO2010/078457, and WO2010/148256.

Nucleic Acids Encoding DXP Pathway Polypeptides

In some aspects of the invention, the cells described in any of the compositions or methods described herein (including host cells that have been engineered for increased carbon flux as described herein) further comprise one or more heterologous nucleic acids encoding a DXS polypeptide or other DXP pathway polypeptides. In some aspects, the cells further comprise a chromosomal copy of an endogenous nucleic acid encoding a DXS polypeptide or other DXP pathway polypeptides. In some aspects, the *E. coli* cells further comprise one or more nucleic acids encoding an IDI polypeptide and a DXS polypeptide or other DXP pathway polypeptides. In some aspects, one nucleic acid encodes the isoprene synthase polypeptide, IDI polypeptide, and DXS polypeptide or other DXP pathway polypeptides. In some aspects, one plasmid encodes the isoprene synthase polypeptide, IDI polypeptide, and DXS polypeptide or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No.: WO 2010/148150

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2, 4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2, 4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). Standard methods can be used to determine whether a polypeptide has HDR polypeptides activity by measuring the ability of the polypeptide to convert HMBPP in vitro, in a cell extract, or in vivo.

Source Organisms for Lower MVA Pathway, Isoprene Synthase, IDI, and DXP Pathway Polypeptides Isoprene synthase, IDI, DXP pathway, and/or lower MVA pathway nucleic acids (and their encoded polypeptides) can be obtained from any organism that naturally contains isoprene synthase, IDI, DXP pathway, and/or lower MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), plants, such as kudzu or poplar (e.g., *Populus alba* or *Populus alba* x *tremula* CAC35696) or aspen (e.g., *Populus tremuloides*). Exemplary sources for isoprene synthases, IDI, and/or MVA pathway polypeptides which can be used are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/078457, and WO2010/148256.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, or strains of Archaea such as *Methanosarcina mazei*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomic reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

In some aspects, the source organism is a gram-positive bacterium. Non-limiting examples include strains of *Streptomyces* (e.g., *S. lividans, S. coelicolor,* or *S. griseus*) and *Bacillus*. In some aspects, the source organism is a gram-negative bacterium, such as *E. coli* or *Pseudomonas* sp.

In some aspects, the source organism is a plant, such as a plant from the family Fabaceae, such as the Faboideae subfamily. In some aspects, the source organism is kudzu, poplar (such as *Populus alba* x *tremula* CAC35696), aspen (such as *Populus tremuloides*), or *Quercus robur*.

In some aspects, the source organism is an algae, such as a green algae, red algae, glaucophytes, chlorarachniophytes, euglenids, chromista, or dinoflagellates.

In some aspects, the source organism is a cyanobacteria, such as cyanobacteria classified into any of the following groups based on morphology: *Chroococcales, Pleurocapsales, Oscillatoriales, Nostocales,* or *Stigonematales.*

Nucleic Acids Encoding Phosphoketolase Polypeptides

In some aspects of the invention, the recombinant cells described in any of the compositions or methods described herein can further comprise one or more nucleic acids encoding a phosphoketolase polypeptide or a polypeptide having phosphoketolase activity. In some aspects, the phosphoketolase polypeptide is an endogenous polypeptide. In some aspects, the endogenous nucleic acid encoding a phosphoketolase polypeptide is operably linked to a constitutive promoter. In some aspects, the endogenous nucleic acid encoding a phosphoketolase polypeptide is operably linked to an inducible promoter. In some aspects, the endogenous nucleic acid encoding a phosphoketolase polypeptide is operably linked to a strong promoter. In some aspects, more than one endogenous nucleic acid encoding a phosphoketolase polypeptide is used (e.g, 2, 3, 4, or more copies of an endogenous nucleic acid encoding a phosphoketolase polypeptide). In a particular aspect, the cells are engineered to overexpress the endogenous phosphoketolase polypeptide relative to wild-type cells. In some aspects, the endogenous nucleic acid encoding a phosphoketolase polypeptide is operably linked to a weak promoter.

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. Thus, without being bound by theory, the expression of phosphoketolase as set forth herein can result in an increase in the amount of acetyl phosphate produced from a carbohydrate source. This acetyl phosphate can be converted into acetyl-CoA which can then be utilized by the enzymatic activities of the MVA pathway to produces mevalonate, isoprenoid precursor molecules, isoprene and/or isoprenoids. Thus the amount of these compounds produced from a carbohydrate substrate may be increased. Alternatively, production of Acetyl-P and AcCoA can be increased without the increase being reflected in higher intracellular concentration. In certain embodiments, intracellular acetyl-P or acetyl-CoA concentrations will remain unchanged or even decrease, even though the phosphoketolase reaction is taking place.

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein.

Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., J. Bact. 183:2929-2936, 2001). Any polypeptide identified as having phosphoketolase peptide activity as described herein is suitable for use in the present invention.

In other aspects, exemplary phosphoketolase nucleic acids include, for example, a phosphoketolase isolated from *Lactobacillus reuteri*, *Bifidobacterium longum*, *Ferrimonas balearica*, *Pedobactor saltans*, *Streptomyces griseus*, and/or *Nocardiopsis dassonvillei*. Additional examples of phosphoketolase enzymes which can be used herein are described in U.S. Pat. No. 7,785,858, which is incorporated by reference herein.

Pathways Involving the Entner-Doudoroff Pathway

The Entner-Doudoroff (ED) pathway is an alternative to the Emden-Meyerhoff-Parnass (EMP-glycolysis) pathway. Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway. 1998. J. Bact. 180:3495-3502; Stulke and Hillen. 2000. Annu. Rev. Microbiol. 54, 849-880; Dawes et al. 1966. Biochem. J. 98:795-803).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. 1992. J. Bact. 174:4638-4646). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or a 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of mevalonate, isoprene, isoprenoid precursor molecules, and/or isoprenoids.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

Pathways Involving the Oxidative Branch of the Pentose Phosphate Pathway

*E. coli* uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pgl) or 6-phosphogluconate dehydrogenase (gnd)) and a non-oxidative branch (with enzymes such as transketolase (tktA), transaldolase (talA or talB), ribulose-5-phosphate-epimerase and (or) ribose-5-phosphate epimerase) (Sprenger. 1995. Arch. Microbiol. 164:324-330).

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase) expression can be modulated (e.g., increase enzyme activity) to allow more carbon to flux towards fructose 6-phosphate and xylulose 5-phosphate, thereby increasing the eventual production of mevalonate, isoprene, isoprenoid precursor molecules, and/or isoprenoids. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

Pathways Involving Phosphofructokinase

Phosphofructokinase is a crucial enzyme of glycolysis which catalyzes the phosphorylation of fructose 6-phosphate. E. coli has two isozymes encoded by pfkA and pfkB. Most of the phosphofructokinase activity in the cell is due to pfkA (Kotlarz et al. 1975, Biochim. Biophys. Acta, 381:257-268).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of mevalonate, isoprene, isoprenoid precursor molecules, and/or isoprenoids. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

Recombinant Cells (Such as Bacterial Cells) Capable of Increased Production of Isoprene The recombinant cells described herein that have been engineered for increased carbon flux to isoprene have the ability to produce isoprene at a concentration greater than that of the same cells that have not been engineered for increased carbon flux to isoprene. In one aspect, the recombinant cells (such as bacterial cells) described herein (e.g., host cells that have been engineered for increased carbon flux to isoprene as described herein) have the ability to produce isoprene at a concentration greater than that of the same cells lacking one or more copies of a heterologous nucleic acid encoding an upper MVA pathway polypeptide (e.g., an mvaE and/or mvaS polypeptide, such as, but not limited to, mvaE and mvaS polypeptides from *L. grayi, E. faecium, E. gallinarum, E. casseliflavus*, and/or *E. faecalis*), one or more copies of a heterologous nucleic acid encoding a lower MVA pathway polypeptide, and one or more heterologous nucleic acids encoding an isoprene synthase polypeptide when cultured in minimal media. In certain aspects, these cells comprise one or more copies of a heterologous nucleic acid encoding an upper MVA pathway polypeptide (e.g., an mvaE and/or mvaS polypeptide, such as, but not limited to, mvaE and mvaS polypeptides from *L. grayi, E. faecium, E. gallinarum, E. casseliflavus*, and/or *E. faecalis*) one or more copies of a heterologous nucleic acid encoding a lower MVA pathway polypeptide, and one or more heterologous nucleic acids encoding an isoprene synthase polypeptide are heterologous nucleic acids. In one aspect, the one or more heterologous nucleic acids are integrated into the host cell's chromosome. The cells can produce at least 5% greater amounts of isoprene compared to isoprene-producing cells that have not been engineered to increase carbon flux to isoprene. In other aspects, the cells (such as bacterial cells) can produce at least 5% greater amounts of isoprene compared to isoprene-producing cells (such as bacterial cells) that do not comprise the mvaE and mvaS polypeptides (such as, but not limited to, mvaE and mvaS polypeptides from *L. grayi, E. faecium, E. gallinarum, E. casseliflavus*, and/or *E. faecalis*). Alternatively, the cells (such as bacterial cells) can produce greater than about 1%, 2%, 3%, 4%, 5%, 6%, 7%, 8%, 9%, 10%, 11%, 12%, 13%, 14%, or 15% of isoprene, inclusive, as well as any numerical value in between these numbers.

In one aspect of the invention, there are provided cells that have been engineered for increased carbon flux to isoprene which comprise one or more heterologous nucleic acids encoding an upper MVA pathway polypeptide, one or more heterologous nucleic acids encoding a lower mevalonate (MVA) pathway polypeptide(s), one or more heterologous nucleic acids encoding a DXP pathway polypeptide(s), and one or more heterologous nucleic acids encoding an isoprene synthase polypeptide. In another aspect of the invention, there are provided cells (such as bacterial cells) comprising one or more heterologous nucleic acids encoding an upper MVA pathway polypeptide (e.g., mvaE and mvaS polypeptides such as, but not limited to, mvaE and mvaS polypeptides from *L. grayi, E. faecium, E. gallinarum, E. casseliflavus*, and/or *E. faecalis*), one or more heterologous nucleic acids encoding a lower mevalonate (MVA) pathway polypeptide(s), one or more heterologous nucleic acids encoding a DXP pathway polypeptide(s), and one or more heterologous nucleic acids encoding an isoprene synthase polypeptide. The cells can further comprise one or more heterologous nucleic acids encoding an IDI polypeptide. The one or more heterologous nucleic acids can be operably linked to constitutive promoters, can be operably linked to inducible promoters, or can be operably linked to a combination of inducible and constitutive promoters. The one or more heterologous nucleic acids can additionally be operably linked strong promoters, weak promoters, and/or medium promoters. One or more of the heterologous nucleic acids encoding mvaE and mvaS polypeptides (such as, but not limited to, mvaE and mvaS polypeptides from *L. grayi, E. faecium, E. gallinarum, E. casseliflavus*, and/or *E. faecalis*), a lower mevalonate (MVA) pathway polypeptide(s), a DXP pathway polypeptide(s), and an isoprene synthase polypeptide can be integrated into a genome of the host cells or can be stably expressed in the cells. The one or more heterologous nucleic acids can additionally be on a vector.

In some aspects, there are provided cells which comprise one or more heterologous nucleic acids encoding an *M. burtonii* MVK polypeptide and one or more nucleic acids encoding an isoprene synthase polypeptide or variants thereof, wherein the cells are capable of producing isoprene.

The production of isoprene by cells that have been engineered for increased carbon flux to isoprene according to any of the compositions or methods described herein can be enhanced (e.g., enhanced by the expression of one or more heterologous nucleic acids encoding an isoprene synthase polypeptide, a lower MVA pathway polypeptide(s), a DXP pathway polypeptide(s), and/or upper MVA pathway polypeptide). In other aspects, the production of isoprene by the cells according to any of the compositions or methods described herein can be enhanced (e.g., enhanced by the expression of one or more heterologous nucleic acids encoding an isoprene synthase polypeptide, a lower MVA pathway polypeptide(s), a DXP pathway polypeptide(s), and/or the mvaE and mvaS polypeptides (such as, but not limited to, mvaE and mvaS polypeptides from *L. grayi, E. faecium, E.* gallinarum, E. casseliflavus*, and/or *E. faecalis*). As used herein, "enhanced" isoprene production refers to an increased cell productivity index (CPI) for isoprene, an increased titer of isoprene, an increased mass yield of isoprene, and/or an increased specific productivity of isoprene by the cells described by any of the compositions and methods described herein compared to cells which do not have one or more heterologous nucleic acids encoding an isoprene synthase polypeptide, a lower MVA pathway polypeptide(s), a DXP pathway polypeptide(s), and/or the mvaE and mvaS polypeptides (such as, but not limited to, mvaE and mvaS polypeptides from *L. grayi, E. faecium, E. gallinarum, E. casseliflavus*, and/or *E. faecalis*) and which have not been engineered for increased carbon flux to isoprene production. The production of isoprene can be enhanced by about 5% to about 1,000,000 folds. The production of isoprene can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by cells that do not express one or more heterologous nucleic acids encoding an upper MVA pathway polypeptide (e.g., an mvaE and/or mvaS polypeptide such as, but not limited to, mvaE and mvaS polypeptides from *L. grayi, E. faecium, E. gallinarum, E. casseliflavus*, and/or *E. faecalis*) and which have not been engineered for increased carbon flux to isoprene production.

The production of isoprene can also enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds.

Methods of Using the Recombinant Cells to Produce Isoprene

Also provided herein are methods of producing isoprene comprising culturing any of the recombinant microorganisms that have been engineered for increased carbon flux to isoprene as described herein. In one aspect, isoprene can be produced by culturing recombinant cells (such as bacterial cells) comprising modulation in any of the enzymatic pathways described herein and one or more heterologous nucleic acids encoding an upper MVA pathway polypeptide (e.g., an mvaE and/or an mvaS polypeptide such as, but not limited to, mvaE and mvaS polypeptides from *L. grayi, E. faecium, E. gallinarum, E. casseliflavus*, and/or *E. faecalis*), a lower MVA pathway polypeptide, and an isoprene synthase polypeptide. In another aspect, isoprene can be produced by culturing recombinant cells (such as bacterial cells) comprising one or more heterologous nucleic acids encoding an upper MVA pathway polypeptide (e.g., an mvaE and/or an mvaS polypeptide such as, but not limited to, mvaE and mvaS polypeptides from *L. grayi, E. faecium, E. gallinarum, E. casseliflavus*, and/or *E. faecalis*), a lower MVA pathway polypeptide, and an isoprene synthase polypeptide. The isoprene can be produced from any of the cells described herein and according to any of the methods described herein. Any of the cells can be used for the purpose of producing isoprene from carbohydrates, including six carbon sugars such as glucose.

Thus, also provided herein are methods of producing isoprene comprising culturing cells that have been engineered for increased carbon flux to isoprene and which comprise one or more heterologous nucleic acids encoding an upper MVA pathway polypeptide; and (b) producing isoprene. In other aspects, provided herein are methods of producing isoprene comprising culturing cells (such as bacterial cells) comprising one or more heterologous nucleic acids encoding an mvaE and an mvaS polypeptide (such as, but not limited to, mvaE and mvaS polypeptides from *L. grayi, E. faecium, E. gallinarum, E. casseliflavus*, and/or *E. faecalis*), in a suitable condition for producing isoprene and (b) producing isoprene. The cells can comprise one or more nucleic acid molecules encoding the lower MVA pathway polypeptide(s) described above (e.g., MVK, PMK, MVD, and/or IDI) and any of the isoprene synthase polypeptide(s) described above (e.g. *Pueraria* isoprene synthase). In some aspects, the cells (such as bacterial cells) can be any of the cells described herein. Any of the isoprene synthases or variants thereof described herein, any of the microorganism (e.g., bacterial) or plant strains described herein, any of the promoters described herein, and/or any of the vectors described herein can also be used to produce isoprene using any of the energy sources (e.g. glucose or any other six carbon sugar) described herein. In some aspects, the method of producing isoprene further comprises a step of recovering the isoprene.

In some aspects, there is provided a method for producing isoprene comprising (a) culturing cells which comprise one or more heterologous nucleic acids encoding an *M. burtonii* MVK and an isoprene synthase; and (b) producing isoprene.

In some aspects, the amount of isoprene produced is measured at the peak absolute productivity time point. In some aspects, the peak absolute productivity for the cells is about any of the amounts of isoprene disclosed herein. In some aspects, the amount of isoprene produced is measured at the peak specific productivity time point. In some aspects, the peak specific productivity for the cells is about any of the amounts of isoprene per cell disclosed herein. In some aspects, the cumulative, total amount of isoprene produced is measured. In some aspects, the cumulative total productivity for the cells is about any of the amounts of isoprene disclosed herein.

In some aspects, any of the cells described herein that have been engineered for increased carbon flux to isoprene (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells that have been engineered for increased carbon flux to isoprene in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h) In some aspects, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some aspects, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h.

In some aspects, the cells that have been engineered for increased carbon flux to isoprene in culture produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some aspects, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some aspects, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some aspects, the isoprene produced by the cells that have been engineered for increased carbon flux to isoprene in culture comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

Provided herein are cells having enhanced isoprene production. The production of isoprene by the cells can be enhanced by the expression of one or more heterologous nucleic acids encoding an upper MVA pathway polypeptide (e.g., but not limited to, an mvaE and/or mvaS polypeptide from *L. grayi, E. faecium, E. gallinarum, E. casseliflavus,* and/or *E. faecalis*), one or more copies of a heterologous nucleic acid encoding a lower MVA pathway polypeptide, and one or more heterologous nucleic acids encoding an isoprene synthase polypeptide. As used herein, "enhanced" isoprene production refers to an increased cell productivity index (CPI) for isoprene, an increased titer of isoprene, an increased mass yield of isoprene, and/or an increased specific productivity of isoprene by the cells described by any of the compositions and methods described herein compared to cells which do not have one or more heterologous nucleic acids encoding an isoprene synthase polypeptide, a lower MVA pathway polypeptide(s), a DXP pathway polypeptide (s), and/or an upper MVA pathway polypeptide (e.g., mvaE and/or mvaS polypeptides such as, but not limited to, mvaE and mvaS polypeptides from *L. grayi, E. faecium, E. gallinarum, E. casseliflavus,* and/or *E. faecalis*) and which have not been engineered for increased carbon flux to isoprene production. The production of isoprene can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by the cells that do not endogenously have one or more heterologous nucleic acids encoding an isoprene synthase polypeptide, a lower MVA pathway polypeptide(s), a DXP pathway polypeptide (s), and/or an upper MVA pathway polypeptide (e.g., mvaE and/or mvaS polypeptides such as, but not limited to, mvaE and mvaS polypeptides from *L. grayi, E. faecium, E. gallinarum, E. casseliflavus,* and/or *E. faecalis*) and which have not been engineered for increased carbon flux to isoprene production.

The production of isoprene by the cells that have been engineered for increased carbon flux to isoprene according to any of the methods described herein can be enhanced (e.g., enhanced by the expression of one or more heterologous nucleic acids encoding the isoprene synthase polypeptide). The production of isoprene can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by the naturally-occurring cells (e.g., the cells without the expression of one or more heterologous nucleic acids encoding an isoprene synthase polypeptide). The production of isoprene can also enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprene by naturally-occurring cells or by cells without the expression of one or more heterologous nucleic acids encoding mvaE and mvaS polypeptides from *L. grayi, E. faecium, E. gallinarum, E. casseliflavus,* and/or *E. faecalis* and which have not been engineered for increased carbon flux to isoprene production.

Recombinant Cells (Such as Bacterial Cells) Capable of Increased Production of Isoprenoid Precursors and/or Isoprenoids Isoprenoids can be produced in many organisms from the synthesis of the isoprenoid precursor molecules which are the end products of the MVA pathway. As stated above, isoprenoids represent an important class of compounds and include, for example, food and feed supplements, flavor and odor compounds, and anticancer, antimalarial, antifungal, and antibacterial compounds.

As a class of molecules, isoprenoids are classified based on the number of isoprene units comprised in the compound. Monoterpenes comprise ten carbons or two isoprene units, sesquiterpenes comprise 15 carbons or three isoprene units, diterpenes comprise 20 carbons or four isoprene units, sesterterpenes comprise 25 carbons or five isoprene units, and so forth. Steroids (generally comprising about 27 carbons) are the products of cleaved or rearranged isoprenoids.

Isoprenoids can be produced from the isoprenoid precursor molecules IPP and DMAPP. These diverse compounds are derived from these rather simple universal precursors and are synthesized by groups of conserved polyprenyl pyrophosphate synthases (Hsieh et al., Plant Physiol. 2011 March; 155(3):1079-90). The various chain lengths of these linear prenyl pyrophosphates, reflecting their distinctive physiological functions, in general are determined by the highly developed active sites of polyprenyl pyrophosphate synthases via condensation reactions of allylic substrates (dimethylallyl diphosphate ($C_5$-DMAPP), geranyl pyrophosphate ($C_{10}$-GPP), farnesyl pyrophosphate ($C_{15}$-FPP), geranylgeranyl pyrophosphate ($C_{20}$-GGPP)) with corresponding number of isopentenyl pyrophosphates ($C_5$-IPP) (Hsieh et al., *Plant Physiol.* 2011 March; 155(3):1079-90).

Production of isoprenoid precursors and/or isoprenoid can be made by using any of the recombinant host cells described here where one or more of the enzymatic pathways have been manipulated such that enzyme activity is modulated to increase carbon flow towards isoprenoid production. In addition, these cells can express one or more copies of a heterologous nucleic acid encoding an upper MVA pathway polypeptide for increased production of mevalonate, isoprene, isoprenoid precursors and/or isoprenoids. In other aspects, these cells can express one or more copies of a heterologous nucleic acid encoding an mvaE and an mvaS polypeptide (such as, but not limited to, mvaE and mvaS polypeptides from *L. grayi, E. faecium, E. gallinarum, E. casseliflavus*, and/or *E. faecalis*) for increased production of mevalonate, isoprene, isoprenoid precursors and/or isoprenoids. Any of the recombinant host cells that have been engineered for increased carbon flux to mevalonate expressing one or more copies of a heterologous nucleic acid encoding an upper MVA pathway polypeptide (e.g., an mvaE and/or an mvaS polypeptide such as, but not limited to, mvaE and mvaS polypeptides from *L. grayi, E. faecium, E. gallinarum, E. casseliflavus*, and/or *E. faecalis*) capable of increased production of mevalonate or isoprene described above can also be capable of increased production of isoprenoid precursors and/or isoprenoids. In some aspects, these cells further comprise one or more heterologous nucleic acids encoding polypeptides of the lower MVA pathway, IDI, and/or the DXP pathway, as described above, and a heterologous nucleic acid encoding a polyprenyl pyrophosphate synthase polypeptide. Without being bound to theory, it is thought that increasing the cellular production of mevalonate in cells (such as bacterial cells) by any of the compositions and methods described above will similarly result in the production of higher amounts of isoprenoid precursor molecules and/or isoprenoids. Increasing the molar yield of mevalonate production from glucose translates into higher molar yields of isoprenoid precursor molecules and/or isoprenoids, including isoprene, produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprene and isoprenoid production.

Types of Isoprenoids

The cells (such as bacterial cells) of the present invention that have been engineered for increased carbon flux to mevalonate are capable of increased production of isoprenoids and the isoprenoid precursor molecules DMAPP and IPP. Examples of isoprenoids include, without limitation, hemiterpenoids, monoterpenoids, sesquiterpenoids, diterpenoids, sesterterpenoids, triterpenoids, tetraterpenoids, and higher polyterpenoids. In some aspects, the hemiterpenoid is prenol (i.e., 3-methyl-2-buten-1-ol), isoprenol (i.e., 3-methyl-3-buten-1-ol), 2-methyl-3-buten-2-ol, or isovaleric acid. In some aspects, the monoterpenoid can be, without limitation, geranyl pyrophosphate, eucalyptol, limonene, or pinene. In some aspects, the sesquiterpenoid is farnesyl pyrophosphate, artemisinin, or bisabolol. In some aspects, the diterpenoid can be, without limitation, geranylgeranyl pyrophosphate, retinol, retinal, phytol, taxol, forskolin, or aphidicolin. In some aspects, the triterpenoid can be, without limitation, squalene or lanosterol. The isoprenoid can also be selected from the group consisting of abietadiene, amorphadiene, carene, α-famesene, β-farnesene, farnesol, geraniol, geranylgeraniol, linalool, limonene, myrcene, nerolidol, ocimene, patchoulo, β-pinene, sabinene, γ-terpinene, terpindene and valencene.

In some aspects, the tetraterpenoid is lycopene or carotene (a carotenoid). As used herein, the term "carotenoid" refers to a group of naturally-occurring organic pigments produced in the chloroplasts and chromoplasts of plants, of some other photosynthetic organisms, such as algae, in some types of fungus, and in some bacteria. Carotenoids include the oxygen-containing xanthophylls and the non-oxygen-containing carotenes. In some aspects, the carotenoids are selected from the group consisting of xanthophylls and carotenes. In some aspects, the xanthophyll is lutein or zeaxanthin. In some aspects, the carotenoid is α-carotene, β-carotene, γ-carotene, β-cryptoxanthin or lycopene.

Heterologous Nucleic Acids Encoding Polyprenyl Pyrophosphate Synthases Polypeptides In some aspects of the invention, the cells that have been engineered for increased carbon flux to isoprenoids described in any of the compositions or methods herein further comprise one or more nucleic acids encoding a lower mevalonate (MVA) pathway polypeptide(s), as described above, as well as one or more nucleic acids encoding a polyprenyl pyrophosphate synthase polypeptides(s). The polyprenyl pyrophosphate synthase polypeptide can be an endogenous polypeptide. The endogenous nucleic acid encoding a polyprenyl pyrophosphate synthase polypeptide can be operably linked to a constitutive promoter or can similarly be operably linked to an inducible promoter. The endogenous nucleic acid encoding a polyprenyl pyrophosphate synthase polypeptide can additionally be operably linked to a strong promoter. Alternatively, the endogenous nucleic acid encoding a polyprenyl pyrophosphate synthase polypeptide can be operably linked to a weak promoter. In particular, the cells can be engineered to over-express the endogenous polyprenyl pyrophosphate synthase polypeptide relative to wild-type cells.

In some aspects, the polyprenyl pyrophosphate synthase polypeptide is a heterologous polypeptide. The cells of the present invention can comprise more than one copy of a heterologous nucleic acid encoding a polyprenyl pyrophosphate synthase polypeptide. In some aspects, the heterologous nucleic acid encoding a polyprenyl pyrophosphate synthase polypeptide is operably linked to a constitutive promoter. In some aspects, the heterologous nucleic acid encoding a polyprenyl pyrophosphate synthase polypeptide is operably linked to an inducible promoter. In some aspects, the heterologous nucleic acid encoding a polyprenyl pyrophosphate synthase polypeptide is operably linked to a strong promoter. In some aspects, the heterologous nucleic acid encoding a polyprenyl pyrophosphate synthase polypeptide is operably linked to a weak promoter.

The nucleic acids encoding a polyprenyl pyrophosphate synthase polypeptide(s) can be integrated into a genome of the host cells or can be stably expressed in the cells. The nucleic acids encoding a polyprenyl pyrophosphate synthase polypeptide(s) can additionally be on a vector.

Exemplary polyprenyl pyrophosphate synthase nucleic acids include nucleic acids that encode a polypeptide, fragment of a polypeptide, peptide, or fusion polypeptide that has at least one activity of a polyprenyl pyrophosphate synthase. Polyprenyl pyrophosphate synthase polypeptides convert isoprenoid precursor molecules into more complex isoprenoid compounds. Exemplary polyprenyl pyrophosphate synthase polypeptides include polypeptides, fragments of polypeptides, peptides, and fusions polypeptides that have at least one activity of an isoprene synthase polypeptide. Exemplary polyprenyl pyrophosphate synthase polypeptides and nucleic acids include naturally-occurring polypeptides and nucleic acids from any of the source organisms described herein. In addition, variants of polyprenyl pyrophosphate synthase can possess improved activity such as improved enzymatic activity. In some aspects, a polyprenyl pyrophosphate synthase variant has other improved properties, such as improved stability (e.g., thermo-stability), and/or improved solubility. Exemplary polyprenyl pyrophosphate synthase nucleic acids can include nucleic acids which encode polyprenyl pyrophosphate synthase polypeptides such as, without limitation, geranyl diphosphate (GPP) synthase, farnesyl pyrophosphate (FPP) synthase, and geranylgeranyl pyrophosphate (GGPP) synthase, or any other known polyprenyl pyrophosphate synthase polypeptide.

In some aspects of the invention, the cells that have been engineered for increased carbon flux to isoprenoids described in any of the compositions or methods herein further comprise one or more nucleic acids encoding a farnesyl pyrophosphate (FPP) synthase. The FPP synthase polypeptide can be an endogenous polypeptide encoded by an endogenous gene. In some aspects, the FPP synthase polypeptide is encoded by an endogenous ispA gene in *E. coli*. The endogenous nucleic acid encoding an FPP synthase polypeptide can be operably linked to a constitutive promoter or can similarly be operably linked to an inducible promoter. The endogenous nucleic acid encoding an FPP synthase polypeptide can additionally be operably linked to a strong promoter. In particular, the cells can be engineered to over-express the endogenous FPP synthase polypeptide relative to wild-type cells.

In some aspects, the FPP synthase polypeptide is a heterologous polypeptide. The cells of the present invention can comprise more than one copy of a heterologous nucleic acid encoding a FPP synthase polypeptide. In some aspects, the heterologous nucleic acid encoding a FPP synthase polypeptide is operably linked to a constitutive promoter. In some aspects, the heterologous nucleic acid encoding a FPP synthase polypeptide is operably linked to an inducible promoter. In some aspects, the heterologous nucleic acid encoding a polyprenyl pyrophosphate synthase polypeptide is operably linked to a strong promoter.

The nucleic acids encoding an FPP synthase polypeptide can be integrated into a genome of the host cells or can be stably expressed in the cells. The nucleic acids encoding an FPP synthase can additionally be on a vector.

Standard methods can be used to determine whether a polypeptide has polyprenyl pyrophosphate synthase polypeptide activity by measuring the ability of the polypeptide to convert IPP into higher order isoprenoids in vitro, in a cell extract, or in vivo. These methods are well known in the art and are described, for example, in U.S. Pat. No. 7,915,026; Hsieh et al., *Plant Physiol.* 2011 March; 155(3):1079-90; Danner et al., *Phytochemistry.* 2011 Apr. 12 [Epub ahead of print]; Jones et al., *J Biol Chem.* 2011 Mar. 24 [Epub ahead of print]; Keeling et al., *BMC Plant Biol.* 2011 Mar. 7; 11:43; Martin et al., *BMC Plant Biol.* 2010 Oct. 21; 10:226; Kumeta & Ito, *Plant Physiol.* 2010 December; 154(4):1998-2007; and Köllner & Boland, *J Org Chem.* 2010 Aug. 20; 75(16):5590-600.

Recombinant Cells (Such as Bacterial Cells) Capable of Increased Production of Isoprenoid Precursors and/or Isoprenoids The recombinant microorganisms (e.g., recombinant bacterial cells) described herein have the ability to produce isoprenoid precursors and/or isoprenoids at a amount and/or concentration greater than that of the same cells without any manipulation to the various enzymatic pathways described herein. In addition, the cells described herein have the ability to produce isoprenoid precursors and/or isoprenoids at an amount and/or concentration greater than that of the same cells that have not been engineered for increased carbon flux to isoprenoids and which lack one or more copies of a heterologous nucleic acid encoding an upper MVA pathway polypeptide, one or more copies of a heterologous nucleic acid encoding a lower MVA pathway polypeptide, and one or more heterologous nucleic acids encoding a polyprenyl pyrophosphate synthase polypeptide. In some aspects, the cells described herein have the ability to produce isoprenoid precursors and/or isoprenoids at an amount and/or concentration greater than that of the same cells lacking one or more copies of a heterologous nucleic acid encoding mvaE and mvaS polypeptides (such as, but not limited to, mvaE and mvaS polypeptides from *L. grayi, E. faecium, E. gallinarum, E. casseliflavus*, and/or *E. faecalis*), one or more copies of a heterologous nucleic acid encoding a lower MVA pathway polypeptide, and one or more heterologous nucleic acids encoding a polyprenyl pyrophosphate synthase polypeptide when cultured in minimal media. In some cases, the one or more copies of a heterologous nucleic acid encoding an upper MVA pathway polypeptide (e.g., an mvaE and/or mvaS polypeptide such as, but not limited to, mvaE and mvaS polypeptides from *L. grayi, E. faecium, E. gallinarum, E. casseliflavus*, and/or *E. faecalis*) one or more copies of a heterologous nucleic acid encoding a lower MVA pathway polypeptide, and one or more heterologous nucleic acid encoding a polyprenyl pyrophosphate synthase polypeptide are heterologous nucleic acids that are integrated into the host cell's chromosome. The cells can produce at least 5% greater amounts of isoprenoid precursors and/or isoprenoids when compared to isoprenoids and/or isoprenoid precursor-producing cells (such as bacterial cells) that have not been engineered for increased carbon flux to isoprenoids. In other aspects, the cells (such as bacterial cells) can produce at least 5% greater amounts of isoprenoid precursors and/or isoprenoids when compared to isoprenoids and/or isoprenoid precursor-producing cells (such as bacterial cells) that do not comprise the mvaE and mvaS polypeptides (such as, but not limited to, mvaE and mvaS polypeptides from *L. grayi, E. faecium, E. gallinarum, E. casseliflavus*, and/or *E. faecalis*). Alternatively, the cells (such as bacterial cells) can produce greater than about 1%, 2%, 3%, 4%, 5%, 6%, 7%, 8%, 9%, 10%, 11%, 12%, 13%, 14%, or 15% of isoprenoid precursors and/or isoprenoids, inclusive, as well as any numerical value in between these numbers.

In one aspect of the invention, there are provided cells that have been engineered for increased carbon flux to isoprenoids and/or isoprenoid precursors comprising one or more heterologous nucleic acids encoding an upper MVA pathway polypeptide, one or more heterologous nucleic acids encoding a lower mevalonate (MVA) pathway polypeptide(s), one or more heterologous nucleic acids encoding a DXP pathway polypeptide(s), and one or more heterologous nucleic acids encoding polyprenyl pyrophosphate synthase. In another aspect of the invention, there are provided cells (such as bacterial cells) comprising one or more heterologous nucleic acids encoding mvaE and mvaS polypeptides (such as, but not limited to, mvaE and mvaS polypeptides from *L. grayi, E. faecium, E. gallinarum, E. casseliflavus*, and/or *E. faecalis*), one or more heterologous nucleic acids encoding a lower mevalonate (MVA) pathway polypeptide (s), one or more heterologous nucleic acids encoding a DXP pathway polypeptide(s), and one or more heterologous nucleic acids encoding polyprenyl pyrophosphate synthase. The cells can further comprise one or more heterologous nucleic acids encoding an IDI polypeptide. Additionally, the polyprenyl pyrophosphate synthase polypeptide can be an FPP synthase polypeptide. The one or more heterologous nucleic acids can be operably linked to constitutive promoters, can be operably linked to inducible promoters, or can be operably linked to a combination of inducible and constitutive promoters. The one or more heterologous nucleic acids can additionally be operably linked strong promoters, weak promoters, and/or medium promoters. One or more of the heterologous nucleic acids encoding an upper MVA pathway polypeptide (e.g., an mvaE and/or mvaS polypeptide such as, but not limited to, mvaE and mvaS polypeptides from *L. grayi, E. faecium, E. gallinarum, E. casseliflavus*, and/or *E. faecalis*), a lower mevalonate (MVA) pathway polypeptide(s), and a DXP pathway polypeptide(s), and a polyprenyl pyrophosphate synthase polypeptide can be integrated into a genome of the host cells or can be stably expressed in the cells. The one or more heterologous nucleic acids can additionally be on a vector.

In some aspects, there are provided cells which comprise one or more heterologous nucleic acids encoding an *M. burtonii* MVK polypeptide and one or more nucleic acids encoding an polyprenyl pyrophosphate synthase, wherein the cells are capable of producing isoprenoids.

Provided herein are methods of using any of the cells that have been engineered for increased carbon flux to isoprenoids and/or isoprenoid precursor described above for enhanced isoprenoid precursor and/or isoprenoid production. The production of isoprenoid precursors and/or isoprenoids by the cells can be enhanced by the expression of one or more heterologous nucleic acids encoding an upper MVA pathway polypeptide, one or more heterologous nucleic acids encoding a lower MVA pathway polypeptide, and one or more heterologous nucleic acids encoding a polyprenyl pyrophosphate synthase polypeptide. In other aspects, the production of isoprenoid precursors and/or isoprenoids by the cells can be enhanced by the expression of one or more heterologous nucleic acids encoding mvaE and mvaS polypeptides (such as, but not limited to, mvaE and mvaS polypeptides from *L. grayi, E. faecium, E. gallinarum, E. casseliflavus*, and/or *E. faecalis*), one or more heterologous nucleic acids encoding a lower MVA pathway polypeptide, and one or more heterologous nucleic acids encoding a polyprenyl pyrophosphate synthase polypeptide. As used herein, "enhanced" isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, and/or an increased specific productivity of isoprenoid precursors and/or isoprenoids by the cells described by any of the compositions and methods described herein compared to cells which do not have one or more heterologous nucleic acids encoding a polyprenyl pyrophosphate synthase polypeptide, a lower MVA pathway polypeptide(s), a DXP pathway polypeptide(s), and/or an upper MVA pathway polypeptide(s) (e.g., mvaE and/or mvaS polypeptides such as, but not limited to, mvaE and mvaS polypeptides from *L. grayi, E. faecium, E. gallinarum, E. casseliflavus*, and/or *E. faecalis*) and which have not been engineered for increased carbon flux to isoprenoids and/or isoprenoid precursor production. The production of isoprenoid precursors and/or isoprenoids can be enhanced by about 5% to about 1,000,000 folds. The production of isoprenoid precursors and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid and/or isoprenoid precursors by cells without the expression of one or more heterologous nucleic acids encoding an upper MVA pathway polypeptide (e.g., mvaE and mvaS polypeptides, such as, but not limited to, mvaE and mvaS polypeptides from *L. grayi, E. faecium, E. gallinarum, E. casseliflavus*, and/or *E. faecalis*) and which have not been engineered for increased carbon flux to isoprenoids and/or isoprenoid precursor production.

The production of isoprenoid precursors and/or isoprenoids by the cells according to any of the methods described herein can be enhanced (e.g., enhanced by the expression of one or more heterologous nucleic acids encoding an upper MVA pathway polypeptide, one or more heterologous nucleic acids encoding a lower MVA pathway polypeptide, and/or one or more heterologous nucleic acids encoding a polyprenyl pyrophosphate synthase polypeptide). In other aspects, the production of isoprenoid precursors and/or isoprenoids by the cells according to any of the methods described herein can be enhanced (e.g., enhanced by the expression of one or more heterologous nucleic acids encoding the mvaE and mvaS polypeptides (such as, but not limited to, mvaE and mvaS polypeptides from *L. grayi, E. faecium, E. gallinarum, E. casseliflavus*, and/or *E. faecalis*), one or more heterologous nucleic acids encoding a lower MVA pathway polypeptide, and one or more heterologous nucleic acids encoding a polyprenyl pyrophosphate synthase polypeptide). The production of isoprenoid precursors and/or isoprenoids can be enhanced by about 5% to about 1,000,000 folds. The production of isoprenoid precursors and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursors and/or isoprenoids by naturally-occurring cells (e.g., cells without the expression of one or more heterologous nucleic acids encoding upper MVA pathway polypeptides, e.g., mvaE and mvaS polypeptides, such as, but not limited to, mvaE and mvaS polypeptides from *L. grayi, E. faecium, E. gallinarum, E. casseliflavus,* and/or *E. faecalis,* and which have not been engineered for increased carbon flux to isoprenoids and/or isoprenoid precursor production).

The production of isoprenoid precursors and/or isoprenoids can also enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursors and/or isoprenoids by naturally-occurring cells or by cells without the expression of one or more heterologous nucleic acids encoding an upper MVA pathway polypeptide (e.g., mvaE and/or mvaS polypeptides, such as, but not limited to, mvaE and mvaS polypeptides from *L. grayi, E. faecium, E. gallinarum, E. casseliflavus,* and/or *E. faecalis*) and which have not been engineered for increased carbon flux to isoprenoids and/or isoprenoid precursor production.

Methods of Using the Recombinant Cells to Produce Isoprenoids and/or Isoprenoid Precursor Molecules Also provided herein are methods of producing isoprenoid precursor molecules and/or isoprenoids comprising culturing recombinant microorganisms (e.g., recombinant bacterial cells) that have been engineered in various enzymatic pathways described herein and/or comprising one or more heterologous nucleic acids encoding an upper MVA pathway polypeptide including, but not limited to, mvaE and an mvaS polypeptide (such as, but not limited to, mvaE and mvaS polypeptides from *L. grayi, E. faecium, E. gallinarum, E. casseliflavus,* and/or *E. faecalis*), a lower MVA pathway polypeptide, and an polyprenyl pyrophosphate synthase polypeptide. The isoprenoid precursor molecules and/or isoprenoids can be produced from any of the cells described herein and according to any of the methods described herein. Any of the cells can be used for the purpose of producing isoprenoid precursor molecules and/or isoprenoids from carbohydrates, including six carbon sugars such as glucose.

Thus, provided herein are methods of making isoprenoid precursor molecules and/or isoprenoids comprising culturing cells that have been engineered for increased carbon flux to isoprenoids and/or isoprenoid precursor; and (b) producing isoprenoid precursor molecules and/or isoprenoids. In other aspects, provided herein are methods of making isoprenoid precursor molecules and/or isoprenoids comprising culturing cells (such as bacterial cells) comprising one or more heterologous nucleic acids encoding an mvaE and an mvaS polypeptide (such as, but not limited to, mvaE and mvaS polypeptides from *L. grayi, E. faecium, E. gallinarum, E. casseliflavus,* and/or *E. faecalis*), in a suitable condition for producing isoprene and (b) producing isoprenoid precursor molecules and/or isoprenoids. The cells can further comprise one or more nucleic acid molecules encoding the lower MVA pathway polypeptide(s) described above (e.g., MVK, PMK, MVD, and/or IDI) and any of the polyprenyl pyrophosphate synthase polypeptide(s) described above. In some aspects, the cells (such as bacterial cells) can be any of the cells described herein. Any of the polyprenyl pyrophosphate synthase or variants thereof described herein, any of the microorganism (e.g., bacterial) or plant strains described herein, any of the promoters described herein, and/or any of the vectors described herein can also be used to produce isoprenoid precursor molecules and/or isoprenoids using any of the energy sources (e.g. glucose or any other six carbon sugar) described herein. In some aspects, the method of producing isoprenoid precursor molecules and/or isoprenoids further comprises a step of recovering the isoprenoid precursor molecules and/or isoprenoids.

The method of producing isoprenoid precursor molecules and/or isoprenoids can comprise the steps of: (a) culturing cells that have been engineered for increased carbon flux to isoprenoids and/or isoprenoid precursors wherein the cells heterologously express one or more copies of a gene encoding an upper MVA pathway polypeptide; and (b) producing isoprenoid precursor molecules and/or isoprenoids, wherein the cells produce greater amounts of isoprenoid precursors and/or isoprenoids when compared to isoprenoids and/or isoprenoid precursor-producing cells that do not comprise one or more heterologous copies of a gene encoding an upper MVA pathway polypeptide and which have not been engineered for increased carbon flux to isoprenoids and/or isoprenoid precursors. In other aspects, the method of producing isoprenoid precursor molecules and/or isoprenoids can similarly comprise the steps of: (a) culturing cells (such as bacterial cells, including, but not limited to, *E. coli* cells) that do not endogenously have an mvaE gene and an mvaS gene (such as, but not limited to, mvaE and mvaS genes from *L. grayi, E. faecium, E. gallinarum, E. casseliflavus,* and/or *E. faecalis*), wherein the cells (such as bacterial cells) heterologously express one or more copies of a gene encoding a mvaE polypeptide and an mvaS polypeptide (such as, but not limited to, mvaE and mvaS polypeptides from *L. grayi, E. faecium, E. gallinarum, E. casseliflavus,* and/or *E. faecalis*); and (b) producing isoprenoid precursor molecules and/or isoprenoids, wherein the cells (such as bacterial cells) produce greater amounts of isoprenoid precursors and/or isoprenoids when compared to isoprenoids and/or isoprenoid precursor-producing cells (such as bacterial cells) that do not comprise the mvaE and mvaS polypeptides (such as, but not limited to, mvaE and mvaS polypeptides from *L. grayi, E. faecium, E. gallinarum, E. casseliflavus,* and/or *E. faecalis*).

The instant methods for the production of isoprenoid precursor molecules and/or isoprenoids can produce at least 5% greater amounts of isoprenoid precursors and/or isoprenoids when compared to isoprenoids and/or isoprenoid precursor-producing cells that have not been engineered for increased carbon flux to isoprenoids and/or isoprenoid precursors and that do not comprise one or more heterologous nucleic acids encoding an upper MVA pathway polypeptide. In other aspects, provided herein are methods for the production of isoprenoid precursor molecules and/or isoprenoids can produce at least 5% greater amounts of isoprenoid precursors and/or isoprenoids when compared to isoprenoids and/or isoprenoid precursor-producing cells (such as bacterial cells) that do not comprise the mvaE and mvaS polypeptides (such as, but not limited to, mvaE and mvaS polypeptides from *L. grayi, E. faecium, E. gallinarum, E. casseliflavus,* and/or *E. faecalis*) and which have not been engineered for increased carbon flux to isoprenoids and/or isoprenoid precursor production. Alternatively, the cells (such as bacterial cells) can produce greater than about 1%, 2%, 3%, 4%, 5%, 6%, 7%, 8%, 9%, 10%, 11%, 12%, 13%, 14%, or 15% of isoprenoid precursors and/or isoprenoids, inclusive. In some aspects, the method of producing isoprenoid precursor molecules and/or isoprenoids further comprises a step of recovering the isoprenoid precursor molecules and/or isoprenoids.

Provided herein are methods of using any of the cells that have been engineered for increased carbon flux to isoprenoids and/or isoprenoid precursors described above for enhanced isoprenoid and/or isoprenoid precursor molecule production. The production of isoprenoid precursor molecules and/or isoprenoids by the cells can be enhanced by the expression of one or more heterologous nucleic acids encoding an upper MVA pathway polypeptide, one or more heterologous nucleic acids encoding a lower MVA pathway polypeptide, and one or more heterologous nucleic acids encoding a polyprenyl pyrophosphate synthase polypeptide. In other aspects, the production of isoprenoid precursor molecules and/or isoprenoids by the cells can be enhanced by the expression of one or more heterologous nucleic acids encoding mvaE and mvaS polypeptides (such as, but not limited to, mvaE and mvaS polypeptides from *L. grayi, E. faecium, E. gallinarum, E. casseliflavus*, and/or *E. faecalis*), one or more heterologous nucleic acids encoding a lower MVA pathway polypeptide, and one or more heterologous nucleic acids encoding a polyprenyl pyrophosphate synthase polypeptide. As used herein, "enhanced" isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, and/or an increased specific productivity of isoprenoid precursors and/ or isoprenoids by the cells described by any of the compositions and methods described herein compared to cells which do not have one or more heterologous nucleic acids encoding a polyprenyl pyrophosphate synthase polypeptide, a lower MVA pathway polypeptide(s), a DXP pathway polypeptide(s), and/or upper MVA pathway polypeptides (e.g., mvaE and/or mvaS polypeptides such as, but not limited to, mvaE and mvaS polypeptides from *L. grayi, E. faecium, E. gallinarum, E. casseliflavus*, and/or *E. faecalis*) and which have not been engineered for increased carbon flux to isoprenoids and/or isoprenoid precursor production. The production of isoprenoid precursor molecules and/or isoprenoids can be enhanced by about 5% to about 1,000, 000 folds. The production of isoprenoid precursor molecules and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursor molecules and/or isoprenoids by cells without the expression of one or more heterologous nucleic acids encoding an upper MVA pathway polypeptide (e.g., mvaE and/or mvaS polypeptides such as, but not limited to, mvaE and mvaS polypeptides from *L. grayi, E. faecium, E. gallinarum, E. casseliflavus*, and/or *E. faecalis*) and which have not been engineered for increased carbon flux to isoprenoids and/or isoprenoid precursor production.

The production of isoprenoid precursor molecules and/or isoprenoids can also enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursor molecules and/or isoprenoids by cells without the expression of one or more heterologous nucleic acids encoding an upper MVA pathway polypeptide (e.g., an mvaE and/or mvaS polypeptide such as, but not limited to, mvaE and mvaS polypeptides from *L. grayi, E. faecium, E. gallinarum, E. casseliflavus*, and/or *E. faecalis*) and which have not been engineered for increased carbon flux to isoprenoids and/or isoprenoid precursor production.

In addition, more specific cell culture conditions can be used to culture the cells in the methods described herein. For example, in some aspects, the method for the production of isoprenoid precursor molecules and/or isoprenoids comprises the steps of (a) culturing cells (such as bacterial cells, including, but not limited to, *E. coli* cells) that have been engineered for increased carbon flux to isoprenoids and/or isoprenoid precursor production that do not endogenously have an mvaE gene and an mvaS gene (such as, but not limited to, mvaE and mvaS genes from *L. grayi, E. faecium, E. gallinarum, E. casseliflavus*, and/or *E. faecalis*) at 34° C., wherein the cells (such as bacterial cells) heterologously express one or more copies of a gene encoding a mvaE polypeptide and an mvaS polypeptide (such as, but not limited to, mvaE and mvaS polypeptides from *L. grayi, E. faecium, E. gallinarum, E. casseliflavus*, and/or *E. faecalis*) on a low to medium copy plasmid and under the control of a strong promoter; and (b) producing isoprenoids and/or isoprenoid precursors. In some aspects, the method of producing isoprenoids and/or isoprenoid precursors further comprises a step of recovering the isoprenoid precursor molecules and/or isoprenoids.

Vectors

Suitable vectors can be used for any of the compositions and methods described herein. For example, suitable vectors can be used to optimize the expression of one or more copies of a gene encoding an upper MVA pathway polypeptide (e.g., an mvaE polypeptide and/or an mvaS polypeptide such as, but not limited to, mvaE and mvaS polypeptides from *L. grayi, E. faecium, E. gallinarum, E. casseliflavus*, and/or *E. faecalis*), an isoprene synthase, a polyprenyl pyrophosphate synthase, and/or one or more MVA pathway polypeptides in anaerobes. In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, one or more copies of an upper MVA pathway polypeptide (e.g., an mvaE polypeptide and/or an mvaS polypeptide such as, but not limited to, mvaE and mvaS polypeptides from *L. grayi, E. faecium, E. gallinarum, E. casseliflavus*, and/or *E. faecalis*), an isoprene synthase, a polyprenyl pyrophosphate synthase, and/or one or more lower MVA pathway polypeptide nucleic acid(s) integrate into the genome of host cells without a selective marker.

Any one of the vectors characterized or used in the Examples of the present disclosure can be used.

Transformation Methods

Nucleic acids encoding one or more copies of an upper MVA pathway polypeptide (e.g., an mvaE and/or an mvaS nucleic acid such as, but not limited to, mvaE and mvaS nucleic acids from *L. grayi, E. faecium, E. gallinarum, E. casseliflavus*, and/or *E. faecalis*), isoprene synthase, and/or lower MVA pathway polypeptides can be inserted into a microorganism using suitable techniques. Additionally, isoprene synthase, IDI, DXP pathway, and/or polyprenyl pyrophosphate synthase nucleic acids or vectors containing them can be inserted into a host cell (e.g., a plant cell, a fungal cell, a yeast cell, or a bacterial cell described herein) using standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (See, e.g., Current Protocols in Molecular Biology (F. M. Ausubel et al. (eds.) Chapter 9, 1987; Sambrook et al., Molecular Cloning: A Laboratory Manual, 2$^{nd}$ ed., Cold Spring Harbor, 1989; and Campbell et al., Curr. Genet. 16:53-56, 1989). The introduced nucleic acids can be integrated into chromosomal DNA or maintained as extra-chromosomal replicating sequences. Transformants can be selected by any method known in the art. Suitable methods for selecting transformants are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716, the disclosures of which are incorporated by reference herein.

Exemplary Purification Methods

In some aspects, any of the methods described herein further include a step of recovering the compounds produced. In some aspects, any of the methods described herein further include a step of recovering the isoprene. In some aspects, the isoprene is recovered by absorption stripping (See, e.g., US Appl. Pub. No. US 2011/0178261 A1, the disclosure of which is incorporated by reference herein). In some aspects, any of the methods described herein further include a step of recovering an isoprenoid. In some aspects, any of the methods described herein further include a step of recovering the terpenoid or carotenoid.

Suitable purification methods are described in more detail in U.S. Patent Application Publication US2010/0196977 A1, the disclosure of which is incorporated by reference herein.

The invention can be further understood by reference to the following examples, which are provided by way of illustration and are not meant to be limiting.

EXAMPLES

Example 1: Construction of E. coli Strain CMP451 (Containing BL21 pgl+PL.2 mKKDyI GI1.2 gltA), CMP452 and CMP453

The promoter in front of the citrate synthase gene (gltA) in BL21 (Novagen) has been replaced by a constitutive low expression promoter, namely GI1.2 (U.S. Pat. No. 7,371,558). Two wild-type promoters have been described for gltA (Wilde, R, and J. Guest. 1986. 1 Gen. Microbiol. 132:3239-3251) and the synthetic promoter was inserted just after the −35 region of the distal promoter. A PCR product was obtained using primers UpgltACm-F (5'-TATTTAATTTT-TAATCATCTAATTTGACAATCATTCAACAAAGTTGT-TACAATTAACCCT CACTAAAGGGCGG-3') (SEQ ID NO:36)) and DngltAl.xgiCm-R (5'-TCAACAGCTGTATCCCCGTTGAGGGT-GAGTTTTGCTTTTGTATCAGCCATATATTCCACC AGCTATTTGTTAGTGAATAAAAGTGGTTGAATTAT-TTGCTCAGGATGTGGCATHGTCAA GGGCTAATACGACTCACTATAGGGCTCG-3') (SEQ ID NO:37)), and plasmid FRT-gb2-Cm-FRT from Gene Bridges (Heidelberg, Germany) as a template. The PCR product was purified and used in a lambda red-mediated recombination as described by the manufacturer (Gene Bridges, Heidelberg, Germany). Several colonies were selected for further characterization. The promoter region was PCR-amplified using primers gltAPromSeqF: 5'-GGCAGTATAGGCTGTT-CACAAAATC-3'(SEQ ID NO:38) and gltApromSeqR: 5'-CTTGACCCAGCGTGCCTTTCAGC-3' (SEQ ID NO: 39) and, as a template, DNA extracted by resuspending a colony in 30 uL H2O, heating at 95 C for 4 min, spinning down, and using 2 uL of that material as a template in a 50 uL reaction. After observing the sequencing results of the PCR products obtained, a colony harboring each of the three different promoters GI1.2, GI1.5 and GI1.6 (U.S. Pat. No. 7,371,558) was saved for further use ((CMP141, CMP142 and CMP143; Table 3).

TABLE 3

E. coli strains

| Strain | Description | Parent |
|---|---|---|
| CMP141 | BL21 Cm-GI1.2 gltA | BL21 |
| CMP142 | BL21 Cm-GI1.5 gltA | BL21 |
| CMP143 | BL21 Cm-GI1.6 gltA | BL21 |
| CMP258 | BL21 pgl+ | BL21 |
| CMP374 | BL21 pgl + PL.2-mKKDyI ldhA::Kan | MD09-314 |
| CMP440 | BL21 pgl + PL.2 mKKDyI Cm-GI1.2 gltA | MD09-314 |
| CMP441 | BL21 pgl + PL.2 mKKDyI Cm-GI1.5 gltA | MD09-314 |
| CMP442 | BL21 pgl + PL.2 mKKDyI Cm-GI1.6 gltA | MD09-314 |
| CMP451 | BL21 pgl + PL.2 mKKDyI GI1.2 gltA | CMP440 |
| CMP452 | BL21 pgl + PL.2 mKKDyI GI1.5 gltA | CMP441 |
| CMP453 | BL21 pgl + PL.2 mKKDyI GI1.6 gltA | CMP442 |
| CMP604 | BL21 pgl + PL.2 mKKDyI GI 1.2 gltA ackA-pta::Cm | CMP451 |
| CMP620 | BL21 pgl + PL.2 mKKDyI GI 1.2 gltA ML ackA-pta::Cm ldhA::Kan | CMP604 |
| CMP635 | BL21 pgl + PL.2 mKKDyI GI 1.2 gltA ML ackA-pta ldhA | CMP620 |
| CMP646 | BL21 attB:Cm (to restore LowerP) col1 | BL21 (Novagen) |
| CMP676 | BL21 pgl + PL.2 mKKDyI GI 1.2 gltA ML ackA-pta ldhA attB::Cm | CMP635 |
| CMP680 | BL21 pg + PL.2 mKKDyI GI 1.2 gltA ML ackA-pta ldhA attB::Cm, pCHL276 | CMP676 |
| MCM521 | BL21 neo-PL.2-mKKDyI | (U.S. patent application No. 12/978,324) |
| MD09-313 | BL21 pgl + neo-PL.2-mKKDyI | CMP258 |

TABLE 3-continued

E. coli strains

| Strain | Description | Parent |
|---|---|---|
| MD09-314 | BL21 pgl + PL.2-mKKDyI | MD09-313 |
| MD491 | BL21 pgl + ackA-pta::Cm | CMP258 |

Strain MD09-313 was built by transducing CMP258 (see U.S. patent application Ser. No. 12/978,324) with a P1 lysate from strain MCM521 (see U.S. patent application Ser. No. 12/978,324) and selecting for colonies on Luria-Bertani plates containing 20 ug/ml kanamycin. P1 lysates are prepared according to the method described in Ausubel, et al., Current Protocols in Molecular Biology, John Wiley and Sons, Inc. The kanamycin marker was removed using the protocol recommended by the manufacturer (Gene Bridges, Heidelberg, Germany) to form strain MD09-314.

A P1 lysate was made from strains CMP141, CMP142 and CMP143 and was used to transduce strain MD09-314, to form CMP440, CMP441 and CMP442 respectively (Table 3). The chloramphenicol marker was removed using the protocol recommended by the manufacturer (Gene Bridges, Heidelberg, Germany) to form strains CMP451, CMP452 and CMP453 respectively (Table 3).

Example 2: Construction of E. coli Strain CMP604 (Containing BL21 pgl+PL.2 mKKDyI GI 1.2 gltA ML ackA-pta::Cm)

A DNA fragment containing the ackA-pta genes interrupted by a chloramphenicol marker was amplified by PCR using strain Triple Triple in which the chloramphenicol marker is still in (U.S. Pat. No. 7,745,184 B2) as a template and primers ackACF (5'-GTGCAAATT-CACAACTCAGCGG) (SEQ ID NO:40) and ptaCR (CAC-CAACGTATCGGGCAT TGCC-3') (SEQ ID NO:41)). The PCR product obtained was used in a recombineering reaction as recommended by the manufacturer (Gene Bridges, Heidelberg, Germany) to integrate the PCR product at the ackA-pta locus in strain CMP258 (See U.S. patent application Ser. No. 12/978,324). Colonies were selected on LB+5 ug/ml of chloramphenicol. One colony was picked and was named MD491. A P1 lysate of MD491 was made and was used to transduce strain CMP451. Colonies were selected on LB+5 ug/ml of chloramphenicol. One colony was picked and was named CMP604.

Example 3: Construction of E. coli Strain CMP620 (Containing BL21 pgl+PL.2 mKKDyI GI 1.2 gltA ML ackA-Pta::Cm ldhA::Kan) and CMP635 (Containing BL21 pgl+PL.2 mKKDyI GI 1.2 gltA ML ackA-Pta ldhA)

A DNA fragment containing the ldhA gene interrupted by a kanamycin marker was amplified by PCR using strain JW 1375 from the Keio collection (Baba et al. 2006. Mol. Syst. Biol. 2: 2006.0008) as a template, and primers ldhAseqR (5'-GGCTTACCGTTTACGCTTTCCAGC-3') (SEQ ID NO:42) and ldhAseqF2 (5'-CTAATGCAATACGTGTCCCGAGC-3') (SEQ ID NO:43). The PCR product obtained was used in a recombineering reaction as recommended by the manufacturer (Gene Bridges, Heidelberg, Germany) to integrate the PCR product at the ldhA locus in strain MD09-313. Colonies were selected on LB+20 ug/ml of kanamycin. One colony was picked and was named CMP374. A P1 lysate of CMP374 was made and was used to transduce CMP604. Colonies were selected on LB+20 ug/ml of kanamycin. One colony was picked and was named CMP620. The chloramphenicol and kanamycin markers were looped out simultaneously by electroporating pCP20 (Datsenko and Wanner. 2000. PNAS 97:6640-5) in the strain, selecting two colonies on LB+50 ug/ml carbenicillin at 30° C., then restreaking those colonies on an LB plate at 42° C. A $Cm^S$ and $Kan^S$ colony was selected from those plates and named CMP635.

Example 4: Construction of E. coli Strain CMP676 (Containing BL21 pgl+PL.2 mKKDyI GI 1.2 gltA ML ackA-Pta ldhA attB::Cm)

A DNA fragment containing a chloramphenicol marker flanked by DNA homologous to the upstream and downstream regions of the λ attachment site attB was amplified by PCR using plasmid pKD3 (Datsenko & Wanner, 2000, PNAS 97:6640-5) as a template, and primers CMP171 (5'-AAAATTTTCAT-TCTGTGACAGAGAAAAAGTAGCCGAA-GATGACGGTTTGTCACATGGA GTTGGCAG-GATGTTTGATTACATGGGAATTAGCCATGGTCC-3') (SEQ ID NO:44) and CMP172 (5'-GACCAGCCGCGTAACCTGGCAAAATCGGT-TACGGTTGAGTAATAAATGGATGCCCTGC GTAAGCGGGGCATTTTTCTTGGTGTAGGCTG-GAGCTGCTTCG-3') (SEQ ID NO:45). The PCR product obtained was used in a recombineering reaction in BL21 (Novagen) as recommended by the manufacturer (Gene Bridges, Heidelberg, Germany) to integrate the PCR product at the λ attachment site attB. Strain CMP646 was thereby generated, selected on LB+5 ug/ml chlroamphenicol. A P1 lysate of CMP646 was made and was used in a transduction reaction on strain CMP635, thereby removing the lower mevalonate pathway (mevalonate kinase, phosphomevalonate kinase, diphosphomevalonate decarboxylase, and isopentenyl diphosphate isomerase) from the chromosome of that strain. The transduction reaction was plated on LB+chloramphenicol 5 ug/ml and one colony was picked and named CMP676.

Example 5: Construction of E. coli Strain CMP680 (BL21 pgl+PL.2 mKKDyI GI 1.2 gltA ML ackA-pta ldhA attB::Cm, pCHL276) and Detection of Mevalonate Plasmid pCHL276 (see Example 6 (iii)) introduced into CMP676 by electroporation. Colonies were selected on LB+50 ug/mL spectinomycin. One colony was picked and named CMP680.

(i) Mevalonate Yield Assay

Overnight cultures of the above-identified strains were inoculated in shake tubes containing 2 mL LB broth supplemented with 50 µg/mL spectinomycin (Novagen). Cultures were then incubated for 14 h at 34° C. at 250 rpm. Next, the cultures were diluted into an 5 mL 48-well plate (Axygen Scientific) containing 2 mL TM3 media supplemented with 1% Glucose, yeast extract to a final concentration of 0.1%, and 200 μM IPTG to final OD of 0.2. The plate was sealed with a Breath Easier membrane (Diversified Biotech) and incubated at 34° C. in a Shel Lab shaker/incubator at 600 rpm for 24 hours. 1 mL of each culture was centrifuged at 3,000×g for 5 min. 250 μl of supernatant was added to 19 μL of 20% sulfuric acid and incubated on ice for 5 min. The mixture was then centrifuged for 5 min at 3000×g and the supernatant was collected for HPLC analysis. 200 μl of supernatant was transferred to a HPLC compatible 96-well conical bottom polypropylene plate (Nunc). The concentration of mevalonate in samples was determined by comparison to a standard curve of mevalonate (Sigma). The glucose concentration was measured by performing a glucose oxidase assay according to the manufacturer's specifications (Pointe Scientific, Inc.)

(ii) HPLC Detection of Mevalonate:

HPLC analysis was performed on an Agilent 1100 series HPLC system containing a refractive index detector using a 300 mm×7.8 mm BioRad-Aminex HPX-87H ion exclusion column (catalog #125-0140) incubated at 50° C. and equipped with a BioRad-Microguard Cation H refill 30 mm×4.6 mm (Catalog #125-0129). Samples were run at a flow rate of 0.6 ml/min in 0.01 N sulfuric acid running buffer. Mevalonate was detected using a refractive index detector.

Example 6: Construction of E. coli Strains MCM1373-1377 Expressing mvaE and mvaS Genes from *Listeria grayi* DSM 20601, *Enterococcus faecium*, *Enterococcus gallinarum* EG2, and *Enterococcus casseliflavus*

(i) Gene Identification and Selection

A primary sequence homology search using the *E. faecalis* mvaE gene product as the query was performed using the BLASTp program located at the NCBI website (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", *Nucleic Acids Res.* 25:3389-3402). Sequences of interest were selected from the search results.

In general, sequences of interest for the mvaE and mvaS genes displayed from 59-66% nucleotide sequence identity (codon optimized; see Table 4) and between 59-71% amino acid sequence identity (Table 5) compared to the wild type *E. faecalis* mvaE and mvaS nucleic acid and protein sequences, respectively.

TABLE 4

Percent identity of mvaE and mvaS nucleotides (codon-optimized) compared to *Enterococcus faecalis* WT

| Species | mvaE gene (% identity) | mvaS gene (% identity) |
| --- | --- | --- |
| Listeria grayi | 62 | 64 |
| Enterococcus faecium | 60 | 59 |
| Enterococcus gallinarum EG2 | 60 | 65 |
| Enterococcus casseliflavus | 60 | 66 |

TABLE 5

Percent identity of mvaE and mvaS amino acid sequences compared to *Enterococcus faecalis* WT

| Species | mvaE gene (% identity) | mvaS gene (% identity) |
| --- | --- | --- |
| Listeria grayi | 59 | 70 |
| Enterococcus faecium | 61 | 60 |
| Enterococcus gallinarum EG2 | 60 | 69 |
| Enterococcus casseliflavus | 59 | 71 |

(ii) Plasmids pDW83, pMCM1223-pMCM1225

The coding sequences of MvaE and MvaS from *Enterococcus casseliflavus* EC10 were optimized for expression in *Escherichia coli* (GeneOracle), and subcloned into the expression vector MCM82 (U.S. Patent Application Publication No. US2010/0196977, para. [1023]) to yield pDW83. Specifically, the cassette harboring the mvaES operon was cut from the cloning vector GcD126 (GeneOracle) using the restriction enzymes BglII and PmeI (Roche) using standard molecular biology techniques. This fragment was then ligated (Roche Rapid Ligation) into MCM82 which had previously been subjected to restriction digest using the enzymes BamHI and PmeI (Roche) followed by agarose gel separation (Invitrogen E-Gel) to remove the expression cassette encoding mvaES from *Enterococcus faecalis* using standard molecular biology techniques. The ligation mixture was transformed into chemically competent Top10 cells (Invitrogen) according to the manufacturer's recommended protocol. Spectinomycin resistant positive transformants were grown in liquid LB medium, and plasmids were purified (Qiagen Miniprep) and verified by sequencing (Quintara Biosciences) using the primers Ec Seq 1F through 4R (Table 6).

TABLE 6

Sequencing Primers

| | |
| --- | --- |
| Ec Seq 1F (SEQ ID NO: 46) | 5'-GGGTATGAAAGCGATTCTGA-3' |
| Ec Seq 2F (SEQ ID NO: 47) | 5'-AGCCCAAGGCGCTATTACCG-3' |
| Ec Seq 3F (SEQ ID NO: 48) | 5'-GGATTAGTTCAAAATTTGGC-3' |
| Ec Seq 4F (SEQ ID NO: 49) | 5'-CGGTTAATGGCACGTTATGA-3' |
| Ec Seq 1R (SEQ ID NO: 50) | 5'-TCGTTCGCCTGTAAACTGCT-3' |
| Ec Seq 2R (SEQ ID NO: 51) | 5'-TGCTCTATTTCAGTACCTTT-3' |
| Ec Seq 3R (SEQ ID NO: 52) | 5'-TGTAAGTTCAGGCCCACGCC-3' |
| Ec Seq 4R (SEQ ID NO: 53) | 5'-CCTCAGCCTTGTTGTAATAA-3' |

Plasmids encoding MvaE and MvaS from *Enterococcus faecium*, *Listeria grayi*, and *Enterococcus gallinarum* were constructed by GeneOracle (Mountain View, Calif.) using the design in Table 7. A synthetic DNA encoding mvaE-RBS-mvaS was created and then cloned into pMCM82 between the NcoI and PstI sites, replacing the existing operon. The vector provided an RBS for mvaE.

TABLE 7

Design for plasmids pMCM1223- pMCM1225 encoding MvaE and MvaS from
Enterococcus faecium, Listeria grayi, and Enterococcus gallinarum

| Plasmid Identifier | Plasmid Name | Source Organism | MvaE | MvaS | Origin and Selection |
|---|---|---|---|---|---|
| pMCM1223 | pCL-Ptrc-Upper_GcM M_161 (Listeria grayi DSM 20601) | L. grayi, DSM 20601 | gi\|229554876\|ref\|ZP_04442665.1\| acetyl-CoA acetyltransferase/ hydroxymethylglutaryl-CoA reductase, degradative [Listeria grayi DSM 20601] | gi\|229554877\|ref\|ZP_04442666.1\| hydroxymethylglutaryl-CoA synthase [Listeria grayi DSM 20601] | pSC101, Spectinomycin (50 ug/mL) |
| pMCM1224 | pCL-Ptrc-Upper_GcM M_162 (Enterococcus faecium) | E. faecium | gi\|9937391\|gb\|AAG02444.1\|AF290094_2 acetyl-CoA acetyltransferase/HMG-CoA reductase [Enterococcus faecium] | gi\|9937390\|gb\|AAG02443.1\|AF290094_1 HMG-CoA synthase [Enterococcus faecium] | pSC101, Spectinomycin (50 ug/mL) |
| pMCM1225 | pCL-Ptrc-Upper_GcM M_163 (Enterococcus gallinarum EG2) | E. gallinarum EG2 | gi\|257869528\|ref\|ZP_05649181.1\| acetyl-CoA acetyltransferase/ hydroxymethylglutaryl-CoA reductase [Enterococcus gallinarum EG2] | gi\|257869527\|ref\|ZP_05649180.1\| hydroxymethylglutaryl-CoA synthase [Enterococcus gallinarum EG2] | pSC101, Spectinomycin (50 ug/mL) |

(iii) pCL_pTrc-Upper(E. faecalis)-Leaderless Construction (pCHL276)

Primers (CL483F: 5'-AGGAGGAATAAACCAT-GAAAACAGTAGTTATTATTGATGCATTAC-3' (SEQ ID NO:54); CL484R: 5'-ACTACTGTTTTCATGGTTTAT-TCCTCCTTATTTAATCGATAC-3' (SEQ ID NO:55)) were designed to remove an extra RBS on pCLpTrc-Upper(E. faecalis), the MCM82 plasmid. The PCR reaction consisted of template DNA, MCM82 (100 ng), 50 uM of each forward and reverse primer, 1 ul of 10 mM dNTPs (Roche), 5 ul of 10× PfuII reaction buffer (Agilent), 1 ul of Pfu II fusion enzyme (Agilent) and 40 ul of water. Eighteen cycles were performed with a temperature profile of 50 seconds at 95 C, and 50 seconds at 60° C., and 9 min at 68° C. and an additional 10 min extension at 68° C. in a Bio-Rad thermocycler. DpnI (1 ul) was added after completion of the PCR reaction and incubated at 37° C. for two hours to remove template DNA. An additional 1 ul of DpnI was added and incubated at 37° C. overnight. Two microliters of the reaction was transformed into TOP10 cells (Invitrogen) and plate of LB+50 g/mL spectinomycin. The correct clone was confirmed by sequencing.

(iv) pCL_pTrc-Upper(E. casseliflavus)-Leaderless Construction (pCHL277)

Primers (CL485F: 5'-AGGAGGAATAAACCATG-GAAGAAGTTGTCATCATTGACGCAC-3' (SEQ ID NO:56); CL486R: 5'-ACTTCTTCCATGGTTTAT-TCCTCCTTATTTAATCG-3' (SEQ ID NO:57)) were designed to remove the extra RBS on pCLpTrc-Upper(E. casseliflavus), pDW83 plasmid. The PCR reaction consisted of template DNA, pDW83 (100 ng), 50 uM of each forward (CL483F) and reverse primer (CL484R), 1 ul of 10 mM dNTPs (Roche), 5 ul of 10× Pfu II reaction buffer (Agilent), 1 ul of Pfu II fusion enzyme (Agilent) and 40 ul of water. Eighteen cycles were performed with a temperature profile of 50 seconds at 95 C, and 50 seconds at 60° C., and 9 min at 68° C. and an additional 10 min extension at 68° C. in a Bio-Rad thermocycler. DpnI (1 ul) was added after PCR reaction and incubate at 37° C. for two hours to remove template DNA. An additional 1 ul of DpnI was added and incubate at 37° C. overnight. Two microliters of the reaction was transformed into TOP 10 cell (Invitrogen) and plate of LA/spec50. The correct clone was confirmed by sequencing.

(v) Construction of High Yield MVA Production Strains MCM1373-1377

Host CMP676 was grown to mid-log in LB at 37 C and prepared for electroporation by washing 3× in one half culture volume iced ddH2O and resuspended in one tenth culture volume of the same. 100 uL of cell suspension was combined with 1 uL plasmid DNA, moved to a 2 mm electroporation cuvette, electroporated at 25 uFD, 200 ohms, 2.5 kV, and immediately quenched with 500 uL LB. Cells were recovered shaking at 37 C for 1 hr and then transformants selected overnight on LB plates with 50 ug/mL spectinomycin at 37 C. Single colonies were grown in LB+50 ug/mL spectinomycin at 37 C to OD600~1. 500 uL of broth was mixed with 1 mL 50% glycerol and frozen on dry ice. Frozen stocks were stored at −80 C.

Example 7: Examination of Mevalonate Productivity Metrics in Engineered E. coli Strains Expressing Genes from the Mevalonate Pathway, Grown in Fed-Batch Culture at the 15-L Scale (i) Materials Medium Recipe (Per Liter Fermentation Medium):

Potassium phosphate $K_2HPO_4$ 7.5 g, Magnesium Sulfate $MgSO_4*7H_2O$ 2 g, citric acid monohydrate $C_6H_8O_7*H_2O$ 2 g, ferric ammonium citrate $NH_4FeC_6H_5O_7$ 0.34 g, yeast extract (from biospringer) 0.5 g, 1000× Modified Trace Metal Solution 1.5 ml, sulfuric acid 50% w/v 2.26 ml, foamblast 882 (Emerald Performance Materials) 0.83 ml, Macro Salts Solution 3.36 ml. All of the components were added together and dissolved in deionized $H_2O$. This solution was heat sterilized (123° C. for 20 minutes). After cooling to run temperature, the pH was adjusted to 7.0 with ammonium hydroxide (28%) and q.s. to volume. Feed solution #1 16.7 g, Vitamin Solution 11.9 mL, and spectinomycin solution 5 ml, were added after sterilization and pH adjustment.

1000× Modified Trace Metal Solution (Per Liter):

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component was dissolved one at a time in deionized $H_2O$, pH was adjusted to 3.0 with HCl/NaOH, and then the solution was q.s. to volume and filter sterilized with a 0.22 micron filter.

Macro Salt Solution (Per Liter):

MgSO$_4$*7H$_2$O 296 g, citric acid monohydrate 296 g, ferric ammonium citrate 49.6 g. All components were dissolved in water, q.s. to volume and filter sterilized with 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Spectinomycin Solution (Per Liter):

50 g spectinomycin was q.s. to volume with deionized water and filter sterilized with 0.22 micron filter.

Feed Solution #1 (Per Kilogram):

Glucose 0.590 kg, Di H2O 0.394 kg, K$_2$HPO$_4$ 7.4 g, and Foamblast882 8.94 g. All components were mixed together and autoclaved.

(ii) Experimental Methods

Fermentation was performed in a 15-L bioreactor with *E. coli* BL21 strains described in Table 8. Each strain was run twice, in identical conditions, so productivity results could be reported as an average of the two results.

TABLE 8

List of mevalonate producing strains examined in fed-batch culture at 15 L scale

| | |
|---|---|
| CMP680 | HMB GI 1.2 gltA ML ackA-pta ldhA attB::Cm, pCLPtrcUpper(rbs) (pCHL276)) |
| MCM1373 | HMB GI 1.2 gltA ML ackA-pta ldhA attB::Cm + pCL-Ptrc-Upper_Ef |
| MCM1374 | HMB GI 1.2 gltA ML ackA-pta ldhA attB::Cm + pCL-Ptrc-Upper_Ec |
| MCM1375 | HMB GI 1.2 gltA ML ackA-pta ldhA attB::Cm + pCL-Ptrc-Upper_Listeria |
| MCM1376 | HMB GI 1.2 gltA ML ackA-pta ldhA attB::Cm + pCL-Ptrc-Upper_Efaecium |
| MCM1377 | HMB GI 1.2 gltA ML ackA-pta ldhA attB::Cm + pCL-Ptrc-Upper_Eg |

A frozen vial of the *E. coli* strain was thawed and inoculated into tryptone-yeast extract medium (LB Miller medium) in a 2.8 L Erlynmeyer flask to be used as the inoculums for the bioreactor. After the inoculum grew to optical density 1.0, measured at 550 nm (OD550), 500 mL was used to inoculate a 15-L bioreactor and bring the initial tank volume to 5 L.

This experiment was carried out to monitor mevalonate formation from glucose at the desired fermentation pH 7.0 and temperature 34° C. Aerobic conditions were maintained for the duration of the run by sparging air at a rate of 8 standard liters per minute, holding back pressure of 0.7 bar gauge, and a stirring rate of 850 rotations per minute, with impellers and baffling to transfer the power to the liquid medium.

The glucose feed solution was fed using a pulse feed program. As soon as the batch glucose was depleted, signaled by a pH rise (pH>=7.05), a pulse of 3 g/min for 20 min was added. Afterwards, a glucose feed pulse was induced by a pH trigger (pH>=7.05). The pulse lasted 30 min and the magnitude (g/min) was equal to the total carbon dioxide evolution rate (mmol/hr) divided by a predetermined factor sufficient to keep the residual glucose in the broth in excess. The total amount of glucose feed delivered to the bioreactor during the 52 hr fermentation varied by strain. Induction was achieved by adding isopropyl-beta-D-1-thiogalactopyranoside (IPTG). A shot of IPTG was added to the tank to bring the concentration to 400 µM when the cells were at an OD550 of 4. The oxygen, nitrogen and carbon dioxide levels in the off-gas from the bioreactors were determined using a Hiden mass spectrometer. A time course of broth samples was taken at 4 hour intervals from each bioreactor. Broth concentration of glucose, citrate, and mevalonate were determined by HPLC. Optical density was determined by measuring the absorbance of dilute broth suspensions at 550 nm and multiplying by the dilution factor, to report the result (OD550). The OD550 reading was converted to dry cell mass by using previously generated factors that compare OD550 to dry cell weight over the time course of a fermentation. Productivity metrics of mass yield, specific productivity, titer, and cell productivity index are reported as an average of two results at comparable time points from each run, using the definitions given above (See "Definitions").

(iii) Small Scale Mevalonate Yield Assay

Overnight cultures were inoculated in shake tubes containing 2 mL LB broth supplemented with 50 µg/mL spectinomycin (Novagen) and 50 µg/mL carbenicillin (Novagen) from frozen stocks. Cultures were then incubated for 14 h at 34° C. at 250 rpm. Next, the cultures were diluted into an 5 mL 48-well plate (Axygen Scientific) containing 2 mL TM3 media supplemented with 1% Glucose, yeast extract to a total concentration of 1%, and 200 µM IPTG to final OD of 0.2. The plate was sealed with a Breath Easier membrane (Diversified Biotech) and incubated at 34° C. in a Shel Lab shaker/incubator at 600 rpm for 24 hours. 1 mL of each culture was centrifuged at 3,000×g for 5 min. 250 µl of supernatant was added to 19 µL of 20% sulfuric acid and incubated on ice for 5 min. The mixture was then centrifuged for 5 min at 3000×g and the supernatant was collected for HPLC analysis. 200 µl of supernatant was transferred to a HPLC compatible 96-well conical bottom polypropylene plate (Nunc). The concentration of mevalonate in samples was determined by comparison to a standard curve of mevalonate (Sigma). The glucose concentration was measured by performing a glucose oxidase assay according to the manufacturer's specifications (Pointe Scientific, Inc.).

(iv) HPLC Detection of Mevalonate:

HPLC analysis was performed on a Waters 2695 Alliance HPLC system containing a Knauer K2301 refractive index detector using a 300 mm×7.8 mm BioRad-Aminex HPX-87H ion exclusion column (catalog #125-0140) incubated at 50° C. and equipped with a BioRad-Microguard Cation H refill 30 mm×4.6 mm (Catalog #125-0129). Samples were run at a flow rate of 0.6 ml/min in 0.01 N sulfuric acid running buffer. Broth levels of mevalonate were able to be quantified by comparing the refractive index response of each sample versus a calibration curve generated by running various mevonate containing solutions of known concentration.

Production of mevalonate in batch culture at mass yields from glucose ranged from 34.8% to 41.1% from *E. coli* containing the mvaE and mvaS genes from the organisms *Listeria grayi* DSM 20601, *Enterococcus faecium*, *Enterococcus gallinarum* EG2, *Enterococcus casseliflavus* (FIG. 1, Table 9).

TABLE 9

Mass yield of mevalonate from glucose.

| Strain | IPTG (µM) | Mass Yield (%) | S.D. |
|---|---|---|---|
| CMP680 | 100 | 33.6 | 0.8 |
| MCM1373 | 100 | 31.8 | 0.8 |

TABLE 9-continued

Mass yield of mevalonate from glucose.

| Strain | IPTG (μM) | Mass Yield (%) | S.D. |
|---|---|---|---|
| MCM1374 | 100 | 35.8 | 3.9 |
| MCM1375 | 100 | 34.6 | 0.2 |
| MCM1376 | 100 | 35.6 | 3.2 |
| MCM1377 | 100 | 41.0 | 0.1 |
| CMP680 | 200 | 35.3 | 0.1 |
| MCM1373 | 200 | 31.9 | 0.2 |
| MCM1374 | 200 | 39.2 | 3.0 |
| MCM1375 | 200 | 34.8 | 1.0 |
| MCM1376 | 200 | 37.9 | 3.3 |
| MCM1377 | 200 | 41.1 | 4.9 |

S.D. represents one standard deviation of two replicates.

The production of mevalonate in fed batch culture in a 15 L fermentor at mass yields from glucose cumulatively ranged from 39.1% to 43.4% in *E. coli* containing the mvaE and mvaS genes from the organisms *Listeria grayi* DSM 20601, *Enterococcus faecium*, *Enterococcus gallinarum* EG2, *Enterococcus casseliflavus* (Table 10).

TABLE 10

Cumulative mass yield results (average of the 3 final points of the 2 runs for each strain)

| Strain | Upper enzymes | Mass Yield (Mevalonate on glucose) (w/w %) | Standard deviation (w/w %) | C.V. % |
|---|---|---|---|---|
| CMP680 | *E. faecalis* | 37.3 | 0.5 | 1.34% |
| MCM1374 | *Enterococcus casseliflavus* | 41.3 | 1.7 | 4.12% |
| MCM1375 | *Listeria grayi* DSM 20601 | 39.1 | 2.0 | 5.12% |
| MCM1376 | *Enterococcus faecium* | 39.7 | 0.7 | 1.76% |
| MCM1377 | *Enterococcus gallinarum* EG2 | 43.4 | 1.1 | 2.53% |

Mevalonate peak specific productivities ranged from 87.5 to 100.1 g/L/h/OD in fed batch culture in a 15 L fermentor in *E. coli* containing the mvaE and mvaS genes from the organisms *Listeria grayi* DSM 20601, *Enterococcus faecium*, *Enterococcus gallinarum* EG2, *Enterococcus casseliflavus* (Table 11).

TABLE 11

Peak specific productivity observed for each strain (average of the peak observed values observed in the 2 runs for each strain)

| Strain | Upper enzymes | Peak Specific productivity (mg/L/hr/OD) | Standard deviation (mg/L/hr/OD) | C.V. % |
|---|---|---|---|---|
| CMP680 | *E. faecalis* | 87.4 | 7.2 | 8.2% |
| MCM1374 | *Enterococcus casseliflavus* | 100.1 | 11.6 | 11.6% |
| MCM1375 | *Listeria grayi* DSM 20601 | 87.5 | 26.7 | 30.5% |
| MCM1376 | *Enterococcus faecium* | 93.9 | 14.2 | 15.1% |
| MCM1377 | *Enterococcus gallinarum* EG2 | 88.6 | 13.9 | 15.7% |

Finally, mevalonate titers ranged from 108.2 to 115.4 g/L (Table 12), and CPIs ranged from 4.86 to 5.80 g mevalonate/g glucose (Table 13) in *E. coli* containing the mvaE and mvaS genes from the organisms *Listeria grayi* DSM 20601, *Enterococcus faecium*, *Enterococcus gallinarum* EG2, *Enterococcus casseliflavus*.

TABLE 12

Peak mevalonate titer observed for each strain (average of the broth titer observed at 48 hrs for each set of runs)

| Strain | Upper enzymes | Peak Mevalonate Titer @ 48 hrs EFT (g/L) | Standard deviation (g/L) | C.V. % |
|---|---|---|---|---|
| CMP680 | *E. faecalis* | 122.8 | 5.8 | 4.7% |
| MCM1374 | *Enterococcus casseliflavus* | 115.4 | 4.1 | 3.6% |
| MCM1375 | *Listeria grayi* DSM 20601 | 108.2 | 4.8 | 4.4% |
| MCM1376 | *Enterococcus faecium* | 110.1 | 12.0 | 10.9% |
| MCM1377 | *Enterococcus gallinarum* EG2 | 111.2 | 6.1 | 5.5% |

TABLE 13

CPI values for each strain (average of the CPI values observed at 44 and 48 hours for each set of runs)

| Strain | Upper enzymes | CPI (g/g) | Standard deviation (g/g) | C.V. % |
|---|---|---|---|---|
| CMP680 | *E. faecalis* | 4.25 | 0.25 | 5.9% |
| MCM1374 | *Enterococcus casseliflavus* | 5.70 | 0.37 | 6.5% |
| MCM1375 | *Listeria grayi* DSM 20601 | 4.86 | 0.73 | 15.0% |
| MCM1376 | *Enterococcus faecium* | 5.29 | 0.12 | 2.3% |
| MCM1377 | *Enterococcus gallinarum* EG2 | 5.80 | 0.52 | 8.9% |

Example 8: Construction of Isoprene-Producing Strains with Host Mutations

Figure 2:
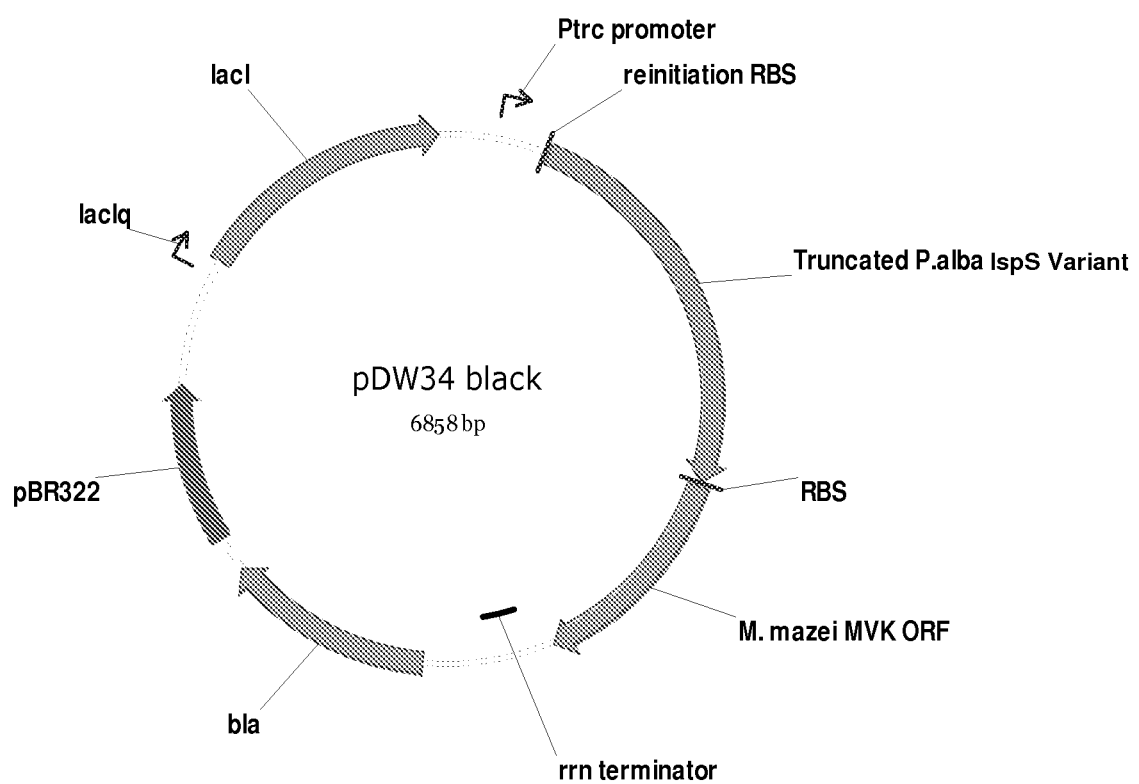
FIG. 2 depicts a plasmid map of pDW34.

A lower mevalonate pathway can be introduced by transduction into CMP676 using a lysate from MCM521 (see Table 3). The kanamycin marker is looped out according to the manufacturer (Gene Bridges, Heidelberg, Germany). The lower pathway from MCM521 can be modified by changing the promoter upstream of the operon by modifying the rbs in front of each gene via the use of alternative genes. Plasmids pMCM1223 (*L. grayi*), pMCM1224 (*E. faecium*), pMCM1225 (*E. gallinarum*), pCHL276 (*E. faecalis*) or pCHL277 (*E. casseliflavus*) are co-electroporated with a variation of plasmid pDW34 (See U.S. Patent Application Publication No: 2010/0196977; FIG. 2). The plasmids, which are variants of pDW34, contain an isoprene synthase variant, which is improved for activity. Colonies can be selected on LB+spectinomycin 50 ug/mL+carbenicillin 50 ug/mL.

The resultant strain is further engineered to modulate the activity of pyruvate dehydrogenase. This strain can be further engineered to increase the activity of one or more genes of the pyruvate dehydrogenase complex. This strain may also be further engineered to decrease the activity of the pyruvate decarboxylase repressor protein. Alternatively, the resultant strain may also be engineered to modulate the activity of citrate synthase. The activity of citrate synthase in the resultant stain can be modulated by decreasing the activity of citrate synthase. Alternatively, the resultant strain may also be engineered to modulate the activity of phosphotransacetylase and/or acetate kinase. The activity of phosphotransacetylase and/or acetate kinase can be modulated by decreasing the activity of phosphotransacetylase and/or acetate kinase. Alternatively, the resultant strain may also be engineered to modulate the activity of lactate dehydrogenase. The activity of lactate dehydrogenase can be modulated by decreasing the activity of lactate dehydrogenase. Alternatively, the resultant strain may also be engineered to modulate the activity of malic enzyme. The activity of lactate dehydrogenase can be modulated by increasing the activity of malic enzyme.

Example 9: Increased Production of Isoprene in Strains Containing the Plasmids with Host Mutations Compared Wild Type *E. faecalis*

(i) Materials
TM3 Media Recipe (Per Liter Fermentation Media):
$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotics are added after sterilization and pH adjustment.
1000× Trace Metal Solution (Per Liter Fermentation Media)
Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure
Cells are grown overnight in Luria-Bertani broth+antibiotics. The day after, they are diluted to an OD600 of 0.05 in 20 mL TM3 medium containing 50 ug/ml of spectinomycin and 50 ug/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. Also, off-gas analysis of isoprene is performed using a gas chromatograph-mass spectrometer (GC-MS) (Agilent) headspace assay. One hundred microliters of whole broth are placed in a sealed GC vial and incubated at 34° C. and 200 rpm for a fixed time of 30 minutes. Following a heat kill step, consisting of incubation at 70° C. for 5 minutes, the sample is loaded on the GC. The reported specific productivity is the amount of isoprene in ug/L read by the GC divided by the incubation time (30 min) and the measured OD600.

(iii) Results:
When the strains containing one or more host mutations are compared to the same background containing pCHL276 (*E. faecalis*), increased specific productivity, yield, CPI and/or titer of isoprene are observed.

Example 10: Construction of Amorphadiene- or Farnesene-Producing Strains

A lower mevalonate pathway is introduced by transduction into CMP676 using a lysate from MCM521 (see Table 3). The kanamycin marker is looped out according to the manufacturer (Gene Bridges, Heidelberg, Germany). The lower pathway from MCM521 can be modified by changing the promoter upstream of the operon by modifying the rbs in front of each gene via the use of alternative genes. Farnesyl diphosphate synthase (ispA) is overexpressed, either by altering the promoter and/or rbs on the chromosome, or by expressing it from a plasmid. Plasmids pMCM1223 (*L. grayi*), pMCM1224 (*E. faecium*), pMCM1225 (*E. gallinarum*), pCHL276 (*E. faecalis*) or pCHL277 (*E. casseliflavus*) are co-electroporated with a variation of plasmid pDW34 (See U.S. Patent Application Publication No: 2010/0196977; FIG. 2). The plasmids which are variants of pDW34 contain the farnesene synthase codon optimized for *E. coli* or amorphadiene synthase codon optimized for *E. coli*, instead of isoprene synthase. Colonies are selected on LB+spectinomycin 50 ug/mL+carbenicillin 50 ug/mL.

The resultant strain is further engineered to modulate the activity of pyruvate dehydrogenase. This strain can be further engineered to increase the activity of one or more genes of the pyruvate dehydrogenase complex. This strain may also be further engineered to decrease the activity of the pyruvate decarboxylase repressor protein. Alternatively, the resultant strain may also be engineered to modulate the activity of citrate synthase. The activity of citrate synthase in the resultant stain can be modulated by decreasing the activity of citrate synthase. Alternatively, the resultant strain may also be engineered to modulate the activity of phosphotransacetylase and/or acetate kinase. The activity of phosphotransacetylase and/or acetate kinase can be modulated by decreasing the activity of phosphotransacetylase and/or acetate kinase. Alternatively, the resultant strain may also be engineered to modulate the activity of lactate dehydrogenase. The activity of lactate dehydrogenase can be modulated by decreasing the activity of lactate dehydrogenase. Alternatively, the resultant strain may also be engineered to modulate the activity of malic enzyme. The activity of lactate dehydrogenase can be modulated by increasing the activity of malic enzyme.

Example 11: Increased Production of Amorphadiene or Farnesene in Strains Containing the Plasmids with Host Mutations Compared to a Wild Type *E. faecalis*

(i) Materials
TM3 media recipe (per liter fermentation media):
$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is then filter-sterilized with a 0.22 micron filter. Glucose 10.0 g and antibiotics are added after sterilization and pH adjustment.
1000× Trace Metal Solution (Per Liter Fermentation Media):
Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure
Cells are grown overnight in Luria-Bertani broth+antibiotics. The day after, they are diluted to an OD600 of 0.05 in 20 mL TM3 medium containing 50 ug/ml of spectinomycin and 50 ug/mL carbenicillin (in a 250-mL baffled Erlenmeyer flask), and incubated at 34° C. and 200 rpm. Prior to inoculation, an overlay of 20% (v/v) dodecane (Sigma-Aldrich) is added to each culture flask to trap the volatile sesquiterpene product as described previously (Newman et. al., 2006).

After 2 h of growth, OD600 is measured and 0.05-0.40 mM isopropyl β-d-1-thiogalactopyranoside (IPTG) is added. Samples are taken regularly during the course of the fermentation. At each timepoint, OD600 is measured. Also, amorphadiene or farnesene concentration in the organic layer is assayed by diluting the dodecane overlay into ethyl acetate. Dodecane/ethyl acetate extracts are analyzed by GC-MS methods as previously described (Martin et. al., *Nat. Biotechnol.* 2003, 21:96-802) by monitoring the molecular ion (204 m/z) and the 189 m/z fragment ion for amorphadiene or the molecular ion (204 m/z) for farnesene. Amorphadiene or farnesene samples of known concentration are injected to produce standard curves for amorphadiene or farnesene, respectively. The amount of amorphadiene or farnesene in samples is calculated using the amorphadiene or farnesene standard curves, respectively.

(iii) Results

When the strains containing one or more host mutations are compared to the same are compared to the same background containing pCHL276 (*E. faecalis*), increased specific productivity, yield, CPI and/or titer of amorphadiene or farnesene are observed.

(iv) References

Newman, J. D., Marshal, J. L., Chang, M. C. Y., Nowroozi, F., Paradise, E. M., Pitera, D. J., Newman, K. L., Keasling, J. D., 2006. High-level production of *amorpha*-4, 11-diene in a two-phase partitioning bioreactor of metabolically engineered *E. coli. Biotechnol. Bioeng.*95, 684-691.

Martin, V. J., Pitera, D. J., Withers, S. T., Newman, J. D., Keasling, J. D., 2003. Engineering a mevalonate pathway in *E. coli* for production of terpenoids. *Nat. Biotechnol.* 21, 796-802.

Example 12: Identification of MvaE Proteins that are not Degraded when Expressed in *E. coli* BL21 or *E. coli* BL21(DE3)

Figure 3:
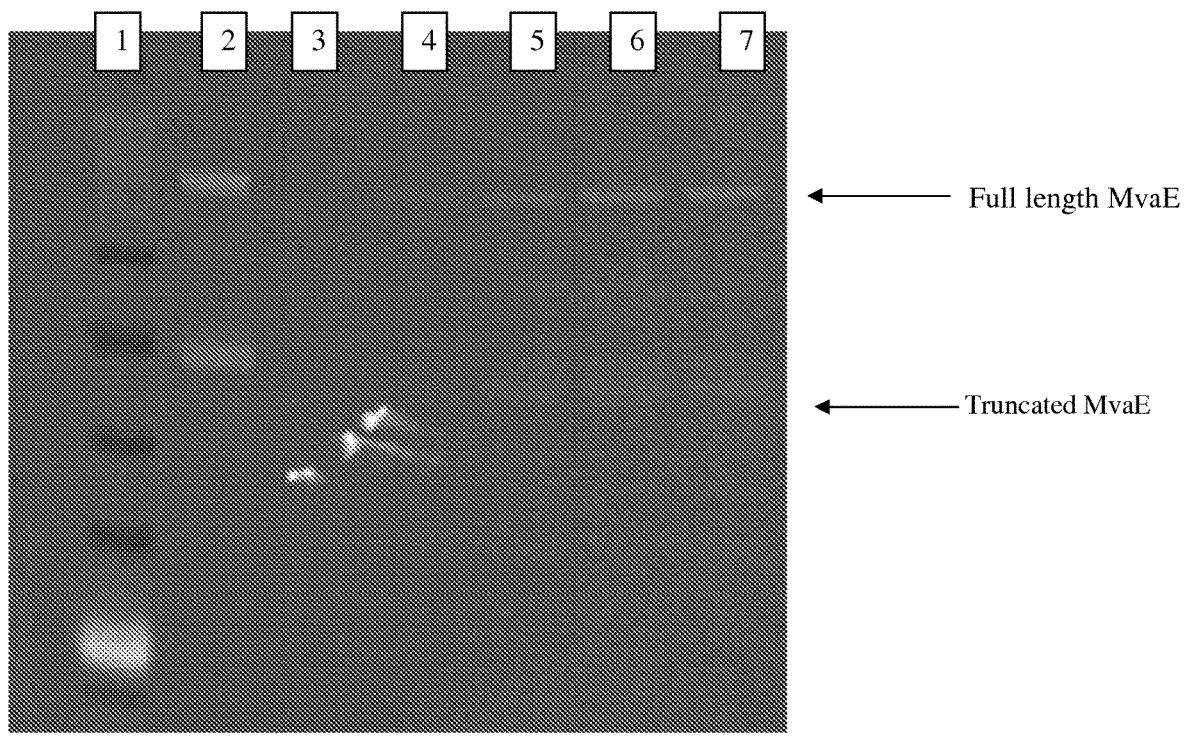
FIG. 3 depicts a Western blot where MvaE from strain DW326 is visualized. Lane 1—Benchmark marker, 2-0.4 ug of purified MvaE, 3-7, Lysate samples from strain DW326 induced with 0, 25, 50, 100, 200 uM IPTG.
Figure 4:
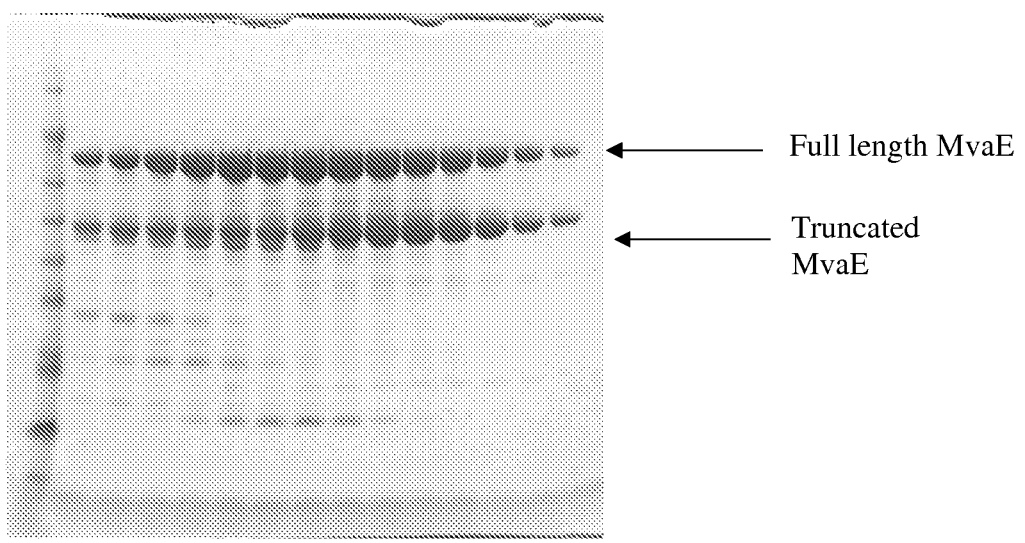
FIG. 4 depicts a SDS-PAGE gel stained with Safestain containing: Lane 1—Benchmark marker, 2-15-His-tag mediated purification of MvaE protein fractions eluted from a nickel column.

Degradation of heterologously expressed protein in a cell can result in loss of ATP due to the futile cycle of protein synthesis and protein degradation, decrease in catalytic activity of the protein being degraded, decrease in the steady state intracellular concentration of the protein of interest, induction of stress responses that can alter the physiology of the cell, and other effects that are potentially deleterious to the commercial production of biologically-derived products (S.-O. Enfors, 2004). Therefore, the expression of full length proteins that are less prone to degrade is beneficial for metabolic engineering. The mvaE gene product from *Enterococcus faecalis* is partially degraded when expressed in *E. coli* BL21 as indicated by fragments that can be identified by western blot (FIG. 3). Cleaved fragments of *E. faecalis* MvaE were also identified by Safestain staining of His-tagged purified material run on an SDS-PAGE gel (FIG. 4). Identification and use of degradation resistant mvaE gene products are beneficial for the increased production of mevalonate, isoprene and isoprenoids.

We demonstrate that the gene products of mvaEs from the organisms *E. faecium, E. gallinarum, E. casseliflavus,* and *L. grayi* are not degraded when expressed in *E. coli* BL21 (DE3) as indicated by absence of fragments that can be identified on Safestain stained SDS-PAGE gels following His-tag mediated purification or when expressed in mevalonate, isoprene or isoprenoid producing *E. coli* BL21 using the methods of detection described.

(i) Methods

Plasmids are constructed that contain DNA encoding His-tagged MvaE from *E. gallinarum, E. faecium, E. casseliflavus,* and *L. grayi.* MvaE is expressed in *E. coli* BL21 (DE3) and is purified by Ni-resin chromatography. Purified samples are analyzed by SDS-PAGE. Samples are further purified by anion exchange chromatography and in some cases gel filtration. Samples purified to >95% homogeneity are sent for production of polyclonal antibodies. Production strains are analysed by western blot and probed using the polyclonal antibodies developed against the MvaE of interest.

(ii) References

Enfors, S. O., Scheper, T. Physiological Stress Responses in Bioprocesses. Springer-Verlag Berlin Heidelberg 2004.

Example 13: Construction of CMP451, (BL21 pgl+PL.2 mKKDyI GI1.2 gltA), CMP452 and CMP453

The promoter in front of the citrate synthase gene (gltA) in BL21 (Novagen) has been replaced by a constitutive low expression promoter, namely GI1.2 (U.S. Pat. No. 7,371, 558). Two wild-type promoters have been described for gltA (Wilde, R, and J. Guest. 1986. J. Gen. Microbiol. 132:3239-3251) and the synthetic promoter was inserted just after the –35 region of the distal promoter. A PCR product was obtained using primers UpgltACm-F (5'-TATTTAATTTT-TAATCATCTAATTTGACAATCATTCAACAAAGTTGT-TACAATTAACCCT CACTAAAGGGCGG-3') (SEQ ID NO:58) and DngltAl.xgiCm-R (5'-TCAACAGCTGTATCCCCGTTGAGGGT-GAGTTTTGCTTTTGTATCAGCCATATATTCCACC AGCTATTTGTTAGTGAATAAAAGTGGTTGAATTAT-TTGCTCAGGATGTGGCATHGTCAA GGGCTAATACGACTCACTATAGGGCTCG-3') (SEQ ID NO:59), and FRT-gb2-Cm-FRT template DNA from Gene Bridges (Heidelberg, Germany) as a template. The PCR product was purified and used in a lambda red-mediated recombination as described by the manufacturer (Gene Bridges, Heidelberg, Germany). Several colonies were selected for further characterization. The promoter region was PCR-amplified using primers gltAPromSeqF (5'-GGCAGTATAGGCTGTTCACAAAATC-3') (SEQ ID NO:60) and gltApromSeqR (5'-CTTGACCCAGCGTGCCTTTCAGC-3') (SEQ ID NO:61) and, as a template, DNA extracted by resuspending a colony in 30 uL H2O, heating at 95 C for 4 min, spinning down, and using 2 uL of that material as a template in a 50 uL reaction. After observing the sequencing results of the PCR products obtained, a colony harboring each of the three different promoters GI1.2, GI1.5 and GI1.6 (U.S. Pat. No. 7,371,558) was saved for further use. Those colonies were named CMP141, CMP142 and CMP143 respectively (Table 14).

TABLE 14

| Strain | Genotype | Parent | Phenotype |
|---|---|---|---|
| CMP141 | BL21 Cm-GI1.2 gltA | BL21 | Lowered expression of citrate synthase |
| CMP142 | BL21 Cm-GI1.5 gltA | BL21 | Lowered expression of citrate synthase |
| CMP143 | BL21 Cm-GI1.6 gltA | BL21 | Increased expression of citrate synthase |
| CMP258 | BL21 pgl+ | BL21 | BL21 strain restored for the presence of phosphogluconolactonase |
| CMP374 | BL21 pgl + PL.2 mKKDyI ldhA::Kan | MD09-314 | Deletion of lactate dehydrogenase |
| CMP440 | BL21 pgl + PL.2 mKKDyI Cm-GI1.2 gltA | MD09-314 | Lowered expression of citrate synthase |
| CMP441 | BL21 pgl + PL.2 mKKDyI Cm-GI1.5 gltA | MD09-314 | Lowered expression of citrate synthase |
| CMP442 | BL21 pgl + PL.2 mKKDyI Cm-GI1.6 gltA | MD09-314 | Increased expression of citrate synthase |
| CMP451 | BL21 pgl + PL.2 mKKDyI GI1.2 gltA | CMP440 | Lowered expression of citrate synthase |
| CMP452 | BL21 pgl + PL.2 mKKDyI GI1.5 gltA | CMP441 | Lowered expression of citrate synthase |
| CMP453 | BL21 pgl + PL.2 mKKDyI GI1.6 gltA | CMP442 | Increased expression of citrate synthase |
| CMP596 | BL21 pgl + PL.2 mKKDyI GI 1.2 gltA ldhA::Kan | CMP451 | Deletion of lactate dehydrogenase |
| CMP604 | BL21 pgl + PL.2 mKKDyI GI1.2 gltA ackA-pta::Cm | CMP451 | Deletion of acetate kinase and phosphotransacetylase |
| CMP620 | BL21 pgl + PL.2 mKKDyI GI1.2 gltA ackA-pta::Cm ldhA::Kan | CMP604 | Deletion of acetate kinase and phosphotransacetylase and lactate dehydrogenase |
| CMP635 | BL21 pgl + PL.2 mKKDyI GI 1.2 gltA ackA-pta ldhA | CMP620 | Deletion of acetate kinase and phosphotransacetylase and lactate dehydrogenase |
| CMP646 | BL21 attB::Cm | BL21 (Novagen) | Chloramphenicol cassette inserted in the chromosome in the attTn7 region |
| CMP662 | BL21 FRT-Cm-FRT-GI1.2 maeB | BL21 (Novagen) | Constitutive low expression of NADPH-dependent malic enzyme |
| CMP671 | BL21 pgl + PL.2 mKKDyI GI1.2 gltA Cm-GI1.2 maeB | CMP451 | Constitutive low expression of NADPH-dependent malic enzyme |
| CMP674 | BL21 pgl + PL.2 mKKDyI GI1.2 gltA attB:Cm | CMP451 | Downregulated citrate synthase and lower pathway removed from chromosome |
| CMP676 | BL21 pgl + PL.2 mKKDyI GI 1.2 gltA ackA-pta ldhA attB::Cm | CMP635 | Downregulated citrate synthase and lower pathway removed from chromosome and deletion of acetate kinase and phosphotransacetylase and lactate dehydrogenase |
| CMP678 | BL21 pgl + PL.2 mKKDyI GI1.2 gltA attB:Cm, pCHL276 | CMP674 | Downregulated citrate synthase and lower pathway removed from chromosome |
| CMP680 | BL21 pgl + PL.2 mKKDyI GI1.2gltA ackA-pta ldhA attB::Cm, pCHL276 | CMP676 | Downregulated citrate synthase, lower pathway removed from chromosome and deletion of acetate kinase and phosphotransacetylase and lactate dehydrogenase |
| CMP681 | BL21 pgl + PL.2 mKKDyI GI1.2 gltA GI1.2 maeB | CMP671 | Constitutive low expression of NADPH-dependent malic enzyme |
| CMP694 | BL21 pgl + PL.2 mKKDyI, pCHL276 | CMP258 | Control. No additional host mutations. |
| CMP706 | BL21 pgl + PL.2 mKKDyI GI1.2 gltA GI1.2 maeB attB::Cm | CMP681 | Lowered expression of citrate synthase, constitutive low expression of NADPH-dependent malic enzyme, and lower pathway removed from chromosome |
| CMP711 | BL21 pgl + PL.2 mKKDyI GI1.2 gltA GI1.2 maeB attB::Cm, pCHL276 | CMP706 | lower pathway removed from chromosome |
| CMP723 | BL21 pgl + PL.2 mKKDyI GI1.2gltA ackA-pta | CMP604 | Acetate kinase and phsophotransacetylase |

TABLE 14-continued

E. coli strains

| Strain | Genotype | Parent | Phenotype |
|---|---|---|---|
| CMP725 | BL21 pgl + PL.2 mKKDyI Gi1.2-gltA pdhR attB::Cm | MD10-435 | Pyruvate decarboxylase repressor deleted, and lower pathway removed from chromosome |
| CMP729 | BL21 pgl + PL.2 mKKDyI Gi1.2-gltA pdhR attB::Cm, pCHL276 | CMP725 | Pyruvate decarboxylase repressor deleted, and lower pathway removed from chromosome |
| CMP735 | BL21 pgl + PL.2 mKKDyI GI1.2gltA ackA-pta attB::Cm | CMP723 | Acetate kinase and phsophotransacetylase deleted, and lower pathway removed from chromosome |
| CMP736 | BL21 pgl + PL.2 mKKDyI GI1.2gltA ackA-pta attB::Cm, pCLPtrcUpper(rbs) | CMP735 | Acetate kinase and phsophotransacetylase deleted, and lower pathway removed from chromosome |
| CMP812 | BL21 pgl + PL.2 mKKDyI GI1.2 gltA ldhA::Kan attB::Cm | CMP596 | Lactate dehydrogenase deleted, and lower pathway removed from chromosome |
| CMP828 | BL21 pgl + PL.2 mKKDyI GI1.2 gltA ldhA attB | CMP812 | Lactate dehydrogenase deleted and lower pathway removed from chromosome |
| CMP832 | BL21 pgl + PL.2 mKKDyI GI1.2 gltA ldhA attB, pCHL276 | CMP828 | Lactate dehydrogenase deleted and lower pathway removed from chromosome |
| MCM521 | BL21 neo-PL.2-mKKDyI | U.S. Patent App. No: 12/978,324 | BL21 strain containing a "lower mevalonate" pathway |
| MCM1002 | BL21 pgl+, pMCM82, pTrcHis2B | CMP258 | Control strain |
| MD09-273 | BL21 pgl + FRT::PL.6-rbs-yIDI-aspA PL.2 mKKDyI | BL21 | Strain used for recombineering of fragments in the chromosome |
| MD09-313 | BL21 pgl + neo-PL.2-mKKDyI | CMP258 | Mevalonate lower pathway on the chromosome, neomycin marker |
| MD09-314 | BL21 pgl + PL.2-mKKDyI | MD09-313 | Mevalonate lower pathway on the chromosome, no antibiotic marker |
| MD10-429 | BL21 wt + pgl + FRT::PL.6-rbs-yIDI-aspA PL.2 mKKDyI pdhR::Kan | MD09-273 | Pyruvate decarboxylase repressor deleted |
| MD10-432 | BL21 pgl + PL.2 mKKDyI Gi1.2-gltA pdhR::Kan | CMP451 | Pyruvate decarboxylase repressor deleted |
| MD10-434 | BL21 pgl + PL.6-rbs-yIDI-aspA PL.2 mKKDyI Cm::PL.6-pdh | MD10-426 | Strong constitutive promoter upstream of pyruvate decarboxylase structural enzymes |
| MD10-435 | BL21 pgl + PL.2 mKKDyI Gi1.2-gltA pdhR | MD10-432 | Pyruvate decarboxylase repressor deleted |
| MD10-440 | BL21 pgl + PL.2 mKKDyI Gi1.2-gltA Cm::PL.6-pdh | MD09-314 | Strong constitutive promoter upstream of pyruvate decarboxylase structural enzymes |
| MD10-446 | BL21 pgl + PL.2 mKKDyI Gi1.2-gltA PL.6-pdh | MD09-314 | Strong constitutive promoter upstream of pyruvate decarboxylase structural enzymes |
| MD10-551 | BL21 pgl + PL.2 mKKDyI Gi1.2-gltA + PL.6-pdh attB::Cm | MD10-446 | Pyruvate decarboxylase repressor deleted |
| MD10-554 | BL21 pgl + PL.2 mKKDyI Gi1.2-gltA + PL.6-pdh attB | MD10-551 | Strong constitutive promoter upstream of pyruvate decarboxylase structural enzymes, and lower pathway removed from chromosome |
| MD10-555 | BL21 pgl + PL.2 mKKDyI Gi1.2-gltA + PL.6-pdh attB, pCHL276 | MD10-554 | Strong constitutive promoter upstream of pyruvate decarboxylase structural enzymes, and lower pathway removed from chromosome |
| MD491 | BL21 pgl + ackA-pta::Cm | CMP258 | Deletion of acetate kinase and phosphotransacetylase |

Strain MD09-313 was built by transducing CMP258 (See U.S. patent application Ser. No. 12/978,324) with a P1 lysate from strain MCM521 (See U.S. patent application Ser. No. 12/978,324) and selecting for colonies on Luria-Bertani plates containing 20 ug/ml kanamycin. P1 lysates were prepared according to the method described in Ausubel, et al., *Current Protocols in Molecular Biology*, John Wiley and Sons, Inc. The kanamycin marker was removed using the protocol recommended by the manufacturer (Gene Bridges, Heidelberg, Germany) to form strain MD09-314.

P1 lysates were made from strains CMP141, CMP142 and CMP143 and were used to transduce strain MD09-314, to form CMP440, CMP441 and CMP442 respectively (Table 3). The chloramphenicol marker was removed using the protocol recommended by the manufacturer (Gene Bridges, Heidelberg, Germany) to form strains CMP451, CMP452 and CMP453 respectively (Table 14).

Example 14: Citrate Synthase Assay and Results

Citrate synthase (gltA) activity was measured by a method similar to that described in Sudgen, P. and Newsholm, E. 1975. *Biochem. J.* 150:105-111. In summary, it measures at 412 nm the release of CoASH from acetyl-CoA by reaction with DTNB.

Strains MD09-313, CMP451, CMP452 and CMP453 were grown overnight in 5 ml LB, at 34° C. and 200 rpm. They were diluted to an OD600 of 0.05 in 20 mL TM3 medium (previously described in U.S. Pat. No. 7,745,184, col. 32, lines 46-61) containing 10 g/L glucose. The cells were grown at 34° C. and 200 rpm to an OD600 of around 2-3. The broth was centrifuged, and the pellet thus obtained was frozen at −80 C. The day of the assay, the pellet was resuspended in assay buffer and the cells were broken using a French pressure cell. The lysate thus obtained was used in the citrate synthase assay.

Figure 6:
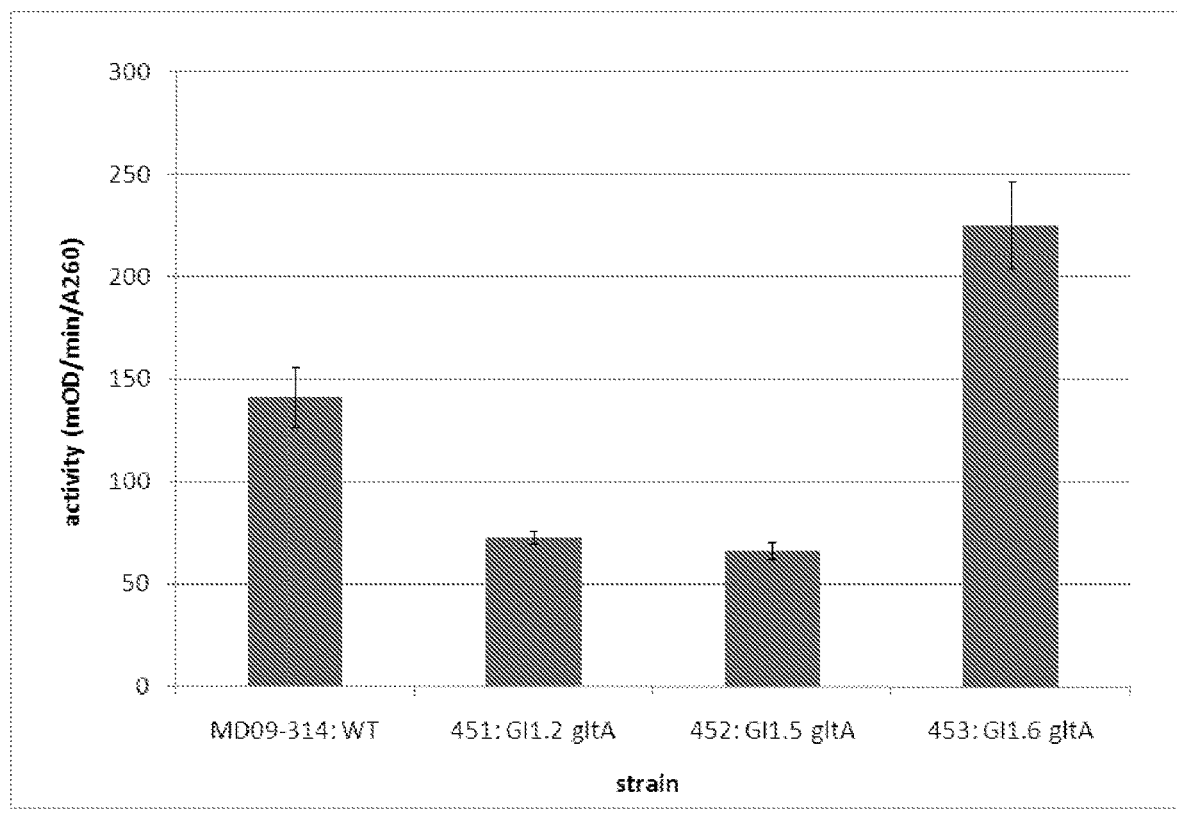
FIG. 6 depicts citrate synthase activity of strains MD09-314, CMP451, CMP452 and CMP453.

Results of the assay are shown in FIG. 6. Strain 451 and 452 had around half the activity of the wild-type, while strain CMP453 had around 1.5× the activity of the wild-type.

Example 15: Construction of Strain MCM1002

Plasmid pMCM82 (pCLPtrcUpper) was electroporated in strain CMP258 and colonies were selected on LB+spectinomycin 50 ug/mL. One colony was picked and electroporated with pTcHis2B (Invitrogen, Carlsbad, Calif.) and transformants were selected on LB+spectinomycin 50 ug/ml and carbenicillin 50 ug/mL. One colony was picked and named MCM1002.

Example 16: Construction of Strain CMP604 (BL21 pgl+PL.2 mKKDyI GI1.2 gltA ackA-Pta::Cm), CMP723 (BL21 pgl+PL.2 mKKDyI GI1.2gltA ackA-Pta), and CMP735 (BL21 pgl+PL.2 mKKDyI GI1.2gltA ackA-Pta attB::Cm)

A DNA fragment containing the ackA-pta genes interrupted by a chloramphenicol marker was amplified by PCR using strain Triple Triple in which the Chloramphenicol marker is still in (U.S. Pat. No. 7,745,184 B2) as a template and primers ackACF (5'-GTGCAAATT-CACAACTCAGCGG-3' (SEQ ID NO:62) and ptaCR (5'-CACCAACGTATCGGGCAT TGCC-3') (SEQ ID NO:63). The PCR product obtained was used in a recombineering reaction as recommended by the manufacturer (Gene Bridges, Heidelberg, Germany) to integrate the PCR product at the ackA-pta locus in strain CMP258 (See U.S. patent application Ser. No. 12/978,324). Colonies were selected on LB+5 ug/ml of chloramphenicol. One colony was picked and was named MD491. A P1 lysate of MD491 was made and was used to transduce strain CMP451. Colonies were selected on LB+5 ug/ml of chloramphenicol. One colony was picked and was named CMP604. The chloramphenicol marker was removed using the protocol recommended by the manufacturer (Gene Bridges, Heidelberg, Germany) to form strain CMP723. CMP723 was transduced with a P1 lysate made from strain CMP646 (see example 18). Colonies were selected on plates containing LB+5 ug/mL chloramphenicol. One colony was picked and named CMP735.

Example 17: Construction of Strain CMP596 (BL21 pgl+PL.2 mKKDyI GI1.2 gltA ldhA::Kan), CMP812 (BL21 pgl+PL.2 mKKDyI GI1.2 gltA ldhA::Kan attB::Cm) and CMP828 (BL21 pgl+PL.2 mKKDyI GI1.2 gltA ldhA attB)

Strain CMP451 was transduced with a P1 lysate made on strain CMP374 (see below) containing a kanamycin marker in the lactate dehydrogenase gene (ldhA). Colonies were plated on LB+20 ug/ml kanamycin. One colony was chosen and named CMP596. CMP596 was transduced with the P1 lysate made from strain CMP646 (see example 18). Transductants were selected on LB+5 ug/ml chloramphenicol. One colony was selected and named CMP812. The kanamycin and chloramphenicol markers were removed in one step using the protocol recommended by the manufacturer (Gene Bridges, Heidelberg, Germany) to form strain CMP828.

Example 18: Construction of Strain CMP620 (BL21 pgl+PL.2 mKKDyI GI1.2 gltA ackA-Pta::Cm ldhA::Kan) and CMP635 (BL21 pgl+PL.2 mKKDyI GI1.2 gltA ackA-Pta ldhA)

A DNA fragment containing the ldhA gene interrupted by a kanamycin marker was amplified by PCR using strain JW 1375 from the Keio collection (Baba et al. 2006. *Mol. Syst. Biol.* 2: 2006.0008) as a template, and primers ldhAseqR (5'-GGCTTACCGTTTACGCTTTCCAGC-3' (SEQ ID NO:64)) and ldhAseqF2 (5'-CTAATGCAATACGTGTCCCGAGC-3' (SEQ ID NO:65)). The PCR product obtained was used in a recombineering reaction as recommended by the manufacturer (Gene Bridges, Heidelberg, Germany) to integrate the PCR product at the ldhA locus in strain MD09-313. Colonies were selected on LB+20 ug/ml of kanamycin. One colony was picked and was named CMP374. A P1 lysate of CMP374 was made and was used to transduce CMP604. Colonies were selected on LB+20 ug/ml of kanamycin. One colony was picked and was named CMP620. The chloramphenicol and kanamycin markers were looped out simultaneously by electroporating pCP20 (Datsenko and Wanner. 2000. *PNAS* 97:6640-5) in the strain, selecting two colonies on LB+50 ug/ml carbenicillin at 30° C., then restreaking those colonies on an LB plate at 42° C. A chloramphenicol- and kanamycin-sensitive colony was selected from those plates and named CMP635.

Example 19: Construction of Strains CMP674 (BL21 pgl+PL.2 mKKDyI GI1.2 gltA attB::Cm) and CMP676 (BL21 pgl+PL.2 mKKDyI GI1.2 gltA ackA-Pta ldhA attB::Cm)

A DNA fragment containing a chloramphenicol marker flanked by DNA homologous to the upstream and downstream regions of the □ attachment site attB was amplified by PCR using plasmid pKD3 (Datsenko, K., and Wanner, B. 2000. *PNAS* 97:6640-6645) as a template, and primers CMP171 (5'-AAAATTTCATTCTGTGACAGAGAAAAAGTAGCCGAA-GATGACGGTTTGTCACATGGA GTTGGCAG-GATGTTTGATTACATGGGAATTAGCCATGGTCC-3' (SEQ ID NO:66)) and CMP172 (5'-GACCAGCCGCGTAACCTGGCAAAATCGGT-TACGGTTGAGTAATAAATGGATGCCCTGC GTAAG CGG GGCATT TTTCTTGGTGTAGGCTG-GAGCTGCTTCG-3' (SEQ ID NO:67)). The PCR product obtained was used in a recombineering reaction in BL21 (Novagen) as recommended by the manufacturer (Gene Bridges, Heidelberg, Germany) to integrate the PCR product at the □ attachment site attB. Strain CMP646 was thereby generated, selected on LB+5 ug/ml chloramphenicol. A P1 lysate of CMP646 was made and was used in a transduction reaction on strains CMP451 and CMP635, thereby removing the lower mevalonate pathway (mevalonate kinase, phosphomevalonate kinase, diphosphomevalonate decarboxylase, and isopentenyl diphosphate isomerase) from the chromosome of that strain. The transduction reaction was plated on LB+chloramphenicol 5 ug/ml and one colony for each transduction was picked and named CMP674 and CMP676 respectively.

Example 20: Construction of Strains CMP678 (BL21 pgl+PL.2 mKKDyI GI 1.2 gltA, pCHL276), CMP680 (BL21 pgl+PL.2 mKKDyI GI 1.2 gltA ackA-Pta ldhA attB::Cm), CMP694 (BL21 pgl+ PL.2 mKKDyI, pCHL276), CMP736 (BL21 pgl+ PL.2 mKKDyI GI1.2 gltA ackA-Pta attB::Cm, pCHL276) and CMP832 (BL21 pgl+PL.2 mKKDyI GI1.2 gltA ldhA attB, pCHL276)

Plasmid pCHL276 was introduced into strains CMP674, CMP676, CMP258, CMP735 and CMP828 by electroporation. Colonies were selected on LB+50 ug/mL spectinomycin. One colony for each transformation was picked and named CMP678, CMP680, CMP694, CMP736 and CMP832 respectively.

Figure 7:
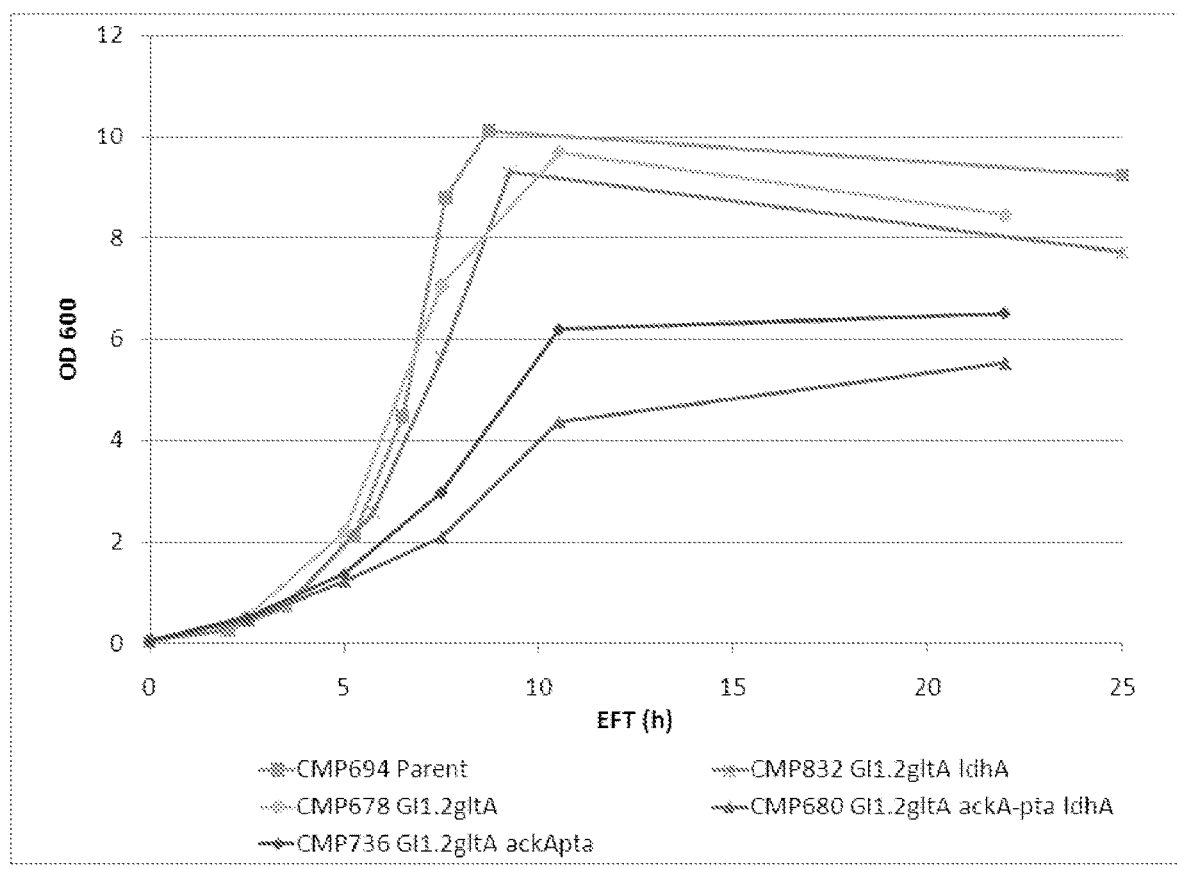
FIG. 7 depicts growth curve of strains CMP694, CMP678, CMP680, CMP736, and CMP832. 100 uM IPTG were added at t=2. Absorbance at 600 nm is plotted as a function of time (EFT=Elapsed Fermentation Time (h)).
Figure 8:
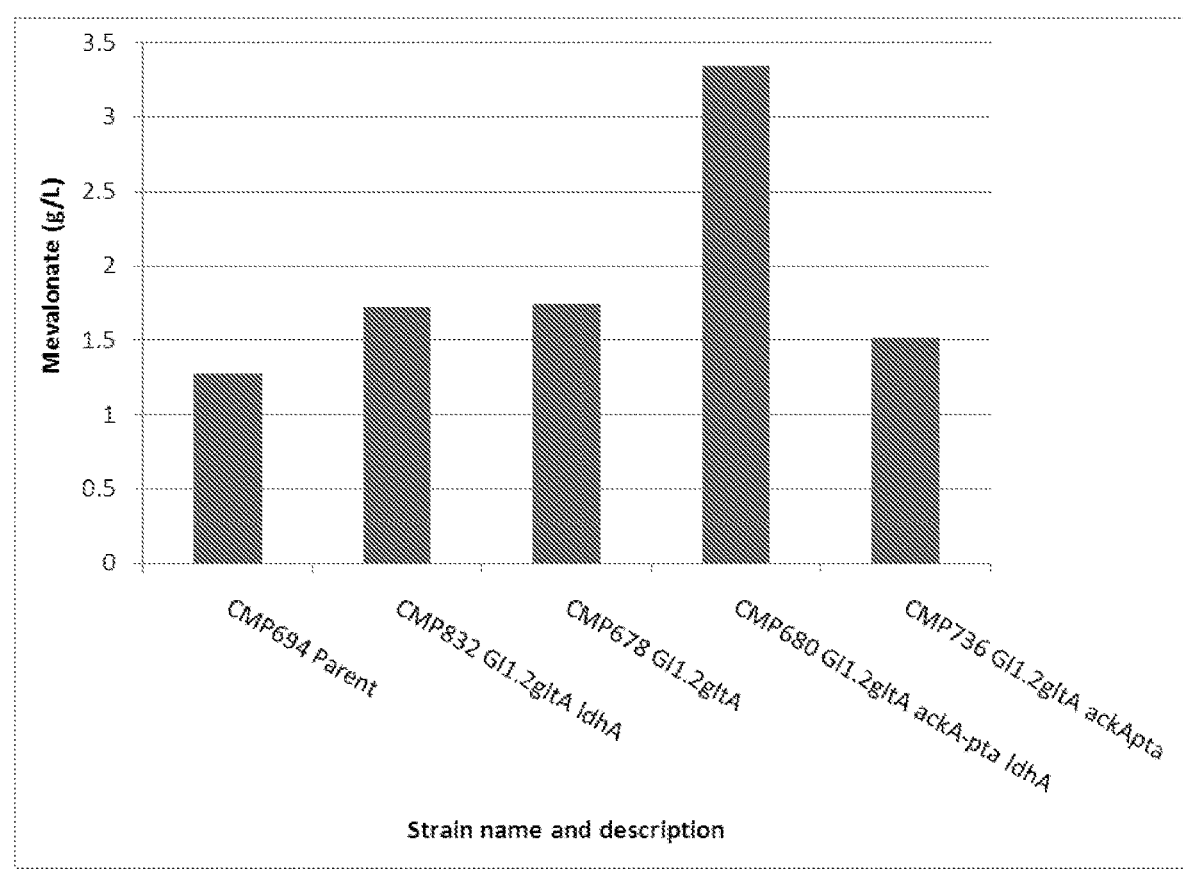
FIG. 8 depicts concentration of mevalonate (g/L) as obtained from 10 g/L glucose after shake flask fermentation of strains CMP694, CMP832, CMP678, CMP680, and CMP736.

Example 21: Increased Production of Mevalonate in a Strain Containing the GI1.2gltA Construct in Comparison to its Parent, and Increased Mevalonate Production in a Strain Containing ackA-Pta ldhA in Comparison to its Parent or a Strain Containing One Mutation at a Time This example shows production of mevalonate in strains CMP678, CMP680, CMP694, CMP736 and CMP832.
(i) Materials
TM3 Media Recipe (Per Liter Fermentation Media):
$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components were added together and dissolved in $diH_2O$. The pH was adjusted to 6.8 with ammonium hydroxide (30%) and brought to volume. Media was filter-sterilized with a 0.22 micron filter. Glucose 10.0 g and antibiotic were added after sterilization and pH adjustment.
1000× Trace Metal Solution (Per Liter Fermentation Media):
Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.
(ii) Experimental Procedure
Cells were grown overnight in Luria-Bertani broth. The day after, they were diluted to an OD600 of 0.05 in 20 mL TM3 medium containing 50 ug/ml of spectinomycin (in a 250-mL baffled Erlenmeyer flask), and incubated at 34° C. and 200 rpm. After 2 h of growth, OD600 was measured and 100 uM IPTG was added. Samples were taken regularly during the course of the fermentation. At each timepoint, OD600 was measured and mevalonate concentration was measured by HPLC. HPLC analysis was performed in the following way: 15 uL of 70% (w/v) perchloric acid was added to 500 uL of broth and the mixture was incubated on ice for 5 minutes. Next, the sample was centrifuged at 14,000×g for 5 minutes and the supernatant collected for HPLC analysis run under the following conditions: (1) BioRad-Aminex HPX-87H Ion Exclusion Column (300 mm×7.8 mm)(Catalog #125-0140)(BioRad, Hercules, Calif.); (2) column temperature=50° C.; (3) BioRad-Microguard Cation H guard column refill (30 mm×4.6 mm) (Catalog #125-0129)(BioRad); (4) running buffer=0.01N $H2SO4$; (5) running buffer flow rate=0.6 ml/min; (6) approximate running pressure=~950 psi; (7) injection volume=100 microliters; (8) runtime=26 minutes.
(iii) Results
Strain CMP678 (GI1.2gltA) was assessed using strain CMP694 (parent) as a control.
The experiment demonstrated that strain CMP678, having the gltA promoter downregulated, showed an increased titer from the same amount of glucose when compared to a strain with a wild-type gltA promoter (CMP694) (FIG. 8). The strains with a downregulated gltA promoter grew to a slightly lower OD than the strain with a WT promoter (FIG. 7).
Strain CMP680 (ackA-pta ldhA), CMP736 (ackA-pta), and CMP832 (ldhA) were assessed using strain CMP678 (parent) as a control. The ackA-pta mutation contributed a slower growth and a lower final OD to the strain, while the ldhA mutation did not affect growth (FIG. 7). The combination of ackA-pta and ldhA mutation slowed growth and decreased final biomass further (FIG. 7) further. By themselves, the ackA-pta or ldhA mutations did not contribute to a higher final concentration of mevalonate, but in combination, they provided a 250% increase in titer (and yield since it is linked to titer in small scale) (FIG. 8).

Example 22: Construction of CMP662 (BL21 FRT-Cm-FRT-GI1.2 maeB)

Figure 9:
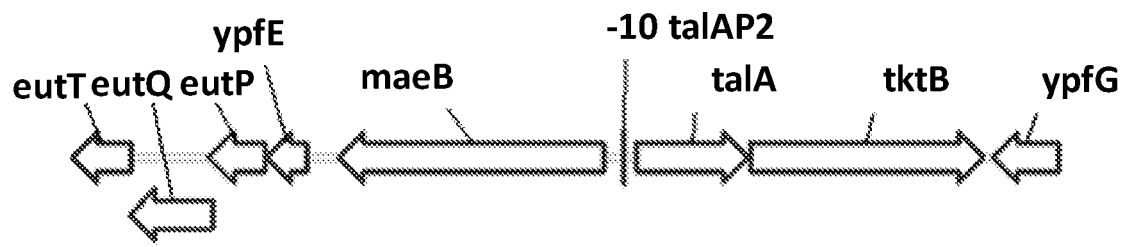
FIG. 9 depicts genome local context of the gene maeB in *E. coli* BL21.
Figure 10:
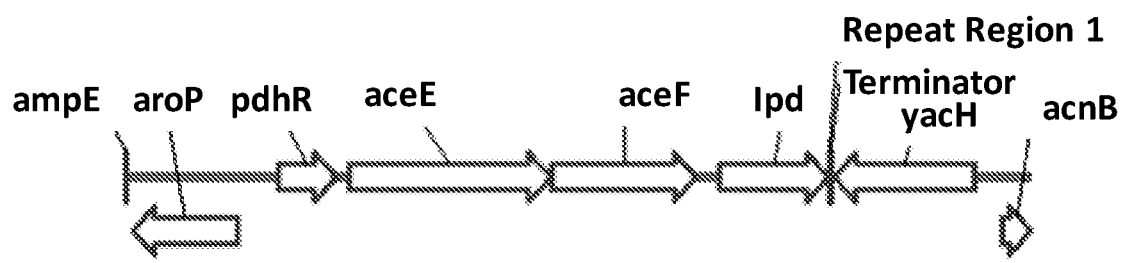
FIG. 10 depicts genome local context of the Pyruvate dehydrogenase complex (pdhR-aceEF-lpd) in *E. coli* K-12.
Figure 11:
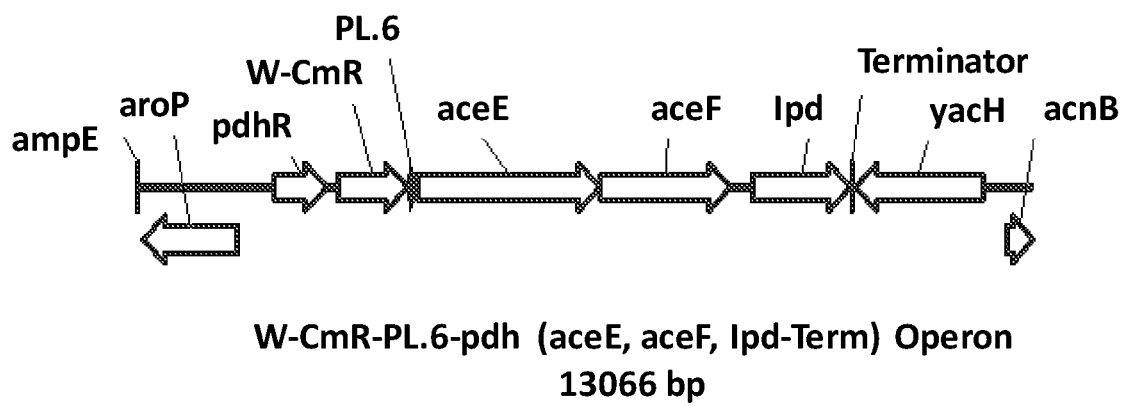
FIG. 11 depicts insertion of a PL.6 promoter upstream of the aceE gene.
Figure 12:
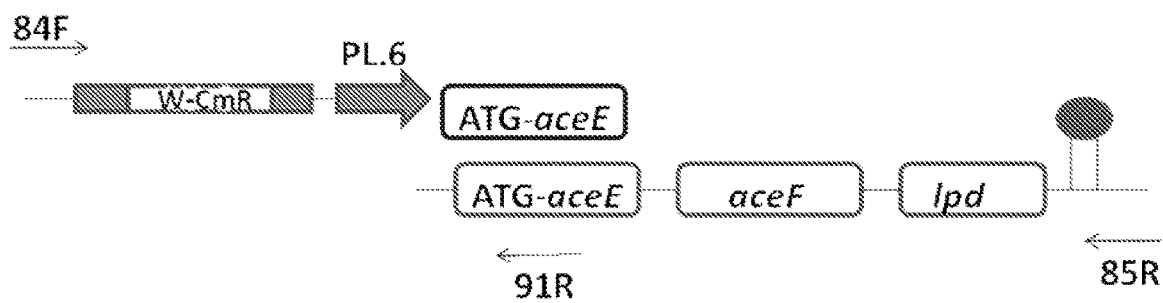
FIG. 12 depicts construction design for the insertion of a PL.6 promoter upstream of the aceE gene.

The native promoter in front of the NADP-dependent malic enzyme (maeB) has been replaced by a constitutive promoter, namely GI1.2 (U.S. Pat. No. 7,371,558). The insertion site of the new promoter has been chosen carefully so as not to alter expression of the gene just upstream (talA) which is translated in the opposite direction (FIG. 9). While the maeB promoter has not been described, the talA promoter has been experimentally determined (Lacour & Landini, 2004, *J. Bact.* 186:7186-7195).
A PCR product has been obtained using primers maeB_GI1.xpKD3 (5'-ACT GGA AAT TCA TGG AAA TCA AGT GCA CTT TGT TTT AAC TGG TCA TCC ATT ATA TAC CTC CTG CTA TTT GTT AGT GAA TAA AAG TGG TTG AAT TAT TTG CTC AGG ATG TGG CAT n GT CAA GGG CGT GTA GGC TGG AGC TGC TTC-3' (SEQ ID NO:68)) and maeBUp_pKD3 (5'-AGA GTT TGG ACT TGC TCA AAG TCT GTA GAC TCC GGC AGG GTA ATA ATG TGC GCC ACG TTG TGG GCA GGG G ATGG-GAATTAGCCATGGTCC-3' (SEQ ID NO:69)), and plasmid pKD3 (Datsenko & Wanner 2000, *PNAS* 97:6640-6645) as a template. The enzyme Herculase II (Agilent, Santa Clara, US) was used according to the manufacturer. The PCR product was purified and used in a lambda red-mediated recombination as described by the manufacturer (Gene Bridges, Heidelberg, Germany). Several colonies were selected for further characterization. The promoter region was PCR-amplified using primers maeBPromseqF: GTGAACTGTTTGATGCCGTC (SEQ ID NO:70) and maeBPromSeqR: ccgtaccgttagagatcacc (SEQ ID NO:116) and, as a template, DNA extracted by resuspending a colony in 30 uL H2O, heating at 95 C for 4 min, spinning down, and using 2 uL of that material as a template in a 50 uL reaction. After observing the sequencing results of the PCR products obtained, a colony harboring the GI1.2 promoter (U.S. Pat. No. 7,371,558) was saved for further use. This colony was named CMP662 (Table 3). A P1 lysate of strain CMP662 was made and was used to transduce CMP451. Colonies were selected on LB+5 ug/ml of chloramphenicol. One colony was picked and was named MDCMP671. The chloramphenicol marker was removed using the protocol recommended by the manufacturer (Gene Bridges, Heidelberg, Germany) to form strain CMP68. CMP681 was transduced with a P1 lysate made from strain CMP646 (see example 18). Colonies were selected on plates containing LB+5 ug/mL chloramphenicol. One colony was picked and named CMP706.

Example 23: Construction of Strain MD10-432 (BL21 pgl+PL.2 mKKDyI Gi1.2-gltA pdhR::Kan), MD10-435 (BL21 pgl+PL.2 mKKDyI Gi1.2-gltA pdhR) and CMP725 (BL21 pgl+PL.2 mKKDyI Gi1.2-gltA pdhR attB::Cm)—pdhR Mutant Cell Line A DNA fragment containing the pdhR gene interrupted by a kanamycin marker was amplified by PCR using strain JW0109 from the Keio collection (Baba et al. 2006 *Mol. Syst. Biol.* 2:2006.0008) using primers MQ10-82F (5'-GGTAAGTGAATCGGTTCAATTCGG-3' (SEQ ID NO:71)) and MQ10-82R (5'-CGCTCAACACCTTCTT-CACGGATG-3' (SEQ ID NO:72)). The PCR product obtained was purified with Qiagen PCR purification Kit (Qiagen, Germantown, Md.) and used in a recombineering reaction as recommended by the manufacturer (Gene Bridges, Heidelberg, Germany) to integrate the PCR product at the pdhR locus in strain MD09-273. Transformants were selected on LA+Kan12.5 ug/ml plates incubated at 37° C. One colony was picked and checked by PCR using primers MQ10-83F (5'-CCTGTATGGACATAAGGTGAATAC-3' (SEQ ID NO:73)) and MQ10-83R (5'-CCTGTCCCATT-GAACTCTCGCCGG-3' (SEQ ID NO:74)) which were about ~250 bp upstream & downstream of pdhR gene region. The correct mutant was named MD10-429.

A P1 lysate of strain MD10-429 was made and used to transduce CMP451. Colonies were selected on LB+Kan12.5 mg/ml. Several transductant colonies were screened by PCR using outside primers MQ10-83F (5'-CCTGTATGGACAT-AAGGTGAATAC-3' (SEQ ID NO:75) and MQ10-83R (5'-CCTGTCCCATTGAACTCTCGCCGG-3' (SEQ ID NO:76)). The correct mutant in CMP451 background strain is named MD10-432.

The Kanamycin marker was removed by FRT recombination by electroporating pCP20 (Datsenko and Wanner, 2000, *PNAS* 97:6640-5), selecting a couple colonies on LA+50 ug/ml Carbenicillin at 30° C., then re-streaking the colony of interest on an LA plate at 37° C. The resulting markerless strain was named MD10-435. Strain MD10-435 was transduced with the P1 lysate made from strain CMP646 (see example 18). Transductants were selected on LB+5 ug/ml chloramphenicol. One colony was selected and named CMP725.

Example 24: Construction of Strain MD10-434 (BL21 pgl+PL.6-Rbs-yIDI-aspA PL.2 mKKDyI+ Cm::PL.6-Pdh), MD10-440 (BL21 pgl+PL.2 mKKDyI Gi1.2-gltA+Cm::PL.6-Pdh) and MD10-446 (BL21 pgl+PL.2 mKKDyI Gi1.2-gltA+PL.6-Pdh)-PL.6-Pdh Mutant Cell Line The promoter in front of the Pdh operon (Pyruvate Dehydrogenase complex) in BL21 (Novagen) has been modified by replacing the native promoter by a constitutive high expression promoter, namely PL.6. A PCR product was obtained using primers MQ10-84F (5'-AGAGTT-CAATGGGACAGGTTCCAGAAAACTCAACGTTATTA-GATAGATAAGGAATAAC CCGTGTAGGCTG-GAGCTGCTTC-3' (SEQ ID NO:77)) and MQ10-84R (5'-CGTCATTTGGGAAACGTTCTGACATGTTTTTTACC TCCTTTGCACCTTCATGGTGGTCA GTGCGTCCTGCTGATGTGCTCAGTAT-CACCGCCAGTGGTATTTATGTCAACACCGCCAG AGATAATTTATCACCGCAGATGGT-TATCTGTATGTTTTTTATATGAATTCATATGAATAT CCTCCTTA-3' (SEQ ID NO:78)) to amplify the chloramphenicol gene flanked by FRT sites from pKD3 plasmid (Datsenko and Wanner. 2000, *PNAS* 97:6640-5). A second PCR product was generated using BL21 as atemplate to amplify the whole PDH operon (aceE, aceF and lpdA) using primers MQ10-85F (5'-ATGTCAGAACGTTTCC-CAAATGACG-3' (SEQ ID NO:79)) and MQ10-85R (5'-GCGGCGTGGTTAGCCGCTTTTTAATTGCCG-GATGTTCCGGCAAACGAAAAATTACTTC TTCTTCGCTTTCGGGTTC-3' (SEQ ID NO:80)). Fusion PCR was used to fuse both pieces of DNA together, with primers MQ10-84F & MQ10-85R. An approximately 1.6 Kbp PCR product was obtained and purified using a Qiagen PCR purification Kit (Qiagen, Germantown, Md.). Approximately, 300-400 ng of purified PCR product was used in a lambda red-mediated recombination as described by the manufacturer (Gene Bridges, Heidelberg, Germany) targeting the PDH promoter in strain MD09-273. When this integration failed to integrate, the PCR product was re-amplified using a shorter reverse primer version (MQ10-91R 5'-GAAGTGGTTAAAGCACAC-3' (SEQ ID NO:81)). As a result, ~1.6 kbp PCR product was successfully integrated in MD09-273. Transformants were selected on LA+chloramphenicol 5 ug/ml. Several colonies were selected for further characterization using primers MQ10-84F & MQ10-84R. The promoter region was PCR-amplified using other primers MQ10-84F & MQ10-91R for further verification. The PCR product obtained was sequenced and shown to be correct, and the strain was named MD10-434.

A P1 lysate of MD10-434 was made and used to transduce CMP451. Transductants were selected on LB+chloramphenicol 5 µg/ml. Several colonies were verified by PCR using primers MQ10-84F & MQ10-84R. One mutant was picked and named MD10-440.

The chloramphenicol marker was removed by FRT recombination (Datsenko & Wanner. 2000. *PNAS* 97:6640-5), using plasmid pCP20. Once the transformants were obtained on LA+50 ug/ml carbenicillin at 30° C., two colonies were re-streaked on a LB plate and incubated at 37° C. A chloramphenicol-sensitive colony was selected from those plates and named MD10-446.

MD10-446 was transduced with a P1 lysate obtained from strain CMP646 (see example 18). Transductants were selected on LB+5 ug/ml chloramphenicol. One colony was selected and named MD10-551. The chloramphenicol marker was removed by FRT recombination (Datsenko & Wanner. 2000. *PNAS* 97:6640-5), using plasmid pCP20. Once the transformants were obtained on LA+50 ug/ml carbenicillin at 30° C., two colonies were re-streaked on a LB plate and incubated at 37° C. A chloramphenicol-sensitive colony was selected from those plates and named MD10-554.

Example 25: Construction of Strains MD10-555 (BL21 pgl+PL.2 mKKDyI GI 1.2 gltA PL.6Pdh attB::Cm, pCHL276), CMP711 (BL21 pgl+PL.2 mKKDyI GI1.2 gltA GI1.2 maeB attB::Cm, pCHL276), CMP729 (BL21 pgl+PL.2 mKKDyI Gi1.2-gltA pdhR attB::Cm, pCHL276)

Plasmid pCHL276 (see example 6 (iii)) was introduced into strains MD10-446, CMP706 and CMP725 by electroporation. Colonies were selected on LB+50 ug/mL spectinomycin. One colony for each transformation was picked and named MD10-555, CMP711 and CMP729 respectively.

Example 26: Increased Production of Mevalonate in Strains Containing the GI1.2maeB, pdhR, and PL.6 Pdh Mutations in Comparison to their Parent This example shows production of mevalonate in strains CMP678, MD10-555, CMP711 and CMP729.

(i) Materials
TM3 Media Recipe (Per Liter Fermentation Media):
$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components were added together and dissolved in $diH_2O$. The pH was adjusted to 6.8 with ammonium hydroxide (30%) and brought to volume. Media was filter-sterilized with a 0.22 micron filter. Glucose 10.0 g and antibiotic were added after sterilization and pH adjustment.
1000× Trace Metal Solution (Per Liter Fermentation Media):
Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure
Cells were grown overnight in Luria-Bertani broth. The day after, they were diluted to an OD600 of 0.05 in 20 mL TM3 medium containing 50 ug/ml of spectinomycin (in a 250-mL baffled Erlenmeyer flask), and incubated at 34° C. and 200 rpm. After 2 h of growth, OD600 was measured and 100 uM IPTG was added. Samples were taken regularly during the course of the fermentation. At each timepoint, OD600 was measured and mevalonate concentration was measured by HPLC. HPLC analysis was performed in the following way: 15 uL of 70% (w/v) perchloric acid was added to 500 uL of broth and the mixture was incubated on ice for 5 minutes. Next, the sample was centrifuged at 14,000×g for 5 minutes and the supernatant collected for HPLC analysis run under the following conditions: (1) BioRad-Aminex HPX-87H Ion Exclusion Column (300 mm×7.8 mm)(Catalog #125-0140)(BioRad, Hercules, Calif.); (2) column temperature=50° C.; (3) BioRad-Microguard Cation H guard column refill (30 mm×4.6 mm) (Catalog #125-0129)(BioRad); (4) running buffer=0.01N $H_2SO_4$; (5) running buffer flow rate=0.6 ml/min; (6) approximate running pressure=~950 psi; (7) injection volume=100 microliters; (8) runtime=26 minutes.

(iii) Results
Strains MD10-555 (PL.6pdh), CMP711 (GI1.2maeB) and CMP729 (pdhR) were assessed using strain CMP678 (parent) as a control.

Figure 13:
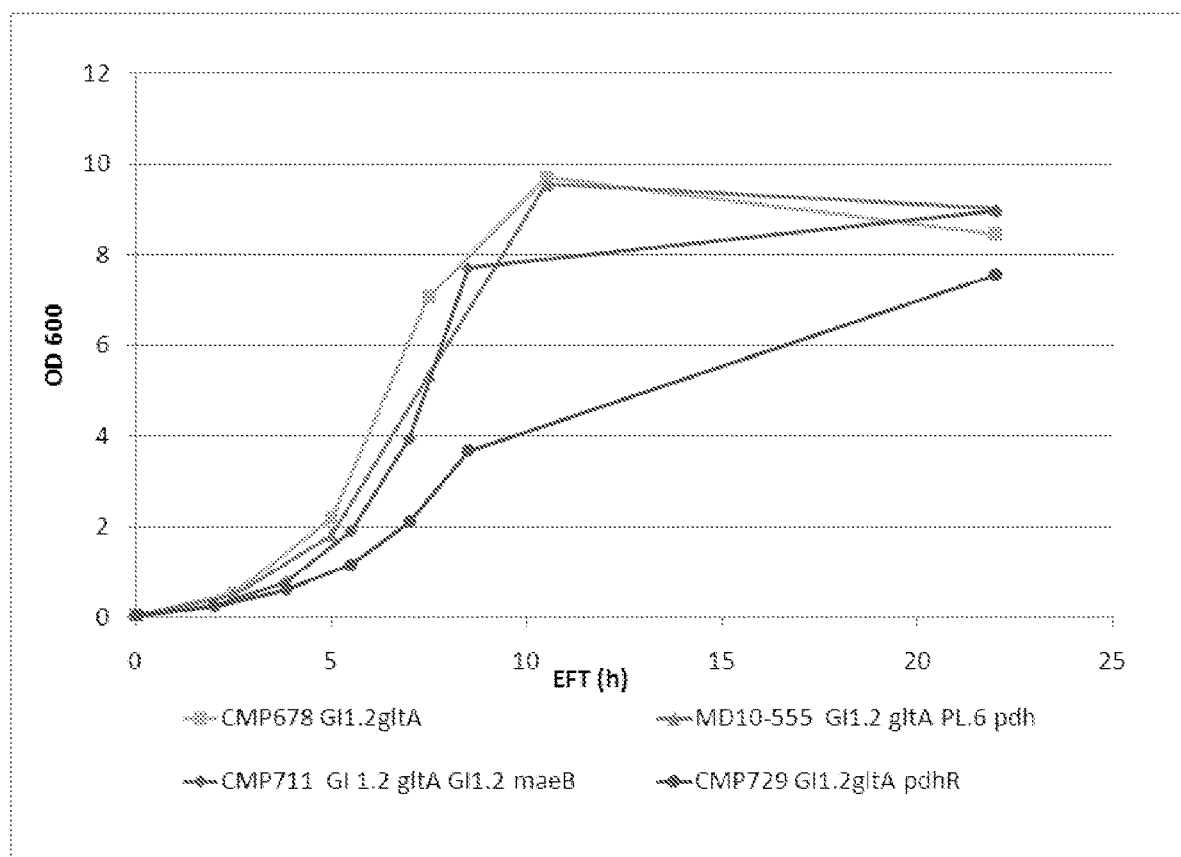
FIG. 13 depicts growth curve of strains CMP678, MD10-555, CMP711, and CMP729. 100 uM IPTG were added at t=2. Absorbance at 600 nm is plotted as a function of time (EFT=Elapsed Fermentation Time (h)).
Figure 14:
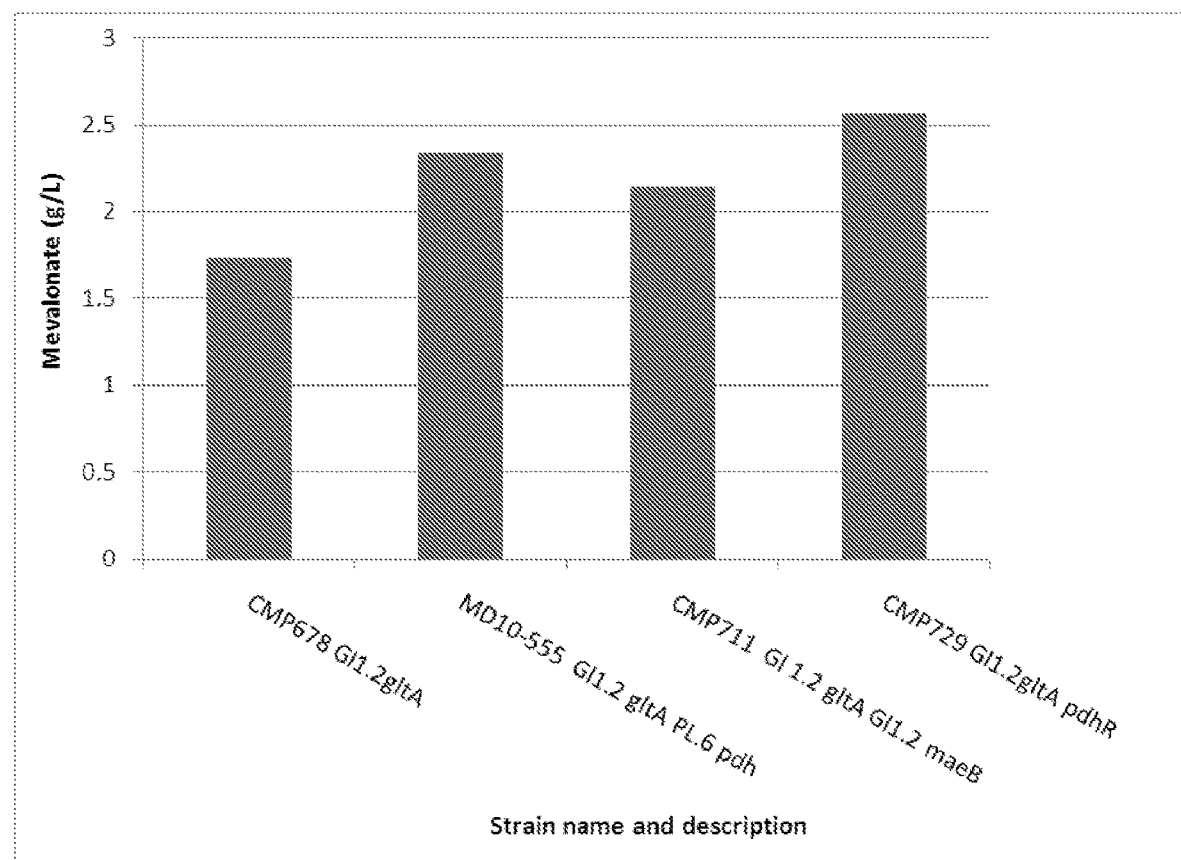
FIG. 14 depicts concentration of mevalonate (g/L) as obtained from 10 g/L glucose after shake flask fermentation of strains CMP678, MD1-555, CMP711 and CMP729.

The experiment demonstrated that strain MD10-555 and CMP729, presumably fluxing more pyruvate towards acetyl-CoA, and CMP711, bringing carbon back from the TCA cycle into pyruvate while generating NADPH, showed an increased titer from the same amount of glucose when compared to a parent strain (CMP678) (FIG. 14). CMP729, with the pdhR mutation, had a slower growth rate than the parent (FIG. 13). The PL.6pdh and GI1.2maeB mutations did not affect growth (FIG. 13).

Example 27: Isoprene Production from *E. coli* Expressing Genes from the Mevalonate Pathway and Isoprene Synthase, Grown in Fed-Batch Culture at the 15-L Scale (i) Materials
Medium Recipe (Per Liter Fermentation Medium):
K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.
1000× Modified Trace Metal Solution (Per Liter):
Citric Acids*H2O 40 g, MnSO4*H2O 30 g, NaCl 10 g, FeSO4*7H2O 1 g, CoCl2* 6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.
Vitamin Solution (Per Liter):
Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.
Feed Solution (Per Kilogram):
Glucose 0.57 kg, Di H2O 0.38 kg, K2HPO4 7.5 g, and 100% Foamblast 10 g. All components were mixed together and autoclaved. Macro Salt Solution 3.4 mL, 1000× Modified Trace Metal Solution 0.8 ml, and Vitamin Solution 6.7 mL were added after the solution had cooled to 25° C.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

(ii) Methods

Fermentation was performed in a 15-L bioreactor with *E. coli* BL21 cells overexpressing the upper MVA pathway (pCLUpper—MCM82), the lower MVA pathway (PL.2-mKKDyI) and truncated isoprene synthase from *P. alba* (pTrcAlba(MEA)) and containing a restored chromosomal pgl gene as well as a knocked-down gltA gene behind the GI1.2 promoter (strain name CMP457). The parental strain, used in the control fermentation, was a strain without the knocked-down gltA gene.

This experiment was carried out to monitor isoprene formation from glucose at the desired fermentation pH 7.0 and temperature 34° C. A frozen vial of the *E. coli* strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L.

The feed solution was fed at an exponential rate until a top feed rate of 6 g/min was reached. After this time, the glucose feed was fed to meet metabolic demands at rates less than or equal to 6 g/min. The total amount of glucose delivered to the bioreactor during the 52 hr fermentation was 6.8 kg. Induction was achieved by adding isopropyl-beta-D-1-thio-galactopyranoside (IPTG). A shot of IPTG was added to the tank to bring the concentration to 100 uM when the cells were at an $OD_{550}$ of 6 and a second shot was added bring the concentration to 100 uM when the cells were at an $OD_{550}$ of 100.

The isoprene level in the off-gas from the bioreactor was determined using an iSCAN (Hamilton Sundstrand) mass spectrometer.

(iii) Results

Figure 15:
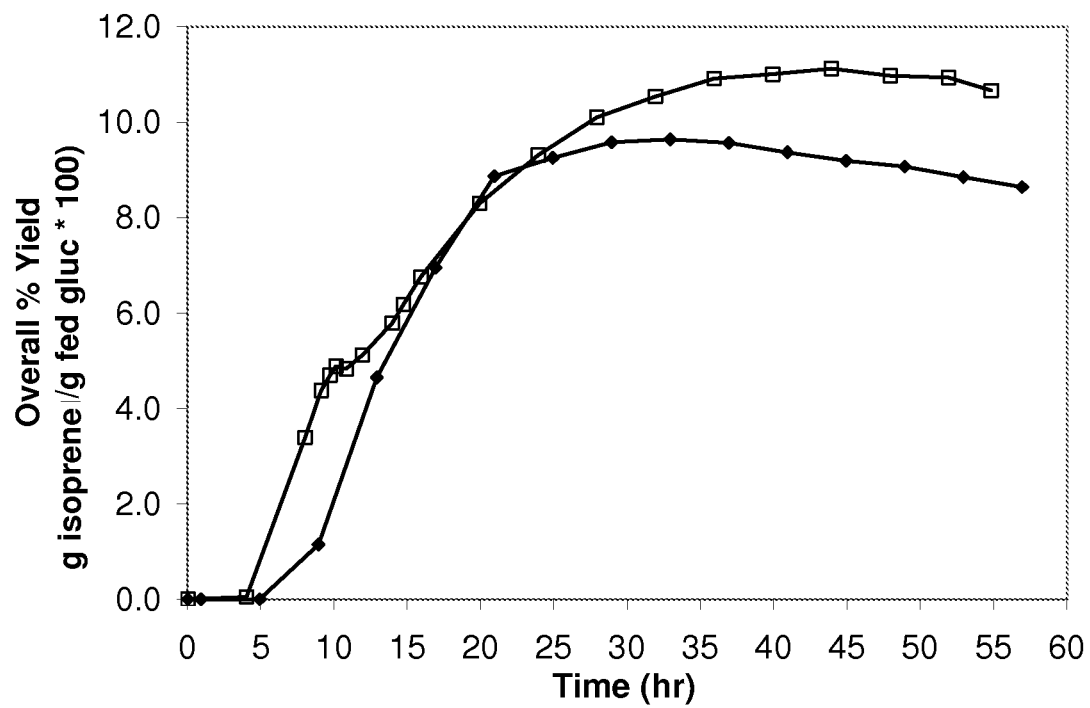
FIG. 15 depicts yield of isoprene on glucose of 1.2 gltA strain (open squares) compared to the parental strain (closed diamonds) in the 15-L fermentation over time. Strains were run under the same conditions. Overall yield was calculated using the following formula: % wt Yield on glucose=Isoprene total(t)/[(Feed Wt(0)−Feed Wt(t)+50) *0.57)], where 0.57 is the wt % of glucose in the glucose feed solution and 50 is the grams of this feed batched into the fermentor at t=0. (20100278: strain CMP457 (open squares); GI1.2gltA20100131: strain MD09-317 (black diamonds) wt gltA).
Figure 16:
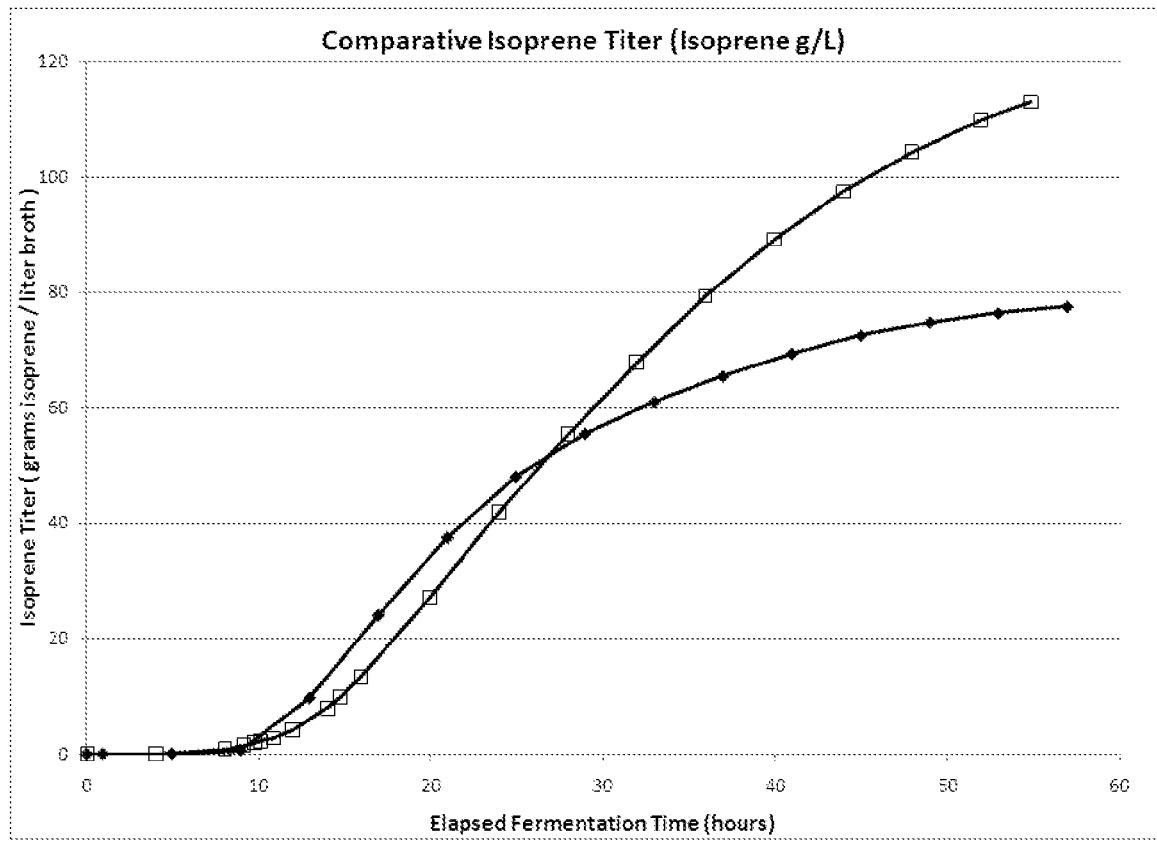
FIG. 16 depicts titer of 1.2 gltA strain (open squares) compared to the parental strain (closed diamonds) in the 15-L fermentation over time. Strains were run under the same conditions. (20100278: strain CMP457 (open squares); GI1.2gltA 20100131: strain MD09-317 (black diamonds) wt gltA).
Figure 17:
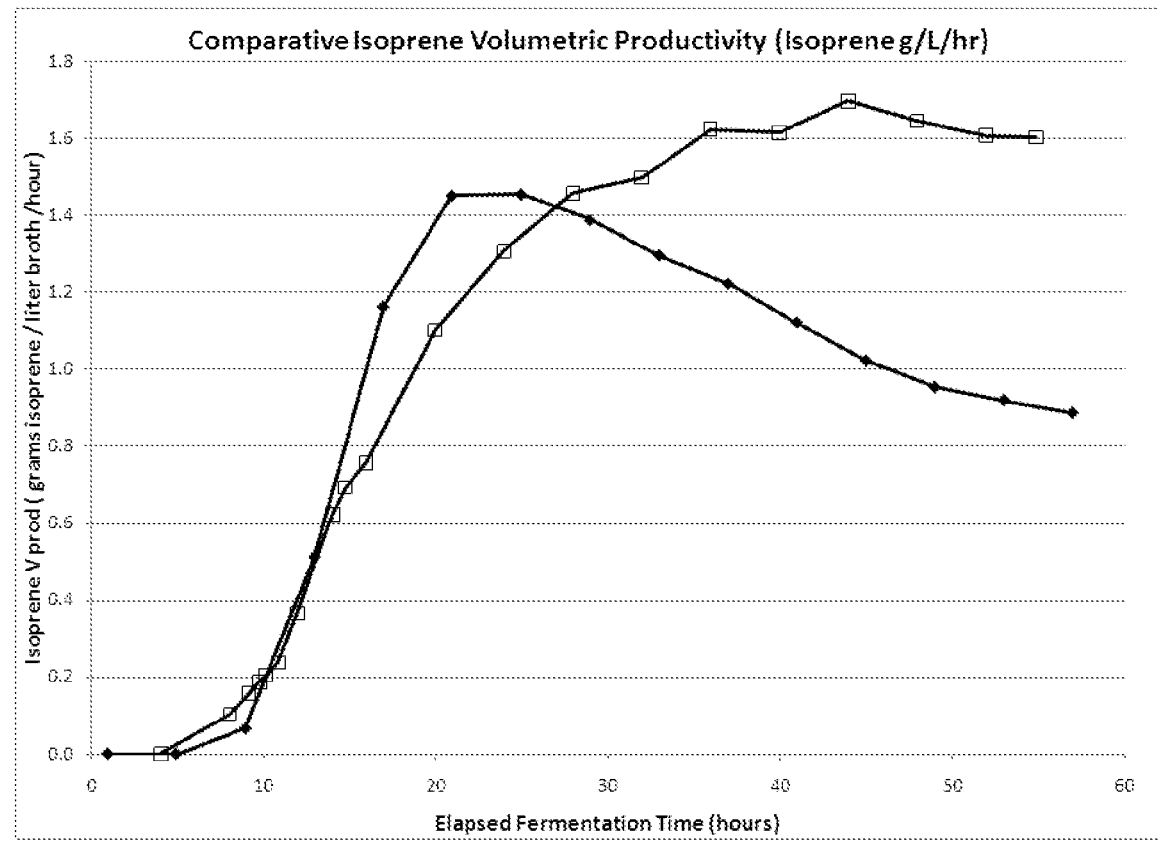
FIG. 17 depicts volumetric productivity of 1.2 gltA strain (open squares) compared to the parental strain (closed diamonds) in the 15-L fermentation over time. Strains were run under the same conditions. (20100278: strain CMP457 (open squares); GI1.2gltA20100131: strain MD09-317 (black diamonds) wt gltA).
Figure 18:
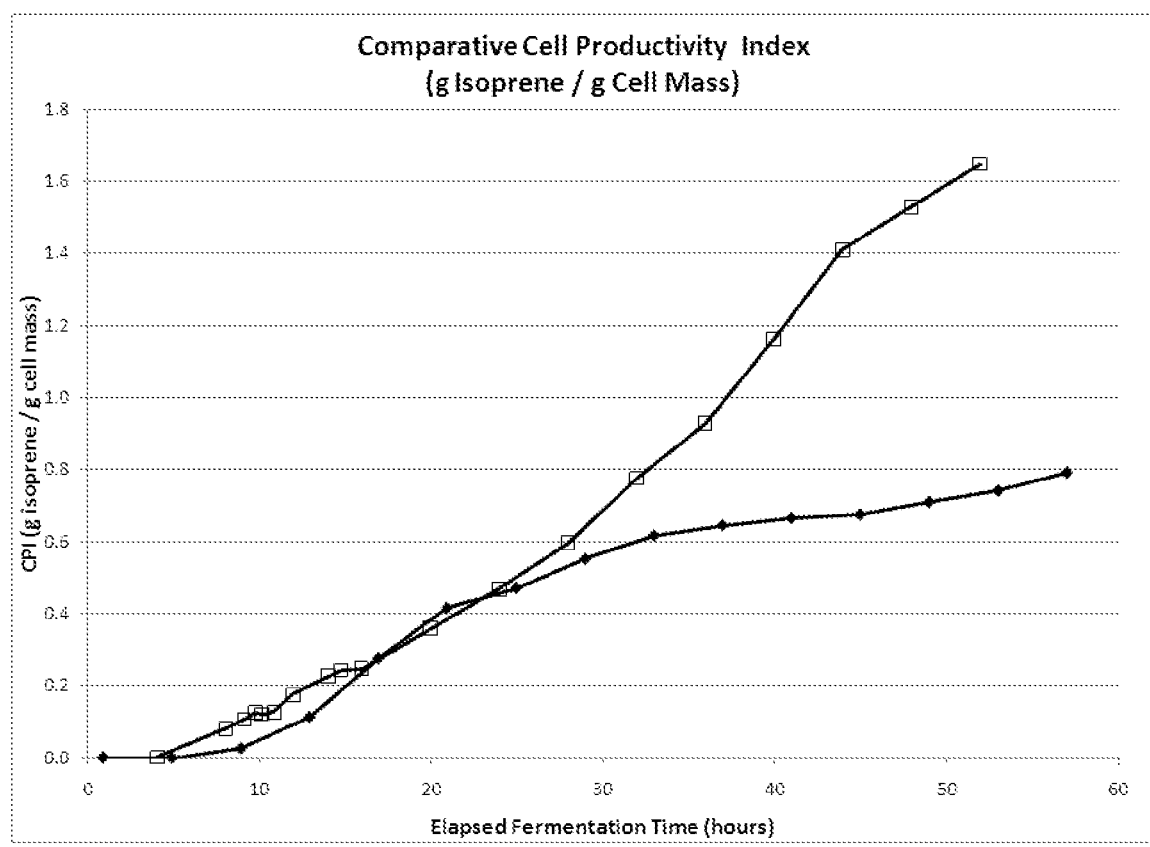
FIG. 18 depicts cell productivity index for isoprene of 1.2 gltA strain (open squares) compared parental strain (closed diamonds) in the 15-L fermentation over time. Strains were run under the same conditions. (20100278: strain CMP457 (open squares); GI1.2gltA20100131: strain MD09-317 (black diamonds) wt gltA). Cell Performance Index (CPI): g isoprene/Avg. gDCW=[HG Total/[OD*Ferm Wt/1.05)/2.7] where 1.05 is the assumed fermentation broth specific gravity (kg/L), and 2.7 has units of OD*L/gDCW.
Figure 19:
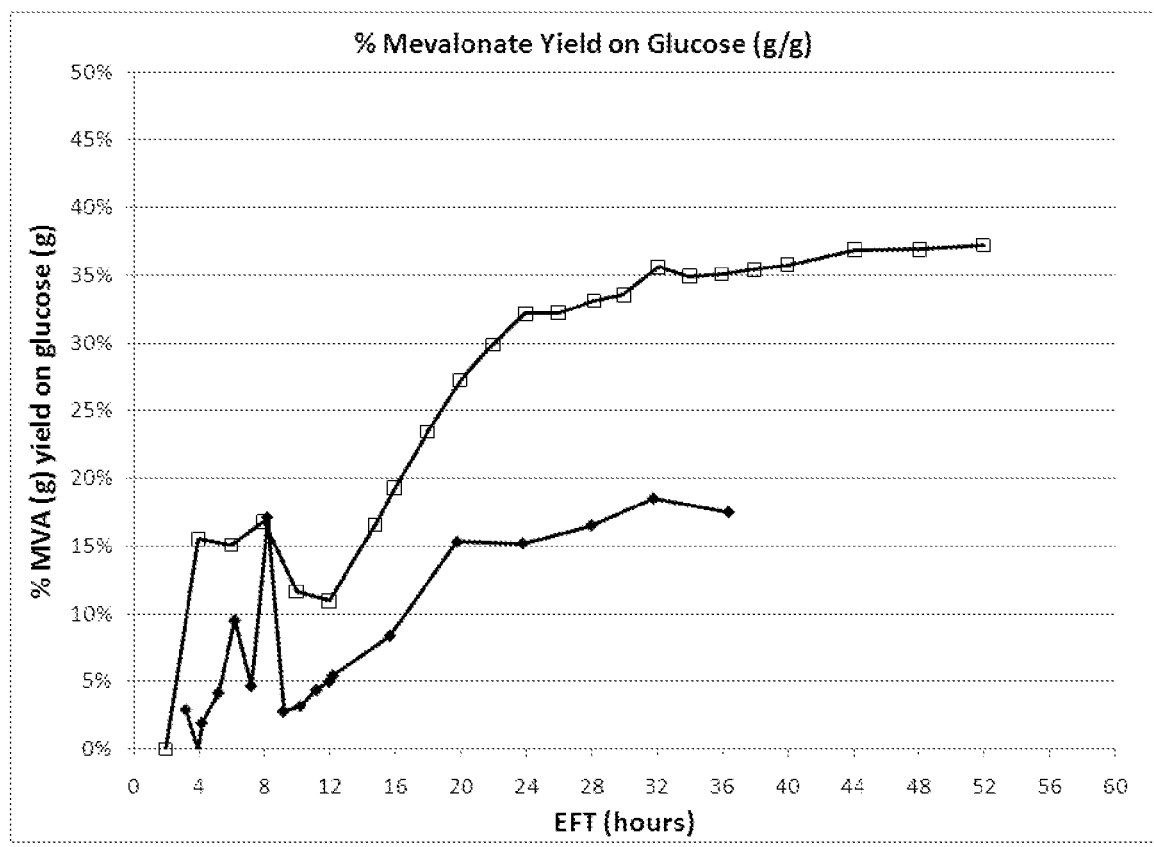
FIG. 19 depicts yield of mevalonate on glucose of 1.2 gltA strain (open squares) compared parental (closed diamonds) in the 15-L fermentation over time. Strains were run under the same conditions. (20100916: strain CMP678 (open squares); GI1.2gltA (20100154: strain MCM1002 (black diamonds) wt gltA). Overall yield was calculated using the following formula: % wt Yield on glucose=Mevalonate total(t)/[(Feed Wt(0)−Feed Wt(t)+50)*0.59)], where 0.59 is the weight fraction of glucose in the glucose feed solution and 50 is the grams of this feed batched into the fermentor at t=0.

The fermentation with the GI1.2 gltA promoter in front of gltA had higher a yield than its parental control (FIG. 15). Isoprene titer, volumetric productivity and cell productivity index were also higher in the GI1.2gltA strain. Results are summarized in Table 15 (below).

Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*H2O 40 g, MnSO4*H2O 30 g, NaCl 10 g, FeSO4*7H2O 1 g, CoCl2* 6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Feed Solution (Per Kilogram):

Glucose 0.590 kg, Di H2O 0.393 kg, K2HPO4 7.4 g, and 100% Foamblast882 8.9 g. All components were mixed together and autoclaved.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter. Addition strategy A (GI1.2gltA runs): Add 16.8 mls directly the tank media before sterilization, with no further addition. Addition strategy B: (wt gltA run) Add 6.895 mls per liter of glucose feed solution.

(ii) Methods

Fermentation was performed in a 15-L bioreactor with *E. coli* BL21 cells expressing the upper MVA pathway (pCLUpper) and containing a restored chromosomal pgl gene. Therefore, three mevalonate producing strains were compared.

MCM1002 (wt promoter in front of gltA, *E. faecalis* upper) (See Example 12)

CMP678 (GI1.2 promoter in front of gltA, *E. faecalis* upper) (See Table 3).

TABLE 15

Isoprene Productivity Metrics (GI1.2gltA vs wild type gltA)

| Strain description | EFT (hrs) | Titer (g/L) | Volumetric Productivity (g/L/hr) | Overall % Yield of MVA on glucose (g/g) | CPI (gMVA/gDCW) |
|---|---|---|---|---|---|
| CMP457 (GI1.2 promoter in front of gltA) | 52 | 113.0 | 1.60 | 10.7% | 1.65 |
| MD09-317 (wt promoter in front of gltA) | 53 | 77.6 | 0.92 | 8.6% | 0.79 |

Example 28: Mevalonate (MVA) Production from *E. coli* Expressing Genes from the Mevalonate Pathway and Grown in Fed-Batch Culture at the 15-L Scale (i) Materials Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal CMP680 (ackA-pta-, ldhA-host, GI1.2gltA, *E. faecalis* upper) (See Example 5)

This experiment was carried out to monitor mevalonate formation from glucose at the desired fermentation pH 7.0 and temperature 34° C. A frozen vial of the *E. coli* strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L.

The batched media had glucose batched in at 9.9 g/L. Induction was achieved by adding isopropyl-beta-D-1-thio-galactopyranoside (IPTG). A shot of IPTG was added to the tank to bring the concentration to 400 uM when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum mevalonate mass yield on glucose, at least 36 hrs elapsed fermentation time.

(iii) Conclusions

Figure 20:
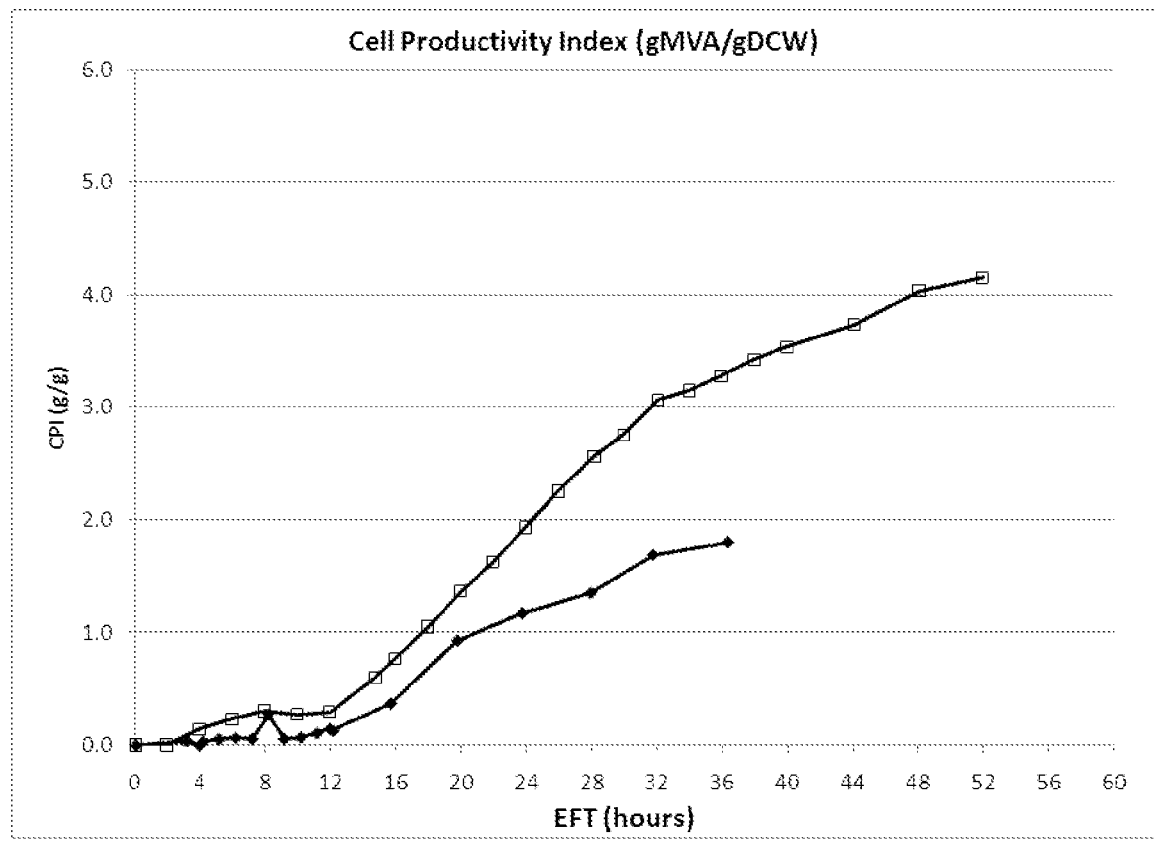
FIG. 20 depicts Cell Productivity Index (CPI) of mevalonate on glucose of 1.2 gltA strain (open squares) compared parental (closed diamonds) in the 15-L fermentation over time. The dry cell weight was not directly measured in these experiments, rather, an experimentally determine optical density to dry cell weight conversion factor was used. This OD to DCW factor was generated in a similar E. coli BL21 host in the same media formulation. Strains were run under the same conditions. (20100916: strain CMP678 (open squares); GI1.2gltA (20100154: strain MCM1002 (black diamonds) wt gltA).
Figure 21:
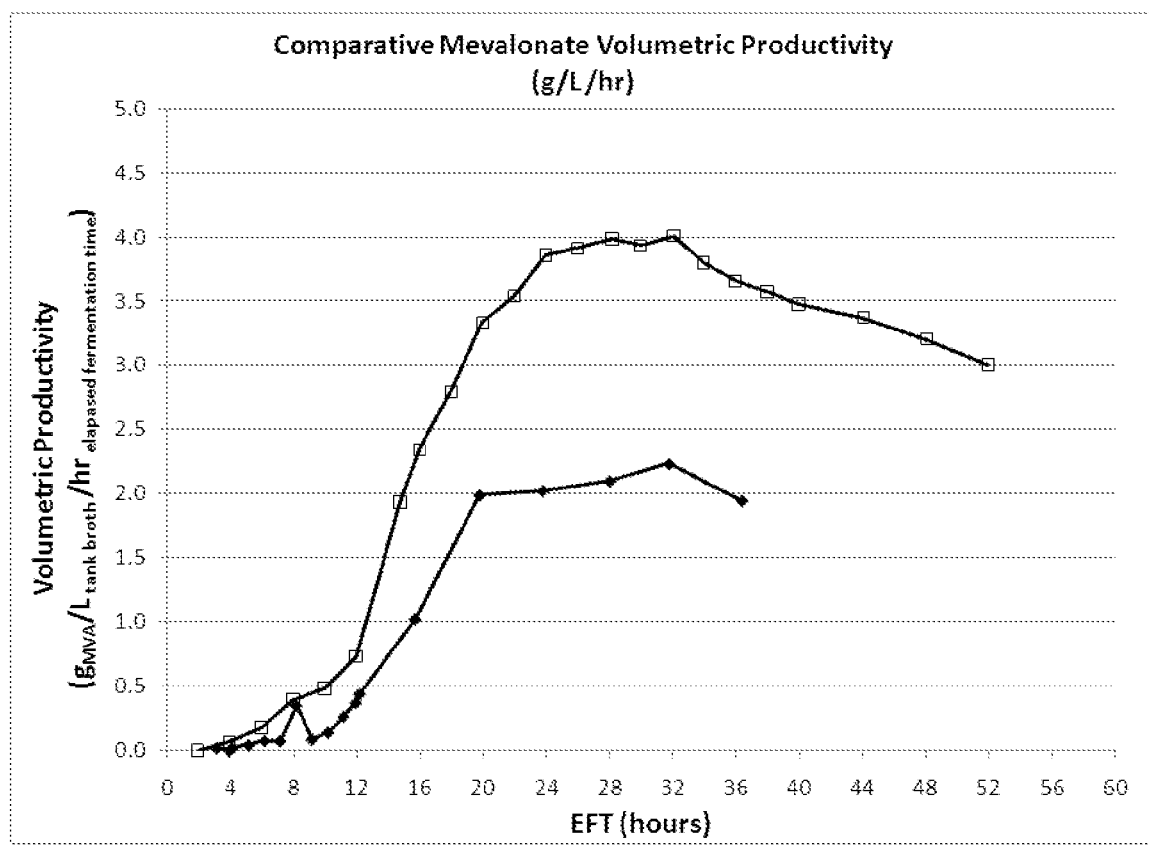
FIG. 21 depicts Volumetric Productivity of mevalonate 1.2 gltA strain (open squares) compared parental (closed diamonds) in the 15-L fermentation over time. Strains were run under the same conditions. (20100916: strain CMP678 (open squares); GI1.2gltA (20100154: strain MCM1002 (black diamonds) wt gltA).
Figure 22:
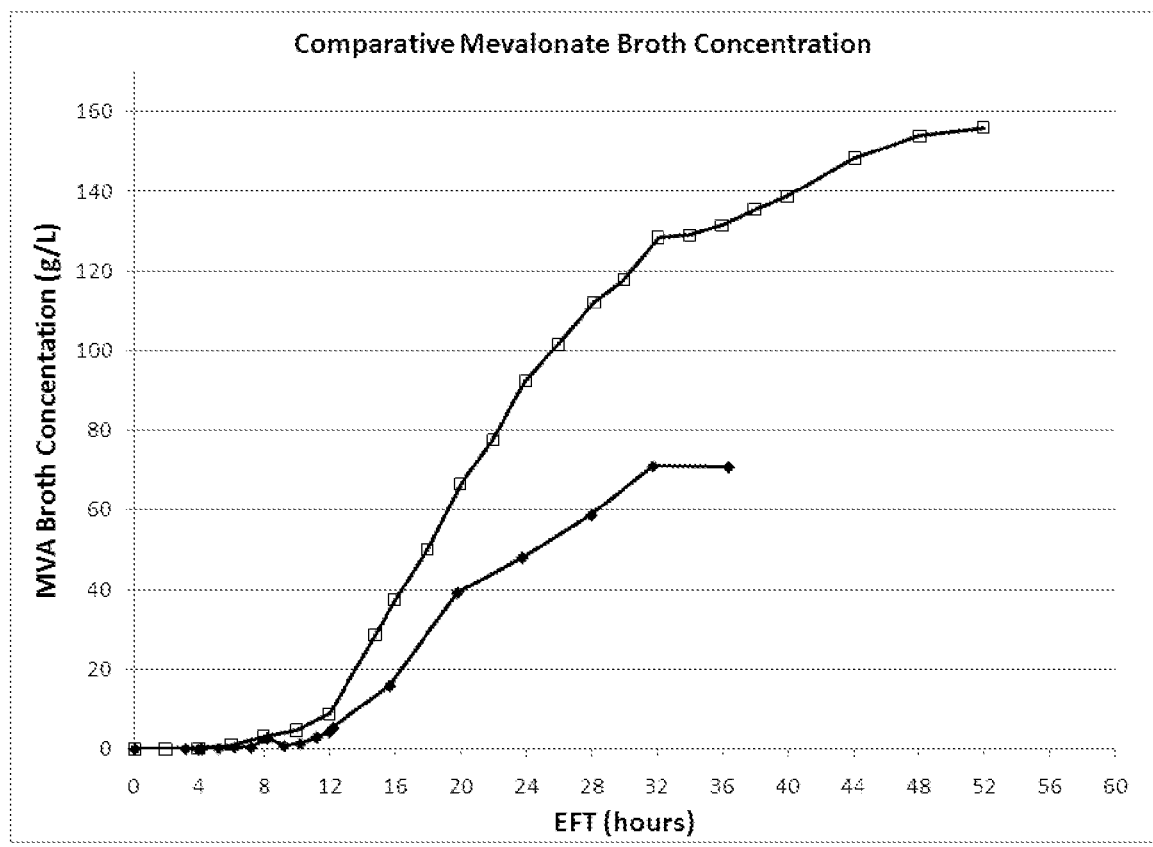
FIG. 22 depicts mevalonate broth titer in 1.2 gltA strain (open squares) compared parental (closed diamonds) in the 15-L fermentation over time. Strains were run under the same conditions. (20100916: strain CMP678 (open squares); GI1.2gltA (20100154: strain MCM1002 (black diamonds) wt gltA).

The fermentation with the GI1.2 gltA knockdown (CMP678) had higher a mevalonate yield on glucose than its parental control (MCM1002). Additionally, a higher cell productivity index, volumetric productivity and mevalonate titer were noted (FIGS. 20, 21 and 24 respectively. Summarized in Table 16).

TABLE 16

MVA Productivity Metrics (GI1.2gltA vs wild type gltA)

| Strain description | EFT (hrs) | Titer (g/L) | Volumetric Productivity (g/L/hr) | Overall % Yield of MVA on glucose (g/g) | CPI (gMVA/gDCW) |
|---|---|---|---|---|---|
| MCM1002 (wt gltA, *E. faecalis* upper) | 36.4 | 70.8 | 1.95 | 17.5% | 1.80 |
| CMP678 (GI1.2gltA, *E. faecalis* upper) | 36.0 | 137.1 | 3.81 | 35.1% | 3.28 |

Figure 23:
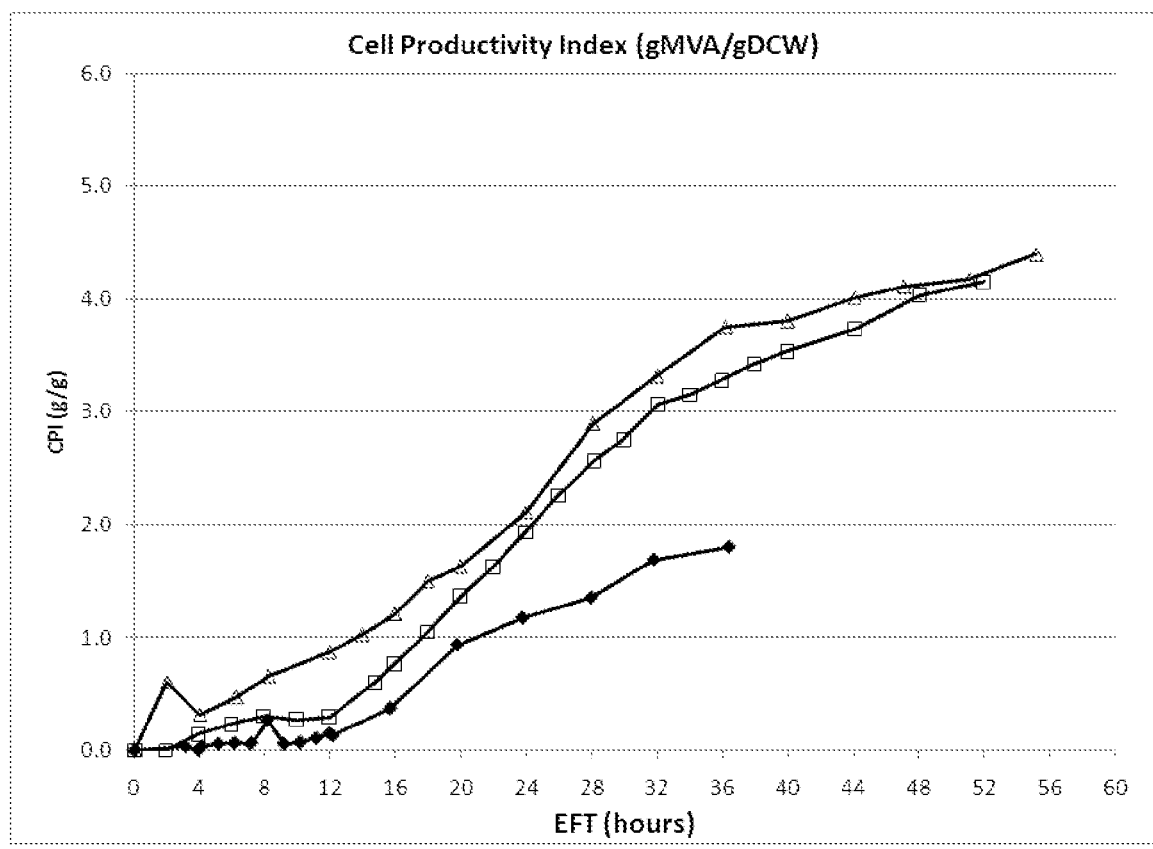
FIG. 23 depicts Cell Productivity Index (CPI) of mevalonate on glucose of 1.2 gltA strain (open squares) compared parental (closed diamonds) in the 15-L fermentation over time. The dry cell weight was not directly measured in these experiments, rather, an experimentally determine optical density to dry cell weight conversion factor was used. This OD to DCW factor was generated in a similar E. coli BL21 host in the same media formulation. Strains in the chart below were run under the same conditions. (20100967: strain CMP680 (open triangles) ackA, pta-, ldh-GI1.2gltA; 20100916: strain CMP678 (open squares) GI1.2gltA; 20100154: strain MCM1002 (black diamonds) wt gltA).
Figure 24:
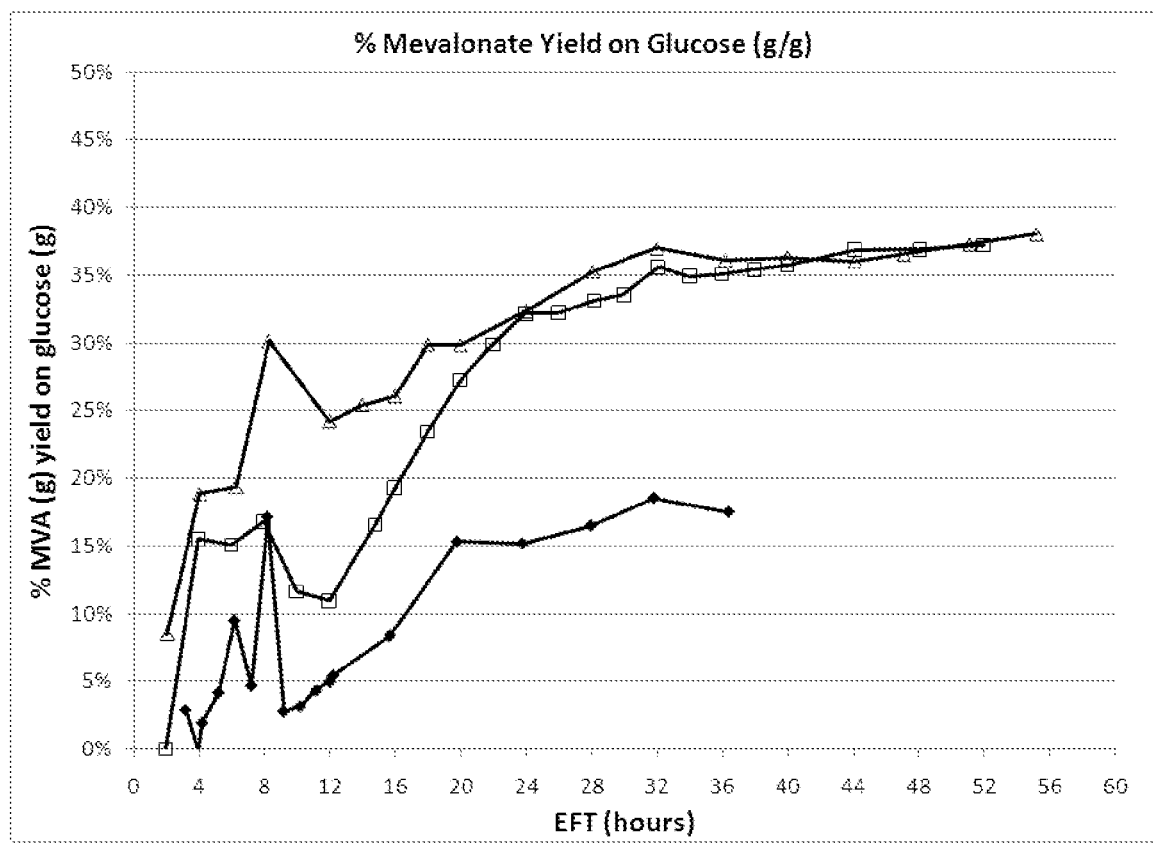
FIG. 24 depicts yield of mevalonate on glucose of the "triple" host (CMP680, open triangles) is better at 36 hrs compared to the 1.2 gltA strain (CMP678, open squares) and both are much improved over the parental (MCM1002, closed diamonds) in the 15-L fermentation. The CMP680 strain is notable for its high initial yield. Strains were run under the same conditions. (20100967: strain CMP680 (open triangles) ackA, pta-, ldh-GI1.2gltA; 20100916: strain CMP678 (open squares) GI1.2gltA; 20100154: strain MCM1002 (black diamonds) wt gltA).
Figure 25:
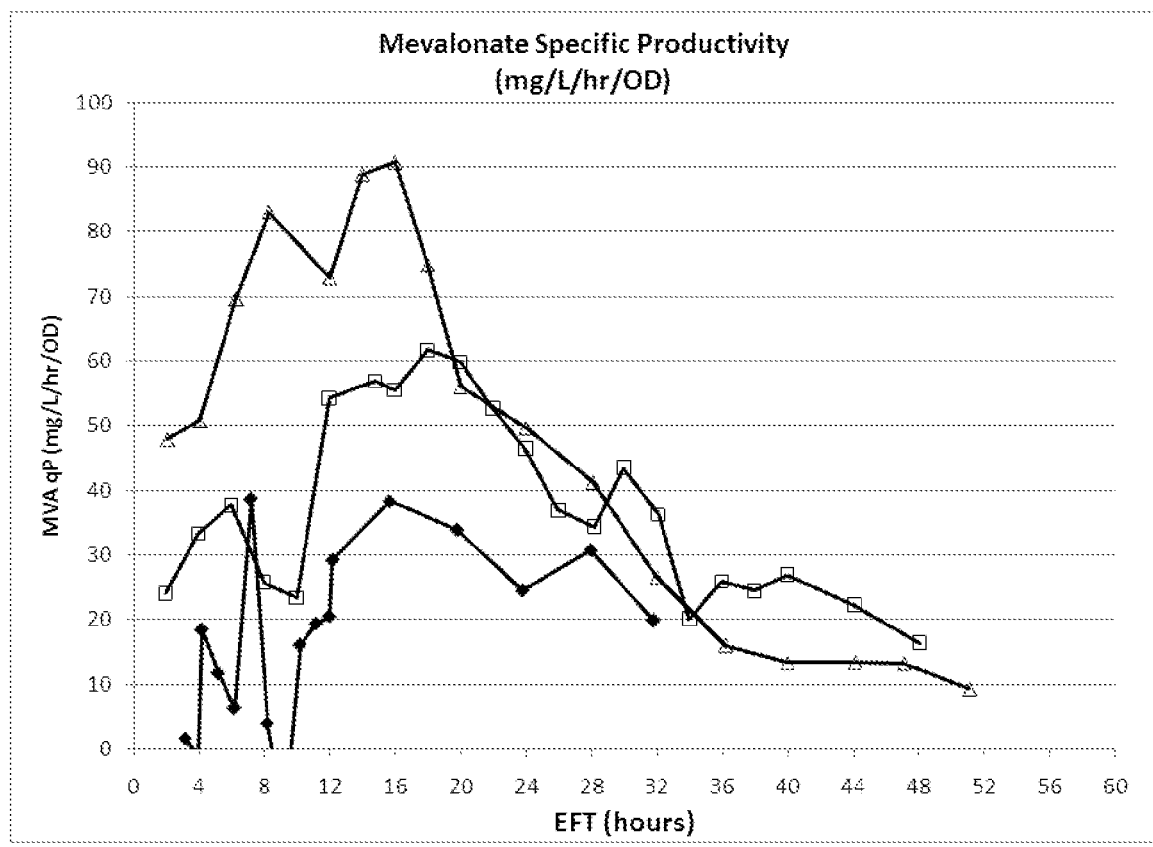
FIG. 25 depicts Specific productivity of mevalonate reported in terms of milligrams mevalonate per liter of fermentor broth per hour per unit of optical density (absorbance at 550 nm). The "triple" host (CMP680, open triangles) shows a much higher specific productivity from 0 to 20 hrs EFT compared to the 1.2 gltA strain (CMP678, open squares) and both are improved over the parental (MCM1002, closed diamonds) in the 15-L fermentation. Strains were run under the same conditions. (20100967: strain CMP680 (open triangles) ackA, pta-, ldh-GI1.2gltA; 20100916: strain CMP678 (open squares) GI1.2gltA; 20100154: strain MCM1002 (black diamonds) wt gltA).
Figure 26:
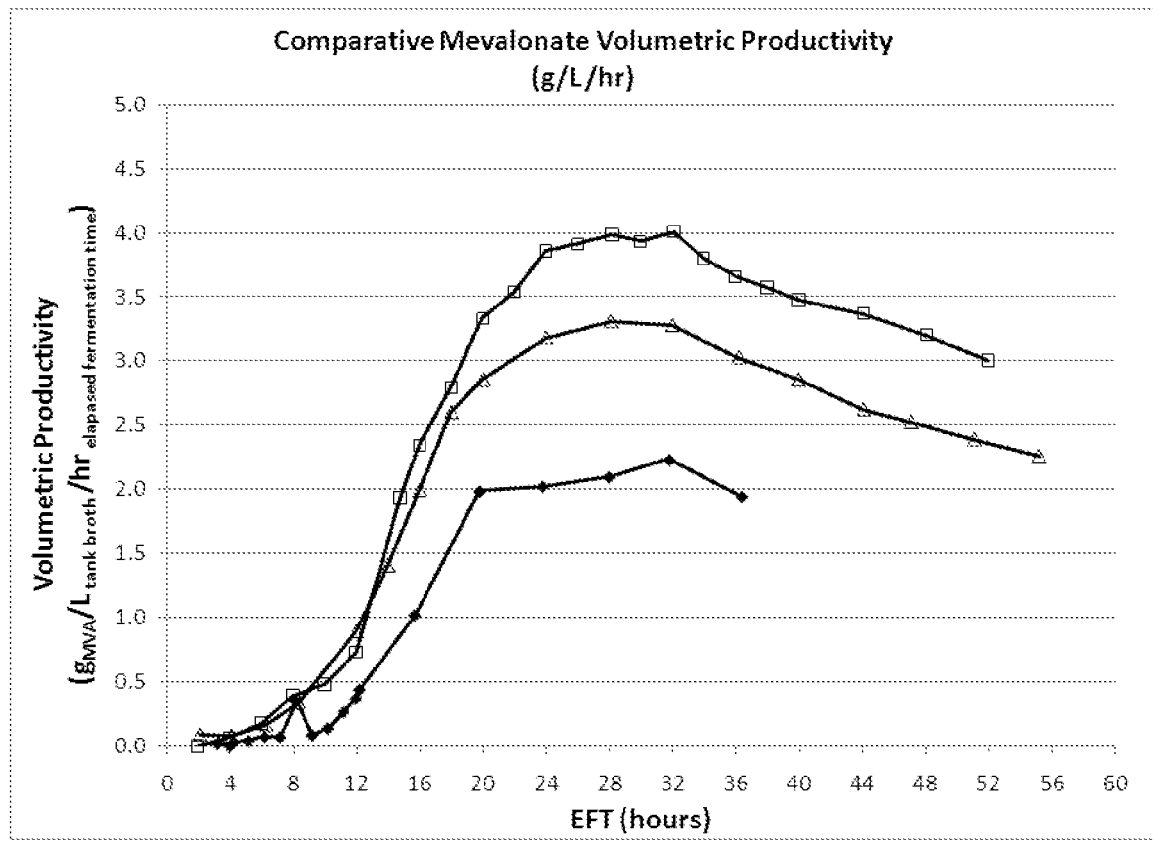
FIG. 26 depicts Volumetric productivity of mevalonate reported in terms of grams mevalonate per liter of fermentor broth per hour of elapsed fermentation time. The "triple" host (CMP680, open triangles) shows a lower volumetric productivity compared to the 1.2 gltA strain (CMP678, open squares) but both are improved over the parental (MCM1002, closed diamonds) in the 15-L fermentation. Strains were run under the same conditions. (20100967: strain CMP680 (open triangles) ackA, pta-, ldh-GI1.2gltA; 20100916: strain CMP678 (open squares) GI1.2gltA; 20100154: strain MCM1002 (black diamonds) wt gltA).
Figure 27:
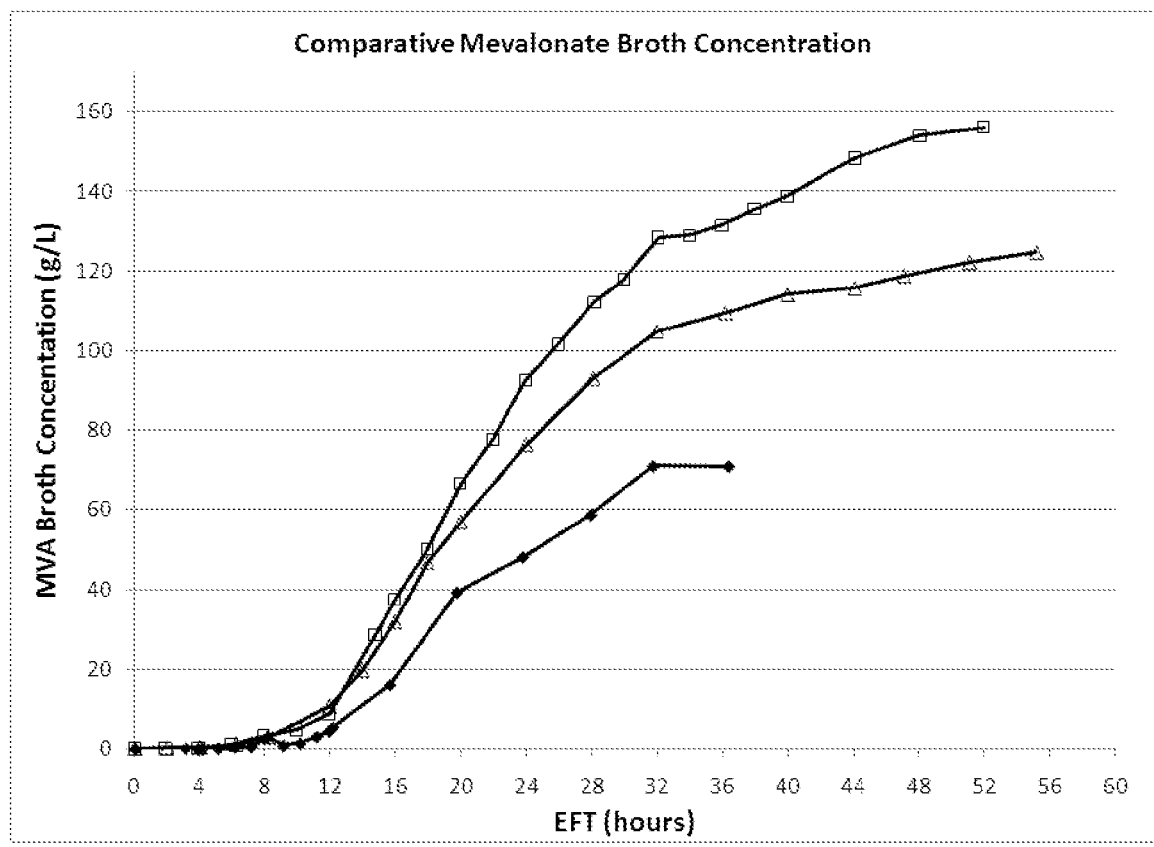
FIG. 27 depicts Mevalonate broth titer (or mevalonate broth concentration) was higher in the 1.2 gltA strain (CMP678, open squares) compared to the "triple" host (CMP680, open triangles). Both were higher than the parental control (MCM1002, closed diamonds) in the 15-L fermentation over time. Strains were run under the same conditions. (20100967: strain CMP680 (open triangles) ackA, pta-, ldh-GI1.2gltA; 20100916: strain CMP678 (open squares) GI1.2gltA; 20100154: strain MCM1002 (black diamonds) wt gltA).

The fermentation with the "triple" host (CMP680) had a higher cell productivity index and a higher overall mevalonate mass yield on glucose than the CMP678 strain (FIG. 23 and FIG. 24, respectively). Very early in the CMP680 fermentation, the mevalonate mass yield on glucose, and the specific productivity of mevalonate (g/L/hr/OD) was much higher than that of CMP678 or MCM1002. (FIG. 24 and FIG. 25, respectively). In the CMP680 fermentation, the mevalonate volumetric productivity and mevalonate broth concentration were down versus CMP678 (FIG. 26 and FIG. 27, respectively). Results summarized in Table 17. The CMP680 strain (or, the host with triple mutation or triple host) is useful for determining maximum mevalonate mass yield on glucose and maximum specific productivity in 15 L fermentation experiments.

TABLE 17

Mevalonate (MVA) Productivity Metrics ("Triple" host vs GI1.2gltA vs wild type gltA)

| Strain description | EFT (hrs) | Titer (g/L) | Volumetric Productivity (g/L/hr) | Overall % Yield of MVA on glucose (g/g) | CPI (gMVA/gDCW) |
|---|---|---|---|---|---|
| MCM1002 (wt gltA, *E. faecalis* upper) | 36.4 | 70.8 | 1.95 | 17.5% | 1.80 |
| CMP678 (GI1.2gltA, *E. faecalis* upper) | 36.0 | 137.1 | 3.81 | 35.1% | 3.28 |
| CMP680 (ackA-, pta-, ldh-host, GI1.2gltA, *E. faecalis* upper) | 36.2 | 109.5 | 3.03 | 36.1% | 3.75 |

36 hr is sufficient to get a read on mevalonate mass yield, but the runs can be extended to increase the mevalonate broth concentration. A table shows the peak titers observed in these experiments. Results observed at the peak titers are summarized in Table 18, below.

TABLE 18

Mevalonate (MVA) Productivity Metrics at peak titer ("Triple" host vs GI1.2gltA vs wild type gltA)

| | EFT at peak titer (hrs) | Peak Titer (g/L) | Volumetric Productivity at peak titer (g/L/hr) | Overall % Yield of MVA on glucose (g/g) at peak titer | CPI at peak titer (gMVA/gDCW) |
|---|---|---|---|---|---|
| MCM1002 (wt gltA, E. faecalis upper) | 36.4 | 70.8 | 1.95 | 17.5% | 1.80 |
| CMP678 (GI1.2gltA, E. faecalis upper) | 52.0 | 156.0 | 3.00 | 37.2% | 4.15 |
| CMP680 (ackA-, pta-, ldh-host, GI1.2gltA, E. faecalis upper) | 55.2 | 124.6 | 2.26 | 38.0% | 4.39 |

(iv) Broth Analysis

The mevalonate concentration in the fermentor broth was determined in broth samples taken at 4 hour intervals by an HPLC analysis. Mevalonate broth concentration in samples was determined by comparison of the refractive index response versus a previously generated calibration curve obtained by running a prepared solution of high purity mevalonate (Sigma Aldrich).

HPLC Information:

System: Waters Alliance 2695; Column: BioRad-Aminex HPX-87H Ion Exclusion Column 300 mm×7.8 mm Catalog #125-0140; Column Temperature: 50 C; Guard column: BioRad-Microguard Cation H refill 30 mm×4.6 mm Catalog #125-0129; Running buffer: 0.01N $H_2SO_4$; Running buffer flow rate: 0.6 ml/min; Approximate running pressure: ~1100-1200 psi; Injection volume: 20 microliters; Detector: Refractive Index (Knauer K-2301); Runtime: 26 minutes.

Example 29: Production of *E. coli* Strains Expressing the Mevalonate Kinase Gene from *Methanococcoides Burtonii* DSM6242

This example details the construction of bacterial strains comprising mevalonate kinase from the psychrotolerant methanogen *M. burtonii* for the production of isoprenoid, isoprenoid precursors, and isoprene through the heterologous mevalonate pathway in *E. coli*.

I. Gene Identification and Pathway Construction

Gene Identification/Selection:

A primary sequence homology search using the *M. mazei* mevalonate kinase gene product as the query was performed via the BLASTp program located at the NCBI website (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs," *Nucleic Acids Res.* 25:3389-3402). Sequences of interest were selected from the search results. *M. burtonii* mevalonate kinase has 61% sequence identity when compared to the mevalonate kinase from *M. mazei*.

Plasmids for the Expression of MVK:

Plasmids for the expression of N-terminally HIS-tagged mMVK and bMVK were synthesized by GeneOracle. Tagged MVK genes were cloned into pET24b under the control of a T7 promoter. Plasmids were introduced into Invitrogen OneShot BL21(DE3) cells (#C6000-03) following the manufacturer's protocol and transformants selected on LA kan50 plates at 37 C overnight.

Lower Isoprenoid Pathways Expressing mMVK and bMVK at Different Levels:

An existing construct (PL.2-mKKDyI, US2011/0159557) expressing the lower MVA pathway (MVK, PMK, MVD, IDI) was modified to express mMVK at different levels and to express bMVK in place of mMVK. The new construct consists of an FRT-flanked chloramphenicol resistance marker, the PL.2 promoter, a bi-cistronic translation initiation sequence, one of two MVK genes, and the PMK, MVD and IDI genes. A PCR product was constructed in two parts to replace the existing promoter, translation initiation sequence and MVK gene with an excisable cmpR marker, promoter, translation initiation sequence and MVK gene. This PCR product was introduced onto the chromosome by double crossover followed by selection of cmpR cells.

The bi-cistronic translation initiation sequence is used to increase expression of MVK by initiating translation of the mRNA independently of the MVK sequence. See Schoner et al., Translation of a synthetic b-cistron mRNA in *Escherichia coli* (*Proc. Natl. Acad. Sci. USA*, Vol. 83, pp. 8506-8510, November 1986). Translation of the MVK ORF is controlled by modulating the strength of the upstream RBS in the bi-cistronic construct. RBSs of varied strength were designed using the RBS Calculator (Salis, et al., *Nat Biotechnol.* 2009 October; 27(10): 946-950.) RBS Calculator optimization software was used with RNA thermodynamic parameters calculated using the Vienna RNA Package v.1.8.4 (see, The University of Vienna website www.tbi.univie.ac.at/~ivo/RNA), Andreas R. Gruber, Ronny Lorenz, Stephan H. Bernhart, Richard Neubuck, and Ivo L. Hofacker (NAR, 2008) and the ViennaRNA module for the RBS Calculator. RBSs were calculated on a Linux server running Python v. 2.4.3. RBSs were designed using the 5' UTR upstream of the RBS (up to 50 nt) and 50 nt of ORF sequence. Multiple RBSs of a given target strength were calculated; one or more was synthesized and tested.

The GeneBridges chloramphenicol template (#A105) was used as template to amplify the upstream half of the construct using primers MCM545 and MCM770. 140 µL ddH$_2$O, 4 µL plasmid DNA (~100 ng/µL), 5 µL 10 µM each primer, 2 µL dNTPs, 40 uL buffer and 4 µL polymerase were combined and aliquoted to 4×50 µL. These reactions were cycled according to manufacturer's protocol (Agilent Herculase II Fusion kit, #600677) in a PCR program consisting of the following cycle: 95° C. 2:00, (95° C. 0:20, 55° C. 0:20, 72° C. 1:15)×30, 72° C. 3:00, 4° C. until cold. Reactions were purified on Qiagen PCR cleanup columns (#28106), eluted in 50 µL and pooled The downstream half of the construct was amplified using the MVK gene as template and primers indicated in Table 22, below. 35 µL ddH$_2$0, 1 µL plasmid DNA (~100 ng/µL), 1.25 µL 10 µM each primer, 0.5 µL dNTPs, 10 uL buffer and 1 µL polymerase were combined and cycled as follows: 95° C. 2:00, (95° C. 0:20, 55° C. 0:20, 72° C. 0:30 (mMVK) or 72° C. 1:00 (bMVK))×30, 72° C. 3:00, 4° C. until cold. Reactions were purified on Qiagen PCR cleanup columns and eluted in 50 µL.

5 µL of upstream and downstream fragments were mixed with 10 µL buffer, 0.5 µL dNTPs and 27 µL ddH$_2$O and PCR cycled: 95° C. 2:00, (95° C. 0:20, 55° C. 0:20, 72° C. 2:00)×5, rt. 1.25 µL of primer MCM120 and either primer MCM162 (mMVK) or MCM790 (bMVK) were added and 25 additional cycles were run. The PCR reaction was brought to 4° C. before purification on Qiagen PCR column and elution in 30 µL EB.

Purified, fused PCR products were electroporated into MCM1332 (for mMVK) or MCM1859 cells (for bMVK). MCM1332 is a subculture of CMP522 (CMP451 (IDN 31588) carrying pRed/ET-carb, GeneBridges) and MCM1859 is a subculture of CMP1103 (CMP1075 (IDN 31308) carrying pRed/ET-carb, GeneBridges). Cultures were grown overnight in LB carb50 at 30° C. 100 µL culture was used to inoculate 5 mL of LB carb50 and cultures were grown at 30° C. until visibly turbid (~2 hr). 150 µL 1M arabinose was added and cultures grown at 37° C. for ~2 hrs. Cells were pelleted, washed three times in sterile, iced ddH$_2$O, and resuspended at 1/10th culture volume in sterile, iced ddH$_2$O. 100 µL cells were mixed with 3 µL PCR product and electroporated in a 2 mm electroporation cuvette, at 25 µFD, 200 ohms, 2.5 kV, and immediately quenched with 500 µL LB. Transformed cells were recovered shaking at 37° C. for ~3 hrs and selected overnight on LB cmp5 plates at 37° C.

Multiple cmpR colonies were streaked to single colonies and screened for the expected integration by PCR and sequencing. Colony purified strains were grown in LA cmp5, brought to 33% glycerol and stored at −80° C.

II. Hosts for Producing Isoprene Using mMVK and bMVK at Different Levels

The modified lower MVA pathways were transduced into MCM2029 (a subculture of CMP1133, IDN 31308) to create isoprene production hosts.

P1 lysates of strains MCM1742, 1753, 1745, 1747 and 1861 (Transduced Pathways) were prepared as follows. 100 µL of overnight culture in LB cmp5 was diluted into 10 mL LB+5 mM CaCl$_2$, 0.2% glucose, cmp5 and shaken at 250 rpm, 37° C. for 30 min. 100 µL of P1 lysate prepared on MG1655 cells was added and culture shaken for at least 3 hours until the media was clear with precipitated lysed cell material. Lysates were vortexed with 100 µL chloroform, spun 5 min at 3000 rpm, and supernatant stored over 100 µL chloroform at 4° C.

Overnight culture of MCM2029 (Recipient for Transduction) was washed into ½ volume sterile 10 mM MgSO$_4$, 5 mM CaCl$_2$. 200 µL cell suspension was mixed with 100 µL lysate and incubated, still, at 30° C. for 30 min. 150 µL 1M NaCitrate and 500 µL LB were added and the reaction recovered, with shaking, at 37° C. for 1-2 hours. Dilutions were plated on LA cmp5 and incubated at 37° C. overnight. Negative controls (no cells or no transducing lysate) were performed in parallel. Chloramphenicol-resistant colonies were picked, restreaked, and single colonies tested by PCR for the presence of the new pathway. The resulting strains, Hosts with Marker, were grown to mid-log in LA and stored at −80° C. in 33% glycerol.

The chloramphenicol resistance marker in the Hosts with Marker was removed using the Flp recombinase expressed from plasmid pCP20 (GeneBridges). Cells were grown to midlog in LB cmp5 at 37° C., electroporated with 1 µL pCP20 (~100 ng/µ1), recovered in LA at 30° C. for 1-3 hrs, and transformants selected on LA carb50 at 30 C overnight or room temperature for 3 days. A single colony was picked, grown at in LA carb50 30 C until visibly turbid, and then shifted to 37° C. for several hours. This culture was streaked out and grown at 37° C. overnight. Single colonies were picked and patched to LA, LA carb50 and LA cmp5. A clone sensitive to carb and cmp was selected for each parent strain. The resulting Isoprene Production Hosts (Table 20) were grown to midlog in LB and stored at −80° C. in 33% glycerol.

TABLE 19

E. coli strains expressing alternative MVK genes

| Strain with modified pathway | MVK | 5' RBS Target Strength | PCR Template | Upstream Up Primer | Upstream Down Primer | Downstream Up Primer | Downstream Down Primer |
|---|---|---|---|---|---|---|---|
| MCM1742 | mazei | 1000 | pMCM376 (12/818,090) | MCM545 | MCM770 | MCM773 | MCM162 |
| MCM1743 | mazei | 100000 | pMCM376 | MCM545 | MCM770 | MCM778 | MCM162 |
| MCM1745 | mazei | 1000000 | pMCM376 | MCM545 | MCM770 | MCM781 | MCM162 |
| MCM1747 | mazei | 10000 | pMCM376 | MCM545 | MCM770 | MCM775 | MCM162 |
| MCM1861 | burtonii | 10000 | pMCM1666 | MCM545 | MCM770 | MCM789 | MCM790 |

TABLE 20

Isoprene production hosts

| Isoprene Production Hosts | Hosts with Marker | Recipient for Transduction | Transduced Pathways |
|---|---|---|---|
| MCM2065 | MCM2050 | MCM2029 | MCM1861 |
| MCM2066 | MCM2053 | MCM2029 | MCM1742 |
| MCM2067 | MCM2054 | MCM2029 | MCM1743 |
| MCM2069 | MCM2057 | MCM2029 | MCM1745 |
| MCM2070 | MCM2059 | MCM2029 | MCM1747 |

III. Plasmids for Expression of Isoprene Synthase without mMVK

Plasmid pDW166 (Trc P. alba IspS variants MEA (Carb50)) was modified to express bMVK rather than mMVK. The bMVK gene was amplified from pMCM1666 with primers MCM810 and MCM811 and the pDW166 vector, minus the mMVK gene, was amplified with primers MCM808 and MCM809 (Herculase II Fusion kit, 35 µL ddH$_2$O, 1 µL template (~100 ng/µL), 0.5 µL dNTPs, 1.25 µL each primer at 10 µM, 1 µL polymerase). Reactions were cycled as follows: 95° C. 2:00, 30×(95° C. 0:20, 55° C. 0:20, 72° C. 0:45 (insert) or 3:00 (vector)), 72° C. 3:00, 4° C. until cold. PCR products were purified on a Qiagen PCR column and eluted in 30 µL EB. The insert was cloned into the vector using the GeneArt Seamless Cloning and Assembly kit (Invitrogen #A13288) in a reaction consisting of 2 µL each PCR product, 4 µL buffer, 10 µL ddH$_2$O and 2 µL enzyme. Reaction was incubated at room temperature for 30 min then 4 µL was transformed into Invitrogen TOP10 chemically competent cells. Following recovery in 250 µL LB at 37° C. for 1 hr, transformants were selected on LA carb50 plates at 37° C. overnight. Miniprepped plasmid was sequenced.

Plasmid pDW166 (pTrcAlba(MEA, IspS variants)-mMVK was modified to delete the majority of the mMVK gene. Plasmid was amplified in a PCR reaction using primers MCM814 and 815 (Herculase II Fusion kit, 35 µL ddH$_2$O, 1 µL template (~100 ng/µL), 0.5 µL dNTPs, 1.25 µL each primer at 10 µM, 1 µL polymerase). Reactions were cycled as follows: 95° C. 2:00, 30×(95° C. 0:20, 55° C. 0:20, 72° C. 3:30 (vector)), 72° C. 3:00, 4° C. until cold. PCR product was desalted on a Millipore VSWP02500 disk floated on ~10 mL ddH2) for ~15 minutes and then 5 µL was electroporated into MCM2065 cells. Following recovery in 500 µL LB at 37° C. for 1 hr, transformants were selected on LA carb50 plates at 37° C. overnight. Miniprepped DNA was sequenced.

IV. Strains for the Production of Isoprene Via mMVK and bMVK at Different Levels Host strains (Table 20) were grown in 5 mL LB at 37° C., 250 rpm to midlog. Iced culture was washed in sterile, iced ddH$_2$O three times and resuspended in $\frac{1}{10}^{th}$ culture volume. 100 µL cell suspension was mixed with 1 µL plasmid DNA (~100 ng/uL) in eppendorf tube. All strains were transformed with pMCM2095. MCM2065 was also transformed with 1 µL each pMCM2020 and pMCM1225 (IDN 31552). Reactions were moved to a 2 mm electroporation cuvette, electroporated at 25 uFD, 200 ohms, 2.5 kV, and immediately quenched with 500 µL LB. Reactions were recovered shaking at 37° C. for at least one hour and transformants selected overnight at 37° C. on LA plates with carb50 (and also spec50 in the case of MCM2065 cotransformed with pMCM2020 and pMCM1225). A colony for each transformation was grown to midlog in LB with antibiotics, brought to 33% glycerol and stored at −80° C. (Host with IspS). Strain MCM2131 was stored in the same manner. The Host with IspS strains were grown in LB carb50 and electroporated with pMCM1225, with transformants selected on LA carb50 spec50. Again, single colonies were grown in LB carb50 spec50, brought to 33% glycerol, and stored at −80° C. (Production Strain, Table 21).

TABLE 21

Production strains

| Production Strain | Upper Pathway Plasmid | Host with IspS | IspS Plasmid | Host |
|---|---|---|---|---|
| MCM2125 | pMCM1225 | MCM2099 | pMCM2095 | MCM2065 |
| MCM2126 | pMCM1225 | MCM2100 | pMCM2095 | MCM2066 |
| MCM2127 | pMCM1225 | MCM2101 | pMCM2095 | MCM2067 |
| MCM2129 | pMCM1225 | MCM2103 | pMCM2095 | MCM2069 |
| MCM2130 | pMCM1225 | MCM2104 | pMCM2095 | MCM2070 |
| MCM2131 | pMCM1225 | N/A | pMCM2020 | MCM2065 |

TABLE 22

Primers used for production of host strains

| | | |
|---|---|---|
| MCM162 | TTAATCTACTTTCAGACCTTGC (SEQ ID NO: 82) | |
| MCM545 | aaagtagccgaagatgacggtttgtcacatggagttggcaggatgtttgattaaaagcAATTAACCCTCACTAAAGGGCGG (SEQ ID NO: 83) | |
| MCM770 | TCCTGCTGATGTGCTCAGTATCACCGCCAGTGGTATTTAAGTCAACACCGCCAGAGATAATTTATCACCGCAGATGGTTATCTTAATACGACTCACTATAGGGCTCG (SEQ ID NO: 84) | |
| MCM773 | ggcggtgatactgagcacatcagcaggacgcactgcTCTAAGGATTAAAGAGGAGAAGATTTCCTGatgtatcgatttaaataaggaggaataacatatggtatcctgttctgcgccg (SEQ ID NO: 85) | |
| MCM775 | ggcggtgatactgagcacatcagcaggacgcactgcTCCTAGGGGCGATTAGGGGACCTACTACatgtatcgatttaaataaggaggaataacatatggtatcctgttctgcgccg (SEQ ID NO: 86) | |
| MCM778 | ggcggtgatactgagcacatcagcaggacgcactgcTCTAGAGCGCACTAAGGAGGCAACTGGatgtatcgatttaaataaggaggaataacatatggtatcctgttctgcgccg (SEQ ID NO: 87) | |

TABLE 22-continued

Primers used for production of host strains

| | |
|---|---|
| MCM781 | ggcggtgatactgagcacatcagcaggacgcactgcTGCAGCGAGGAGGTAAGGGatgtatcgattta aataaggaggaataacatatggtatcctgttctgcgccg (SEQ ID NO: 88) |
| MCM789 | ggcggtgatactgagcacatcagcaggacgcactgcTCCTAGGGGCGATTAGGGGACCTACT ACatgtatcgatttaaataaggaggaataacatATGATAACGTGCTCTGCGCC (SEQ ID NO: 89) |
| MCM790 | GGCTCTCAACTCTGACATGTTTTTTTCCTCCTTAAGGGTGCAGGCCTATCG CAAATTAGCttactgacattctacgcgaaca (SEQ ID NO: 90) |
| MCM810 | GTTTAAACTTTAACTAGACTTTACTGACATTCTACGCGAACACCG (SEQ ID NO: 91) |
| MCM811 | cataaaggaggtaaaaaaacATGATAACGTGCTCTGCGCCG (SEQ ID NO: 92) |
| MCM814 | gggtaagattagtctagttaaagtttaaac (SEQ ID NO: 93) |
| MCM815 | TAACTAGACTAATCTTACCCGGCGCAGAAC (SEQ ID NO: 94) |

V. Protein Purification

Protein expression and purification: E. coli strain MCM1666 harboring M. burtonii mevalonate kinase gene was grown at 34° C. in 1-L of Terrific broth containing 50 mg/L kanamycin. Cells were induced with 50 µM IPTG at $OD_{600}$=0.6 and harvested by centrifugation 5 hours after induction. Cell pellets were resuspended in 0.05 M sodium phosphate, 0.3 M sodium chloride, 0.02 M imidazole (pH 8.0) buffer containing 0.2 mg/ml DNaseI and 0.5 mM of 4-(2-Aminoethyl) benzenesulfonyl fluoride hydrochloride (AEBSF) following a freeze-thaw cycle. Lysis was achieved by repeated passes through a French Pressure cell at 20,000 psi. Cell lysates were clarified by ultracentrifugation at 229,000×g for one hour. The supernatants were filtered through a 0.2µ filter and loaded onto a HiTrap IMAC HP column charged with nickel sulfate and equilibrated with 0.05 M sodium phosphate, 0.3 M sodium chloride, 0.02 M imidazole (pH 8.0). Mevalonate kinase was isolated using a linear gradient from 0.02 to 0.5 M of imidazole. Fractions containing the mevalonate kinase were identified using SDS-PAGE (Invitrogen) and desalted into 0.05 M Tris, 0.05 M sodium chloride (pH 7.4) using a Hi Prep 26/10 desalting column. Final mevalonate kinase fraction was 95% when assessed by SDS-PAGE and coomassie staining. Quantitation was performed using spectrophotometer readings at 280 nm (conversion factor equal to 0.3 OD/mg/ml, VectorNTI.

Isolation, purification and kinetic analysis of M. mazei MVK was previously described in U.S. Patent Application Publication No. 2010/0086978.

Example 30: Solubility of M. burtonii and M. mazei Mevalonate Kinases from pET24b Plasmid in MCM1666 and MCM1669 Strains This example examines the respective solubility of mevalonate kinases derived from M. burtonii and M. mazei.
(i) Materials and Methods Strains MCM1666 and MCM1669 were grown at 34° C. in 5 ml of LB medium containing 50 mg/L kanamycin. Cells were induced with 50 µM IPTG at OD(600)=0.6 and harvested by centrifugation 4 hours after induction. Cell lysates were prepared in 50 mM Tris, 50 mM NaCl (pH 7.4) with 0.2 mg/ml DNaseI and 0.5 mM AEBSF and passed twice through the French Pressure Cell set at 700 psi to achieve lysis. Protein solubility was analyzed by SDS-PAGE gel.

(ii) Results

Figure 28:
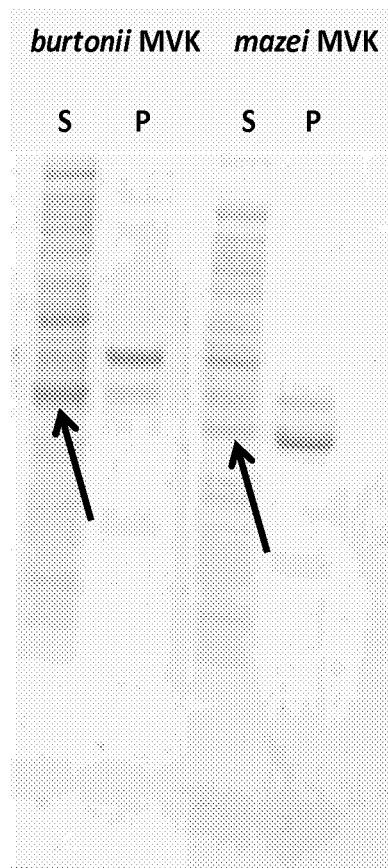
FIG. 28 depicts solubility of M. burtonii and M. mazei mevalonate kinases (MVK) in MCM1666 and MCM1669 strains respectively.

When expressed of pET24b vector M. burtonii mevalonate kinase was 70% soluble, where as mevalonate kinase from M. mazei had a solubility of about 5% and the rest of the protein was located in the pellet fraction (FIG. 28).

Example 31: Kinetic Analysis and Inhibition of Mevalonate Kinases from M. burtonii and M. mazei This example details the respective kinetics of catalytic activity and inhibition of mevalonate kinases derived from M. burtonii and M. mazei.
(i) Materials and Methods Kinetics were performed using SpectraMax 190 platereader (Molecular Devices). All kinetic data were analyzed using Kaleidagraph 4.0 graphing program from Synergy software. Adenosine triphosphate (ATP), phosphoenolpyruvate (PEP), NADH, magnesium chloride, sodium chloride, Tris, HEPE, DNase I, as well as MVP and MVPP were purchased from Sigma. Dithiothreitol was purchased from Fluka. Lactate dehydrogenase was purchased from Calbiochem and pyruvate kinase was purchased from MD biomedicals. DMAPP, IPP and GPP were synthesized in-house.

The catalytic activities of both M. burtonii and M. mazei mevalonate kinase were measured using a modified spectrophotometric assay that couples ADP formation to pyruvate synthesis and reduction to lactate. The initial rate of disappearance of NADH serves as a measure of phosphorylation of mevalonate by MVK. The assays were performed in triplicate in a 96-well non-binding plate (Costar catalog #9017) format, at 30° C. Each 100 µl reaction contained 0.4 mM PEP, 0.05 mM DTT, 0.32 mM NADH, 10 mM $MgCl_2$, 2.5 units of LDH and 2.5 units of PK in 50 mM HEPES, 50 mM NaCl (pH 7.4).

The kinetic constants for the mevalonate kinases from M. burtonii and M. mazei were determined by applying random bireactant system kinetics model using varying amounts of both mevalonate and ATP substrates. The following concentrations were tested: 0.4 mM, 0.2 mM, 0.1 mM and 0.05 mM of mevalonate and 2 mM, 1 mM, 0.5 mM and 0.25 mM of ATP. The reaction was initiated with the addition of 40 nM of purified M. burtonii mevalonate kinase or 80 nM (0.25 µg) of purified M. mazei mevalonate kinase. Absorbance changes associated with the amount of NADH oxidized to NAD+ were monitored continuously at 340 nm and plotted against time to determine the rate of the mevalonate kinase coupled reactions. Protein inhibition studies were performed by adding terpenyl diphosphates (DMAPP, IPP, GPP, MVPP) as well as terpenyl monophosphate MVP at various concentrations to the reaction mix. Previously purified *S. cerevisiae* mevalonate kinase was used as a positive control for DMAPP, IPP and GPP inhibition where as *S. pneumoniae* mevalonate kinase was used as a positive control for MVP and MVPP inhibition.

(ii) Results

Kinetic constants were evaluated for *M. burtonii* and *M. mazei* mevalonate kinases with respect to both mevalonate and ATP using random bireactant system model (Table 23). *M. burtonii* mevalonate kinase has a $k_{cat}$ of 44.4 $s^{-1}$ for mevalonate and a $k_{cat}$ of 74.3 $s^{-1}$ for ATP, whereas *M. mazei* mevalonate kinase has $k_{cat}$ of 18.3 $s^{-1}$ for mevalonate and a $k_{cat}$ of 26.8 $s^{-1}$ for ATP at 34° C. $K_{a(Mev)}$ values for *M. burtonii* and *M. mazei* mevalonate kinases were very similar, 391 μM and 397 μM respectively. $K_{b(ATP)}$ were 212 μM for *M. burtonii* mevalonate kinase and 460 μM for *M. mazei*.

TABLE 23

Kinetic and inhibition data for mevalonate kinases derived from *M. burtonii* and *M. mazei*

| Mevalonate kinase | Substrate | $k_{cat}$ ($s^{-1}$) | $K_{a/b}$ (μM) | $V_{max}$ (μM/sec) | α | $K_i$ DMAPP (μM) | $K_i$ IPP (μM) | $K_i$ GPP (μM) | $K_i$ MVP (μM) | $K_i$ MVPP (μM) |
|---|---|---|---|---|---|---|---|---|---|---|
| *M. burtonii* | Mevalonate | 44.4 | 391 | 1.78 | 0.52 | >5000 | >5000 | >5000 | >3000 | >5000 |
|  | ATP | 74.3 | 212 | 2.97 | 3.74 |  |  |  |  |  |
| *M. mazei* | Mevalonate | 18.3 | 397 | 1.46 | 0.23 | >5000 | >5000 | >5000 | >3000 | >1000 |
|  | ATP | 26.8 | 460 | 2.14 | 1.62 |  |  |  |  |  |

Example 32: Growth and Isoprene Productivity of *E. coli* Strains Expressing *M. burtonii* or *M. mazei* Mevalonate Kinase on the *E. coli* Chromosome This example details an examination of the growth and isoprene productivity in engineered *E. coli* strains expressing *M. burtonii* mevalonate kinase or *M. mazei* mevalonate kinase on the *E. coli* chromosome at small scale.

Materials and Methods

Growth Assays:

Overnight cultures were inoculated in shake tubes containing 2 mL of LB broth supplemented with 50 μg/mL carbenicillin (Novagen) and 50 μg/mL spectinomycin (Novagen) from frozen stocks. Cultures were then incubated for 14 h at 34° C. at 240 rpm. Next, the cultures were diluted into a 5 mL 48-well plate (Axygen Scientific) containing 2 mL TM3 media supplemented with 1% glucose, 0.02% yeast extract, 50 μg/mL carbenicillin and 50 μg/mL spectinomycin to a final OD of 0.2. The plate was sealed with Breath Easier membrane (Diversified Biotech) and incubated at 34° C. in a Shel Lab shaker/incubator at 600 rpm. The cultures were induced with 200 μM IPTG at OD of 0.4. One hour after induction mevalonate was added to the cultures to a final concentration of 0, 2, 4, 8, 16, 32 mM. OD measurements were taken at 0, 1, 2, 3, 4, and 5 hrs after induction with IPTG.

TABLE 24

List of the engineered *E. coli* strains examined at small scale

| Strain Name | Abbreviated Genotype |
|---|---|
| CMP1136 | pgl- + pTrcAlba(MEA, G491S)-mMVK + pCL-Ptrc-Upper_Ef |
| DW708 | pgl- + pTrcAlba(MEA, IspS variants)-mMVK + pCL-Ptrc-Upper_gallinarum |
| MCM2131 | pgl- FRT-PL.2-2cis-RBS10000-MVK(burtonii) + pTrcAlba(MEA, IspS variants)-bMVK + pCL-Ptrc-Upper_gallinarum |
| MCM2125 | pgl- FRT-PL.2-2cis-RBS10000-MVK(burtonii) + pTrcAlba(MEA, IspS variants)-mMVK(del) + pCL-Ptrc-Upper_gallinarum |
| MCM2126 | pgl- FRT-PL.2-2cis-RBS1000-mMVK + pTrcAlba(MEA, IspS variants)-mMVK(del) + pCL-Ptrc-Upper_gallinarum |
| MCM2127 | pgl- FRT-PL.2-2cis-RBS100000-mMVK + pTrcAlba(MEA, IspS variants)-mMVK(del) + pCL-Ptrc-Upper_gallinarum |
| MCM2129 | pgl- FRT-PL.2-2cis-RBS1000000-mMVK + pTrcAlba(MEA, IspS variants)-mMVK(del) + pCL-Ptrc-Upper_gallinarum |
| MCM2130 | pgl- FRT-PL.2-2cis-RBS10000-mMVK + pTrcAlba(MEA, IspS variants)-mMVK(del) + pCL-Ptrc-Upper_gallinarum |

Isoprene Productivity:

Samples for analysis of isoprene productivity by GC/MS from the engineered *E. coli* strains were taken at 1, 2, 3, 4, and 5 hrs after induction. 100 μL of culture broth was pippeted into deep-98-well glass block and sealed with aluminum sealer (Beckman Coulter). The glass block was incubated for 30 min at 34° C. water bath, after which it was transferred to 80° C. water bath for a 2 min heat-kill incubation. The glass block was cooled and transferred to the GC/MS for isoprene measurements.

Isoprene Detection by GC/MS:

GC/MS was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 μm film thickness) was used for separation of analytes. The GC/MS method utilized helium as the carrier gas at a flow of 1 ml/min. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 2000 μg/L. The limit of detection was estimated to be 50 to 100 ng/L using this method.

(ii) Results

Growth of MCM2131 is not inhibited by mevalonate concentrations ranging between 0 and 16 mM. MCM2131 has the highest specific productivity ranging between 30-42 mg/L/h/OD with 32 mM mevalonate added, therefore is able to support very high flux from the upper pathways.

Figure 29:
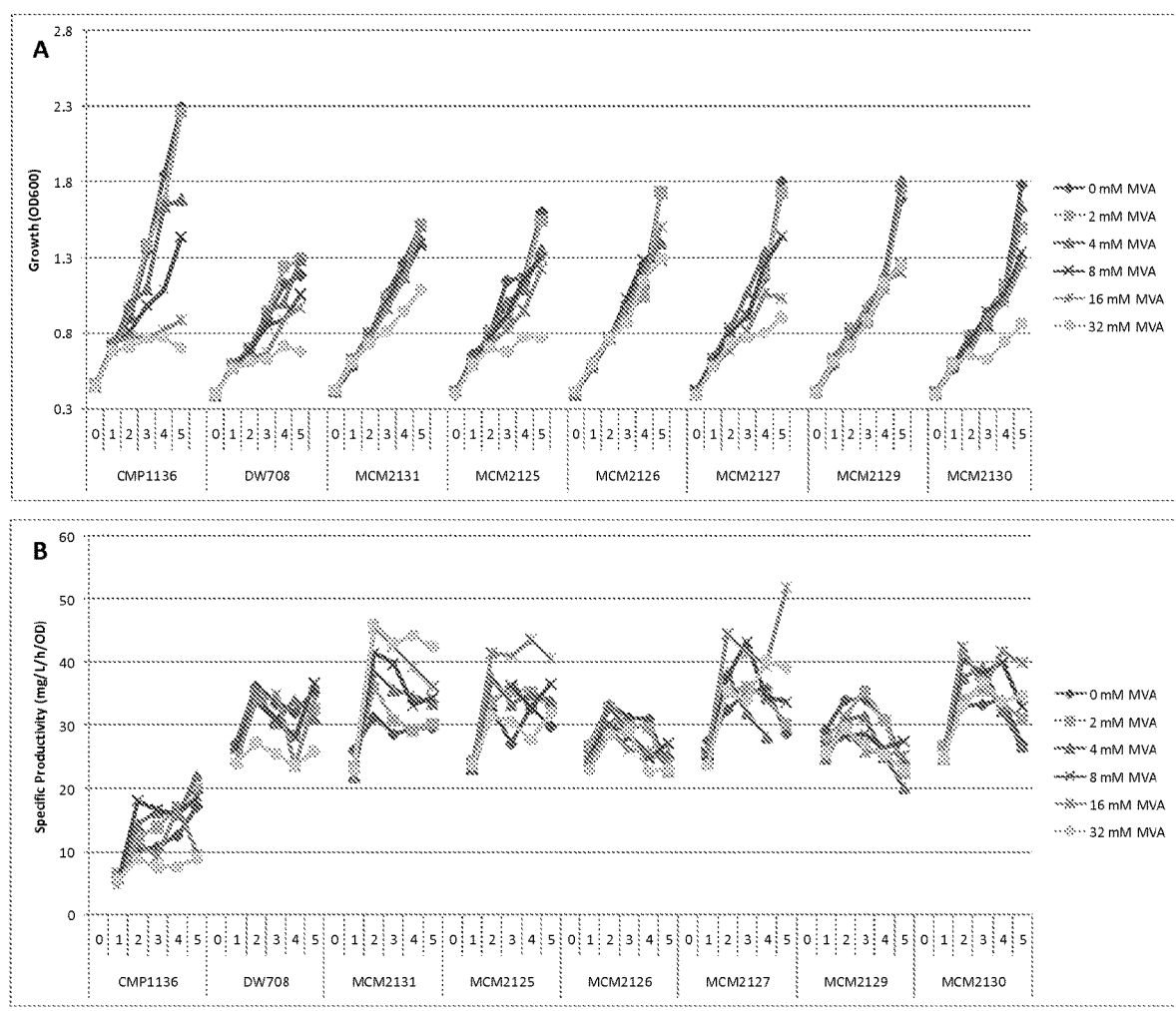
FIG. 29 depicts growth and isoprene productivity in engineered E. coli strains expressing M. burtonii mevalonate kinase (A) or M. mazei mevalonate kinase (B) on the E. coli chromosome at small scale.

Engineered strains MCM2125, MCM2127 and MCM2130 with one copy of chromosomal mevalonate kinase are able to achieve specific productivities of 40 mg/L/h/OD with 16 mM mevalonate feed. Their growth is also not inhibited by mevalonate concentrations between 0-16 mM (FIG. 29).

Example 33: Plasmid and Chormosomal Expression of *M. mazei* and *M. burtonii* Mevalonate Kinases in *E. coli*

Strains MCM2126 and MCM2127 were run to determine if any benefit can be obtained by expressing the *mazei* MVK off of the chromosome only.

Materials and Methods (i) Solutions

Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di $H_2O$. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO^4*2H_2O$ 100 mg. Each component was dissolved one at a time in Di H2O, pH was adjusted to 3.0 with HCl/NaOH, and then the solution was q.s. to volume and filter sterilized with a 0.22 micron filter.

Macro Salt Solution (Per Liter):

$MgSO4*7H_2O$ 296 g, citric acid monohydrate 296 g, ferric ammonium citrate 49.6 g. All components were dissolved in water, q.s. to volume and filter sterilized with 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di $H_2O$, pH was adjusted to 3.0 with HCl/NaOH, and then the solution was q.s. to volume and filter sterilized with 0.22 micron filter.

Feed Solution #1 (Per Kilogram):

Glucose 0.590 kg, Di $H_2O$ 0.393 kg, $K_2HPO_4$ 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Methods

Samples were thawed and normalized to OD=20 in 100 mM Tris, 100 mM NaCl, pH 7.6, 0.1 mg/ml DNaseI, 1 mg/ml lysozyme, and 0.5 mM AEBSF (4-(2-Aminoethyl) benzenesulfonyl fluoride hydrochloride). OD normalized cell suspensions were lysed by repeated pass through the French pressure cell at 700 psi. Lysates were clarified by centrifugation at 14,000 rpm for 10 minutes. Clarified lysates were evaluated for total protein content using Bradford assay (BioRad, 500-0006). Samples were then protein normalized and ran on 4-12% SDS-PAGE gels (Life Technologies). Proteins were transferred onto Nitrocellulose membrane using iBlot transfer apparatus (Life Technologies). Nitrocellulose was developed using BenchPro™ 4100 Western Card Processing Station (Life Technologies), probing for either *M. mazei* and *M. burtonii* MVKs with primary polyclonal antibodies produced in rabbits by ProSci incorporated against purified enzymes and a secondary fluorescent antibody Alexa Fluor 488 goat anti-rabbit IgG (Life Technologies, A-11008). Specific protein quantitation was achieved using Storm imager and ImageQuant TL software from GE Healthcare.

(iii) Results

Figure 30:
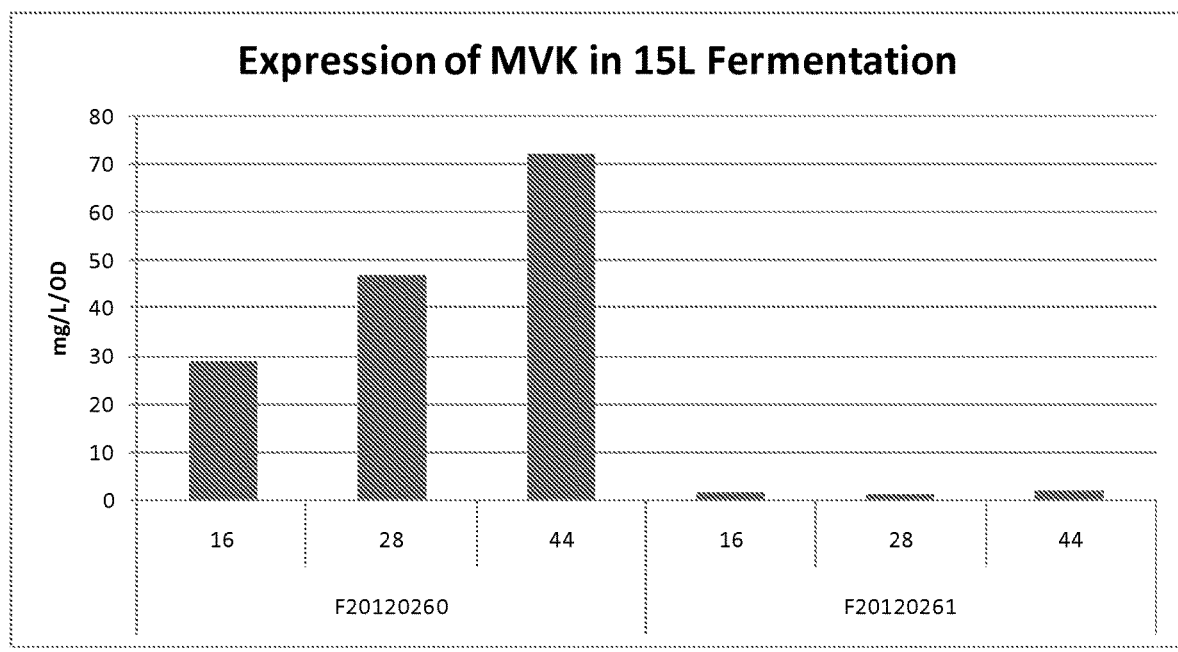
FIG. 30 depicts expression of M. mazei and M. burtonii mevalonate kinases in E. coli 15-L fermentations.

Expression of *M. burtonii* mevalonate kinase in MCM2125 is at least 15 fold lower then expression of *M. mazei* mevalonate kinase in DW708 strain, based on protein quantitation by western blot analysis (FIG. 30).

Example 34: Isoprene Production in *E. coli*

This example evaluates isoprene production in *E. coli* (BL21) expressing introduced genes from the mevalonate pathway and grown in fed-batch culture at the 15-L scale. Isoprene producing strains were run in a standard isoprene production process, described below. The performance metrics of strain DW708 (cumulative isoprene yield on glucose, instantaneous isoprene yield on glucose, volumetric productivity of isoprene, specific productivity and cell productivity index) are compared here to experimental strains, MCM2125, MCM2126 and MCM2127. These strains were run in the same conditions to determine if any yield improvement can be attributed to the use of the *burtonii* mevalonate kinase (MVK) in strain MCM2125, compared to a strain that used only *mazei* MVK (DW708). Additionally, strains MCM2126 and MCM2127 were run in the same conditions to determine if any benefit can be obtained by expressing the *mazei* MVK off of the chromosome only.

TABLE 25

List of strains

| Strain Name | Host | MVK in host chromosome | Upper plasmid | Lower plasmid | MVK on lower plasmid | Run numbers |
|---|---|---|---|---|---|---|
| DW708 | pgl- | *Mazei* | pCL Ptrc *E. gallinarum* Upper (pMCM1225) | pTrc *P. alba* IspS (MEA IspS variants)-mMVK (pDW166) | Yes (*Mazei*) | 20120187 20120260 |
| MCM2125 | pgl- FRT-PL.2-2cis-RBS10000-MVK(*burtonii*) | *Burtonii* | pCL-Ptrc-Upper_*gallinarum* | pTrcAlba(MEA, IspS variants)-mMVK(del) | No | 20120188 20120261 |
| MCM2126 | pgl- FRT-PL.2-2cistron-RBS1000-mMVK | *Mazei* (lower strength chromosomal promoter) | pCL-Ptrc-Upper_*gallinarum* | pTrcAlba(MEA, IspS variants)-mMVK(del) | No | 20120262 |
| MCM2127 | pgl- FRT-PL.2-2cistron-RBS100000-mMVK+ | *Mazei* (higher strength chromosomal promoter) | +pCL-Ptrc-Upper_*gallinarum* | pTrcAlba(MEA, IspS variants)-mMVK(del) | No | 20120263 |

(ii) Solutions

Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di $H_2O$. This solution was heat sterilized (123 C for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*$H_2O$ 40 g, $MnSO_4*H2O$ 30 g, NaCl 10 g, $FeSO4*7H2O$ 1 g, $CoCl2*6H2O$ 1 g, $ZnSO*7H2O$ 1 g, $CuSO4*5H2O$ 100 mg, $H3BO3$ 100 mg, $NaMoO4*2H2O$ 100 mg. Each component was dissolved one at a time in Di $H_2O$, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

$MgSO4*7H2O$ 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Method

A frozen vial of the *E. coli* strain was thawed and inoculated into a flask with tryptone-yeast extract medium and the appropriate antibiotics. After the inoculum grew to optical density 1.0, measured at 550 nm (OD550), 500 mL was used to inoculate a 15-L bioreactor and bring the initial tank volume to 5 L.

The inlet gas using to maintain bioreactor backpressure at 0.7 bar gauge and to provide the oxygen to the production organisms was supplied by Matheson Tri-Gas, Inc in compressed gas cylinders.

The batched media had glucose batched in at 9.7 g/L. Induction was achieved by adding isopropyl-beta-D-1-thiogalactopyranoside (IPTG). A shot of IPTG was added to the tank to bring the concentration to 200 uM when the cells were at an OD550 of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 52 to 69 hrs elapsed fermentation time.

(iii) Analysis

Isoprene is volatile and can be efficiently swept from the tank by the inlet gas. The isoprene level in the bioreactor off-gas was determined using two mass spectrometers, an iSCAN (Hamilton Sundstrand), and a Hiden HPR20 (Hiden Analytical) mass spectrometer. Oxygen, Nitrogen, and CO2 levels in the offgas were determined by the same mass spec units.

Dissolved Oxygen in the fermentation broth is measured by sanitary, sterilizable probe with an optical sensor provided Hamilton Company.

The citrate, glucose, acetate, and mevalonate concentrations in the fermentor broth was determined in broth samples taken at 4 hour intervals by an HPLC analysis. Concentration in broth samples were determined by comparison of the refractive index response versus a previously generated calibration curve using standard of a known concentration HPLC Information:

System: Waters Alliance 2695; Column: BioRad-Aminex HPX-87H Ion Exclusion Column 300 mm×7.8 mm Catalog #125-0140; Column Temperature: 50 C; Guard column: BioRad-Microguard Cation H refill 30 mm×4.6 mm Catalog #125-0129; Running buffer: 0.01N $H_2SO_4$; Running buffer flow rate: 0.6 ml/min; Approximate running pressure: ~1100-1200 psi; Injection volume: 20 microliters; Detector: Refractive Index (Knauer K-2301); Runtime: 26 minute.

(iv) Results

Figure 31:
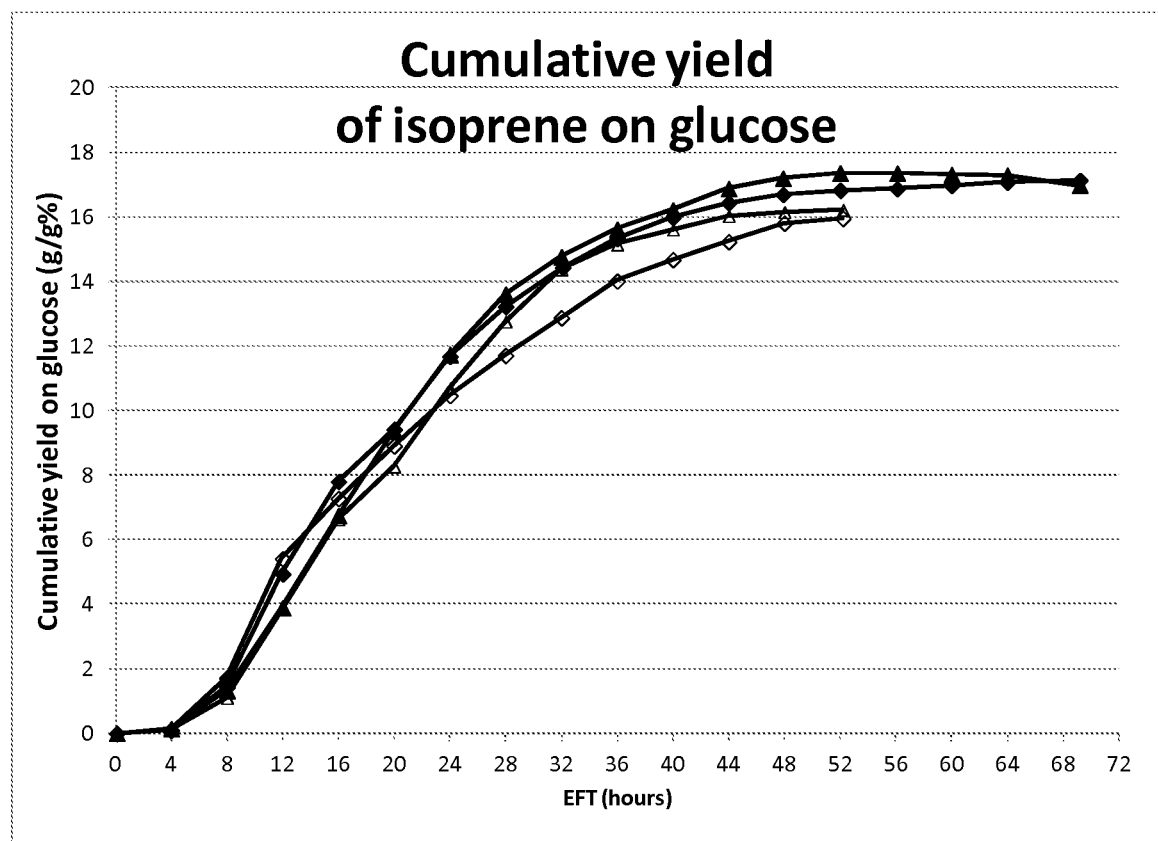
FIG. 31 depicts yield of isoprene on glucose achieved in each 15-L fermentation over time. % wt Yield on glucose=Isoprene total (t)/[(Feed Wt(0)−Feed Wt(t)+83.5)*0.59)], where 0.59 is the wt % of glucose in the glucose feed solution and 83.5 is the grams of this feed batched into the fermentor at t=0. Each feed had its weight % measured independently. DW708: mazei MVK on plasmid and chromosome (closed diamonds); DW708: mazei MVK on plasmid and chromosome (open diamonds); MCM2125: burtonii MVK on chromosome only (closed triangles); MCM2125: burtonii MVK on chromosome only (open triangles).
Figure 32:
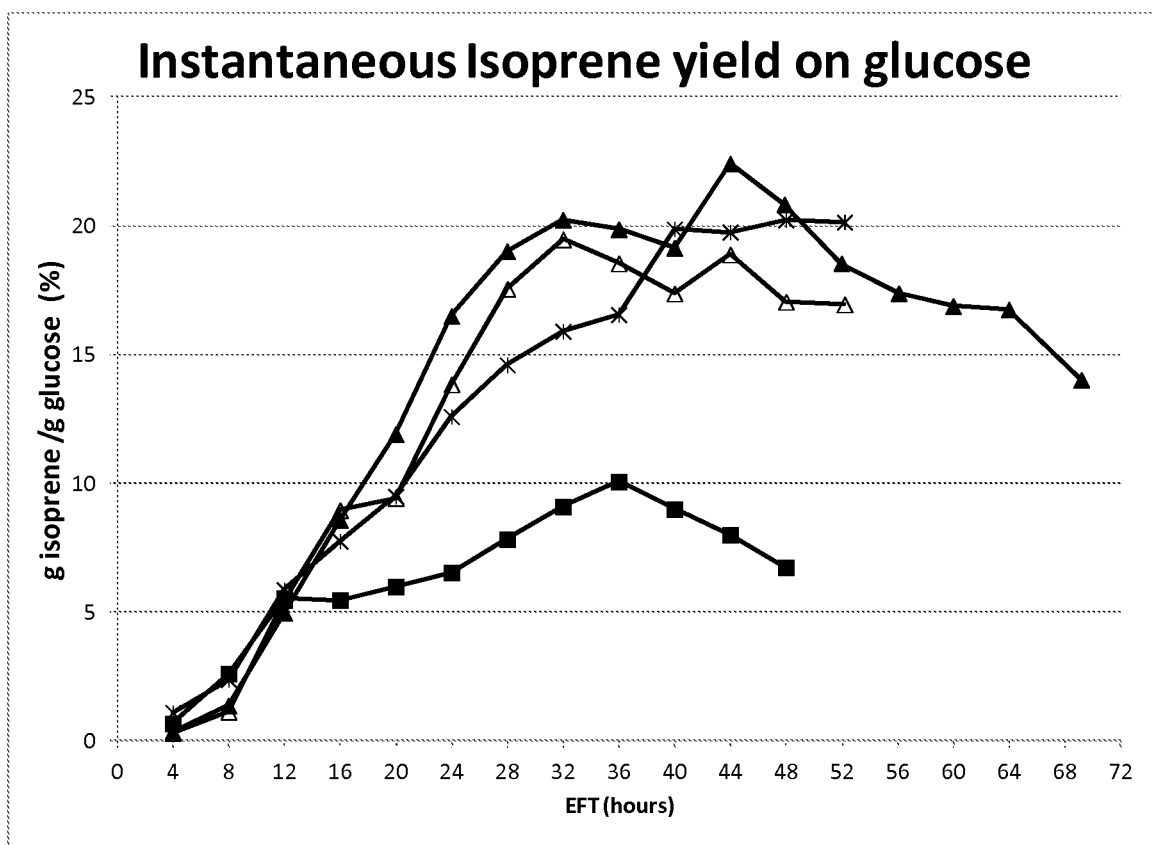
FIG. 32 depicts instantaneous yield of isoprene on glucose achieved in each 15-L fermentation over time. Isoprene Instantaneous yield was calculated using the formula: Isoprene Inst. yield (g/g %)=Isoprene produced $(t_1-t_0)$/consumed glucose $(t_1-t_0)*100$. DW708: mazei MVK on plasmid and chromosome (closed diamonds); DW708: mazei MVK on plasmid and chromosome (open diamonds); MCM2125: burtonii MVK on chromosome only (closed triangles); MCM2125: burtonii MVK on chromosome only (open triangles).
Figure 33:
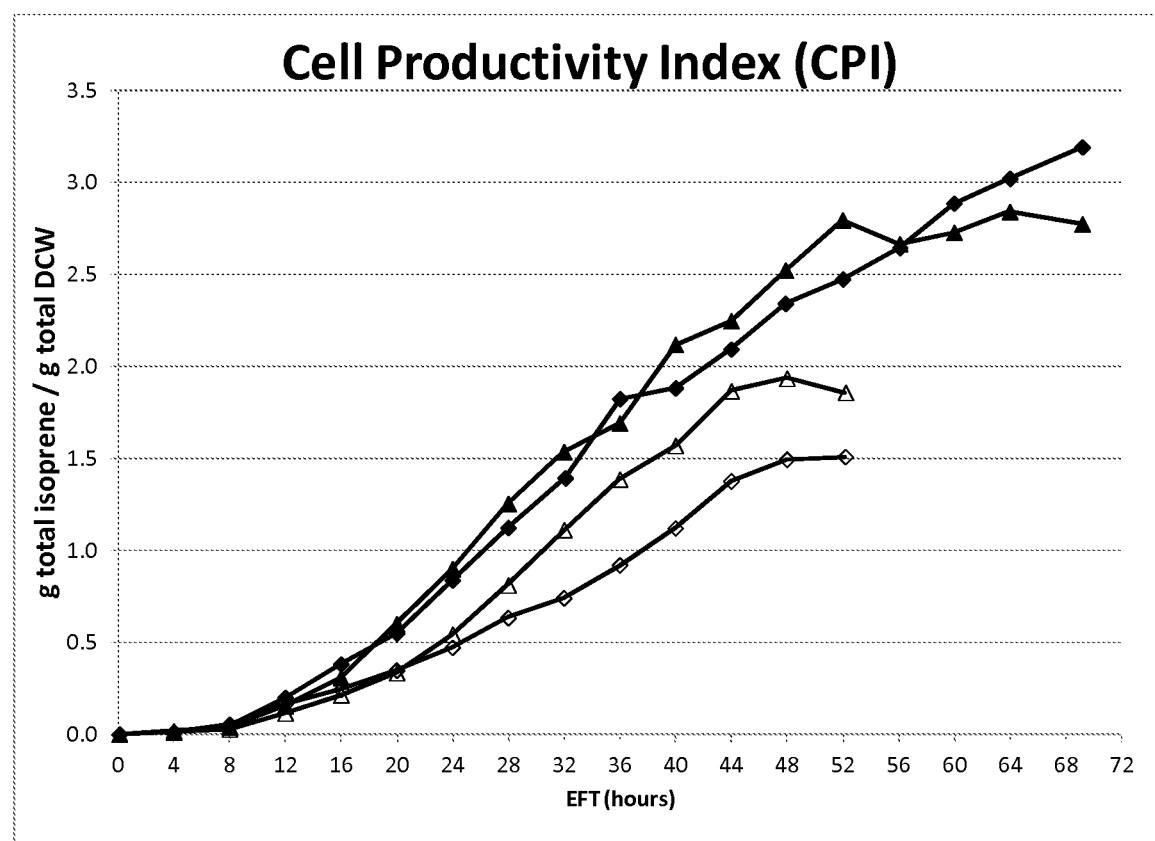
FIG. 33 depicts cell productivity index (CPI) achieved in each 15-L fermentation over time. Cell Productivity Index (CPI) was calculated using the following formula: CPI=total grams Isoprene/total grams dry cell weight. DW708: mazei MVK on plasmid and chromosome (closed diamonds); DW708: mazei MVK on plasmid and chromosome (open diamonds); MCM2125: burtonii MVK on chromosome only (closed triangles); MCM2125: burtonii MVK on chromosome only (open triangles).
Figure 34:
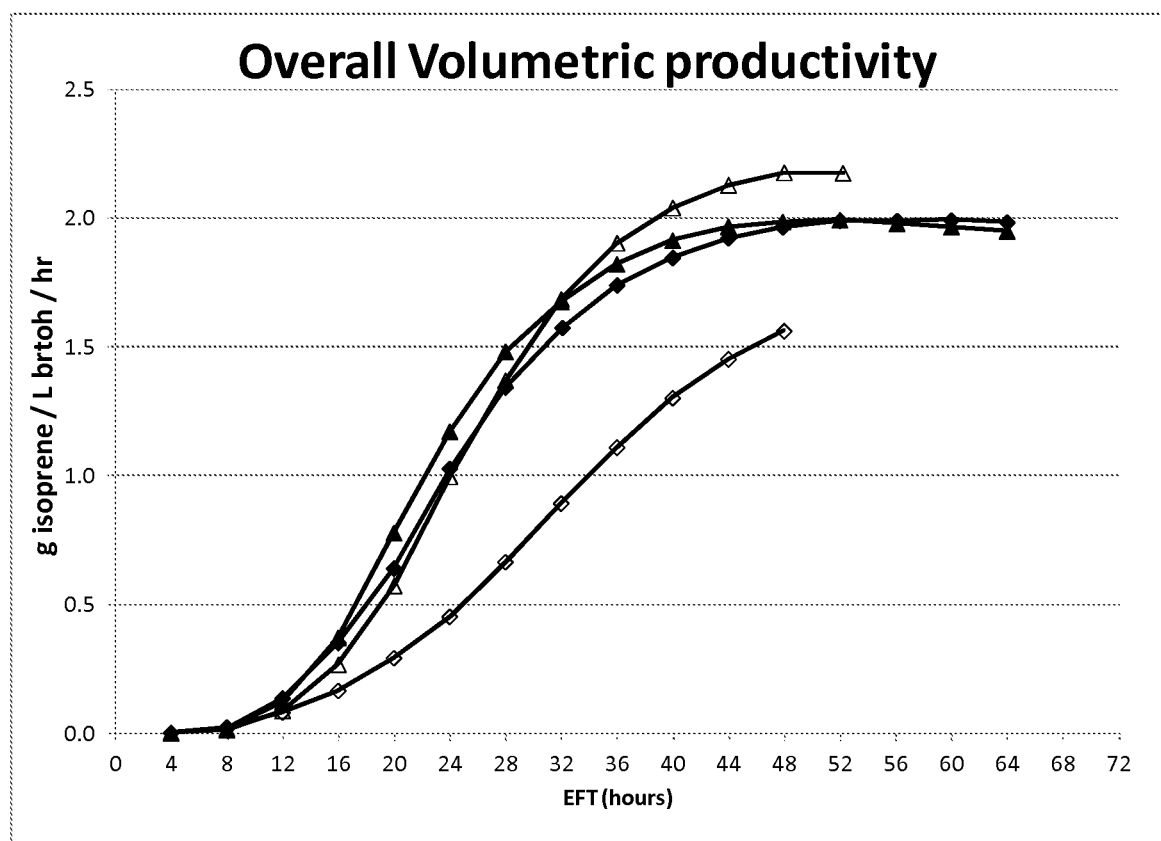
FIG. 34 depicts volumetric productivity achieved in each 15-L fermentation over time. Volumetric Productivity was calculated using the following formula: [ΣHGER(t)/1000*68.117)]/[t−t$_0$], where the summation is from t$_0$ to t. Tank turnaround time is not factored in. DW708: *mazei* MVK on plasmid and chromosome (closed diamonds); DW708: *mazei* MVK on plasmid and chromosome (open diamonds); MCM2125: *burtonii* MVK on chromosome only (closed triangles); MCM2125: *burtonii* MVK on chromosome only (open triangles).
Figure 35:
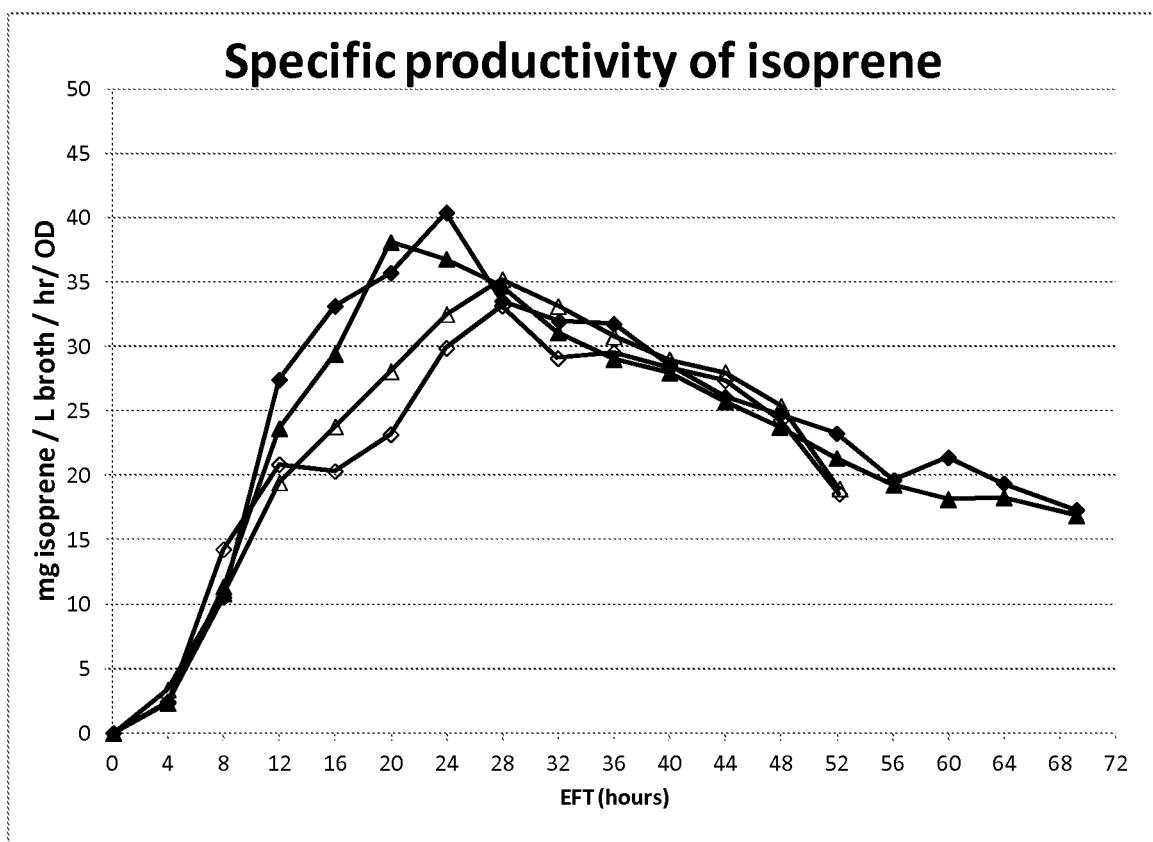
FIG. 35 depicts specific productivity achieved in each 15-L fermentation over time. Specific Productivity was calculated using the following formula: Specific productivity (mg/L/hr/OD)=HgER*68.117 g/mol/OD. HgER is the Isoprene Evolution Rate in (mmol/L/hr). OD=optical density=Absorbance at 550 nm*dilution factor in water. DW708: *mazei* MVK on plasmid and chromosome (closed diamonds); DW708: *mazei* MVK on plasmid and chromosome (open diamonds); MCM2125: *burtonii* MVK on chromosome only (closed triangles); MCM2125: *burtonii* MVK on chromosome only (open triangles).

The results are summarized in Table 26. The strain expressing *burtonii* MVK (MCM2125) achieved a comparable cumulative % yield of isoprene on glucose (FIG. 31), a comparable instantaneous % yield of isoprene on glucose (FIG. 32), a comparable cell performance index (CPI; FIG. 33), a comparable overall volumetric productivity (FIG. 34), and a comparable specific productivity (FIG. 35) versus the strain expressing *mazei* MVK (DW708).

TABLE 26

Isoprene productivity metrics

| Strain description/ Run Number | Overall Isoprene Volumetric Productivity (g/L/hr) at time of max overall isoprene yield | Max Cumulative % Yield of Isoprene on glucose (g/g) | Peak instantaneous % yield of isoprene on glucose (g/g %) | CPI (g Isoprene/ gDCW) at time of max overall isoprene yield | Peak Specific Productivity (mg isoprene/ L/hr/OD) |
|---|---|---|---|---|---|
| DW708 20120187 | 1.96 | 17.1 | 19.5 | 3.19 | 40.39 |
| DW708 20120260 | 1.61 | 16.0 | 19.0 | 1.51 | 28.95 |
| MCM2125 20120188 | 1.95 | 17.3 | 22.4 | 2.84 | 38.1 |
| MCM2125 20120261 | 2.18 | 16.2 | 19.5 | 1.86 | 35.2 |
| MCM2126 20120262 | 0.65 | 7.5 | 10.08 | 0.70 | 19.34 |
| MCM2127 20120263 | 1.94 | 15.5 | 20.23 | 1.92 | 28.95 |

Figure 36:
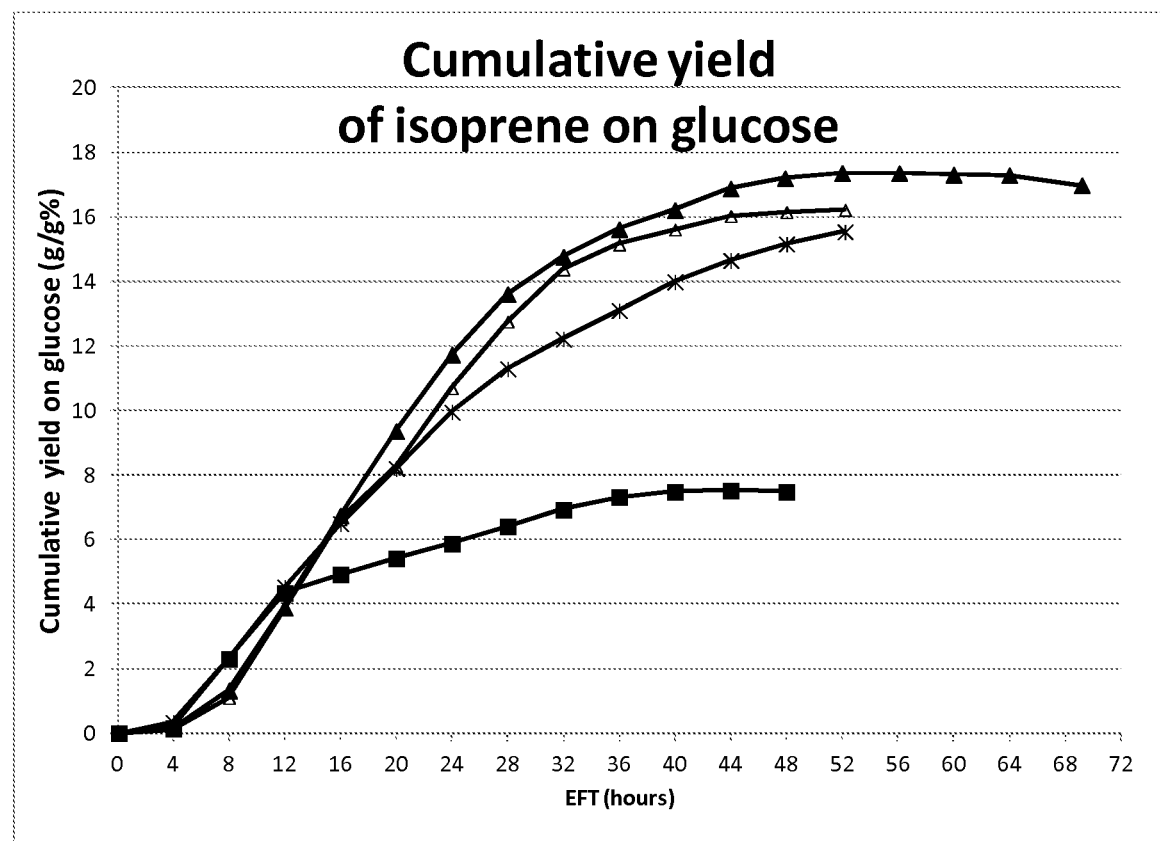
FIG. 36 depicts yield of isoprene on glucose achieved in each 15-L fermentation over time. % wt Yield on glucose=Isoprene total (t)/[(Feed Wt(0)−Feed Wt(t)+83.5)*0.59)], where 0.59 is the wt % of glucose in the glucose feed solution and 83.5 is the grams of this feed batched into the fermentor at t=0. Each feed had its weight % measured independently. MCM2125: *burtonii* MVK on chromosome only (closed triangles); MCM2125: *burtonii* MVK on chromosome only (open triangles); MCM2126: *mazei* MVK on chromosome only (closed squares); MCM2127: *mazei* MVK on chromosome only (stars).
Figure 37:
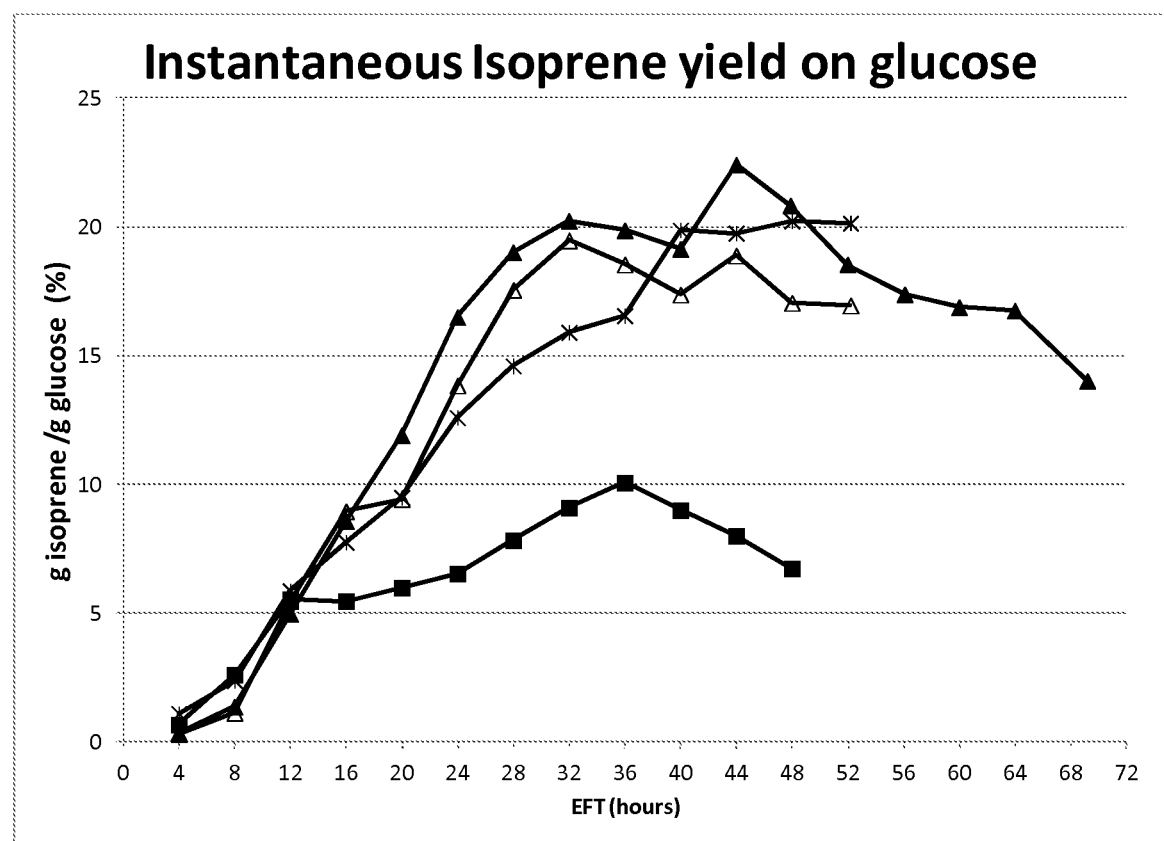
FIG. 37 depicts instantaneous yield of isoprene on glucose achieved in each 15-L fermentation over time. Isoprene Instantaneous yield was calculated using the formula: Isoprene Inst. yield (g/g %)=Isoprene produced (t$_1$-t$_0$)/consumed glucose (t$_1$-t$_0$)*100. MCM2125: *burtonii* MVK on chromosome only (closed triangles); MCM2125: *burtonii* MVK on chromosome only (open triangles); MCM2126: *mazei* MVK on chromosome only (closed squares); MCM2127: *mazei* MVK on chromosome only (stars).
Figure 38:
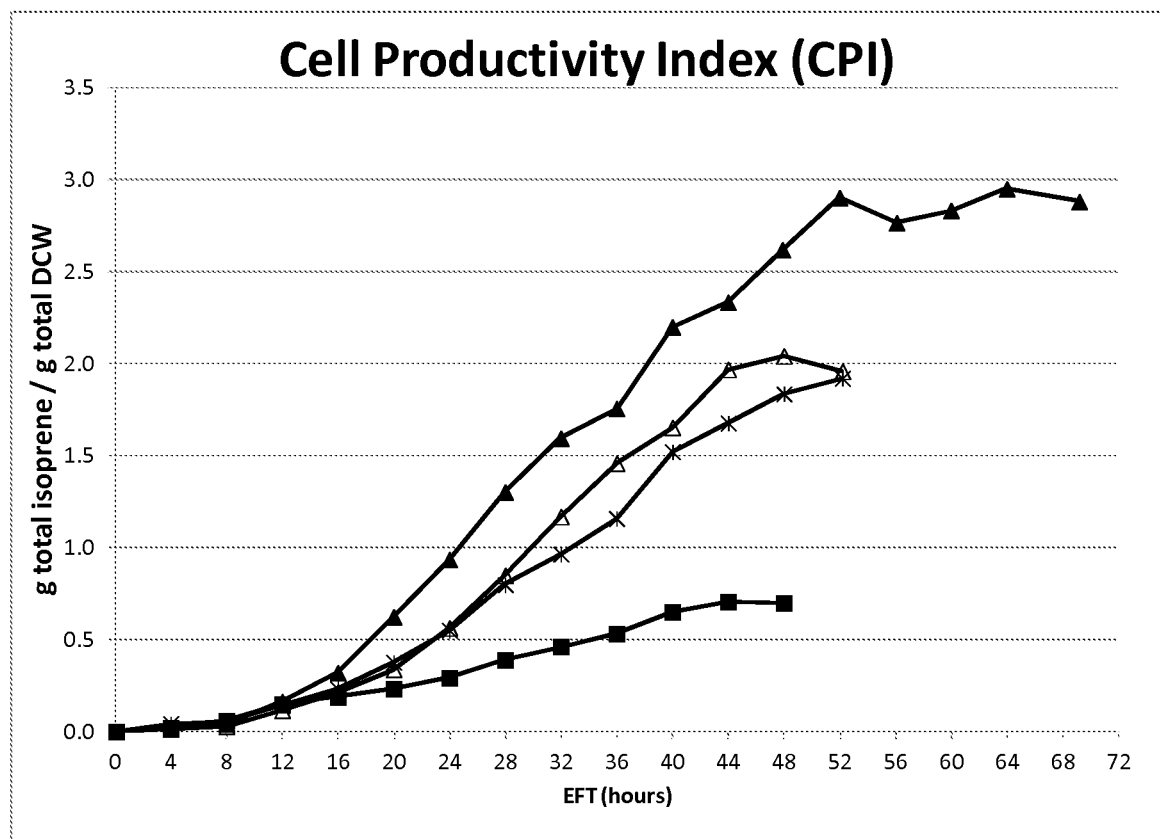
FIG. 38 depicts cell productivity index (CPI) achieved in each 15-L fermentation over time. Cell Productivity Index (CPI) was calculated using the following formula: CPI=total grams Isoprene/total grams dry cell weight. MCM2125: *burtonii* MVK on chromosome only (closed triangles); MCM2125: *burtonii* MVK on chromosome only (open triangles); MCM2126: *mazei* MVK on chromosome only (closed squares); MCM2127: *mazei* MVK on chromosome only (stars).
Figure 39:
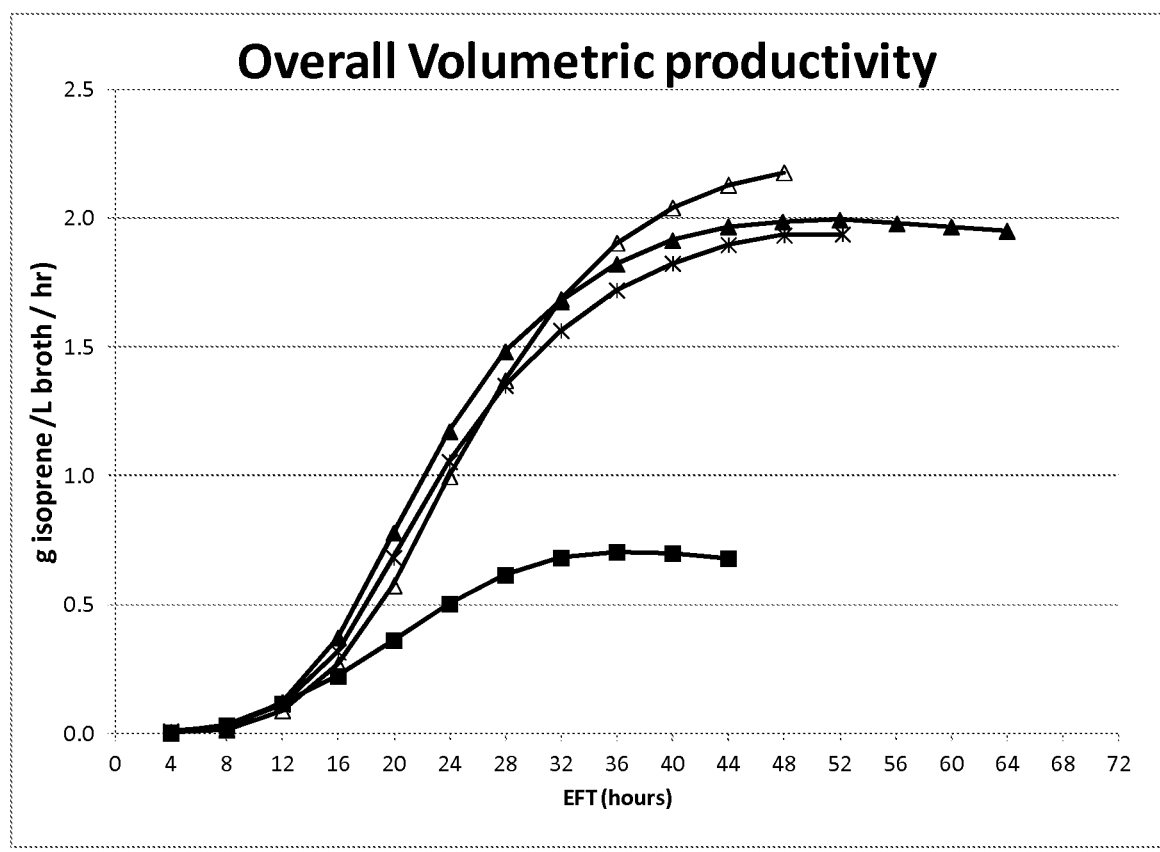
FIG. 39 depicts volumetric productivity achieved in each 15-L fermentation over time. Volumetric Productivity was calculated using the following formula: [ΣHGER(t)/1000*68.117)]/[t−t$_0$], where the summation is from t$_0$ to t. Tank turnaround time is not factored in. MCM2125: *burtonii* MVK on chromosome only (closed triangles); MCM2125: *burtonii* MVK on chromosome only (open triangles); MCM2126: *mazei* MVK on chromosome only (closed squares); MCM2127: *mazei* MVK on chromosome only (stars).
Figure 40:
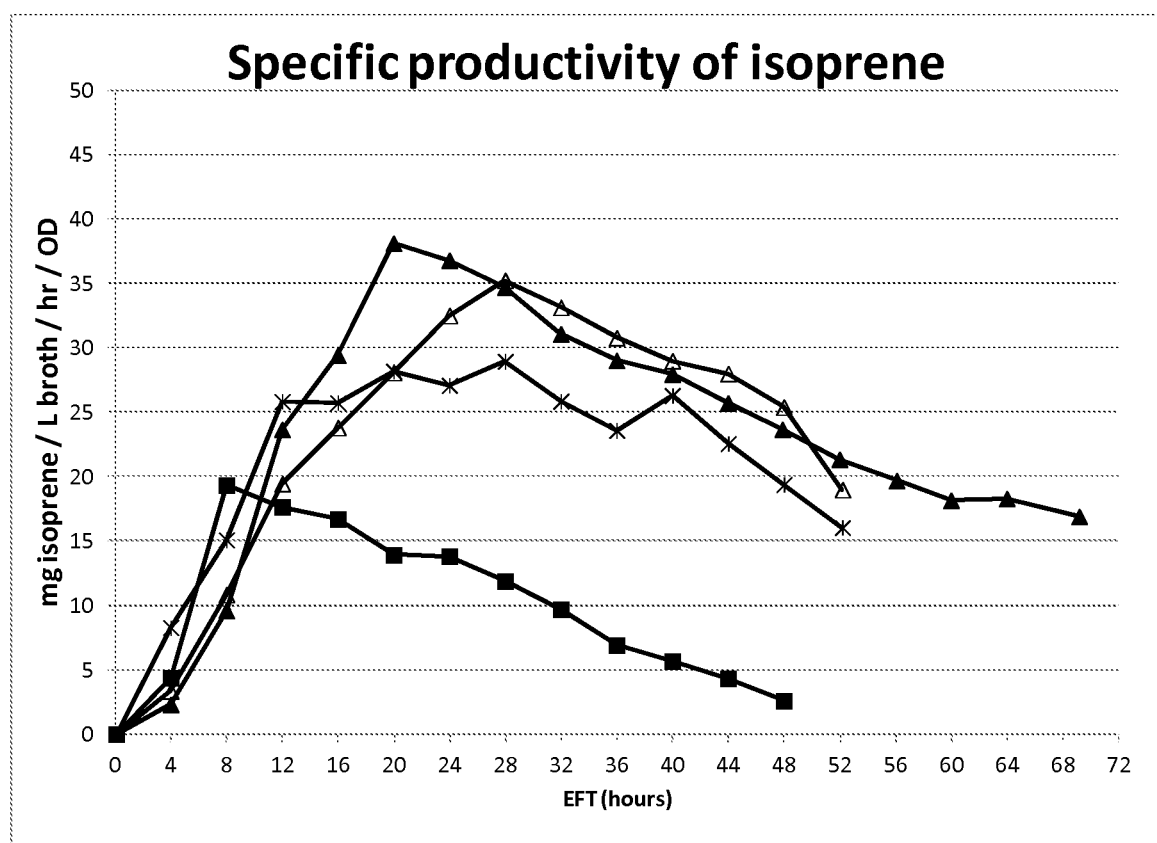
FIG. 40 depicts specific productivity achieved in each 15-L fermentation over time. Specific Productivity was calculated using the following formula: Specific productivity (mg/L/hr/OD)=HgER*68.117 g/mol/OD. HgER is the Isoprene Evolution Rate in (mmol/L/hr). OD=optical density=Absorbance at 550 nm*dilution factor in water. MCM2125: *burtonii* MVK on chromosome only (closed triangles); MCM2125: *burtonii* MVK on chromosome only (open triangles); MCM2126: *mazei* MVK on chromosome only (closed squares); MCM2127: *mazei* MVK on chromosome only (stars).

Comparing strains that expressed MVK off of the chromosome only, strain MCM2125, (expressing *burtonii* MVK) achieved a better cumulative % yield of isoprene on glucose (FIG. 36), a comparable instantaneous % yield of isoprene on glucose (FIG. 37), a higher cell performance index (CPI; FIG. 38), a slightly better volumetric productivity (FIG. 39), and a slightly higher specific productivity versus strain MCM2127 (FIG. 40), which expressed *mazei* MVK.

Example 35: Construction of Strain CMP1136 (-PGL)

A PCR product containing a Kanamycin cassette flanked by FRT sites and regions homologous to upstream and downstream of pgl (ybhE) was obtained, using the PCR method described in example 4, Keio strain JW0750 (Baba et al. 2006. Mol. Syst. Biol. 2:1-11) which contains a kanamycin cassette in the pgl locus, and primers pglAmpF (5'-cagcaaatagcaggtgtatccagc-3' (SEQ ID NO:95)) and pglAmpR (5'-GCA ACC GAC TGT TGA TAG AAC AAC-3' (SEQ ID NO:96)). This PCR product was used in a recombineering reaction (see protocol described above) with *E. coli* CMP1075. A colony was selected on LB+kanamycin 10 mg/L and named CMP1125. The kanamycin marker was removed using the protocol recommended by the manufacturer (Gene Bridges, Heidelberg, Germany) to form strain CMP1133.

CMP1133 was checked by PCR with primers pglAmpF and pglRecCheck (5'-GGT TAC AAA ATG ATT GGC GTA CGC-3' (SEQ ID NO:97)) to demonstrate deletion of the pgl gene. Plasmids MCM82 and pCHL243 were electroporated concomitantly into CMP1133. A colony growing on LB+carbenicilin 50 mg/L and spectinomycin 50 mg/L was selected and named CMP1136.

Example 36: Large Scale Fermentation of CMP1136

This experiment was performed to evaluate isoprene production from *E. coli*(BL21) expressing introduced genes from the mevalonate pathway and grown in fed-batch culture at the 15-L scale. An isoprene producing strain CMP1082 (HMB GI1.2gltA, PyddVIspA_GO, truncIspA, pMCM82, pDW72) was run in a standard isoprene production process, described below. The performance metrics (cumulative isoprene yield on glucose, instantaneous isoprene yield on glucose, volumetric productivity of isoprene, specific productivity and cell productivity index) are compared to an experimental strain CMP1136 (HMB GI1.2gltA, PyddVIspA_GO, truncIspA,pgl-, pMCM82, pDW72) that was run in the same conditions to identify yield improvement attributed to the deletion of the pgl gene in CMP1136.

Medium Recipe (Per Liter Fermentation Medium):
K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):
Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):
Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):
MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):
Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

This experiment was carried out to monitor isoprene formation from glucose at the desired fermentation pH (7.0) and temperature (34° C.). A frozen vial of the E. coli strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L.

The batched media had glucose batched in at 9.7 g/L. Induction was achieved by adding isopropyl-beta-D-1-thio-galactopyranoside (IPTG). IPTG was added to the tank to bring the concentration to 200 uM when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 68 to 72 hrs elapsed fermentation time.

Results

Figure 41:
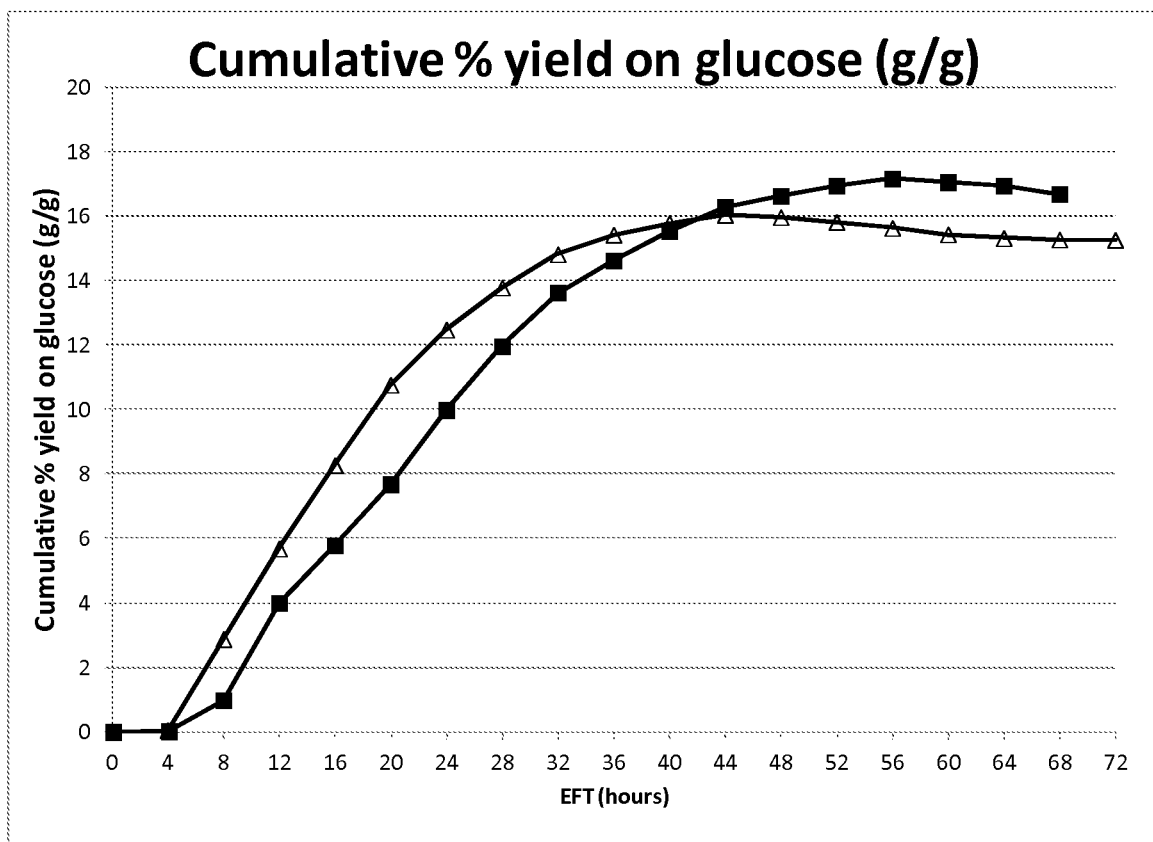
FIG. 41 depicts yield of isoprene on glucose achieved in each 15-L fermentation over time. CMP1082 (pgl+) is depicted by open triangles and CMP1136 (pgl−) is depicted by closed squares.
Figure 42:
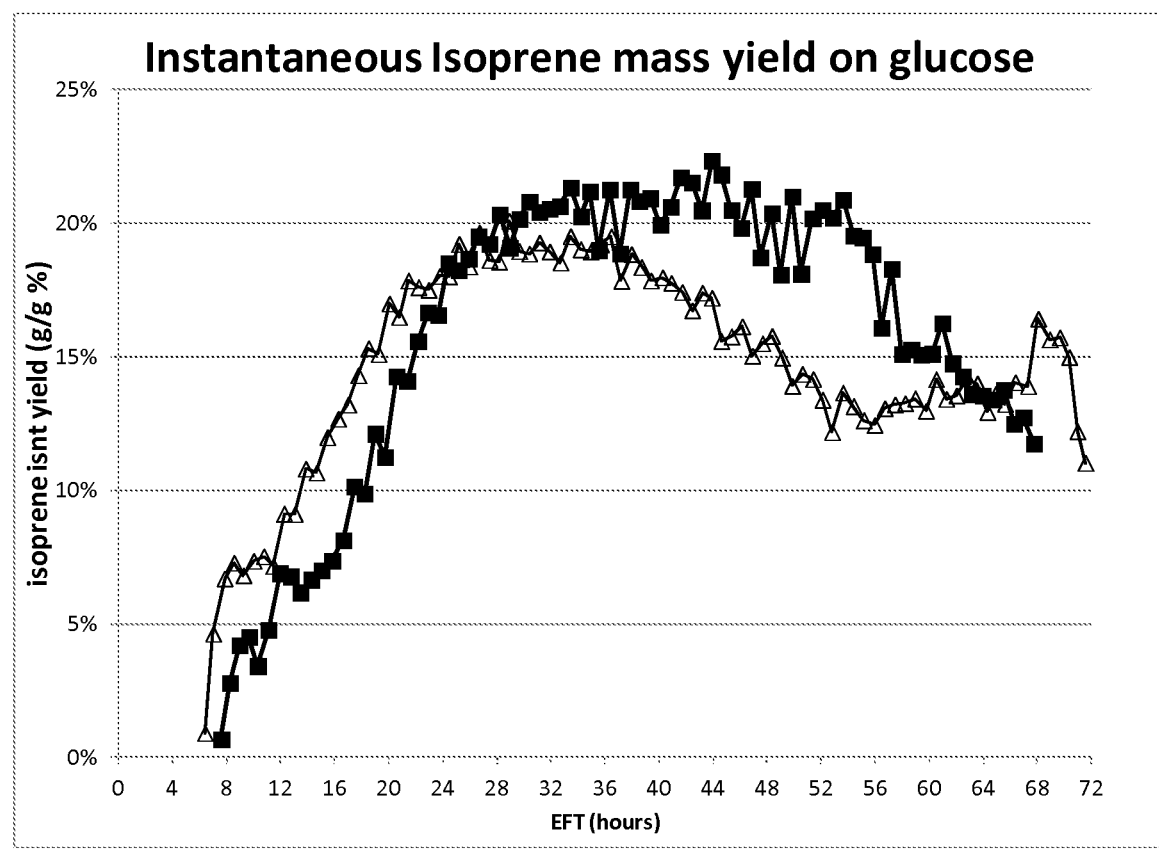
FIG. 42 depicts instantaneous yield of isoprene on glucose achieved in each 15-L fermentation over time. CMP1082 (pgl+) is depicted by open triangles and CMP1136 (pgl−) is depicted by closed squares.
Figure 43:
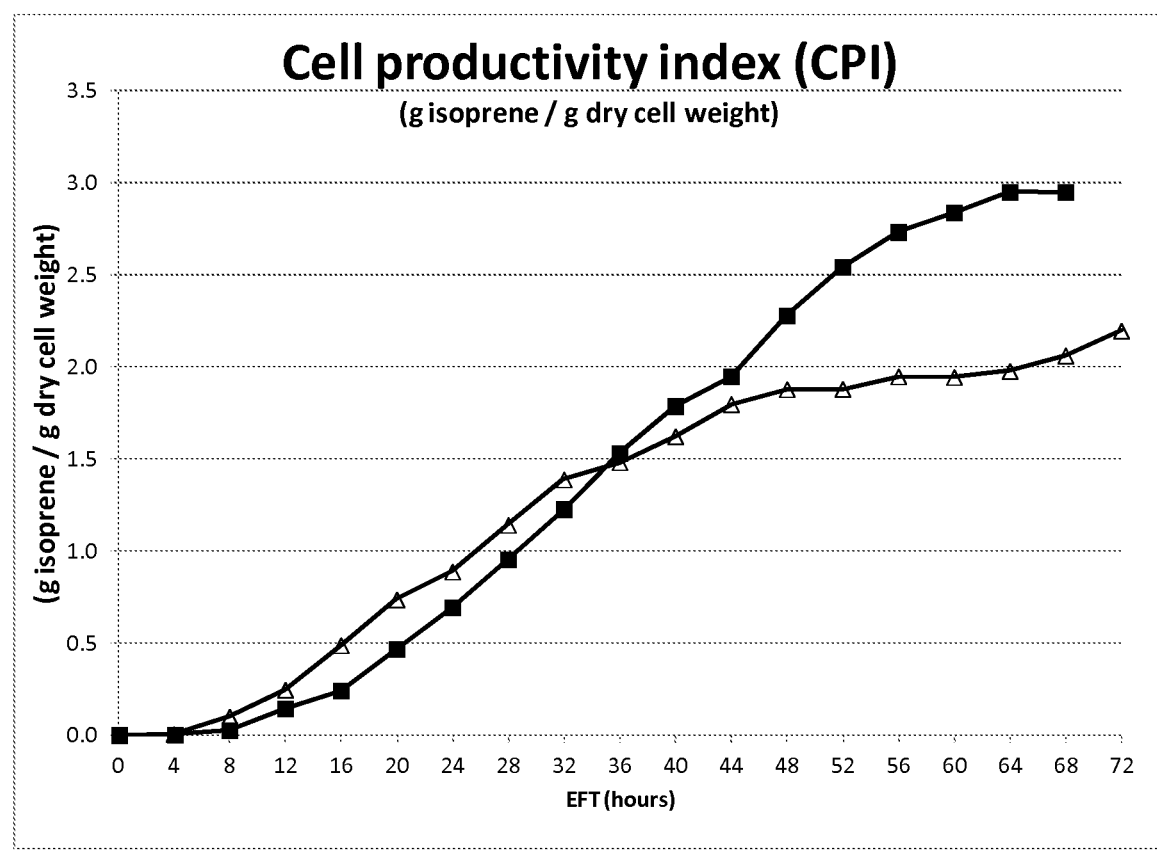
FIG. 43 depicts Cell Productivity Index (CPI) achieved in each 15-L fermentation over time. CMP1082 (pgl+) is depicted by open triangles and CMP1136 (pgl−) is depicted by closed squares.
Figure 44:
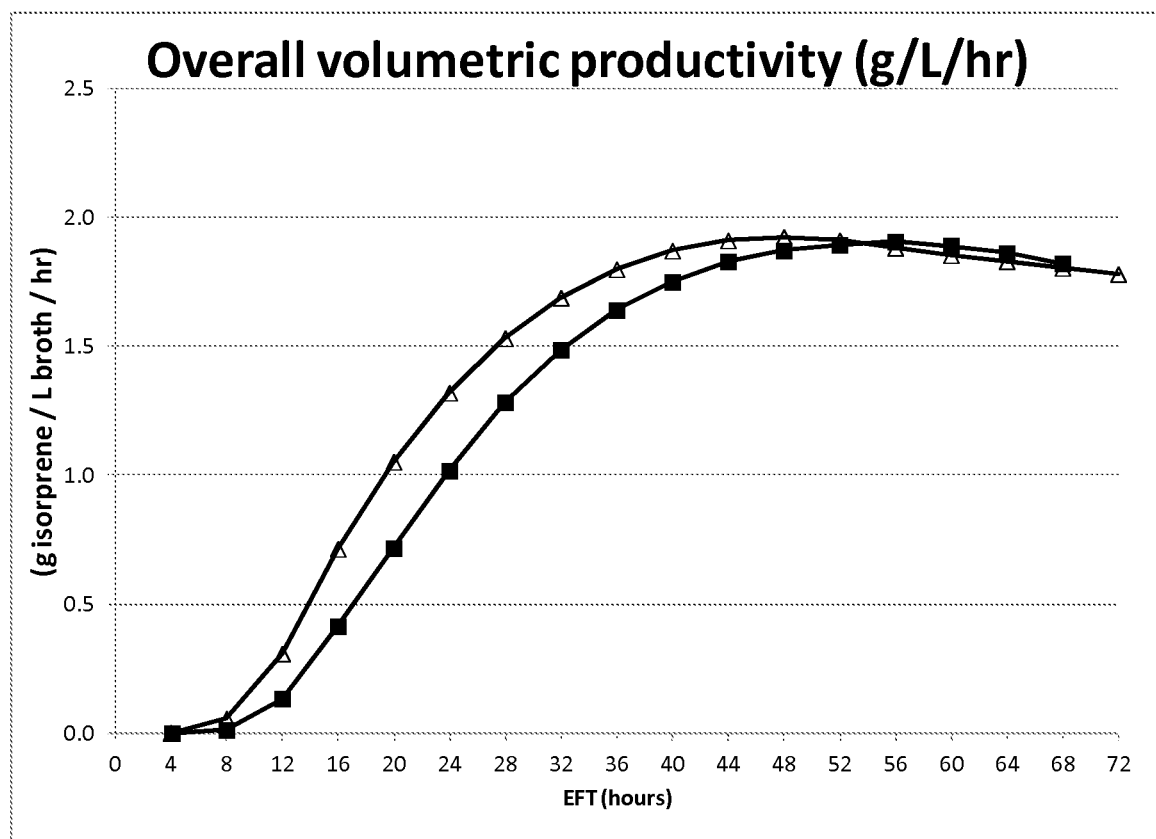
FIG. 44 depicts volumetric productivity achieved in each 15-L fermentation over time. CMP1082 (pgl+) is depicted by open triangles and CMP1136 (pgl−) is depicted by closed squares.
Figure 45:
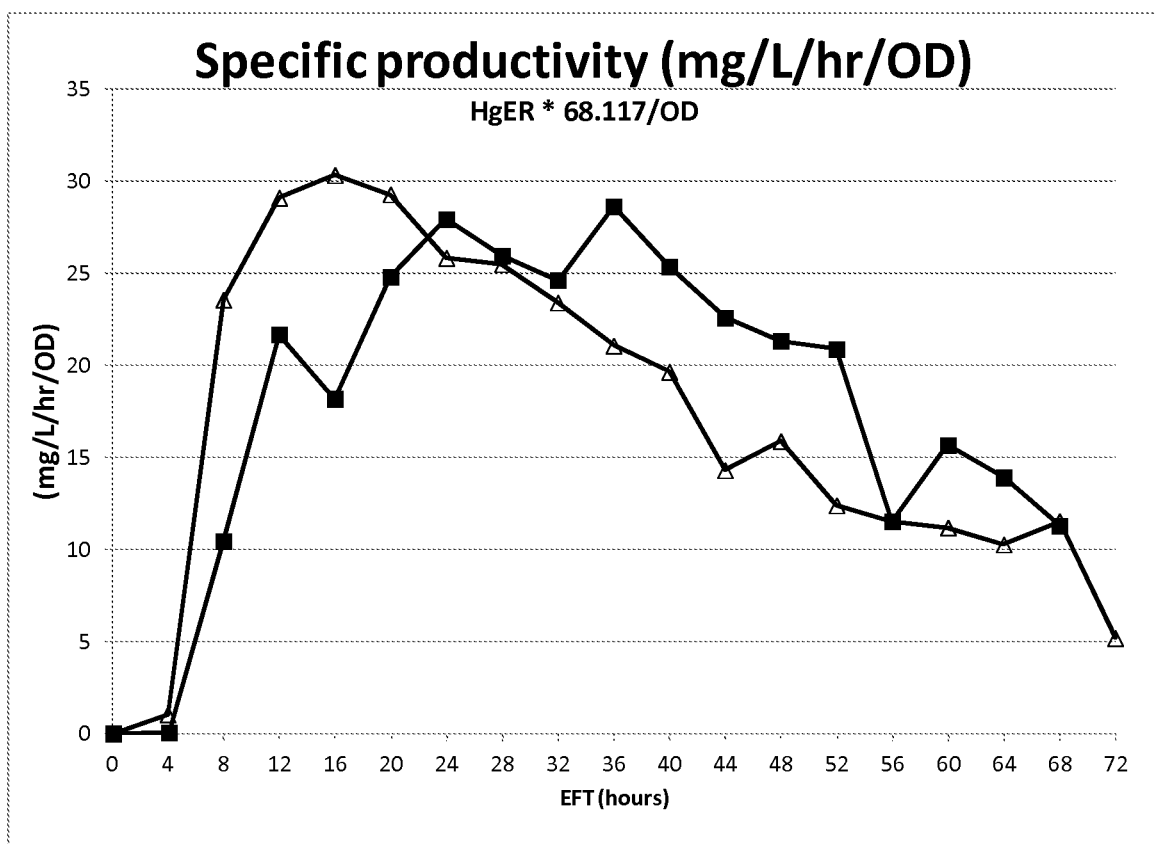
FIG. 45 depicts specific productivity achieved in each 15-L fermentation over time. CMP1082 (pgl+) is depicted by open triangles and CMP1136 (pgl−) is depicted by closed squares.

The pgl− strain (CMP1136) achieved a higher % yield of isoprene on glucose than the pgl+strain (CMP1082). See Table 27 and FIG. 41. The pgl− strain (CMP1136) achieved a higher instantaneous % yield of isoprene on glucose than the pgl+strain (CMP1082) and was able to maintain this high productivity for a longer period of time (~24 hrs at max for pgl− versus ~12 hrs at max for pgl+). See Table 27 and FIG. 42. The pgl− strain (CMP1136) achieved a higher cell productivity index than the pgl+strain (CMP1082). At the end of fermentation 68 to 72 hrs, the pgl− strain had a much higher CPI. Also, at the time of maximum cumulative yield of isoprene on glucose (44 hrs for the pgl+strain and 56 hrs for the pgl− strain) the CPI is higher in the pgl− strain. See Table 27 and FIG. 43. The pgl− strain (CMP1136) achieved about the same overall volumetric productivity as the pgl+ strain (CMP1082). See Table 27 and FIG. 44. The pgl− strain (CMP1136) achieved about the same peak specific productivity as the pgl+strain (CMP1082). However, the pgl− strain (CMP1136) was able to maintain this high productivity for a longer period of time than the pgl+strain (CMP1082) and was notably better late in the fermentation. See Table 27 and FIG. 45.

Example 37: Construction of Strains CMP1237 and CMP1238, Having an Engineered Phosphoenolpyruvate Carboxylase (Ppc) Promoter The chloramphenicol cassette FRT-gb2-Cm-FRT from GeneBridges (Heidelberg, Germany) was amplified with primers 1.2ppcR2 (5'-cgggctttgcttttcgtCAGTGGTTGAAT-TATTTGCTCAGGATGTGGCATCGT-CAAGGGCTAATAC GACTCACTATAGGGCTCG-3' (SEQ ID NO:98)) and ppcF (5'-gttacttggggcgatttttaacatttc-cataagttacgcttatttaaagcAATTAACCCT-CACTAAAGGGCGG-3' (SEQ ID NO:99)). The PCR product thus obtained was purified and used in a recombineering reaction according to the manufacturer's recommendation (GeneBridges) to introduce the construct in strain MG1655 1.6ppc (see U.S. Pat. No. 7,745,184, issued Jun. 29, 2010). A PCR product was amplified from the resulting strain (CMP3_49) using primers CMP79 (5'-GGA AAC ACG GTT TAT CAA GCC CAC C-3' (SEQ ID NO:100)) and CMP80 (5'-cgtgaagatttcgacaacttacgg-3' (SEQ ID NO:101)) and was and used in a recombineering reaction according to the manufacturer's recommendation (GeneBridges) to introduce the construct in BL21(DE3). A P1 lysate was prepared from the latter strain and was used to transduce CMP1133 (U.S. application Ser. No. 13/725,949, filed Dec. 21, 2012, now U.S. Pat. No. 8,865,442, issued Oct. 21, 2014). P1 lysates were prepared and used according to the method described in Ausubel, et al., *Current Protocols in Molecular Biology*, John Wiley and Sons, Inc. A colony was selected on LB+chloramphenicol 5 mg/L and named CMP 1230. The chloramphenicol marker was removed using the protocol recommended by the manufacturer (Gene Bridges, Heidelberg, Germany) to form strain CMP1234. Plasmid pairs pMCM82 (US2011/0159557) and pDW72 (See U.S. patent application Ser. No. 13/283,564), and pMCM1225 (See Table 25) and pDW240 were introduced by electroporation and selection on LB+50 mg/L carbenicillin+50 mg/L spectinomycin. The strains thus obtained were named CMP1237 and CMP1238 respectively.

Example 38: Isoprene Production in Strains Containing an Engineered Ppc Promoter-CMP1237 vs CMP1136

This example examines isoprene production in strains having an engineered phosphoenolpyruvate carboxylase (ppc) promoter.

TABLE 27

| | Isoprene productivity metrics | | | | |
|---|---|---|---|---|---|
| Strain description/ Run Number | Peak instantaneous % yield of isoprene on glucose (g/g %) | Overall Isoprene Volumetric Productivity (g/L/hr) at time of max overall isoprene yield | Max Overall % Yield of Isoprene on glucose (g/g) | CPI (g Isoprene/ gDCW) at time of max overall isoprene yield | Peak Specific Productivity (mg isoprene/ L/hr/OD) |
| CMP1082/ 20111110 | 20.1 | 1.91 | 16.3 | 1.81 | 30.31 |
| CMP1136/ 20111225 | 22.3 | 1.82 | 17.2 | 2.73 | 28.61 |

(i) Solutions

TM3 media recipe (per liter fermentation media): K2HPO4 13.6 g, KH2PO4 13.6 g, MgSO4*7H2O 2 g, citric acid monohydrate 2 g, ferric ammonium citrate 0.3 g, (NH4)2SO4 3.2 g, yeast extract 0.2 g, 1000× Trace Metals Solution 1 ml. All of the components are added together and dissolved in diH2O. The pH is adjusted to 6.8 with ammonium hydroxide (30%) and brought to volume. Media is filter-sterilized with a 0.22 micron filter. Glucose 10.0 g and antibiotics are added after pH adjustment and sterilization.

1000× Trace Metal Solution (Per Liter Fermentation Media):

Citric Acid*H2O 40 g, MnSO4*H2O 30 g, NaCl 10 g, FeSO4*7H2O 1 g, CoCl2*6H2O 1 g, ZnSO4*7H2O 1 g, CuSO4*5H2O 100 mg, H3BO3 100 mg, NaMoO4*2H2O 100 mg. Each component is dissolved one at a time in diH2O. The pH is adjusted to 3.0 with HCl/NaOH, and then the solution is brought to volume and filter-sterilized with a 0.22 micron filter.

(ii) Methods

Cells are grown overnight in Luria-Bertani broth+antibiotics. The day after, they are diluted to an OD600 of 0.1 in 20 mL TM3 medium containing 50 µg/ml of spectinomycin and 50 µg/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. Also, off-gas analysis of isoprene is performed using a gas chromatograph-mass spectrometer (GC-MS) (Agilent) headspace assay (see U.S. Patent Application Publication No.: US 2005/0287655, the contents of which are incorporated herein by reference in its entirety). One hundred microliters of whole broth are placed in a sealed GC vial and incubated at 34° C. and 200 rpm for a fixed time of 30 minutes. Following a heat kill step, consisting of incubation at 70° C. for 7 minutes, the sample is loaded on the GC. The reported specific productivity is the amount of isoprene in µg/L read by the GC divided by the incubation time (30 min) and the measured OD600.

(iii) Results

Figure 46:
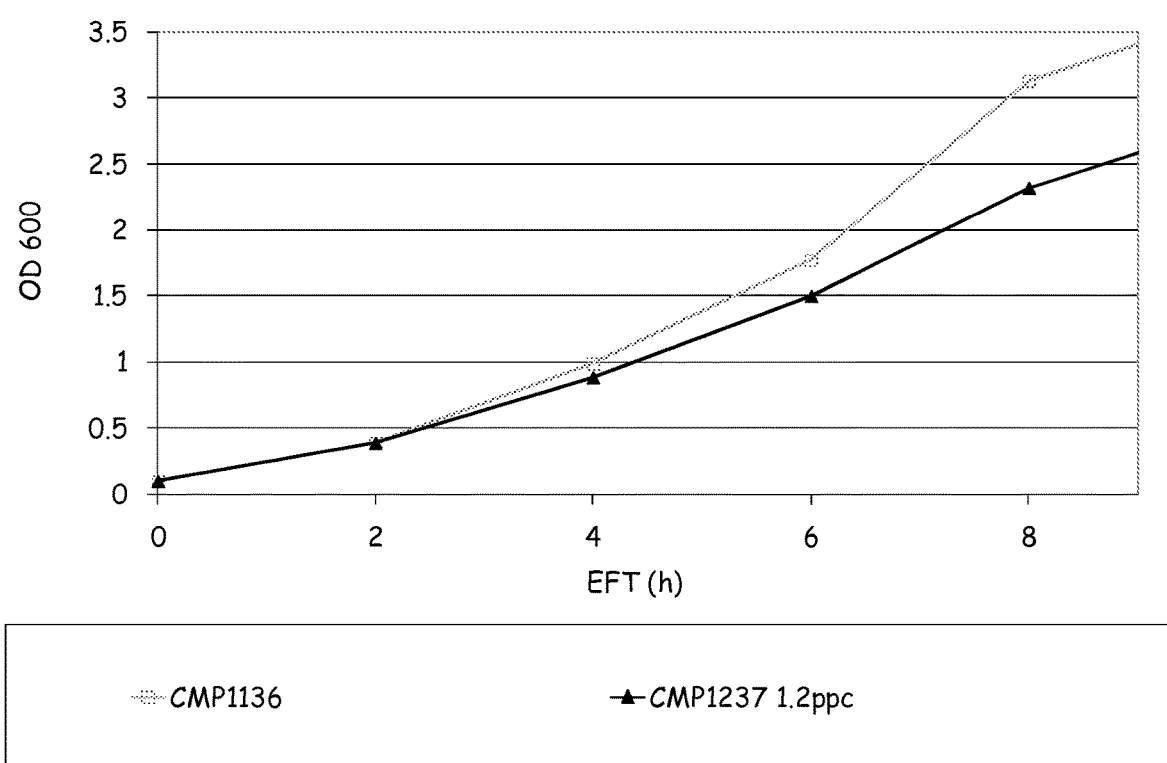
FIG. 46 depicts OD600 of isoprene-producing cultures as a function of time, in a 250-mL Erlenmeyer shake flask, filled with 25 mL of medium, and incubated at 34° C. and 200 rpm.
Figure 47:
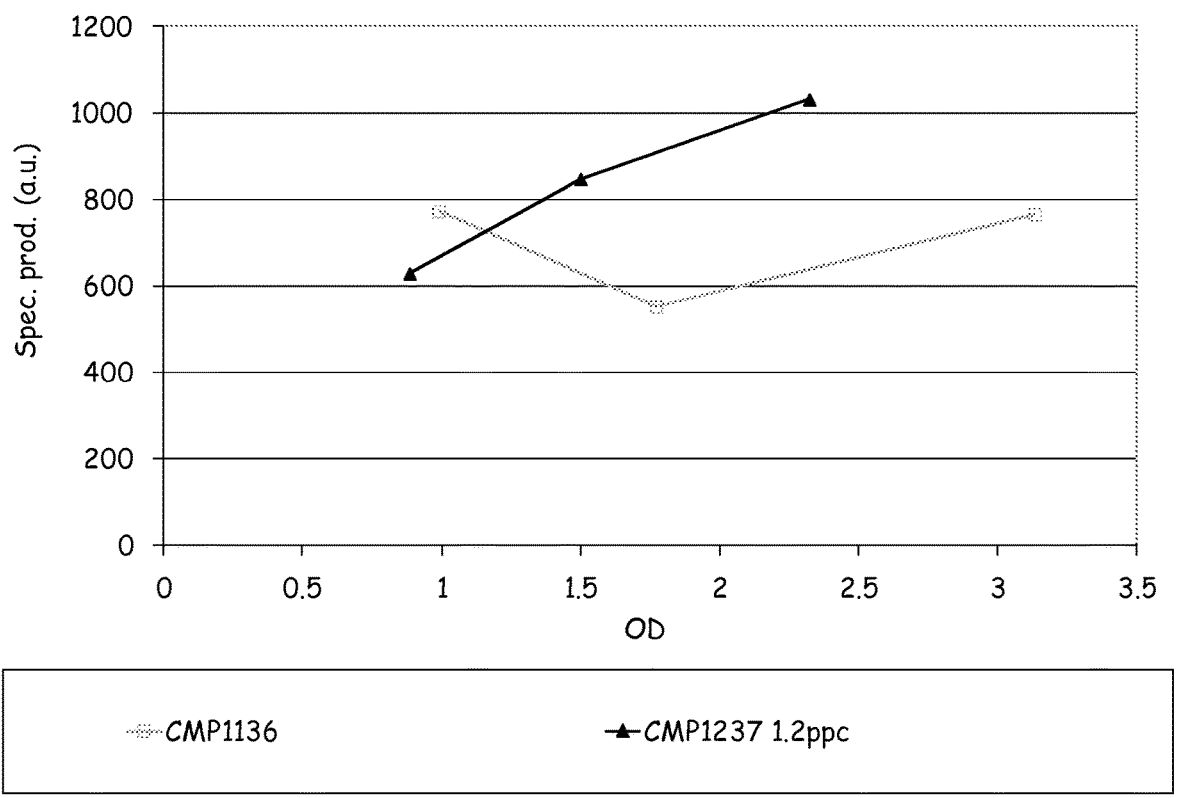
FIG. 47 depicts specific productivity (in arbitrary units) of isoprene-producing cultures as a function of OD. Cultures were incubated in a 250-mL Erlenmeyer shake flask, filled with 25 mL of medium, at 34° C. and 200 rpm.

Strains with engineered ppc promoter (CMP1237) grew slightly slower than the strains with wild-type ppc, CMP1136 (FIG. 46). Specific productivity of CMP1237 strains was higher than the specific productivity of CMP1136 (FIG. 47).

Example 39: Isoprene Production in Strains Containing an Engineered Ppc Promoter on 15 L Scale This experiment was performed to evaluate isoprene production from E. coli (BL21) expressing introduced genes from the mevalonate pathway and grown in fed-batch culture at the 15-L scale. An isoprene producing strain CMP1136 (HMB GI1.2gltA, PyddVIspA_GO, truncIspA, pgl–, pMCM82, pDW72) was run in a standard isoprene production process, described below. The performance metrics (cumulative isoprene yield on glucose, instantaneous isoprene yield on glucose, volumetric productivity of isoprene, specific productivity and cell productivity index) are compared here to an experimental strain that was run in the same conditions to see if any yield improvement can be attributed to the expression of the phosphoenolpyruvate carboxylase gene behind the GI1.2 promoter in the experimental strain, CMP1237(HMB GI1.2gltA, GI1.2ppc, PyddVIspA_GO, truncIspA, pgl–, pMCM82, pDW72).

(i) Solutions

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123 C for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Methods

This experiment was carried out to monitor isoprene formation from glucose at the desired fermentation pH (7.0) and temperature (34° C.). A frozen vial of the E. coli strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L.

The inlet gas using to maintain bioreactor backpressure at 0.7 bar gauge and to provide the oxygen to the production organisms oxygen concentration of 8-10% by volume with the balance of the gas being nitrogen.

The batched media had glucose batched in at 9.7 g/L. Induction was achieved by adding isopropyl-beta-D-1-thiogalactopyranoside (IPTG). A shot of IPTG was added to the tank to bring the concentration to 200 uM when the cells were at an $OD_{550}$ of 6. Once the glucose was consumed by the culture, as signaled by a rise in pH, the glucose feed solution was fed to meet metabolic demands at rates less than or equal to 6 g/min. The fermentation was run long enough to determine the maximum isoprene mass yield on glucose, a total of 68 to 72 hrs elapsed fermentation time.

(iii) Analysis

Isoprene is volatile and can be efficiently swept from the tank by the inlet gas. The isoprene level in the bioreactor off-gas was determined using two mass spectrometers, an iSCAN (Hamilton Sundstrand), and a Hiden HPR20 (Hiden Analytical) mass spectrometer. Oxygen, Nitrogen, and CO2 levels in the offgas were determined by the same mass spec units.

Dissolved Oxygen in the fermentation broth is measured by sanitary, sterilizable probe with an optical sensor provided Hamilton Company.

The citrate, glucose, acetate, and mevalonate concentrations in the fermentor broth was determined in broth samples taken at 4 hour intervals by an HPLC analysis. Concentration in broth samples were determined by comparison of the refractive index response versus a previously generated calibration curve using standard of a known concentration.

(iii) Results

Figure 48:
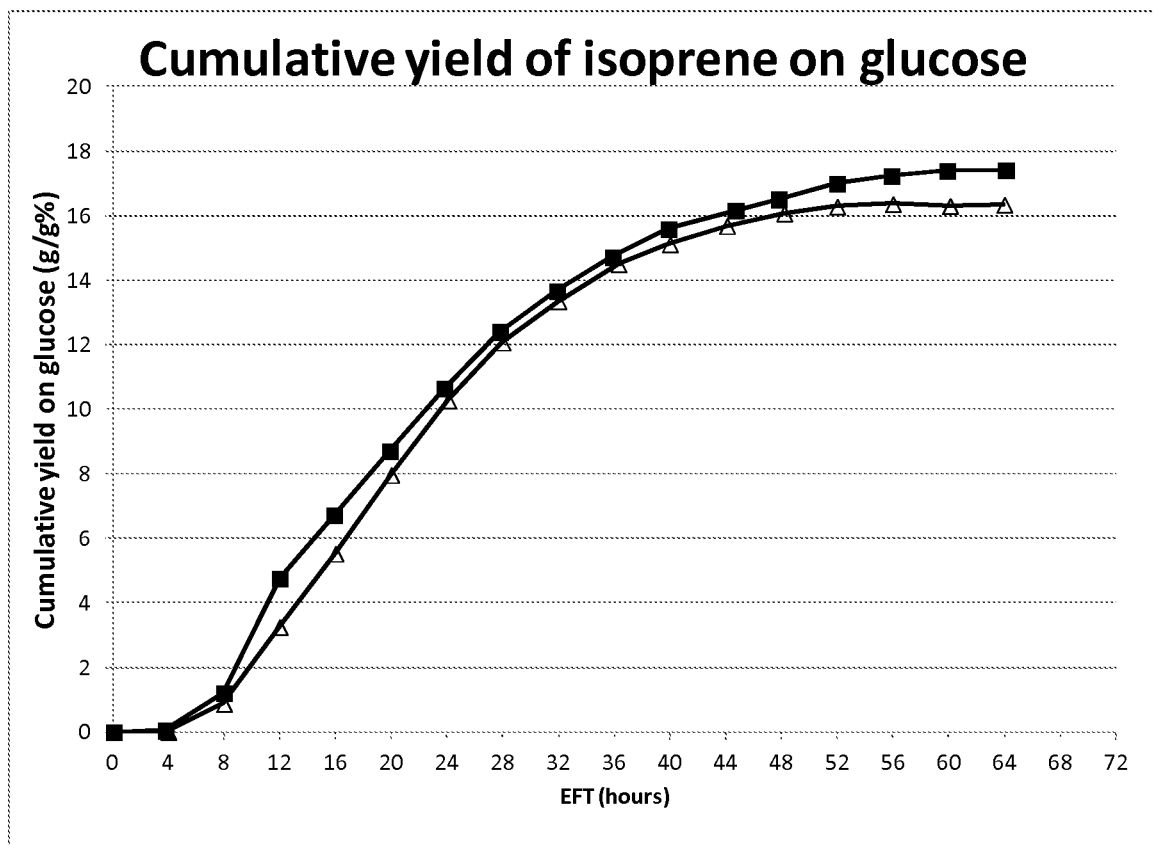
FIG. 48 depicts yield of isoprene on glucose achieved in each 15-L fermentation over time. % wt Yield on glucose=Isoprene total (t)/[(Feed Wt(0)−Feed Wt(t)+83.5)*0.59)], where 0.59 is the wt % of glucose in the glucose feed solution and 83.5 is the grams of this feed batched into the fermentor at t=0. Each feed had its weight % measured independently. CMP1136: wild type ppc promoter (open triangles); CMP1237: GI1.2ppc promoter (closed squares).
Figure 49:
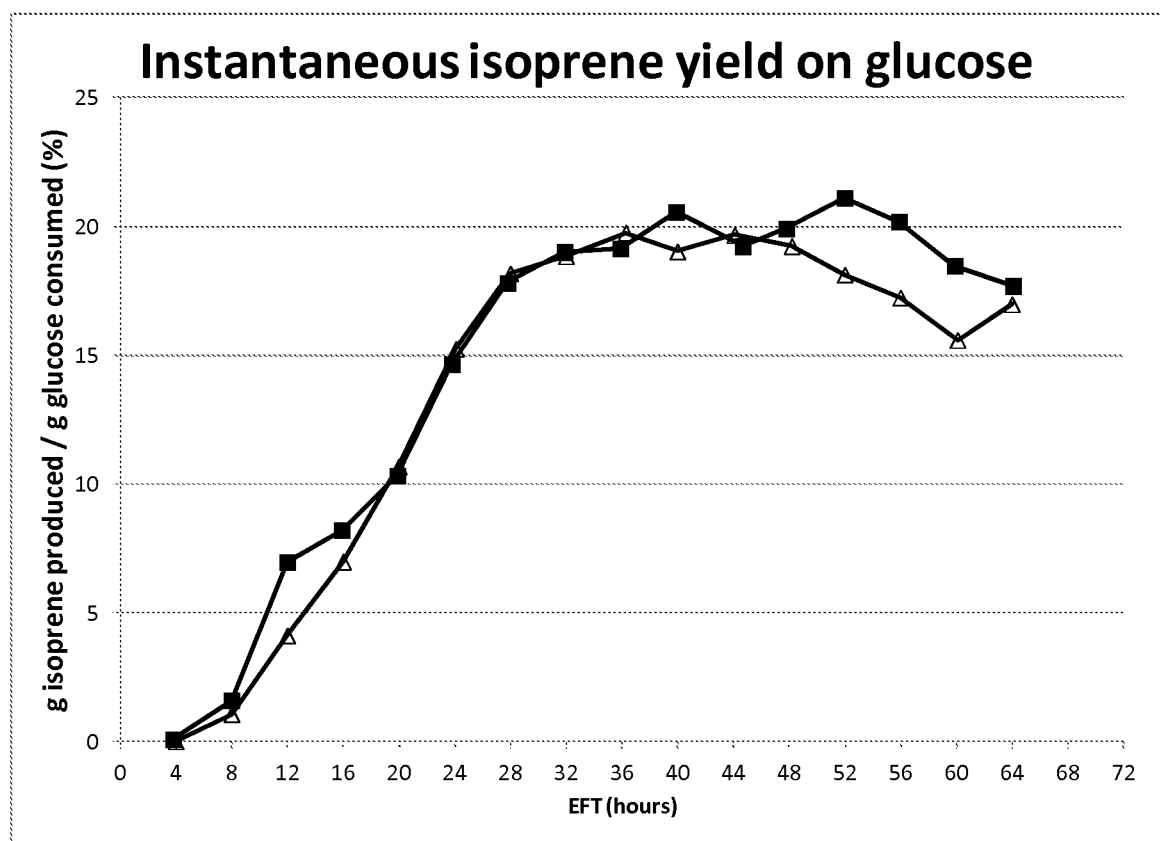
FIG. 49 depicts instantaneous yield of isoprene on glucose achieved in each 15-L fermentation over time. Isoprene Instantaneous yield was calculated using the formula: Isoprene Inst. yield (g/g %)=Isoprene produced (t$_1$−t$_0$)/consumed glucose (t$_1$−t$_0$)*100. CMP1136: wild type ppc promoter (open triangles); CMP1237: GI1.2ppc promoter (closed squares).
Figure 50:
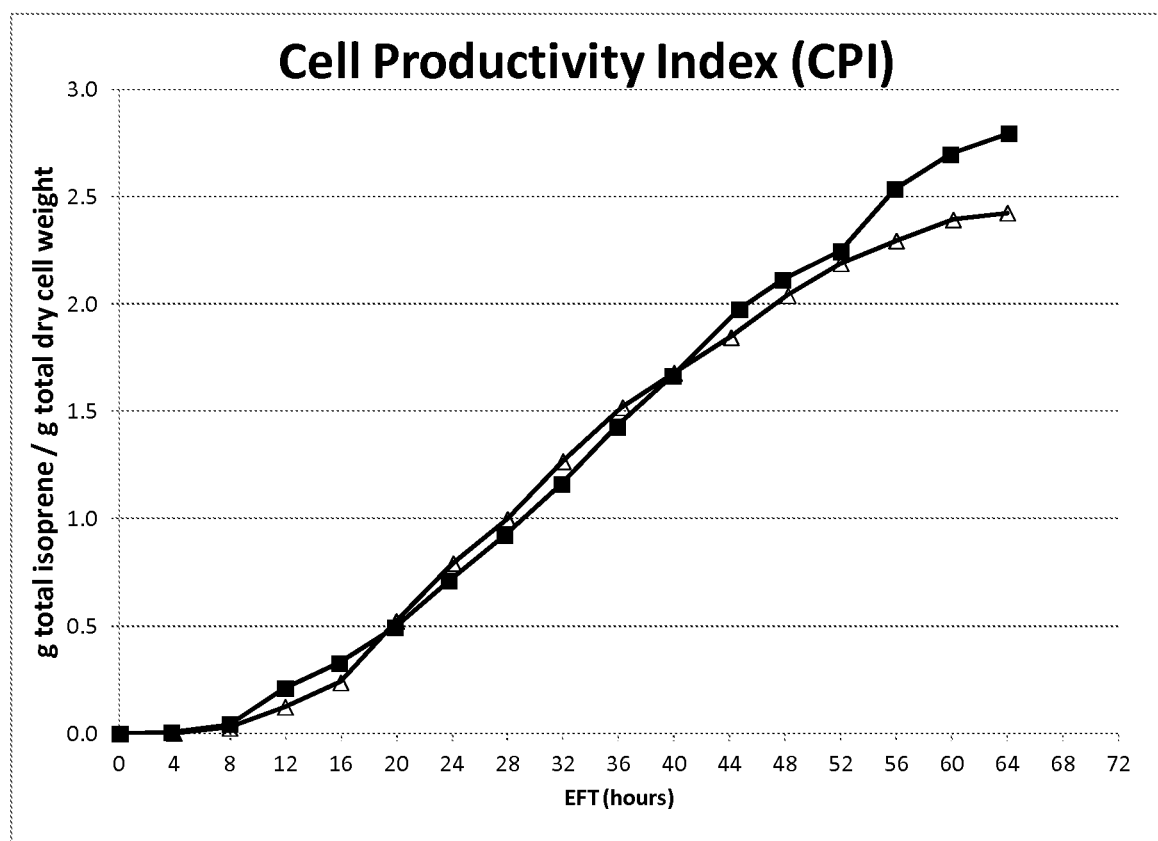
FIG. 50 depicts cell productivity index (CPI) achieved in each 15-L fermentation over time. Cell Productivity Index (CPI) was calculated using the following formula: CPI=total grams Isoprene/total grams dry cell weight. CMP1136: wild type ppc promoter (open triangles); CMP1237: GI1.2ppc promoter (closed squares).
Figure 51:
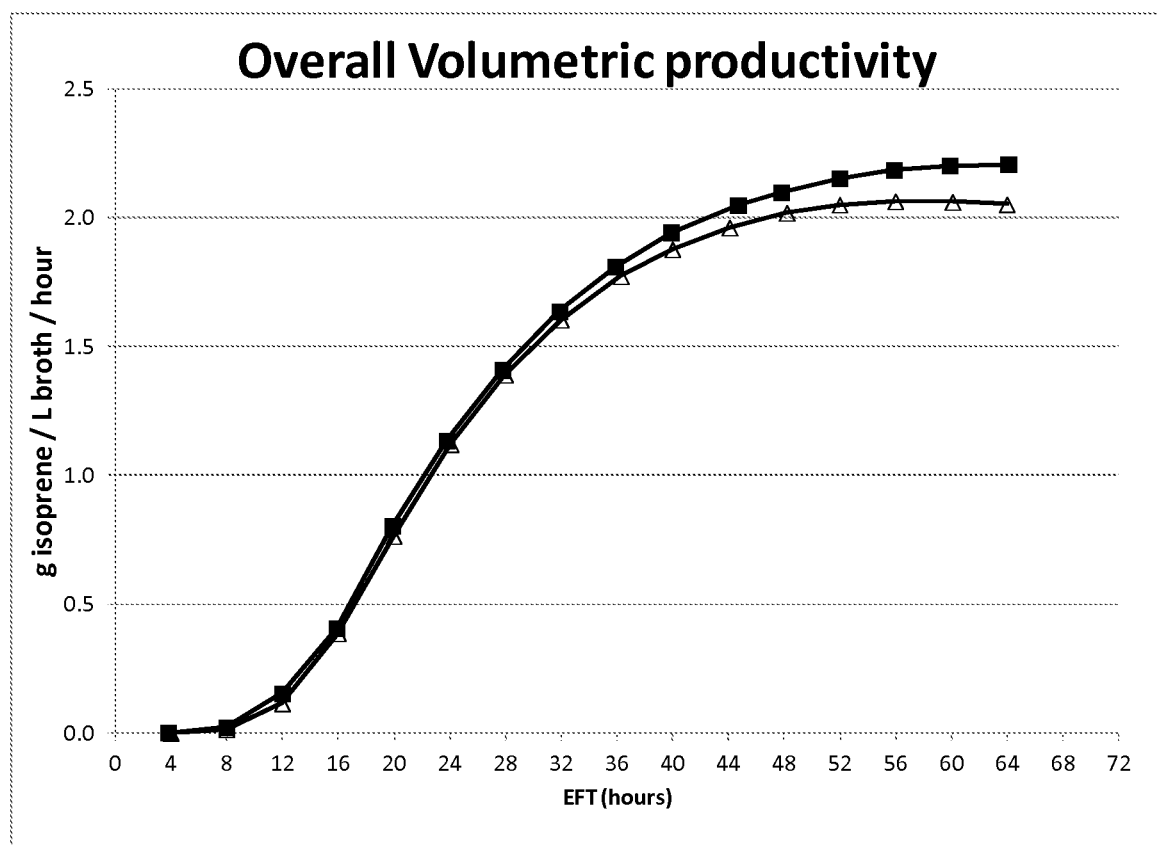
FIG. 51 depicts volumetric productivity achieved in each 15-L fermentation over time. Volumetric Productivity was calculated using the following formula: [ΣHGER(t)/1000*68.117)]/[t−t$_0$], where the summation is from t$_0$ to t. Tank turnaround time is not factored in. CMP1136: wild type ppc promoter (open triangles); CMP1237: GI1.2ppc promoter (closed squares).
Figure 52:
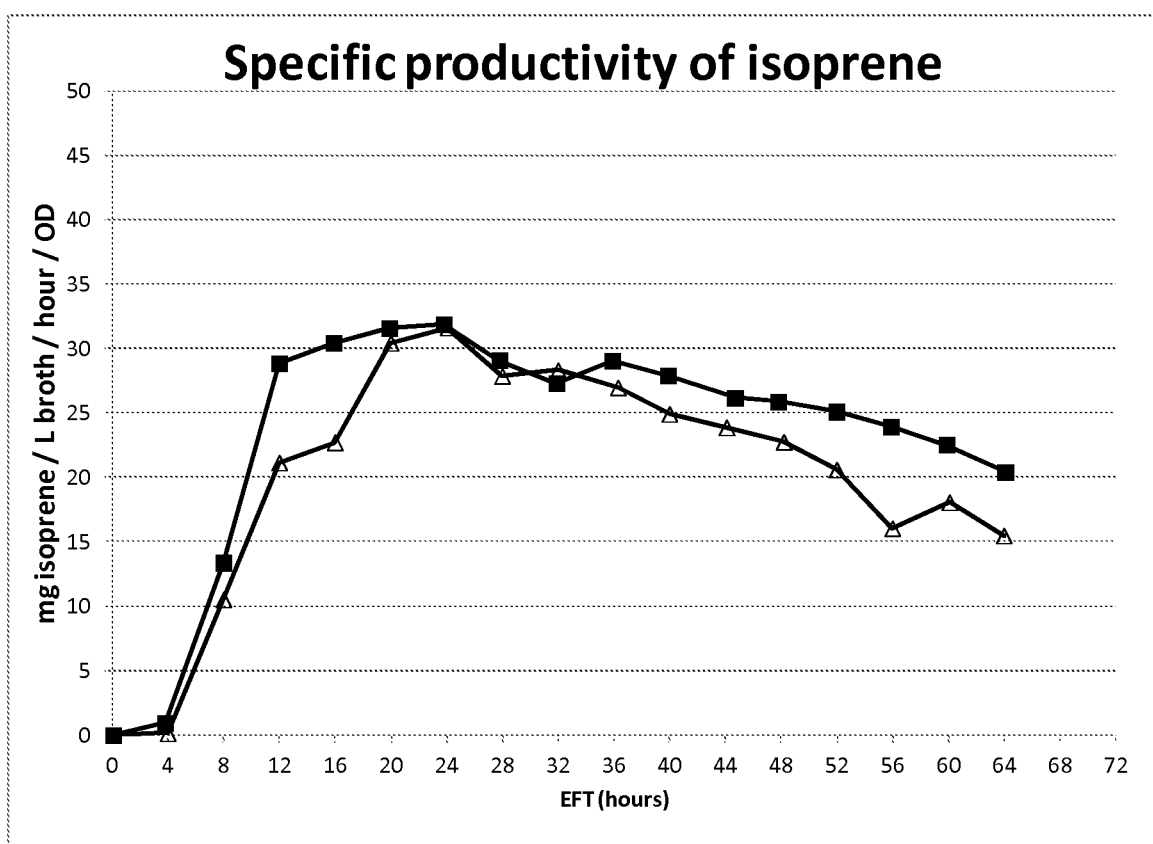
FIG. 52 depicts specific productivity achieved in each 15-L fermentation over time. Specific Productivity was calculated using the following formula: Specific productivity (mg/L/hr/OD)=HgER*68.117 g/mol/OD. HgER is the Isoprene Evolution Rate in (mmol/L/hr). OD=optical density=Absorbance at 550 nm*dilution factor in water. CMP1136: wild type ppc promoter (open triangles); CMP1237: GI1.2ppc promoter (closed squares).

The results are summarized in Table 28. The GI1.2 ppc strain (CMP1237) achieved a higher % yield of isoprene on glucose (FIG. 48), a higher instantaneous % yield of isoprene on glucose (FIG. 49), a higher cell productivity index (FIG. 50), a higher overall volumetric productivity (FIG. 51), and about the same peak specific productivity (FIG. 52) of isoprene compared to the wildtype ppc promoter strain (CMP1136).

TABLE 28

Isoprene productivity metrics

| Strain description/ Run Number | Peak instantaneous % yield of isoprene on glucose (g/g %) | Overall Isoprene Volumetric Productivity (g/L/hr) at time of max overall isoprene yield | Max Overall % Yield of Isoprene on glucose (g/g) | CPI (g Isoprene/ gDCW) at time of max overall isoprene yield | Peak Specific Productivity (mg isoprene/ L/hr/OD) |
|---|---|---|---|---|---|
| CMP1237/ 20120407 | 21.1 | 2.21 | 17.4 | 2.80 | 31.86 |
| CMP1136/ 20120135 | 19.7 | 2.05 | 16.3 | 2.43 | 31.62 |

Example 40: GI1.2 Ppc Construct has Less Phosphoenolpyruvate Carboxylase Activity than a Wild-Type Ppc Promoter (i) Materials and Methods Cells from 15-L fermentations with strains CMP1237 (engineered ppc promoter) and DW719 (wild-type ppc) have been harvested by centrifugation. Supernatant was discarded and the pellet was resuspended in lysis buffer (50 mM Tris HCl, pH 8, 1 mg/ml lysozyme, 1 mM DTT, 10 µg/ml DNAse, 1 mM PMSF). Cells were subject one freeze/thaw cycle, before centrifugation to remove cell debris. Supernatant was collected and stored on ice.

The assay monitors the conversion of phosphenolpyruvate (PEP) to oxaloacetate (OAA) by coupling the conversion of OAA to malate by malate dehydrogenase (MDH) and monitoring the oxidation of NADH to $NAD^+$.

The assay was carried out in a microtiter plate with the following reagents: 0.1 M Tris pH 8, 0.1 mM NADH, 10 mM $KHCO_3$, 10 mM $MgCL_2$, 5 mM PEP, 0.5 mM Acetyl-CoA, 5 u/ml Malate dehydrogenase, 10-20 µL sample. The decrease in absorbance at 340 nm was observed over 100 sec.

(ii) Results

At around 48 h in the fermentation, phosphoenolpyruvate carboxylase activity of DW719 was 49 activity/$OD_{260}$ while activity of CMP1237 was 34 activity/$OD_{260}$.

Figure 53:
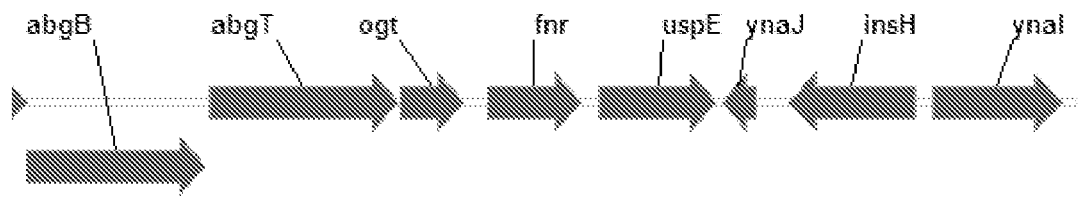
FIG. 53 depicts genome organization of *E. coli* MG1655 around FNR (source: GenBank U00096)

Example 41: Construction of Strains CMP1189 and CMP1191, Having a Restored FNR Protein, and Production of Isoprene by the Latter A P1 lysate was prepared from strain JW1326 from the Keio collection (Baba et al. 2006. *Mol. Syst. Biol.* 2: 2006.0008) and was used to transduce CMP1133 (U.S. patent application Ser. No. 13/725,949, filed Dec. 21, 2012, now U.S. Pat. No. 8,865,442, issued Oct. 21, 2014). P1 lysates were prepared and used according to the method described in Ausubel, et al., *Current Protocols in Molecular Biology*, John Wiley and Sons, Inc. A colony was selected on LB+kanamycin 10 mg/L and named CMP1180. A P1 transduction is able to transduce up to 100 kB DNA. As ynaJ is in close proximity of FNR (FIG. 53), selecting for a mutation in ynaJ will most probably also bring the DNA encoding FNR from the strain the lysate was made. The Keio collection has been built in a K-12 strain, which has a functional FNR. That is unlike *E. coli* BL21 in which FNR contains a stop codon in the protein (Studier et al. 2009. *J Mol. Biol.* 394:653-680). FNR was amplified from CMP1180 with primers CMP51 (5'-CAG GTA ATG CAT TAC GGC CAA CTG-3' (SEQ ID NO:102)) and CMP52 (5'-caggctgtacgctggctgatgac-3' (SEQ ID NO:103)) and sequenced with CMP53 (5'-ATG ATC CCG GAA AAG CGA ATT ATA CG-3' (SEQ ID NO:104)). The sequence proved that a functional FNR allele had been restored. The kanamycin marker was removed using the protocol recommended by the manufacturer (Gene Bridges, Heidelberg, Germany) to form strain CMP1189. Plasmid pairs pMCM82 (US2011/0159557) and pDW72 (See U.S. patent application Ser. No. 13/283,564) were introduced by electroporation and selection on LB+50 mg/L carbenicillin+50 mg/L spectinomycin. The strains thus obtained were named CMP1191.

Isoprene production by strain CMP1191 was compared to CMP1136 using the protocol described in Example 38. As FNR is an oxygen sensor, another set of shake flask was done with the same medium but the flasks were incubated at 50 rpm rather than 200 rpm. That led to an oxygen-limited culture.

Results

Figure 54:
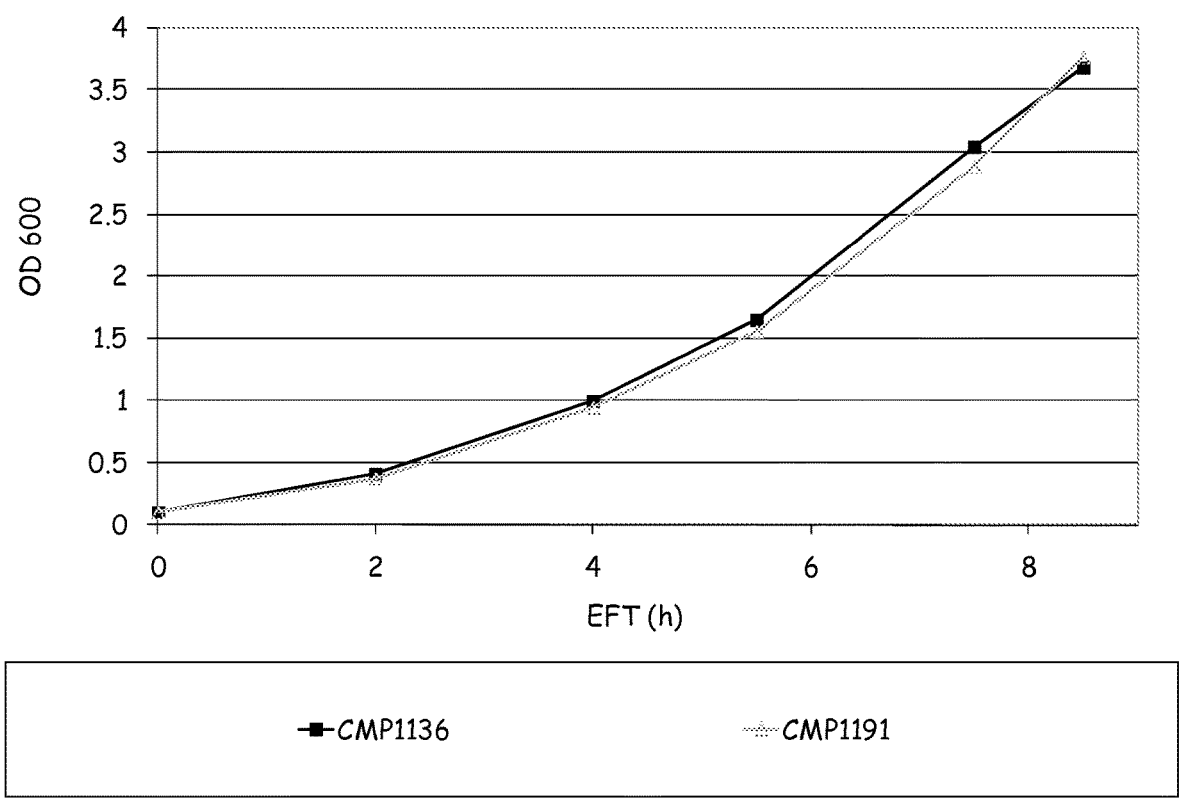
FIG. 54 depicts OD600 of isoprene-producing cultures as a function of time, in a 250-mL Erlenmeyer shake flask, filled with 25 mL of medium, and incubated at 34° C. and 200 rpm.
Figure 55:
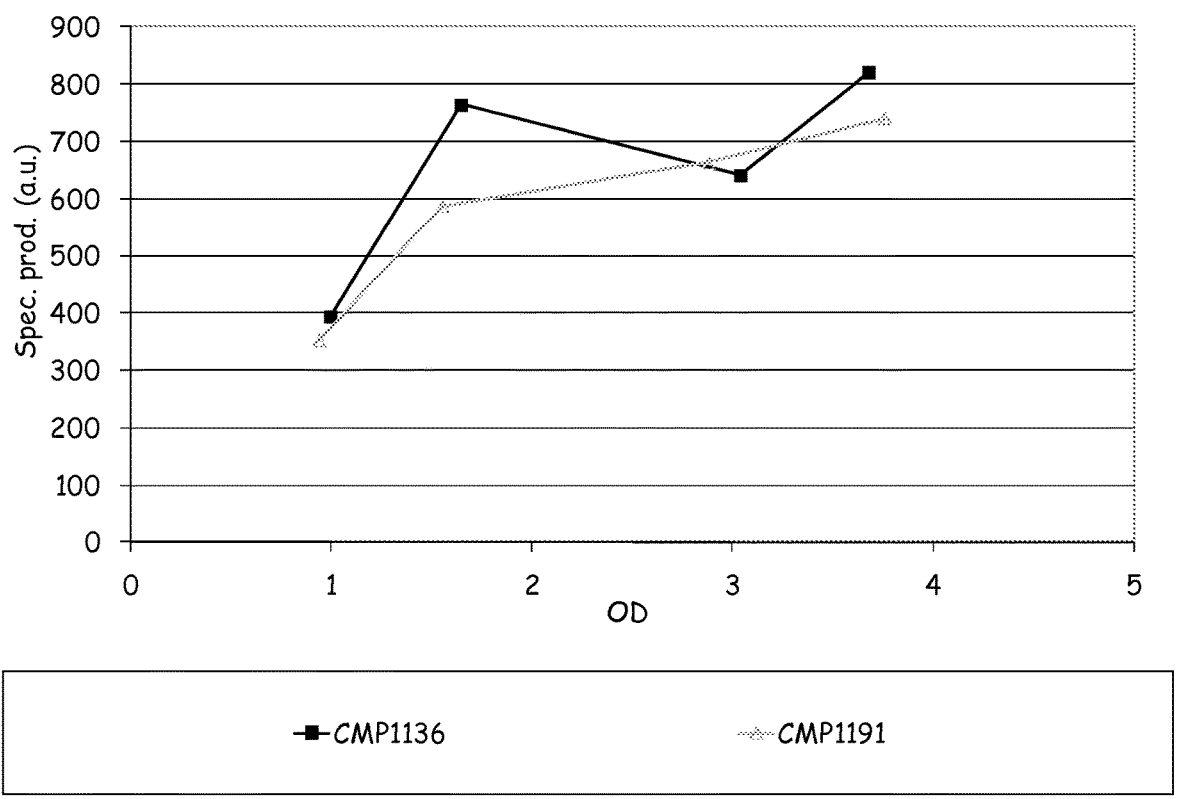
FIG. 55 depicts specific productivity (in arbitrary units) of isoprene-producing cultures as a function of OD. Cultures were incubated in a 250-mL Erlenmeyer shake flask, filled with 25 mL of medium, at 34° C. and 200 rpm.
Figure 56:
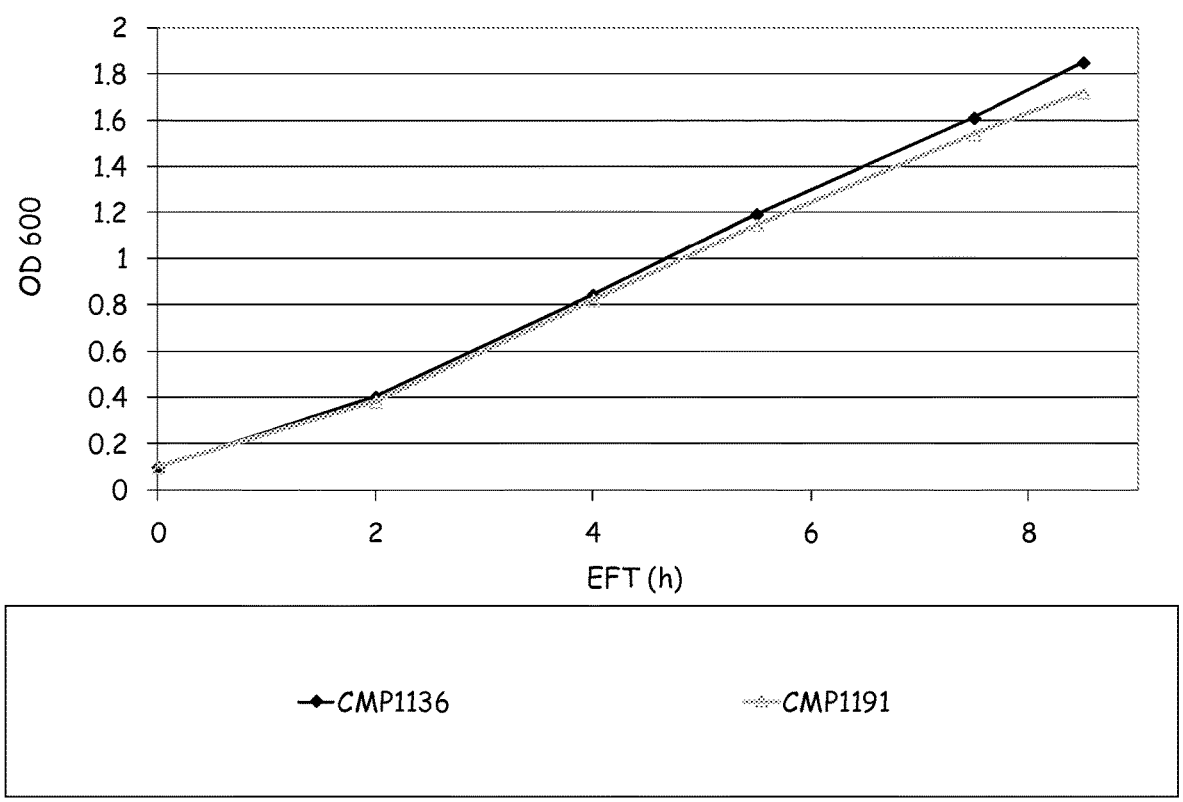
FIG. 56 depicts OD600 of isoprene-producing cultures as a function of time, in a 250-mL Erlenmeyer shake flask, filled with 25 mL of medium, and incubated at 34° C. and 50 rpm.
Figure 57:
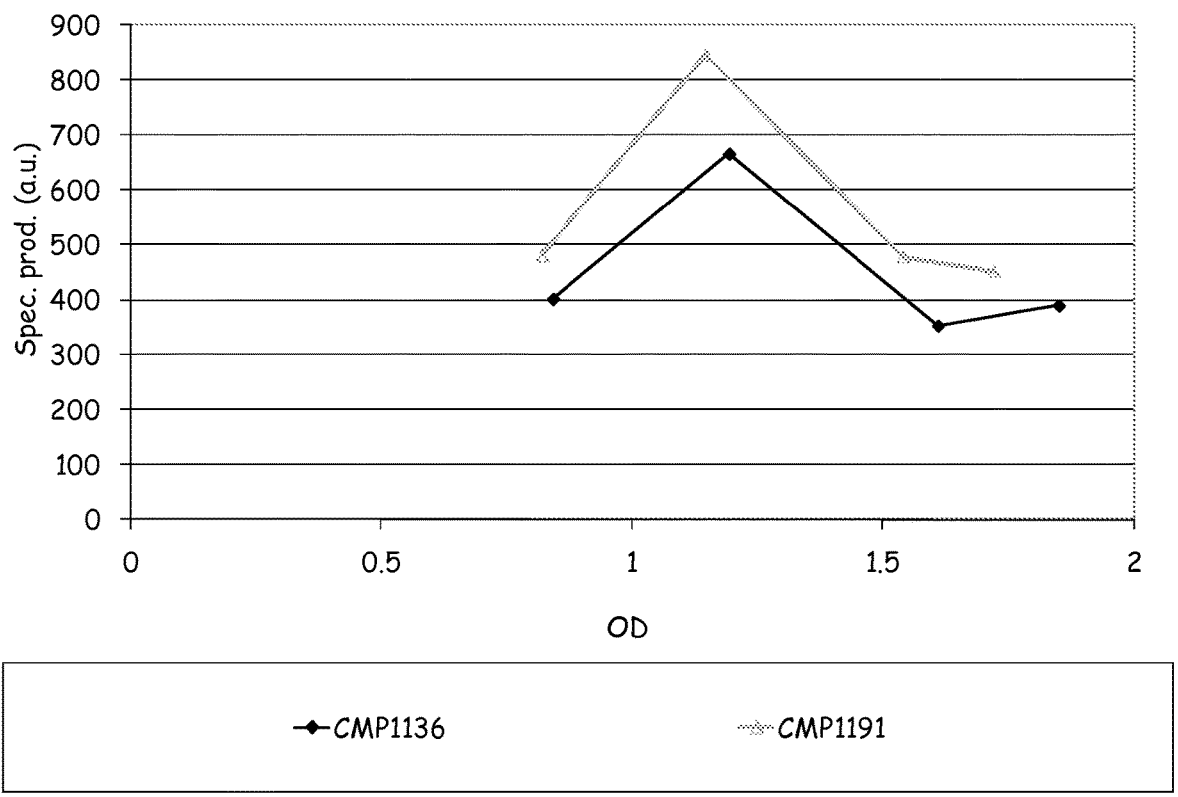
FIG. 57 depicts specific productivity (in arbitrary units) of isoprene-producing cultures as a function of OD. Cultures were incubated in a 250-mL Erlenmeyer shake flask, filled with 25 mL of medium, at 34° C. and 50 rpm.

Growth of strain with functional FNR was similar to growth of strain with mutated FNR in well-aerated flask (FIG. 54). When oxygen was limited by reducing agitation, growth of strain with functional FNR was a bit slower (FIG. 55). Specific productivity of CMP1136 (mutated FNR) and CMP1191 (functional FNR) was similar in well-aerated flask (FIG. 56). When oxygen was limited by reducing agitation, the strain with the functional FNR had an improved specific productivity (FIG. 57).

Example 42: Construction of MD12-746 (Having an ackA-Pta Mutation)

A DNA fragment containing the ackA-pta genes interrupted by a chloramphenicol marker was amplified by PCR using strain MG1655 AackA-pta::Cm (see U.S. Pat. No. 7,745,184, issued Jun. 29, 2010) as a template, and primers ackACF (5'-gtgcaaattcacaactcagcgg-3' (SEQ ID NO:105)) and ptaCR (5'-CAC CAA CGT ATC GGG CAT TGC-3' (SEQ ID NO:106)). The PCR product obtained was used in a recombineering reaction as recommended by the manufacturer (Gene Bridges, Heidelberg, Germany) to integrate the PCR product at the ackA-pta locus in strain CMP258 (U.S. Patent Application Publication No. 2012/0045812, filed Aug. 5, 2011). Colonies were selected on LB+5 µg/ml of chloramphenicol. One colony was picked and was named MD10-491. A P1 lysate was made from this strain and used to transduce CMP1133. The chloramphenicol marker was looped out by electroporating pCP20 (Datsenko and Wanner. 2000. *PNAS* 97:6640-5) in the strain, selecting two colonies on LB+50 ug/ml carbenicillin at 30° C., then restreaking those colonies on an LB plate at 42° C. A Chloramphenicol sensitive colony was selected from those plates and named MD12-746.

Isoprene production by strain MD12-746 was compared to DW719 using the protocol described in Example 38.

Results

Figure 58:
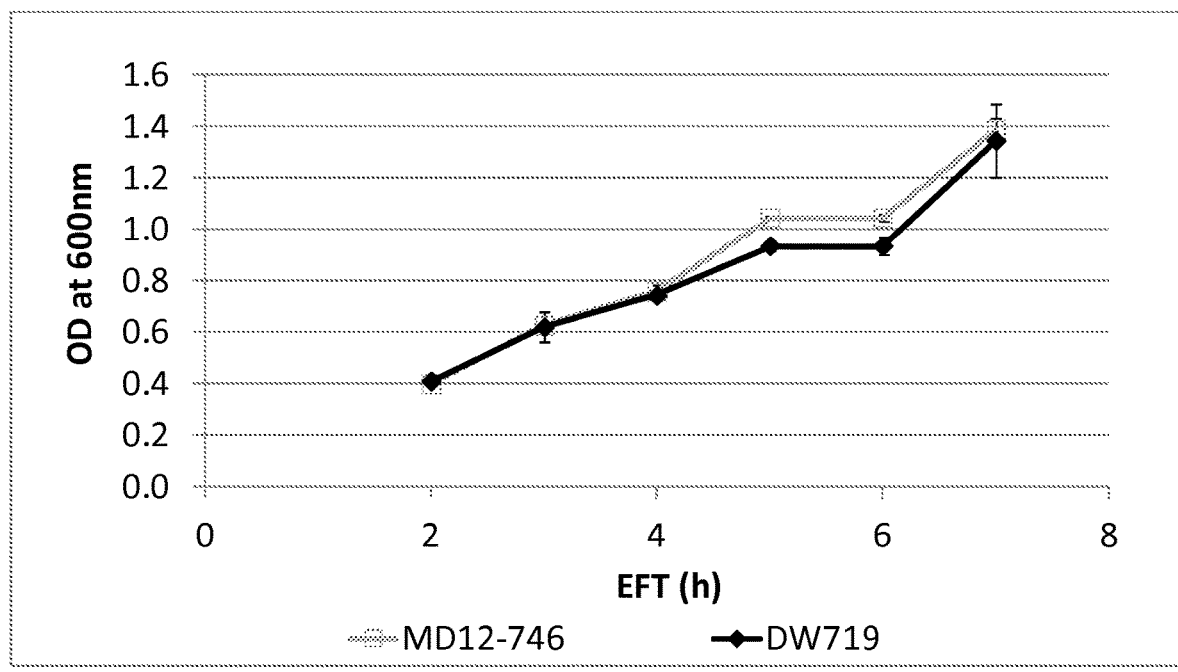
FIG. 58 depicts OD600 of isoprene-producing cultures as a function of time.
Figure 59:
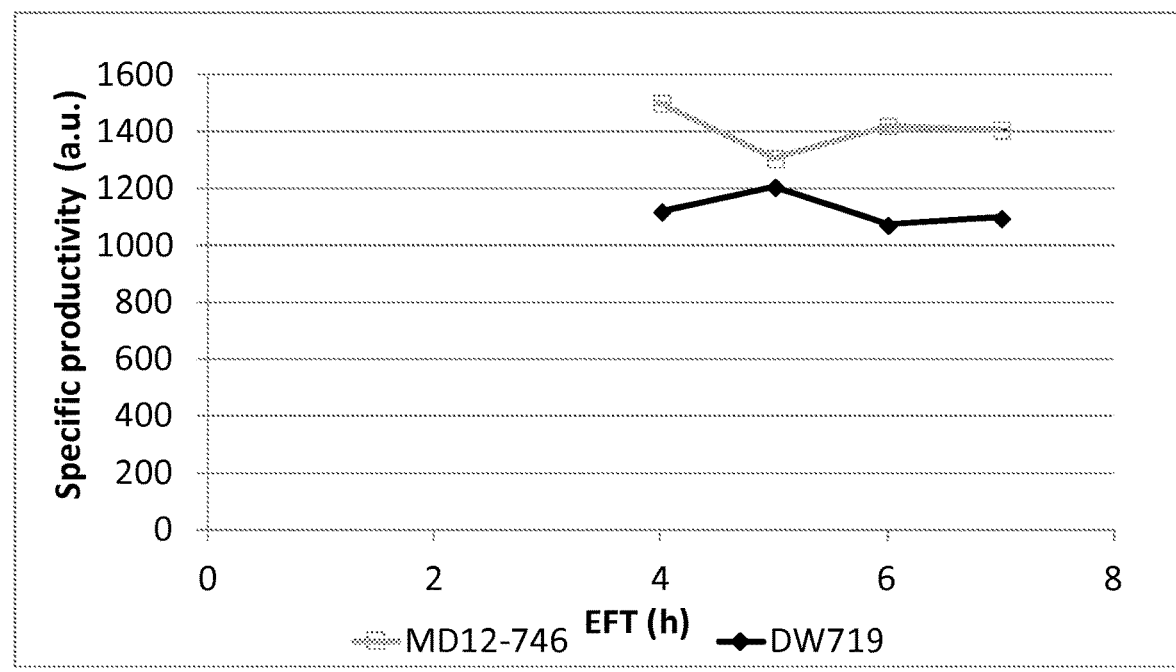
FIG. 59 depicts specific productivity (in arbitrary units) of isoprene-producing cultures as a function of time.

Increased specific productivity of isoprene was observed in MD12-746 versus DW719 (FIGS. 58-59).

Example 43: Increased Specific Productivity of Isoprene in a Strain Overexpressing iraM This example details a microarray analyses of 15-L fermentations performed by the method below.

(i) Methods

Strains used in this genome-wide transcription study are CMP457 and MCM1020. Strain MCM1020 was constructed by electroporating plasmids pTrcHis2B (Invitrogen, Carlsbad, Calif.) and pCL1920 (see U.S. Patent Application Publication No. 2009/0203102, the contents of which is incorporated herein by reference) into strain CMP258 (see International Patent Application No. PCT/US2011/058188, the contents of which is incorporated herein by reference) and selecting a colony on LB+50 mg/L spectinomycin+50 mg/L carbenicillin.

Fermentation samples were quickly diluted 1:5 in RNALater (Qiagen, Valencia, Calif.) and frozen at −20° C. Cells were harvested and lysed in Trizol (Invitrogen) and incubated at room temperature for 5 minutes. Nucleic acids were isolated by extracting by adding 20% ice cold chloroform. The solution was mixed and incubated for 5 minutes at room temperature followed by centrifugation at 13,000 rpm at 4° C. for 15 minutes. The top water phase was isolated and an equal volume of ice cold ethanol was added. RNA was isolated using the RNEasy mini kit (Qiagen). Following the manufactures instructions, DNA was degraded during the procedure by adding a DNase solution (10 µL DNase I stock in 70 µL RDD buffer) (Qiagen) and incubating at room temperature for 30 minutes. RNA was eluted from the RNeasy column in nuclease-free water. A minimum of 20 µg of RNA was collected from each sample as measured using a Nanodrop instrument. RNA was further purified by precipitation by adding ⅒th volume if 3M sodium acetate. Glycogen (RNA grade from Fermentas) was added to a final concentration of 1 ug/uL followed by the addition of 2.5 volume of ice cold ethanol. The solution was incubated for 60 minutes at −80° C. and then centrifuged for 15 minutes at 10.000 rpm. The supernatant was discarded and the RNA pellet was washed briefly with ice cold 70% ethanol. The RNA pellet was air dried for 20 minutes and dissolved in nuclease-free water at a concentration of 1 µg/µL. Quality and concentration was measured using a Nanodrop instrument and by gel electrophoresis. Synthesis of cDNA, labeling and transcription analysis was performed by Roche NimbleGen (Iceland) using a 385K 4-plex microarray designed specifically for *E. coli* BL21. The resulting data was analyzed using the GenespringGX Version 11 (Agilent).

(ii) Results

Figure 60:
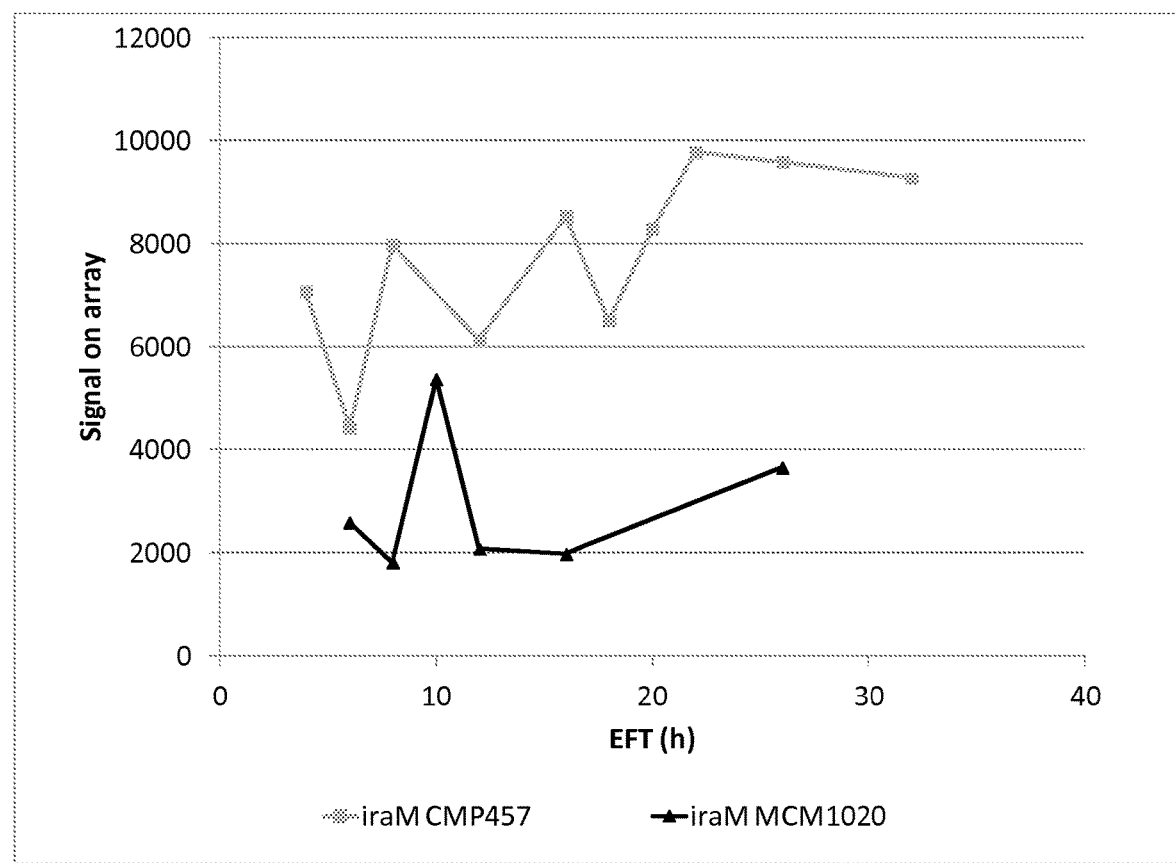
FIG. 60 depicts RNA hybridization signal on the array form CMP457 (producing isoprene) vs MCM1020 (control strain).

By analyzing the data, it was found that the proteolysis inhibitor iraM was induced in isoprene producing strains (FIG. 60).

Example 44: Construction of Strains MD11-610 and MD11-612

MD11-610: PL.6 Promoter in Front of iraM.

A PCR product (#1) was generated using primers MQ10-127F (5'-GTT AAC TGG TTG CAG TCA CCT GGA GGC ACC AGG CAC CGC ATC AAC AAA GTT CAT TTG TAA AAA TGG AGA TAA TTG TGT AGG CTG GAG CTG CTT C-3' (SEQ ID NO:107)) and MQ10-127R (5'-TCG TGT CAA TTA CTA TCC ACT TCA TGT TTT TTT ACC TCC TTT GCA CCT TCA TGG TGG TCA GTG CGT CCT GCT GAT GTG CTC AGT ATC ACC GCC AGT GGT ATT TAT GTC AAC ACC GCC AGA GAT AAT TTA TCA CCG CAG ATG GTT ATC TGT ATG TTT TTT ATA TGA ATT CAT ATG AAT ATC CTC CTT A-3' (SEQ ID NO:108)) with plasmid pKD3 (Datsenko and Wanner. 2000. *PNAS* 97:6640-5) as a template. PCR product #2 was generated using primers MQ10-128F (5'-ATG AAG TGG ATA GTA ATT GAC ACG A-3' (SEQ ID NO:109)) and MQ11-128R (5'-GCA TTC TTT CAA TAG CTT TGC TTT CTT CAA CGT CTT TTT TGC AAA GGT GGT AAG CAC ATT TTA TTT CTT AGT CAA GTC AAA AGC CTC CGG TCG GAG GCT TTT GAC TTT ACT TGA GCC CAT ATG GGC ATA TAT T-3' (SEQ ID NO:110)), with chromosomal DNA of BL21 (Novagen) as template. Primers MQ10-127F and MQ11-128R-term (5'-GCATTCTTT-CAATAGCTTTGCTTTCTT-CAACGTCTTTTTTGCAAAGGTGGTAAGCACATT TTATTTCTTAGTCAAGTCAAAAGCCTCCGGTCG-GAGGCTTTTGACTTTACTTGAGCCCA TATGGGCAT-ATT-3' (SEQ ID NO:111)) were used to amplify a third PCR product (PCR #3) using a mixture of PCR #1 and PCR #2 fragments as a template. The PCR product thus obtained was used in a recombineering reaction according to the manufacturer's protocol (GeneBridges, Heidelberg, Germany) to integrate it at the kill locus in strain CMP451 (BL21 pgl+PL.2 mKKDyI GI1.2 gltA) to form strain MD11-597. The chloramphenicol marker was looped out with pCP20 to form strain MD11-604. The latter was transformed by electroporation with plasmids pMCM82 and pDW166. A colony was isolated on LB+50 □g/mL carbenicillin+50 □g/mL spectinomycin and named MD11-610.

MD11-612: GI1.6 Promoter in Front of iraM.

A PCR product (#4) was generated using primers MQ11-127F (5'-GTT AAC TGG TTG CAG TCA CCT GGA GGC ACC AGG CAC CGC ATC AAC AAA GTT CAT TTG TAA AAA TGG AGA TAA TTG TGT AGG CTG GAG CTG CTT C-3' (SEQ ID NO:112)) and MQ11-129R (5'-TCG TGT CAA TTA CTA TCC ACT TCA TTT TAT ATA CCT CCT GCT ATT TGT TAG TGA ATA AAA GTG GTT GAA TTA TTT GCT CAG GAT GTG GCA TTG TCA AGG GCC ATA TGA ATA TCC TCC TTA-3' (SEQ ID NO:113)) with plasmid pKD3 (Datsenko and Wanner. 2000. *PNAS* 97:6640-5) as a template. Primers MQ11-127F and MQ11-128R-term were used to amplify a new PCR product (PCR #5) using a mixture of PCR #4 and PCR #2 fragments as a template. The PCR product thus obtained was used in a recombineering reaction according to the manufacturer's protocol (GeneBridges, Heidelberg, Germany) to integrate it at the kill locus in strain CMP451 to form strain MD11-599. The chloramphenicol marker was looped out with pCP20 to form strain MD11-606. The latter was transformed by electroporation with plasmids pMCM82 and pDW166. A colony was isolated on LB+50 mg/mL carbenicillin+50 mg/mL spectinomycin and named MD11-612.

Figure 61:
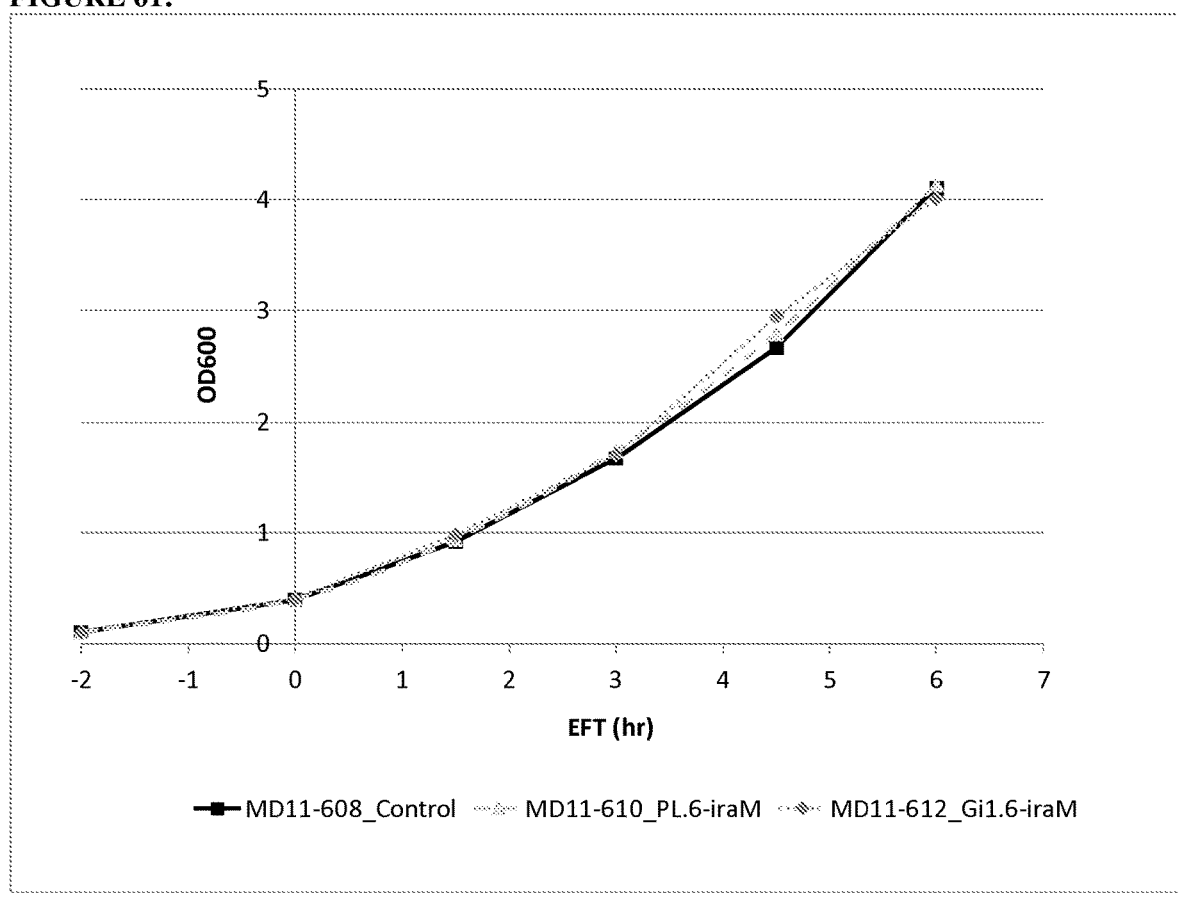
FIG. 61 depicts OD600 of cultures as a function of time.
Figure 62:
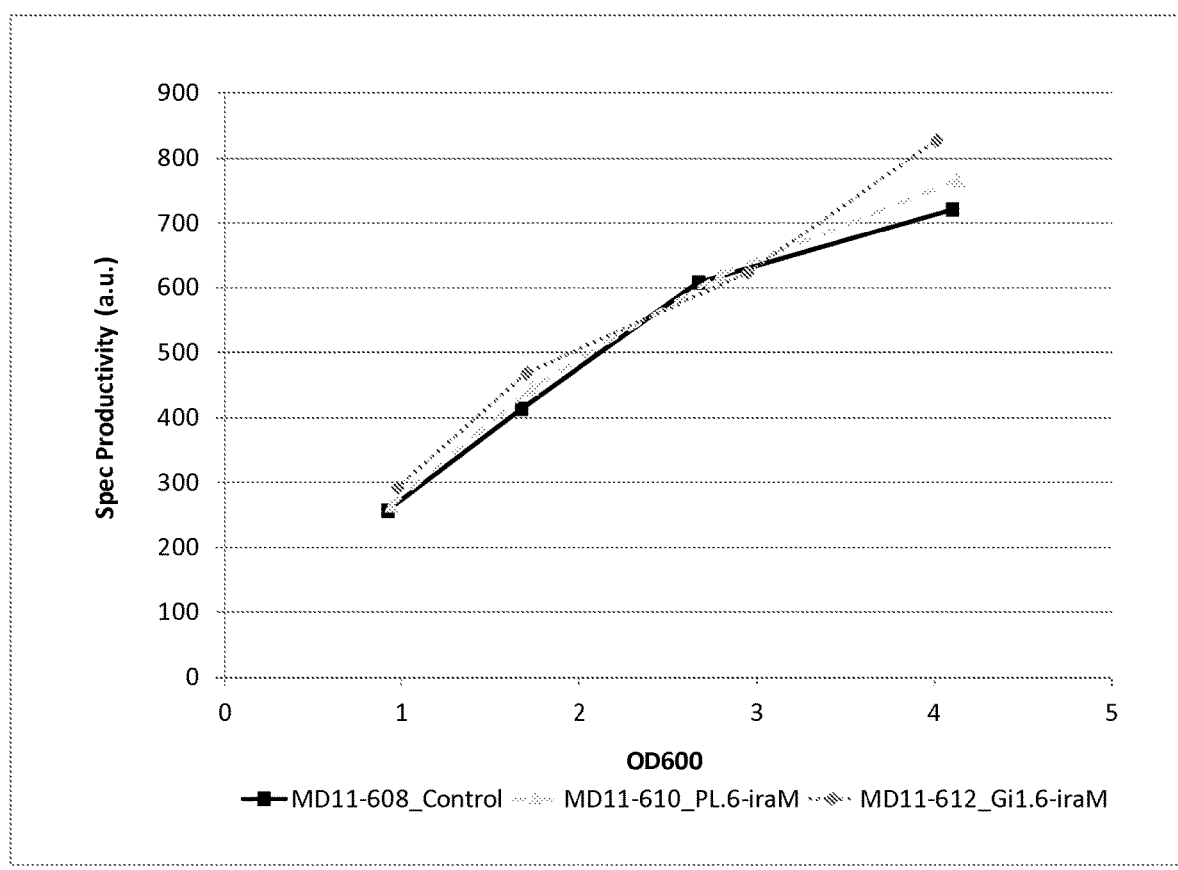
FIG. 62 depicts specific productivity (in arbitrary units) of isoprene-producing cultures as a function of time.
Figure 63:
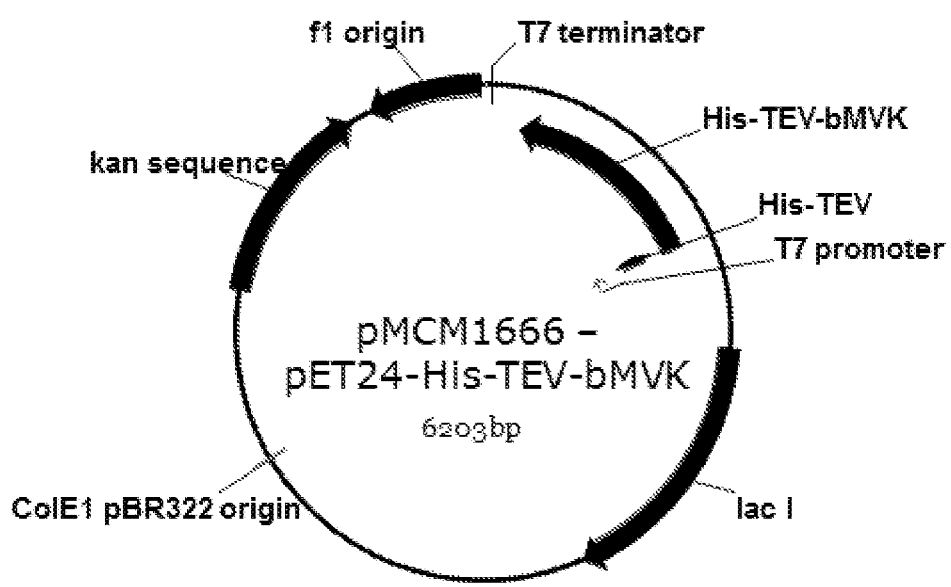
FIG. 63 depicts a map of plasmid pMCM1666-pET24-His-TEV-bMVK.
Figure 64:
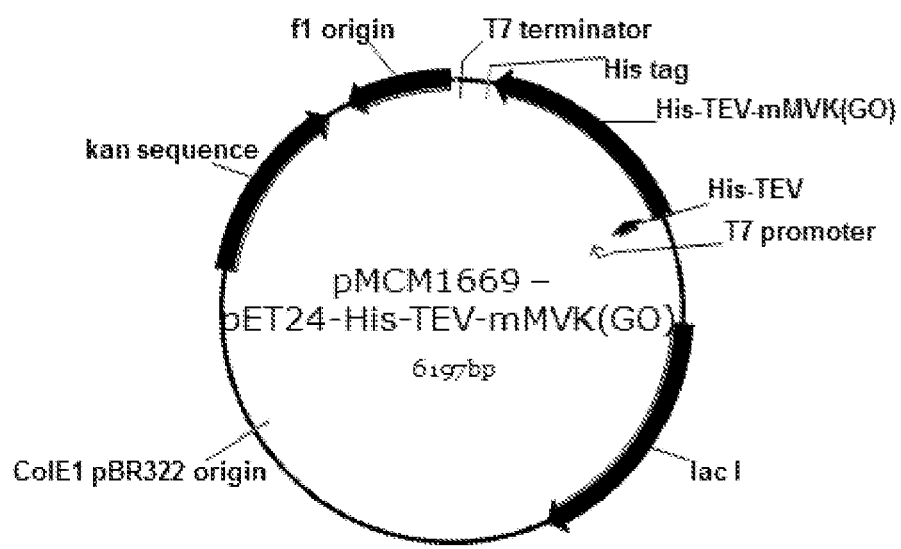
FIG. 64 depicts a map of plasmid pMCM1669-pET24-His-TEV-mMVK(GO).
Figure 65:
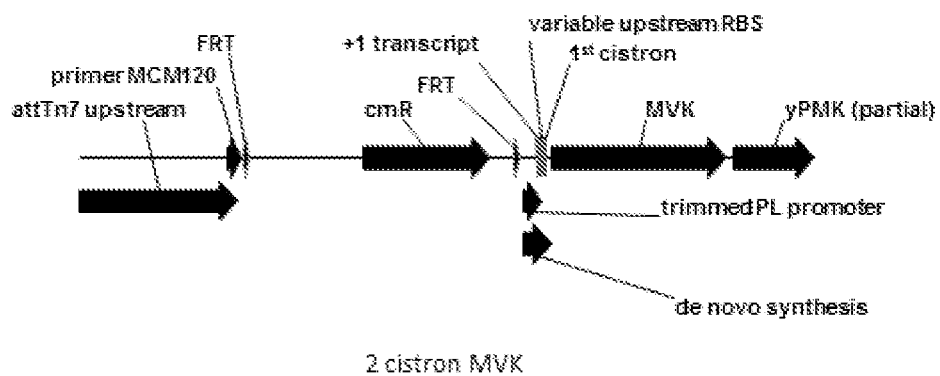
FIG. 65 depicts a schematic of the two cistron MVK construct.
Figure 66:
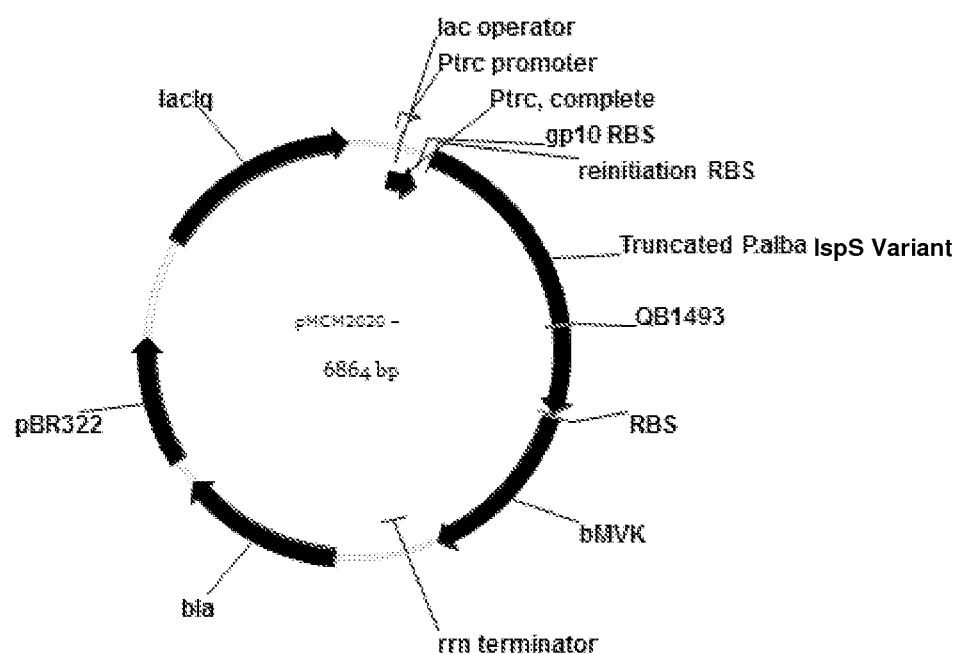
FIG. 66 depicts a map of plasmid pMCM2020-pTrcAlba-bMVK.
Figure 67:
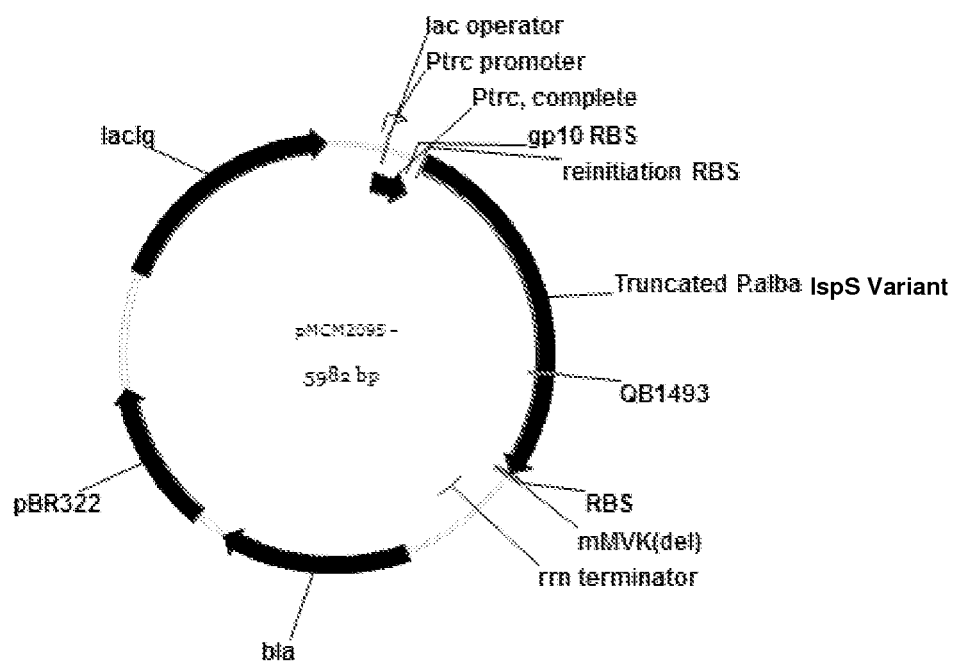
FIG. 67 depicts a map of plasmidpMCM2095-pTrcAlba-mMVK(del).

Strains MD11-610 and MD11-612 were tested in small scale (shake flasks) in comparison to MD11-608 (CMP451 harboring plasmids pMCM82 and pDW166) as a control, using the protocol described in Example 38 (above). All the strains had a similar growth profile (FIG. 61). The strains with the engineered iraM promoter had an increased specific productivity (FIG. 62).

Example 45: Increased Specific Productivity of Isoprene in a Strain MD11-607, with Deleted acrA acrA is a component of the multidrug efflux pump acrAB-TolC. This complex has been associated with resistance to solvents, dyes and detergents. Intuitively, overexpression of this pump could increase resistance to stress by chemicals such as butanol or isoprene. Counterintuitively, mutation of acrA has been credited with increased butanol resistance Atsumi et al., 2010, *Mol Sys Biol.*, 6:449)

As isoprene might have a toxic effect similar to butanol, we tested the effect of acrA deletion on isoprene specific productivity.

A DNA fragment containing the acrA gene interrupted by a kanamycin marker was amplified by PCR using strain JW0452 from the Keio collection (Baba et al. 2006. *Mol. Syst. Biol.* 2: 2006.0008) as a template, and primers MQ10-121F (5'-GTT CGT GAA TTT ACA GGT GTT AGA TTT AC-3' (SEQ ID NO:114)) and MQ10-121R (5'-GTG CAA TCG TAG GAT ATT GCG CCA CCG GC-3' (SEQ ID NO:115)). The PCR product obtained was used in a recombineering reaction as recommended by the manufacturer (Gene Bridges, Heidelberg, Germany) to integrate the PCR product at the acrA locus in strain CMP451 (See U.S. patent application Ser. No. 13/283,564). Colonies were selected on LB+10 ug/ml of kanamycin. One colony was picked and was named MD11-589. The kanamycin marker was looped out by electroporating pCP20 (Datsenko and Wanner. 2000. *PNAS* 97:6640-5) in the strain, selecting two colonies on LB+50 ug/ml carbenicillin at 30° C., then restreaking those colonies on an LB plate at 42° C. A KanS colony was selected from those plates and named MD11-602. Plasmids pMCM82 (US2011/0159557) and pDW166 were introduced by electroporation and selection on LB+50 mg/L carbenicillin+50 mg/L spectinomycin. The strain thus obtained was named MD11-607.

Figure 68:
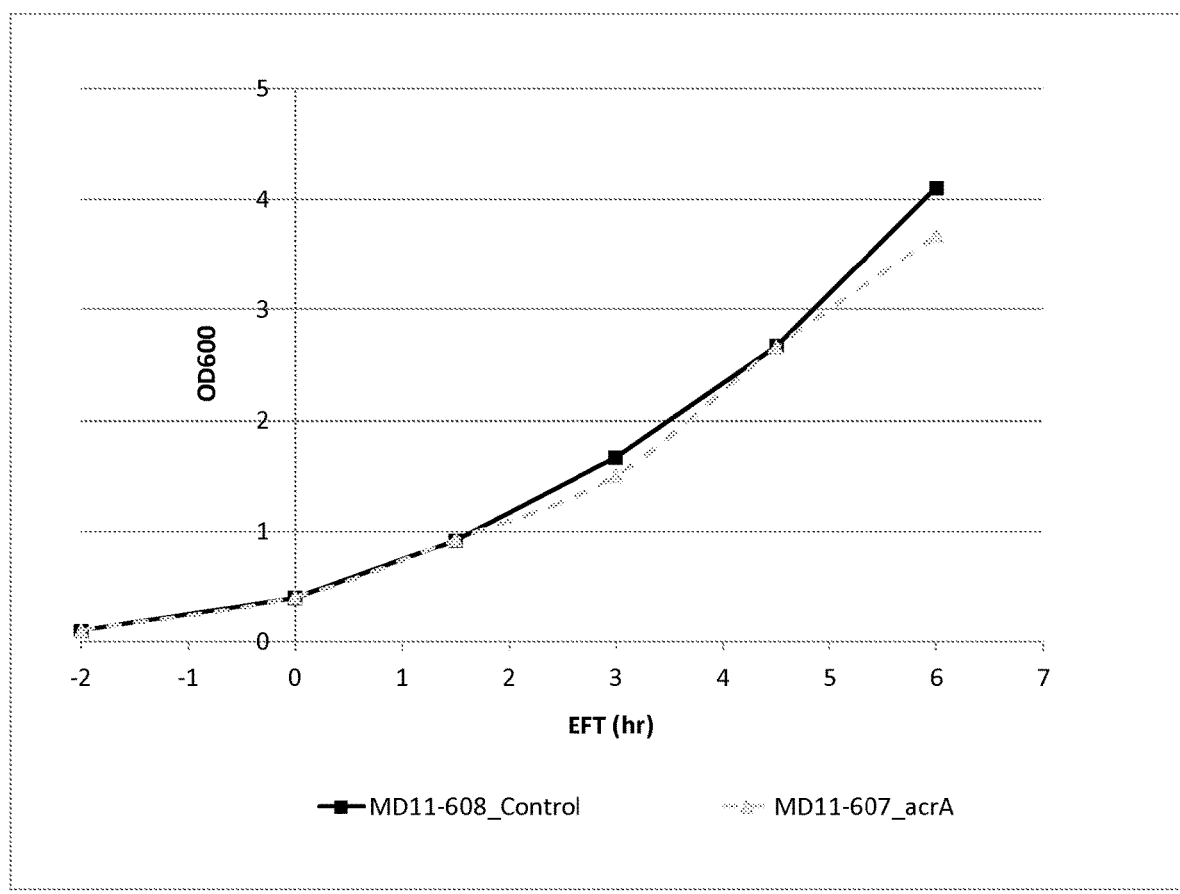
FIG. 68 depicts OD600 of cultures as a function of time.
Figure 69:
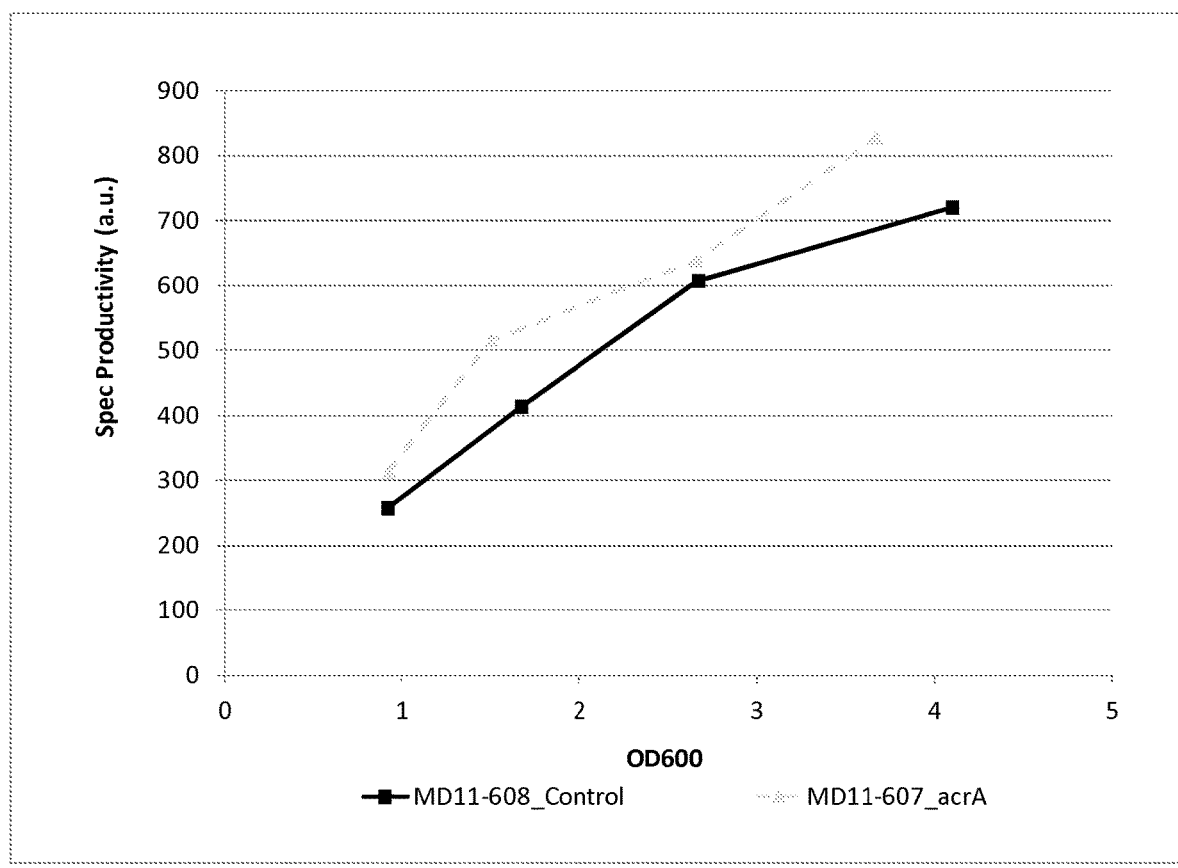
FIG. 69 depicts specific productivity (in arbitrary units) of isoprene-producing cultures as a function of time.

Strain MD11-607 was tested in small scale (shake flasks) in comparison to MD11-608 (CMP451 harboring plasmids pMCM82 and pDW166) as a control, using the protocol described in Example 38 (above). Growth was similar early in the fermentation but acrA mutant started to slow down later in the fermentation (FIG. 68). MD11-607 had an increased specific productivity compared to MD11-608 (FIG. 69).

SEQUENCES

L. grayi mvaE:
atggttaagagacattgtaataattgatgcctccgtactcccatccggtaagtaccggtcagctctcaaagatgacggcggtggaattgggaaccgcagttcaaaggctcgt
tcgagaagagacgaccaggccaaagaccatgtagaacaagtcattttggcctgaacaagtcctgtgttctgcctgaaagcaatagcatggcgcgcaacagatcctactggagaaagcggaagtaatagtagcagg
agtatcgatccgatcgacgaatgcgccgattattacatcatataatcaagaagaagacaaccccctccaaagcctgttctcctacgatgacctcgattactcgtcgacgcgttagcg
gaaagattatgggttaacagcgaaaatttgccgaacagtacgggacgcgttcacgtgaggcaaggaccctttgcgtatgatgacaccacctgaaaaataagtcgttcggac
acaggcatttccagcctgaactactgtcacgagggacaacgctacaatcaatgatggcccctcagccgtgatcattgcatcaaggagtttgctgagacaaaccagattccctac
cttgcgatcgtacatgatattaatagagatgcatgcatccatcaataatggccgtgatgatcatcccgatgaaatgtatgatcgtaccaaatccgatgtaacccaaattagcactgaagaaat
cgatccttgaaattaatagggcattgtaagcaccctcagcgcaccagttgaaccacccagagagagaagctacacaccgacgctagtcccctaggacaagccgttatgctccgtattcactaggccatcct
attaataagacggagcggcattgaaccagcggttaaaaaaatttatcaattggcccggtaggaccgtctgaactagacttcaggagcaagccgtgatcagccgtacaaaca
tgtactgcagaagacacactcctgaagatattccgaagatcgatcgaaatcaatcctgtgaaatgaatcaccccttgtggattgaatctgaggtgatagag
ttataccatcccacagccagcgagtcgagtctgctgtcgctgtactcagcagagcaacaccacgggcgtttcagtcagaataaaagatgtttccgc
gtgggcaaattgtacttatgaacctcaaagaaccgcaagtctatcgagcatcgacgatgatccgacgttctgtcatgttcgtgatactcaagacgcaatggcgctaactcatcaac
accattctcgaggtgggcctaaagagagtagtgcgcgcggcttctgaagggaaatccttctgcaaggacacatgccgcggtagccggtttcttattcattactcaacgaatcaattgtgaccgtgtcgcatacctta
cgaagcactgagtgtatctcgcgctatgcgcaagccaatcgcaagaaatatcgcgaagaaatctatcagcgctatcaacgcacagctgaccatcaaggggcatcaaccagatattcagcccaacccaacaagagttatg
aatgtattgaggcgtcgtttggcctcaggaaaatgacacacggccgtcgcgtgcggcagcgcagccgcatcagcgactgatcacgcagctcagcagtaagccagtgc
aggtgcagaaggcgtacacggagatgcctggcagagtggagtcacagcggcagcccggctaaagaaaatgcttcgatttcgaaggaagcggcattcgaaagtcacatgt
gatcagaggccgaaggaggctggcagaagtcacagcggtaacagctactatatcgtatgaggagagcgctggccagcgcattcgaaggaaattacaaggtcacatgt
cgctccaggctcgctcttcttgcattatcgtaggcgtcaggcaaggaagtgaaatcctggccaagaaagtgaaatctggctatgaatacaggcgaacgccagaccac
tcgcagagatcagatcgcaaaagttgaattgtga SEQ ID NO: 1

L. grayi mvaS:
atgaccgaacgttggaatcgataaaatgtcattcttcttgtccaccttacttctttgacatgactgatctggacatagaagacggatgtcgatccaataagttctgattggtattgg
ccaggaccgatgcagtcagttaatccgcagagtcggaataacgcaaaaacgcaggattattcgtgaccatgtgcaaaacatactgtcagctgaggacctgatcagctgaaaattgatgtcatagtc
ggcaccgagagtgaatccgatgaatcgtgaccgcaagcgagtgcctagtgcatttcacagtgcttccagtcaaaggttctgcgctcctttgaaatcaaagaagccgtgtgtatgggta
gcggattacagtcgccctgtaacccatctaggaatcatccgataacccagtctgaaatcgtcagtgcataagatatcgcgaaacaacagaagccgtgcttctggagtgaaccaacgaa
ggtgcagcggctagctcacgggttcgacccctctcaactgacgatcgtcgaagatattgtctccaagctggtgacttcttgagaccagtgacatga
cctcctatgtcgacgggctcttagtacaagacacatccgcgttagtcagacccgtatggagggcaatcagagaggcgcagtcgtatcgtgactgcagccaattcgcgcccct
agcttcatatccctgctatactaaaatggccaaaaggcctacagccacaaggggtactcgtatacccggtgtatcggtcaggcggtagccttatttcacggtcgcatagaaactggaggtatctctgaaaaatgctcagagcctaaaggtgcagatctaataggtctattttcttacggttc
cgcgtgctgtgccggagttttctcaggaaggtcatccgagcacgcatgaaaaagcttcagacaaccagacgagacagtagcagacaccatccaactgcagag
agtacgaaacatgttctccgatcgctgcttgacgtggacagaaccgattacgtgacaagacacatagcttatgcattctcgtcagccgaacacctactgagtacaggagtt
ga SEQ ID NO: 2

E. faecium mvaE:
atgaaagaagtggttatgattgatgcggctcgcacaccattgggaaatcacagagagtagtcttagtccttttcacgcggtggagctggggacactggtcacgaaaggctgctg
gataaaacaaagcttaagagaagacaagatgacaagtgatcacggcatgtgatcaggcaggaaacggacaaagtcgcaagacaaaacgttcaagacaaacggctta
ggtgacctcgccgcgatgagcgtactattaacgaagtttgccggttgcgggtgcagagaacggggatttagccccgcagttagccgtccagagttggcagttggcattcca
ggtacgtcaatggccagttaccagtcagagacaaattgcagtcgcgcgaagaagcggtacgcatcatcaatggttaatgacggatgcgtttc
caatgtccatgggtgttcagtctccagaagattattccgtaaccgctgcaatggcgacctcttcagtgagattcgtgcacagatccgtaggaccggaacgaacactcagcccaatgtgtcagccaatctgaaagcgccggtt
gaagccggggtgttgctttctcgaagaaggcacggtaccgtggaagtcggaaggagcaccggcatctgtgaatgacgcgcgtgtcgtccaaatacccagggcatgatccatcaaatggacgaggcagaatcccgagaacataatcct
tccacgattcgtttccgacgatgaaggggccattaatgaagcatcgcgatactccaaggctgcaatgaattgcatcatcatgccccaatacgtaacgatgcggcgatcatgcgggcgatagatta
ggccatccatgcgcaagcgaaattccatgggcgggcatccttggatgtcattcgcgtgagcaagacgtttataccccgtgcatcagctatgcagaaacgt
ctgcccgtgctgtagaaacggcactttcattgtccaggagcagcagacgttgctccgaagaattcgtcgatatcacatgattgagaattgggaagtgggaatttccaatgaattcggagtgcacaa -continued

SEQUENCES aatttcagattaatggcaagaaaaatgattcctatgcgactgaagaacctcagtaatagcggcagcatgcaacggccaaaatctgcggaaac
gcctcagcggcttatgcgctggcagcgggggagtgttcaggatattcacgcggagttcttttcacgcgtatttcaatgacttctgttgaagtcaaggacgcaatg
gtaccgagtattgttaaacgccagcactccgaaagctgccaataaactgcgtgaagaccgtgcaatgtcccgaaggagaaatactgttctccatctgtcaaactcgctcggatcccttaccg
catctcgcatgttcgagattccUttgaaagactgtcgtgaaccgatcgaacggcgtgcgttgcccgcaacggaaacacacacggggtgtttccgcttcattcaccgcatacgcgcccgtaat
gcggcaaccatacaaggggtatgacggatattggccaagcgatcgtgaagcgctgtaaataacagtcccactggtcgtgtgcgacatcgcgtaggttaacagacagaatcgcgcgcgttagtcagtgacagaa
ggcttgtaccaaggtttaacggattggcagatattgatccgcaaagaactggtcatcagcgtcatgatgcggcatgcgcatgcggcgttacgcattagtacagaa
gccaagcttccctgcatgctggatattgatccgcaaagaactggtcgatcagcgctgtaaaccaagcgcaaaaatcgcgaagtgcgaaatactaaaaat
gcattcagaaaggcaatacaatttagaaaaatccgagaaaatg SEQ ID NO: 3

E. faecium mvaS:
atgaaaatcgtattgacctgtcctcttcatcccgaattgtatttgacatgactgagtcgcagaatcacgcgggatgatccagtcagctaaatatcattggaatcggacaa
gatgagtgcagtgcaatgcgcaaacctgcacacactggtagatccgacgagtaaatcgtgatgatgcaatggacagatcggcttg
gcacggaatcaggaattgccaccctccaaagcaagccgtgattattccagacaaacccaagtgtagctccttcgaggtaaagaagttgctaggcggaact
gctgcccgctgcacatgccgaaggagctatgtgatgattacaaccaaaacccgattattcgattctggagacgatatgtgttttcacagaggatcatgatttctcggcggcgtgattactccgag
ttccctgctgatgagggcgccttcaaacttccagaggtattcagaggaatcaagcgaaatgtccgcaaggggctggaagatgtccaagctatg
cttttcacatacctatacgaagtatggtaagaagcagctgtaacccagtgtttaagatgtttaacaagatgtcttacaagagtcattaccaagtgacctgtcgctcaaaacttcaaagcatcaggggagctccagtcattccttaatggctaattcgcat
gtcgggtccgagttcttaccggtattagaagaaaattaccaagtcgagacgcgcgattaccagcgacgacattcgtattattaaaaatcga
SEQ ID NO: 4

E. gallinarum mvaE:
atggaagaagtggtaattataagatgtcacgtcggactcggactccgattggtaaatatcacggtcgttgaagaagtttcagcggtcgttggcgtggcgtcgtgctaaagcatgttc
gaacgcaacccagaaaatcaaagagagatgcgcagttctgcgccaggtcatatggggtctgtgcaagcaggtaatgcagtgtctcaatcaggggtgt
ccgttgcattcccgcttctacaattacagaggttgtgggtcgttttggtgcgtcatcctgaaagtactcttgaaaggcatgcaactactggcagcagaggagcgtggcaggcgg
catgaatcaatgacaaatgcgccaagcctgtcccactacaaggcggagatacgcagtgtccagtgccaagatatgggcaactcggatgactgcagagcgcattctctagt
aaactatggattaacaggggaaatgtccatgcggaacagggggatctccgtgaggcgcaagctacacatcacgcgatgatgtcgatatcaaatcaacacggatgaagcaggcaag
aaacaaatcgctaaggaaatgcgccactggcagtgtaaccgaagggagtcagatcgaagagatggcagatgtatgaggatcagatcccaaacaacgatggaaagcatcaaaccc
tgtttaaacgatgcagtacagggcactgtaaccgcaggaatgctaaccgaggatgcgatcggaatatatgggctctgtctccgataaaagcgatacaaatcgatcttacaaaatagcctcgaagatattg
gagttgttaaaataatgaagccttgccgcaagagtagtgtcgcaagagctagctgttgaatctagctggaatagtccgtcaagtctggattaaccgttaacgttatatcctcagttcatgcaat
tgggcaaccggcgtcctggcctgccactgttagcagagctgagcctgtgtggtcgtcatggtgctgagccagccaatgct
tttagaacgtccaactattgagaaggctaaaccgacagacaaagaaaaaagttctatgactgttcaccagctgcaagagtcagagctcccagttcccgaaactcagtccgaaact
aaacagcagtatctccagatgatatgccgaggacgatgagccggaagaacgtgaaatggccgcatgtccaaaatggccagccgaattcaaccaccgagccagtccgaaatggagatccaaaccccgaagggcgtgttcgcgccaaatgggccatgtcactcagtcagaagttgatgcct
cagaggtccagattcagcgggccagaatgtcttcagccgaacaggaatgctagaaaccgaaaatccgccaaagttcctccctcccgcatttcaaatcctgtgtgaaaa
gagggaagtgctgtcctcgcgcattgaactcctcgttcattaaacaaggagctgaaccgatttatcagtgaccttttagagtggaaagacgcga
tgggggcaataatcaataatgtctgcagggcaacctccgaatgttccgaccagagtttcgccccatattttctcttcgaactggccgcaaagacagcccaccgcag
tacctgttgtgaaaaaggattaacgtctatagcacctagcgtaagggtgccacaaggagtgcatccgcatccatcagccgctgttgaggcgtaccaagtgtgcccaagctc
ctatccaggggcatgagattgtgctgactaaactggtagctgttcatcctttcaagctgccggctcagatgggcgaattcgggtgcgcctggtcaaaagcgagactgtcatgtacaaatctgggcctacaaagtgcggccaagctc
aagcagggcacatgtccatgcagcccgttcctgcgccatgttgagctggtttgccactgttccgaaggtata
tcagcaggcaggcgcgttctgttctggcagagatccgcgaacaatga SEQ ID NO: 5

E. gallinarum mvaS:
atgaacgtcggcattgacaaaatcaatttttttgtcccaccgtattattattggtgacctgatatggtgactctgcccacgcacggcgaagtggacccgaacaaattacaatggaattggacag
gatcagatggcttgagcaagaagacgcacgatcgtaacattcgcggctagcgctgaacaactgagacctgcaagctatagaactggtatagttggt

SEQUENCES acggaatcggcattgacgagagcaaagatccggtcgtttacatcgttgtggcgtacaaccttcgctcgcagttgaaataaagaagctgttacgggcaaccg
caggcattgcagttgcccaagactcatatcaagcgagcagcaagctccggtaatgcaagcgatatagctcgtatgtcttggtcttcggtaacgcccacaa
ggcgcagggcagttgctatgctcacgcgatcttctcacggcaaatccgactctcgaaacgacaatgatgtgatgtaaccgaggatattatgactctggagacccatcttgggtcacg
ctacccctggtagatggcacccttccaatcaagtctatatgacagttcaagaaggtcggaccacatgcgaacgcaatccagcttctatccgactatccgcgattag
tttcataccgttcaataaaaatgggtaagaaagccctgtcctcgctgttttgcagatagaaggtgaaactgaagcaatgaacagcagtgctaacagcgtatgaagagtctatgtatattca
cgcccgatcgcaacttgtacggatcattgtaccggtcgtttagtgcagtgtcagggctataaaatcaatgaacaaagaggcgcatacccagctcctgatcagcgtcagaagattccatcgaagagtag
cgctgcagcgaatttttctccggtcgtcttagaaattgatcaggatgcagcgtctccgaaagtcgagcttcatctccgagataaaaaacgattcgtacttacatataaggaggagctga
aggcgattttacagattcctagaaatgtgatcaggatgcagcgtctccgaaagtcgagcttcatctccgagataaaaaacgattcgtactaataggaggagctga
SEQ ID NO: 6

E. casseliflavus mvaE:

atggaagaagtgtcatcattgacgactgctactccaataggaaagtaccacgttcgctgaaagattacacgtgttgaactgggacagtagcagcaaggcgttgctg
gcacgaaatcagcagcaagcaacacatagcgcaagttattattggcaacgtcctgccaagccgaagtgggcagaatccaggcgacaagtcagttacagtcaggattgt
ctctgatatccccgcacgcagcgatcaatagtgtgctcggttatgaaagctctgattggtgaggacccaaaatccagcgaacaaagcctctggttcaacaggcgg
aattgaaagcatgacaaacgcgcctgttagttattacaacaaggctgaggactgaatcatttcggcgccggttagcacaatgatgcacaagatgatcagttcca
aaccaatggcttacccgcagagaccgtctgctgagagatacggttcctcccaggacgaaacggttcatcagagccgcgacaagcgtgaagaaagctagctgtgagcttaaaac
gaaaaagttgatcaggaaattgtacccctgacggaaaaattccggaaacggttctccaggacgcgaagagccctcgatgttattaatgacgaactcatatgcgaagaacaccagaatcttatc
ggtgtcaaaaagcgcgaacagtcacgtacgatacgcgaacctctcagcgctgctctatgttatataagggcgaaaatcctattgcgaagaacaccagaatcttatc
tggccgtataaaggagaacgtcagtggggttgcccccgaaataatggtatttcccccattaaggctataagacacacccctgctgaaaatcaagcactgaccatagaggatata
gaataaaaagagagatataagaagcattgctgcgagttcgtgcgaattcgaggacgaccgagacaaaaaagttatcgctatggcgtggtggggtcttggattggcga
caatgggcgacggagccgcgacaagtcgcgctcgcccaacaattcttatgaggactgcttccgaaaaatacggcgcagaagcgctatagctatagtgatctcctcatgcagaacccctagcgg
tgtctctgaaaaccatccggccagcgctattaccggctatgatggtggagtctcagacgatggaaagagagcgccatcaatcacgggccaaaatgtccgaagtga
atctcttaggcgtgggctgaactaccaggtcgaagcgatctagagaggcggtgaataatggtataaactgaatagcacgagccagggacaccgcggcgaatggct
ggcagcttgctaagatagatcctacacgagcgtccaacacaagggcgaatggcggcgtcccacacaagccaaagccgtggaacaatgcttctccccaaagttaatctacgcccatctgcactgacccccgggtgcggct
gcgatgcctaagttgcacgggacatgggcacggcgccatgcccaaagcacaaggagcgccatcagcaaggcacatagtcagcgttgaagcaccatgccacagtgtgacagtcgcagtag
ggggctcacaaaatcctgcaaaagcacaggcgcgccagccaatgaccgccccagcgtgagcatcagcagggcgcgcccgccatgcagtagccagtcgaaactgtgggcaagcctgcaatcaacaatagcaactt
ggccgcttacgagcactagtgagcgggagcggagggcattcagcaagcgcacatgaatcacaccagcagcgtgaccgtccttccggaccgctttcggaactactgaaatagagcaacta
gctcgaagctgagggcacgcgacgacgccaaatgaatcaggacaggcgcaggctcgtaatctctgaccgaataagaattaa SEQ ID NO: 7

E. casseliflavus mvaS:

atgaacgttggaattgataaaatcaattttttcgttccgcctattcattgatgatggtggatctcgctcgtcaagaggaagtgaccccaacaagtcactaggaataggccaag
atcagtgcagtaacaagaaacgcaagatatcgcaagttcgcgatgcacgccgaaggatatcctgactaaggaagattcacaggccacagatatggtaatagtgggg
actgagtctggaatcggaaatcctgaggaagtgctgctgtgctatgcgatcggcttaggtatgcagctcagcctttgcgcgctcccttgaaattaaggaggccatgctatgggcccactgc
cggcttcagttcgcaaaagtcatgcagccggcaatcccagacaagtcctggctgacgactgcgtatgaccccgtgagggagaaccgactcaag
gtagtgtgtgacgcgccatcgtgattccccgtcagtttccgctgcctatctttgagcgccttagaaaagtgatatatcatgtagacccaagataatactcatgtgacccaagaataccaacgctggcggcatcaatat
cctatggtagacgtacacgagaaagctcgtcatggctgaagctgcgggctaaaacgtcggagagatgcagaagatcaggagacaaaagcggttaatgcgacagcgacatagtcagcgtgaccgactggcggcataaatagcggcaaggcagacacagcgcccatgccaaaactgctcatatcctcgaacgcgcaaaaactctgagtcatgcagcgcatatgttcagg
cgtcggactcagtggaattttcagtgcgtcttggtgcctctggtaccggaaaacaattagcgcaaggcctactgcaaagatcttccggaccgtcttccatcgcagtac
gaagccatgtttaatgaacctgatattgatgaacgtgtaatattctgaggatgatcattcaggagagaccttactgaccctactgctactcccagagatcaaaaacactatcgctactataacgaggaatgaa
attcccgaatgacggtcaagatgccgtggcggaagctcaagatgaatgacgatgcgcgtattggcgaaacaaatcaagcggaagcggaagtttaattgctgggaattgagaa E. faecalis mvaE:

atgaaaacagtagttattattgatgcattacgaaccaccaccaattgaacaaaatataaaggcagcttagatcaagtgccgtagacttaggaacacatgttacaacacttttaaaa
agacattccactatttctgaagaattgatcaagtatttggaatgtttcacaagctggcaaatcccgcacgacaaatagcaatcaaaacagcggttgtctcatgaa
attcccgcaatgacggttaatgaggtctgcgatgcaggaatgaggcgtatttggccgcaaattgattcaattaggaagaagcggaagtttaattgctgggattgaagaa SEQUENCES
-continued E. faecalis mvaS:

```
Atgacaatggattgataaaatagttttttgccccctattattagttgatgacgcactggctgaagctgaaccctggaaatctggaaatgttgtattgggcaaga
ccaatggcggaaccccatcagccaagtcaaagcggccaatgccgcagaacggatcttcagccaggcaagaggcgcccaagagaccaatgataatgtgtcggga
ctgagtccagtccgatgctgaagaactcacgtgcaaagcgccgcagttcttaatcgtcttaatgggattccaatccttcgctcgctcgaaatcaaggagagctgttacggagcaacagca
ggcttacagttagtcacgtgcctagcctactcaatccagataaaaaagtcctgtcagcgagatgttaaaggagatatgcgacagaagactgctaaattcggcggtgagctacaccaaggag
ctgggcggttgctgctttgcaaagcggccctacccaacgctactcatgactttgatttgcagatataggaactccaagcgtctctaagcgcttatgatgattagcgttccat
attcctaacacaaaatggcaaaaagcttatcttggcatttctttatagaaagtctccgaccaactagcaagtccccgctgaatagaagaacgactttaggcgcaatgatcgcctatgtgctg
gcgtaggaacttgtatacgggttcacttatcagcgttgttcaaaatcctttaagaaaatgaactcattagcactgcggataatcggacagacttccatcgctgaatatgaagccatgttcg
cagaaattttcagcagacagcatttgtataccggtcaacgttgaagtagaactgagagtgaattaaatatgtattctgctattaataatacccgtccctggcttgaaactaa SEQ ID NO: 9
```

E. gallinarum EG2 (mvaE):

```
MEEVVIIDARRTPIGKYHGSLKKFSAVALGTAVAKDMFERNQKIKEEIAQVIIGNVLQAGNGQNPARQVA
LQSGLSVDIPASTINEVCGSGLKAILMGMEQIQLGKAQVVLAGGIESMTNAPSLLSHYNKAEDTYSVPVSS
MTLDGLTDAFSSKPMGLTAENVAQRYGISREAQDQFAYQSQMKAAKAQAAENKFAKEIVPLAGETKTITAD
EGIRSQTTMEKLASLKPVFKTDGTVTAGNASTINDGAALVLLASKTYCETNDIPYLATIKEIVEVGIDPE
IMGIGPIKAIQTLLQNQKVSLEDIGVFEINEAFAASSIVVESELGLDPAKVNRYGGGISLGHAIGATGAR
LATSLVYQMQEIQARYGIASLCVGGGLGLAMLLERPTIEKAKPTDKFYELSPAERLQELENQQKISSET
KQQLSQMMLAEDTANHLIENQISEIELPMGVGMNLKVDGKAYVVPMATEPSVIAAMSNGAKMAGEIHTQ
SKERLLRGQIVFSAKNPNEIEQRIAENQALIFERAEQSYPSIVKREGGLRRIALRHFPADSQQESADQST
FLSVDLFVDVKDAMGANIINAILEGVAALFREWFPNEEILFSILSNLATESLVTAVCEVPFSALSKRGGA
TVAQKIVQASLFAKTDPYRAVTHNKGIMNGVEAVMLATGNDTRAVSAACHGYAARTGSYQGLTNWTIESD
RLVGEITLPLAIATVGGATKVLPKAQAALEISDVHSSQELAALAASVGLVQNLAALRALVSEGIQKGHMS
MQARSLAIAVGAEKAEIEQVAEKLRQNPMNQQQALRFLGEIREQ SEQ ID NO: 11
```

E. gallinarum EG2 (mvaS):

```
MNVGIDKINFFVPPYYLDMVDLAHAREVDPNKFTIGIGQDQMAVSKKTHDIVTFAASAAKEILEPEDLQA
IDMVIVGTESGIDESKASAVVLHRLLGVQPFARSFEIKEACYGATAGIQFAKTHIQANPESKVLVIASDI
ARYGLRSGGEPTQGAGAVAMLLTANPRIILTFENDNLMLTQDIYDFWRPLGHAYPMVDGHLSNQVYIDSFK
KVVWQAHCERNQASISDYAAISFHIPYTKMGKKALLAVFADEVETBQERVMARYEESIVYSRRIGNLYTGS
```

SEQUENCES
-continued

LYLGLISLLENSSHLSAGDRIGLFSYGSGAVSEFFSGRLVAGYENQLNKEAHTQLLDQRQKLSIEEYEAI
FTDSLEIDQDAAFSDDLPYSIREIKNTIRYYKES SEQ ID NO: 12

L. grayi (mvaE):
MVKDIVIIDALRTPIGKYRGQLSKMTAVELGTAVTKALFEKNDQVKDHVEQVIFGNVLQAGNGQNPARQI
ALNSGLSAEIPASTINQVCGSGLKAISMARQQILLGEAEVIVAGGIESMTNAPSITYYNKEEDTLSKPVP
TMTFDGLTDAFSGKIMGLTAENVAEQYGVSREAQDAFAYGSQMKAKAQEQGIFAAEILPLEIGDEVITQ
DEGVRQETTLEKLSLLRTIFKEDGTVTAGNASTINDGASVIIASKEFAETNQIPYLAIVHDITEIGIDP
SIMGIAPVSAINKLLIDRNQISMEEIDLFEINEAFAASSVVVQKELSIPDEKINIGGSGIALGHPLGATGA
RIVTTLAHQLKRTHGRYGIASLCIGGGLGAILIEVPQEDQVKKFYQLAREDRIARLQEQAVISPATKH
VLAEMTLPEDIADNLIENQISEMEIPLGVALNLRVNDKSYTIPLATEEPPSVIAACNNGAKMANHLGGFQS
ELKDGFLRGQIVLMNVKEPATIEHTITABKKAAIFRAAAQSHPSIVKRGGGLKEIVVRTFDDDPTFLSIDL
IVDTKDAMGANIINTILEGVAGFLREILTBEILFSILSNYATESIVTASCRIPYEALSKKKGDGKRIABKV
AAASKFAQLDPYRAATHNKGIMNGIEAVVLASGNDTRAVAAAAHAYASRDQHYRGLSQMQVAEGALHGEI
SLPLALGSVGGAIEVLPKAKAAFEIMGITEAKELAEVTAAVGLAQNLAALRALVSEGIQQGHMSLQARSL
ALSVGATGKEVEILAEKLQGSRMNQANAQTILAEIRSQKVEL SEQ ID NO: 13

L. grayi (mvaS):
MTMNVGIDKMSFFVPPYFVDMTDLAVARDVDPNKFPLIGIGQDQMAVNPKTQDIVTFATNAAKNILSAEDL
DKIDMVIVGTESGIDESKASAVVLHRLLGIQKFARSFEIKEACYGGTAALQFAVNHIRNHPESKVLVVAS
DIAKYGLASGGEPTQGAGAVAMLVSTDPKIIAFNDDSLALTQDIYDFWRPVGHDYPMVDGPLSTETYIQS
FQTVWQEYTKRSQHALADFAALSFHIPYTKMGKKALLALLEGESEEAQNRILAKYEKSIAYSRKAGNLYT
GSLYIGLISLLENAEDLKAGDLIGLFSYGSGAVAEFFSGRLIVEDYQEQLLKTKHAEQLAHRKQLTIEEYE
TMFSDRLDVDKDAERYEDTLAYSISSVRNTVREYRS SEQ ID NO: 14

E. faecium (mvaE):
MKEVVMIDAARTPIGKYRGSLSPFTAVELGTLVTKGLLDKTKLKKDIDQVIFGNVLQAGNGQNVARQIA
LNSGLPVDVPAMTINEVCGSGMKAVILARQLIQLGEAELVIAGGTESMSQAPMLKPYQSETNEYGEPISS
MVNDGLTDAFSNAHMGLTAEKVATQFSVSREEQDRYALSSQLKAAHAVEAGVFSBEIIPVKISDEDVLSE
DEAVRGNSTLEKLGTLRTVFSEEGTVTAGNASPLNDGASVVILASKEYAENNNLPYLATIKEVAEVGIDP
SIMGIAPIKAIQKLTDRSGMNLSTIDLFEINEAFAASSIVVSQELQLDEEKVNIYGGAIALGHPIGASGA
RILTTLAYGLLREQKRYGIASLCIGGGLGLAVLLEANMEQTHKDVQKKKFYQLTPSERRSQLIEKNVLTQ
ETALIFQEQTLSEELSDHMIENQVSEVEIPMGIAQNFQINGKKKWIPMATEEPSVIAASNGAKICGNIC
AETPQRLMRGQIVLSGKSEYQAVINAVNHRKEELICANESYPSIVKRGGGVQDISTREFMGSFHAYLSI
DFLVDKDAGANMNSILESVANKLREWFPEEELESIISNFATESLASACCEIPFERLGRNKEIGEQI
AKKIQQAGEYAKLDPYRAATHNKGIMNGIEAVVAATGNDTRAVSASIHAYAARNGLYQGLTDWQIKGDKL
VGKLTVPLAVATVGGASNLLPKAKASLAMLDIDSAKELAQVIAAVGLAQNLAALRALVTEGIQKGHMGLQ
ARSLAISIGAIGEEIEQVAKKLREAEKMNQQTAIQILEKIREK SEQ ID NO: 15

E. faecium (mvaS):
MKIGIDRLSFFIPNLYLDMTELAESRGDDPAKYHIGIGQDQMAVNRANEDIITLGANAASKIVTEKDREL
IDMVIVGTESHSKASAVIIHHILLKIQSFARSFEVKEACYGGTAALHMAKEYVKNHPERKVLVIASDI
ARYGLASGGEVTQGVGAVAMMITQNPRILSIEDDSVFLTEDIYDEWRPDYSEFPVDGPLSNSTYIESFQ
KVWNRHKELSGRGLEDYQAIAFHIPYTKMGKKALQSVLDQTDEDNQERLMARYEESIRYSRRIGNLYTGS
LYLGLTSLLENSKSLQPGDRIGLFSYGSGAVSEFFTGYLEENYQEYLFAQSHQEMLDSRTRITVDEYETI
FSETLPEHGSCAEYTSDVPFSITKIENDIRYYKI SEQ ID NO: 16

E. casseliflavus (mvaE):
MEEVVIIDALRTPIGKYHGSLKDYTAVELGTVAAKALLARNQQAKEHIAQVIIGNVLQAGSGQNPGRQVS
LQSGLSSDIPASTINEVCGSGMKAILMGMEQIQLNKASVVLTGGIESMTNAPLFSYYNKAEDQYSAPVST
MMHDGLTDAFSKPMGLTAETVABRYGITRKEQDEFAYHSQMKAAKAQAAKKFDQEIVPLTEKSGTVLQD

SEQUENCES

EGIRAATTVEKLAELKTVFKKDGTVTAGNASTINDGAAMVLIASKSYCEHQIPYLAVIKEIVEVGFAPE
IMGISPIKAIDTLLKNQALTIEDIGIFEINEAFAASSIVVERELGLDPKKVNRYGGGISLGHAIGATGAR
IATTVAYQLKDTQERYGIASLCVGGGLGLAMLLENPSATASQTNEDEESASEKTEKKKEYALAPNERLAF
LEAQGAITAAETLVFQEMTLNKETANHLIENQISEVEIPLGVGLNLQVNGKAYNVPLATEEPSVIAAMSN
GAKMAGPITTTSQERLLRGGIVFMDVQDPEAILAKVESEQATIPAVANETYPSIVKRGGGLRRVIGRNFS
PAESDLATAYVSIDIMVDVKDAMGANIINSILEGVAELFRKWFPBEEILESILSNLATESLVTATCSVPF
DKLSKTGNGRQVAGKIVHAADFAKIDPYRAATHNKGIMNGVEALILATGNDTRAVSAACHGYAARNGRMQ
GLTSWTIIEDRLIGSITLPLAIATVGGATKILPLKAQAALALTGVETASELASLAASVGLVQNLAALRALV
SEGIQQGHMSMQARSLAISVGAKGTEIEQLAAKLRAATQMNQEQARKFLTEIRN SEQ ID NO: 17

*E. casseliflavus* (mvaS):
MNVGIDKINFFVPPYFIDMVDLAHAREVDPNKFTIGIGQDQMAVNKKTQDIVTFAMHAAKDILTKEDLQA
IDMVIGTESGIDESKASAVVLHRLLGIQPFARSFEIKEACYGATAGLQPAKAHVQANPQSKVLVASDI
ARYGLASGGEPTQGVGAVAMLISADPAILQLENDNLMLTQDIYDFWRPVGHQYPMVDGHLSNAVYIDSFK
QVWQAHCEKNQRTAKDYAALSFHIPYTKMGKKALLAVFAEEDETEQKRLMARYEBSIVYSRRTGNLYTGS
LYLGLISLLENSSLQANDRIGLFSYGSGAVAEFFSGLLVPGYEKQLAQAAHQALLDDRQKLITAEYEAM
FNETIDIDQDSFEDDLLYSIREIKNTIRYNEENE SEQ ID NO: 18

Aceto acetyl-CoA-synthase:
MTDVRFRIIGTGAYVPERIVSNDEVGAPAGVDDDWITRKTGIRQ
RRWAADDQATSDLATAAGRAALKAAGITPEQLTVIAVATSPDRPQPPTAAYVQHHLG
ATGTAAFDVNAVCSGTVFALSSVAGTLVRGGYALVIGADLYSRILNPADRKTVVLFG
DGAGAMVLGPTSTGTGPIVRRVALHTFGGLTDLIRVPAGGSRQPLDTDGLDAGLQYFA
MDGREVRRFVTEHLPQLIKGFLHEAGVDAADISHFVPHQANGVMLDEVFGELHLPRAT
MHRTVETYGNTGAASIPITMDAAVRAGSFRPGELVLLAGFGGGMAASFALIEW SEQ ID NO: 19

Isoprene synthase:
Atggaagctcgtcttctgcgaactacgaacctacagctgggactatgattacctgctgtcctccgacacgagtccatcgaagtataccaaagacaaagcgaaaagct
ggaagccgaagttctgcgcgaagttctgcgcagatcagaaattctgaccctgctgaactgattgacaacgtccagctgacaacgcccactgtattcgtcgtggtcaacaggttcgtcaactcctgaag
cgtgtggctgatcgttcgtgttgcaagcgatcgcaaagaccggcttcaaagaccaacctcctggagaggaaactccttcaaagctatccgagggcagctcctctggctctggaag
caggaagcgttcagcgctcaaagaccaacctcctggagaggcaacctcaaagatctcaaagatcgtgaaagagagctgcaaaggaccgttctggtcggctgcgagctgcaacatctgaattcaacat
gccactcagctctgatccagccgtgactcagcgtgcagtggctgaaaccgtctgctatccgaggcctaccggcaaacgccgtttggttgctgtgagcagcagcgcacttgagagctttctactgg
gccgggtgagcattcgaacctcgacgcctgaaccatctgggagccgatatcctacgacatgtacgaccctggacgacacccgtgctcctaccacttatgaccctgaccgtggtgaaccgcagatgccaaatagcgttcttcttta
actgaaggtcctgctcctgtccgactcctcctgaccctcggtaaagtaaaggacgcagactgctcaacattaaaaggaagaagatcgaaacct
cgaaaactgaaaagtaaagctggcggctggcggcaacgccatggaaatcctcttctggccgcctgaactggtgtcgtgctgcgtcgtgcaagaacattaaaaggaagaagatcgaaacct
gcaaaataccagcgctgaaccatctccgtcctccatatccgtctccatatctcccgaaatgggcgactgcgccatgtagagaccggcgaatcaggagagcgcaatggctttctcttta
catgcgcactcaaaggtatctcgagaagctggctacgcaaactggctacgcagctcactgcttatcgatcgatgctgaatctgatcgatgacactgcctgcctgtgaaaggatgaacaaggaaaaaactggtgtgagcctgttcgcg
aaaccgttcgtggaaaccccgatcaaccgcatgccgcactgcagtcaatctcactgcacctcctccggatcagtgagccgacccgcaaacgcgttcgtctgtgta
atcactgaaccgattctgccgtttgaaccgcta (SEQ ID NO: 20)

ispA:
tggacttccgcagcaactcgaaccggttaaggcagcctgaagcggtgccaaccggcgctgagccgtttatcgccccactgccctttcaggaagacttcccggttgtcgaaaccatgagtgatg
gccattaaggcctgtaagcgctcgctgcgacttccctggttataccaccggctgaatatgtttggcgtagacacgcgcaccctgcgccgagagtgtatccac
gctactactcattatgatgattaccgcgatgatgaccgcgatctgccggaccgatcgcgaccccgaagttggcgagccaaacgccgattctgccgacg
ctttacaaacgctggctgctccgattctaagcagcgatgcggatgccgataccggaagtgtcggatcgcgacagaattctgatgattctgaactgcgtgacgcagcgtatcgcgcgaat
gtcgggtggtcagcagcgcactagattgagcgccaaggtcgtgctctgcgacaagtacctctcgacgccgttgacgcgctgagcgtatttcatcgtcaataaaaccggcgcattcatcgtcataaaccggcgtattgcgccttc
tggtgcattaagcgccggagataaagggcgttgtctcgcaagtgcgacaagtacagagagcatcggctcttcaagatgacatcctgatggtag -continued

SEQUENCES gagatactgcaaacgttgggaaaacgccaggtgccgaccagcaacttggtaaagtacctacctggtgagcaacttctggatgagcccggaagaaagcccggatctgat
cgacgatgcccgtcagtcgctgaacaactggctgaacagtcgataccctcggcactgcggcaaggccgcagcggactacatccatccagcgctaataa
(SEQ ID NO: 21)

Amorphadiene synthase codon-optimized for E. coli:
ATGAGCCTGACCGAAGAAAACCGATTCGTCCGATTCGAAATTTTCCGCCTAGCATTGGGTGATCAGTT
TCTGATTTATGACGAGAAACAGTTGAACAGGCCGTTGAGCAGATTGTAATGATCTGAAAAAAGAAGTTCGC
CAGCTGCTGAAAGAAGCACTGGATATTCCGATGAAACATGCCAATCTGCTGAACTGTGATTGATAAATTC
AGCGTCTGGGTATCCCGATCATTTTGAACGTGAAATTGATCATGCCCCTGCCAGTTGATCATTTATGAAACCTAT
GGTGATAATTGGAATGGTGATCGTAGCAGCCGTGTGTTTCTGTATGCGTAAACAGGGGTTATTATGTTAC
CTGCGACCGTGTTTAACAACTATAAGCAACCAGCATGCGTGTTCCGGGTGAAATTATTCGGAAGATGCACTGG
GGTCTGCTGGAACTGTATGAAGCACTGGAGCTGTGAAACAGCAATTTAGCACCAATCCGGCACTGTTTACCGAA
GTTTTTACCCGTAGCCGTCTGAAACAGCCCGTGTGAAACAGCCTCTGCGCTGTGATTGACGACGCAGTATATTCCGT
ATCCAGCCGTCACTGAACAGCCGTTGTAAGAAAACCCCTGCTGAAAACTGGCAAACTGGAATTTAATCTGCTGCA
TTTATCAGCAGGATAGCCATAACAAAAAACCCTGTAAATGTGAAAGCCTTCGACATCAAAAAACGC
GAGCCTGCATAAAGAGACTGAGCCACGTTGTGAATGTATTTTTGGGGTCTGGGTAGCGTGTTTTGAACCGCAGTATA
GCCGTGCACGTGTGTTTTTACCAAGCAGTGTGATTATACCCTGATAATGATCACCTATGAGCCATATT
GGCACCCCTATGAGGAACTGAAAAATCTTTACCGAAGCCCGTTGAACGTTGGAGCATTACCGTCTGGATACCC
TGCCGGAATATATGGAAACCGACTCGTTTAATTGCGGTAAAGAATGTCCGGATGAAGAATGGCACGCCATTATAC
AAAGAAGGTCGTACCGACGTCAATGAAGGTCATATTCCGACCACCGAAGAAACATGATCCGGTTGTGATTATTA
CCGGTGTGCAAAATCGGTCCCCTCGTGTTTCGTTATAGCCGTATCTGGGTGGTATTCTGGGTCGTCTGAACATCTGAT
GAATGGGCAGTTAGCGCACCGAACGTAAAACATAGCCAGCCAGCGATCTATGAAAAGCTATATAGAAGAATATATA
CGTGAAACGAGAGTATGCCAGACCCTGATTTACCAAGAAGTTGACGACCGTTTGAAAAGATATCAACCGT
GAATATCTGACACCGAAAAACATTCCGCGTACGCTTACGCGTATGGGCGACGATATATATATAAACATCTGATTATTCCTGA
AGTTCAGTATGCCAGTGAAGATACCTTACGGTTATTTATCTGCTGTTCAGTTTCCTGATTAAAGCCTG
CTGGTGTATCCGATGAAGCATTTAA (SEQ ID NO: 22)

Farnesene synthase codon-optimized for E. coli:
ATGAGCACCCTGCCGATTAGCAGCGTTAGCTTAGCCAGCAGCACCAGTCCGCTGGTTGTTGATGATAAAG
TTAGCACCAAACCCGGATGTATTTCGTCCAACATGAACTTTAAATGCAAGCCATTTGGGGTGATCAGTTTCTG
ACCTATGATGAACGGAAGATCTGGTGATGAAAAAACAGCTGGTTGAAGAACTGAAAGAAGATGTTAAA
AAAGAGCTGATCAACCATCAAGGTAGCACGTCAGCGATGCAGCGTCAGCGATCATGTTAACTGATTGAACTGATCGATG
CCGGTTCAGCCTGCTGGTGATTCTGCATATCATTTGAAGAGAAGTCATAGCATCCTGCAGCATATTCATGTT
ACCTATGGTGAACAGTGGTGGTTAGCAGCGGTGATAAAGAAAATTGCAGAGAATTTTATGGACGAGAAGGCAAATTCAAAGAAAG
AGCAGGGTTTTAATGTTAGCAGCGGTATTCTGCACTGTATGAAGCAGCATTTATGCGTGTTGAAGATGAAACC
CCTGTGTAATGATGCCAGAGTATTCGGCACCGATGTGCACGGTATGCAAAGATCCCCGAGCTGTGATGA
GCAGCCTGCTGCCAGATTTATCATGCAACGAGAAACCAGCCCATAATGAGATCTGCTGAAACTGGCAAACTG
GATTTAGCGTTCTGCAGTGCAACGCAAAAAAGACTGAGCCATATTTGTAAATGGTGAAAAGATCTGG
ATCTGCAGAATAAACTGCCCGTATGTCTGATCGTGTTCTGATGAAAACCTTTACGAGCTGCTGGATCATCAT
ATGAACCGCAGCATGCACGTACCGATGTATGTTTCTGCCGGAAACTGTGCAGTTGAACCTTGGAGCATT
TACGTTTGATTAATGCCACAACATGAAACCTGATTATCAAGAAACTGATTTATCACGAATGAAACCTGGAAA
AGTGTGTCTGATATGCTCCGCGAAAGTGGCCAAGGTGTTAAAAATGGCCAAAACCGTGAAACCTGGAAAG
TGGAAGAAAGTCTGGCACAATTACCCTGCTTTGTTGAACCCTGAATAAACCGTGGTTCATGCCCAGCCGCTGGA
AACTGGGTAGCGATCAGATTACCCTGTAGCCGTTGTTAGCATGGTGAGGTCGCACCGCACTCGAGATGATTCAGAT
AGAGTATAGCGCCCGTCGCTATCCGCCTATTATCGCCTATTATCAAGCAAGCTGTGTT ATTGTTCGCCTGATGATATATTGTGAGCCACAAAGAAGAACAAGAACGCGGTCATGTTGCCAGCAGCA
TTGAAATGTTTATAGCAAAGAAAGTGGTGCAAGCGAAGAAGAAGCCTTGCGAATTATATCAGCCGTAAAGTGG
AAGATGCCTGGAAAGTTAATTAATCGTGAAAGCCTGCGTCCGACCGCAGTTCCGTTCCGCTGCTGATGCT
GCAATTAACCTGGCACGTATGTGTGAAGTTCTGTATAGCGTTAATGATGTTTTACCCATGCCGAAGGTGA
TATGAAATCCTATATGAAAAGCTTCTTCCGTCCATCCGATCGTTGTTTAA (SEQ ID NO: 23)

pMCM1223-pCL-Ptrc-Upper_GcMM_161 (Listeria grayi DSM 20601):
cccgcttactgtcgggaattcgcgttggcgattcattaatgcagatctgaaatgagctgtgacaattaatcatccggctcgtataatgtggaattgtgagcggataacaattt
caccacaggaaacagcgccgttgagaaacaggaagcggaccctgctcttttacaattttatcagacaatcgtgtgggcactcgaccgaattatcgattaacttattaaaaatt
aaagaggtatatataattaatgattaataaggacggatacatgtctataaggacatcgtaaagaactatgcccctccgatcgtactccccatcgtaagtaccggcgctcaaa
gatgacggcggtggaattggaaccgcagtcctgctcgttcgagaagacgaccaggtcaaagacccatgtagaacaagtcattttgcaacgtttacaggcagga
acgccagatcccgcccctcagatcgccccctaattctggcctgccgctcagataccggctcgactattaaccaggtgtggttcggcctgaaagcaataagcatggcgc
gccaacagatcctctgccggaagtaatagtcaggaggtatcgaatcatgacaaatcgccgagttattacatattataaaggaagagaacaccctcaaag
cctgtcctgcagtaccctcgatgctgaccgcggttaacgacggtgttgggttaaccaagtgttgccgaacgatacggcgtatcccgtaggccagggac
gccttgcgtatgatgcagatgcagatgaaagcagcaaagagcccaagaagcaggcatttctcggcaccatttaaagaagatggctactgttacagataggtcctcttgaaatactgccaacgatattactactcaggacgaggg
ggtcgtcaaggagaccaccctgaaaaattaagctcttccggaccatttcctacctcgtctgcgcgtctgagcgcaacgctgtcctcacgcgctcagccgtg
atcattgcatccaagaggttgctgagaacaaacagattcccctaccttcgtctcgtacatgttactagaagatggcagagcttgtgatccatcaatagggccaccatgctaccaatatggccaacaggcaagttctcccgat
atcaataaactgatcaacaaattgcagaagaacattgatcatcatcgaagcatcatcaagcaaggtgtagcctccaaaaaaaaacattcccgat
gaaaagatcaatatttggcgttccgtccattgggcgtgtggtcaggtgccttgccttggcctgagcactgtcacagcgcatccaaaaatttatcaatggcccgtgaacgcgtcaagcgtcctgg
ctagactttcaggacggaacagggtggacatcagccagtgcagtgaaagatatttgtactccgcagaaacctccatatatgttaaaatcgtactcaatatctgaaatgg
aaatccctcggttgtggcttttgagttctcggggctctaatgaaagctgcttcaggttataccatccccactaggagcggatccgcctaataagtgtcaaaaatgcca
aaccactcggcggttcagtccgccagccagtccatcgaaattaaaagatggtttcctcgtcgtggggtcaaacgagtaggggcctaaaagagatgctaaaagagtccaactcgcaagaccgcactacgagagaaa
gcgcaatttctgccgcagtggttcgtgccagcagggctctaaccatcatcggcgcatatgggggcgcatacaagacccgaaggatcttcctatatagaatctctgttctcatttatcta
attacgcaaccgaatcaatttgcagcttcgaccgtcgacccaccacaaaggtattatcaatgagtcgcagtgcagaaaggtgtcagacactgagagtgttaaaagaagaatggttcgcatctaaatttgc
ccgtagaatcctcacgcgatcagcactatcggggcttaagcaactggggcttaagcctgaaatcatggggatccacagaggcgaaagcgagtgcagaaagccagtgcagcaggcaagagtgcagtcgcgtgaggcgtgcgccaatg
cgtatgcttttcagaccgttgcaggtgcctggcg
aatggagctcttccaagcgaaacatagcaggctcttagtgaggaaataacctcggggatccatcagccaagttcgagggcagagaaggagcggaggccaatctggccaaa
cgttaagaggcttgtttagtgaagaatacaacaagcgccagtctgcatagggctgctatccgctctggtcagttggctacaggaggcgcaaggaagttgaaatccgtcggccgaaa
aattacagggctcctcgtataaggcagccggcgaacgctcagaccataactaccagaacagtgaattgaattgtgctagcgactaggaggatataccaatgaccat
gaacgttgaatcgataaaatgtcattattgttccaccttacttgtgacatgctgatctggcaggagcacgatctgcagcagcaccagacctcgacctgtaaatcaaagaagcttctgattggtattggccaggacc
agatggcagttgaatccgaaaacgcaggatattgtgacattgtccagtcgtgccaaaacatatgctcagctgaggacctgatcagtcgcctcttgaaatcaaagaagcctgtatggggtaccgcgct
ttacagttcgctgaacccatttagaatcatcctgaactcaaagttctcgtgctgcatcagatctgcgttagtgcaaatcccaaatacgccgcttaccacgacgatagctccgcttcacgacgatactctatgactctatattttatagtacttttatagtacttttattattg
cgctggtggctatgtcgtcaactgagaccctactcatcacgacaccaattctatgactactcccgctgcagatatacataggcgttggccctagcaaactggtgcgctagtatactgtgcgcgctatctatg
gccacggctactaatagggcaaaaatgggcgtcgtctcaatcttcaggacctcgggctacaaatcctgaggaggagccggataccggcatttactgaatgtaaaaagagtactagacttcctcagaa
aggcggtaccgtaaccgtatccgaggcgtttcctcgatcctctccttccaatctaagcctgttaatggcctctatttaaggggcgatttcaagttcccggtctgctgttt
gcgcaggtttctcaggaaggctgttgaggaactcagggaggacaacagctgcgaacagcagctacttaaaacaacatgccatagaaagcaactgacaatcgaggagtacgaaa
cgatgtttccgatcgctgacgctgaaggcttggaccggtgagaacaaagcgccgaataagcccgaattatggcgatcccatggcgggcaccgaatgagggcgaatt
ttggtaccatatggaatttgaagctgtaatgcagggccgaactgaacctgataagcgccgaagagggtcgccgaggatctcccgaatgccgaaaaagcctaagcgggtcattcagggcccggttaaacggtcccag
ctggcctgtttggcggatgggaagaatttcacaagcctgatgcctgtattcacaccgatctgcgtaatttcaccagcatctcgtctgaatgcagctcgtgcggccatttgcctgccgcacacccgc
caacaccgctgatcggtattcctccctaccgatctgtagatttaaatgcggatttttaatgcgactgtctgtagatttgcctagattttcagtgggcctaaacaaagcaagctttcataaccgccttaagcgcgcccgca
attgtgtaggggtcttattgcgaccacgttagacattattgcctcgacatcgtgcgcatggcgtgaccgatagttgcaagctgcagcaattatgctgctatgactatgctgctgaggccttggctgtgagctgtgatctcccactgatccgcgcctgcggccaagcgatct
aagcggcgtcggctggttggggctgaaccagcagttgggcaggctatcgatgagatctgcgtcttggttcacagtggacacaaatcttccactagttgcgccgagcgaccagaaaggccttggctgtgagctgctgaccgaagacctgtgacatctttcctcaactgatcggccatcttccgccaagcgatct -continued

SEQUENCES tcttcttgtccaagataagcctgtctagcttcaagtatgacgggtgatactgcgcagggcgctccattgccagctcggcagtcggcagcgacatcctcggcgcgatttgccggttac
tgcgctgtaccaaatgcgggacaacgtaagcactacattcgctcatcgcagccgcagcgcggacttccatagccgccgagttcattagcgctcaagatcctgt
caggaaccggatcaaagagttcctccgcgtggaccctccaatgcagtcgcgctccaaggtcgtcgcagcgcatagccagataagctagtcagccagccagccgagat
acctgcgtctccaggggaagccaagttccaaaaggtcgttgatcaagccaacaatgtcgtcgtcgcacacaatggccttcaccgtcaccagcaataatcactgtgtgg
atctcgctctccaggggaagccgaagttccaaaaggtcgttgatcaaggtcgccgcccgtgtttcatcaagcctcgatgagccaactacctctgtagtgatgatcttcggcga
ctccaggccgccatccactcgatgattgttaacttgttagggcgactgctgctgcgtctgcctgtaacatcgtgcctgctgccacgccgtcggtcaaggtctgaccagtgcgtga
tgcccaggcatagactgtaccgcattgcattcagcttacggacgcaacaagcttatgcaccgaacaagcctgaaacgctgtttcatccgttccaccggtgccaacctgggcagcagccgaag
tcgaggcattcgcctggctgggaacggaaagctccgtctccagcgcttgcctccacgcaggtgggcgcctggtctcctccccgcaaggtgtgcacggatctgcc
ctggcttcaggagtcggaagaccccggtcgtgcgcgtgtacctggtcgatgaagttggcatctgacccgggtcgctcctcggtttctgaaggcgagcatcgttgtcgc
ccagcttctgtatggaacgggcatgcggtccagatggggcttcgcaactgcgggacagtgagggtttgctgcgccaaacggctgttctggttctgctagtttgtat
caggatccggtcttcagccggttcgtccagcgccctgaaaacgcgtattttctccagaatggccgatgccagctcttctccaaggaggctgctctcccgtgttcggcagctt
gatcgataagcagcatcgcctgtcatcgtcatcgttcagctgtcagctgtgtgcccagaaacgctgatatatctcagttctggttctgtcaatttgcactgttcatcgctctat
taggtgttactgtcgtctgctgtcgctgaacagtcgcgtagtctcaggtgaacagatgaatgccaacaaaactcgtaaacgtctgtatccatctttcttacaccgtttcatcgtgc
atatggacaagttcccctttgatagtaacggtaacgtgtactttggtttgttactgttgtagtcgtgatcactgatagaatcactgacgtagcccataaagccaagccacgatctccgattage
cagtgtctctcggtcgtttcgtgttttcgtgcgaccagacgagtgagcaactgaaatcactttgcatgcatcaaaatatttgcctcaaacgtgagcgaattttg
cagtttaagcatcgcgtagttggttttcttgaaaatcaaacctgatctacgtcagtcagtagtcgggagatcgggcgctcctattgtgtattttgtcaccaatcatctgtaagtttcatacttactgttctcaagtcgttacaaccatt
ggtaagctcttcaacttgaaaatcaatgcagtagttatttcaagcattaactctcatcaagcgaccttaaatcatcaagcaacaattgctcgtagttgtagttattttaataacactcat
aaatcctcagagtatttcttcaaaagatcatactagttccttctttgagttgggtattcgtaaactctgctagacctctaaattctgcgaaaacttccgtgaaaactgttttatgactcaaaatcattcataattttttcgctt
gagaactggcatagttgcccacctgagcgttcatcatctgaacgctaccgtctgcttaggtgattgcacagcagcagcatagtacaccataaaattagcttg
tcctactgagtcgcatccgttaagcataacgacgactagtcacatctgcatctatatctgtagcaaacaactaattcaatccgtagcgtagacaaaaatgtagccactaatacaatttggggg
gttcatgccgaccggtaagctattagtccttcctttctttctgagtgtgggtatttctggattggggaaaactgactctcgtgaaaccctgtaaatcctgctagacctttgt
ctagtcaataatactatagtccttcctttctttgagtgtcgggtatttctggattggggaaaactgactctcgtgaaaccctgtaaatctcgtagacctttgt
gtgtttttttgtctatatcaagctgctcttttgtccctacaaaacagacctcaaaacctcaaaaccctaaagttagctgcctcgactggacgcUtctaagctgatactagctttgt
tacaaaagatgtcgcaacctgagtcgcctcttttcgtgaccattcagtcgcgtcgcgcgcgcttgcctcggcatcaggcatggcattggcggcagatattcagtcgccggaacagcgagagcagaga
ggaaactaccactaatacaagaaaaagcgtaattagcgaacaattagaaaaagccgtaatggcgcaggggcttctcagggcgtttatggggtcctcaaggccttcaggccgctgacccctcgatttt
ccagctgaccacttcggattatccgtgacgaggcattcagaaggctaatgccaccagtaagcagcggtatctcaacaggtta (SEQ ID NO: 24)

pMCM1224 - pCL-Ptrc-Upper GcMM 162 (Enterococcus faecium):
ccgttcttactgtcggaatttgcgtggccgattcattaatgcagattctgaaatgagctgtgacaattaatcatccggctcgtataatgtggaattgtgagcggataacaattt
cacacaggaaacagcgatgaaaatgctgagaaactgctgtcttatcagaccatgaaaacaatgtacggtgacaattaagcactcaagaaactgtcgatcatgattga
aaagaggtatatttaattgtatcgattaaataaggaggaataaaccatgaaagaagttgtatgtgatgcggtcgcacaccatggaataacagagtattagtcatt
cggacaaaaacgtggggcaacactgtgctgaagaaacagcagacctgtctagctggaggcaccctctttcgcttcagcgcagcaagcgctggcaaagtactgattcggattcctgggtttagggaaatcacaaggtataatacactaacggctcagcaggaaa
gcagtaatcacagaagcagacacctggacactgtgctcacaagaccaccctactgcagagaaccgaatacgaga
gccgatcaatggttaatgacgcgtgacgactgcggtcgttccaatgggcttcgaaaaaggctgcgacccagttccgtcgcggaggaacaaga
ccgtacgacttgctcagcaatggaaaaagcacctgggaaaatgcgtggtcttccagaatcgcgaagaaaagaggaaagtaaagaccgcgtcggctggcagcgcacaagagcgtaagcgaaagcgagggaggatgttcgttcgcgcggacacgtaaaaacg
tgtctgatttgctaagcgaggcaagaaaaaagaagacacttctgtctgcccgggcgttttgcaaaggatatctccagcatgcgaaagctgcgctatgcgccccaat
aaggccattcaaaaagttaacagctccggtcaggcatgaacctgttccacgttgcacaaatttcgattaatgcaagaaaaatggattcctcatcgctgactaataagcagca
gaatcaggcggccaaaatgcggaatgaactgcagaaagaaagttcaagatctcaatctctcatggaaaatgcggggcaaatgctgtcgaataatcaacgggtggcaagttactcacgcgcggtagtcctgaagccctcgtactcaggatttcagccgctccctcc
gcgggcgcaaaaaaaggaaactcgtccaaccccggctctcaggctggaggctgctcaagcccgctgattcctccgcgattttgaacaagtgtgtaaccccggct
aatcatcgccaaaggaggacttgatttattcgcaaccgccgagtggttaacgtcgttccaagcggtaatcatgatcaagtccggtaacgcgcacctcactcagccggtaatatcaccgatcaactccatttatctcattgatctgttctaacgtcaacatgacggcatcaactccagcagcctgcagcaggtgcggcatcaactccaccgatcagcggttctgttccaatcgaactcccgccatcgtgttttattactggggatcgtctgcacgaaccggtaatcatgatcaacttgatctggcgtcacatctctaatatccggcgacttgacctgacgtcgaatgcgctcatactcacatccctcacggctaatcctgtgtgttttctcaagctgtgcaagttgtgatgccaaattaaggactctcagagaagtgggctagccgcgatccatagagcaggtacaggccgatccagttctgtagtcacaggatagatgtgctcaacgcgtcagcgtgcagcttctcagattaatccaccacggagatcatttaacgtgaaggcagatagacgctggcatcaactttcacgcgt
gaatcatcgactgattgtcgggcaaatcgcgtaccgactcgttaacgcggtgaaatcatcagcgatcaactccatgcgcacctcattctccgcggagcaaatcaaaccgttgaaaccactcgaaatcctattctcagacgacgcaactatccaccctccagcaggtcagt
gtttatccatcgactUctggtggacgtcaaggacgtcaatggggcaacatgatccgattattcgcaacagcgtaaacgcggggagctggctaccgatattctacgcggggagttcaggatattctacgcgggagttcaaaagcgtcaactatccaccctccagcaggtcagc
gtatttcaatcgactUctggtggacgtcaaggacgtcaatggggcaacatgatccgattattcgcaaccagcgtcaactcactcattctgcaccccagacttaaagcgtcaaatcaactattcatgctgtcccgaaggaa -continued

SEQUENCES

```
atactgttcccatcctcgctcacggagtccctgcatcctcatgttgcgagattccttttgaaagactttgtgtaacaagaaattggtgaacagatcgccaagaaa
attcaacaggcaggggaaatgctaagcttgacccttaccgcgcaacccataacaaggggattaacgatgtgaacggtatcgagccctgttgccgcaacggaaacgacaca
cgggctgtttccgttcctcattcacgcatacgcgcccaatggcttgtaccaaggttaacgattggcagatcaaggggtaaaatggttggtaaattaacagtcccactggc
tgtggcgactgtcggtgggcgtcgaactattaccaaagccaagatccctcgctgatattgatccgcaaagaactgccaagtgatcgcgccgtaggttt
agcacaagaattcggggcgtacggcgcattagtgacagaaggcacacagaggtcttcaagcacgttcttagcgatttcgataggtgccatcgtgaggagat
agagcaagtcgcgaaaaaacttcgtgaaagctgaagtgcaatcacgatttagaaaaaatcgcgagaatgatctagacgcactcaggaggatac
caatgaaaatcggattgacccgttctctcctcatccgaattgtattggacatgactgagctgcgaatccacggggatgtcagaatcaccggagttgatgatcatattggtatcgt
aagatcaggtggcagtgagtcggcgcaaacgaggcatcataacatgggccgcaagatgtgcgagtaagatctgacagaagaccccgagtgatgatatcgt
tggcctgggatcaggaattgaccactcaaggcagtggacactccttcaaatttcagtcgttcgcccgttatctcgaggtaaaagaagcttgctatggcggaa
ctgcgcccgcacacgtggcaagtgatgtcaaaatctcccggaggcgtgatttcgttgatcgtcgacatgcgcgtatgttggccagcggagaagttactc
aaggcgtgggggccctagccatgatgattaccaacaaacccccgattaattcgattgaagacgtagtgtttctcacaaggaaaagttctatggcgctgattactccg
agtccctgagtggcgggccccttcaaactcaacgatatagaagagttttcagaagttgtaaccggcacaagaataaccaggagcgcttatggcgaaagatggctgaagattagagtctcattgct
atagccggataatttgtcacacgcagctgtcgcctgtcttgaaacttcaagtttcaacccggagacgtcttgctgatagatagcgcgaaggacttccctatgga
gtggtgccggtcccagtattacgggtatttagaagaaaatataccaagagtacctgtcgtcgtcaagccatcaagaaagtgtcgatacgcggactcggactcgatga
ataggagaaccatctttcagagaccctgccagaacatgtggcccgagaacatggtcagaagatgatcgagaacgatttctataacaagatgagaacgacatctgtattataaaactg
actgaagctgtaacatatgggaattcgaagctgggctggccccgaaaacctcatctcagaagaggatcttcagcagatcgaaaagggatgttgataaacagtattgaaaacg
gtctccagcttgctgcggtgatgagaagaagttcagccgaccagaagttcgataaaacagaattcgcagagcagtgggcgtgaggcagtaagcggcggt
ggtcccaccctgccaccggaaccagaagccgtagcgcgatgtagtgggctttgcctgtctccctgagtagtaccctagtcgatagcgggagagccagcaaacgaa
agtgcagtcgaagactggccttcgtttattcgtgtttctcggtgaacctctcggagcgtactcccagctcaaattaaggcagaagggcccgattgcgaagcaacggccgg
agggtggcgggcaggaacgccgcccgccattaagaccaggggcatccaaatcaaggcagaaggcccatccgggcgttgcgttctcaaatctttggttattttctaaatac
attcaaatagtatccgtcatgagacaataaccctgataatgaagctaaatgccaagatagcgagaagaggcccgccacaccccaaactgcgcagctgaat
ggcgaatggcgcctgatgggtcggtatttcttcctaccgcatctgggtattcacacggtatttaatgcggatgtgcgattactcccaaatatcgcgcatggcgcagccgga
caccgccaacacccgctgagactgtagaagctgtctatgaatctgtcgactactggcctttcacgtaactagggctgagcaatatgggctagtgcctctaacgctgagtaagccg
atcccccaatttgtagggcttatatcaccgcgaaaaactaataaagcacgcttagaacgtcatattgcacgctcgcctattcggcctacactctccaactcttcatgatatat
cgcgcgaagcctggggcggctcggagcctctgcggcggagaagcggcggtagaccgaatttcaaagcagttcgcgcagctgatatgctgtagtgctccgactctaacgcttgagtaagcco
gatcctgtcaggaccgagcctcaaagagttccctcgcgcaagcgatgcattgcctgcagcgaccttcccaagacaacaaggcagcgaacaatggcgactagcagc
tcgaagatacctggcaggcggaaaactcggcaatgtcgaggcccatcatttgcgcccgaagccgagaagcttccaaaaggtcgcggatcactcacagcaacacatcaatatca
gcggagaattctgcctctcaagggaaggcgaagttccaaaaggtcgtgatcaaaagtcgtgatgccgcgagttgttcatcaagcgtcaccgtaccagaaatcaattca
gtgtggcttcaggcgcatcaggccgcccatccatgatgttaacttgttaagcgcgaccaaggcaacgtatctgttccttcaaaggccgtaacctctgatagtgatact
tcggccgataccgccgttcccccagtcctcctcaatgttgttttaggcgactgcctgcgtcgctccataacatcgacccacgcgtaacgcgttgct
gcttggatcccgaggcactgcttcaccccaaaaacgtcatacaacaagcatgaaaaacgcatgcgcacctcgctgctgcgcgccactgcgtcggtcgacagttg
cgtgagccgcatacgtggcattccaacagcaaggtcatgctcgttcctcccgttccaccaaggctgtgccctccacccggcaacctggccagca
gcgaagtcgaggcattctgtcctgctggaacgagcccaaggttcgtcgccgagccgctgccgggtcgccgagcgcaagtggctgttcaccaaggggtgtgcacg
atcgccctggctcaggagtcgaaggacgggctcggagtgcggatcagtgcggatttgcaaacggttgcaatcaaggtaaacaggtaggctacagagccagcatcgtt
tgttcgccccagtcgtgatgaacgggcagtcgcgaggtttgcaactgtgcaaggggtcgcaaacgcgctttctgtgttgtcgg
tccaaggatcggcggttcggccccgtcagcggcttgcgcgaactaatcccagaaaatcacctctccagaatgccagatcttcctcagggcgtcactggcaggggcgaggccaaggc
tttgtatcagaatgcagattccggcttcaggagctctctgatgtagtgctgtgtcaagttgactgccctgaaactcgatcgtccagattgtgacgttacttggtgtcccgttgtcgg
cagattgattcgataagcagcatcgccctttcaggctctctatgtgactgtgaactgagcgcgcctgtccaagtgtccactgtcaattcatgtttgatgttactggtttcacct
gttccattaggtcgtacatgtacatcgtccgaaaagctcatggtgaactgtggtcttcaggagaacagtgccctgaacagtcgtaaaagctccatgtgaatgcaccaaaaatcgtaaaagctctgatgtactatcttttaccaccgtttcat
ctgtgccatcaacgtctcctgatgatgtgacactgtgtacagctgttgtttgttgagcattagctaactgcgtgacccccggcatcatcactaccaggctccgtacttgcgtctggctgttgctag
cttagccagtatgtctctcagtgttgttttagtccggtgtgtgtcagtctctgttctcgttgttcgatccatgttgcctcatctcctcatcctcactggttcatgcctcaaaactggccgcagtcgagcga
atttgcagtcagtaaccgcagtatcgtagtcgtcactggaaattcagtggttgtccaccatttcatcgttgtcttcaccttaagtctggtattgcacccgcttcaagtgtcatcactggttcgg
agatcatgtaaaagccatcgatctctagtccaacttggaaatcaacaacgtatccaggcccgcctccgttaacaccaattcatgctgaaagtctttaaactttaaagcttattgttctaaaaac
ccattgtaagcttaaactctgaatgctactgttaatgtgaccattaactaacgactccataactaaagatgaactcatatttatgaattttttaactgaaaataaggtaagcaatcaatcaattttaataccagagc
ctcataaatcctcatagaatagttcttcaaagactcaacactgtacaaagcttaacacatgaacctcaaagatatatttatgaattttttaactggaaaataaggtaataatacacaacatccagaattctaatttcc
gcttgaaaactggcatagttgtcactgacttgtggcatcgccctgcttaacgtctgggcatttcaatcgttaatcgtcaaccaagctctggttgttctgtgtctggtagtgcagtcgtcaagcagtagcctcaggtcatcatcactaccaggctccgtacttgcgtctggctgttgctag
atttccccatctaagcttaaactcacgtcaaaaactgggattgttgcctatggtaagtgaacgatacccgttatttccgttaggggctgttgttttagtgctgtgtgctagtgttattaataacca
ttggttcatgctccgttaagtcatagactaaccgctaagcatctcaaccttgttcaatttgcttaagtccaggctaccacatctcaattggttaattaattctcattaccaattgagatg
``` ggctagtcaatgatgattactagtccttttccttgagttgtgggtatcgtgaattctgctagacccttgtaaattctgctagaccctctgtaaattccgctagacctttgtgtgtttttgttatatttcaagtcgttgctatatttagaataagaaagaccttaaaaaaagaatagatccgacccctgtatcaactcactacttagtcagtccgcagtattacaaagatgtcgcaactgcgttgctcctctacaaaacgaccttaaaacctaaaggcttaagtagcaccctgaagctcggcaaatcctgataatccttttgtctccgaccatcaggcactgcgtcgtgctcttttcgtgacattcagttccgctgctcacggcacccgtcagtgacacaggcgcctttatggattcatgcaaggaaactacccataactacaagaaaagccctcagggcttcaggcgttctaaggcgtttatggcgtgctcatgttgtgctcactttttgacttttgcgcagttccccctgattttccagtcctgaccactccgattccctgacgaggtctcagacggtcaatcagcctaatgcaccgtcaaggcgcggtcatcaatccaacgacctta (SEQ ID NO: 25)

pMCM1225-pCL-Ptrc-Upper GcMM 163 (Enterococcus gallinarum EG2):

ccgtccttactgtcggaatctcggtctggccgattcgtcattaatgcagtcgtgacaattcatcatccggctcgtataatgtgaattgtgagcggataacaatttcacacaggaaacagcgccgtgaactcagacatgtctcaacaattatcagaccatctgtgggcactgcaccgacaatatcgattaacttattaaaatattaagaggtatattaatgtcgataagagaatcacctgaaattatattgaagacctttgtaattatcacggtcgttgaagaagtttcagcgcgtgggcagctggacacccgctaagaacatgctgctgaaagacagtgcgccagcgtccttcaatcaggttgccgtaagctgcgtcgttaacgaggagcggcaggcatataattaacgaggagcgactatctgatgggcatggaacaatccaactgacaaagcgcaaagcgcatcctttgccagtgcgtctgacagacgcaaaaggcgaggaaacagcgcaggcagaaacaaatcgtcaaggcgcagaaacaaatcgtcaaggcgtgaaacgtgcaaccatcaataatcgtaaagcctaagatcgagataccattcaatctgtgagtgcggaacttaccaaaccaagatgtgccactcgcccaagcggaatgtggaatcgatccgagcctgtcgctgacactttcgaagtcgatatgagagcttgccagaaccgctcactcactggttgcagggtaattcagcgtcatcagtgcgtgcccgtcagttacccaatcaagctgaaactgaggaaatgcagcctgtctgacaggagctctatcgcaattgtcaggagttcactcctctccaagagttcagcgtcagtgcagcagtgcaatcctttgccccaatcagtatgatatttcgaagatcagatgtgagcggctacccaaagttgcccaaagcggatggtcttcactctccacctgagagcgttcaccaacatttgggcgttgcactcgatgcttgtgagccatactttgtaccgacccccaagctgtagtgttggggtagctcatgcttgtcagatatggccgttcagacttcaggggcctttcacggagatcaagcctgttgactgctagtgccatcaagctcaagtgaagatccccatgggtgcggtgtcaaattagtcaccggctagcctctcaaaagccgcaacgcaccaggccatgcggcagcgcggagtcaagacaaactacgatatgctaaaaggctcgagccagagattactctaactaaaaggtgcagtccgccactgctatgcaactctcaaacgggtgcgaaccatccgcgaacaatccggcccacagactaacgaggcggggaaacagtgtgtaggcctaccttcgcatagatcctctgctgtccagcctagaggttacagtcccattcactattcaacccatgacagcctttctaccacaggatcacttgtctcccgttgagggctatctgaagcagggtttgtccccttttgagcaaggtctctgagaccacctgtcgcggtacgaccaggaaaccaacactggaacggctgttagctgtgccctgtagctattcatcagcgtctagaacggtgtaagctgctctaccacactccgcgcatggcctctaatcttcaggcggcgcattgccgatgttagtatgttagtatgggcatacgccctcaaaccgatttgactgagttctggagtcagaatagcccctcgggagtgaacccgatgcatcgagatcgctgaccaggttctgagctttgtctgtgacatttggcggatcgcttagctcatccagaaacaagaccacaaggttcccaagcatcaagttaaggactattcagcgtaacagcgtaaccgcaagcgggtgatgacggtaggagctttgcgctagtttaagaaatgaagccaccgtatattcgcatcacgcatcagccctggggaacggatacgccaatgtcatcagctgactgccctacagctgtttgctcctgaacctgcttacagatcgcccgatccgctcaatcgttccatatcctaagcttatgcaactcagcccgataattcaatattctacctgttgaaacagattctgtggactttcgcagtctaacgggcatgttcctcccatctgatacctaaagcatacctcgaagcgttgagttgatccgggcatgtcatctggcccactgccgcgaatccgctatcgagatatcgctacctccaatattgcccatcgggcatcaggcaatacttcatacacgcgaacagggttgtttaagctttcaaggcaggattgcgagcgtcactagggtaaatatcagccggccggggagttggcaatgaccgaagaatcaacagattaccggcaccgctagccttgagggtagagtgaagcagcacccgaagcgggctcccatggaagtcgagaggtcagggcccattgcgtattgagagcgtacaagccgtgcgcccagcaccttcgcctggagaggctactattcgatcatcgaatcaatcgggagatcttctcctccgcaccaacagttcacacgttcccatcatggtccaatctagatcatatgtgcttctggtcactcggccgctgctgataacgagacagagcagagatcacaagtcagaatcgctttaaagtagcgacagatatcttctcctcaagagcgcttaatggaagtattgcaaccgatcgctcatccgcccacaatatcactgactgaacgcaacttgtagacccgtgagtagttaggccacgcatcaagacaaagacgacctgaccaagtcaatcgtcattactaccagtgacttgcagagagcaaccaatgtatagacctgatctggcccaatgccgaagggctgctctgacctccatcttaacctccgccttacatggcagcttagggctaatcctcagagagtcagtgccgtcaagtagttacgactcatcacggcagatcgtcatgtctagtttgccccgtagtgcgaaatggcagcctaccgctgttccaatggtatcactcgatgtatgggcccgcagttcgcagacgcgcatcgtctaacatcagatcgcatcagccatctgctcaggccatcactgtaagcaggagaaagcttactactcgcatcaggctcactatcactccatgccagcgcaaagattcctccgttaccattgcagcggctcctactcctcgtcagtaataagcccaggagtatcgccatcatcactgcacgtgtaccaacagactccaccacatggtaatagcgccttgcgagcaattaccgcagccctgacctatccggaggaacgaagctaccccagggcactcgctggctcacctatcggcagaagcttcatggtgtcgccggtaccggcgatgcttttgccaggtatctgctagagatccgcaacactgcctgtggagtctctaactacctacgctgcagaccgcaaagatcaccattgtaaaaaactcatctcgatgattgttgagcaatctcactttgccccgctatatcctgcgtgatcgccaagcaaccctctctaggccttgtaatgaggatctcttgtgatttagagctcatccggccaccggttaattacaacctgcgaatctgagggtgcaatagtattacagacttagagcaactccgatttgatggcagccgcatgccatggagcaccgcttgccactgagaagtatgagagtcgttatcagaaccggtggatagagtgaagcactcagagtcagttggcgcagccaccgcgatggggtggtcgggtgagttgaccttagcagaagctgcaccgtcacacttttaagacagcgtaatctctgctactgtcatcaccaagtgcgcaataaagttttcaggctctcctgccactgatcactttggatagggggtagaagccagggactcagactgagacccctacgaggccttgttggttcgttacgacgatcgggtgcagttctacatacacactgggccgttagtatggcgacaggggactctgacttgctcttacctcgtctggcggtctacttagcgcgagacccctgcctggcgacgcggacaagccaagccccggtatcttcctggacatatttttctaccgcctctatcccagaagctgtacagccttagttaggcaatcaaggcttaagtgcctgatgggtgaaagcgaataattccgctcttgaagccagacatcgtcttttaacatcttcatcccgacccggagcgatacaccagacaataaacctaccacccgatacctgccgaacaatagacacgaaactcggcttccctcatatcttttgagatcgatacatgccgcagtaccgcatatccagtcatcatatcaatcatctactgagcatcaacccatctcattttaccacatcactagccatttcactctccatgaactactatctcgcctctattggtatctacatcttgacaggcttggagctatcctatttaaatttgaatggaagggtttcggggcactgcgcacatcgctagcaagatcaagaaattagcaaatccaagtttttaaatatcaccgatgatgtagaaaatccatcgatatcatgcaaaactatacttcagtggttctgttgaggtttgtaaaattcgcactacatcacagttcagtaagcatcacttagcaggcgagtaatactctaaacccacaagagtatactgattggtattcttagcagcgcaaggtcggtcaccagtgaccgtgtgcggtatctctaacacagcaacgtgccagcccaacccgttactaagcaagcgactggatggtttacgttacagaacacaatttatcctggtttagggagtctccggtcgtcatccgccctgtagcatccaggttatgctccgatcatcacccgcacgtccttaaacttgcctgggtaaccaactaccctaacttaatcggaagtgctaattttgatatatctctcaatagtatacccccatatgagtttctaaataactccgcggtccgatatgcgccaactcaagccttgcatcgttcatggtccgtctatgccgagcggtgcactctagagcagccgttttttagagaccttttttcctccccatttgttagtccccataacctgccaagagcctacgctcccaatagcttcaaaagatcgcccctaccgtttggcggatcagtgcgttggtctaaagctgtggagatcaatggctgcatccaatagcaatacctggagtaagacgagggatatgacccgataatcaatatgtgcttttgcatatcgccaatccgccttttttgagatccgtgcgtaagttaatctgcaactgactgccccaacagtgcgcagcccgaccccgaatagctgctatgaatagcagagcacaataaatgcgcatgagaacaagaatgcgggcgggcataaaacgatttattcctgggcaccctcaaaactcattttgtttatttttcaaaatacatttccaaactgttgatccgcatctgtatcagcgatgctgcgggtattttcctttacgactctcgttggtgcactccacacagtggcgacttaatgcggtactcctgcgataactaaggccgcaatcgctcgataacagggttcacccaaccctactcaatccagacaatggacgctgaccccaagctgctattaccacgccccatgctactcttatatatgtgagccctgtcagttccctcaacatgccgcatggtgtaagcaggacgaagtaacgagaaatggtcctcaagcgattcagtactaaccccaatccccacctgatgcgagtcaagctgcggaccacagcgtttgtctcaacggacagtaagctcagacgtaatgacagaccatattgccttgtaaccagcaaatctccgaaactacgagccggtctaagtcaatattcccaaactcgacgatgtcaacgcgcccgcacccccagcttgatcctcaagtccctgacattgcgcaactgcatcattgttctaaaaatgaaactcaaccccttcttcaagaacaagcgcccgcgagcagcttcgtttgccgagaaggcactcctcctgatccgagcctccgtctcaaaacgtgcggtagtagtaggcaccctgaagcaggtggaatgttaagagttctaaatacattgcggcggcatgtgcctgatgcaagactcgctgaatcaatattgcggattttcctttaaatgcgtagttggctggcttgtggttggctgtgtgagcgtattgtccattagtcatcttactgccagcatgctcaacgcttagatggcatcttgttggctgtcgttgcgtgtgagcttgagttaa gccgcgccgcgaagcggcgtcggcttgaacgaagttgtagacattattgccgactacctggtgatctcgccttcagtagtggacaaatttcttcaactgatctcgcgcgag
gccaagcgacctctcttcctgccaagataagctctccagatagacgggctgatactgacgggtcgcagcgcttcccagtcggcagcgacatctcttcggcgcg
atttgccggttactgcggtgtgtaccaaatgcggagagagtcctccgccgcgatgcaacgtaggcaactcgcttactgcgtctcttgcttgcagcaagaagccgatcaatgtcgatctgg
aaagatactcgtcaggaacggatcaagaatcgcttgctgctgctgatgcattttccaaatttcctcaaatcgcctgatttctcaaaaggctcgtggatatatcttgtcgaacacctgacttct
ctggtctgaagatcctgcactctcgccctctcaggggaaggcgaagttcccattctccattctgcgcttagcgtgacttagtaacgttcgcgcgtgttcatcaagcttacgcaccagcttcga
acagcgggagaatctcgctctgcagcccgaagttcccagggaaggaagtttccaaaggtcgtgatcaaagtcgccgcgtgttcatcaagcctacgcaccagcagcaaatca
atatcactgtgtggcttcaggcgccatccatgatgttcttaacttgtttaggggaaactcggggagaccgtacgacgtacggccagcgatcgtgcgtcgaatccaactaaacatcgaccaccgcgtacgc
gatgctgtgctggattcggtgatcgaccgagggctgccaagcttccaagacgtgtaaccacagcatatcgtgtgctcccaagtcgtcgtgcgtgtcggtcaaggttctga
ccagttcggggtggaccaaggatagcgcatgtgccgaggctctcgtacgacgtgacgacgagcgaactgcggtctgcccggcgctctctcgccggggtcaccgcaacttgtgg
gcagcagcagcagcgaaggagcgaattctccgtcgcctcggcggcaacgagcgaagtcggctcgccagcatcgttccggtgctgacccgcaggcattgtcgctatctcttccgccacgagcaagtgctgt
gccaggatctcgcctggcttcaggagtcctgatggaaacggggctctatgaacagctggactgaggtcccaggccagactgtcaacctgggtgtcgatgttcaacctggcggtctgactcgtcctcaagcagcaacgtgtttcaggggtctgaagcgcga
caagggctccaaggatgctgggccctgatgccagaggtggcccggagctgccgacgcaggagcgaggagcaccccgcagagcagcagaggatcgtggccccaacgggctgtctcggt
gttgctcagttttgtatcagaatcgagatccggctcgagcctcatcgccctgatcagtgtccactgttgccggtcatatgccatgtgcgtcaattcatgttcagtgcttgttttactg
gtccacctgtctcattagtgtcaatgccactgaccatcggtgtgtccgcgaactgtcagacgcagatatctcttatccagtgtgtgaatccgtgaacagcttgaatgcaacagtcttgaatcgtaaagctctgatgtatctgattcgattttttacac
gatcatctgtgacgaatgcatatgatggtctgataatgtcaaccggaactgcggagacacaacaatgagatacactacttgcatgcatctcactttgcctcaaaatttgcctcaaaactgg
ctccgttgctatttgaatcttagcagtgttctcctagtggtccgtgtgtagttttgcgtgagcatgaggtagagtatcctcagtgttgtgttgaggtgtggtgtgtaatgtattgagagttttcatcattacctgtaaggtgtatctgatgctgtaaggtgaatgatgaaatcttactattggttagagttttcttgttgtctatgtcgagggctatgcagctagttgatgtgtaatcgtgtaatcgttgtgtgtgtgtcaggtactcgcggtggaggatacatcagcgtgtgtagagatcgtgtaatcgtcggaattaacgaccatactgtaattgtgtaagggttcccatgtgaatcatcgggattgcttgatgatttcgccttcctcagtggttagtcagaatcggtccccagggtttcctgagacgtcgctgtttttctgccccttctgaactgtcgaatcgttcaatcgttgttcagcagtcctg
ggttacgagatcctttgctctctgtgttagctcgttaatgagtattcagcgattaaccacgcaatcaccacgcctgtaagtgcaaatgctgagctgatatcctatgtaccactgctcacactcacgagccattaatgaactgcggaatcccagcatccaagtcagtaaagagcaatatccctgccttgcacttaatattttcacaaagatagtcgtcaccatactgctgcttgagatctctatttgctcttgtgagattctttgtatcctttccactcaaaactaattc
ataacactccttgctaatatagctaccactctgagaactggcatagtttgtcaactgctctgtcactgcgataataaaagactattgcgcaatatcaaaggacgtcgagcgatgcgtcagctagcttcacaaaagctcctgagggtatcactggcactgagtgtgcaacacacata
aattacttggttggttagttagtgagtcaattactactagtcaaggcgtgcttgagtctgagctgtcttggtgtgtggaatatagaagaaaaagacaggaactggccaattcctcaattgtcagcggtaaaccctggggccggagtaaaaaactaaagatcactcgcccaaagctgaaaactgtaaatctgcgtagacctcctgtataactactattgctgctgccaatcgtgtaactactttagtcag
tgagcctttgttcaatgggtcaagtcagtggaattatctgtcttccgtaagaaaatctgagcgaactctcgagcgttgtgggagccttgagctgtttctgcttgatcgactttctgtttcagcagtcctg
accggagtattacaaaagtcatgtcgcaacgtgtcgagctcctcacaaacacagacctgtaagacgaggacactcgcaagtcggcgcaagctgcaccacgcgctgaattcctcacaagtcgatt
ccatgtctccgaccatcagcgttctccgtcttgaccagtcaagttttgacggtagtcgagtcgtccgcaggctcgacaggggcttaagtctggtgtggggatgcactaagggcactatg
gattcatgcaaggatgtctggaagcaacgcccgtcacggggttcaccacatgaccgcatcgtgcgtacgatcacccgtacaaaaatcatgcatccgttggtctcagcagttgttcagcagtcctg
ccctctgattttccagtctgaccactcgcgattatctcggtcagcaggtcattcagactgtgcaaatgctgtcaggtcaccctggatgaagcaggatcaggcaggttcaacgagtta
(SEQ ID NO: 26)

pMCM1666 pET24-His-TEV-bMVK:

atccgatatagaccttccttcagcaaaaaaccctcaagaccctttagaggccccaagggttatgctagctagttattgctcagcggtggcagcagccaactcagctcttccttcgg
gctgtgttagcggccggatccagcggttggtggtggtggccgactagctcgagatcgtgacagccggaactgcggaactggatctcggtgacaacacacccagcctgccaccggcat
ccctattgctcagcggcgacgtatccacattttcacgggcctcaggagtttcaacgggaactgcatacaaatccacgactcccccccgcctcgtaattctagaaccgtagctaatcagcctgatcagccggacgtat
aaatcagacgatcgtcagcgaaagaatcagcatcatccaatatggaatctaacagccgccacactcggaatccgaaccagctcgaaatcccatttcgcaccctccg
attacaactcagtttcccataggaataagactcggaactcagcttaactttcgctcgggatcggtgggtatcagcgtacctacacacacatgtcggccacaacacctccctcggacgagaatattggttgtta
ccgatcaaaatcatgccccgcagctatcgttcaacctcgtcttagctgccagtcaaggatgctagcctatagccatagccatagctcgcacgcatagtcgccaacatggccgcaatatcggccggaagcggggaagcgtgtgcctgaacagcgagcaagacggat
ttcaaccctcatggccgcttcaagcgctattcgtcagcgagcctccaccgcgcaaaagtgaaatatcccgaaagactgtcgaaaccatgcaaggaatttgccgaccacgatcggaacgcaagcatgcggccagcgacacataggatgaacatctcgaaatgccgtt
gtgccagatgtgaagagctcgagttgcgcccgcagagcgtatcatcgcgagagagcctgaatagccccctatgtgagccgtcacccatatgagctggaagtgccggccatcccgagggaacactcgccgaaccactctcagcagcattccgatcaatatcggcacagcatcgcaccgtccgtatcgactgcatgttcgcg
aagagatacttctgagggggaaattgttacccgcgagcccagtcaaccgcaacctcctcgctattggcgatcgctcaactcatctatcgagtcatactctgccgaacaccatctcgcggagactgagacctccagtcctgggcaggtgatggcatatgcatcctacgccagacccggggccatcatcacgctgcgcccgcatggaggtcaaacggtggaagtgaag
acaggatacttcatcctgagggggactcgatcgtcgaggcgcctcagccgcagccatcaccaacacccattcaccccaggaaagacacgcgtactatacctcggaatccttcgatgtgatcaccatcgcgtgcatcaaggtcgagatagcccaacctccagcgcacgaatttcgcaggagatactacggccgacgctgcgtcgttctctacggtctgatcgagccgcgtcgcgacccggaagtctctggagtttaccgtgtaacggttgcactcactactacttcaatcagcagatccccgcaggaatgcggaaaactgacgaaagctacccgtgatgtgctgctctttcagctcggatagaagacgtaccgaccccccaaatatatagtgactgaaccccaagtaaaccactagggaagcaaggccagcctactatgggacgaccgctacgccaacccggcgctcaccgtactcactactttagtcag
caggcccccggccgcccgggggactcagcctctcagatatcagcgaatgacgggccgaactcatcagccaaatgggccaaactgttcgcttcacctcgtaatcagcacacgtgggaacctgacatttcggaaacgtggaagacttgtctccaattgctgcaaacactactatgcgccagcgtctcaacctactacgcctgctccctaaatggtcaaccttcctactcggcatatcgacgcctgatgtcggacgaaatgcgagaaccgcgacgaaaactgatgttcgcg
tcgcataaggagggagctggcgttagcgagctgagcgggcactgaatctctgccaaaatcctgtagcaaaactctggtcgtccgagtcggagatgcggtgcccatcgcctatcagacgcaccgccagccagccgctcgacccgcccccgtacaaaccatggctgtgatgatcatagcgcagccatccgggaagccaccagaaggcttttgcgccgcatggag
caggcccccggccgcccgggggactcagcctctcagatatcagcgaatgacgggccgaactcatcagccaaatgggccaaactgttcgcttcacctcgtaatcagcacacgtgggaacctgacatttcggaaacgtggaagacttgtctccaattgctgcaaacactactatgcgccagcgtctcaacctactacgcctgctccctaaatggtcaaccttcctactcggcatatcgacgcctgatgtcggacgaaatgcgagaaccgcgacgaaaactgatgttcgcg
tcgcataaggagggagctggcgttagcgagctgagcgggcactgaatctctgccaaaatcctgtagcaaaactctggtcgtccgagtcggagatgcggtgcccatcgcctatcagacgcaccgccagccagccgctcgacccgcccccgtacaaaccatggctgtgatgatcatagcgcagccatccgggaagccaccagaaggcttttgcgccgcatggag
accagaacgtatacgatgcgagagctatgatgcgtatccacctcccgtcttgcataatgcgcagtggcatgaccaccgccagagaaagtgatcatactgctcatgaaaaaacgacaccctttctcactacgtactgagcgggaatggttgtgaagacacgcggaaaaagtgaag
cgggatgggagctggaattgcgtgaattacattcccaaccgcgtggcacaacaactggcgggcaaacagtcgttgctgctgctgctcttgcgttcactactacgtgttgcacctcagtcggtgccctgccgtc

| SEQUENCES |
|---|
| gcaaattgtgcggcggtgattaaatctcgcgcggatcaactggtgcagctggtgcagctggtgtcgatggtagaacgaagcggctgaagcctgaaagcgcggtcacaatctt
ctcgcgcaacgtcagtggctgatcattactccatgaagacgtgactggcggatgaccaggatccattgctggtgaaagctgcctgcactaatgaccgcgtattctgatgtctgaccag
acaccatcaacagtattattcccatagacgactggtgtcggactggtgagcactctggtcgcattggtcaacagcaaatcggcgtgcgtcgtcgtcgttcaacaaaca
tctcggcgcgtctcgtctcggctgctgcgcataatatccactcagccgatcgcaatcagccgatcggatgcgctggatgccatgtccggttcggttcagccgaggtgcgga
tgcaaagctgaatagacgcgatcacgacgaagacgacagctccgaagaccggtggttgccaacgatattcgcctgcgagtcgctggggcaacagcgtgaccggtgct
tatccggtagtgggatggacacagcgtcgaaggcaggcaatcagtgagccgctccaccttccactgtgaaagaaacccctggcgcccaatacgcaaaccgctctccccgcgtt
gcaactcctcaggcgccagccgctaatgacgtacgcagacgggcaagctccacggcgaaggcgacggcgaacgcaattaagtaagctactgtctcttcttatcatgcaacctgcaccg
ggccggatttcattaatgaccgctgaagcctcaaccagtcagccttacccgtggcgaccagcgatcaagtcatcgtgccgatactgctcctcaaggcctaggcacagggctgcggg
atgccttgaaggcttcaaccagtcagccttcccgagggaatggggcgatgactatcgtgccgaacctggtgctgcagcgccctctggcggaaccctgcgccaagctgcactg
cagcgcctggctcattttgggcggaggcagcgactcgcgtggtattcccgaggaagcagcctgggaaagctggcgaatcctgaatctgccatggccgatgcagcacatgtgccaggttgggaccccgcgtaaggcgcgccgttaggtgcgcggtaagaccgcgtatgccatttcggttccgtgtt
tcgtaaagtctggaaacggtgaattcttccgctccgcaccattagttccggatctgctggtgcttacccctcagcgatgctgcctggcacactcccggcggcagtaagaaaactgcctactattaacgaagctg
gcgatgacccgacgtgaatttctccgccgcgcaccaatgaacgaaatctctcctgcctcgcgttttaccccaaccttacccagcggcatcagtagcatcatcagtacgacgtgagcat
ccctctcgttcatcggtatcattaccccatgacgaaatatcacagacgcatcgttgaatgtgccatcagaaaacggccctttacacatggcgattatcagaagc
cagactaacgcttctgggagaaaccttcgacacatgcagtcccgagacggtcacagttggctcctgaggagatgcagagcaacatgcagaactcagtttcatcggagacaagaacggcgcgatgagcttaccaggctactcgcgcagg
gttggcgggtggggcggagcgtggcgcaggaggcgccagggatgatgccggatggaggcgttcccgaagcgtgctgcttccctcggaaagcggtgcgcttccgagagcgggtaggtattacga
gtcgatgaatacccgcacagatcgtaaggagaaatcaccgcatcaggaaaatacgcagggatataaagataccagggcgttccc
actgcagccagtagcagatgcaggcaatggtaggacagagagccgttttcgggccagagatgttgtgctgcctcggcctggcaactcaactacagcgtagacaca
gtagtagcagcaactctgagctcggctgctgaacagctgtaagcctggtacgacctgctgaagcagttgagccacacccctggctcgctttttcggtgcctgccaagcagggttttttgtcttatgggccgg
gatttggtatctcggcctgcaagcagtcagcgctgcttcgtccggagaaaaggatggtcagcccagcgcttttaggattggtattaggatggtgttttggttgaacaatgtcagcgagcat
ctgctacataaaaatgtcggcaataaatcggcaatcagtaatgccggacaataactctatatactgcagcgaattcctgcactaaggatgagtggttgaacaacacccgagctcaaactacaactcaggatttgaaaaccctctattataggcagtacattaacggtgcagcggtcggcggacgcagcgtaaggtaccctgaataacatgctgcaagaaaaccataaggaagaacagtggtactcgcagagaatactacatctgactctcttacccaacccccgcggaacggccgataaggtggagcgcgctgagcggaactataccgtacaggttaagcagcagcccgcctaactgttatgcgcctctcaggggaacacaaagttaggcagaggcgagcgtcagaaggcagcgcggtcaaaaggtcgttctacaggcaaatgctctttttatcgttttgcttatctcttgatcgatcagtggacgcagaacgccaacctatccaggcggcgtgctgaaggtactaaatgctccacctcaggacaggcgcaagggcatcgagagttgattgcgatgaagttggtagatttgcgcacatggatgaagttgagaagcagtgaaaatcatccctcaccatggcagatcgcgataatgaggatgtcgcgctgatttgggtatcgactatcctcagagaccctactgcagtgcccccgcaatacccaacgagagatatgattattaccgaagtggatttcctcgcctctgctggctgaagcatcttacacacatcctgctaaggagatattcggcgactattaaactcgccatccaaatgcagtatgcttgttgagatgcagagccacaactctctctctctgctctgcagctctggccagaggaacgccattagcgcactaccccctcctggcccgtaatggcgacgaccgcagcagcttgggtggccatctcctcaaagttggcctcaatgaggcagcttgttgtagcctgagacttgaaagaggcgcgatattggctagcgagtcaccatgctagccgccgactcagtaagcgtgcgggccctttaagcgatgaaggcaggagttatcttctatgtcgccccgaagcaactaccatcggcgctatcagggcatcgagccgcggcggaatcgaagcactcccggttaatgcaaactggggtgaaaataacagcagccactctgccagcgggcccatctgcccccactcagtgaaccatccacct
aatcaagttttttggggtcgaggtgccgtaaggcgctaagcgcgttggggaatcctgcatgcaggcggccaagtgtagcggtcacgctgcgcgtaaccaccaccacccgcctcgaaggcttagaggttcgatcaggcgacgagcgagcgacgtgccc
ggaagagaaagcgaaagggaggtggcaacaggtttacactttaggctttggccccccctggaaagcgcccca
attcgcca (SEQ ID NO: 27)

pMCM1669 — pET24-His-TEV-mMVK(GO):
atccggatagtctcctccttcagcaaaaaaccccctcaagaccccgttagaggcccccaagggtttatgctagtattgctcagcggtcagcag
ccaatcagcttacgttccgcagttgtcagccggatccagtggtggtggtcagctgatcattaatccacctttaaaccgctctcgtc
ggcttggttactcttaccgcaactgcttcggcaactgcttcggatacattttccggtgcagtaagagctcacacatccgccccc
accggcaccccgctatcttagcgcagccccagcggcggctgaagaacatagtcagtgagaccaaggttgtctcgcaacgctgtcaatgga
cgcataggctgcatcaatcggtcagagaccctaaccggtgatgatctcaactggcaacactggccaactcgtgttgggaggaaaaaaccctgtgcc
cgtcataaagcgtcaacatccggtttgagatcgtaagctggcgtcaccactaaaaactgcagaaagtggccatagtgctgtttgatgctgc
aataacaatgccactcgatttcaatctcgtgtccaatttcctgtcgatcgcattcgaactcacacaaggccgaatcgtaaactatcgcatt
accttgcacctgattgaactgccaaccagtccgagctacagttgtcgagctaccaacactcctggatagattgcatcttct
gtcagcagctgacctgcccagcagcgcctacgagtcgatgttttcgaagtcgagcgacgtcctattcggacatcgtcagttcagcgaac

| SEQUENCES |
|---|
| tctagtaccgcagttgactgcactgcacatgcgatggcagtttcaccgtactactgctgatgctcaccaaacagatatcttccgggcgcagcagctc |
| accatgccccggaaatagaggttccaccccagtccatgatgatgtgcatatggtgatggtgcatatgtatcctcttaaagttaacaaaattattctag |
| agggaattgttatccgtcacaattccctatagtgagtcgtattaatttcgcggatcgaatctcgatcctctagcgccgacgatcgtggccg |
| gctcgtttcggcgtgcagtggctggtcgccacagggagcgggttgcggccctatcgccgacaccaccgatgggaagatcggctgcactcggtcatgagc |
| gctcgttttcggcgtgggtatggtggcaggcccgtggccgggggactgtgggcgtcattgggcgcctctctgcatgcaccattcctgccggggtgc |
| tcaacgccccaacctactactggctgcttcctaatgcaggagagctgcataaggagagcgtcgagatccggaatccggacaccatcgaatggcgcaaa |
| acctttcgcgtgatggcatggatgatagcgccggaagagagtcaattcaggtgtgaatgtgaaaccagtagtacgatgtcgagtatgc |
| cgtgtctcttatcagaccgttttcccgcgtggtgaaccaggccagccagtcgttggtttgccacctccagtctgcctgacgcg |
| gctgaattactattcccaaccgtggcacaaccaactggcggcaaactggccacagtcgttgcttggcgttcaccccagtcgctccagtcgacggcc |
| ccgtcgcaaatgtcgcgggattaaatctccgcgattcgcgcaactcgcgcgggctgatttaacatctgcgtcagcggggatctgtagaacgatggtgagcc |
| tgtaagcgggtggtgcacaatctctccgcaacgcatggtgcagtgggctgatcattaactatcgctggattgaccaggatgcaattgcgtgggagc |
| tgcctgcataatgttccggcattgcgtcattttcttgatgtctctgaccagacaccaacagtatattctctccatgaagacgtgcctggctggcata |
| aatatctcactcgacatgcaaatcgcgttagcggcctattcgttacggccattaagttctgctcggggcgtctgctgtctggctggcata |
| gagggcatcgtgcccactcgatcgtgcctgcaaacgatcagatgccgccgcattggcgcaatgcgctgctgcggcggcccctacccggctcgggtggt |
| gcaatatccggtgggatacgacgatacccgaagaacgacgattgctatatatccgcgttaaccaccaaacaggtttcgcctgtggg |
| caaaccaagtgggaccgcctttgcgtggtaccttgcgatcctgcgcccgcgcagatccaacgtgctttgtttccccgtcgtgccgtcactggtgtgcgga |
| acctgaccgggacgtggcccgggcggtcgcatggctttcacttgcactaggtagttaagtaaggcacccgatcgctgctctcgtgcgcaaac |
| gcagtgcagcccaacgcaattaatgtaagttctgcgcccaggcaattcatggacggatcgccgattctgcgccggaaacgccctgagggcctgtcaaaccccagtcagctcc |
| ttccgtggcgcccgcagcggcatgactacgtcgcgccaacctgccctgcgcgacgatgacgcgccggaaggctgtccgcgcgcagcggtc |
| atttttcgggcgaggaccgcgttcccttaccctgtttttattcgcgcgtgcagtcttcatcatcagtcagtgcgagctctatcctgaaccctcgtttc |
| gcccgcatcatattacccccatgagcagacaataacgcttctgccgcctgcctcaacgagcgcagttgttcaccggcatccagtaacccgctccttacaggccttat |
| gccgcatcatattacccccatgagcagacaataacgcttctgccgcgctttacccggacaacagagagaaaaccgcccttacatcgccccttat |
| cagaaggccagacattaaccgtctctgaagaaactaacgcttctctgccgcgtttcggtgatgacggtgaaacctcgacacatgcagctcctccgggagacggtcacagagttgctgtaag |
| tgagcttaccgccggatgacaagcccgtcagggcgtctcagggtggcgggtgtcagggctgcagccagtcacgtagcgata |
| gcgagtgtactgctaactactgccagcatatgcgggcatcagcaagatttactgagagtcaactatgcgggtgaaataccgcaagagtgttaag |
| gagaaaataccgcatcaggcgctcttccgcttcctcgctcactgactcgctgcgtcgttcggctgcgcgagcggtatcagctcactcaa |
| agcggtaatacggttatccacagaatcaggggataacgcaggaaagaacatgtgagcaaaaggccagcaaaaggccaggaacccgacagg |
| gcccgttctggccttttgctgcggtttctttccataggctccgccccctgaagctcctcgcgtcagaggtggcgaaacccgacagg |
| actataaagatacccaggcgttccccgctggaagctcccttcgtgcgctctcctgttccgaccctgccgcttaccggatacctgtccgcctttctccctt |
| cggaagcgtggcgctttctcatagctcacgctgtaggtatctcagttcggtgtaggtcgttcgctccaagctgggctgtgtgcacgaaccccc |
| gttcagcccgaccgctgcgcctcatccggtaactatcgtcttgagtccaacccggtaagacacgacttatcgccactggcagcagccactggtatct |
| caggattagcagagcgaggtatgtaggcggtgctacagagtttcttgaagtggtggcctaactacggctacactagaagaacagtattggtatct |
| gcgctctgctgaagccagttaccttcggaaaaagagttggtagctcttgatccggcaaacaaaccaccgctggtagcggtggttttttttgtttgcaa |
| gcagcagattaccgccagaaaaaaggatctcaagaagatctcttgatcctttttctacggggtctgacgctcagtggaacgaaaactcacgttaag |
| ggattttggtcatgcatcatcccccatcttcagcattttgatcgatgatgtttttattctgtgaatgtagcagaaaccaactctgctggaccaagcgaattg |
| ggattttggtcatgagattatcaaaatgaagttttaaatcaatctaaagtatatatatgagtaaacttgggtctgacagttaccaatgcttaatcagtgaggcacctatcctgattatggg |
| aacaagtccgcccgaagtttctgaaacatgcaaagtgccaaatccctgatgtcagtgcttaatacctgataacctattttgacgaggg |
| gaaataagtggtgattatcggacatgaaaatatgctaccggataccgacagactaccgagacacctccggatcagtggtaggcctcgattctcctt |
| cattacagaaacggctttttcaaaaaatatgtattgagaaataccatgcgggctattattgaagcatttatcagggtgtaccttactgtcaagg |
| tgagcggatacatattgaatgtattagaaaaataaacaatagggggttccgcgcaccatttccccgaaaagtgccacctgacgtctaagaaattaattca |
| atttgttaaattcgcgttaaattttgtaaatcagcttcatttttaaccaataggccgaaatcggcaaaatccctatattaaatcaaaagaatagaccga |

-continued

SEQUENCES

MCM1742:

aaagtagccgaagatgaccggtttgtcacatggagtggcaggatgtttgattaaagcaattaaccctcactaaagggcggcgcgaagttcctat
tcctctagaaagtataggaacttcattctcaccgggtaggggaggcgcttctcccaaggcagtcggagcatgcccttgagcagcccgctgggcac
ttggcgctcacaagtggcctcgcctcgcacacattccacactccacggctaggcgccaaccgctcgccttcttggtggcccccttcgcgccac
cctccactcctcccctgcaggaagttccccccccgacaatggaagcggtgtcaggagcggtgacaaatagcagctttgctcctttgctcactagtctc
gtgcagatggacagcaccgtgagcaatgaaccggtaggctttgggcagcggcgggcgggcgcgggaagctcctctgcagcccgagct
ggctggaaggggtggtccgggcggtccaggcgcgggtccaggcgtcttcctctcctatcctcgggcttcgacctgcagcagcacgtgtgacaattaatcatc
tctgacgcttcaaaagcgcacgtcgcgcgtccgtgttcctccatccgggatgcagcgcaaggagtgctgtgacacgtgtgacaattaatcatc
ggcatagtatcggcatagtatatacgacaagtgaggaaataaacatgaaaaaaatcactgatatatatcccaatg
gcatcgtaaagaacattgagcatttgagccatcagttgtcatgtaccatcttcccgcgctaccatatgaatgctcccggctcagctggatattacggccttttaagaccgtaaa
gaaaataagcacaagttatccggcttatcacattcttgcccgcgtatgaaactgaaacgtttcatcagcgctcagttaataccacgacgttccgg
ctggtgatatggatagtgttcaccctgtacaccgtttccatgagcaaactggaaacgtttcatcagcgctcggagtgaataccacgacgattccgg
cagttctcacatattcgaaagtggcaatgaccaactcttcgccccgttttcatccatgaagtttattgagatatgttttcgtctcgagcca
atccctgggtgagttcatcgcggctcggcggtgtctcatgcggttgatggttcatgtcgggcaagatgttaatgaatacaactacggccaaggc
gacaaggtctctgatgccgtgggcgcattcaggttcatcagcgggactctgggttggtgcgcgggcggaagtttcagtccaaggcgatctgaacagcgct
atgaggcagtttttcatgatctctgtgggtgtgttgggcgcgggaagtcctattctctagaaagtataggaactcttctgagccctag
tgagtcgtatcaagataaccatctcgggtgataatatctcggggttgactgaataccactgcgggtgatactgagcacatcagcaggac
gcatcgcTCTAAGATTAAAGAGAAGATTCCTGatgtatcgatttaatcaaggaggaataacatatggatcct
tgctgcgcgggtaagattttaccgttcggtgaacacccgtagtttatggcgaactgcaatgcgtgcgtcggtgaactgcgtacccgtgttc
gcgggaaccttaatgactctatcactattcagagccaaggcggccaccggtcgcaaccgttcgaaaaagcaccttatgtctcggtaattgaga
aaatgcaaaatctattccattaacgagctgtgtttctttgaccgtcgcattcgacatccgcagctccagaagtcctaaactgggccacgaaatcggactactatc
gcgtctattgtgcgctaatcgactactgttcggctttgcctgctgcccctcgcggcgtgggtgttaccctcgggctgggtaccaccgaaaatcgaaatcggactgggcatctg
tgcgcgtcccaaccgatcgctatgtttctcctccaccaaagagttagtagcgaactgttcagctgcgcaaagctcacccggattgatcgaaccgctga
tgacctctattggcaaaatctctcgatccgcgacaacctgtctgtcggcgactaacgcatccatccgccgcctgatgaacgcaacaggtc
tcctggacccgtggcctatggtgcctgaccgctccggaaaatgcaaccaagtcgcaaccaagtggcagaagcggtagcagcgccgtggcgttggcctaaatcacgggcgcc
ggcggccggcgctggcctgatggtgcctgaccgctccggaaaatgcaaccaagtcgcagaagcggtagcagcgcggtaagtgactat
cactaaaccgaccgagcaaggtctgaaagtagagattaa (SEQ ID NO: 29)

MCM1743:

aaagcagccgaagatgaccggtttgtcacatggagtggcaggatgtttgattaaagcaattaaccctcactaaagggcggcgcgaagttcctat
tcctctagaaagtataggaacttcattctcaccgggtaggggaggcgcttctcccaaggcagtcggagcatgcccttgagcagcccgctgggcac
ttggcgctcacaagtggcctcgcctcgcacacattccacactccacggctaggcgccaaccgctcgccttcttggtggcccccttcgcgccac
cctccactcctcccctgcaggaagttccccccccgacaatggaagcggtgtcaggagcggtgacaaatagcagctttgctcctttgctcactagtctc
gtgcagatggacagcaccgtgagcaatgaaccggtaggctttgggcagcggcgggcgggcgcgggaagctcctctgcagcccgagct
ggctggaaggggtggtccgggcggtccaggcgcgggtccaggcgtcttcctctcctatcctcgggcttcgacctgcagcagcacgtgtgacaattaatcatc
tctgacgcttcaaaagcgcacgtcgcgcgtccgtgttcctccatccgggatgcagcgcaaggagtgctgtgacacgtgtgacaattaatcatc
ggcatagtatcggcatagtatatacgacaagtgaggaaataaacatgaaaaaaatcactgatatatatcccaatg
gcatcgtaaagaacattgagcatttgagccatcagttgtcatgtaccatcttcccgcgctaccatatgaatgctcccggctcagctggatattacggccttttaagaccgtaaa
gaaaataagcacaagttatccggcttatcacattcttgcccgcgtatgaaactgaaacgtttcatcagcgctcagttaataccacgacgttccgg
ctggtgatatggatagtgttcaccctgtacaccgtttccatgagcaaactggaaacgtttcatcagcgctcggagtgaataccacgacgattccgg
cagttctcacatattcgcaagatggcgttaaacgtggcaatgaccaactcttcgccccgttttcatccatgaagtttattgagatatgttttcgtctcgagcca
atccctgggtgagttcatcgcggctcggcggtgtctcatgcggttgatggttcatgtcgggcaagatgttaatgaatacaactacggccaaggc
gacaaggtggcaggtctggcgctggcatctcaggttcatcagcgggactctgggttggtgcgcgggcggaagtttcagtccaaggcgatctgaacagcgct
atgaggcagtttttcatgatctctgtgggtgtgttgggcgcgggaagtcctattctctagaaagtataggaactcttctgagccctag

SEQUENCES

```
aataaaagagcttatttcatgatctgtgttgtttgtgcggcggaagttcctattctctagaaagtataggaacttcctcgagccctatag
tgagtcgtataagataaccatctcggtgataaattatctctggcggtttgactgataaactactgcggtgatactgagcacatcagcaggac
gcactgcTCTAGAGCGCACTAAGGAGCCACTGatgtatcgattaaataaggaggataacatatgtatcctgttct
gcgcggtcaagattacctgtcggtgaactaccgtagttatggcgaactgcaattgcgtgtgcggtgaactgcgtaccgtgttcgcgc
ggaactcaatgactcttatcactattcagagccagatcggccgcagatcggccgacactctgattcgaaaagcacccttatgtgtcggtaattgagaaaat
gcgcaaatcattccttattaacggtgttctcggtttcggctttggccctgagcctgcagcagcaaaatcgtaagctggccacgaatcgaaattgaaagtacaagggtgc
tctattggtcgccaaccgatacgtatgtttcctccacaaagagttagtagctaagtgacatctccggaacctgctcagctcgcgaaagactgcaaactccggattgatgaacgctgatga
ttggcgatccggcttttccctcgatcggcgaacaactggtctctgcctggcgatcatctgcgcatcaccgaaagcacccgattgacgaacagggtctcc
cctctatggcaaatctctgactacatcttagaactgagccagtgatcattccgtcgtgcgcagtgcgtttggccgctaaaatcacggccgctgc
ggcggtggcctgtatggtgcgctgaccgctccgaaaatggcaaccaagtggcagaagcggtagcaggccgtgcaggcgctgcggtaaagtgactatcac
taaaccgaccgagcaaggctctgaaagtagattaa (SEQ ID NO: 30)

MCM1745:
aaagtagcgcgaagatgacggtttgtcacatggagtggcaggatggtttgattaaaagcaattaaccctcactaaaggcgcgcgaagttcctat
tcctcagaaagtataggaactctcattctcacgggtagggaggcgtttccccaaggcagtgcgaccatgcgcttagcagcccgtgggcac
ttggcgctacacaaggccctctggcctcgcacacatttcaacctcaccagtagcggccaactgctccgtcttcttggttggccccttcgcgcac
cttccactcctccccctagtcaggaagttcccccgccgcagctcgcttgggcagccgcaatgacagcgcttgctccttgctcctcactagtctc
gtcagatgacagcagcccctgacccagtgaaggtagcgggcggagcccttcaggggtcgggccggggcggtcaggaagcctctcgagcccgcat
gctgccgcttcaaaagccgcgcaacgtgccgcgcttctcctctctccctccgggcttcgacctcgaggacacctttgacaattaatcatc
ggcatcgtatcggcatagtatataacgacaagtgagggaactaaaacatggagaaaaaaatcactgctatataccccttgatatatccaatg
gaaaataagcacaagttgaggcattttatccgccctattcatcttctcccgcgcttatcataccccctgaatcgccatgcgacacgaagacgtgag
ctggatatgagctagcgtgtcacccttgttacgggtgtcagtgtggtacgggcattttcatccgtcgagtgaatcaccacgacgattccgg
cagttctacacatatattcgaaagtgtgcgtttgattaaacgtggcaatatggcccaattcttccctaaaggggtctcctcgccccgccttcacccgttcgtcagcca
atccctggtgagtctgatgccgtggcagttcaggtctcatggcgctttgtatgtctccatggcggcagaagcggtcgcagaatgtctaatgaatacaacagtactgcg
gacaaggtgcaggcccggcgtaagcggggacttcaggttccgaatataagacgaccaagcagctgagcctcttgagcccctggtacc
aatgagtggcagggccaagtggtctaattccatgatcgtgtagttttgctgcgcgggcggaaagcttcctgtcctgcgcagaagaatcgagttagcccctggtacg
tgagctgttaagataaccatctgcggtgataaattatctctggcgtgttcgactgataaactactgcggtaaagacggggtgagcacatcagcaggc
gcactgcTCTAGAGCGAAAAGAGCCGAATATACTAGatgtatcgattaataaggaggataacatatggctacctgtctcgcg
ccgggtagatttagctgtcggtgaacagccaaactactggcttatggcgaactgcaattgcgtgtgcggtgaactgcgtaccgttgcgcga
actcaatgactcttattaacggttctcggcgccatctgagcatcagacgccacccgtcagcgcaaagcacctcatgtgtcgcgtaattgagaaaatgcg
caaatcattccttattaacggtgttctcggcttcggccacgctcgcacgttcgacgtgattgcgatctgaacgtgcaagaatcgtaaactggccacgaatcgaaatggaaaaagcg
ttggcgctgaacgagctgtgttccgggctttcggcctcgaactctcggcgtgatcctgcaagacacatcctcggaagtgcaagagtgcggccatgattgg
cgataccggctcttcctcccaccaagagttagtgcagcaaagatgatctcaacgcaaccgcgttgatcgaaccgctgatgacctc
tatggcaaaatctctgatcggcgaacaactgtcctcgggatcttgccgaccagccgcgcagactgcgcagggtctcctga
cgcctggcgtgtatgttgcgcctgaccgctccgaaaaatggcaacccgcgatcagcggaagcggctgaaagtgactactactac
ccgaccgagcaaggctctgaaagtagattaa (SEQ ID NO: 31)

MCM1747:
aaagtagcgcgaagatgacggtttgtcacatggagtggcaggatggtttgattaaaagcaattaaccctcactaaaggcgcgcgaagttcctat
tcctcagaaagtataggaactctcattctcacgggtagggaggcgtttccccaaggcagtgcgaccatgcgcttagcagcccgtgggcac
ttggcgctacacaaggccctctggcctcgcacacatttcaacctcaccagtagcggccaactgctccgtcttcttggttggccccttcgcgcac
cttccactcctccccctagtcaggaagttcccccgccgcagctcgcttgggcagccgcaatgacagcgcttgctccttgctcctcactagtctc
gtcagatgacagcagcccctgacccagtgaaggtagcgggcggagcccttcaggggtcgggccggggcggtcaggaagcctctcgagcccgcat
```

-continued

SEQUENCES tctgcacgcttcaaagcgctgcgcacgtctgccgcttctctcttcctcatctccggcgcttcgacctgcagcagcacgtgtgacaattaatcatc
ggcatcagtatcggcatagtataacgacaaggtgagaactaaaccatggagaaaaaaatcactgatataccaccgttgatatatccatg
gcatcgtaaagaacatttgaggcatttcagtcagttgctcaatgtacctataccagacgtcagtgatattacggcctttaaagacgctaaa
gaaaataagcacaagtttatccggcctttatccacattccttgccgctgatgaatgctcatccggaattcgtatggcagcggtgag
ctggtgatatggaagatgtcaccctgttcacaccgttttccatgagcaaactgaaaacgtttcatcctctgagtgaataccaacgactttccgg
cagttctcacatatattcgcaagatgtgcgttacggtgttacggccaatcgccattccctaaggggttattgagaatatgttttcgtctcagcca
atccctgggtgagttctgatgccgctggcgattcaggttcatcatgcgcgttgtgatggtccatgtcggcagaatgtcttaatgaatacaacagtatgcg
gacaaggtcgcaggggggtaaggcggactctggggttcgaataaagacggcagacgacgtgagccgacgtgagcctcctgaattcggtacc
atgagtcgcaggcgtctaattcatttcatgacgctgtgttttcatgtgcgggcgaagttctatttattccgtatactgttgacacagaatcctcgagccctatag
aataaaagagctttttcatgacctgctgtgtttttcatgtgcgggcgaagttctatttattccgtatactgttgacacagaatcctcgagccctatag
tgagtcgtattaagataaccatccggcgtgataaattatcctcgcgtgttgacgtaataccactggcgtgatactgagcacatcagcaggac
gcactgcTCCTAGGGCGATTAGGGACCTACTACatgtatcgattcaattaaggaggaataacatatgtatcctgtc
gcgcccggcaagattacctgtcggtgaacacggcccgagtgttatggcgaaactgcaattgcgtgcgtggaactgcgctaccgtgttccgc
ggaaaccaatgaccctaatcactattcagatccagatgccgccgcacccgctgaattcgaaaagcaacagtcgtctgcgtaattgagaaat
gcgcaaatctattcctattaacggtgttctctgaccggtgttcttcgacctttgccttctcgaccttgaccatcccgtgggctccggtgagcagcgttactatcgcg
tctatcggtcgcgctgaacagcgctgtccggctttcgcctttgcctcagccgcggcgtggttaccatccggaaacgctcaaactgggcacgacgtcgaaactccggactgcgcattgtga
tggcgataccggtatgctttctcccaccaaagatagactagcagcagagtgcgaaagctaccggatttgatcgaacctgatga
cctcattggcaaaatctctcgtatcggcgaacaactggttctgtctggagactacgcatccggcagccctgatgaacgtcaaccaggggctccc
tggacgcctggcgttaacatcttagaactgaccgctccggaaaatgcaccagtggcagcaagtgcagaagcgctgcaggttcaaccacggccgctggc
ggcggtggtgattatggtgcctgacggtcaaggtgaaaatgcgcagcagcagaaagtctgtaagctgatataccgctgaacagaagaagcagcaaaatcacgggcgctggtactatcac
taaaccgaccgagccgagcaagtctgaaagtagattaa (SEQ ID NO: 32)

MCM1861:
aaagtagccgaagatgacgagtttgcacactggaggatgaccagattcagattgattaagacaattaaccctcactaaaggccggaagttcctat
tctctagaaagttatgcaacactcattctccgggtaggggagcgctttccagggtttaaaccgtctaactgagctagcccgacgcgcaaaatgccagcccggtctgccc
tggcctcacaaagtgcctgctcgctcgctcgcacattccatccaccgtagcgcaacccgtctcctcttggtgccccctcggcac
ctctctccgaagctcccatatgacggtgctccccccgcctcctgccgcgcagttgagagcgtgtgcagcagcagtggcggcggaagtcaccagttcc
ctgtagagatagacaggcaccacccactatgcaagaatgcaatatgagccgtcggggcaacgtgtcggagcgctcccagaagttgctcccttgcctttcgctccttgctcctcttggctcaga
gtgcagatggaggcgggtgtgggtcagggcgggtgcagggcgggtcaggcgggcgggcgggtgcggggcccccgaaagtctcctccgagccccgcat
tctgcacgcttcaaagcgctgcgcacgtctgccgcttctctcttcctcatctccggcgcttcgacctgcagcagcacgtgtgacaattaatcatc
ggcatcagtatcggcatagtataacgacaaggtgagaactaaaccatggagaaaaaaatcactgatataccaccgttgatatatccatg
gcatcgtaaagaacatttgaggcatttcagtcagttgctcaatgtacctataccagacgtcagtgatattacggcctttaaagacgctaaa
gaaaataagcacaagtttatccggcctttatccacattccttgccgctgatgaatgctcatccggaattcgtatggcagcggtgag
ctggtgatatggaagatgtcaccctgttcacaccgttttccatgagcaaactgaaaacgtttcatcctctgagtgaataccaacgactttccgg
cagttctcacatatattcgcaagatgtgcgttacggtgttacggccaatcgccattccctaaggggttattgagaatatgttttcgtctcagcca
atccctgggtgagttctgatgccgctggcgattcaggttcatcatgcgcgttgtgatggtccatgtcggcagaatgtcttaatgaatacaacagtatgcg
gacaaggtcgcaggggggtaaggcggactctggggttcgaataaagacggcagacgacgtgagccgacgtgagcctcctgaattcggtacc
atgagtcgcaggcgtctaattcatttcatgacgctgtgttttcatgtgcgggcgaagttctatttattccgtatactgttgacacagaatcctcgagccctatag
aataaaagagctttttcatgacctgctgtgtttttcatgtgcgggcgaagttctatttattccgtatactgttgacacagaatcctcgagccctatag
tgagtcgtattaagataaccatccggcgtgataaattatcctcgcgtgttgacgtaataccactggcgtgatactgagcacatcagcaggac
gcactgcTCCTAGGGCGATTAGGGACCTACTACatgtatcgattcaattaaggaggaataacatatgatataacgtgct
ctgccggccaaagtatatcctctgggaacagtgtatcagaggagccgcgatatgtgtcgcgatattagaacgccgtgac
agtcctccgccgataccataccatcctttgacggggatcgagaatacggaactccgacaagtggatcagttcgaggttcatccccatgtcggccgtgttggagcgtt
tccaggatatttcatctttgacgggatgatctgagaatcagtcgagacatccgacatcaagaagtccggatcgcagagtggtcggatctatcgcgcagtaaacattcaggc
gactatataaggctatgaccacatgtctgtgacccgggtggagttgcacggaacgatatcgcaagatggccatgaggtgaacaaaacattcaggc
acggcttctctacgcactatttctcgcccaccaagagtgtggggcttggtcaatgaccggatattagccgatttcgaacaacgttcccgatgtgtaggtccgttcta
atcggtaacaccataattcctcgcccaaagcatctggtgtgggtaatgaccggatattagccgatttcgaacaacgttcccgatgtgtaggtccgttcta
gttctattgggaaactgagtgaatcgaagaggcttagtcaatgaccggattaatgaccggattacgtgacgggaactgatgaacatgacagggcttg
ttaagtcaataggtgttcctgcaagctgatttacgccccgtgaattacgcccgtgaattaccgccctatgagctttatggtcaaagattacagaagcggagcgggtg

SEQUENCES pMCM2020 - pTrcAlba-bMVK:
gttgacagcttatcatcgactgcacgttgcaccaatgctctcgcgtcaggcagcatcggaagctggtagctgtgcagtcgtaaatcac
tgcataattcgtgtcgctcaaggcgcactccgttctgataatgttttgccgcatcataacgttctggcaaatatctgaaatgagctgttg
acaattaatcatccggctcgtataatgtggaattgtgagcggataacaattcacacaggaaacagcgccgtgaaaaagcgaagcgca
ctgcttttaacaattatcagacaatctgtgtgggcactcgaccggaatatgcttacttattaaaaatttaaagagtatatattaatgtatcga
ttaaataaggagatacaaacaaagtcgaaaagcgaaaaagtcgaagccgaagtcgtcgcgaacctaacagctgaccgtatattctgaccct
cgagtccatcgaagtatacaaagacaaagcagaaagcctgggcctgacggctacggacttcctcgtctctaccgtcggatgatccgcgg
gctgaactgattgacaacgtcaaccaagactttcctgaccagcttcctccgtctgcgtggactgtttgaggttctcaggaagcgttcagc
ggcttcaaagaacaacgcaaagccaagtgcaaagataatccaaagctgtcgaagcgaatcggtaaagcgtcctgctgg
aaggcgaaaacatcctggagcagggcgaaggtttcgcaatctcatcgaaagaactgtctgaagaaagatcggtaaagagctgcagaaac
agtgaactggttctgtgtggagctggcaatctcggattacaacatgatccagtctgtataacagcgtgaaacgtccgttggtggcgtc
gtgtgtctcgtggacgcccaaccgccacctcctctcgacgtgagcgtctggtgctgagcaatcggcattcgaaaccgcaatactccg
actgcgtaactccgcgcaaaatgttttcgtaacattcgtaacgatatctgcgatgtacgcacctcgacgaactggagctgtttact
gatcgttcgaagcgttggaacgtaaagcatcaacgaccctgcgtatctgcgacaatctgaaatcggcttctgtataacatttaacgaatcg
cctacgacaacctccaagataaagtagaagaacacctgcgtatctgaccaagccctggcgtgcgacctgtgcaacgcttccctgaagaagcaa
gtggcgtgtacaaatctctccgacaactactctggcaaaacccttcgcaacgtcgaaatcctctctggccgccaactggtcgttcgcttacttcg
ctgtcgtcgagaacattaaaaaggagagatcgaaaacctgcggtgaactgacgaaaaacctggtgtagccgtcgcgaacctggtac
cgaaagcgtagcgctgatgatctcgatgaacctggaaacctgaaacgacgacaactgcgtcggattgacgcctatcctcgcaaacgttcgttctg
taatcactgaacgatctccggttgaacgctaactgcttgaagcgcatcaaggaggtcataaagaaaacatgatacgcgtgaagtgtatctcttc
ggcgaacactgcagttgtatcgaagagcggcgatatgctgtgcgtgacctacatcgtcggccgtgaagctcctccgcagtctctcgatacctaactat
ctctcaagctccggcacaacggggatcgattcgaggtctccatccctatgtgcggtgaggctcaggacgttcaggatattccatctttgacgggt
agattcgagaataagctccgacataccggtgggatcagtgagcggtaacctcaaggtgggactataagcgttatggatacactg
cttgacctggtgagtagacatatacgtaagatgcatgagtggcatgagaatcaaagcaccagggccgcggcctctctacgacacttatgt
gtgtaccatggagcgtcgtcctgataccccagcggaaaagtaagctaggcgcggatttgatcggtaacaccaatatattcctgtc
cacgaaggagtggtgggatggctaatgagcgggatactagggaaactcccatgtgttaggtcttagtctatggaaactcagtgtaatc
ggaaccgtcaagctgttagcatctcaacgcgccctgagctaccggggcttatggcctgagcgcgggggagggtatgtttgctatca
gaactgtcaagtcgaattacgcgccctgagctctgacagcgcttaatgcgacacgagcggggatgtatggttcgcg
gtccgcgtgaaatggaggtgctcgcgaagcaatgggatcgcgcgaaggtgtgtggcaagtggttgcaacgcaacagatatcgtgtcgcg
tagaatgtcagtcagttcgctgataaacgaatttaaacgttaaagtttggcggatgaggagaagatttcagcctgatacagattaatcag
aacgcagaagcggctgatacagcggaaatgtcgtcctcggcgcagtagcgcggtgcccacctgaccctgcaacctcagaagtgaaacgc
cgtagccgcaggagccctggcatgacgtgatagaggaacctcccatcgcagtagaaagctcagtcgaagactggg
cctttcgtttatcgtcgtcgtcgtgagcgagacccggctcctgactaaacctcgggagacggttagagcagggatgaacgcccgag
ggtgcgggcaggagcgccgcgaccgcccccataaactcggccatccggggcatgcagagaccatctaaatggcttgaacgttcctacaaactctt
ttgttttattttctcaaatcacattttctaatatggccccatgataaaaccttgatcatatatggccttaataatattcgaaaaggaagagtaagtattc
aacatttcctgtcgctcaatatatgcttaccgtgctttaccgttgaattcctgtggtgaaaagtggtgaacgtgtgaagatcca
gttggtgcagtgggtggtttcgcgatggctcctggatattatcccgtttgaccaactgaagatttcgcccgcggaagaacttcccaatgatgagcac
tttttaagtctgatagcgcgaataccgggttgtcgtcgtcgatgtgcgatacttttttgatacgagtgatctgcatgatggtccgtccgtcggtcag
gaaggtgcagactttcatctcctttctcgcgtagtccacactaccattttgccgtccgcctacgtatcgtcagcatgagtgatccgatcgtcgtcggg
gtatactcacccgggtaaagcggcgcatatatacgcaggctggcaatgcagcgcagcgtcgatcggggctgcgatatgaattgcatcaaaccgcag
ttagcagccacctcccggaagaaattatgtcagttggcagtcagcactcaaatacggacactcaaagctggctgcaataatgttccagcagg
tttactactccggagaaagcagcgcatcattggcagcaatgatccgcatctctcaacaacaacgtaggtccaactatttaactggcgaacta
cgactatagtctactgccctaagatcgtgagcggcgcaataggcagcactgacctgtcgatagtaagaaggttactcttcaagatggcgtcctct
atggtgctatgaagttggttccacagcatatcgggaagcagatgtggccgggcactgcttctctgcaatgcaaagcaccatgcatcggagtacgacg
acgacggggcgcaggccaactatggatgaacgaaatagacagatcgctgagatggcaagctttaatgcggtagtttatcac -continued

SEQUENCES tttactcatatacttttagattgatttaaaacttcatttttaattaaaggatctagtgaagatcctttgataatctcatgaccaaatccctaacgt
gagtttcgttccactacgtgtcagaccggtcagaccgcggtggttgttgccagcaccacttcaagaactctgagctctgctctcatcgtgaaaat
aaacaccgctaccagtcggtagctgtccacctctcaagaactctgagccgcctacaagacccgctctgctaatccgtaccagtggctgc
actgccctctagtgcagctagtcgtctttaccgcggttggactcaagacgatagttaccggataaggcgcagcggtcggctgaacggggtcgtg
tgccagtgcgataagtcgtgtcttacccggttggactcaagacgatagttaccggataaggcgcagcggtcggctgaacggggtcgtg
cacacagcccagctggagcgaacgacctcaccaccgaactgagatcctcacgcggctgagcatgaaaagcgccacgcttcccgaaggaga
aaggcggacaggtatccgtaagcggcaggtcggaacaggagcggcacgagggagttccagggggaaaacctgtatctttatagtc
ctgtcggggtgtcgccacctgacctgacctgattttgtgactctcttccctgctgatgctcgcaggggcggacctcaggaaaacgccagcaaacgcggcctttt
tacgtcctcctgcccgccgaacctgacctcttctgtcctcacatgttcttccctgctatccctgattctgtgataaccgcttgagtgagctgata
ccgctcgccgcgaacccgcgaacctgacctcagccgagcggaggacggcgctatgacgctattttctcattacgcactg
tgccgtattttcacaccgcatatgctgcactctcagtacaatctgtctctgatgccgccgacgggcttgctgctcccgacacaagctgacc
gccatggctgccgccccgcaccgctgtcgagtcgcgcaggagggatgggaaccttcacaaccgctgtcaagacaagtcgttgctgattg
gtctccggagcgctgtcaagggctgatcaccaccgcgttgtcaccacacgggatcatcgccaagcgcgaaatgtgcgggcgatcaactctcggcgattaatctggtgcagcggtgt
tgcattcactgaacaccgaaccgcagacgctcccggatgcaagacctttaggggtgtgaagaagtcctagggtgtgaatgtgaa
accagtaacgtatacgatgcgagcggcagagtgcgctgtctctatcagacgttctctgatgccgatgtgagccagccaccagctctctcggaaaac
gcggaaaaagtgaagcggcgatgggagcgatgcgagctcggcacgcgcggatgttcgcggcaataatctcgcgtaagcgcagtcgttgctgattg
gcgttgccatccccggtgccgccctgcaggcaggtccccgctgactgatgtccctctttcggggaatctcgcctaatggtgcagcggaggtggtcgcagcgt
gcgtgccgagtggtgaaaagcggctgcgaacgcgtaaaggcggcggaccggcagtgagctcccactcgttgccaatgcg
cggcattacccggtcgggctgcgttgcgcggcgtgcggatatctcggattggtgccgggcaaaccagcggcttgtgaccccgtgagtgggataga
ccaccatcaaaacaggatttcgctgcgttcgctggggaaagaaacccctggcccaatacgaaccctgctcctcccggcctcggtctcttgctactgcagc
tttcccggctctcactggtgaaagacggatgcgaacctgagctgtgacggcagtagcacgctctcccctttctgccgactcatataagtcagctg
gcacgcaggtttccggactggaaagcgggcagtgagcgcaacgcaattaatgtgagttagctcactcattaggcaccccaggctttacactttatgcttccggctcgtatgttgtgtggaattgtgagcggataacaatttcacacaggaaacagctatgaccatgattacgaattgatctg (SEQ ID NO: 34)

pMCM2095 - pTrcAlba-mMVK(del):

gtttgacagcttatcatcgactgacggtgcaccaatgcttctggcgtcaggcagcatgcttctggcgttgtggcgttgtggctgtcgcgtcaaatcac
tgcataattcgtgtcgtccaaggcgcactcgttctggataatgttttgcgcgacatcataacggttctgccaaatattctgaaatgagctgttg
acaattaatcatccggctcatatgtgagaatgtgagcggataacaattcacaccaggaaacagccagtaaccgaagcggca
ctgctcttaacaattatcagacaatcgtgtggcactcgaccggaattatcgattaacttcattattaaaatttaaagagtatattaatgtatcga
ttaataaggaggaataaaccatggaagtataaacgaaaagggggagcgaacctaacactgtggactactcgtcctcccgacacga
cgagtcccagctgaaatgtacaacagagcgaagtcgtcggactaacagatcgcgagattaataacgaaaacagaattctgaccct
gctggaactgtgacaacctcagcgctggaccgcttccagtttctgcaccctgtatccaggggtatccgctgccggtcgttcctccgcgcgg
cttcgatgcggtaaccaaaacgcacctccgcgtaaccaaagagaccgcaagtccgctccgctgctctccggggttcagacttcagagcgttcagc
ggcttcaaagaccccaaaaccctgacgaggcaacttcgacgaaagtttcgcaatcctcgtcgaaaccgacgctctgaaggaaacgtgctgaaaagctgcaagtcctcctg
aaggcgaaaacatcctgaccgagcgaaggtttctgcaatctcagtcgccgcagatgctgctaccgcgccaaacagatcctgaaaagagaccg
agtgagccctgcctcatcgctcgctcgcatgcgatctcatcgtcatccatcgtggtcaaggagacg
cgaatcagttctgctggagctgcaattctgattacaacatgatctgtataccagcgctgctgcagagctgccatcccgtgtggcgtgcatactccg
gtgtggtttggcgaccaaacctcgcacctgctcttcttcctgaccgcctgattgagagttctctactgaccgatgtagcacccggctgctgctagcgcaatacccg
agtcgttgaggcggttggggacgaaccatcaacgaccgcgatttcatgatggacgaaatcccggacattaacattaacctcaatgaagtcagaaaaccgc
atcagatgcggtgaaccgggtgacctgaccgtgtcaacgctttctgaccgtgaccggtcaacgcttcctctgcaagagcaag
tggtgtacaaacatctactccgacctttgacgactactcggcaacatgacaactactctctgcgaccgttgtcttcttctattcgc
tgtctgcagaacattaaaagaggagacgagagacgacgctgagaaccgctggaaaaccgcaaatacacctccgactccgctgcaatgac
ctgctagccgttcgcggaaattcgcggtgaccgatattctgtatccgctctcgtgctcgactctataacactatttaaacgaaatcgc
atgcagtgagcggtgggagcgaccgccatcacgaccgccgattcatatcgacgatgtatccgacagttgtgaacgcgtttcctgaagaacaag
cctacgacaactgggaaatctcccacttctactccgacctttgacgactactcggcaacatgactttcctgtcaacgcttcctctgcaagagcaag
gaaagcggctgtcgtgcgaatgaacgggtgaagaaagtgaacaaggaaaactgagtggtgagctacccctgcaaaccgttcgtgaaacc
gcgatcaactgcgacgtcaatctactccgtcactgcagactgcgtgaacgtggaggacgacgtagcgatgcgtcaatgac
aatcactgaaacgatcctgccgatccgttttgaacgtgtgaactggtatcctgcttcactctctgcgccgggtaggattagctagtta
aagttaaacggtctccagttcgtgcgcttggctgttttggcggatgagagaagatttcagctgcagattaaatcagaattaacgaaccagaggctgataaa

SEQUENCES acagaatttgcctggcggcagtagcgcggtggtccacctgaccctgaccctgcgactcagaagtgaaacgccgtagcgcgatgtagtgg
ggtctcccatgcggagagtagggaactgccaggcatcaaataaacgaaaggctcagtcgaaagactgggccttcgtttatcgtgttgtcg
gtgaacgctctcctgagtaggacaaatccgcgggagcggattgaagcttgaagcaacgcccgaaggggtggcggcagaacgccg
ccataaactgccaggcatcagcgaaggccatccgacggatggccatctggtttcacaaactcttttgttttatttttctaaatacattca
aatatgtatccgcttcatgagacaataaacctgataaaatgcttcaataattgaaaaaggaagagtagtaattcaacattccgtgtcgccctatt
cccttttgcggcatttgccttctctgttttgtcaccagaaacgctggtgaaagtatgaagatcagttggtgcacagtgggttac
atcgaactgaatccaacagcggtaagatccttgagattttcgccccgaagaacgttttccaatgatgagcacttttaaagttctgctatgtggcgc
ggtattatccgttgacgccggcaagaagcaactcggtcgccgcgcatcaccctattccagaatgacttggtgagtactcaccagtcacagaaaa
gcatcttacggatggcatcgatgacagtaagaagaattatgcagtgctgccatcacgtagtgataacactcggcaacttacctgacaacgatcgg
aggaccgaaggagctaaccgctttttgcacaacatggggatcatgtaactcgcctgatggcgttggaccggagctaagcatacca
aacgacgagcgtgacaccacgatgcctgagcaatgcaggaccacctcgcctcgctggtcgccctcgggctggctggtttatgcgaaagggatttccggcaac
aataataactgatgactgtctcgcgtatcattgcgcactggggcagatgtaagcctccgatcgtagtattctcacacgggagtcaggcaac
tatgataatgacaaatagacaatcgtgagatgtgcctcactgattaagcagtgcctcagacaagttactcatataactttagattg
attaaaactcattttttaatttaaaaggatctaggtgaagatctcttttgataatctcatgaccaaaatcccttaacgtgagttttcgttccactgagcgtc
agaacccgtagaaaagatcaaaggatctcttgatcctttttttctgcgcgtaactctttttccgaaggtaactggcttcagcagagcgcagataccaaatactgtcc
gttgttgccggtcaagctaccaactcttttccgaaggtaactggcttcagcagagcgcagataccaaatactgttccctcctagtgtagccgta
gttaggccacctcacttcaagaactctgtagcaccgcctacatacctcgctgttaccagtggctgctgccagtggcgataagtcgtgt
cttaccgggttggactcaagacgatagttaccggataaggcgcagcggtcgggctgaacggggggttcgtgcacacagcccagcttggagcg
aacgacctacaccgaactgagatacctacagcgtgagctgagaaagcggaacagcggacaaagcggacaggtatccgtaaggggagcagcaaagcggacaggtatccgcacctctga
agcggcagggtcggaacaggaggagcgcacgagggagcttccagggggaaacgcctggtatctttatagtcctgtcgggtttcgccacctctga
cttgagcgtcgatttttgttagtgcgtcgattgagctgagtgggggaagcctcagcaacgcggcctttcgttcacgttcctgcgttcctttgctgg
cctttgctcacatgttctttcctgcgttatccctgattctgtggataaaacgcctttacccgcgttgagtgagctcatacgttacgcgcagcgaacg
acgagcgagcgagtcagtgagcgaggaagcggaagagcgcatccgtaagccagtatacactccgctatcgctacggtacactcgtgcggtatccacacgacgatat
ggtgcactctcagtacaatctgctcgacgtactatgccgagatctacggcgttaaccctgctagaccgtctacgtcgccccgaca
cccgcaacaactccgtgacgccctctcaccgcatcaccgaaacgcgaggcgagcagagagatcaattcgccgcgaaggcgaggcagcgtgaaacccgccgaacggcatgcattacgttactgacaccatcg
cagagggttttcaccgtaccgccagccgcgaaattgcgcggaattgcgcgaaatgccgccggcatgaccggcatgcattacgttactgacaccatcg
aatgtgcaaaacctttcgcggtgtccttatcagacgcggttcccgcggtgctgaacaacggcgaacactgggtgaaccagcccgcagatcagcacagccggtgtgaaccagttatacgatgtc
gcagagtatgcggagcgtttgaattacattccagacaccgttatccctggctgaaccagcgcaaacagtcgttgctgattggcgttgccactccagtctgg
cctctgacgcgccgcaatcgcggcgattaattcgcgcgggatcaaatctctcgccacgcccgccgatcaatcagcgtcagcgtagaacgaagcg
gcgtcgaagcctgtaaagcgctgtaaaggcggcggtgacaatcctctcgccaacgctcagtgggctgatcattaactatcgtgagtgatcaccaggatgccatt
gctggaagctgcctgcactaagttccgggcatggtctgcgttagcggcccattaagtctgctccgccggctgctgcgctgctgctgc
tgactgggtcgtcggtgagcattggcatcggtcaccagcaaatcgcgttagcggcgaactgagtgcgcatgcgctgctgcttcaacaaccatgc
tggcggcatcaaatatctcactgcgctgctacatcagcccagcgaacggcggagtcggcatgcgctgcgccattaccgagtccggct
aatgctgaaatgagggcatcgttccacctgagtctgttgcaacgatcagatggcggctgcgctgcgccattaccgagtccggct
gcgcgttggtgcggatatccggatagtgggatacgacgataccgaagacagctcatgttatatccgccgctcaccaccatcaaacaggatttc
gcctgctgggcaaacaccgtgggcgcctgctcaactcctcaggcggcggcgcggtaggcggccaatcagcgttgcccgtctcactggtga
aaagaaaaaaccaccgctaccagcggtggtttgtttgccggatcaagagctaccaactctttttccgaaggtaactggcttcagcagccgccagtttcccgact
ggaaagcgggcagtgagcgcaacgcaattaatgtgagttagcgcgaattgatctg (SEQ ID NO: 35)

What is claimed is:

1. Recombinant bacterial or yeast cells capable of increased production of mevalonate, wherein the cells comprise an attenuated activity of phosphogluconolactonase (PGL), wherein the recombinant bacterial or yeast cells further comprise (i) and (ii):
   (i) modulated activity of two or more enzymes from the group consisting of:
      (a) decreased activity of citrate synthase,
      (b) attenuated activity of phosphotransacetylase,
      (c) attenuated activity of acetate kinase,
      (d) attenuated activity of lactate dehydrogenase,
      (e) increased activity of malate dehydrogenase,
      (f) increased activity of pyruvate dehydrogenase,
      (g) attenuated activity of phosphoenolpyruvate carboxylase, resulting in increased carbon flux towards mevalonate production; and
   (ii) one or more nucleic acids encoding one or more upper mevalonate (MVA) pathway polypeptides; and wherein the cells produce increased amounts of mevalonate compared to mevalonate-producing cells that do not comprise (i) and (ii).

2. The cells of claim 1, wherein the one or more nucleic acids encoding an upper MVA pathway polypeptide are an mvaE gene and an mvaS gene.

3. The cells of claim 2, wherein the 3-hydroxymethyl-3-glutaryl-CoA reductase gene (HMG-CoA reductase, mvaE) and the 3-hydroxy-3-methyl-glutaryl-CoA synthase gene (HMG-CoA synthase, mvaS) are selected from the group consisting of: (a) an mvaE gene and an mvaS gene from *Listeria grayi* (*L. grayi*); (b) an mvaE gene and an mvaS gene from *Enterococcus faecium* (*E. faecium*); (c) an mvaE gene and an mvaS gene from *Enterococcus gallinarum* (*E. gallinarum*); (d) an mvaE gene and an mvaS gene from *Enterococcus casseliflavus* (*E. casseliflavus*); and (e) an mvaE gene and an mvaS gene from *Enterococcus faecalis* (*E. faecalis*).

4. The cells of claim 1, wherein the activity of citrate synthase is decreased by decreasing the expression of an endogenous citrate synthase gene as compared to cells that have not been engineered.

5. The cells of claim 1, wherein the activity of phosphotransacetylase and/or acetate kinase is attenuated by attenuating the expression of an endogenous phosphotransacetylase gene and/or an endogenous acetate kinase gene.

6. The cells of claim 1, wherein the activity of lactate dehydrogenase is attenuated by attenuating the expression of an endogenous lactate dehydrogenase gene.

7. The cells of claim 1, wherein the activity of malate dehydrogenase is increased by increasing the expression of a malate dehydrogenase gene as compared to cells that have not been engineered.

8. The cells of claim 1, wherein the activity of pyruvate dehydrogenase is increased by increasing the expression of one or more genes of the pyruvate dehydrogenase complex consisting of (a) pyruvate dehydrogenase (E1), (b) dihydrolipoyl transacetylase, and (c) dihydrolipoyl dehydrogenase as compared to cells that have not been engineered.

9. The cells of claim 1, wherein the activity of PGL is attenuated by attenuating the expression of an endogenous PGL gene.

10. The cells of claim 1, wherein the activity of phosphoenolpyruvate carboxylase is attenuated by attenuating the expression of an endogenous phosphoenolpyruvate carboxylase gene.

11. The cells of claim 1, wherein the modulated activity of three or more enzymes comprises:
   (I) decreased activity of citrate synthase;
   (II) attenuated activity of one or more of (A) phosphotransacetylase, (B) acetate kinase, and (C) lactate dehydrogenase; and
   (III) modulated activity of one or more enzymes from the group consisting of (D) increased activity of malate dehydrogenase, (E) increased activity of pyruvate dehydrogenase, and (F) attenuated activity of phosphoenolpyruvate carboxylase, wherein the activities of three or more enzymes comprising (I), (II), and (III) are in comparison to cells that have not been engineered.

12. The cells of claim 11, wherein the (III) modulated activity of one or more enzymes comprises (E) increased activity of pyruvate dehydrogenase is in comparison to cells that have not been engineered.

13. The cells of claim 1, wherein the cells are gram-positive bacterial cells, *Streptomyces*, gram-negative bacterial cells, *Escherichia, Pantoea*, or yeast cells.

14. The cells of claim 13, wherein the cells are *Bacillus subtilis, Escherichia coli*, or *Pantoea citrea*.

15. The cells of claim 13, wherein the cells are *Saccharomyces cerevisiae*.

16. A method of producing mevalonate, comprising: (a) culturing the cells of claim 1 under suitable culture conditions for production of mevalonate; and (b) producing the mevalonate.

17. The method of claim 16, further comprising (c) recovering the mevalonate.

* * * * *

SEQUENCE LISTING

<160> NUMBER OF SEQ ID NOS: 117

<210> SEQ ID NO 1
<211> LENGTH: 2439
<212> TYPE: DNA
<213> ORGANISM: L. grayi

<400> SEQUENCE: 1

| | | | | | | |
|---|---|---|---|---|---|---|
| atggttaaag | acattgtaat | aattgatgcc | ctccgtactc | ccatcggtaa | gtaccgcggt | 60 |
| cagctctcaa | agatgacggc | ggtggaattg | ggaaccgcag | ttacaaaggc | tctgttcgag | 120 |
| aagaacgacc | aggtcaaaga | ccatgtagaa | caagtcattt | ttggcaacgt | tttacaggca | 180 |
| gggaacggcc | agaatcccgc | ccgtcagatc | gcccttaatt | ctggcctgtc | cgcagagata | 240 |
| ccggcttcga | ctattaacca | ggtgtgtggt | tctggcctga | agcaataag | catggcgcgc | 300 |
| caacagatcc | tactcggaga | agcggaagta | atagtagcag | gaggtatcga | atccatgacg | 360 |
| aatgcgccga | gtattacata | ttataataaa | gaagaagaca | ccctctcaaa | gcctgttcct | 420 |
| acgatgacct | tcgatggtct | gaccgacgcg | tttagcggaa | agattatggg | tttaacagcc | 480 |
| gaaaatgttg | ccgaacagta | cggcgtatca | cgtgaggccc | aggacgcctt | tgcgtatgga | 540 |
| tcgcagatga | aagcagcaaa | ggcccaagaa | cagggcattt | tcgcagctga | aatactgcct | 600 |
| cttgaaatag | gggacgaagt | tattactcag | gacgaggggg | ttcgtcaaga | gaccaccctc | 660 |
| gaaaaattaa | gtctgcttcg | gaccattttt | aaagaagatg | gtactgttac | agcgggcaac | 720 |
| gcctcaacga | tcaatgatgg | cgcctcagcc | gtgatcattg | catcaaagga | gtttgctgag | 780 |
| acaaaccaga | ttccctacct | tgcgatcgta | catgatatta | cagagatagg | cattgatcca | 840 |
| tcaataatgg | gcattgctcc | cgtgagtgcg | atcaataaac | tgatcgatcg | taaccaaatt | 900 |
| agcatggaag | aaatcgatct | cttttgaaatt | aatgaggcat | ttgcagcatc | ctcggtggta | 960 |
| gttcaaaaag | agttaagcat | tcccgatgaa | aagatcaata | ttggcggttc | cggtattgca | 1020 |
| ctaggccatc | ctcttggcgc | cacaggagcg | cgcattgtaa | ccaccctagc | gcaccagttg | 1080 |
| aaacgtacac | acggacgcta | tggtattgcc | tccctgtgca | ttggcggtgg | ccttggccta | 1140 |
| gcaatattaa | tagaagtgcc | tcaggaagat | cagccggtta | aaaaatttta | tcaattggcc | 1200 |
| cgtgaggacc | gtctggctag | acttcaggag | caagccgtga | tcagcccagc | tacaaaacat | 1260 |
| gtactggcag | aaatgacact | tcctgaagat | attgccgaca | atctgatcga | aaatcaaata | 1320 |
| tctgaaatgg | aaatccctct | tggtgtggct | ttgaatctga | gggtcaatga | taagagttat | 1380 |
| accatcccac | tagcaactga | ggaaccgagt | gtaatcgctg | cctgtaataa | tggtgcaaaa | 1440 |
| atggcaaacc | acctgggcgg | ttttcagtca | gaattaaaag | atggtttcct | gcgtgggcaa | 1500 |
| attgtactta | tgaacgtcaa | agaacccgca | actatcgagc | atacgatcac | ggcagagaaa | 1560 |
| gcggcaattt | ttcgtgccgc | agcgcagtca | catccatcga | ttgtgaaacg | aggtgggggt | 1620 |
| ctaaaagaga | tagtagtgcg | tacgttcgat | gatgatccga | cgttcctgtc | tattgatctg | 1680 |
| atagttgata | ctaaagacgc | aatgggcgct | aacatcatta | acaccattct | cgagggtgta | 1740 |
| gccggctttc | tgagggaaat | ccttaccgaa | gaaattctgt | tctctatttt | atctaattac | 1800 |
| gcaaccgaat | caattgtgac | cgccagctgt | cgcataccct | tacgaagcact | gagtaaaaaa | 1860 |
| ggtgatggta | aacgaatcgc | tgaaaaagtg | gctgctgcat | ctaaatttgc | ccagttagat | 1920 |
| ccttatcgag | ctgcaaccca | caacaaaggt | attatgaatg | gtattgaggc | cgtcgttttg | 1980 |
| gcctcaggaa | atgacacacg | ggcggtcgcg | gcagccgcac | atgcgtatgc | ttcacgcgat | 2040 |
| cagcactatc | ggggcttaag | ccagtggcag | gttgcagaag | gcgcgttaca | cggggagatc | 2100 |

| | |
|---|---|
| agtctaccac ttgcactcgg cagcgttggc ggtgcaattg aggtcttgcc taaagcgaag | 2160 |
| gcggcattcg aaatcatggg gatcacagag gcgaaggagc tggcagaagt cacagctgcg | 2220 |
| gtagggctgg cgcaaaacct ggcggcgtta agagcgcttg ttagtgaagg aatacagcaa | 2280 |
| ggtcacatgt cgctccaggc tcgctctctt gcattatcgg taggtgctac aggcaaggaa | 2340 |
| gttgaaatcc tggccgaaaa attacagggc tctcgtatga atcaggcgaa cgctcagacc | 2400 |
| atactcgcag agatcagatc gcaaaaagtt gaattgtga | 2439 |

<210> SEQ ID NO 2
<211> LENGTH: 1158
<212> TYPE: DNA
<213> ORGANISM: L. grayi

<400> SEQUENCE: 2

| | |
|---|---|
| atgaccatga acgttggaat cgataaaatg tcattctttg ttccacctta ctttgtggac | 60 |
| atgactgatc tggcagtagc acgggatgtc gatcccaata agtttctgat tggtattggc | 120 |
| caggaccaga tggcagttaa tccgaaaacg caggatattg tgacatttgc cacaaatgct | 180 |
| gccaaaaaca tactgtcagc tgaggacctt gataaaattg atatggtcat agtcggcacc | 240 |
| gagagtggaa tcgatgaatc caaagcgagt gccgtagtgc ttcacaggtt gctcggtatc | 300 |
| cagaagtttg ctcgctcctt tgaaatcaaa gaagcctgtt atgggggtac cgcggcttta | 360 |
| cagttcgctg taaaccacat taggaatcat cctgaatcaa aggttcttgt agttgcatca | 420 |
| gatatcgcga aatacggcct ggcttctgga ggtgaaccaa cgcaaggtgc aggcgctgtg | 480 |
| gctatgctcg tctcaactga ccctaagatc attgctttca cgacgatag cctcgcgctt | 540 |
| acacaagata tctatgactt ctggcgacca gttggacatg actatcctat ggtcgacggg | 600 |
| cctcttagta cagagaccta catccagtca tttcagaccg tatggcagga atacacaaaa | 660 |
| cggtcgcagc atgcactggc agactttgct gcccttagct ttcatatccc gtatactaaa | 720 |
| atgggcaaaa aggcgctgct tgcaatcctt gaaggcgaat cagaggaggc tcagaaccgt | 780 |
| atactagcaa aatatgaaaa agtatagcc tactccagaa aggcgggtaa cctgtatacc | 840 |
| ggtagcctgt atctaggact tatttcactt ctggaaaatg cagaagacct taaagctggt | 900 |
| gatttaatag gcctctttc ttacggttcc ggtgctgttg cggagttttt ctcaggaagg | 960 |
| ctggttgagg actatcagga acagctactt aaaacaaaac atgccgaaca gctggcccat | 1020 |
| agaaagcaac tgacaatcga ggagtacgaa acgatgttct ccgatcgctt ggacgtggac | 1080 |
| aaagacgccg aatacgaaga cattagct tatagcattt cgtcagtccg aaacaccgta | 1140 |
| cgtgagtaca ggagttga | 1158 |

<210> SEQ ID NO 3
<211> LENGTH: 2442
<212> TYPE: DNA
<213> ORGANISM: E. faecium

<400> SEQUENCE: 3

| | |
|---|---|
| atgaaagaag tggttatgat tgatgcggct cgcacaccca ttgggaaata cagaggtagt | 60 |
| cttagtcctt ttacagcggt ggagctgggg acactggtca cgaaagggct gctggataaa | 120 |
| acaaagctta agaaagacaa gatagaccaa gtgatattcg gcaatgtgct tcaggcagga | 180 |
| aacggacaaa acgttgcaag acaaatagcc ctgaacagtg gcttaccagt tgacgtgccg | 240 |
| gcgatgacta ttaacgaagt ttgcgggtcc ggaatgaaag cggtgattt agcccgccag | 300 |

```
ttaatacagt tagggagggc agagttggtc attgcagggg gtacggagtc aatgtcacaa    360
gcacccatgc tgaaaccta ccagtcagag accaacgaat acggagagcc gatatcatca    420
atggttaatg acgggctgac ggatgcgttt tccaatgctc acatgggtct tactgccgaa    480
aaggtggcga cccagttttc agtgtcgcgc gaggaacaag accggtacgc attgtccagc    540
caattgaaag cagcgcacgc ggttgaagcc ggggtgttct cagaagagat tattccggtt    600
aagattagcg acgaggatgt cttgagtgaa gacgaggcag taagaggcaa cagcactttg    660
gaaaaactgg gcaccttgcg gacggtgttt tctgaagagg gcacggttac cgctggcaat    720
gcttcaccgc tgaatgacgg cgctagtgtc gtgattcttg catcaaaaga atacgcggaa    780
aacaataatc tgccttacct ggcgacgata aaggaggttg cggaagttgg tatcgatcct    840
tctatcatgg gtattgcccc aataaaggcc attcaaaagt taacagatcg gtcgggcatg    900
aacctgtcca cgattgatct gttcgaaatt aatgaagcat tcgcggcatc tagcattgtt    960
gtttctcaag agctgcaatt ggacgaagaa aaagtgaata tctatggcgg ggcgatagct   1020
ttaggccatc caatcggcgc aagcggagcc cggatactga caaccttagc atacggcctc   1080
ctgcgtgagc aaaagcgtta tggtattgcg tcattatgta tcggcggtgg tcttggtctg   1140
gccgtgctgt tagaagctaa tatggagcag acccacaaag acgttcagaa gaaaaagttt   1200
taccagctta ccccctccga gcggagatcg cagcttatcg agaagaacgt tctgactcaa   1260
gaaacggcac ttattttcca ggagcagacg ttgtccgaag aactgtccga tcacatgatt   1320
gagaatcagg tctccgaagt ggaaattcca atgggaattg cacaaaattt tcagattaat   1380
ggcaagaaaa aatggattcc tatggcgact gaagaacctt cagtaatagc ggcagcatcg   1440
aacggcgcca aatctgcgg gaacatttgc gcggaaacgc ctcagcggct tatgcgcggg   1500
cagattgtcc tgtctggcaa atcagaatat caagccgtga taaatgccgt gaatcatcgc   1560
aaagaagaac tgattctttg cgcaaacgag tcgtacccga gtattgttaa acgcggggga   1620
ggtgttcagg atatttctac gcgggagttt atgggttctt ttcacgcgta tttatcaatc   1680
gactttctgg tggacgtcaa ggacgcaatg ggggcaaaca tgatcaactc tattctcgaa   1740
agcgttgcaa ataaactgcg tgaatggttc ccggaagagg aaatactgtt ctccatcctg   1800
tcaaacttcg ctacggagtc cctggcatct gcatgttgcg agattccttt tgaaagactt   1860
ggtcgtaaca agaaattgg tgaacagatc gccaagaaaa ttcaacaggc agggaatat    1920
gctaagcttg acccttaccg cgcggcaacc cataacaagg ggattatgaa cggtatcgaa   1980
gccgtcgttg ccgcaacggg aaacgacaca cgggctgttt ccgcttctat tcacgcatac   2040
gccgcccgta atggcttgta ccaaggttta acggattggc agatcaaggg cgataaactg   2100
gttggtaaat taacagtccc actggctgtg gcgactgtcg gtggcgcgtc gaacatatta   2160
ccaaaagcca aagcttccct cgccatgctg gatattgatt ccgcaaaaga actggcccaa   2220
gtgatcgccg cggtaggttt agcacagaat ctggcggcgt tacgtgcatt agtgacagaa   2280
ggcattcaga aggacacat gggcttgcaa gcacgttctt tagcgatttc gataggtgcc    2340
atcggtgagg agatagagca agtcgcgaaa aaactgcgtg aagctgaaaa aatgaatcag   2400
caaacggcaa tacagatttt agaaaaaatt cgcgagaaat ga                      2442
```

<210> SEQ ID NO 4
<211> LENGTH: 1155
<212> TYPE: DNA
<213> ORGANISM: E. faecium

<400> SEQUENCE: 4

```
atgaaaatcg gtattgaccg tctgtccttc ttcatcccga atttgtatttt ggacatgact    60
gagctggcag aatcacgcgg ggatgatcca gctaaatatc atattggaat cggacaagat   120
cagatggcag tgaatcgcgc aaacgaggac atcataacac tgggtgcaaa cgctgcgagt   180
aagatcgtga cagagaaaga ccgcgagttg attgatatgg taatcgttgg cacggaatca   240
ggaattgacc actccaaagc aagcgccgtg attattcacc atctccttaa aattcagtcg   300
ttcgcccgtt ctttcgaggt aaaagaagct tgctatggcg aactgctgc cctgcacatg    360
gcgaaggagt atgtcaaaaa tcatccggag cgtaaggtct tggtaattgc gtcagacatc   420
gcgcgttatg gtttggccag cggaggagaa gttactcaag gcgtgggggc cgtagccatg   480
atgattacac aaaaccccg gattctttcg attgaagacg atagtgtttt tctcacagag    540
gatatctatg atttctggcg gcctgattac tccgagttcc ctgtagtgga cgggccctt    600
tcaaactcaa cgtatataga gagttttcag aaagtttgga accggcacaa ggaattgtcc   660
ggaagagggc tggaagatta tcaagctatt gcttttcaca taccctatac gaagatgggt   720
aagaaagcgc tccagagtgt tttagaccaa accgatgaag ataaccagga gcgcttaatg   780
gctagatatg aggagtctat tcgctatagc cggagaattg gtaacctgta cacaggcagc   840
ttgtaccttg gtcttacaag cttgttggaa aactctaaaa gtttacaacc gggagatcgg   900
atcggcctct tttcctatgg cagtggtgcg cgtgtccgagt tctttaccgg gtatttagaa   960
gaaaattacc aagagtacct gttcgctcaa agccatcaag aaatgctgga tagccggact  1020
cggattacgg tcgatgaata cgagaccatc ttttcagaga ctctgccaga acatggtgaa  1080
tgcgccgaat atacgagcga cgtccccttt tctataacca agattgagaa cgacattcgt  1140
tattataaaa tctga                                                   1155

<210> SEQ ID NO 5
<211> LENGTH: 2448
<212> TYPE: DNA
<213> ORGANISM: E. gallinarum

<400> SEQUENCE: 5
atggaagaag tggtaattat agatgcacgt cggactccga ttggtaaata tcacgggtcg    60
ttgaagaagt tttcagcggt ggcgctgggg acggccgtgg ctaaagacat gttcgaacgc   120
aaccagaaaa tcaaagagga gatcgcgcag gtcataattg gtaatgtctt gcaggcagga   180
aatggccaga accccgcgcg gcaagttgct cttcaatcag ggttgtccgt tgacattccc   240
gcttctacaa ttaacgaggt ttgtgggtct ggttttgaaag ctatcttgat gggcatggaa   300
caaatccaac tcggcaaagc gcaagtagtg ctggcaggcg gcattgaatc aatgacaaat   360
gcgccaagcc tgtcccacta taacaaggcg aggatacgt atagtgtccc agtgtcgagc   420
atgacactgg atggtctgac agacgcattt tctagtaaac ctatgggatt aacagcggaa   480
aacgtcgcac agcgctacgg tatctcccgt gaggcgcaag atcaattcgc atatcaatct   540
cagatgaaag cagcaaaagc gcaggcagaa acaaattcg ctaaggaaat tgtgccactg    600
gcgggtgaaa ctaaaaccat cacagctgac gaagggatca gatcccaaac aacgatggag   660
aaactggcaa gtctcaaacc tgttttaaa accgatggca ctgtaaccgc agggaatgct   720
agcaccatta tgacggggc cgcccttgtg ctgcttgcta gcaaaactta ctgcgaaact   780
aatgacatac cgtaccttgc gacaatcaaa gaaattgttg aagttggaat cgatccggag   840
attatgggca tctctccgat aaaagcgata caaacattgt tacaaaatca aaaagttagc   900
```

```
ctcgaagata ttggagtttt tgaaataaat gaagcctttg ccgcaagtag catagtggtt      960
gaatctgagt tgggattaga tccggctaaa gttaaccgtt atgggggtgg tatatcctta     1020
ggtcatgcaa ttggggcaac cggcgctcgc ctggccactt cactggtgta tcaaatgcag     1080
gagatacaag cacgttatgg tattgcgagc tgtgcgttg tggtggact tggactggca      1140 atgcttttag aacgtccaac tattgagaag ctaaaccga cagacaaaaa gttctatgaa     1200
ttgtcaccag ctgaacggtt gcaagagctg gaaaatcaac agaaaatcag ttctgaaact     1260
aaacagcagt tatctcagat gatgcttgcc gaggacactg caaaccattt gatagaaaat     1320
caaatatcag agattgaact cccaatgggc gtcgggatga acctgaaggt tgatgggaaa     1380
gcctatgttg tgccaatggc gacggaagag ccgtccgtca tcgcggccat gtctaatggt     1440
gccaaaatgg ccggcgaaat tcacactcag tcgaaagaac ggctgctcag aggtcagatt     1500
gttttcagcg cgaagaatcc gaatgaaatc gaacagagaa tagctgagaa ccaagctttg     1560
attttcgaac gtgccgaaca gtcctatcct tccattgtga aaagagaggg aggtctccgc     1620
cgcattgcac ttcgtcattt tcctgccgat tctcagcagg agtctgcgga ccagtccaca     1680
tttttatcag tggaccttt tgtagatgtg aaagacgcga tgggggcaaa tatcataaat     1740
gcaatacttg agggcgtcgc agccctgttt cgcgaatggt tccccaatga ggaaattctt     1800
ttttctattc tctcgaactt ggctacggag agcttagtca cggctgtttg tgaagtccca     1860
tttagtgcac ttagcaagag aggtggtgca acggtgcccc agaaaattgt gcaggcgtcg     1920
ctcttcgcaa agacagaccc ataccgcgca gtgacccaca caaagggat tatgaacggt     1980 gtagaggctg ttatgcttgc cacaggcaac gacacgcgcg cagtctcagc cgcttgtcat     2040
ggatacgcag cgcgcaccgg tagctatcag ggtctgacta actggacgat tgagtcggat     2100
cgcctggtag gcgagataac actgccgctg gccatcgcta cagttggagg cgctaccaaa     2160
gtgttgccca agctcaagc ggcactggag attagtgatg ttcactcttc tcaagagctt      2220
gcagccttag cggcgtcagt aggtttagta caaaatctcg cggccctgcg cgcactggtt     2280
tccgaaggta tacaaaaagg gcacatgtcc atgcaagccc ggtctctcgc aatcgcggtc     2340
ggtgctgaaa aagccgagat cgagcaggtc gccgaaaagt tgcggcagaa cccgccaatg     2400
aatcagcagc aggcgctccg ttttcttggc gagatccgcg aacaatga                  2448
```

<210> SEQ ID NO 6
<211> LENGTH: 1155
<212> TYPE: DNA
<213> ORGANISM: E. gallinarum

<400> SEQUENCE: 6

```
atgaacgtcg gcattgacaa aattaattt ttcgttccac cgtattatct ggatatggtc       60
gacctggccc acgcacgcga agtggaccg aacaaattta caattggaat tggacaggat      120
cagatggctg tgagcaaaaa gacgcacgat atcgtaacat tcgcggctag tgccgcgaag     180
gaaattttag aacctgagga cttgcaagct atagacatgg ttatagttgg taccgaatcg     240
ggcattgacg agagcaaagc atccgcggtc gttttacatc gttgttggg cgtacaacct      300 ttcgctcgca gttttgaaat taagaagcc tgttacgggg caaccgcagg cattcagttt      360
gccaagactc atatacaagc gaacccggag agcaaggtcc tggtaattgc aagcgatata     420
gctcggtatg tgcttcggtc aggtggagag cccacacaag gcgcaggggc agttgctatg     480
cttctcacgc aaatcccag aatcctgacc ttcgaaaacg acaatctgat gttaacgcag      540
gatatttatg acttctggag accacttggt cacgcttacc ctatggtaga tggccacctt     600
```

| | | | |
|---|---|---|---|
| tccaatcaag | tctatattga | cagttttaag aaggtctggc aagcacattg cgaacgcaat | 660 |
| caagcttcta | tatccgacta | tgccgcgatt agttttcata ttccgtatac aaaaatgggt | 720 |
| aagaaagccc | tgctcgctgt | ttttgcagat gaagtggaaa ctgaacagga acgcgttatg | 780 |
| gcacggtatg | aagagtctat | cgtatattca cgccggatcg gcaacttgta tacgggatca | 840 |
| ttgtacctgg | ggctgatatc | cttattggaa aacagttctc acctgtcggc gggcgaccgg | 900 |
| ataggattgt | ttagttatgg | gagtggcgct gtcagcgaat ttttctccgg tcgtttagtg | 960 |
| gcaggctatg | aaaatcaatt | gaacaaagag gcgcataccc agctcctgga tcagcgtcag | 1020 |
| aagctttcca | tcgaagagta | tgaggcgatt tttacagatt ccttagaaat tgatcaggat | 1080 |
| gcagcgttct | cggatgacct | gccatattcc atccgcgaga taaaaaacac gattcggtac | 1140 |
| tataaggaga | gctga | | 1155 |

<210> SEQ ID NO 7
<211> LENGTH: 2475
<212> TYPE: DNA
<213> ORGANISM: E. casseliflavus

<400> SEQUENCE: 7

| | | | |
|---|---|---|---|
| atggaagaag | ttgtcatcat | tgacgcactg cgtactccaa taggaaagta ccacggttcg | 60 |
| ctgaaagatt | acacagctgt | tgaactgggg acagtagcag caaaggcgtt gctggcacga | 120 |
| aatcagcaag | caaaagaaca | catagcgcaa gttattattg gcaacgtcct gcaagccgga | 180 |
| agtgggcaga | atccaggccg | acaagtcagt ttacagtcag gattgtcttc tgatatcccc | 240 |
| gctagcacga | tcaatgaagt | gtgtggctcg ggtatgaaag cgattctgat gggtatggag | 300 |
| caaattcagc | tgaacaaagc | ctctgtggtc ttaacaggcg gaattgaaag catgaccaac | 360 |
| gcgccgctgt | ttagttatta | caacaaggct gaggatcaat attcggcgcc ggttagcaca | 420 |
| atgatgcacg | atggtctaac | agatgctttc agttccaaac caatgggctt aaccgcagag | 480 |
| accgtcgctg | agagatatgg | aattacgcgt aaggaacaag atgaatttgc ttatcactct | 540 |
| caaatgaagg | cggccaaagc | ccaggcggcg aaaaagtttg atcaggaaat tgtaccc ctg | 600 |
| acggaaaaat | ccggaacggt | tctccaggac gaaggcatca gagccgcgac aacagtcgag | 660 |
| aagctagctg | agcttaaaac | ggtgttcaaa aaagacggaa cagttacagc gggtaacgcc | 720 |
| tctacgataa | atgatggcgc | tgctatggta ttaatagcat caaaatctta ttgcgaagaa | 780 |
| caccagattc | cttatctggc | cgttataaag gagatcgttg aggtgggttt tgccccccgaa | 840 |
| ataatgggta | tttccccccat | taaggctata gacaccctgc tgaaaaatca agcactgacc | 900 |
| atagaggata | taggaatatt | tgagattaat gaagcctttg ctgcgagttc gattgtggta | 960 |
| gaacgcgagt | tgggcctgga | ccccaaaaaa gttaatcgct atggcggtgg tatatcactc | 1020 |
| ggccacgcaa | ttggggcgac | gggagctcgc attgcgacga ccgttgctta tcagctgaaa | 1080 |
| gatacccagg | agcgctacgg | tatagcttcc ttatgcgttg gtggggtct tggattggcg | 1140 |
| atgcttctgg | aaaacccatc | ggccactgcc tcacaaacta attttgatga ggaatctgct | 1200 |
| tccgaaaaaa | ctgagaagaa | gaagtttttat gcgctagctc ctaacgaacg cttagcgttt | 1260 |
| ttggaagccc | aaggcgctat | taccgctgct gaaaccctgg tcttccagga gatgaccttta | 1320 |
| aacaaagaga | cagccaatca | cttaatcgaa aaccaaatca gcgaagttga aattcctta | 1380 |
| ggcgtgggcc | tgaacttaca | ggtgaatggg aaagcgtata atgttcctct ggccacggag | 1440 |
| gaaccgtccg | ttatcgctgc | gatgtcgaat ggcgccaaaa tggctggtcc tattacaaca | 1500 |

```
acaagtcagg agaggctgtt acggggtcag attgtcttca tggacgtaca ggacccagaa    1560
gcaatattag cgaaagttga atccgagcaa gctaccattt tcgcggtggc aaatgaaaca    1620
tacccgtcta tcgtgaaaag aggaggaggt ctgcgtagag tcattggcag gaatttcagt    1680
ccggccgaaa gtgacttagc cacggcgtat gtatcaattg acctgatggt agatgttaag    1740
gatgcaatgg gtgctaatat catcaatagt atcctagaag gtgttgcgga attgtttaga    1800
aaatggttcc cagaagaaga aatcctgttc tcaattctct ccaatctcgc gacagaaagt    1860
ctggtaacgg cgacgtgctc agttccgttt gataaattgt ccaaaactgg gaatggtcga    1920
caagtagctg gtaaaatagt gcacgcggcg gactttgcta agatagatcc atacagagct    1980
gccacacaca ataaaggtat tatgaatggc gttgaagcgt taatcttagc caccggtaat    2040
gacacccgtg cggtgtcggc tgcatgccac ggttacgcgg cacgcaatgg gcgaatgcaa    2100
gggcttacct cttggacgat tatcgaagat cggctgatag gctctatcac attacctttg    2160
gctattgcga cagtgggggg tgccacaaaa atcttgccaa aagcacaggc cgccctggcg    2220
ctaactggcg ttgagacggc gtcggaactg gccagcctgg cggcgagtgt gggattagtt    2280
caaaatttgg ccgctttacg agcactagtg agcgagggca ttcagcaagg gcacatgagt    2340
atgcaagcta gatccctggc cattagcgta ggtgcgaaag gtactgaaat agagcaacta    2400
gctgcgaagc tgagggcagc gacgcaaatg aatcaggagc aggctcgtaa atttctgacc    2460
gaaataagaa attaa                                                    2475

<210> SEQ ID NO 8
<211> LENGTH: 1161
<212> TYPE: DNA
<213> ORGANISM: E. casseliflavus

<400> SEQUENCE: 8
atgaacgttg gaattgataa aatcaattt ttcgttccgc cctatttcat tgatatggtg      60
gatctcgctc atgcaagaga agttgacccc aacaagttca ctataggaat aggccaagat    120
cagatggcag taaacaagaa aacgcaagat atcgtaacgt tcgcgatgca cgccgcgaag    180
gatattctga ctaaggaaga tttacaggcc atagatatgg taatagtggg gactgagtct    240
gggatcgacg agagcaaggc aagtgctgtc gtattgcatc ggcttttagg tattcagcct    300
tttgcgcgct ccttttgaaat taaggaggca tgctatgggg ccactgccgg ccttcagttt    360
gcaaaagctc atgtgcaggc taatccccag agcaaggtcc tggtggtagc ttccgatata    420
gcacgctacg gactggcatc cggaggagaa ccgactcaag gtgtaggtgc tgtgcaatg    480 ttgatttccg ctgatccagc tatcttgcag ttagaaaatg ataatctcat gttgacccaa    540
gatatatacg atttttggcg cccggtcggg catcaatatc ctatggtaga cggccatctg    600
tctaatgccg tctatataga cagctttaaa caagtctggc aagcacattg cgagaaaaac    660
caacggactg ctaaagatta tgctgcattg tcgttccata ttccgtacac gaaaatgggt    720
aagaaagctc tgttagcggt ttttgcggag gaagatgaga cagaacaaaa gcggttaatg    780
gcacgttatg aagaatcaat tgtatacagt cgtcggactg gaaatctgta tactggctca    840
ctctatctgg gcctgatttc cttactggag aatagtagca gtttacaggc gaacgatcgc    900
ataggtctgt ttagctatgg ttcaggggcc gttgcggaat ttttcagtgg cctcttggta    960
ccgggttacg agaaacaatt agcgcaagct gcccatcaag ctcttctgga cgaccggcaa   1020
aaactgacta tcgcagagta cgaagccatg tttaatgaaa ccattgatat tgatcaggac   1080
cagtcatttg aggatgactt actgtactcc atcagagaga tcaaaaacac tattcgctac   1140
```

```
tataacgagg agaatgaata a                                               1161
```

<210> SEQ ID NO 9
<211> LENGTH: 2412
<212> TYPE: DNA
<213> ORGANISM: E. faecalis

<400> SEQUENCE: 9

```
atgaaaacag tagttattat tgatgcatta cgaacaccaa ttggaaaata taaaggcagc      60
ttaagtcaag taagtgccgt agacttagga acacatgtta caacacaact tttaaaaaga    120
cattccacta tttctgaaga aattgatcaa gtaatctttg gaaatgtttt acaagctgga    180
aatggccaaa atcccgcacg acaaatagca ataaacagcg gtttgtctca tgaaattccc    240
gcaatgacgg ttaatgaggt ctgcggatca ggaatgaagg ccgttatttt ggcgaaacaa    300
ttgattcaat taggagaagc ggaagtttta attgctggcg ggattgagaa tatgtcccaa    360
gcacctaaat tacaacgttt taattacgaa acagaaagct acgatgcgcc ttttctagt    420
atgatgtatg atggattaac ggatgccttt agtggtcagg caatgggctt aactgctgaa    480
aatgtggccg aaaagtatca tgtaactaga gaagagcaag atcaatttc tgtacattca    540
caattaaaag cagctcaagc acaagcagaa gggatattcg ctgacgaaat agccccatta    600
gaagtatcag gaacgcttgt ggagaaagat gaagggattc gccctaattc gagcgttgag    660
aagctaggaa cgcttaaaac agttttaaa gaagacggta ctgtaacagc agggaatgca    720
tcaaccatta tgatggggc ttctgctttg attattgctt cacaagaata tgccgaagca    780
cacggtcttc cttatttagc tattattcga gacagtgtgg aagtcggtat tgatccagcc    840
tatatgggaa tttcgccgat taagccatt caaaaactgt tagcgcgcaa tcaacttact    900
acggaagaaa ttgatctgta tgaaatcaac gaagcatttg cagcaacttc aatcgtggtc    960
caaagagaac tggctttacc agaggaaaag gtcaacattt atggtggcgg tatttcatta   1020
ggtcatgcga ttggtgccac aggtgctcgt ttattaacga gtttaagtta tcaattaaat   1080
caaaagaaa agaaatatgg agtggcttct ttatgtatcg gcggtggctt aggactcgct   1140
atgctactag agagacctca gcaaaaaaaa aacagccgat tttatcaaat gagtcctgag   1200
gaacgcctgg cttctcttct taatgaaggc cagatttctg ctgatacaaa aaaagaattt   1260
gaaaatacgg ctttatcttc gcagattgcc aatcatatga ttgaaaatca atcagtgaa   1320
acagaagtgc cgatgggcgt tggcttacat ttaacagtgg acgaaactga ttatttggta   1380
ccaatggcga cagaagagcc ctcagttatt gcggctttga gtaatggtgc aaaaatagca   1440
caaggattta aaacagtgaa tcaacaacgc ttaatgcgtg gacaaatcgt tttttacgat   1500
gttgcagatc ccgagtcatt gattgataaa ctacaagtaa gagaagcgga agttttcaa   1560
caagcagagt taagttatcc atctatcgtt aaacggggcg gcggcttaag agatttgcaa   1620
tatcgtactt ttgatgaatc attttgtatct gtcgacttt tagtagatgt taaggatgca   1680
atgggggcaa atatcgttaa cgctatgttg gaaggtgtgg ccgagttgtt ccgtgaatgg   1740
tttgcggagc aaaagatttt attcagtatt ttaagtaatt atgccacgga gtcggttgtt   1800
acgatgaaaa cggctattcc agtttcacgt ttaagtaagg ggagcaatgg ccgggaaatt   1860
gctgaaaaaa ttgtttttagc ttcacgctat gcttcattag atccttatcg ggcagtcacg   1920
cataacaaag gaatcatgaa tggcattgaa gctgtagttt tagctacagg aaatgataca   1980
cgcgctgtta gcgcttcttg tcatgctttt gcggtgaagg aaggtcgcta ccaaggcttg   2040
```

```
actagttgga cgctggatgg cgaacaacta attggtgaaa tttcagttcc gcttgcttta   2100
gccacggttg gcggtgccac aaaagtctta cctaaatctc aagcagctgc tgatttgtta   2160
gcagtgacgg atgcaaaaga actaagtcga gtagtagcgg ctgttggttt ggcacaaaat   2220
ttagcggcgt tacgggcctt agtctctgaa ggaattcaaa aaggacacat ggctctacaa   2280
gcacgttctt tagcgatgac ggtcggagct actggtaaag aagttgaggc agtcgctcaa   2340
caattaaaac gtcaaaaaac gatgaaccaa gaccgagcca tggctatttt aaatgattta   2400
agaaaacaat aa                                                       2412

<210> SEQ ID NO 10
<211> LENGTH: 1152
<212> TYPE: DNA
<213> ORGANISM: E. faecalis

<400> SEQUENCE: 10
atgacaattg ggattgataa aattagtttt tttgtgcccc cttattatat tgatatgacg     60
gcactggctg aagccagaaa tgtagaccct ggaaaattttc atattggtat tgggcaagac   120
caaatggcgg tgaacccaat cagccaagat attgtgacat ttgcagccaa tgccgcagaa   180
gcgatcttga ccaagaaga taagaggcc attgatatgg tgattgtcgg gactgagtcc      240
agtatcgatg agtcaaaagc ggccgcagtt gtcttacatc gtttaatggg gattcaacct    300
ttcgctcgct ctttcgaaat caaggaagct tgttacggag caacagcagg cttacagtta    360
gctaagaatc acgtagcctt acatccagat aaaaaagtct tggtcgtagc ggcagatatt    420
gcaaaatatg gcttaaattc tggcggtgag cctacacaag gagctggggc ggttgcaatg    480
ttagttgcta gtgaaccgcg cattttggct ttaaaagagg ataatgtgat gctgacgcaa    540
gatatctatg acttttggcg tccaacaggc cacccgtatc ctatggtcga tggtcctttg    600
tcaaacgaaa cctacatcca atcttttgcc caagtctggg atgaacataa aaaacgaacc    660
ggtcttgatt tgcagatta tgatgccttta gcgttccata ttccttacac aaaaatgggc    720
aaaaaagcct tattagcaaa aatctccgac caaactgaag cagaacagga acgaattta     780
gcccgttatg aagaaagtat cgtctatagt cgtcgcgtag gaaacttgta tacgggttca    840
ctttatctgg gactcatttc ccttttagaa aatgcaacga ctttaaccgc aggcaatcaa    900
attggtttat tcagttatgg ttctggtgct gtcgctgaat ttttcactgg tgaattagta    960
gctggttatc aaaatcattt acaaaaagaa actcatttag cactgctgga taatcggaca   1020
gaactttcta tcgctgaata tgaagccatg tttcagaaaa ctttagacac agacattgat   1080
caaacgttag aagatgaatt aaaatatagt atttctgcta ttaataatac cgttcgttct   1140
tatcgaaact aa                                                       1152

<210> SEQ ID NO 11
<211> LENGTH: 815
<212> TYPE: PRT
<213> ORGANISM: E. gallinarum

<400> SEQUENCE: 11

Met Glu Glu Val Val Ile Ile Asp Ala Arg Arg Thr Pro Ile Gly Lys
1               5                   10                  15

Tyr His Gly Ser Leu Lys Lys Phe Ser Ala Val Ala Leu Gly Thr Ala
                20                  25                  30

Val Ala Lys Asp Met Phe Glu Arg Asn Gln Lys Ile Lys Glu Glu Ile
            35                  40                  45
```

```
Ala Gln Val Ile Ile Gly Asn Val Leu Gln Ala Gly Asn Gly Gln Asn
     50                  55                  60

Pro Ala Arg Gln Val Ala Leu Gln Ser Gly Leu Ser Val Asp Ile Pro
65                  70                  75                  80

Ala Ser Thr Ile Asn Glu Val Cys Gly Ser Gly Leu Lys Ala Ile Leu
                    85                  90                  95

Met Gly Met Glu Gln Ile Gln Leu Gly Lys Ala Gln Val Val Leu Ala
                100                 105                 110

Gly Gly Ile Glu Ser Met Thr Asn Ala Pro Ser Leu Ser His Tyr Asn
            115                 120                 125

Lys Ala Glu Asp Thr Tyr Ser Val Pro Val Ser Ser Met Thr Leu Asp
130                 135                 140

Gly Leu Thr Asp Ala Phe Ser Ser Lys Pro Met Gly Leu Thr Ala Glu
145                 150                 155                 160

Asn Val Ala Gln Arg Tyr Gly Ile Ser Arg Glu Ala Gln Asp Gln Phe
                165                 170                 175

Ala Tyr Gln Ser Gln Met Lys Ala Ala Lys Ala Gln Ala Glu Asn Lys
            180                 185                 190

Phe Ala Lys Glu Ile Val Pro Leu Ala Gly Glu Thr Lys Thr Ile Thr
195                 200                 205

Ala Asp Glu Gly Ile Arg Ser Gln Thr Thr Met Glu Lys Leu Ala Ser
210                 215                 220

Leu Lys Pro Val Phe Lys Thr Asp Gly Thr Val Thr Ala Gly Asn Ala
225                 230                 235                 240

Ser Thr Ile Asn Asp Gly Ala Ala Leu Val Leu Leu Ala Ser Lys Thr
                245                 250                 255

Tyr Cys Glu Thr Asn Asp Ile Pro Tyr Leu Ala Thr Ile Lys Glu Ile
            260                 265                 270

Val Glu Val Gly Ile Asp Pro Glu Ile Met Gly Ile Ser Pro Ile Lys
            275                 280                 285

Ala Ile Gln Thr Leu Leu Gln Asn Gln Lys Val Ser Leu Glu Asp Ile
290                 295                 300

Gly Val Phe Glu Ile Asn Glu Ala Phe Ala Ala Ser Ser Ile Val Val
305                 310                 315                 320

Glu Ser Glu Leu Gly Leu Asp Pro Ala Lys Val Asn Arg Tyr Gly Gly
                325                 330                 335

Gly Ile Ser Leu Gly His Ala Ile Gly Ala Thr Gly Ala Arg Leu Ala
            340                 345                 350

Thr Ser Leu Val Tyr Gln Met Gln Glu Ile Gln Ala Arg Tyr Gly Ile
            355                 360                 365

Ala Ser Leu Cys Val Gly Gly Gly Leu Gly Leu Ala Met Leu Leu Glu
370                 375                 380

Arg Pro Thr Ile Glu Lys Ala Lys Pro Thr Asp Lys Lys Phe Tyr Glu
385                 390                 395                 400

Leu Ser Pro Ala Glu Arg Leu Gln Glu Leu Asn Gln Gln Lys Ile
                405                 410                 415

Ser Ser Glu Thr Lys Gln Gln Leu Ser Gln Met Met Leu Ala Glu Asp
                420                 425                 430

Thr Ala Asn His Leu Ile Glu Asn Gln Ile Ser Glu Ile Glu Leu Pro
            435                 440                 445

Met Gly Val Gly Met Asn Leu Lys Val Asp Gly Lys Ala Tyr Val Val
450                 455                 460

Pro Met Ala Thr Glu Glu Pro Ser Val Ile Ala Ala Met Ser Asn Gly
```

```
            465                 470                 475                 480
Ala Lys Met Ala Gly Glu Ile His Thr Gln Ser Lys Glu Arg Leu Leu
                485                 490                 495

Arg Gly Gln Ile Val Phe Ser Ala Lys Asn Pro Asn Glu Ile Glu Gln
                500                 505                 510

Arg Ile Ala Glu Asn Gln Ala Leu Ile Phe Glu Arg Ala Glu Gln Ser
                515                 520                 525

Tyr Pro Ser Ile Val Lys Arg Glu Gly Leu Arg Arg Ile Ala Leu
                530                 535                 540

Arg His Phe Pro Ala Asp Ser Gln Gln Glu Ser Ala Asp Gln Ser Thr
545                 550                 555                 560

Phe Leu Ser Val Asp Leu Phe Val Asp Val Lys Asp Ala Met Gly Ala
                565                 570                 575

Asn Ile Ile Asn Ala Ile Leu Glu Gly Val Ala Ala Leu Phe Arg Glu
                580                 585                 590

Trp Phe Pro Asn Glu Glu Ile Leu Phe Ser Ile Leu Ser Asn Leu Ala
                595                 600                 605

Thr Glu Ser Leu Val Thr Ala Val Cys Glu Val Pro Phe Ser Ala Leu
610                 615                 620

Ser Lys Arg Gly Gly Ala Thr Val Ala Gln Lys Ile Val Gln Ala Ser
625                 630                 635                 640

Leu Phe Ala Lys Thr Asp Pro Tyr Arg Ala Val Thr His Asn Lys Gly
                645                 650                 655

Ile Met Asn Gly Val Glu Ala Val Met Leu Ala Thr Gly Asn Asp Thr
                660                 665                 670

Arg Ala Val Ser Ala Ala Cys His Gly Tyr Ala Ala Arg Thr Gly Ser
                675                 680                 685

Tyr Gln Gly Leu Thr Asn Trp Thr Ile Glu Ser Asp Arg Leu Val Gly
                690                 695                 700

Glu Ile Thr Leu Pro Leu Ala Ile Ala Thr Val Gly Gly Ala Thr Lys
705                 710                 715                 720

Val Leu Pro Lys Ala Gln Ala Ala Leu Glu Ile Ser Asp Val His Ser
                725                 730                 735

Ser Gln Glu Leu Ala Ala Leu Ala Ala Ser Val Gly Leu Val Gln Asn
                740                 745                 750

Leu Ala Ala Leu Arg Ala Leu Val Ser Glu Gly Ile Gln Lys Gly His
                755                 760                 765

Met Ser Met Gln Ala Arg Ser Leu Ala Ile Ala Val Gly Ala Glu Lys
770                 775                 780

Ala Glu Ile Glu Gln Val Ala Glu Lys Leu Arg Gln Asn Pro Pro Met
785                 790                 795                 800

Asn Gln Gln Gln Ala Leu Arg Phe Leu Gly Glu Ile Arg Glu Gln
                805                 810                 815

<210> SEQ ID NO 12
<211> LENGTH: 384
<212> TYPE: PRT
<213> ORGANISM: E. gallinarum

<400> SEQUENCE: 12

Met Asn Val Gly Ile Asp Lys Ile Asn Phe Phe Val Pro Pro Tyr Tyr
1               5                   10                  15

Leu Asp Met Val Asp Leu Ala His Ala Arg Glu Val Asp Pro Asn Lys
                20                  25                  30
```

Phe Thr Ile Gly Ile Gly Gln Asp Gln Met Ala Val Ser Lys Lys Thr
 35                  40                  45

His Asp Ile Val Thr Phe Ala Ala Ser Ala Ala Lys Glu Ile Leu Glu
 50                  55                  60

Pro Glu Asp Leu Gln Ala Ile Asp Met Val Ile Val Gly Thr Glu Ser
 65                  70                  75                  80

Gly Ile Asp Glu Ser Lys Ala Ser Ala Val Val Leu His Arg Leu Leu
                 85                  90                  95

Gly Val Gln Pro Phe Ala Arg Ser Phe Glu Ile Lys Glu Ala Cys Tyr
                100                 105                 110

Gly Ala Thr Ala Gly Ile Gln Phe Ala Lys Thr His Ile Gln Ala Asn
            115                 120                 125

Pro Glu Ser Lys Val Leu Val Ile Ala Ser Asp Ile Ala Arg Tyr Gly
130                 135                 140

Leu Arg Ser Gly Gly Glu Pro Thr Gln Gly Ala Gly Ala Val Ala Met
145                 150                 155                 160

Leu Leu Thr Ala Asn Pro Arg Ile Leu Thr Phe Glu Asn Asp Asn Leu
                165                 170                 175

Met Leu Thr Gln Asp Ile Tyr Asp Phe Trp Arg Pro Leu Gly His Ala
                180                 185                 190

Tyr Pro Met Val Asp Gly His Leu Ser Asn Gln Val Tyr Ile Asp Ser
            195                 200                 205

Phe Lys Lys Val Trp Gln Ala His Cys Glu Arg Asn Gln Ala Ser Ile
210                 215                 220

Ser Asp Tyr Ala Ala Ile Ser Phe His Ile Pro Tyr Thr Lys Met Gly
225                 230                 235                 240

Lys Lys Ala Leu Leu Ala Val Phe Ala Asp Glu Val Glu Thr Glu Gln
                245                 250                 255

Glu Arg Val Met Ala Arg Tyr Glu Glu Ser Ile Val Tyr Ser Arg Arg
                260                 265                 270

Ile Gly Asn Leu Tyr Thr Gly Ser Leu Tyr Leu Gly Leu Ile Ser Leu
            275                 280                 285

Leu Glu Asn Ser Ser His Leu Ser Ala Gly Asp Arg Ile Gly Leu Phe
290                 295                 300

Ser Tyr Gly Ser Gly Ala Val Ser Glu Phe Phe Ser Gly Arg Leu Val
305                 310                 315                 320

Ala Gly Tyr Glu Asn Gln Leu Asn Lys Glu Ala His Thr Gln Leu Leu
                325                 330                 335

Asp Gln Arg Gln Lys Leu Ser Ile Glu Glu Tyr Glu Ala Ile Phe Thr
                340                 345                 350

Asp Ser Leu Glu Ile Asp Gln Asp Ala Ala Phe Ser Asp Asp Leu Pro
            355                 360                 365

Tyr Ser Ile Arg Glu Ile Lys Asn Thr Ile Arg Tyr Tyr Lys Glu Ser
370                 375                 380

<210> SEQ ID NO 13
<211> LENGTH: 812
<212> TYPE: PRT
<213> ORGANISM: L. grayi

<400> SEQUENCE: 13

Met Val Lys Asp Ile Val Ile Asp Ala Leu Arg Thr Pro Ile Gly
 1               5                  10                  15

Lys Tyr Arg Gly Gln Leu Ser Lys Met Thr Ala Val Glu Leu Gly Thr
                 20                  25                  30

```
Ala Val Thr Lys Ala Leu Phe Glu Lys Asn Asp Gln Val Lys Asp His
        35                  40                  45
Val Glu Gln Val Ile Phe Gly Asn Val Leu Gln Ala Gly Asn Gly Gln
        50                  55                  60
Asn Pro Ala Arg Gln Ile Ala Leu Asn Ser Gly Leu Ser Ala Glu Ile
65                  70                  75                  80
Pro Ala Ser Thr Ile Asn Gln Val Cys Gly Gly Leu Lys Ala Ile
                    85                  90                  95
Ser Met Ala Arg Gln Gln Ile Leu Leu Gly Glu Ala Glu Val Ile Val
                    100                 105                 110
Ala Gly Gly Ile Glu Ser Met Thr Asn Ala Pro Ser Ile Thr Tyr Tyr
                    115                 120                 125
Asn Lys Glu Glu Asp Thr Leu Ser Lys Pro Val Pro Thr Met Thr Phe
        130                 135                 140
Asp Gly Leu Thr Asp Ala Phe Ser Gly Lys Ile Met Gly Leu Thr Ala
145                 150                 155                 160
Glu Asn Val Ala Glu Gln Tyr Gly Val Ser Arg Glu Ala Gln Asp Ala
                    165                 170                 175
Phe Ala Tyr Gly Ser Gln Met Lys Ala Ala Lys Ala Gln Glu Gln Gly
                    180                 185                 190
Ile Phe Ala Ala Glu Ile Leu Pro Leu Glu Ile Gly Asp Glu Val Ile
                    195                 200                 205
Thr Gln Asp Glu Gly Val Arg Gln Glu Thr Thr Leu Glu Lys Leu Ser
        210                 215                 220
Leu Leu Arg Thr Ile Phe Lys Glu Asp Gly Thr Val Thr Ala Gly Asn
225                 230                 235                 240
Ala Ser Thr Ile Asn Asp Gly Ala Ser Ala Val Ile Ile Ala Ser Lys
                    245                 250                 255
Glu Phe Ala Glu Thr Asn Gln Ile Pro Tyr Leu Ala Ile Val His Asp
                    260                 265                 270
Ile Thr Glu Ile Gly Ile Asp Pro Ser Ile Met Gly Ile Ala Pro Val
        275                 280                 285
Ser Ala Ile Asn Lys Leu Ile Asp Arg Asn Gln Ile Ser Met Glu Glu
        290                 295                 300
Ile Asp Leu Phe Glu Ile Asn Glu Ala Phe Ala Ala Ser Ser Val Val
305                 310                 315                 320
Val Gln Lys Glu Leu Ser Ile Pro Asp Glu Lys Ile Asn Ile Gly Gly
                    325                 330                 335
Ser Gly Ile Ala Leu Gly His Pro Leu Gly Ala Thr Gly Ala Arg Ile
                    340                 345                 350
Val Thr Thr Leu Ala His Gln Leu Lys Arg Thr His Gly Arg Tyr Gly
                    355                 360                 365
Ile Ala Ser Leu Cys Ile Gly Gly Leu Gly Leu Ala Ile Leu Ile
        370                 375                 380
Glu Val Pro Gln Glu Asp Gln Pro Val Lys Lys Phe Tyr Gln Leu Ala
385                 390                 395                 400
Arg Glu Asp Arg Leu Ala Arg Leu Gln Glu Gln Ala Val Ile Ser Pro
                    405                 410                 415
Ala Thr Lys His Val Leu Ala Glu Met Thr Leu Pro Glu Asp Ile Ala
                    420                 425                 430
Asp Asn Leu Ile Glu Asn Gln Ile Ser Glu Met Glu Ile Pro Leu Gly
        435                 440                 445
```

```
Val Ala Leu Asn Leu Arg Val Asn Asp Lys Ser Tyr Thr Ile Pro Leu
    450                 455                 460

Ala Thr Glu Glu Pro Ser Val Ile Ala Ala Cys Asn Asn Gly Ala Lys
465                 470                 475                 480

Met Ala Asn His Leu Gly Gly Phe Gln Ser Glu Leu Lys Asp Gly Phe
                485                 490                 495

Leu Arg Gly Gln Ile Val Leu Met Asn Val Lys Glu Pro Ala Thr Ile
                500                 505                 510

Glu His Thr Ile Thr Ala Glu Lys Ala Ala Ile Phe Arg Ala Ala Ala
                515                 520                 525

Gln Ser His Pro Ser Ile Val Lys Arg Gly Gly Leu Lys Glu Ile
    530                 535                 540

Val Val Arg Thr Phe Asp Asp Pro Thr Phe Leu Ser Ile Asp Leu
545                 550                 555                 560

Ile Val Asp Thr Lys Asp Ala Met Gly Ala Asn Ile Ile Asn Thr Ile
                565                 570                 575

Leu Glu Gly Val Ala Gly Phe Leu Arg Glu Ile Leu Thr Glu Glu Ile
                580                 585                 590

Leu Phe Ser Ile Leu Ser Asn Tyr Ala Thr Glu Ser Ile Val Thr Ala
    595                 600                 605

Ser Cys Arg Ile Pro Tyr Glu Ala Leu Ser Lys Lys Gly Asp Gly Lys
    610                 615                 620

Arg Ile Ala Glu Lys Val Ala Ala Ala Ser Lys Phe Ala Gln Leu Asp
625                 630                 635                 640

Pro Tyr Arg Ala Ala Thr His Asn Lys Gly Ile Met Asn Gly Ile Glu
                645                 650                 655

Ala Val Val Leu Ala Ser Gly Asn Asp Thr Arg Ala Val Ala Ala Ala
                660                 665                 670

Ala His Ala Tyr Ala Ser Arg Asp Gln His Tyr Arg Gly Leu Ser Gln
    675                 680                 685

Trp Gln Val Ala Glu Gly Ala Leu His Gly Ile Ser Leu Pro Leu
    690                 695                 700

Ala Leu Gly Ser Val Gly Gly Ala Ile Glu Val Leu Pro Lys Ala Lys
705                 710                 715                 720

Ala Ala Phe Glu Ile Met Gly Ile Thr Glu Ala Lys Glu Leu Ala Glu
                725                 730                 735

Val Thr Ala Ala Val Gly Leu Ala Gln Asn Leu Ala Ala Leu Arg Ala
                740                 745                 750

Leu Val Ser Glu Gly Ile Gln Gln Gly His Met Ser Leu Gln Ala Arg
    755                 760                 765

Ser Leu Ala Leu Ser Val Gly Ala Thr Gly Lys Glu Val Glu Ile Leu
    770                 775                 780

Ala Glu Lys Leu Gln Gly Ser Arg Met Asn Gln Ala Asn Ala Gln Thr
785                 790                 795                 800

Ile Leu Ala Glu Ile Arg Ser Gln Lys Val Glu Leu
                805                 810

<210> SEQ ID NO 14
<211> LENGTH: 385
<212> TYPE: PRT
<213> ORGANISM: L. grayi

<400> SEQUENCE: 14

Met Thr Met Asn Val Gly Ile Asp Lys Met Ser Phe Phe Val Pro Pro
1               5                   10                  15
```

```
Tyr Phe Val Asp Met Thr Asp Leu Ala Val Ala Arg Asp Val Asp Pro
            20                  25                  30

Asn Lys Phe Leu Ile Gly Ile Gly Gln Asp Gln Met Ala Val Asn Pro
            35                  40                  45

Lys Thr Gln Asp Ile Val Thr Phe Ala Thr Asn Ala Ala Lys Asn Ile
 50                  55                  60

Leu Ser Ala Glu Asp Leu Asp Lys Ile Asp Met Val Ile Val Gly Thr
 65                  70                  75                  80

Glu Ser Gly Ile Asp Glu Ser Lys Ala Ser Ala Val Val Leu His Arg
                 85                  90                  95

Leu Leu Gly Ile Gln Lys Phe Ala Arg Ser Phe Glu Ile Lys Glu Ala
                100                 105                 110

Cys Tyr Gly Gly Thr Ala Ala Leu Gln Phe Ala Val Asn His Ile Arg
            115                 120                 125

Asn His Pro Glu Ser Lys Val Leu Val Val Ala Ser Asp Ile Ala Lys
130                 135                 140

Tyr Gly Leu Ala Ser Gly Gly Glu Pro Thr Gln Gly Ala Gly Ala Val
145                 150                 155                 160

Ala Met Leu Val Ser Thr Asp Pro Lys Ile Ile Ala Phe Asn Asp Asp
                165                 170                 175

Ser Leu Ala Leu Thr Gln Asp Ile Tyr Asp Phe Trp Arg Pro Val Gly
            180                 185                 190

His Asp Tyr Pro Met Val Asp Gly Pro Leu Ser Thr Glu Thr Tyr Ile
        195                 200                 205

Gln Ser Phe Gln Thr Val Trp Gln Glu Tyr Thr Lys Arg Ser Gln His
210                 215                 220

Ala Leu Ala Asp Phe Ala Ala Leu Ser Phe His Ile Pro Tyr Thr Lys
225                 230                 235                 240

Met Gly Lys Lys Ala Leu Leu Ala Ile Leu Glu Gly Ser Glu Glu
                245                 250                 255

Ala Gln Asn Arg Ile Leu Ala Lys Tyr Glu Lys Ser Ile Ala Tyr Ser
                260                 265                 270

Arg Lys Ala Gly Asn Leu Tyr Thr Gly Ser Leu Tyr Leu Gly Leu Ile
            275                 280                 285

Ser Leu Leu Glu Asn Ala Glu Asp Leu Lys Ala Gly Asp Leu Ile Gly
290                 295                 300

Leu Phe Ser Tyr Gly Ser Gly Ala Val Ala Glu Phe Phe Ser Gly Arg
305                 310                 315                 320

Leu Val Glu Asp Tyr Gln Glu Gln Leu Leu Lys Thr Lys His Ala Glu
                325                 330                 335

Gln Leu Ala His Arg Lys Gln Leu Thr Ile Glu Glu Tyr Glu Thr Met
            340                 345                 350

Phe Ser Asp Arg Leu Asp Val Asp Lys Asp Ala Glu Tyr Glu Asp Thr
            355                 360                 365

Leu Ala Tyr Ser Ile Ser Ser Val Arg Asn Thr Val Arg Glu Tyr Arg
        370                 375                 380

Ser
385

<210> SEQ ID NO 15
<211> LENGTH: 813
<212> TYPE: PRT
<213> ORGANISM: E. faecium
```

```
<400> SEQUENCE: 15

Met Lys Glu Val Val Met Ile Asp Ala Ala Arg Thr Pro Ile Gly Lys
1               5                   10                  15

Tyr Arg Gly Ser Leu Ser Pro Phe Thr Ala Val Glu Leu Gly Thr Leu
            20                  25                  30

Val Thr Lys Gly Leu Leu Asp Lys Thr Lys Leu Lys Lys Asp Lys Ile
        35                  40                  45

Asp Gln Val Ile Phe Gly Asn Val Leu Gln Ala Gly Asn Gly Gln Asn
    50                  55                  60

Val Ala Arg Gln Ile Ala Leu Asn Ser Gly Leu Pro Val Asp Val Pro
65                  70                  75                  80

Ala Met Thr Ile Asn Glu Val Cys Gly Ser Gly Met Lys Ala Val Ile
                85                  90                  95

Leu Ala Arg Gln Leu Ile Gln Leu Gly Glu Ala Glu Leu Val Ile Ala
            100                 105                 110

Gly Gly Thr Glu Ser Met Ser Gln Ala Pro Met Leu Lys Pro Tyr Gln
        115                 120                 125

Ser Glu Thr Asn Glu Tyr Gly Glu Pro Ile Ser Ser Met Val Asn Asp
    130                 135                 140

Gly Leu Thr Asp Ala Phe Ser Asn Ala His Met Gly Leu Thr Ala Glu
145                 150                 155                 160

Lys Val Ala Thr Gln Phe Ser Val Ser Arg Glu Glu Gln Asp Arg Tyr
                165                 170                 175

Ala Leu Ser Ser Gln Leu Lys Ala Ala His Ala Val Glu Ala Gly Val
            180                 185                 190

Phe Ser Glu Glu Ile Ile Pro Val Lys Ile Ser Asp Glu Asp Val Leu
        195                 200                 205

Ser Glu Asp Glu Ala Val Arg Gly Asn Ser Thr Leu Glu Lys Leu Gly
    210                 215                 220

Thr Leu Arg Thr Val Phe Ser Glu Glu Gly Thr Val Thr Ala Gly Asn
225                 230                 235                 240

Ala Ser Pro Leu Asn Asp Gly Ala Ser Val Val Ile Leu Ala Ser Lys
                245                 250                 255

Glu Tyr Ala Glu Asn Asn Asn Leu Pro Tyr Leu Ala Thr Ile Lys Glu
            260                 265                 270

Val Ala Glu Val Gly Ile Asp Pro Ser Ile Met Gly Ile Ala Pro Ile
        275                 280                 285

Lys Ala Ile Gln Lys Leu Thr Asp Arg Ser Gly Met Asn Leu Ser Thr
    290                 295                 300

Ile Asp Leu Phe Glu Ile Asn Glu Ala Phe Ala Ala Ser Ser Ile Val
305                 310                 315                 320

Val Ser Gln Glu Leu Gln Leu Asp Glu Glu Lys Val Asn Ile Tyr Gly
                325                 330                 335

Gly Ala Ile Ala Leu Gly His Pro Ile Gly Ala Ser Gly Ala Arg Ile
            340                 345                 350

Leu Thr Thr Leu Ala Tyr Gly Leu Leu Arg Glu Gln Lys Arg Tyr Gly
        355                 360                 365

Ile Ala Ser Leu Cys Ile Gly Gly Gly Leu Gly Leu Ala Val Leu Leu
    370                 375                 380

Glu Ala Asn Met Glu Gln Thr His Lys Asp Val Gln Lys Lys Phe
385                 390                 395                 400

Tyr Gln Leu Thr Pro Ser Glu Arg Arg Ser Gln Leu Ile Glu Lys Asn
                405                 410                 415
```

-continued

Val Leu Thr Gln Glu Thr Ala Leu Ile Phe Gln Glu Gln Thr Leu Ser
            420                 425                 430

Glu Glu Leu Ser Asp His Met Ile Glu Asn Gln Val Ser Glu Val Glu
            435                 440                 445

Ile Pro Met Gly Ile Ala Gln Asn Phe Gln Ile Asn Gly Lys Lys Lys
450                 455                 460

Trp Ile Pro Met Ala Thr Glu Glu Pro Ser Val Ile Ala Ala Ala Ser
465                 470                 475                 480

Asn Gly Ala Lys Ile Cys Gly Asn Ile Cys Ala Glu Thr Pro Gln Arg
            485                 490                 495

Leu Met Arg Gly Gln Ile Val Leu Ser Gly Lys Ser Glu Tyr Gln Ala
            500                 505                 510

Val Ile Asn Ala Val Asn His Arg Lys Glu Glu Leu Ile Leu Cys Ala
            515                 520                 525

Asn Glu Ser Tyr Pro Ser Ile Val Lys Arg Gly Gly Val Gln Asp
            530                 535                 540

Ile Ser Thr Arg Glu Phe Met Gly Ser Phe His Ala Tyr Leu Ser Ile
545                 550                 555                 560

Asp Phe Leu Val Asp Val Lys Asp Ala Met Gly Ala Asn Met Ile Asn
            565                 570                 575

Ser Ile Leu Glu Ser Val Ala Asn Lys Leu Arg Glu Trp Phe Pro Glu
            580                 585                 590

Glu Glu Ile Leu Phe Ser Ile Leu Ser Asn Phe Ala Thr Glu Ser Leu
            595                 600                 605

Ala Ser Ala Cys Cys Glu Ile Pro Phe Glu Arg Leu Gly Arg Asn Lys
            610                 615                 620

Glu Ile Gly Glu Gln Ile Ala Lys Lys Ile Gln Gln Ala Gly Glu Tyr
625                 630                 635                 640

Ala Lys Leu Asp Pro Tyr Arg Ala Ala Thr His Asn Lys Gly Ile Met
            645                 650                 655

Asn Gly Ile Glu Ala Val Val Ala Thr Gly Asn Asp Thr Arg Ala
            660                 665                 670

Val Ser Ala Ser Ile His Ala Tyr Ala Ala Arg Asn Gly Leu Tyr Gln
            675                 680                 685

Gly Leu Thr Asp Trp Gln Ile Lys Gly Asp Lys Leu Val Gly Lys Leu
            690                 695                 700

Thr Val Pro Leu Ala Val Ala Thr Val Gly Gly Ala Ser Asn Ile Leu
705                 710                 715                 720

Pro Lys Ala Lys Ala Ser Leu Ala Met Leu Asp Ile Asp Ser Ala Lys
            725                 730                 735

Glu Leu Ala Gln Val Ile Ala Ala Val Gly Leu Ala Gln Asn Leu Ala
            740                 745                 750

Ala Leu Arg Ala Leu Val Thr Glu Gly Ile Gln Lys Gly His Met Gly
            755                 760                 765

Leu Gln Ala Arg Ser Leu Ala Ile Ser Ile Gly Ala Ile Gly Glu Glu
            770                 775                 780

Ile Glu Gln Val Ala Lys Lys Leu Arg Glu Ala Glu Lys Met Asn Gln
785                 790                 795                 800

Gln Thr Ala Ile Gln Ile Leu Glu Lys Ile Arg Glu Lys
            805                 810

<210> SEQ ID NO 16
<211> LENGTH: 384

<212> TYPE: PRT
<213> ORGANISM: E. faecium

<400> SEQUENCE: 16

```
Met Lys Ile Gly Ile Asp Arg Leu Ser Phe Phe Ile Pro Asn Leu Tyr
1               5                   10                  15

Leu Asp Met Thr Glu Leu Ala Glu Ser Arg Gly Asp Asp Pro Ala Lys
            20                  25                  30

Tyr His Ile Gly Ile Gly Gln Asp Gln Met Ala Val Asn Arg Ala Asn
        35                  40                  45

Glu Asp Ile Ile Thr Leu Gly Ala Asn Ala Ala Ser Lys Ile Val Thr
50                  55                  60

Glu Lys Asp Arg Glu Leu Ile Asp Met Val Ile Val Gly Thr Glu Ser
65                  70                  75                  80

Gly Ile Asp His Ser Lys Ala Ser Ala Val Ile His His Leu Leu
                85                  90                  95

Lys Ile Gln Ser Phe Ala Arg Ser Phe Glu Val Lys Glu Ala Cys Tyr
            100                 105                 110

Gly Gly Thr Ala Ala Leu His Met Ala Lys Glu Tyr Val Lys Asn His
        115                 120                 125

Pro Glu Arg Lys Val Leu Val Ile Ala Ser Asp Ile Ala Arg Tyr Gly
    130                 135                 140

Leu Ala Ser Gly Gly Glu Val Thr Gln Gly Val Gly Ala Val Ala Met
145                 150                 155                 160

Met Ile Thr Gln Asn Pro Arg Ile Leu Ser Ile Glu Asp Asp Ser Val
                165                 170                 175

Phe Leu Thr Glu Asp Ile Tyr Asp Phe Trp Arg Pro Asp Tyr Ser Glu
            180                 185                 190

Phe Pro Val Val Asp Gly Pro Leu Ser Asn Ser Thr Tyr Ile Glu Ser
        195                 200                 205

Phe Gln Lys Val Trp Asn Arg His Lys Glu Leu Ser Gly Arg Gly Leu
    210                 215                 220

Glu Asp Tyr Gln Ala Ile Ala Phe His Ile Pro Tyr Thr Lys Met Gly
225                 230                 235                 240

Lys Lys Ala Leu Gln Ser Val Leu Asp Gln Thr Asp Glu Asp Asn Gln
                245                 250                 255

Glu Arg Leu Met Ala Arg Tyr Glu Glu Ser Ile Arg Tyr Ser Arg Arg
            260                 265                 270

Ile Gly Asn Leu Tyr Thr Gly Ser Leu Tyr Leu Gly Leu Thr Ser Leu
        275                 280                 285

Leu Glu Asn Ser Lys Ser Leu Gln Pro Gly Asp Arg Ile Gly Leu Phe
    290                 295                 300

Ser Tyr Gly Ser Gly Ala Val Ser Glu Phe Phe Thr Gly Tyr Leu Glu
305                 310                 315                 320

Glu Asn Tyr Gln Glu Tyr Leu Phe Ala Gln Ser His Gln Glu Met Leu
                325                 330                 335

Asp Ser Arg Thr Arg Ile Thr Val Asp Glu Tyr Glu Thr Ile Phe Ser
            340                 345                 350

Glu Thr Leu Pro Glu His Gly Glu Cys Ala Glu Tyr Thr Ser Asp Val
        355                 360                 365

Pro Phe Ser Ile Thr Lys Ile Glu Asn Asp Ile Arg Tyr Tyr Lys Ile
    370                 375                 380
```

<210> SEQ ID NO 17

```
<211> LENGTH: 824
<212> TYPE: PRT
<213> ORGANISM: E. casseliflavus

<400> SEQUENCE: 17

Met Glu Glu Val Val Ile Ile Asp Ala Leu Arg Thr Pro Ile Gly Lys
1               5                   10                  15

Tyr His Gly Ser Leu Lys Asp Tyr Thr Ala Val Glu Leu Gly Thr Val
            20                  25                  30

Ala Ala Lys Ala Leu Leu Ala Arg Asn Gln Gln Ala Lys Glu His Ile
        35                  40                  45

Ala Gln Val Ile Ile Gly Asn Val Leu Gln Ala Gly Ser Gly Gln Asn
    50                  55                  60

Pro Gly Arg Gln Val Ser Leu Gln Ser Gly Leu Ser Ser Asp Ile Pro
65                  70                  75                  80

Ala Ser Thr Ile Asn Glu Val Cys Gly Ser Gly Met Lys Ala Ile Leu
                85                  90                  95

Met Gly Met Glu Gln Ile Gln Leu Asn Lys Ala Ser Val Val Leu Thr
            100                 105                 110

Gly Gly Ile Glu Ser Met Thr Asn Ala Pro Leu Phe Ser Tyr Tyr Asn
        115                 120                 125

Lys Ala Glu Asp Gln Tyr Ser Ala Pro Val Ser Thr Met Met His Asp
    130                 135                 140

Gly Leu Thr Asp Ala Phe Ser Ser Lys Pro Met Gly Leu Thr Ala Glu
145                 150                 155                 160

Thr Val Ala Glu Arg Tyr Gly Ile Thr Arg Lys Glu Gln Asp Glu Phe
                165                 170                 175

Ala Tyr His Ser Gln Met Lys Ala Ala Lys Ala Gln Ala Ala Lys Lys
            180                 185                 190

Phe Asp Gln Glu Ile Val Pro Leu Thr Glu Lys Ser Gly Thr Val Leu
        195                 200                 205

Gln Asp Glu Gly Ile Arg Ala Ala Thr Val Glu Lys Leu Ala Glu
    210                 215                 220

Leu Lys Thr Val Phe Lys Lys Asp Gly Thr Val Thr Ala Gly Asn Ala
225                 230                 235                 240

Ser Thr Ile Asn Asp Gly Ala Ala Met Val Leu Ile Ala Ser Lys Ser
                245                 250                 255

Tyr Cys Glu Glu His Gln Ile Pro Tyr Leu Ala Val Ile Lys Glu Ile
            260                 265                 270

Val Glu Val Gly Phe Ala Pro Glu Ile Met Gly Ile Ser Pro Ile Lys
        275                 280                 285

Ala Ile Asp Thr Leu Leu Lys Asn Gln Ala Leu Thr Ile Glu Asp Ile
    290                 295                 300

Gly Ile Phe Glu Ile Asn Glu Ala Phe Ala Ala Ser Ser Ile Val Val
305                 310                 315                 320

Glu Arg Glu Leu Gly Leu Asp Pro Lys Lys Val Asn Arg Tyr Gly Gly
                325                 330                 335

Gly Ile Ser Leu Gly His Ala Ile Gly Ala Thr Gly Ala Arg Ile Ala
            340                 345                 350

Thr Thr Val Ala Tyr Gln Leu Lys Asp Thr Gln Glu Arg Tyr Gly Ile
        355                 360                 365

Ala Ser Leu Cys Val Gly Gly Gly Leu Gly Leu Ala Met Leu Leu Glu
    370                 375                 380

Asn Pro Ser Ala Thr Ala Ser Gln Thr Asn Phe Asp Glu Glu Ser Ala
```

```
385                 390                 395                 400
Ser Glu Lys Thr Glu Lys Lys Phe Tyr Ala Leu Ala Pro Asn Glu
                405                 410             415

Arg Leu Ala Phe Leu Glu Ala Gln Gly Ala Ile Thr Ala Ala Glu Thr
            420                 425             430

Leu Val Phe Gln Glu Met Thr Leu Asn Lys Glu Thr Ala Asn His Leu
        435                 440             445

Ile Glu Asn Gln Ile Ser Glu Val Glu Ile Pro Leu Gly Val Gly Leu
    450                 455                 460

Asn Leu Gln Val Asn Gly Lys Ala Tyr Asn Val Pro Leu Ala Thr Glu
465             470              475                 480

Glu Pro Ser Val Ile Ala Ala Met Ser Asn Gly Ala Lys Met Ala Gly
                485                 490                 495

Pro Ile Thr Thr Thr Ser Gln Glu Arg Leu Leu Arg Gly Gln Ile Val
            500                 505                 510

Phe Met Asp Val Gln Asp Pro Glu Ala Ile Leu Ala Lys Val Glu Ser
        515                 520                 525

Glu Gln Ala Thr Ile Phe Ala Val Ala Asn Glu Thr Tyr Pro Ser Ile
    530                 535                 540

Val Lys Arg Gly Gly Gly Leu Arg Arg Val Ile Gly Arg Asn Phe Ser
545             550                 555                 560

Pro Ala Glu Ser Asp Leu Ala Thr Ala Tyr Val Ser Ile Asp Leu Met
                565                 570                 575

Val Asp Val Lys Asp Ala Met Gly Ala Asn Ile Ile Asn Ser Ile Leu
            580                 585                 590

Glu Gly Val Ala Glu Leu Phe Arg Lys Trp Phe Pro Glu Glu Glu Ile
        595                 600                 605

Leu Phe Ser Ile Leu Ser Asn Leu Ala Thr Glu Ser Leu Val Thr Ala
    610                 615                 620

Thr Cys Ser Val Pro Phe Asp Lys Leu Ser Lys Thr Gly Asn Gly Arg
625             630                 635                 640

Gln Val Ala Gly Lys Ile Val His Ala Ala Asp Phe Ala Lys Ile Asp
                645                 650                 655

Pro Tyr Arg Ala Ala Thr His Asn Lys Gly Ile Met Asn Gly Val Glu
            660                 665                 670

Ala Leu Ile Leu Ala Thr Gly Asn Asp Thr Arg Ala Val Ser Ala Ala
        675                 680                 685

Cys His Gly Tyr Ala Ala Arg Asn Gly Arg Met Gln Gly Leu Thr Ser
    690                 695                 700

Trp Thr Ile Ile Glu Asp Arg Leu Ile Gly Ser Ile Thr Leu Pro Leu
705             710                 715                 720

Ala Ile Ala Thr Val Gly Gly Ala Thr Lys Ile Leu Pro Lys Ala Gln
                725                 730                 735

Ala Ala Leu Ala Leu Thr Gly Val Glu Thr Ala Ser Glu Leu Ala Ser
            740                 745                 750

Leu Ala Ala Ser Val Gly Leu Val Gln Asn Leu Ala Ala Leu Arg Ala
        755                 760                 765

Leu Val Ser Glu Gly Ile Gln Gln Gly His Met Ser Met Gln Ala Arg
    770                 775                 780

Ser Leu Ala Ile Ser Val Gly Ala Lys Gly Thr Glu Ile Glu Gln Leu
785             790                 795                 800

Ala Ala Lys Leu Arg Ala Ala Thr Gln Met Asn Gln Glu Gln Ala Arg
                805                 810                 815
```

Lys Phe Leu Thr Glu Ile Arg Asn
            820

<210> SEQ ID NO 18
<211> LENGTH: 386
<212> TYPE: PRT
<213> ORGANISM: E. casseliflavus

<400> SEQUENCE: 18

Met Asn Val Gly Ile Asp Lys Ile Asn Phe Phe Val Pro Pro Tyr Phe
1               5                   10                  15

Ile Asp Met Val Asp Leu Ala His Ala Arg Glu Val Asp Pro Asn Lys
            20                  25                  30

Phe Thr Ile Gly Ile Gly Gln Asp Gln Met Ala Val Asn Lys Lys Thr
        35                  40                  45

Gln Asp Ile Val Thr Phe Ala Met His Ala Ala Lys Asp Ile Leu Thr
    50                  55                  60

Lys Glu Asp Leu Gln Ala Ile Asp Met Val Ile Val Gly Thr Glu Ser
65                  70                  75                  80

Gly Ile Asp Glu Ser Lys Ala Ser Ala Val Val Leu His Arg Leu Leu
                85                  90                  95

Gly Ile Gln Pro Phe Ala Arg Ser Phe Glu Ile Lys Glu Ala Cys Tyr
            100                 105                 110

Gly Ala Thr Ala Gly Leu Gln Phe Ala Lys Ala His Val Gln Ala Asn
        115                 120                 125

Pro Gln Ser Lys Val Leu Val Val Ala Ser Asp Ile Ala Arg Tyr Gly
    130                 135                 140

Leu Ala Ser Gly Gly Glu Pro Thr Gln Gly Val Gly Ala Val Ala Met
145                 150                 155                 160

Leu Ile Ser Ala Asp Pro Ala Ile Leu Gln Leu Glu Asn Asp Asn Leu
                165                 170                 175

Met Leu Thr Gln Asp Ile Tyr Asp Phe Trp Arg Pro Val Gly His Gln
            180                 185                 190

Tyr Pro Met Val Asp Gly His Leu Ser Asn Ala Val Tyr Ile Asp Ser
        195                 200                 205

Phe Lys Gln Val Trp Gln Ala His Cys Glu Lys Asn Gln Arg Thr Ala
    210                 215                 220

Lys Asp Tyr Ala Ala Leu Ser Phe His Ile Pro Tyr Thr Lys Met Gly
225                 230                 235                 240

Lys Lys Ala Leu Leu Ala Val Phe Ala Glu Glu Asp Glu Thr Glu Gln
                245                 250                 255

Lys Arg Leu Met Ala Arg Tyr Glu Glu Ser Ile Val Tyr Ser Arg Arg
            260                 265                 270

Thr Gly Asn Leu Tyr Thr Gly Ser Leu Tyr Leu Gly Leu Ile Ser Leu
        275                 280                 285

Leu Glu Asn Ser Ser Leu Gln Ala Asn Asp Arg Ile Gly Leu Phe
    290                 295                 300

Ser Tyr Gly Ser Gly Ala Val Ala Glu Phe Phe Ser Gly Leu Leu Val
305                 310                 315                 320

Pro Gly Tyr Glu Lys Gln Leu Ala Gln Ala His Gln Ala Leu Leu
                325                 330                 335

Asp Asp Arg Gln Lys Leu Thr Ile Ala Glu Tyr Glu Ala Met Phe Asn
            340                 345                 350

Glu Thr Ile Asp Ile Asp Gln Asp Gln Ser Phe Glu Asp Asp Leu Leu

```
                    355                 360                 365
Tyr Ser Ile Arg Glu Ile Lys Asn Thr Ile Arg Tyr Tyr Asn Glu Glu
            370                 375                 380

Asn Glu
385

<210> SEQ ID NO 19
<211> LENGTH: 329
<212> TYPE: PRT
<213> ORGANISM: E. coli

<400> SEQUENCE: 19

Met Thr Asp Val Arg Phe Arg Ile Ile Gly Thr Gly Ala Tyr Val Pro
1               5                   10                  15

Glu Arg Ile Val Ser Asn Asp Glu Val Gly Ala Pro Ala Gly Val Asp
            20                  25                  30

Asp Asp Trp Ile Thr Arg Lys Thr Gly Ile Arg Gln Arg Arg Trp Ala
        35                  40                  45

Ala Asp Asp Gln Ala Thr Ser Asp Leu Ala Thr Ala Ala Gly Arg Ala
    50                  55                  60

Ala Leu Lys Ala Ala Gly Ile Thr Pro Glu Gln Leu Thr Val Ile Ala
65                  70                  75                  80

Val Ala Thr Ser Thr Pro Asp Arg Pro Gln Pro Pro Thr Ala Ala Tyr
                85                  90                  95

Val Gln His His Leu Gly Ala Thr Gly Thr Ala Ala Phe Asp Val Asn
            100                 105                 110

Ala Val Cys Ser Gly Thr Val Phe Ala Leu Ser Val Ala Gly Thr
        115                 120                 125

Leu Val Tyr Arg Gly Gly Tyr Ala Leu Val Ile Gly Ala Asp Leu Tyr
    130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
            180                 185                 190

Leu Ile Arg Val Pro Ala Gly Gly Ser Arg Gln Pro Leu Asp Thr Asp
        195                 200                 205

Gly Leu Asp Ala Gly Leu Gln Tyr Phe Ala Met Asp Gly Arg Glu Val
    210                 215                 220

Arg Arg Phe Val Thr Glu His Leu Pro Gln Leu Ile Lys Gly Phe Leu
225                 230                 235                 240

His Glu Ala Gly Val Asp Ala Asp Ile Ser His Phe Val Pro His
                245                 250                 255

Gln Ala Asn Gly Val Met Leu Asp Glu Val Phe Gly Glu Leu His Leu
            260                 265                 270

Pro Arg Ala Thr Met His Arg Thr Val Glu Thr Tyr Gly Asn Thr Gly
        275                 280                 285

Ala Ala Ser Ile Pro Ile Thr Met Asp Ala Ala Val Arg Ala Gly Ser
    290                 295                 300

Phe Arg Pro Gly Glu Leu Val Leu Leu Ala Gly Phe Gly Gly Gly Met
305                 310                 315                 320

Ala Ala Ser Phe Ala Leu Ile Glu Trp
                325
```

<210> SEQ ID NO 20
<211> LENGTH: 1635
<212> TYPE: DNA
<213> ORGANISM: Populus alba

<400> SEQUENCE: 20

| | | | | | |
|---|---|---|---|---|---|
| atggaagctc | gtcgttctgc | gaactacgaa | cctaacagct | gggactatga | ttacctgctg | 60 |
| tcctccgaca | cggacgagtc | catcgaagta | tacaaagaca | aagcgaaaaa | gctggaagcc | 120 |
| gaagttcgtc | gcgagattaa | taacgaaaaa | gcagaatttc | tgaccctgct | ggaactgatt | 180 |
| gacaacgtcc | agcgcctggg | cctgggttac | cgtttcgagt | ctgatatccg | tggtgcgctg | 240 |
| gatcgcttcg | tttcctccgg | cggcttcgat | gcggtaacca | agacttccct | gcacggtacg | 300 |
| gcactgtctt | ccgtctgct | gcgtcaacac | ggttttgagg | tttctcagga | agcgttcagc | 360 |
| ggcttcaaag | accaaaacgg | caacttcctg | agaaccctga | aggaagatat | caaagctatc | 420 |
| ctgagcctgt | acgaggccag | cttcctggct | ctggaaggcg | aaaacatcct | ggacgaggcg | 480 |
| aaggttttcg | caatctctca | tctgaaagaa | ctgtctgaag | aaaagatcgg | taagagctg | 540 |
| gcagaacagg | tgaaccatgc | actggaactg | ccactgcatc | gccgtactca | gcgtctggaa | 600 |
| gcagtatggt | ctatcgaggc | ctaccgtaaa | aaggaggacg | cgaatcaggt | tctgctggag | 660 |
| ctggcaattc | tggattacaa | catgatccag | tctgtatacc | agcgtgatct | gcgtgaaacg | 720 |
| tcccgttggt | ggcgtcgtgt | gggtctggcg | accaaactgc | actttgctcg | tgaccgcctg | 780 |
| attgagagct | tctactgggc | cgtgggtgta | gcattcgaac | cgcaatactc | cgactgccgt | 840 |
| aactccgtcg | caaaaatgtt | ttctttcgta | accattatcg | acgatatcta | cgatgtatac | 900 |
| ggcaccctgg | acgaactgga | gctgtttact | gatgcagttg | agcgttggga | cgtaaacgcc | 960 |
| atcaacgacc | tgccggatta | catgaaactg | tgctttctgg | ctctgtataa | cactattaac | 1020 |
| gaaatcgcct | acgacaacct | gaaagataaa | ggtgagaaca | tcctgccgta | tctgaccaaa | 1080 |
| gcctgggctg | acctgtgcaa | cgcttttcctg | caagaagcca | gtggctgta | caacaaatct | 1140 |
| actccgacct | ttgacgacta | cttcggcaac | gcatggaaat | cctcttctgg | cccgctgcaa | 1200 |
| ctggtgttcg | cttacttcgc | tgtcgtgcag | aacattaaaa | aggaagagat | cgaaaacctg | 1260 |
| caaaaatacc | atgacaccat | ctctcgtcct | tcccatatct | tccgtctgtg | caatgacctg | 1320 |
| gctagcgcgt | ctgcggaaat | tgcgcgtggt | gaaaccgcaa | atagcgtttc | ttgttacatg | 1380 |
| cgcactaaag | gtatctccga | agaactggct | accgaaagcg | tgatgaatct | gatcgatgaa | 1440 |
| acctggaaaa | agatgaacaa | ggaaaaactg | ggtggtagcc | tgttcgcgaa | accgttcgtg | 1500 |
| gaaaccgcga | tcaacctggc | acgtcaatct | cactgcactt | atcataacgg | cgacgcgcat | 1560 |
| acctctccgg | atgagctgac | ccgcaaacgc | gttctgtctg | taatcactga | accgattctg | 1620 |
| ccgtttgaac | gctaa | | | | | 1635 |

<210> SEQ ID NO 21
<211> LENGTH: 900
<212> TYPE: DNA
<213> ORGANISM: E. coli

<400> SEQUENCE: 21

| | | | | | |
|---|---|---|---|---|---|
| atggacttc | cgcagcaact | cgaagcctgc | gttaagcagg | ccaaccaggc | gctgagccgt | 60 |
| tttatcgccc | cactgccctt | tcagaacact | cccgtggtcg | aaaccatgca | gtatggcgca | 120 |
| ttattaggtg | gtaagcgcct | gcgacctttc | ctggtttatg | ccaccggtca | tatgtttggc | 180 |
| gttagcacaa | acacgctgga | cgcacccgct | gctgccgtag | agtgtatcca | cgcttactca | 240 |

| | |
|---|---|
| ttaattcatg atgatttacc ggcgatggat gatgacgatc tgcgccgcgg tttgccgacc | 300 |
| tgccatgtga agtttggcga agcaaacgcg attctcgctg gcgacgcttt acaaacgctg | 360 |
| gcgttctcga ttctaagcga tgccgatatg ccggaagtgt cggatcgcga cagaatttcg | 420 |
| atgatttctg aactggcgag cgccagcggt attgccggaa tgtgcggtgg tcaggcacta | 480 |
| gatttagacg cggaaggcaa acacgtacct ctggacgcgc ttgagcgtat tcatcgtcat | 540 |
| aaaaccggcg cattgattcg cgccgccgtt cgccttggtg cattaagcgc cggagataaa | 600 |
| gggcgtcgtg ctctgccagt actcgacaag tacgcagaga gcatcggcct tgccttccag | 660 |
| gttcaagatg acatcctgga tgtggtagga gatactgcaa cgttgggaaa cgccagggt | 720 |
| gccgaccagc aacttggtaa aagtacctac cctgcacttc tgggtcttga gcaagcccgg | 780 |
| aagaaagccc gggatctgat cgacgatgcc cgtcagtcgc tgaaacaact ggctgaacag | 840 |
| tcactcgata cctcggcact ggaagcgcta gcggactaca tcatccagcg taataaataa | 900 |

<210> SEQ ID NO 22
<211> LENGTH: 1641
<212> TYPE: DNA
<213> ORGANISM: Artificial Sequence
<220> FEATURE:
<223> OTHER INFORMATION: Synthetic Construct

<400> SEQUENCE: 22

| | |
|---|---|
| atgagcctga ccgaagaaaa accgattcgt ccgattgcaa attttccgcc tagcatttgg | 60 |
| ggtgatcagt ttctgattta tgagaaacag gttgaacagg gcgttgagca gattgttaat | 120 |
| gatctgaaaa aagaagttcg ccagctgctg aaagaagcac tggatattcc gatgaaacat | 180 |
| gccaatctgc tgaaactgat tgatgaaatt cagcgtctgg gtatcccgta tcattttgaa | 240 |
| cgtgaaattg atcatgccct gcagtgcatt tatgaaacct atggtgataa ttggaatggt | 300 |
| gatcgtagca gcctgtggtt tcgtctgatg cgtaaacagg ttattatgt tacctgcgac | 360 |
| gtgtttaaca actataaaga taaaaacggt gcctttaaac agagcctggc aaatgatgtt | 420 |
| gaaggtctgc tggaactgta tgaagcaacc agcatgcgtg ttccgggtga attattctg | 480 |
| gaagatgcac tgggttttac ccgtagccgt ctgagcatga tgaccaaaga tgcatttagc | 540 |
| accaatccgg cactgtttac cgaaatccag cgtgcactga acagccgct gtggaaacgt | 600 |
| ctgcctcgta ttgaagcagc acagtatatt ccgtttatc agcagcagga tagccataac | 660 |
| aaaaccctgc tgaaactggc aaaactggaa tttaatctgc tgcagagcct gcataaagaa | 720 |
| gaactgagcc acgtttgtaa atggtggaaa gccttcgaca tcaaaaaaaa cgcaccgtgt | 780 |
| ctgcgtgatc gtattgttga atgttatttt tggggtctgg tagcggttt tgaaccgcag | 840 |
| tatagccgtg cacgtgtgtt ttttaccaaa gcagttgcag ttattaccct gatcgatgat | 900 |
| acctatgacg catatggcac ctatgaggaa ctgaaaatct ttaccgaagc cgttgaacgt | 960 |
| tggagcatta cctgtctgga tacccctgccg gaatatatga aaccgatcta taaactgttc | 1020 |
| atggacacct ataccgagat ggaagaattt ctggcaaaag aaggtcgtac cgacctgttt | 1080 |
| aattgcggta agaatttgt gaaagaattc gtgcgtaacc tgatggttga agcaaaatgg | 1140 |
| gccaatgaag gtcatattcc gaccaccgaa gaacatgatc cggttgtgat tattaccggt | 1200 |
| ggtgcaaacc tgctgaccac cacctgttat ctgggtatga gcgatatttt caccaaagaa | 1260 |
| agcgttgaat gggcagttag cgcaccggcct ctgtttcgtt atagcggtat tctgggtcgt | 1320 |
| cgtctgaacg atctgatgac ccataaagca gaacaagaac gtaaacatag cagcagcagc | 1380 |

| | |
|---|---:|
| ctggaaagct atatgaaaga atataacgtg aacgaagagt atgcacagac cctgatttac | 1440 |
| aaagaagttg aggacgtttg gaaagatatc aaccgtgaat atctgaccac gaaaaacatt | 1500 |
| ccgcgtccgc tgctgatggc agttatttat ctgtgtcagt tcctggaagt tcagtatgca | 1560 |
| ggtaaagata actttacgcg tatgggcgac gaatataaac atctgattaa aagcctgctg | 1620 |
| gtgtatccga tgagcattta a | 1641 |

<210> SEQ ID NO 23
<211> LENGTH: 1734
<212> TYPE: DNA
<213> ORGANISM: Artificial Sequence
<220> FEATURE:
<223> OTHER INFORMATION: Synthetic Construct

<400> SEQUENCE: 23

| | |
|---|---:|
| atgagcaccc tgccgattag cagcgttagc tttagcagca gcaccagtcc gctggttgtt | 60 |
| gatgataaag ttagcaccaa accggatgtt attcgtcaca ccatgaactt taatgcaagc | 120 |
| atttggggtg atcagtttct gacctatgat gaaccggaag atctggtgat gaaaaaacag | 180 |
| ctggttgaag aactgaaaga agaagttaaa aaagagctga tcaccatcaa aggtagcaat | 240 |
| gaaccgatgc agcatgttaa actgattgaa ctgatcgatg ccgttcagcg tctgggtatt | 300 |
| gcatatcatt ttgaagaaga aatcgaagaa gccctgcagc atattcatgt tacctatggt | 360 |
| gaacagtggg tggataaaga aaatctgcag agcattagcc tgtggtttcg tctgctgcgt | 420 |
| cagcagggtt ttaatgttag cagcggtgtg tttaaagatt ttatggacga gaaaggcaaa | 480 |
| ttcaaagaaa gcctgtgtaa tgatgcacag ggtattctgg cactgtatga agcagcattt | 540 |
| atgcgtgttg aagatgaaac cattctggat aatgcactgg aatttaccaa agtgcacctg | 600 |
| gatatcattg caaagatcc gagctgtgat agcagcctgc gtacccagat tcatcaggca | 660 |
| ctgaaacagc cgctgcgtcg tcgtctggca cgcattgaag cactgcatta tgccgatt | 720 |
| tatcagcaag aaaccagcca taatgaagat ctgctgaaac tggcaaaact ggattttagc | 780 |
| gttctgcagt ccatgcacaa aaaagaactg agccatattt gtaaatggtg aaagatctg | 840 |
| gatctgcaga taaaactgcc gtatgttcgt gatcgtgttg ggaaggtta ttttttggatt | 900 |
| ctgagcatct attatgaacc gcagcatgca cgtacccgta tgtttctgat gaaaacctgt | 960 |
| atgtggctgg ttgtgctgga tgatacgttt gataattatg gcacctacga ggaactggaa | 1020 |
| atctttaccc aggcagttga cgttggagc attagttgtc tggatatgct gccggaatac | 1080 |
| atgaaactga tttatcaaga actggtgaac ctgcacgttg aaatgaaga agtctgggc | 1140 |
| aaaggtggta aaaacattag caatagtctg tgtcagggtc gttggcagaa agaactgggt | 1200 |
| agtcagatta ccctggttga aaccaaaatg caaaacgtg tgttcatgc ccagccgctg | 1260 |
| gaagagtata tgagcgttag catggttacc ggcacctatg gtctgatgat tgcacgtagc | 1320 |
| tatgttggtc gtggtgatat tgttaccgaa gataccttta atgggtgag cagctatccg | 1380 |
| cctattatca aagcaagctg tgttattgtt cgcctgatgg atgatattgt gagccacaaa | 1440 |
| gaagaacaag aacgcggtca tgttgccagc agcattgaat gttatagcaa agaaagtggt | 1500 |
| gcaagcgaag aagaagcctg cgaatatatc agccgtaaag tggaagatgc ctggaaagtt | 1560 |
| attaatcgtg aaagcctgcg tccgaccgca gttccgtttc cgctgctgat gcctgcaatt | 1620 |
| aacctggcac gtatgtgtga agttctgtat agcgttaatg atggttttac ccatgccgaa | 1680 |
| ggtgatatga atcctatat gaaaagcttc ttcgtgcatc cgatggttgt ttaa | 1734 |

<210> SEQ ID NO 24
<211> LENGTH: 8712
<212> TYPE: DNA
<213> ORGANISM: Artificial Sequence
<220> FEATURE:
<223> OTHER INFORMATION: Synthetic Construct

<400> SEQUENCE: 24

| | | | | | |
|---|---|---|---|---|---|
| cccgtcttac | tgtcgggaat | tcgcgttggc | cgattcatta | atgcagattc | tgaaatgagc | 60 |
| tgttgacaat | taatcatccg | gctcgtataa | tgtgtggaat | tgtgagcgga | taacaatttc | 120 |
| acacaggaaa | cagcgccgct | gagaaaaagc | gaagcggcac | tgctctttac | aatttatcag | 180 |
| acaatctgtg | tgggcactcg | accggaatta | tcgattaact | ttattattaa | aaattaaaga | 240 |
| ggtatatatt | aatgtatcga | ttaaataagg | aggaataaac | catggttaaa | gacattgtaa | 300 |
| taattgatgc | cctccgtact | cccatcggta | agtaccgcgg | tcagctctca | agatgacgg | 360 |
| cggtggaatt | gggaaccgca | gttacaaagg | ctctgttcga | gaagaacgac | caggtcaaag | 420 |
| accatgtaga | acaagtcatt | tttggcaacg | ttttacaggc | agggaacggc | cagaatcccg | 480 |
| cccgtcagat | cgcccttaat | tctggcctgt | ccgcagagat | accggcttcg | actattaacc | 540 |
| aggtgtgtgg | ttctggcctg | aaagcaataa | gcatggcgcg | ccaacagatc | ctactcggag | 600 |
| aagcggaagt | aatagtagca | ggaggtatcg | aatccatgac | gaatgcgccg | agtattacat | 660 |
| attataataa | agaagaagac | accctctcaa | agcctgttcc | tacgatgacc | ttcgatggtc | 720 |
| tgaccgacgc | gtttagcgga | aagattatgg | gtttaacagc | cgaaaatgtt | gccgaacagt | 780 |
| acggcgtatc | acgtgaggcc | caggacgcct | ttgcgtatgg | atcgcagatg | aaagcagcaa | 840 |
| aggcccaaga | acagggcatt | tcgcagctg | aaatactgcc | tcttgaaata | ggggacgaag | 900 |
| ttattactca | ggacgagggg | gttcgtcaag | agaccaccct | cgaaaaatta | agtctgcttc | 960 |
| ggaccatttt | taaagaagat | ggtactgtta | cagcgggcaa | cgcctcaacg | atcaatgatg | 1020 |
| gcgcctcagc | cgtgatcatt | gcatcaaagg | agtttgctga | caaaccag | attccctacc | 1080 |
| ttgcgatcgt | acatgatatt | acagagatag | gcattgatcc | atcaataatg | ggcattgctc | 1140 |
| ccgtgagtgc | gatcaataaa | ctgatcgatc | gtaaccaaat | tagcatggaa | gaaatcgatc | 1200 |
| tctttgaaat | taatgaggca | tttgcagcat | cctcggtggt | agttcaaaaa | gagttaagca | 1260 |
| ttcccgatga | aaagatcaat | attggcggtt | ccggtattgc | actaggccat | cctcttggcg | 1320 |
| ccacaggagc | gcgcattgta | accaccctag | cgcaccagtt | gaaacgtaca | cacggacgct | 1380 |
| atggtattgc | ctccctgtgc | attggcggtg | gccttggcct | agcaatatta | atagaagtgc | 1440 |
| ctcaggaaga | tcagccggtt | aaaaaatttt | atcaattggc | ccgtgaggac | cgtctggcta | 1500 |
| gacttcagga | gcaagccgtg | atcagcccag | ctacaaaaca | tgtactggca | gaaatgacac | 1560 |
| ttcctgaaga | tattgccgac | aatctgatcg | aaaatcaaat | atctgaaatg | gaaatccctc | 1620 |
| ttggtgtggc | tttgaatctg | agggtcaatg | ataagagtta | taccatccca | ctagcaactg | 1680 |
| aggaaccgag | tgtaatcgct | gcctgtaata | atggtgcaaa | aatggcaaac | cacctgggcg | 1740 |
| gttttcagtc | agaattaaaa | gatggtttcc | tgcgtgggca | aattgtactt | atgaacgtca | 1800 |
| aagaacccgc | aactatcgag | catacgatca | cggcagagaa | agcggcaatt | tttcgtgccg | 1860 |
| cagcgcagtc | acatccatcg | attgtgaaac | gaggtgggg | tctaaaagag | atagtagtgc | 1920 |
| gtacgttcga | tgatgatccg | acgttcctgt | ctattgatct | gatagttgat | actaaagacg | 1980 |
| caatgggcgc | taacatcatt | aacaccattc | tcgagggtgt | agccggcttt | ctgagggaaa | 2040 |
| tccttaccga | agaaattctg | ttctctattt | tatctaatta | cgcaaccgaa | tcaattgtga | 2100 |

```
ccgccagctg tcgcatacct tacgaagcac tgagtaaaaa aggtgatggt aaacgaatcg    2160
ctgaaaaagt ggctgctgca tctaaatttg cccagttaga tccttatcga gctgcaaccc    2220
acaacaaagg tattatgaat ggtattgagg ccgtcgtttt ggcctcagga aatgacacac    2280
gggcggtcgc ggcagccgca catgcgtatg cttcacgcga tcagcactat cggggcttaa    2340
gccagtggca ggttgcagaa ggcgcgttac acggggagat cagtctacca cttgcactcg    2400
gcagcgttgg cggtgcaatt gaggtcttgc ctaaagcgaa ggcggcattc gaaatcatgg    2460
ggatcacaga ggcgaaggag ctggcagaag tcacagctgc ggtagggctg gcgcaaaacc    2520
tggcggcgtt aagagcgctt gttagtgaag gaatacagca aggtcacatg tcgctccagg    2580
ctcgctctct tgcattatcg gtaggtgcta caggcaagga agttgaaatc ctggccgaaa    2640
aattacaggg ctctcgtatg aatcaggcga acgctcagac catactcgca gagatcagat    2700
cgcaaaaagt tgaattgtga tctagacgca ctaggaggat ataccaatga ccatgaacgt    2760
tggaatcgat aaaatgtcat tctttgttcc accttacttt gtggacatga ctgatctggc    2820
agtagcacgg gatgtcgatc ccaataagtt tctgattggt attggccagg accagatggc    2880
agttaatccg aaaacgcagg atattgtgac atttgccaca aatgctgcca aaaacatact    2940
gtcagctgag gaccttgata aaattgatat ggtcatagtc ggcaccgaga gtggaatcga    3000
tgaatccaaa gcgagtgccg tagtgcttca caggttgctc ggtatccaga agtttgctcg    3060
ctcctttgaa atcaaagaag cctgttatgg gggtaccgcg gctttacagt tcgctgtaaa    3120
ccacattagg aatcatcctg aatcaaaggt tcttgtagtt gcatcagata tcgcgaaata    3180
cggcctggct tctggaggtg aaccaacgca aggtgcaggc gctgtggcta tgctcgtctc    3240
aactgaccct aagatcattg ctttcaacga cgatagcctc gcgcttacac aagatatcta    3300
tgacttctgg cgaccagttg gacatgacta tcctatggtc gacgggcctc ttagtacaga    3360
gacctacatc cagtcatttc agaccgtatg gcaggaatac acaaaacggt cgcagcatgc    3420
actggcagac tttgctgccc ttagctttca tatcccgtat actaaaatgg caaaaaggc    3480
gctgcttgca atccttgaag gcgaatcaga ggaggctcag aaccgtatac tagcaaaata    3540
tgaaaagagt atagcctact ccagaaaggc gggtaacctg tataccggta gcctgtatct    3600
aggacttatt tcacttctgg aaaatgcaga agaccttaaa gctggtgatt taataggcct    3660
cttttcttac ggttccggtg ctgttgcgga gttttttctca ggaaggctgg ttgaggacta    3720
tcaggaacag ctacttaaaa caaaacatgc cgaacagctg gcccatagaa agcaactgac    3780
aatcgaggag tacgaaacga tgttctccga tcgcttggac gtggacaaag acgccgaata    3840
cgaagacaca ttagcttata gcatttcgtc agtccgaaac accgtacgtg agtacaggag    3900
ttgactgcag ctggtaccat atgggaattc gaagcttggg cccgaacaaa aactcatctc    3960
agaagaggat ctgaatagcg ccgtcgacca tcatcatcat catcattgag tttaaacggt    4020
ctccagcttg gctgttttgg cggatgagag aagattttca gcctgataca gattaaatca    4080
gaacgcagaa gcggtctgat aaaacagaat ttgcctggcg gcagtagcgc ggtggtccca    4140
cctgacccca tgccgaactc agaagtgaaa cgccgtagcg ccgatggtag tgtggggtct    4200
ccccatgcga gagtagggaa ctgccaggca tcaaataaaa cgaaaggctc agtcgaaaga    4260
ctgggccttt cgttttatct gttgtttgtc ggtgaacgct ctcctgagta ggacaaatcc    4320
gccgggagcg gatttgaacg ttgcgaagca acggcccgga gggtggcggg caggacgccc    4380
gccataaact gccaggcatc aaattaagca gaaggccatc ctgacggatg ccttttttgc    4440
gtttctacaa actcttttg tttatttttc taaatacatt caaatatgta tccgctcatg    4500
```

```
agacaataac cctgataaat gcttcaataa tctggcgtaa tagcgaagag gcccgcaccg      4560
atcgcccttc ccaacagttg cgcagcctga atggcgaatg gcgcctgatg cggtattttc      4620
tccttacgca tctgtgcggt atttcacacc gcatatggtg cactctcagt acaatctgct      4680
ctgatgccgc atagttaagc cagccccgac acccgccaac acccgctgac gagcttagta      4740
aagccctcgc tagattttaa tgcggatgtt gcgattactt cgccaactat tgcgataaca      4800
agaaaaagcc agcctttcat gatatatctc ccaatttgtg tagggcttat tatgcacgct      4860
taaaaataat aaaagcagac ttgacctgat agtttggctg tgagcaatta tgtgcttagt      4920
gcatctaacg cttgagttaa gccgcgccgc gaagcggcgt cggcttgaac gaattgttag      4980
acattatttg ccgactacct tggtgatctc gcctttcacg tagtggacaa attcttccaa      5040
ctgatctgcg cgcgaggcca agcgatcttc ttcttgtcca agataagcct gtctagcttc      5100
aagtatgacg ggctgatact gggccggcag gcgctccatt gcccagtcgg cagcgacatc      5160
cttcggcgcg attttgccgg ttactgcgct gtaccaaatg cgggacaacg taagcactac      5220
atttcgctca tcgccagccc agtcgggcgg cgagttccat agcgttaagg tttcatttag      5280
cgcctcaaat agatcctgtt caggaaccgg atcaaagagt tcctccgccg ctggacctac      5340
caaggcaacg ctatgttctc ttgcttttgt cagcaagata gccagatcaa tgtcgatcgt      5400
ggctggctcg aagatacctg caagaatgtc attgcgctgc cattctccaa attgcagttc      5460
gcgcttagct ggataacgcc acggaatgat gtcgtcgtgc acaacaatgg tgacttctac      5520
agcgcggaga atctcgctct ctccagggga agccgaagtt ccaaaaggt cgttgatcaa       5580 agctcgccgc gttgtttcat caagccttac ggtcaccgta accagcaaat caatatcact      5640
gtgtggcttc aggccgccat ccactgcgga gccgtacaaa tgtacggcca gcaacgtcgg      5700
ttcgagatgg cgctcgatga cgccaactac ctctgatagt tgagtcgata cttcggcgat      5760
caccgcttcc ctcatgatgt taactttgt tttagggcga ctgccctgct gcgtaacatc       5820
gttgctgctc cataacatca aacatcgacc cacggcgtaa cgcgcttgct gcttggatgc      5880
ccgaggcata gactgtaccc caaaaaaaca gtcataacaa gccatgaaaa ccgccactgc      5940
gccgttacca ccgctgcgtt cggtcaaggt tctggaccag ttgcgtgagc gcatacgcta      6000
cttgcattac agcttacgaa ccgaacaggc ttatgtccac tgggttcgtg ccttcatccg      6060
tttccacggt gtgcgtcacc cggcaacctt gggcagcagc gaagtcgagg catttctgtc      6120
ctggctggcg aacgagcgca aggtttcggt ctccacgcat cgtcaggcat ggcggccttt      6180
gctgttcttc tacggcaagg tgctgtgcac ggatctgccc tggcttcagg agatcggaag      6240
acctcggccg tcgcggcgct tgccggtggt gctgaccccg gatgaagtgg ttcgcatcct      6300
cggttttctg gaaggcgagc atcgtttgtt cgcccagctt ctgtatggaa cgggcatgcg      6360
gatcagtgag ggtttgcaac tgcgggtcaa ggatctggat ttcgatcacg gcacgatcat      6420
cgtgcgggag ggcaagggct ccaaggatcg ggccttgatg ttacccgaga gcttggcacc      6480
cagcctgcgc gagcagggga attaattccc acgggttttg ctgcccgcaa acgggctgtt      6540
ctggtgttgc tagtttgtta tcagaatcgc agatccggct tcagccggtt tgccggctga      6600
aagcgctatt tcttccagaa ttgccatgat ttttccccca cggaggcgt cactggctcc       6660 cgtgttgtcg gcagctttga ttcgataagc agcatcgcct gtttcaggct gtctatgtgt      6720
gactgttgag ctgtaacaag ttgtctcagg tgttcaattt catgttctag ttgctttgtt      6780
ttactggttt cacctgttct attaggtgtt acatgctgtt catctgttac attgtcgatc      6840
```

```
tgttcatggt gaacagcttt gaatgcacca aaaactcgta aaagctctga tgtatctatc    6900
ttttttacac cgttttcatc tgtgcatatg gacagttttc cctttgatat gtaacggtga    6960
acagttgttc tactttgtt tgttagtctt gatgcttcac tgatagatac aagagccata    7020
agaacctcag atccttccgt atttagccag tatgttctct agtgtggttc gttgttttg     7080 cgtgagccat gagaacgaac cattgagatc atacttactt tgcatgtcac tcaaaaattt    7140
tgcctcaaaa ctggtgagct gaattttgc agttaaagca tcgtgtagtg ttttcttag      7200 tccgttatgt aggtaggaat ctgatgtaat ggttgttggt attttgtcac cattcatttt    7260
tatctggttg ttctcaagtt cggttacgag atccatttgt ctatctagtt caacttggaa    7320
aatcaacgta tcagtcgggc ggcctcgctt atcaaccacc aatttcatat tgctgtaagt    7380
gtttaaatct ttacttattg gtttcaaaac ccattggtta agccttttaa actcatggta    7440
gttattttca agcattaaca tgaacttaaa ttcatcaagg ctaatctcta tatttgcctt    7500
gtgagttttc ttttgtgtta gttcttttaa taaccactca taaatcctca tagagtattt    7560
gttttcaaaa gacttaacat gttccagatt atatttatg aattttttta actggaaaag     7620
ataaggcaat atctcttcac taaaaactaa ttctaatttt tcgcttgaga acttggcata    7680
gtttgtccac tggaaaatct caaagccttt aaccaaagga ttcctgattt ccacagttct    7740
cgtcatcagc tctctggttg ctttagctaa tacaccataa gcattttccc tactgatgtt    7800
catcatctga gcgtattggt tataagtgaa cgataccgtc cgttctttcc ttgtagggtt    7860
ttcaatcgtg gggttgagta gtgccacaca gcataaaatt agcttggttt catgctccgt    7920
taagtcatag cgactaatcg ctagttcatt tgctttgaaa acaactaatt cagacataca    7980
tctcaattgg tctaggtgat tttaatcact ataccaattg agatgggcta gtcaatgata    8040
attactagtc cttttccttt gagttgtggg tatctgtaaa ttctgctaga cctttgctgg    8100
aaaacttgta aattctgcta gaccctctgt aaattccgct agacctttgt gtgttttttt    8160
tgtttatatt caagtggtta taatttatag aataaagaaa gaataaaaaa agataaaaag    8220
aatagatccc agccctgtgt ataactcact actttagtca gttccgcagt attacaaaag    8280
gatgtcgcaa acgctgtttg ctcctctaca aaacagacct taaaacccta aaggcttaag    8340
tagcaccctc gcaagctcgg gcaaatcgct gaatattcct tttgtctccg accatcaggc    8400
acctgagtcg ctgtcttttt cgtgacattc agttcgctgc gctcacggct ctggcagtga    8460
atgggggtaa atggcactac aggcgccttt tatggattca tgcaaggaaa ctacccataa    8520
tacaagaaaa gcccgtcacg ggcttctcag ggcgttttat ggcgggtctg ctatgtggtg    8580
ctatctgact ttttgctgtt cagcagttcc tgccctctga ttttccagtc tgaccacttc    8640
ggattatccc gtgacaggtc attcagactg gctaatgcac ccagtaaggc agcggtatca    8700
tcaacaggct ta                                                       8712
```

<210> SEQ ID NO 25
<211> LENGTH: 8712
<212> TYPE: DNA
<213> ORGANISM: Artificial Sequence
<220> FEATURE:
<223> OTHER INFORMATION: Synthetic Construct

<400> SEQUENCE: 25

```
cccgtcttac tgtcgggaat tcgcgttggc cgattcatta atgcagattc tgaaatgagc      60
tgttgacaat taatcatccg gctcgtataa tgtgtggaat tgtgagcgga taacaatttc     120
acacaggaaa cagcgccgct gagaaaaagc gaagcggcac tgctctttac aatttatcag    180
```

| | | | | | |
|---|---|---|---|---|---|
| acaatctgtg | tgggcactcg | accggaatta | tcgattaact | ttattattaa | aaattaaaga | 240 |
| ggtatatatt | aatgtatcga | ttaaataagg | aggaataaac | catgaaagaa | gtggttatga | 300 |
| ttgatgcggc | tcgcacaccc | attgggaaat | acagaggtag | tcttagtcct | tttacagcgg | 360 |
| tggagctggg | gacactggtc | acgaaagggc | tgctggataa | acaaagctt | aagaaagaca | 420 |
| agatagacca | agtgatattc | ggcaatgtgc | ttcaggcagg | aaacggacaa | aacgttgcaa | 480 |
| gacaaatagc | cctgaacagt | ggcttaccag | ttgacgtgcc | ggcgatgact | attaacgaag | 540 |
| tttgcgggtc | cggaatgaaa | gcggtgattt | tagcccgcca | gttaatacag | ttaggggagg | 600 |
| cagagttggt | cattgcaggg | ggtacggagt | caatgtcaca | agcacccatg | ctgaaacctt | 660 |
| accagtcaga | gaccaacgaa | tacggagagc | cgatatcatc | aatggttaat | gacgggctga | 720 |
| cggatgcgtt | ttccaatgct | cacatgggtc | ttactgccga | aaaggtggcg | acccagtttt | 780 |
| cagtgtcgcg | cgaggaacaa | gaccggtacg | cattgtccag | ccaattgaaa | gcagcgcacg | 840 |
| cggttgaagc | cggggtgttc | tcagaagaga | ttattccggt | taagattagc | gacgaggatg | 900 |
| tcttgagtga | agacgaggca | gtaagaggca | acagcacttt | ggaaaaactg | gcaccttgc | 960 |
| ggacggtgtt | ttctgaagag | ggcacggtta | ccgctgcaa | tgcttcaccg | ctgaatgacg | 1020 |
| gcgctagtgt | cgtgattctt | gcatcaaaag | aatacgcgga | aaacaataat | ctgccttacc | 1080 |
| tggcgacgat | aaaggaggtt | gcggaagttg | gtatcgatcc | ttctatcatg | ggtattgccc | 1140 |
| caataaaggc | cattcaaaag | ttaacagatc | ggtcgggcat | gaacctgtcc | acgattgatc | 1200 |
| tgttcgaaat | taatgaagca | ttcgcggcat | ctagcattgt | tgtttctcaa | gagctgcaat | 1260 |
| tggacgaaga | aaaagtgaat | atctatggcg | gggcgatagc | tttaggccat | ccaatcggcg | 1320 |
| caagcggagc | ccggatactg | acaaccttag | catacggcct | cctgcgtgag | caaaagcgtt | 1380 |
| atggtattgc | gtcattatgt | atcggcggtg | gtcttggtct | ggccgtgctg | ttagaagcta | 1440 |
| atatggagca | gacccacaaa | gacgttcaga | agaaaaagtt | ttaccagctt | acccctccg | 1500 |
| agcggagatc | gcagcttatc | gagaagaacg | ttctgactca | agaaacggca | cttatttcc | 1560 |
| aggagcagac | gttgtccgaa | gaactgtccg | atcacatgat | tgagaatcag | gtctccgaag | 1620 |
| tggaaattcc | aatgggaatt | gcacaaaatt | ttcagattaa | tggcaagaaa | aaatggattc | 1680 |
| ctatggcgac | tgaagaacct | tcagtaatag | cggcagcatc | gaacggcgcc | aaaatctgcg | 1740 |
| ggaacatttg | cgcggaaacg | cctcagcggc | ttatgcgcgg | gcagattgtc | ctgtctggca | 1800 |
| aatcagaata | tcaagccgtg | ataaatgccg | tgaatcatcg | caaagaagaa | ctgattcttt | 1860 |
| gcgcaaacga | gtcgtacccg | agtattgtta | acgcgggg | aggtgttcag | gatatttcta | 1920 |
| cgcgggagtt | tatgggttct | tttcacgcgt | atttatcaat | cgactttctg | gtggacgtca | 1980 |
| aggacgcaat | gggggcaaac | atgatcaact | ctattctcga | aagcgttgca | aataaactgc | 2040 |
| gtgaatggtt | cccggaagag | gaaatactgt | tctccatcct | gtcaaacttc | gctacggagt | 2100 |
| ccctggcatc | tgcatgttgc | gagattcctt | ttgaaagact | tggtcgtaac | aaagaaattg | 2160 |
| gtgaacagat | cgccaagaaa | attcaacagg | caggggaata | tgctaagctt | gacccttacc | 2220 |
| gcgcggcaac | ccataacaag | gggattatga | acggtatcga | agccgtcgtt | ccgcaacgg | 2280 |
| gaaacgacac | acgggctgtt | tccgcttcta | ttcacgcata | cgccgcccgt | aatggcttgt | 2340 |
| accaaggttt | aacggattgg | cagatcaagg | gcgataaact | ggttggtaaa | ttaacagtcc | 2400 |
| cactggctgt | ggcgactgtc | ggtggcgcgt | cgaacatatt | accaaaagcc | aaagcttccc | 2460 |
| tcgccatgct | ggatattgat | tccgcaaaag | aactggccca | agtgatcgcc | gcggtaggtt | 2520 |

```
tagcacagaa tctggcggcg ttacgtgcat tagtgacaga aggcattcag aaaggacaca    2580
tgggcttgca agcacgttct ttagcgattt cgataggtgc catcggtgag gagatagagc    2640
aagtcgcgaa aaaactgcgt gaagctgaaa aatgaatcga gcaaacggca atacagattt    2700
tagaaaaaat tcgcgagaaa tgatctagac gcactaggag gatataccaa tgaaaatcgg    2760
tattgaccgt ctgtccttct tcatcccgaa tttgtatttg gacatgactg agctggcaga    2820
atcacgcggg gatgatccag ctaaatatca tattggaatc ggacaagatc agatggcagt    2880
gaatcgcgca aacgaggaca tcataacact gggtgcaaac gctgcgagta agatcgtgac    2940
agagaaagac cgcgagttga ttgatatggt aatcgttggc acggaatcag gaattgacca    3000
ctccaaagca agcgccgtga ttattcacca tctccttaaa attcagtcgt tcgcccgttc    3060
tttcgaggta aaagaagctt gctatggcgg aactgctgcc ctgcacatgg cgaaggagta    3120
tgtcaaaaat catccggagc gtaaggtctt ggtaattgcg tcagacatcg cgcgttatgg    3180
tttggccagc ggaggagaag ttactcaagg cgtgggggcc gtagccatga tgattacaca    3240 aaaccccgg attctttcga ttgaagacga tagtgttttt ctcacagagg atatctatga    3300
tttctggcgg cctgattact ccgagttccc tgtagtggac gggccccttt caaactcaac    3360
gtatatagag agttttcaga aagtttggaa ccggcacaag gaattgtccg gaagagggct    3420
ggaagattat caagctattg cttttcacat accctatacg aagatgggta agaaagcgct    3480
ccagagtgtt ttagaccaaa ccgatgaaga taaccaggag cgcttaatgg ctagatatga    3540
ggagtctatt cgctatagcc ggagaattgg taacctgtac acaggcagct tgtaccttgg    3600
tcttacaagc ttgttggaaa actctaaaag tttacaaccg ggagatcgga tcggcctctt    3660
ttcctatggc agtggtgcgg tgtccgagtt ctttaccggg tatttagaag aaaattacca    3720
agagtacctg ttcgctcaaa gccatcaaga aatgctggat agccggactc ggattacggt    3780
cgatgaatac gagaccatct tttcagagac tctgccagaa catggtgaat gcgccgaata    3840
tacgagcgac gtccccttt ctataaccaa gattgagaac gacattcgtt attataaaat    3900
ctgactgcag ctggtaccat atgggaattc gaagcttggg cccgaacaaa aactcatctc    3960
agaagaggat ctgaatagcg ccgtcgacca tcatcatcat catcattgag tttaaacggt    4020
ctccagcttg gctgttttgg cggatgagag aagattttca gcctgataca gattaaatca    4080
gaacgcagaa gcggtctgat aaaacagaat ttgcctggcg gcagtagcgc ggtggtccca    4140
cctgacccca tgccgaactc agaagtgaaa cgccgtagcg ccgatggtag tgtggggtct    4200
ccccatgcga gagtagggaa ctgccaggca tcaaataaaa cgaaaggctc agtcgaaaga    4260
ctgggccttt cgttttatct gttgtttgtc ggtgaacgct ctcctgagta ggacaaatcc    4320
gccgggagcg gatttgaacg ttgcgaagca acggcccgga gggtggcggg caggacgccc    4380
gccataaact gccaggcatc aaattaagca gaaggccatc ctgacggatg gcctttttgc    4440
gtttctacaa actcttttg tttattttc taaatacatt caaatatgta tccgctcatg    4500
agacaataac cctgataaat gcttcaataa tctggcgtaa tagcgaagag gcccgcaccg    4560 atcgccttc ccaacagttg cgcagcctga atggcgaatg gcgcctgatg cggtattttc    4620
tccttacgca tctgtgcggt atttcacacc gcatatggtg cactctcagt acaatctgct    4680
ctgatgccgc atagttaagc cagccccgac acccgccaac acccgctgac gagcttagta    4740
aagccctcgc tagattttaa tgcggatgtt gcgattactt cgccaactat tgcgataaca    4800
agaaaaagcc agcctttcat gatatatctc ccaatttgtg tagggcttat tatgcacgct    4860
taaaaataat aaaagcagac ttgacctgat agtttggctg tgagcaatta tgtgcttagt    4920
```

```
gcatctaacg cttgagttaa gccgcgccgc gaagcggcgt cggcttgaac gaattgttag   4980
acattatttg ccgactacct tggtgatctc gcctttcacg tagtggacaa attcttccaa   5040
ctgatctgcg cgcgaggcca agcgatcttc ttcttgtcca agataagcct gtctagcttc   5100
aagtatgacg ggctgatact gggccggcag gcgctccatt gcccagtcgg cagcgacatc   5160
cttcggcgcg attttgccgg ttactgcgct gtaccaaatg cgggacaacg taagcactac   5220
atttcgctca tcgccagccc agtcgggcgg cgagttccat agcgttaagg tttcatttag   5280
cgcctcaaat agatcctgtt caggaaccgg atcaaagagt tcctccgccg ctggacctac   5340
caaggcaacg ctatgttctc ttgcttttgt cagcaagata gccagatcaa tgtcgatcgt   5400
ggctggctcg aagatacctg caagaatgtc attgcgctgc cattctccaa attgcagttc   5460
gcgcttagct ggataacgcc acggaatgat gtcgtcgtgc acaacaatgg tgacttctac   5520
agcgcggaga atctcgctct ctccagggga agccgaagtt tccaaaaggt cgttgatcaa   5580
agctcgccgc gttgtttcat caagcctac ggtcaccgta accagcaaat caatatcact   5640
gtgtggcttc aggccgccat ccactgcgga gccgtacaaa tgtacggcca gcaacgtcgg   5700
ttcgagatgg cgctcgatga cgccaactac ctctgatagt tgagtcgata cttcggcgat   5760
caccgcttcc ctcatgatgt ttaactttgt tttagggcga ctgccctgct gcgtaacatc   5820
gttgctgctc cataacatca aacatcgacc cacggcgtaa cgcgcttgct gcttggatgc   5880
ccgaggcata gactgtaccc caaaaaaaca gtcataacaa gccatgaaaa ccgccactgc   5940
gccgttacca ccgctgcgtt cggtcaaggt tctggaccag ttgcgtgagc gcatacgcta   6000
cttgcattac agcttacgaa ccgaacaggc ttatgtccac tgggttcgtg ccttcatccg   6060
tttccacggt gtgcgtcacc cggcaacctt gggcagcagc gaagtcgagg catttctgtc   6120
ctggctggcg aacgagcgca aggtttcggt ctccacgcat cgtcaggcat ggcggcctt    6180 gctgttcttc tacggcaagg tgctgtgcac ggatctgccc tggcttcagg agatcggaag   6240
acctcggccg tcgcggcgct tgccggtggt gctgaccccg gatgaagtgg ttcgcatcct   6300
cggttttctg gaaggcgagc atcgtttgtt cgcccagctt ctgtatggaa cgggcatgcg   6360
gatcagtgag ggtttgcaac tgcgggtcaa ggatctggat ttcgatcacg gcacgatcat   6420
cgtgcgggag ggcaagggct ccaaggatcg ggccttgatg ttacccgaga gcttggcacc   6480
cagcctgcgc gagcagggga attaattccc acgggttttg ctgcccgcaa acgggctgtt   6540
ctggtgttgc tagtttgtta tcagaatcgc agatccggct tcagccggtt gccggctga   6600 aagcgctatt tcttccagaa ttgccatgat ttttcccca cggagggcgt cactggctcc    6660
cgtgttgtcg gcagctttga ttcgataagc agcatcgcct gtttcaggct gtctatgtgt   6720
gactgttgag ctgtaacaag ttgtctcagg tgttcaattt catgttctag ttgctttgtt   6780
ttactggttt cacctgttct attaggtgtt acatgctgtt catctgttac attgtcgatc   6840
tgttcatggt gaacagcttt gaatgcacca aaaactcgta aaagctctga tgtatctatc   6900 tttttacac cgttttcatc tgtgcatatg gacagttttc cctttgatat gtaacggtga    6960
acagttgttc tacttttgtt tgttagtctt gatgcttcac tgatagatac aagagccata   7020
agaacctcag atccttccgt atttagccag tatgttctct agtgtggttc gttgtttttg   7080
cgtgagccat gagaacgaac cattgagatc atacttactt tgcatgtcac tcaaaaattt   7140
tgcctcaaaa ctggtgagct gaattttgc agttaaagca tcgtgtagtg tttttcttag    7200
tccgttatgt aggtaggaat ctgatgtaat ggttgttggt attttgtcac cattcatttt   7260
```

-continued

```
tatctggttg ttctcaagtt cggttacgag atccatttgt ctatctagtt caacttggaa    7320
aatcaacgta tcagtcgggc ggcctcgctt atcaaccacc aatttcatat tgctgtaagt    7380
gtttaaatct ttacttattg gtttcaaaac ccattggtta agccttttaa actcatggta    7440
gttattttca agcattaaca tgaacttaaa ttcatcaagg ctaatctcta tatttgcctt    7500
gtgagttttc ttttgtgtta gttctttttaa taaccactca taaatcctca tagagtattt    7560
gttttcaaaa gacttaacat gttccagatt atattttatg aattttttta actggaaaag    7620
ataaggcaat atctcttcac taaaaactaa ttctaatttt tcgcttgaga acttggcata    7680
gtttgtccac tggaaaatct caaagccttt aaccaaagga ttcctgattt ccacagttct    7740
cgtcatcagc tctctggttg ctttagctaa tacaccataa gcattttccc tactgatgtt    7800
catcatctga gcgtattggt tataagtgaa cgataccgtc cgttcttttcc ttgtagggtt    7860 ttcaatcgtg gggttgagta gtgccacaca gcataaaatt agcttggttt catgctccgt    7920
taagtcatag cgactaatcg ctagttcatt tgctttgaaa acaactaatt cagacataca    7980
tctcaattgg tctaggtgat tttaatcact ataccaattg agatgggcta gtcaatgata    8040
attactagtc ctttttccttt gagttgtggg tatctgtaaa ttctgctaga cctttgctgg    8100
aaaacttgta aattctgcta gaccctctgt aaattccgct agacctttgt gtgtttttt    8160 tgtttatatt caagtggtta taatttatag aataaagaaa gaataaaaaa agataaaaag    8220
aatagatccc agccctgtgt ataactcact actttagtca gttccgcagt attacaaaag    8280
gatgtcgcaa acgctgtttg ctcctctaca aaacagacct taaaacccta aaggcttaag    8340
tagcaccctc gcaagctcgg gcaaatcgct gaatattcct tttgtctccg accatcaggc    8400
acctgagtcg ctgtcttttt cgtgacattc agttcgctgc gctcacggct ctggcagtga    8460 atggggtaa atggcactac aggcgccttt tatggattca tgcaaggaaa ctacccataa    8520
tacaagaaaa gcccgtcacg ggcttctcag ggcgttttat ggcgggtctg ctatgtggtg    8580
ctatctgact ttttgctgtt cagcagttcc tgccctctga ttttccagtc tgaccacttc    8640
ggattatccc gtgacaggtc attcagactg gctaatgcac ccagtaaggc agcggtatca    8700
tcaacaggct ta                                                        8712
```

<210> SEQ ID NO 26
<211> LENGTH: 8719
<212> TYPE: DNA
<213> ORGANISM: Artificial Sequence
<220> FEATURE:
<223> OTHER INFORMATION: Synthetic Construct

<400> SEQUENCE: 26

```
cccgtcttac tgtcgggaat tcgcgttggc cgattcatta atgcagattc tgaaatgagc     60
tgttgacaat taatcatccg gctcgtataa tgtgtggaat tgtgagcgga taacaatttc    120
acacaggaaa cagcgccgct gagaaaaagc gaagcggcac tgctctttaa caatttatca    180
gacaatctgt gtgggcactc gaccggaatt atcgattaac tttattatta aaaattaaag    240
aggtatatat taatgtatcg attaaataag gaggaataaa ccatggaaga agtggtaatt    300
atagatgcac gtcggactcc gattggtaaa tatcacgggt cgttgaagaa gttttcagcg    360
gtggcgctgg ggacggccgt ggctaaagac atgttcgaac gcaaccagaa aatcaaagag    420
gagatcgcgc aggtcataat tggtaatgtc ttgcaggcag gaaatggcca gaaccccgcg    480
cggcaagttg ctcttcaatc aggggttgtcc gttgacattc ccgcttctac aattaacgag    540
gtttgtgggt ctggtttgaa agctatcttg atgggcatgg aacaaatcca actcggcaaa    600
```

```
gcgcaagtag tgctggcagg cggcattgaa tcaatgacaa atgcgccaag cctgtcccac    660
tataacaagg cggaggatac gtatagtgtc ccagtgtcga gcatgacact ggatggtctg    720
acagacgcat tttctagtaa acctatggga ttaacagcgg aaaacgtcgc acagcgctac    780
ggtatctccc gtgaggcgca agatcaattc gcatatcaat ctcagatgaa agcagcaaaa    840
gcgcaggcag aaaacaaatt cgctaaggaa attgtgccac tggcgggtga aactaaaacc    900
atcacagctg acgaagggat cagatcccaa acaacgatgg agaaactggc aagtctcaaa    960
cctgttttta aaaccgatgg cactgtaacc gcagggaatg ctagcaccat taatgacggg   1020
gccgcccttg tgctgcttgc tagcaaaact tactgcgaaa ctaatgacat accgtacctt   1080
gcgacaatca agaaattgt tgaagttgga atcgatccgg agattatggg catctctccg   1140
ataaaagcga tacaaacatt gttacaaaat caaaaagtta gcctcgaaga tattggagtt   1200
tttgaaataa atgaagcctt tgccgcaagt agcatagtgg ttgaatctga gttgggatta   1260
gatccggcta aagttaaccg ttatgggggt ggtatatcct taggtcatgc aattggggca   1320
accggcgctc gcctggccac ttcactggtg tatcaaatgc aggagataca agcacgttat   1380
ggtattgcga gcctgtgcgt tggtggtgga cttggactgg caatgctttt agaacgtcca   1440
actattgaga aggctaaacc gacagacaaa aagttctatg aattgtcacc agctgaacgg   1500
ttgcaagagc tggaaaatca acagaaaatc agttctgaaa ctaaacagca gttatctcag   1560
atgatgcttg ccgaggacac tgcaaaccat ttgatagaaa atcaaatatc agagattgaa   1620
ctcccaatgg gcgtcgggat gaacctgaag gttgatggga agcctatgt tgtgccaatg   1680 gcgacggaag agccgtccgt catcgcggcc atgtctaatg gtgccaaaat ggccggcgaa   1740
attcacactc agtcgaaaga acggctgctc agaggtcaga ttgttttcag cgcgaagaat   1800
ccgaatgaaa tcgaacagag aatagctgag aaccaagctt tgattttcga acgtgccgaa   1860
cagtcctatc cttccattgt gaaaagagag ggaggtctcc gccgcattgc acttcgtcat   1920
tttcctgccg attctcagca ggagtctgcg gaccagtcca catttttatc agtggacctt   1980
tttgtagatg tgaaagacgc gatgggggca aatatcataa atgcaatact tgagggcgtc   2040
gcagccctgt ttcgcgaatg gttccccaat gaggaaattc ttttttctat tctctcgaac   2100
ttggctacgg agagcttagt cacggctgtt tgtgaagtcc catttagtgc acttagcaag   2160
agaggtggtg caacggtggc ccagaaaatt gtgcaggcgt cgctcttcgc aaagacagac   2220
ccataccgcg cagtgaccca caacaaaggg attatgaacg gtgtagaggc tgttatgctt   2280
gccacaggca acgacacgcg cgcagtctca gccgcttgtc atggatacgc agcgcgcacc   2340
ggtagctatc agggtctgac taactggacg attgagtcgg atcgcctggt aggcgagata   2400
acactgccgc tggccatcgc tacagttgga ggcgctacca agtgttgcc caaagctcaa   2460 gcggcactgg agattagtga tgttcactct tctcaagagc ttgcagcctt agcggcgtca   2520
gtaggtttag tacaaaatct cgcggccctg cgcgcactgg tttccgaagg tatacaaaaa   2580
gggcacatgt ccatgcaagc ccggtctctc gcaatcgcgg tcggtgctga aaaagccgag   2640
atcgagcagg tcgccgaaaa gttgcggcag aacccgccaa tgaatcagca gcaggcgctc   2700
cgttttcttg gcgagatccg cgaacaatga tctagacgca ctaggaggat ataccaatga   2760
acgtcggcat tgacaaaatt aatttttttcg ttccaccgta ttatctggat atggtcgacc   2820
tggcccacgc acgcgaagtg gacccgaaca aatttacaat tggaattgga caggatcaga   2880
tggctgtgag caaaaagacg cacgatatcg taacattcgc ggctagtgcc gcgaaggaaa   2940
```

```
ttttagaacc tgaggacttg caagctatag acatggttat agttggtacc gaatcgggca    3000
ttgacgagag caaagcatcc gcggtcgttt tacatcgttt gttgggcgta caacctttcg    3060
ctcgcagttt tgaaattaaa gaagcctgtt acggggcaac cgcaggcatt cagtttgcca    3120
agactcatat acaagcgaac ccggagagca aggtcctggt aattgcaagc gatatagctc    3180
ggtatggtct tcggtcaggt ggagagccca cacaaggcgc aggggcagtt gctatgcttc    3240
tcacggcaaa tcccagaatc ctgaccttcg aaaacgacaa tctgatgtta acgcaggata    3300
tttatgactt ctggagacca cttggtcacg cttaccctat ggtagatggc cacctttcca    3360
atcaagtcta tattgacagt tttaagaagg tctggcaagc acattgcgaa cgcaatcaag    3420
cttctatatc cgactatgcc gcgattagtt ttcatattcc gtatacaaaa atgggtaaga    3480
aagccctgct cgctgttttt gcagatgaag tggaaactga acaggaacgc gttatggcac    3540
ggtatgaaga gtctatcgta tattcacgcc ggatcggcaa cttgtatacg ggatcattgt    3600
acctggggct gatatcctta ttggaaaaca gttctcacct gtcggcgggc gaccggatag    3660
gattgtttag ttatgggagt ggcgctgtca gcgaattttt ctccggtcgt ttagtggcag    3720
gctatgaaaa tcaattgaac aaagaggcgc atacccagct cctggatcag cgtcagaagc    3780
tttccatcga agagtatgag gcgattttta cagattcctt agaaattgat caggatgcag    3840
cgttctcgga tgacctgcca tattccatcc gcgagataaa aaacacgatt cggtactata    3900
aggagagctg actgcagctg gtaccatatg ggaattcgaa gcttgggccc gaacaaaaac    3960
tcatctcaga gaggatctg aatagcgccg tcgaccatca tcatcatcat cattgagttt    4020
aaacggtctc cagcttggct gttttggcgg atgagaagat ttttcagcc tgatacagat    4080 taaatcagaa cgcagaagcg gtctgataaa acagaatttg cctggcggca gtagcgcggt    4140
ggtcccacct gaccccatgc cgaactcaga agtgaaacgc cgtagcgccg atggtagtgt    4200
ggggtctccc catgcgagag tagggaactg ccaggcatca aataaaacga aaggctcagt    4260
cgaaagactg gcctttcgt tttatctgtt gtttgtcggt gaacgctctc ctgagtagga    4320
caaatccgcc gggagcggat ttgaacgttg cgaagcaacg gcccggaggg tggcgggcag    4380
gacgcccgcc ataaactgcc aggcatcaaa ttaagcagaa ggccatcctg acggatggcc    4440 ttttttgcgtt tctacaaact cttttttgtt tatttttctaa atacattcaa atatgtatcc    4500
gctcatgaga caataaccct gataaatgct tcaataatct ggcgtaatag cgaagaggcc    4560
cgcaccgatc gcccttccca acagttgcgc agcctgaatg gcgaatggcg cctgatgcgg    4620
tattttctcc ttacgcatct gtgcggtatt tcacaccgca tatggtgcac tctcagtaca    4680
atctgctctg atgccgcata gttaagccag ccccgacacc cgccaacacc cgctgacgag    4740
cttagtaaag ccctcgctag attttaatgc ggatgttgcg attacttcgc caactattgc    4800
gataacaaga aaaagccagc cttttcatgat atatctccca atttgtgtag gcttattat    4860 gcacgcttaa aaataataaa agcagacttg acctgatagt ttggctgtga caattatgt    4920 gcttagtgca tctaacgctt gagttaagcc gcgccgcgaa gcggcgtcgg cttgaacgaa    4980
ttgttagaca ttatttgccg actaccttgg tgatctcgcc tttcacgtag tggacaaatt    5040
cttccaactg atctgcgcgc gaggccaagc gatcttcttc ttgtccaaga taagcctgtc    5100
tagcttcaag tatgacgggc tgatactggg ccggcaggcg ctccattgcc cagtcggcag    5160
cgacatcctt cggcgcgatt ttgccggtta ctgcgctgta ccaaatgcgg gacaacgtaa    5220
gcactacatt tcgctcatcg ccagcccagt cgggcggcga gttccatagc gttaaggttt    5280
catttagcgc ctcaaataga tcctgttcag gaaccggatc aaagagttcc tccgccgctg    5340
```

```
gacctaccaa ggcaacgcta tgttctcttg cttttgtcag caagatagcc agatcaatgt    5400
cgatcgtggc tggctcgaag atacctgcaa gaatgtcatt gcgctgccat tctccaaatt    5460
gcagttcgcg cttagctgga taacgccacg gaatgatgtc gtcgtgcaca caatggtga     5520 cttctacagc gcggagaatc tcgctctctc caggggaagc cgaagtttcc aaaaggtcgt    5580
tgatcaaagc tcgccgcgtt gtttcatcaa gccttacggt caccgtaacc agcaaatcaa    5640
tatcactgtg tggcttcagg ccgccatcca ctgcggagcc gtacaaatgt acggccagca    5700
acgtcggttc gagatggcgc tcgatgacgc caactacctc tgatagttga gtcgatactt    5760
cggcgatcac cgcttccctc atgatgttta actttgtttt agggcgactg ccctgctgcg    5820
taacatcgtt gctgctccat aacatcaaac atcgacccac ggcgtaacgc gcttgctgct    5880
tggatgcccg aggcatagac tgtaccccaa aaaaacagtc ataacaagcc atgaaaaccg    5940
ccactgcgcc gttaccaccg ctgcgttcgg tcaaggttct ggaccagttg cgtgagcgca    6000
tacgctactt gcattacagc ttacgaaccg aacaggctta tgtccactgg gttcgtgcct    6060
tcatccgttt ccacggtgtg cgtcacccgg caaccttggg cagcagcgaa gtcgaggcat    6120
ttctgtcctg gctggcgaac gagcgcaagg tttcggtctc cacgcatcgt caggcattgg    6180
cggccttgct gttcttctac ggcaaggtgc tgtgcacgga tctgccctgg cttcaggaga    6240
tcggaagacc tcggccgtcg cggcgcttgc cggtggtgct gacccggat gaagtggttc     6300 gcatcctcgg ttttctggaa ggcgagcatc gtttgttcgc ccagcttctg tatggaacgg    6360
gcatgcggat cagtgagggt ttgcaactgc gggtcaagga tctggatttc gatcacggca    6420
cgatcatcgt gcgggagggc aagggctcca aggatcgggc cttgatgtta cccgagagct    6480
tggcacccag cctgcgcgag caggggaatt aattcccacg ggttttgctg cccgcaaacg    6540
ggctgttctg gtgttgctag tttgttatca gaatcgcaga tccggcttca gccggtttgc    6600
cggctgaaag cgctatttct tccagaattg ccatgatttt tcccccacgg gaggcgtcac    6660
tggctcccgt gttgtcggca gctttgattc gataagcagc atcgcctgtt tcaggctgtc    6720
tatgtgtgac tgttgagctg taacaagttg tctcaggtgt tcaatttcat gttctagttg    6780
ctttgtttta ctggtttcac ctgttctatt aggtgttaca tgctgttcat ctgttacatt    6840
gtcgatctgt tcatggtgaa cagctttgaa tgcaccaaaa actcgtaaaa gctctgatgt    6900
atctatcttt tttacaccgt tttcatctgt gcatatggac agttttccct ttgatatgta    6960
acggtgaaca gttgttctac ttttgtttgt tagtcttgat gcttcactga tagatacaag    7020
agccataaga acctcagatc cttccgtatt tagccagtat gttctctagt gtggttcgtt    7080 gttttttgcgt gagccatgag aacgaaccat tgagatcata cttactttgc atgtcactca    7140
aaaattttgc ctcaaaactg gtgagctgaa ttttgcagt taaagcatcg tgtagtgttt    7200
ttcttagtcc gttatgtagg taggaatctg atgtaatggt tgttggtatt ttgtcaccat    7260
tcatttttat ctggttgttc tcaagttcgg ttacgagatc catttgtcta tctagttcaa    7320
cttggaaaat caacgtatca gtcgggcggc ctcgcttatc aaccaccaat ttcatattgc    7380
tgtaagtgtt taaatcttta cttattggtt tcaaaaccca ttggttaagc cttttaaact    7440
catggtagtt attttcaagc attaacatga acttaaattc atcaaggcta atctctatat    7500
ttgccttgtg agttttcttt tgtgttagtt cttttaataa ccactcataa atcctcatag    7560
agtatttgtt ttcaaaagac ttaacatgtt ccagattata ttttatgaat ttttttaact    7620
ggaaaagata aggcaatatc tcttcactaa aaactaattc taattttcg cttgagaact     7680
```

| | |
|---|---:|
| tggcatagtt tgtccactgg aaaatctcaa agcctttaac caaaggattc ctgatttcca | 7740 |
| cagttctcgt catcagctct ctggttgctt tagctaatac accataagca ttttccctac | 7800 |
| tgatgttcat catctgagcg tattggttat aagtgaacga taccgtccgt tctttccttg | 7860 |
| tagggttttc aatcgtgggg ttgagtagtg ccacacagca taaaattagc ttggtttcat | 7920 |
| gctccgttaa gtcatagcga ctaatcgcta gttcatttgc tttgaaaaca actaattcag | 7980 |
| acatacatct caattggtct aggtgatttt aatcactata ccaattgaga tgggctagtc | 8040 |
| aatgataatt actagtcctt ttcctttgag ttgtgggtat ctgtaaattc tgctagacct | 8100 |
| ttgctggaaa acttgtaaat tctgctagac cctctgtaaa ttccgctaga cctttgtgtg | 8160 |
| ttttttttgt ttatattcaa gtggttataa tttatagaat aaagaaagaa taaaaaaga | 8220 |
| taaaagaat agatcccagc cctgtgtata actcactact ttagtcagtt ccgcagtatt | 8280 |
| acaaaggat gtcgcaaacg ctgtttgctc ctctacaaaa cagaccttaa aaccctaaag | 8340 |
| gcttaagtag caccctcgca agctcgggca aatcgctgaa tattccttt gtctccgacc | 8400 |
| atcaggcacc tgagtcgctg tctttttcgt gacattcagt tcgctgcgct cacggctctg | 8460 |
| gcagtgaatg ggggtaaatg gcactacagg cgccttttat ggattcatgc aaggaaacta | 8520 |
| cccataatac aagaaaagcc cgtcacgggc ttctcagggc gttttatggc gggtctgcta | 8580 |
| tgtggtgcta tctgactttt tgctgttcag cagttcctgc cctctgattt tccagtctga | 8640 |
| ccacttcgga ttatcccgtg acaggtcatt cagactggct aatgcaccca gtaaggcagc | 8700 |
| ggtatcatca acaggctta | 8719 |

<210> SEQ ID NO 27
<211> LENGTH: 6203
<212> TYPE: DNA
<213> ORGANISM: Artificial Sequence
<220> FEATURE:
<223> OTHER INFORMATION: Synthetic Construct

<400> SEQUENCE: 27

| | |
|---|---:|
| atccggatat agttcctcct ttcagcaaaa aaccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtcattac tgacattcta | 180 |
| cgcgaacacc gatatctgtt gcgtttgcaa ccaccacctt gccaccggcc atccctattg | 240 |
| cttcagcgac gctatccaca ttttcacgcg gactgatagc aaccatacat ccccctccac | 300 |
| ccgctcctgt aatcttagac ccataagcgc ctgattcacg ggcggcgtaa atcagacttg | 360 |
| acagttctgc acaggaaaca cctattgcat ctaacagacc ctggtcgatg ttcatcagtt | 420 |
| cccccacgct aacgtaatcc cggtcattga ctaagccctc tccgattaca ctcagtttcc | 480 |
| caatagaact aagaactgga cctacaacat cggggaaccg ttcgttcaga tccgctacat | 540 |
| tacccaccaa ctccttcgtg gacgagaata tattggtgtt accgatcaaa atcccgcagt | 600 |
| ctatcagctc taactttttc cgctggggta tcaggacgac acctcccatg gtacacacat | 660 |
| aagtgtccgt aggagaagcc gtgccctgaa tgttttgttc aacctcatgg cccatcttag | 720 |
| cgatatcgtc taactccagc cccaggtcaa gcagtgtatc catagccttt atagtcgcca | 780 |
| ccgttactgc ggcggatgag ccaagaccgg atcccaccgg tatgtcggag cttattctca | 840 |
| gatctacccc gtcaaaagat gaaatatcct ggaaacgctc caacacggcc gacacatagg | 900 |
| gatgaacctc gaaatcgatc cccgttgtgc cgagacttga agagatagtt atggtatcgg | 960 |
| caggagagac tgtcacgcgc gttctaatat cgaccgcaca gcatatcgcc ggctctccgt | 1020 |

```
atacaactgc atgttcgccg aagagatata ctttgcccgg cgcagagcac gttatcatgc    1080
cctggaaata gaggttctca cctccagctc catgatgatg gtgatggtgc atatgtatat    1140
ctccttctta aagttaaaca aaattatttc tagaggggaa ttgttatccg ctcacaattc    1200
ccctatagtg agtcgtatta atttcgcggg atcgagatct cgatcctcta cgccggacgc    1260
atcgtggccg gcatcaccgg cgccacaggt gcggttgctg gcgcctatat cgccgacatc    1320
accgatgggg aagatcgggc tcgccacttc gggctcatga gcgcttgttt cggcgtgggt    1380
atggtggcag gccccgtggc cgggggactg ttgggcgcca tctccttgca tgcaccattc    1440
cttgcggcgg cggtgctcaa cggcctcaac ctactactgg gctgcttcct aatgcaggag    1500
tcgcataagg gagagcgtcg agatcccgga caccatcgaa tggcgcaaaa cctttcgcgg    1560
tatggcatga tagcgcccgg aagagagtca attcagggtg gtgaatgtga aaccagtaac    1620
gttatacgat gtcgcagagt atgccggtgt ctcttatcag accgtttccc gcgtggtgaa    1680
ccaggccagc cacgtttctg cgaaaacgcg ggaaaaagtg gaagcggcga tggcggagct    1740
gaattacatt cccaaccgcg tggcacaaca actggcgggc aaacagtcgt tgctgattgg    1800
cgttgccacc tccagtctgg ccctgcacgc gccgtcgcaa attgtcgcgg cgattaaatc    1860
tcgcgccgat caactgggtg ccagcgtggt ggtgtcgatg gtagaacgaa gcggcgtcga    1920
agcctgtaaa gcggcggtgc acaatcttct cgcgcaacgc gtcagtgggc tgatcattaa    1980
ctatccgctg gatgaccagg atgccattgc tgtggaagct gcctgcacta atgttccggc    2040
gttatttctt gatgtctctg accagacacc catcaacagt attatttcc cccatgaaga    2100 cggtacgcga ctgggcgtgg agcatctggt cgcattgggt caccagcaaa tcgcgctgtt    2160
agcgggccca ttaagttctg tctcggcgcg tctgcgtctg gctggctggc ataaatatct    2220
cactcgcaat caaattcagc cgatagcgga acgggaaggc gactggagtg ccatgtccgg    2280
ttttcaacaa accatgcaaa tgctgaatga gggcatcgtt cccactgcga tgctggttgc    2340
caacgatcag atgcgctggg cgcaatgcg cgccattacc gagtccgggc tgcgcgttgg    2400
tgcggatatc tcggtagtgg gatacgacga taccgaagac agctcatgtt atatcccgcc    2460
gttaaccacc atcaaacagg attttcgcct gctggggcaa accagcgtgg accgcttgct    2520
gcaactctct cagggccagg cggtgaaggg caatcagctg ttgcccgtct cactggtgaa    2580
aagaaaaacc accctggcgc ccaatacgca aaccgcctct ccccgcgcgt tggccgattc    2640
attaatgcag ctggcacgac aggtttcccg actggaaagc gggcagtgag cgcaacgcaa    2700
ttaatgtaag ttagctcact cattaggcac cgggatctcg accgatgccc ttgagagcct    2760
tcaacccagt cagctccttc cggtgggcgc ggggcatgac tatcgtcgcc gcacttatga    2820
ctgtcttctt tatcatgcaa ctcgtaggac aggtgccggc agcgctctgg gtcattttcg    2880
gcgaggaccg ctttcgctgg agcgcgacga tgatcggcct gtcgcttgcg gtattcggaa    2940
tcttgcacgc cctcgctcaa gccttcgtca ctggtcccgc caccaaacgt ttcggcgaga    3000
agcaggccat tatcgccggc atggcggccc cacgggtgcg catgatcgtg ctcctgtcgt    3060
tgaggacccg gctaggctgg cggggttgcc ttactggtta gcagaatgaa tcaccgatac    3120
gcgagcgaac gtgaagcgac tgctgctgca aacgtctgcg acctgagca acaacatgaa    3180 tggtcttcgg tttccgtgtt tcgtaaagtc tggaaacgcg gaagtcagcg ccctgcacca    3240
ttatgttccg gatctgcatc gcaggatgct gctggctacc ctgtggaaca cctacatctg    3300
tattaacgaa gcgctggcat tgaccctgag tgatttttct ctggtcccgc cgcatccata    3360
```

```
ccgccagttg tttaccctca caacgttcca gtaaccgggc atgttcatca tcagtaaccc    3420
gtatcgtgag catcctctct cgtttcatcg gtatcattac ccccatgaac agaaatcccc    3480
cttacacgga ggcatcagtg accaaacagg aaaaaaccgc ccttaacatg cccgctttta    3540
tcagaagcca gacattaacg cttctggaga aactcaacga gctggacgcg gatgaacagg    3600
cagacatctg tgaatcgctt cacgaccacg ctgatgagct ttaccgcagc tgcctcgcgc    3660
gtttcggtga tgacggtgaa aacctctgac acatgcagct cccggagacg gtcacagctt    3720
gtctgtaagc ggatgccggg agcagacaag cccgtcaggg cgcgtcagcg ggtgttggcg    3780
ggtgtcgggg cgcagccatg acccagtcac gtagcgatag cggagtgtat actggcttaa    3840
ctatgcggca tcagagcaga ttgtactgag agtgcaccat atatgcggtg tgaaataccg    3900
cacagatgcg taaggagaaa ataccgcatc aggcgctctt ccgcttcctc gctcactgac    3960
tcgctgcgct cggtcgttcg gctgcggcga gcggtatcag ctcactcaaa ggcggtaata    4020
cggttatcca cagaatcagg ggataacgca ggaaagaaca tgtgagcaaa aggccagcaa    4080
aaggccagga accgtaaaaa ggccgcgttg ctggcgtttt tccataggct ccgcccccct    4140
gacgagcatc acaaaaatcg acgctcaagt cagaggtggc gaaacccgac aggactataa    4200
agataccagg cgtttccccc tggaagctcc ctcgtgcgct ctcctgttcc gaccctgccg    4260
cttaccggat acctgtccgc ctttctccct tcgggaagcg tggcgctttc tcatagctca    4320
cgctgtaggt atctcagttc ggtgtaggtc gttcgctcca agctgggctg tgtgcacgaa    4380
ccccccgttc agcccgaccg ctgcgcctta tccggtaact atcgtcttga gtccaacccg    4440
gtaagacacg acttatcgcc actggcagca gccactggta acaggattag cagagcgagg    4500
tatgtaggcg gtgctacaga gttcttgaag tggtggccta actacggcta cactagaagg    4560
acagtatttg gtatctgcgc tctgctgaag ccagttacct tcggaaaaag agttggtagc    4620
tcttgatccg gcaaacaaac caccgctggt agcggtggtt tttttgtttg caagcagcag    4680
attacgcgca gaaaaaaagg atctcaagaa gatcctttga tcttttctac ggggtctgac    4740
gctcagtgga acgaaaactc acgttaaggg attttggtca tgaacaataa aactgtctgc    4800
ttacataaac agtaatacaa ggggtgttat gagccatatt caacgggaaa cgtcttgctc    4860
taggccgcga ttaaattcca acatggatgc tgatttatat gggtataaat gggctcgcga    4920
taatgtcggg caatcaggtg cgacaatcta tcgattgtat gggaagcccg atgcgccaga    4980
gttgtttctg aaacatggca aaggtagcgt tgccaatgat gttacagatg agatggtcag    5040
actaaactgg ctgacggaat ttatgcctct tccgaccatc aagcatttta tccgtactcc    5100
tgatgatgca tggttactca ccactgcgat ccccgggaaa acagcattcc aggtattaga    5160
agaatatcct gattcaggtg aaaatattgt tgatgcgctg gcagtgttcc tgcgccggtt    5220
gcattcgatt cctgtttgta attgtccttt taacagcgat cgcgtatttc gtctcgctca    5280
ggcgcaatca cgaatgaata acggtttggt tgatgcgagt gattttgatg acgagcgtaa    5340
tggctggcct gttgaacaag tctggaaaga atgcataaac ttttgccat ctcaccgga    5400
ttcagtcgtc actcatggtg atttctcact tgataacctt attttgacg aggggaaatt    5460
aataggttgt attgatgttg gacgagtcgg aatcgcagac cgataccagg atcttgccat    5520
cctatggaac tgcctcggtg agttttctcc ttcattacag aaacggcttt ttcaaaaata    5580
tggtattgat aatcctgata tgaataaatt gcagtttcat ttgatgctcg atgagttttt    5640
ctaagaatta attcatgagc ggatacatat ttgaatgtat ttagaaaaat aaacaaatag    5700
gggttccgcg cacatttccc cgaaaagtgc cacctgaaat tgtaaacgtt aatattttgt    5760
```

| | |
|---|---:|
| taaaattcgc gttaaatttt tgttaaatca gctcattttt taaccaatag gccgaaatcg | 5820 |
| gcaaaatccc ttataaatca aaagaataga ccgagatagg gttgagtgtt gttccagttt | 5880 |
| ggaacaagag tccactatta aagaacgtgg actccaacgt caagggcga aaaaccgtct | 5940 |
| atcagggcga tggcccacta cgtgaaccat caccctaatc aagttttttg gggtcgaggt | 6000 |
| gccgtaaagc actaaatcgg aaccctaaag ggagcccccg atttagagct tgacggggaa | 6060 |
| agccggcgaa cgtggcgaga aggaaggga agaaagcgaa aggagcgggc gctagggcgc | 6120 |
| tggcaagtgt agcggtcacg ctgcgcgtaa ccaccacacc cgccgcgctt aatgcgccgc | 6180 |
| tacagggcgc gtcccattcg cca | 6203 |

<210> SEQ ID NO 28
<211> LENGTH: 6197
<212> TYPE: DNA
<213> ORGANISM: Artificial Sequence
<220> FEATURE:
<223> OTHER INFORMATION: Synthetic Construct

<400> SEQUENCE: 28

| | |
|---|---:|
| atccggatat agttcctcct ttcagcaaaa aaccccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtcattaa tccaccttta | 180 |
| aaccctgctc cgtcggcttg gttatcgtta ctttaccgcc agcacctgca actgcttcgg | 240 |
| caacctgatt acatttttcc ggtgcagtaa gagctaccat acatccgccc ccaccggcac | 300 |
| ccgttatctt agcgccaaag gctcccgcag cgcgggctga ataaatcagc tgagacagct | 360 |
| ccaaaatgtt cacacccagc gcatccaaca ggccttgatt gacgttcatc agacgaccta | 420 |
| tagaagcata gtcaccactg agaacaagtt gttcgccaat ccggctgatc tttccaatgg | 480 |
| acgtcataag cggttcaata aggtctggat atgactctct caactggcga acattggcca | 540 |
| ccagctcttt ggttgaggaa atacccccg tgtcgccaat aacaatgcca caatccggtg | 600 |
| ttttgagttt tctacgctca ggtatcgtca ctacaccccc aaacgtgctc acataagtgt | 660 |
| ctgttggtga tgctgcacct tgcaccttga tttcaatctc gtgtcccaat ttcgcaattt | 720 |
| cctgtaaact aaggccgaat ccgaaaagct cgtttaacgc tccaatactc gcaattgtca | 780 |
| cagctgctga actgcccaac ccagaaccta caggtatgtc cgaatctaca gtaaggaaca | 840 |
| ctccgttgat tgggatagat ttgcgcatct tctcgattac tgccgagacg tacggatgtt | 900 |
| tttcgaagtc gagccctgta cggcctattt gagactgaat cgtgatgctg tcgttcagtt | 960 |
| cagcgcgaac tctagtacgc agttcgactg cacatgcgat ggcagtttca ccgtatacta | 1020 |
| ctgcatgctc accaaacaga tatatctttc cgggcgcaga gcagctcacc atgccctgga | 1080 |
| aatagaggtt ctcacctcca gctccatgat gatggtgatg gtgcatatgt atatctcctt | 1140 |
| cttaaagtta aacaaaatta tttctagagg ggaattgtta tccgctcaca attccctat | 1200 |
| agtgagtcgt attaatttcg cgggatcgag atctcgatcc tctacgccgg acgcatcgtg | 1260 |
| gccggcatca ccggcgccac aggtgcggtt gctggcgcct atatcgccga catcaccgat | 1320 |
| ggggaagatc gggctcgcca cttcgggctc atgagcgctt gtttcggcgt gggtatggtg | 1380 |
| gcaggccccg tggccggggg actgttgggc gccatctcct tgcatgcacc attccttgcg | 1440 |
| gcggcggtgc tcaacggcct caacctacta ctgggctgct tcctaatgca ggagtcgcat | 1500 |
| aagggagagc gtcgagatcc cggacaccat cgaatggcgc aaaaccttc gcggtatggc | 1560 |

```
atgatagcgc ccggaagaga gtcaattcag ggtggtgaat gtgaaaccag taacgttata   1620
cgatgtcgca gagtatgccg gtgtctctta tcagaccgtt tcccgcgtgg tgaaccaggc   1680
cagccacgtt tctgcgaaaa cgcgggaaaa agtggaagcg gcgatggcgg agctgaatta   1740
cattcccaac cgcgtggcac aacaactggc gggcaaacag tcgttgctga ttggcgttgc   1800
cacctccagt ctggccctgc acgcgccgtc gcaaattgtc gcggcgatta atctcgcgc    1860 cgatcaactg ggtgccagcg tggtggtgtc gatggtagaa cgaagcggcg tcgaagcctg   1920
taaagcggcg gtgcacaatc ttctcgcgca acgcgtcagt gggctgatca ttaactatcc   1980
gctggatgac caggatgcca ttgctgtgga agctgcctgc actaatgttc cggcgttatt   2040
tcttgatgtc tctgaccaga cacccatcaa cagtattatt ttctcccatg aagacggtac   2100
gcgactgggc gtggagcatc tggtcgcatt gggtcaccag caaatcgcgc tgttagcggg   2160
cccattaagt tctgtctcgg cgcgtctgcg tctggctggc tggcataaat atctcactcg   2220
caatcaaatt cagccgatag cggaacggga aggcgactgg agtgccatgt ccggttttca   2280
acaaaccatg caaatgctga atgagggcat cgttcccact gcgatgctgg ttgccaacga   2340
tcagatggcg ctgggcgcaa tgcgcgccat taccgagtcc gggctgcgcg ttggtgcgga   2400
tatctcggta gtgggatacg acgataccga agacagctca tgttatatcc cgccgttaac   2460
caccatcaaa caggattttc gcctgctggg gcaaaccagc gtggaccgct tgctgcaact   2520
ctctcagggc caggcggtga agggcaatca gctgttgccc gtctcactgg tgaaaagaaa   2580
aaccaccctg cgcgcccaata cgcaaaccgc ctctccccgc gcgttggccg attcattaat   2640
gcagctggca cgacaggttt cccgactgga aagcgggcag tgagcgcaac gcaattaatg   2700
taagttagct cactcattag gcaccgggat ctcgaccgat gcccttgaga gccttcaacc   2760
cagtcagctc cttccggtgg gcgcggggca tgactatcgt cgccgcactt atgactgtct   2820
tctttatcat gcaactcgta ggacaggtgc cggcagcgct ctgggtcatt tcggcgagg    2880 accgctttcg ctggagcgcg acgatgatcg gcctgtcgct tgcggtattc ggaatcttgc   2940
acgccctcgc tcaagccttc gtcactggtc ccgccaccaa acgtttcggc gagaagcagg   3000
ccattatcgc cggcatggcg gccccacggg tgcgcatgat cgtgctcctg tcgttgagga   3060
cccggctagg ctggcggggt tgccttactg gttagcagaa tgaatcaccg atacgcgagc   3120
gaacgtgaag cgactgctgc tgcaaaacgt ctgcgacctg agcaacaaca tgaatggtct   3180
tcggtttccg tgtttcgtaa agtctggaaa cgcggaagtc agcgccctgc accattatgt   3240
tccggatctg catcgcagga tgctgctggc taccctgtgg aacacctaca tctgtattaa   3300
cgaagcgctg gcattgaccc tgagtgattt ttctctggtc ccgccgcatc cataccgcca   3360
gttgtttacc ctcacaacgt tccagtaacc gggcatgttc atcatcagta acccgtatcg   3420
tgagcatcct ctctcgtttc atcggtatca ttaccccccat gaacagaaat ccccttaca   3480 cggaggcatc agtgaccaaa caggaaaaaa ccgcccttaa catggcccgc tttatcagaa   3540
gccagacatt aacgcttctg gagaaactca acgagctgga cgcggatgaa caggcagaca   3600
tctgtgaatc gcttcacgac cacgctgatg agctttaccg cagctgcctc gcgcgtttcg   3660
gtgatgacgg tgaaaacctc tgacacatgc agctcccgga gacggtcaca gcttgtctgt   3720
aagcggatgc cgggagcaga caagcccgtc agggcgcgtc agcgggtgtt ggcgggtgtc   3780
ggggcgcagc catgacccag tcacgtagcg atagcggagt gtatactggc ttaactatgc   3840
ggcatcagag cagattgtac tgagagtgca ccatatatgc ggtgtgaaat accgcacaga   3900
tgcgtaagga gaaaataccg catcaggcgc tcttccgctt cctcgctcac tgactcgctg   3960
```

```
cgctcggtcg ttcggctgcg gcgagcggta tcagctcact caaaggcggt aatacggtta    4020
tccacagaat cagggataa cgcaggaaag aacatgtgag caaaaggcca gcaaaaggcc    4080
aggaaccgta aaaaggccgc gttgctggcg tttttccata ggctccgccc ccctgacgag    4140
catcacaaaa atcgacgctc aagtcagagg tggcgaaacc cgacaggact ataaagatac    4200
caggcgtttc ccctggaag ctccctcgtg cgctctcctg ttccgaccct gccgcttacc    4260
ggatacctgt ccgcctttct cccttcggga agcgtggcgc tttctcatag ctcacgctgt    4320
aggtatctca gttcggtgta ggtcgttcgc tccaagctgg gctgtgtgca cgaaccccc    4380 gttcagcccg accgctgcgc cttatccggt aactatcgtc ttgagtccaa cccggtaaga    4440
cacgacttat cgccactggc agcagccact ggtaacagga ttagcagagc gaggtatgta    4500
ggcggtgcta cagagttctt gaagtggtgg cctaactacg gctacactag aaggacagta    4560
tttggtatct gcgctctgct gaagccagtt accttcggaa aaagagttgg tagctcttga    4620
tccggcaaac aaaccaccgc tggtagcggt ggttttttg tttgcaagca gcagattacg    4680
cgcagaaaaa aaggatctca agaagatcct ttgatctttt ctacggggtc tgacgctcag    4740
tggaacgaaa actcacgtta agggattttg gtcatgaaca ataaaactgt ctgcttacat    4800
aaacagtaat acaaggggtg ttatgagcca tattcaacgg gaaacgtctt gctctaggcc    4860
gcgattaaat tccaacatgg atgctgattt atatgggtat aaatgggctc gcgataatgt    4920
cgggcaatca ggtgcgacaa tctatcgatt gtatgggaag cccgatgcgc cagagttgtt    4980
tctgaaacat ggcaaaggta gcgttgccaa tgatgttaca gatgagatgg tcagactaaa    5040
ctggctgacg gaatttatgc ctcttccgac catcaagcat tttatccgta ctcctgatga    5100
tgcatggtta ctcaccactg cgatccccgg gaaaacagca ttccaggtat tagaagaata    5160
tcctgattca ggtgaaaata ttgttgatgc gctggcagtg ttcctgcgcc ggttgcattc    5220
gattcctgtt tgtaattgtc ctttttaacag cgatcgcgta tttcgtctcg ctcaggcgca    5280
atcacgaatg aataacggtt tggttgatgc gagtgatttt gatgacgagc gtaatggctg    5340
gcctgttgaa caagtctgga agaaaatgca taaactttg ccattctcac cggattcagt    5400
cgtcactcat ggtgatttct cacttgataa ccttattttt gacgagggga aattaatagg    5460
ttgtattgat gttggacgag tcggaatcgc agaccgatac caggatcttg ccatcctatg    5520
gaactgcctc ggtgagtttt ctccttcatt acagaaacgg cttttttcaaa aatatggtat    5580 tgataatcct gatatgaata aattgcagtt tcatttgatg ctcgatgagt ttttctaaga    5640
attaattcat gagcggatac atatttgaat gtatttagaa aaataaacaa ataggggttc    5700
cgcgcacatt tccccgaaaa gtgccacctg aaattgtaaa cgttaatatt tgttaaaat    5760 tcgcgttaaa ttttgttaa atcagctcat ttttaacca ataggccgaa atcggcaaaa    5820
tcccttataa atcaaaagaa tagaccgaga tagggttgag tgttgttcca gtttggaaca    5880
agagtccact attaaagaac gtggactcca acgtcaaagg gcgaaaaacc gtctatcagg    5940
gcgatggccc actacgtgaa ccatcaccct aatcaagttt tttggggtcg aggtgccgta    6000
aagcactaaa tcggaaccct aaagggagcc cccgatttag agcttgacgg ggaaagccgg    6060
cgaacgtggc gagaaaggaa gggaagaaag cgaaaggagc gggcgctagg gcgctggcaa    6120
gtgtagcggt cacgctgcgc gtaaccacca cacccgccgc gcttaatgcg ccgctacagg    6180
gcgcgtccca ttcgcca                                                  6197
```

<210> SEQ ID NO 29

<211> LENGTH: 2609
<212> TYPE: DNA
<213> ORGANISM: Artificial Sequence
<220> FEATURE:
<223> OTHER INFORMATION: Synthetic Construct

<400> SEQUENCE: 29

| | | | | | |
|---|---|---|---|---|---|
| aaagtagccg | aagatgacgg | tttgtcacat | ggagttggca | ggatgtttga | ttaaaagcaa | 60 |
| ttaaccctca | ctaaagggcg | gccgcgaagt | tcctattctc | tagaaagtat | aggaacttca | 120 |
| ttctaccggg | taggggaggc | gcttttccca | aggcagtctg | gagcatgcgc | tttagcagcc | 180 |
| ccgctgggca | cttggcgcta | cacaagtggc | ctctggcctc | gcacacattc | acatccacc | 240 |
| ggtaggcgcc | aaccggctcc | gttctttggt | ggcccttcg | cgccaccttc | cactcctccc | 300 |
| ctagtcagga | agttcccccc | cgccccgcag | ctcgcgtcgt | gcaggacgtg | acaaatggaa | 360 |
| gtagcacgtc | tcactagtct | cgtgcagatg | gacagcaccg | ctgagcaatg | gaagcgggta | 420 |
| ggcctttggg | gcagcggcca | atagcagctt | tgctccttcg | ctttctgggc | tcagaggctg | 480 |
| ggaaggggtg | ggtccggggg | cgggctcagg | ggcgggctca | ggggcggggc | gggcgcccga | 540 |
| aggtcctccg | gaggcccggc | attctgcacg | cttcaaaagc | gcacgtctgc | cgcgctgttc | 600 |
| tcctcttcct | catctccggg | cctttcgacc | tgcagcagca | cgtgttgaca | attaatcatc | 660 |
| ggcatagtat | atcggcatag | tataatacga | caaggtgagg | aactaaacca | tggagaaaaa | 720 |
| aatcactgga | tataccaccg | ttgatatatc | ccaatggcat | cgtaaagaac | attttgaggc | 780 |
| atttcagtca | gttgctcaat | gtacctataa | ccagaccgtt | cagctggata | ttacggcctt | 840 |
| tttaaagacc | gtaaagaaaa | ataagcacaa | gttttatccg | gcctttattc | acattcttgc | 900 |
| ccgcctgatg | aatgctcatc | cggaattccg | tatggcaatg | aaagacggtg | agctggtgat | 960 |
| atgggatagt | gttcacccc tt | gttacaccgt | tttccatgag | caaactgaaa | cgttttcatc | 1020 |
| gctctggagt | gaataccacg | acgatttccg | gcagtttcta | cacatatatt | cgcaagatgt | 1080 |
| ggcgtgttac | ggtgaaaacc | tggcctattt | ccctaaaggg | tttattgaga | atatgttttt | 1140 |
| cgtctcagcc | aatccctggg | tgagtttcac | cagttttgat | ttaaacgtgg | ccaatatgga | 1200 |
| caacttcttc | gccccgttt | tcaccatggg | caaatattat | acgcaaggcg | acaaggtgct | 1260 |
| gatgccgctg | gcgattcagg | ttcatcatgc | cgtttgtgat | ggcttccatg | tcggcagaat | 1320 |
| gcttaatgaa | ttacaacagt | actgcgatga | gtggcagggc | ggggcgtaag | cgggactctg | 1380 |
| gggttcgaat | aaagaccgac | caagcgacgt | ctgagagctc | cctggcgaat | tcggtaccaa | 1440 |
| taaaagagct | ttatttttcat | gatctgtgtg | ttggttttg | tgtgcggcgc | ggaagttcct | 1500 |
| attctctaga | aagtatagga | acttcctcga | gccctatagt | gagtcgtatt | aagataacca | 1560 |
| tctgcggtga | taaattatct | ctggcggtgt | tgacgtaaat | accactggcg | gtgatactga | 1620 |
| gcacatcagc | aggacgcact | gctctaagga | ttaaagagga | gaagatttcc | tgatgtatcg | 1680 |
| atttaaataa | ggaggaataa | catatggtat | cctgttctgc | gccgggtaag | atttacctgt | 1740 |
| tcggtgaaca | cgccgtagtt | tatggcgaaa | ctgcaattgc | gtgtgcggtg | gaactgcgta | 1800 |
| cccgtgttcg | cgcggaactc | aatgactcta | tcactattca | gagccagatc | ggccgcaccg | 1860 |
| gtctggattt | cgaaaagcac | ccttatgtgt | ctgcggtaat | tgagaaaatg | cgcaaatcta | 1920 |
| ttcctattaa | cggtgttttc | ttgaccgtcg | attccgacat | cccggtgggc | tccggtctgg | 1980 |
| gtagcagcgc | agccgttact | atcgcgtcta | ttggtgcgct | gaacgagctg | ttcggctttg | 2040 |
| gcctcagcct | gcaagaaatc | gctaaactgg | gccacgaaat | cgaaattaaa | gtacagggtg | 2100 |
| ccgcgtcccc | aaccgatacg | tatgtttcta | ccttcggcgg | cgtggttacc | atcccggaac | 2160 |

```
gtcgcaaact gaaaactccg gactgcggca ttgtgattgg cgataccggc gttttctcct    2220
ccaccaaaga gttagtagct aacgtacgtc agctgcgcga aagctacccg gatttgatcg    2280
aaccgctgat gacctctatt ggcaaaatct ctcgtatcgg cgaacaactg gttctgtctg    2340
gcgactacgc atccatcggc cgcctgatga acgtcaacca gggtctcctg gacgccctgg    2400
gcgttaacat cttagaactg agccagctga tctattccgc tcgtgcggca ggtgcgtttg    2460
gcgctaaaat cacgggcgct ggcggcggtg gctgtatggt tgcgctgacc gctccggaaa    2520
aatgcaacca agtggcagaa gcggtagcag cgctggcgg taaagtgact atcactaaac    2580
cgaccgagca aggtctgaaa gtagattaa                                      2609
```

<210> SEQ ID NO 30
<211> LENGTH: 2606
<212> TYPE: DNA
<213> ORGANISM: Artificial Sequence
<220> FEATURE:
<223> OTHER INFORMATION: Synthetic Construct

<400> SEQUENCE: 30

```
aaagtagccg aagatgacgg tttgtcacat ggagttggca ggatgtttga ttaaaagcaa      60
ttaaccctca ctaaagggcg gccgcgaagt tcctattctc tagaaagtat aggaacttca     120
ttctaccggg taggggaggc gcttttccca aggcagtctg gagcatgcgc tttagcagcc     180
ccgctgggca cttggcgcta cacaagtggc ctctggcctc gcacacattc cacatccacc     240
ggtaggcgcc aaccggctcc gttctttggt ggccccttcg cgccaccttc cactcctccc     300
ctagtcagga agttccccc cgccccgcag ctcgcgtcgt gcaggacgtg acaaatggaa     360
gtagcacgtc tcactagtct cgtgcagatg acagcaccg ctgagcaatg gaagcgggta     420
ggcctttggg gcagcggcca atagcagctt tgctccttcg ctttctgggc tcagaggctg     480
ggaaggggtg gtccgggg cgggctcagg ggcgggctca ggggcgggc gggcgcccga     540 aggtcctccg gaggcccggc attctgcacg cttcaaaagc gcacgtctgc cgcgctgttc     600
tcctcttcct catctccggg cctttcgacc tgcagcagca cgtgttgaca attaatcatc     660
ggcatagtat atcggcatag tataatacga caaggtgagg aactaaacca tggagaaaaa     720 atcactgga taccaccg ttgatatatc ccaatggcat cgtaaagaac attttgaggc     780
atttcagtca gttgctcaat gtacctataa ccagaccgtt cagctggata ttacggcctt     840
tttaaagacc gtaaagaaaa ataagcacaa gttttatccg gcctttattc acattcttgc     900
ccgcctgatg aatgctcatc cggaattccg tatggcaatg aaagacggtg agctggtgat     960
atgggatagt gttcacccct tgttacaccg ttttccatgag caaactgaaa cgttttcatc    1020
gctctggagt gaataccacg acgatttccg gcagtttcta cacatatatt cgcaagatgt    1080
ggcgtgttac ggtgaaaacc tggcctattt ccctaaaggg tttattgaga atatgttttt    1140
cgtctcagcc aatccctggg tgagtttcac cagttttgat ttaaacgtgg ccaatatgga    1200
caacttcttc gcccccgttt tcaccatggg caaatattat acgcaaggcg acaaggtgct    1260
gatgccgctg gcgattcagg ttcatcatgc cgtttgtgat ggcttccatg tcggcagaat    1320
gcttaatgaa ttacaacagt actgcgatga gtggcagggc ggggcgtaag cgggactctg    1380
gggttcgaat aaagaccgac caagcgacgt ctgagagctc cctggcgaat tcggtaccaa    1440
taaaagagct ttattttcat gatctgtgtg ttggttttg tgtgcggcgc ggaagttcct    1500
attctctaga aagtatagga acttcctcga gccctatagt gagtcgtatt aagataacca    1560
```

| | |
|---|---|
| tctgcggtga taaattatct ctggcggtgt tgacgtaaat accactggcg gtgatactga | 1620 |
| gcacatcagc aggacgcact gctctagagc gcactaagga ggcaactgga tgtatcgatt | 1680 |
| taaataagga ggaataacat atggtatcct gttctgcgcc gggtaagatt tacctgttcg | 1740 |
| gtgaacacgc cgtagtttat ggcgaaactg caattgcgtg tgcggtggaa ctgcgtaccc | 1800 |
| gtgttcgcgc ggaactcaat gactctatca ctattcagag ccagatcggc cgcaccggtc | 1860 |
| tggatttcga aaagcaccct tatgtgtctg cggtaattga gaaaatgcgc aaatctattc | 1920 |
| ctattaacgg tgttttcttg accgtcgatt ccgacatccc ggtgggctcc ggtctgggta | 1980 |
| gcagcgcagc cgttactatc gcgtctattg gtgcgctgaa cgagctgttc ggctttggcc | 2040 |
| tcagcctgca agaaatcgct aaactgggcc acgaaatcga attaaagta cagggtgccg | 2100 |
| cgtccccaac cgatacgtat gtttctacct tcggcggcgt ggttaccatc ccggaacgtc | 2160 |
| gcaaactgaa aactccggac tgcggcattg tgattggcga taccggcgtt ttctcctcca | 2220 |
| ccaaagagtt agtagctaac gtacgtcagc tgcgcgaaag ctaccggat tgatcgaac | 2280 |
| cgctgatgac ctctattggc aaaatctctc gtatcggcga caactggtt ctgtctggcg | 2340 |
| actacgcatc catcggccgc ctgatgaacg tcaaccaggg tctcctggac gccctgggcg | 2400 |
| ttaacatctt agaactgagc cagctgatct attccgctcg tgcggcaggt gcgtttggcg | 2460 |
| ctaaaatcac gggcgctggc ggcggtggct gtatggttgc gctgaccgct ccggaaaaat | 2520 |
| gcaaccaagt ggcagaagcg gtagcaggcg ctggcggtaa agtgactatc actaaaccga | 2580 |
| ccgagcaagg tctgaaagta gattaa | 2606 |

<210> SEQ ID NO 31
<211> LENGTH: 2604
<212> TYPE: DNA
<213> ORGANISM: Artificial Sequence
<220> FEATURE:
<223> OTHER INFORMATION: Synthetic Construct

<400> SEQUENCE: 31

| | |
|---|---|
| aaagtagccg aagatgacgg tttgtcacat ggagttggca ggatgtttga ttaaaagcaa | 60 |
| ttaaccctca ctaaagggcg ccgcgaagt tcctattctc tagaaagtat aggaacttca | 120 |
| ttctaccggg taggggaggc gcttttccca aggcagtctg gagcatgcgc tttagcagcc | 180 |
| ccgctgggca cttggcgcta cacaagtggc ctctggcctc gcacacattc acatccacc | 240 |
| ggtaggcgcc aaccggctcc gttctttggt ggcccctttcg cgccaccttc cactcctccc | 300 |
| ctagtcagga agttccccccc cgccccgcag ctcgcgtcgt gcaggacgtg acaaatggaa | 360 |
| gtagcacgtc tcactagtct cgtgcagatg gacagcaccg ctgagcaatg gaagcgggta | 420 |
| ggcctttggg gcagcggcca atagcagctt tgctccttcg ctttctgggc tcagaggctg | 480 |
| ggaaggggtg ggtccggggg cgggctcagg ggcgggctca gggcggggc gggcgcccga | 540 |
| aggtcctccg gaggcccggc attctgcacg cttcaaaagc gcacgtctgc cgcgctgttc | 600 |
| tcctcttcct catctccggg cctttcgacc tgcagcagca cgtgttgaca attaatcatc | 660 |
| ggcatagtat atcggcatag tataatacga caaggtgagg aactaaacca tggagaaaaa | 720 |
| aatcactgga tataccaccg ttgatatatc ccaatggcat cgtaaagaac attttgaggc | 780 |
| atttcagtca gttgctcaat gtacctataa ccagaccgtt cagctggata ttacggcctt | 840 |
| tttaaagacc gtaaagaaaa ataagcacaa gttttatccg gcctttattc acattcttgc | 900 |
| ccgcctgatg aatgctcatc cggaattccg tatggcaatg aaagacgtg agctggtgat | 960 |
| atgggatagt gttcacccct tgttacaccgt tttccatgag caaactgaaa cgttttcatc | 1020 |

```
gctctggagt gaataccacg acgatttccg gcagtttcta cacatatatt cgcaagatgt    1080
ggcgtgttac ggtgaaaacc tggcctattt ccctaaaggg tttattgaga atatgttttt    1140
cgtctcagcc aatccctggg tgagtttcac cagtttgat ttaaacgtgg ccaatatgga    1200
caacttcttc gcccccgttt tcaccatggg caaatattat acgcaaggcg acaaggtgct    1260
gatgccgctg gcgattcagg ttcatcatgc cgtttgtgat ggcttccatg tcggcagaat    1320
gcttaatgaa ttcaacagt actgcgatga gtggcagggc ggggcgtaag cgggactctg    1380
gggttcgaat aaagaccgac caagcgacgt ctgagagctc cctggcgaat tcggtaccaa    1440
taaaagagct ttattttcat gatctgtgtg ttggttttg tgtgcggcgc ggaagttcct    1500
attctctaga aagtatagga acttcctcga gccctatagt gagtcgtatt aagataacca    1560
tctgcggtga taaattatct ctggcggtgt tgacgtaaat accactggcg gtgatactga    1620
gcacatcagc aggacgcact gctctagaga aagagccgaa atactagatg tatcgattta    1680
aataaggagg aataacatat ggtatcctgt tctgcgccgg gtaagattta cctgttcggt    1740
gaacacgccg tagtttatgg cgaaactgca attgcgtgtg cggtggaact gcgtacccgt    1800
gttcgcgcgg aactcaatga ctctatcact attcagagcc agatcggccg caccggtctg    1860
gatttcgaaa agcacccta tgtgtctgcg gtaattgaga aaatgcgcaa atctattcct    1920
attaacggtt ttttcttgac cgtcgattcc gacatcccgg tgggctccgg tctgggtagc    1980
agcgcagccg ttactatcgc gtctattggt gcgctgaacg agctgttcgg ctttggcctc    2040
agcctgcaag aaatcgctaa actgggccac gaaatcgaaa ttaaagtaca gggtgccgcg    2100
tccccaaccg atacgtatgt ttctaccttc ggcggcgtgg ttaccatccc ggaacgtcgc    2160
aaactgaaaa ctccggactg cggcattgtg attggcgata ccggcgtttt ctcctccacc    2220
aaagagttag tagctaacgt acgtcagctg cgcgaaagct acccggattt gatcgaaccg    2280
ctgatgacct ctattggcaa aatctctcgt atcggcgaac aactggttct gtctggcgac    2340
tacgcatcca tcggccgcct gatgaacgtc aaccagggtc tcctggacgc cctgggcgtt    2400
aacatcttag aactgagcca gctgatctat tccgctcgtg cggcaggtgc gtttggcgct    2460
aaaatcacgg gcgctggcgg cggtggctgt atggttgcgc tgaccgctcc ggaaaaatgc    2520
aaccaagtgg cagaagcggt agcaggcgct ggcggtaaag tgactatcac taaaccgacc    2580
gagcaaggtc tgaaagtaga ttaa                                          2604

<210> SEQ ID NO 32
<211> LENGTH: 2607
<212> TYPE: DNA
<213> ORGANISM: Artificial Sequence
<220> FEATURE:
<223> OTHER INFORMATION: Synthetic Construct

<400> SEQUENCE: 32
aaagtagccg aagatgacgg tttgtcacat ggagttggca ggatgtttga ttaaaagcaa      60
ttaaccctca ctaaagggcg gccgcgaagt tcctattctc tagaaagtat aggaacttca     120
ttctaccggg taggggaggc gcttttccca aggcagtctg gagcatgcgc tttagcagcc     180
ccgctgggca cttggcgcta cacaagtggc ctctggcctc gcacacattc cacatccacc     240
ggtaggcgcc aaccggctcc gttctttggt ggccccttcg cgccaccttc cactcctccc     300
ctagtcagga agttccccc cgccccgcag ctcgcgtcgt gcaggacgtg acaaatggaa     360
gtagcacgtc tcactagtct cgtgcagatg gacagcaccg ctgagcaatg gaagcgggta     420
```

```
ggcctttggg gcagcggcca atagcagctt tgctccttcg ctttctgggc tcagaggctg    480
ggaaggggtg ggtccggggg cgggctcagg ggcgggctca ggggcgggc gggcgcccga    540 aggtcctccg gaggcccggc attctgcacg cttcaaaagc gcacgtctgc cgcgctgttc    600
tcctcttcct catctccggg cctttcgacc tgcagcagca cgtgttgaca attaatcatc    660
ggcatagtat atcggcatag tataatacga caaggtgagg aactaaacca tggagaaaaa    720
aatcactgga tataccaccg ttgatatatc ccaatggcat cgtaaagaac attttgaggc    780
atttcagtca gttgctcaat gtacctataa ccagaccgtt cagctggata ttacggcctt    840
tttaaagacc gtaaagaaaa ataagcacaa gttttatccg gcctttattc acattcttgc    900
ccgcctgatg aatgctcatc cggaattccg tatggcaatg aaagacggtg agctggtgat    960
atgggatagt gttcacccct tgtacaccgt tttccatgag caaactgaaa cgttttcatc   1020
gctctggagt gaataccacg acgatttccg gcagtttcta cacatatatt cgcaagatgt   1080
ggcgtgttac ggtgaaaacc tggcctattt ccctaaaggg tttattgaga atatgttttt   1140
cgtctcagcc aatccctggg tgagtttcac cagttttgat ttaaacgtgg ccaatatgga   1200
caacttcttc gcccccgttt tcaccatggg caaatattat acgcaaggcg acaaggtgct   1260
gatgccgctg gcgattcagg ttcatcatgc cgtttgtgat ggcttccatg tcggcagaat   1320
gcttaatgaa ttacaacagt actgcgatga gtggcagggc ggggcgtaag cgggactctg   1380
gggttcgaat aaagaccgac caagcgacgt ctgagagctc cctggcgaat tcggtaccaa   1440
taaaagagct ttattttcat gatctgtgtg ttggtttttg tgtgcggcgc ggaagttcct   1500
attctctaga agtataggaa cttcctcga gccctatagt gagtcgtatt aagataacca   1560
tctgcggtga taaattatct ctggcggtgt tgacgtaaat accactggcg gtgatactga   1620
gcacatcagc aggacgcact gctcctaggg gcgattaggg gacctactac atgtatcgat   1680
ttaaataagg aggaataaca tatggtatcc tgttctgcgc cgggtaagat ttacctgttc   1740
ggtgaacacg ccgtagttta tggcgaaact gcaattgcgt gtgcggtgga actgcgtacc   1800
cgtgttcgcg cggaactcaa tgactctatc actattcaga gccagatcgg ccgcaccggt   1860
ctggatttcg aaaagcaccc ttatgtgtct gcggtaattg agaaaatgcg caaatctatt   1920
cctattaacg gtgttttctt gaccgtcgat tccgacatcc cggtgggctc cggtctgggt   1980
agcagcgcag ccgttactat cgcgtctatt ggtgcgctga cgagctgtt cggctttggc   2040 ctcagcctgc aagaaatcgc taaactgggc cacgaaatcg aaattaaagt acagggtgcc   2100
gcgtccccaa ccgatacgta tgtttctacc ttcggcggcg tggttaccat cccgaacgt    2160 cgcaaactga aaactccgga ctgcggcatt gtgattggcg ataccggcgt tttctcctcc   2220
accaaagagt tagtagctaa cgtacgtcag ctgcgcgaaa gctacccgga tttgatcgaa   2280
ccgctgatga cctctattgg caaaatctct cgtatcggcg aacaactggt tctgtctggc   2340
gactacgcat ccatcggccg cctgatgaac gtcaaccagg gtctcctgga cgccctgggc   2400
gttaacatct agaactgag ccagctgatc tattccgctc gtgcggcagg tgcgtttggc   2460
gctaaaatca cgggcgctgg cggcggtggc tgtatggttg cgctgaccgc tccggaaaaa   2520
tgcaaccaag tggcagaagc ggtagcaggc gctggcggta aagtgactat cactaaaccg   2580
accgagcaag gtctgaaagt agattaa                                      2607
```

<210> SEQ ID NO 33
<211> LENGTH: 2673
<212> TYPE: DNA
<213> ORGANISM: Artificial Sequence
<220> FEATURE:
<223> OTHER INFORMATION: Synthetic Construct

<400> SEQUENCE: 33

| | | | | |
|---|---|---|---|---|
| aaagtagccg | aagatgacgg | tttgtcacat | ggagttggca | ggatgtttga ttaaaagcaa | 60 |
| ttaaccctca | ctaaagggcg | gccgcgaagt | tcctattctc | tagaaagtat aggaacttca | 120 |
| ttctaccggg | tagggaggc | gcttttccca | aggcagtctg | gagcatgcgc tttagcagcc | 180 |
| ccgctgggca | cttggcgcta | cacaagtggc | ctctggcctc | gcacacattc acatccacc | 240 |
| ggtaggcgcc | aaccggctcc | gttctttggt | ggcccttcg | cgccaccttc cactcctccc | 300 |
| ctagtcagga | agttcccccc | cgccccgcag | ctcgcgtcgt | gcaggacgtg acaaatggaa | 360 |
| gtagcacgtc | tcactagtct | cgtgcagatg | gacagcaccg | ctgagcaatg aagcgggta | 420 |
| ggcctttggg | gcagcggcca | atagcagctt | tgctccttcg | ctttctgggc tcagaggctg | 480 |
| ggaaggggtg | ggtccggggg | cgggctcagg | ggcgggctca | ggggcggggc gggcgcccga | 540 |
| aggtcctccg | gaggcccggc | attctgcacg | cttcaaaagc | gcacgtctgc cgcgctgttc | 600 |
| tcctcttcct | catctccggg | cctttcgacc | tgcagcagca | cgtgttgaca attaatcatc | 660 |
| ggcatagtat | atcggcatag | tataatacga | caaggtgagg | aactaaacca tggagaaaaa | 720 |
| aatcactgga | tataccaccg | ttgatatatc | ccaatggcat | cgtaaagaac attttgaggc | 780 |
| atttcagtca | gttgctcaat | gtacctataa | ccagaccgtt | cagctggata ttacggcctt | 840 |
| tttaaagacc | gtaaagaaaa | ataagcacaa | gttttatccg | gcctttattc acattcttgc | 900 |
| ccgcctgatg | aatgctcatc | cggaattccg | tatggcaatg | aaagacggtg agctggtgat | 960 |
| atgggatagt | gttcaccctt | gttacaccgt | tttccatgag | caaactgaaa cgttttcatc | 1020 |
| gctctggagt | gaataccacg | acgatttccg | gcagtttcta | cacatatatt cgcaagatgt | 1080 |
| ggcgtgttac | ggtgaaaacc | tggcctattt | ccctaaaggg | tttattgaga atatgttttt | 1140 |
| cgtctcagcc | aatccctggg | tgagtttcac | cagttttgat | ttaaacgtgg ccaatatgga | 1200 |
| caacttcttc | gccccgtttt | tcaccatggg | caaatattat | acgcaaggcg acaaggtgct | 1260 |
| gatgccgctg | gcgattcagg | ttcatcatgc | cgtttgtgat | ggcttccatg tcggcagaat | 1320 |
| gcttaatgaa | ttacaacagt | actgcgatga | gtggcagggc | ggggcgtaag cgggactctg | 1380 |
| gggttcgaat | aaagaccgac | caagcgacgt | ctgagagctc | cctggcgaat tcggtaccaa | 1440 |
| taaaagagct | ttattttcat | gatctgtgtg | ttggttttg | tgtgcggcgc ggaagttcct | 1500 |
| attctctaga | aagtatagga | acttcctcga | gccctatagt | gagtcgtatt aagataacca | 1560 |
| tctgcggtga | taaattatct | ctggcggtgt | tgacgtaaat | accactggcg gtgatactga | 1620 |
| gcacatcagc | aggacgcact | gctcctaggg | gcgattaggg | gacctactac atgtatcgat | 1680 |
| ttaataagg | aggaataaca | tatgataacg | tgctctgcgc | cgggcaaagt atatctcttc | 1740 |
| ggcgaacatg | cagttgtata | cggagagccg | gcgatatgct | gtgcggtcga tattagaacg | 1800 |
| cgcgtgacag | tctctcctgc | cgataccata | actatctctt | caagtctcgg cacaacgggg | 1860 |
| atcgatttcg | aggttcatcc | ctatgtgtcg | gccgtgttgg | agcgtttcca ggatatttca | 1920 |
| tcttttgacg | gggtagatct | gagaataagc | tccgacatac | cggtgggatc cggtcttggc | 1980 |
| tcatccgccg | cagtaacggt | ggcgactata | aaggctatga | tacactgct tgacctgggg | 2040 |
| ctggagttag | acgatatcgc | taagatgggc | catgaggttg | aacaaaacat tcagggcacg | 2100 |
| gcttctccta | cggacactta | tgtgtgtacc | atgggaggtg | tcgtcctgat accccagcgg | 2160 |
| aaaaagttag | agctgataga | ctgcgggatt | ttgatcggta | acaccaatat attctcgtcc | 2220 |

```
acgaaggagt tggtgggtaa tgtagcggat ctgaacgaac ggttccccga tgttgtaggt      2280
ccagttctta gttctattgg gaaactgagt gtaatcggag agggcttagt caatgaccgg      2340
gattacgtta gcgtggggga actgatgaac atcgaccagg gtctgttaga tgcaataggt      2400
gtttcctgtg cagaactgtc aagtctgatt tacgccgccc gtgaatcagg cgcttatggg      2460
tctaagatta caggagcggg tggaggggga tgtatggttg ctatcagtcc gcgtgaaaat      2520
gtggatagcg tcgctgaagc aatagggatg gccggtggca aggtggtggt tgcaaacgca      2580
acagatatcg gtgttcgcgt agaatgtcag taagctaatt tgcgataggc ctgcacccct      2640
aaggaggaaa aaacatgtc agagttgaga gcc                                   2673
```

<210> SEQ ID NO 34
<211> LENGTH: 6864
<212> TYPE: DNA
<213> ORGANISM: Artificial Sequence
<220> FEATURE:
<223> OTHER INFORMATION: Synthetic Construct

<400> SEQUENCE: 34

```
gtttgacagc ttatcatcga ctgcacggtg caccaatgct tctggcgtca ggcagccatc        60
ggaagctgtg gtatggctgt gcaggtcgta aatcactgca taattcgtgt cgctcaaggc       120
gcactcccgt tctggataat gttttttgcg ccgacatcat aacggttctg gcaaatattc       180
tgaaatgagc tgttgacaat taatcatccg gctcgtataa tgtgtggaat tgtgagcgga       240
taacaatttc acacaggaaa cagcgccgct gagaaaaagc gaagcggcac tgctctttaa       300
caatttatca gacaatctgt gtgggcactc gaccggaatt atcgattaac tttattatta       360
aaaattaaag aggtatatat taatgtatcg attaaataag gaggaataaa ccatggaaac       420
gcgtcgttct gcgaactacg aacctaacag ctgggactat gattacctgc tgtcctccga       480
cacggacgag tccatcgaag tatacaaaga caaagcgaaa aagctggaag ccgaagttcg       540
tcgcgagatt aataacgaaa aagcagaatt tctgaccctg ctggaactga ttgacaacgt       600
ccagcgcctg ggcctgggtt accgtttcga gtctgatatc cgtggtgcgc tggatcgctt       660
cgtttcctcc ggcggcttcg atgcggtaac caagacttcc ctgcacggta cggcactgtc       720
tttccgtctg ctgcgtcaac acggttttga ggtttctcag gaagcgttca gcggcttcaa       780
agaccaaaac ggcaacttcc tggagaacct gaaggaagat atcaaagcta tcctgagcct       840
gtacgaggcc agcttcctgg ctctggaagg cgaaaacatc ctggacgagg cgaaggtttt       900
cgcaatctct catctgaaag aactgtctga agaaaagatc ggtaaagagc tggcagaaca       960
ggtgaaccat gcactggaac tgccactgca tcgccgtact cagcgtctgg aagcagtatg      1020
gtctatcgag gcctaccgta aaaggagga gcgcgaatcag gttctgctgg agctggcaat      1080
tctggattac aacatgatcc agtctgtata ccagcgtgat ctgcgtgaaa cgtcccgttg      1140
gtggcgtcgt gtgggtctgg cgaccaaact gcactttgct cgtgaccgcc tgattgagag      1200
cttctactgg gccgtgggtg tagcattcga accgcaatac tccgactgcc gtaactccgt      1260
cgcaaaaatg ttttgtttcg taaccattat cgacgatatc tacgatgtat acggcacccct     1320 ggacgaactg gagctgttta ctgatgcagt tgagcgttgg gacgtaaacg ccatcaacga      1380
cctgccggat tacatgaaac tgtgctttct ggctctgtat aacactatta cgaaatcgc      1440 ctacgacaac ctgaaagata aggtgagaa catcctgccg tatctgacca agcctgggc      1500 tgacctgtgc aacgctttcc tgcaagaagc caagtggctg tacaacaaat ctactccgac      1560
ctttgacgac tacttcggca acgcatggaa atcctcttct ggcccgctgc aactggtgtt      1620
```

```
cgcttacttc gctgtcgtgc agaacattaa aaaggaagag atcgaaaacc tgcaaaaata  1680
ccatgacacc atctctcgtc cttcccatat cttccgtctg tgcaatgacc tggctagcgc  1740
gtctgcggaa attgcgcgtg gtgaaaccgc aaatagcgtt tcttgttaca tgcgcactaa  1800
aggtatctcc gaagaactgg ctaccgaaag cgtgatgaat ctgatcgatg aaacctggaa  1860
aaagatgaac aaggaaaaac tgggtggtag cctgttcgcg aaaccgttcg tggaaaccgc  1920
gatcaacctg gcacgtcaat ctcactgcac ttatcataac ggcgacgcgc atacctctcc  1980
ggatgagctg acccgcaaac gcgttctgtc tgtaatcact gaaccgattc tgccgtttga  2040
acgctaactg cataaaggag gtaaaaaaac atgataacgt gctctgcgcc gggcaaagta  2100
tatctcttcg gcgaacatgc agttgtatac ggagagccgg cgatatgctg tgcggtcgat  2160
attagaacgc gcgtgacagt ctctcctgcc gataccataa ctatctcttc aagtctcggc  2220
acaacgggga tcgatttcga ggttcatccc tatgtgtcgg ccgtgttgga gcgtttccag  2280
gatatttcat cttttgacgg ggtagatctg agaataagct ccgacatacc ggtgggatcc  2340
ggtcttggct catccgccgc agtaacggtg gcgactataa aggctatgga tacactgctt  2400
gacctggggc tggagttaga cgatatcgct aagatgggcc atgaggttga acaaaacatt  2460
cagggcacgg cttctcctac ggacacttat gtgtgtacca tgggaggtgt cgtcctgata  2520
ccccagcgga aaaagttaga gctgatagac tgcgggattt tgatcggtaa caccaatata  2580
ttctcgtcca cgaaggagtt ggtgggtaat gtagcggatc tgaacgaacg gttccccgat  2640
gttgtaggtc cagttcttag ttctattggg aaactgagtg taatcggaga gggcttagtc  2700
aatgaccggg attacgttag cgtgggggaa ctgatgaaca tcgaccaggg tctgttagat  2760
gcaataggtg tttcctgtgc agaactgtca agtctgattt acgccgcccg tgaatcaggc  2820
gcttatgggt ctaagattac aggagcgggt ggaggggggat gtatggttgc tatcagtccg  2880
cgtgaaaatg tggatagcgt cgctgaagca atagggatgg ccggtggcaa ggtggtggtt  2940
gcaaacgcaa cagatatcgg tgttcgcgta gaatgtcagt aaagtctagt taaagtttaa  3000
acggtctcca gcttggctgt tttggcggat gagagaagat tttcagcctg atacagatta  3060
aatcagaacg cagaagcggt ctgataaaac agaatttgcc tggcggcagt agcgcggtgg  3120
tcccacctga ccccatgccg aactcagaag tgaaacgccg tagcgccgat ggtagtgtgg  3180
ggtctcccca tgcgagagta gggaactgcc aggcatcaaa taaaacgaaa ggctcagtcg  3240
aaagactggg cctttcgttt tatctgttgt ttgtcggtga acgctctcct gagtaggaca  3300
aatccgccgg gagcggattt gaacgttgcg aagcaacggc ccgagggtg gcgggcagga  3360
cgcccgccat aaactgccag gcatcaaatt aagcagaagg ccatcctgac ggatggcctt  3420
tttgcgtttc tacaaactct ttttgtttat ttttctaaat acattcaaat atgtatccgc  3480
tcatgagaca ataaccctga taaatgcttc aataatattg aaaaaggaag agtatgagta  3540
ttcaacattt ccgtgtcgcc cttattccct tttttgcggc attttgcctt cctgtttttg  3600
ctcacccaga aacgctggtg aaagtaaaag atgctgaaga tcagttgggt gcacgagtgg  3660
gttacatcga actggatctc aacagcggta agatccttga gttttcgc cccgaagaac  3720
gttttccaat gatgagcact tttaaagttc tgctatgtgg cgcggtatta tcccgtgttg  3780
acgccgggca agagcaactc ggtcgccgca tacactattc tcagaatgac ttggttgagt  3840
actcaccagt cacagaaaag catcttacgg atggcatgac agtaagagaa ttatgcagtg  3900
ctgccataac catgagtgat aacactgcgg ccaacttact tctgacaacg atcggaggac  3960
```

```
cgaaggagct aaccgctttt ttgcacaaca tgggggatca tgtaactcgc cttgatcgtt      4020
gggaaccgga gctgaatgaa gccataccaa acgacgagcg tgacaccacg atgcctgtag      4080
caatggcaac aacgttgcgc aaactattaa ctggcgaact acttactcta gcttcccggc      4140
aacaattaat agactggatg gaggcggata agttgcagg accacttctg cgctcggccc       4200
ttccggctgg ctggtttatt gctgataaat ctggagccgg tgagcgtggg tctcgcggta      4260
tcattgcagc actggggcca gatggtaagc cctcccgtat cgtagttatc tacacgacgg      4320
ggagtcaggc aactatggat gaacgaaata gacagatcgc tgagataggt gcctcactga      4380
ttaagcattg gtaactgtca gaccaagttt actcatatat actttagatt gatttaaaac      4440
ttcattttta atttaaaagg atctaggtga agatccttt tgataatctc atgaccaaaa       4500
tcccttaacg tgagttttcg ttccactgag cgtcagaccc cgtagaaaag atcaaaggat      4560
cttcttgaga tcctttttt ctgcgcgtaa tctgctgctt gcaaacaaaa aaaccaccgc       4620
taccagcggt ggtttgtttg ccggatcaag agctaccaac tcttttttccg aaggtaactg     4680
gcttcagcag agcgcagata ccaaatactg tccttctagt gtagccgtag ttaggccacc      4740
acttcaagaa ctctgtagca ccgcctacat acctcgctct gctaatcctg ttaccagtgg      4800
ctgctgccag tggcgataag tcgtgtctta ccgggttgga ctcaagacga tagttaccgg      4860
ataaggcgca gcggtcgggc tgaacggggg gttcgtgcac acagcccagc ttggagcgaa      4920
cgacctacac cgaactgaga tacctacagc gtgagctatg agaaagcgcc acgcttcccg      4980
aagggagaaa ggcggacagg tatccggtaa gcggcagggt cggaacagga gagcgcacga      5040
gggagcttcc agggggaaac gcctggtatc tttatagtcc tgtcgggttt cgccacctct      5100
gacttgagcg tcgatttttg tgatgctcgt cagggggggcg gagcctatgg aaaaacgcca     5160
gcaacgcggc cttttttacgg ttcctggcct tttgctggcc ttttgctcac atgttctttc     5220
ctgcgttatc ccctgattct gtggataacc gtattaccgc ctttgagtga gctgataccg      5280
ctcgccgcag ccgaacgacc gagcgcagcg agtcagtgag cgaggaagcg gaagagcgcc      5340
tgatgcggta ttttctcctt acgcatctgt gcggtatttc acaccgcata tggtgcactc      5400
tcagtacaat ctgctctgat gccgcatagt taagccagta tacactccgc tatcgctacg      5460
tgactgggtc atggctgcgc cccgacaccc gccaacaccc gctgacgcgc cctgacgggc      5520
ttgtctgctc ccggcatccg cttacagaca agctgtgacc gtctccggga gctgcatgtg      5580
tcagaggttt tcaccgtcat caccgaaacg cgcgaggcag cagatcaatt cgcgcgcgaa      5640
ggcgaagcgg catgcattta cgttgacacc atcgaatggt gcaaaacctt cgcggtatg      5700
gcatgatagc gcccggaaga gagtcaattc agggtggtga atgtgaaacc agtaacgtta      5760
tacgatgtcg cagagtatgc cggtgtctct tatcagaccg tttcccgcgt ggtgaaccag      5820
gccagccacg tttctgcgaa aacgcgggaa aaagtggaag cggcgatggc ggagctgaat      5880
tacattccca accgcgtggc acaacaactg gcgggcaaac agtcgttgct gattggcgtt      5940
gccacctcca gtctggccct gcacgcgccg tcgcaaattg tcgcggcgat taaatctcgc      6000
gccgatcaac tgggtgccag cgtggtggtg tcgatggtag aacgaagcgg cgtcgaagcc      6060
tgtaaagcgg cggtgcacaa tcttctcgcg caacgcgtca gtgggctgat cattaactat      6120
ccgctggatg accaggatgc cattgctgtg gaagctgcct gcactaatgt tccggcgtta      6180
tttcttgatg tctctgacca gacacccatc aacagtatta ttttctccca tgaagacggt      6240
acgcgactgg gcgtggagca tctggtcgca ttgggtcacc agcaaatcgc gctgttagcg      6300
ggcccattaa gttctgtctc ggcgcgtctg cgtctggctg gctggcataa atatctcact      6360
```

```
cgcaatcaaa ttcagccgat agcggaacgg gaaggcgact ggagtgccat gtccggtttt   6420
caacaaacca tgcaaatgct gaatgagggc atcgttccca ctgcgatgct ggttgccaac   6480
gatcagatgg cgctgggcgc aatgcgcgcc attaccgagt ccgggctgcg cgttggtgcg   6540
gatatctcgg tagtgggata cgacgatacc gaagacagct catgttatat cccgccgtca   6600
accaccatca aacaggattt tcgcctgctg ggcaaacca gcgtggaccg cttgctgcaa   6660
ctctctcagg gccaggcggt gaagggcaat cagctgttgc ccgtctcact ggtgaaaaga   6720
aaaaccaccc tggcgcccaa tacgcaaacc gcctctcccc gcgcgttggc cgattcatta   6780
atgcagctgg cacgacaggt ttcccgactg gaaagcgggc agtgagcgca acgcaattaa   6840
tgtgagttag cgcgaattga tctg                                         6864
```

<210> SEQ ID NO 35
<211> LENGTH: 5982
<212> TYPE: DNA
<213> ORGANISM: Artificial Sequence
<220> FEATURE:
<223> OTHER INFORMATION: Synthetic Construct

<400> SEQUENCE: 35

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatggaagc    420
tcgtcgttct gcgaactacg aacctaacag ctgggactat gattacctgc tgtcctccga    480
cacggacgag tccatcgaag tatacaaaga caaagcgaaa aagctggaag ccgaagttcg    540 tcgcagagatt aataacgaaa aagcagaatt tctgaccctg ctggaactga ttgacaacgt    600
ccagcgcctg ggcctggggtt accgtttcga gtctgatatc cgtggtgcgc tggatcgctt    660
cgtttcctcc ggcggcttcg atgcggtaac caagacttcc ctgcacggta cggcactgtc    720
tttccgtctg ctgcgtcaac acggttttga ggtttctcag gaagcgttca gcggcttcaa    780
agaccaaaac ggcaacttcc tggagaacct gaaggaagat atcaaagcta tcctgagcct    840
gtacgaggcc agcttcctgg ctctggaagg cgaaaacatc ctggacgagg cgaaggtttt    900
cgcaatctct catctgaaag aactgtctga agaaagatc ggtaaagagc tggcagaaca    960
ggtgaaccat gcactggaac tgccactgca tcgccgtact cagcgtctgg aagcagtatg   1020
gtctatcgag gcctaccgta aaaggagga cgcgaatcag ttctgctgg agctggcaat   1080 tctggattac aacatgatcc agtctgtata ccagcgtgat ctgcgtgaaa cgtcccgttg   1140
gtggcgtcgt gtgggtctgg cgaccaaact gcactttgct cgtgaccgcc tgattgagag   1200
cttctactgg gccgtgggtg tagcattcga accgcaatac tccgactgcc gtaactccgt   1260
cgcaaaaatg ttttctttcg taaccattat cgacgatatc tacgatgtat acggcaccct   1320
ggacgaactg gagctgtttta ctgatgcagt tgagcgttgg gacgtaaacg ccatcaacga   1380
cctgccggat tacatgaaac tgtgcttttct ggctctgtat aacactatta acgaaatcgc   1440
ctacgacaac ctgaaagata aggtgagaa catcctgccg tatctgacca agcctgggc   1500
```

```
tgacctgtgc aacgctttcc tgcaagaagc caagtggctg tacaacaaat ctactccgac    1560
ctttgacgac tacttcggca acgcatggaa atcctcttct ggcccgctgc aactggtgtt    1620
cgcttacttc gctgtcgtgc agaacattaa aaaggaagag atcgaaaacc tgcaaaaata    1680
ccatgacacc atctctcgtc cttcccatat cttccgtctg tgcaatgacc tggctagcgc    1740
gtctgcggaa attgcgcgtg gtgaaaccgc aaatagcgtt tcttgttaca tgcgcactaa    1800
aggtatctcc gaagaactgg ctaccgaaag cgtgatgaat ctgatcgatg aaacctggaa    1860
aaagatgaac aaggaaaaac tgagtggtag cctgttcgcg aaaccgttcg tggaaaccgc    1920
gatcaacctg gcacgtcaat ctcactgcac ttatcataac ggcgacgcgc atacctctcc    1980
ggatgagctg acccgcaaac gcgttctgtc tgtaatcact gaaccgattc tgccgtttga    2040
acgctaactg cataaaggag gtaaaaaaac atggtatcct gttctgcgcc gggtaagatt    2100
agtctagtta agtttaaacg gtctccagc ttggctgttt tggcggatga gaagatttc    2160 tcagcctgat acagattaaa tcagaacgca gaagcggtct gataaaacag aatttgcctg    2220
gcggcagtag cgcggtggtc ccacctgacc ccatgccgaa ctcagaagtg aaacgccgta    2280
gcgccgatgg tagtgtgggg tctccccatg cgagagtagg gaactgccag gcatcaaata    2340
aaacgaaagg ctcagtcgaa agactgggcc tttcgtttta tctgttgttt gtcggtgaac    2400
gctctcctga gtaggacaaa tccgccggga gcggatttga acgttgcgaa gcaacggccc    2460
ggagggtggc gggcaggacg cccgccataa actgccaggc atcaaattaa gcagaaggcc    2520
atcctgacgg atggcctttt tgcgtttcta caaactcttt ttgtttattt ttctaaatac    2580
attcaaatat gtatccgctc atgagacaat aaccctgata atgcttcaa taatattgaa    2640 aaaggaagag tatgagtatt caacatttcc gtgtcgccct tattccttt tttgcggcat    2700 tttgccttcc tgtttttgct cacccagaaa cgctggtgaa agtaaaagat gctgaagatc    2760
agttgggtgc acgagtgggt tacatcgaac tggatctcaa cagcggtaag atccttgaga    2820
gttttcgccc cgaagaacgt tttccaatga tgagcacttt taaagttctg ctatgtggcg    2880
cggtattatc ccgtgttgac gccgggcaag agcaactcgg tcgccgcata cactattctc    2940
agaatgactt ggttgagtac tcaccagtca cagaaaagca tcttacggat ggcatgacag    3000
taagagaatt atgcagtgct gccataacca tgagtgataa cactgcggcc aacttacttc    3060
tgacaacgat cggaggaccg aaggagctaa ccgcttttt gcacaacatg ggggatcatg    3120
taactcgcct tgatcgttgg gaaccggagc tgaatgaagc cataccaaac gacgagcgtg    3180
acaccacgat gcctgtagca atggcaacaa cgttgcgcaa actattaact ggcgaactac    3240
ttactctagc ttcccggcaa caattaatag actggatgga ggcggataaa gttgcaggac    3300
cacttctgcg ctcggccctt ccggctggct ggtttattgc tgataaatct ggagccggtg    3360
agcgtgggtc tcgcggtatc attgcagcac tggggccaga tggtaagccc tcccgtatcg    3420
tagttatcta cacgacgggg agtcaggcaa ctatggatga acgaaataga cagatcgctg    3480
agataggtgc ctcactgatt aagcattggt aactgtcaga ccaagtttac tcatatatac    3540
tttagattga tttaaaactt cattttaat ttaaaggat ctaggtgaag atccttttg    3600 ataatctcat gaccaaaatc ccttaacgtg agttttcgtt ccactgagcg tcagaccccg    3660
tagaaaagat caaaggatct tcttgagatc cttttttct gcgcgtaatc tgctgcttgc    3720
aaacaaaaaa accaccgcta ccagcggtgg tttgtttgcc ggatcaagag ctaccaactc    3780
tttttccgaa ggtaactggc ttcagcagag cgcagatacc aaatactgtc cttctagtgt    3840
agccgtagtt aggccaccac ttcaagaact ctgtagcacc gcctacatac ctcgctctgc    3900
```

```
taatcctgtt accagtggct gctgccagtg gcgataagtc gtgtcttacc gggttggact    3960
caagacgata gttaccggat aaggcgcagc ggtcgggctg aacgggggt tcgtgcacac    4020
agcccagctt ggagcgaacg acctacaccg aactgagata cctacagcgt gagctatgag   4080
aaagcgccac gcttcccgaa gggagaaagg cggacaggta tccggtaagc ggcagggtcg   4140
gaacaggaga gcgcacgagg gagcttccag ggggaaacgc ctggtatctt tatagtcctg   4200
tcgggtttcg ccacctctga cttgagcgtc gattttgtg atgctcgtca ggggggcgga    4260
gcctatggaa aaacgccagc aacgcggcct ttttacggtt cctggccttt tgctggcctt   4320
ttgctcacat gttctttcct gcgttatccc ctgattctgt ggataaccgt attaccgcct   4380
ttgagtgagc tgataccgct cgccgcagcc gaacgaccga gcgcagcgag tcagtgagcg   4440
aggaagcgga gagcgcctg atgcggtatt ttctccttac gcatctgtgc ggtatttcac    4500
accgcatatg gtgcactctc agtacaatct gctctgatgc cgcatagtta gccagtata    4560
cactccgcta tcgctacgtg actgggtcat ggctgcgccc cgacacccgc caacacccgc   4620
tgacgcgccc tgacgggctt gtctgctccc ggcatccgct tacagacaag ctgtgaccgt   4680
ctccgggagc tgcatgtgtc agaggttttc accgtcatca ccgaaacgcg cgaggcagca   4740
gatcaattcg cgcgcgaagg cgaagcggca tgcatttacg ttgacaccat cgaatggtgc   4800
aaaacctttc gcggtatggc atgatagcgc ccggaagaga gtcaattcag ggtggtgaat   4860
gtgaaaccag taacgttata cgatgtcgca gagtatgccg gtgtctctta tcagaccgtt   4920
tcccgcgtgg tgaaccaggc cagccacgtt tctgcgaaaa cgcgggaaaa agtggaagcg   4980
gcgatggcgg agctgaatta cattcccaac cgcgtggcac aacaactggc gggcaaacag   5040
tcgttgctga ttggcgttgc cacctccagt ctggccctgc acgcgccgtc gcaaattgtc   5100
gcggcgatta aatctcgcgc cgatcaactg ggtgccagcg tggtggtgtc gatggtagaa   5160
cgaagcggcg tcgaagcctg taaagcggcg gtgcacaatc ttctcgcgca acgcgtcagt   5220
gggctgatca ttaactatcc gctggatgac caggatgcca ttgctgtgga agctgcctgc   5280
actaatgttc cggcgttatt tcttgatgtc tctgaccaga cacccatcaa cagtattatt   5340
ttctcccatg aagacggtac gcgactgggc gtggagcatc tggtcgcatt gggtcaccag   5400
caaatcgcgc tgttagcggg cccattaagt tctgtctcgg cgcgtctgcg tctggctggc   5460
tggcataaat atctcactcg caatcaaatt cagccgatag cggaacggga aggcgactgg   5520
agtgccatgt ccggttttca acaaaccatg caaatgctga atgagggcat cgttcccact   5580
gcgatgctgg ttgccaacga tcagatggcg ctgggcgcaa tgcgcgccat taccgagtcc   5640
gggctgcgcg ttggtgcgga tatctcggta gtgggatacg acgataccga agacagctca   5700
tgttatatcc cgccgtcaac caccatcaaa caggattttc gcctgctggg caaaccagc   5760
gtggaccgct tgctgcaact ctctcagggc caggcggtga agggcaatca gctgttgccc   5820
gtctcactgg tgaaaagaaa aaccacccctg gcgcccaata cgcaaaccgc ctctccccgc   5880
gcgttggccg attcattaat gcagctggca cgacaggttt cccgactgga aagcgggcag   5940
tgagcgcaac gcaattaatg tgagttagcg cgaattgatc tg                      5982
```

<210> SEQ ID NO 36
<211> LENGTH: 73
<212> TYPE: DNA
<213> ORGANISM: Artificial Sequence
<220> FEATURE:
<223> OTHER INFORMATION: Synthetic Construct

```
<400> SEQUENCE: 36
tatttaattt ttaatcatct aatttgacaa tcattcaaca aagttgttac aattaaccct    60
cactaaaggg cgg                                                      73

<210> SEQ ID NO 37
<211> LENGTH: 147
<212> TYPE: DNA
<213> ORGANISM: Artificial Sequence
<220> FEATURE:
<223> OTHER INFORMATION: Synthetic Construct

<400> SEQUENCE: 37
tcaacagctg tatccccgtt gagggtgagt tttgcttttg tatcagccat atattccacc    60
agctatttgt tagtgaataa aagtggttga attatttgct caggatgtgg cathgtcaag   120
ggctaatacg actcactata gggctcg                                      147

<210> SEQ ID NO 38
<211> LENGTH: 25
<212> TYPE: DNA
<213> ORGANISM: Artificial Sequence
<220> FEATURE:
<223> OTHER INFORMATION: Synthetic Construct

<400> SEQUENCE: 38
ggcagtatag gctgttcaca aaatc                                         25

<210> SEQ ID NO 39
<211> LENGTH: 23
<212> TYPE: DNA
<213> ORGANISM: Artificial Sequence
<220> FEATURE:
<223> OTHER INFORMATION: Synthetic Construct

<400> SEQUENCE: 39
cttgacccag cgtgcctttc agc                                           23

<210> SEQ ID NO 40
<211> LENGTH: 22
<212> TYPE: DNA
<213> ORGANISM: Artificial Sequence
<220> FEATURE:
<223> OTHER INFORMATION: Synthetic Construct

<400> SEQUENCE: 40
gtgcaaattc acaactcagc gg                                            22

<210> SEQ ID NO 41
<211> LENGTH: 22
<212> TYPE: DNA
<213> ORGANISM: Artificial Sequence
<220> FEATURE:
<223> OTHER INFORMATION: Synthetic Construct

<400> SEQUENCE: 41
caccaacgta tcgggcattg cc                                            22

<210> SEQ ID NO 42
<211> LENGTH: 24
<212> TYPE: DNA
<213> ORGANISM: Artificial Sequence
<220> FEATURE:
<223> OTHER INFORMATION: Synthetic Construct

<400> SEQUENCE: 42
```
ggcttaccgt ttacgctttc cagc                                            24

<210> SEQ ID NO 43
<211> LENGTH: 23
<212> TYPE: DNA
<213> ORGANISM: Artificial Sequence
<220> FEATURE:
<223> OTHER INFORMATION: Synthetic Construct

<400> SEQUENCE: 43
ctaatgcaat acgtgtcccg agc                                             23

<210> SEQ ID NO 44
<211> LENGTH: 99
<212> TYPE: DNA
<213> ORGANISM: Artificial Sequence
<220> FEATURE:
<223> OTHER INFORMATION: Synthetic Construct

<400> SEQUENCE: 44
aaaattttca ttctgtgaca gagaaaaagt agccgaagat gacggtttgt cacatggagt     60
tggcaggatg tttgattaca tgggaattag ccatggtcc                            99

<210> SEQ ID NO 45
<211> LENGTH: 100
<212> TYPE: DNA
<213> ORGANISM: Artificial Sequence
<220> FEATURE:
<223> OTHER INFORMATION: Synthetic Construct

<400> SEQUENCE: 45
gaccagccgc gtaacctggc aaaatcggtt acggttgagt aataaatgga tgccctgcgt     60
aagcggggca ttttcttgg tgtaggctgg agctgcttcg                           100

<210> SEQ ID NO 46
<211> LENGTH: 20
<212> TYPE: DNA
<213> ORGANISM: Artificial Sequence
<220> FEATURE:
<223> OTHER INFORMATION: Synthetic Construct

<400> SEQUENCE: 46
gggtatgaaa gcgattctga                                                 20

<210> SEQ ID NO 47
<211> LENGTH: 20
<212> TYPE: DNA
<213> ORGANISM: Artificial Sequence
<220> FEATURE:
<223> OTHER INFORMATION: Synthetic Construct

<400> SEQUENCE: 47
agcccaaggc gctattaccg                                                 20

<210> SEQ ID NO 48
<211> LENGTH: 20
<212> TYPE: DNA
<213> ORGANISM: Artificial Sequence
<220> FEATURE:
<223> OTHER INFORMATION: Synthetic Construct

<400> SEQUENCE: 48
ggattagttc aaaatttggc                                                 20

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct

<400> SEQUENCE: 49
cggttaatgg cacgttatga                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic Construct

<400> SEQUENCE: 50
tcgttcgcct gtaaactgct                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic Construct

<400> SEQUENCE: 51
tgctctattt cagtaccttt                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic Construct

<400> SEQUENCE: 52
tgtaagttca ggcccacgcc                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct

<400> SEQUENCE: 53
cctcagcctt gttgtaataa                                              20

<210> SEQ ID NO 54
<211> LENGTH: 45
<212> TYPE: DNA
<213> ORGANISM: Artificial Sequence
<220> FEATURE:
<223> OTHER INFORMATION: Synthetic Construct

<400> SEQUENCE: 54
aggaggaata aaccatgaaa acagtagtta ttattgatgc attac                  45

<210> SEQ ID NO 55
<211> LENGTH: 42
<212> TYPE: DNA
<213> ORGANISM: Artificial Sequence
<220> FEATURE:
<223> OTHER INFORMATION: Synthetic Construct

<400> SEQUENCE: 55
actactgttt tcatggttta ttcctcctta tttaatcgat ac                           42

<210> SEQ ID NO 56
<211> LENGTH: 42
<212> TYPE: DNA
<213> ORGANISM: Artificial Sequence
<220> FEATURE:
<223> OTHER INFORMATION: Synthetic Construct

<400> SEQUENCE: 56
aggaggaata aaccatggaa gaagttgtca tcattgacgc ac                           42

<210> SEQ ID NO 57
<211> LENGTH: 35
<212> TYPE: DNA
<213> ORGANISM: Artificial Sequence
<220> FEATURE:
<223> OTHER INFORMATION: Synthetic Construct

<400> SEQUENCE: 57
acttcttcca tggtttattc ctccttattt aatcg                                   35

<210> SEQ ID NO 58
<211> LENGTH: 73
<212> TYPE: DNA
<213> ORGANISM: Artificial Sequence
<220> FEATURE:
<223> OTHER INFORMATION: Synthetic Construct

<400> SEQUENCE: 58
tatttaattt ttaatcatct aatttgacaa tcattcaaca aagttgttac aattaaccct        60
cactaaaggg cgg                                                           73

<210> SEQ ID NO 59
<211> LENGTH: 147
<212> TYPE: DNA
<213> ORGANISM: Artificial Sequence
<220> FEATURE:
<223> OTHER INFORMATION: Synthetic Construct

<400> SEQUENCE: 59
tcaacagctg tatccccgtt gagggtgagt tttgcttttg tatcagccat atattccacc        60
agctatttgt tagtgaataa aagtggttga attatttgct caggatgtgg cathgtcaag       120
ggctaatacg actcactata gggctcg                                           147

<210> SEQ ID NO 60
<211> LENGTH: 25
<212> TYPE: DNA
<213> ORGANISM: Artificial Sequence
<220> FEATURE:
<223> OTHER INFORMATION: Synthetic Construct

<400> SEQUENCE: 60
ggcagtatag gctgttcaca aaatc                                              25

<210> SEQ ID NO 61
<211> LENGTH: 23
<212> TYPE: DNA
<213> ORGANISM: Artificial Sequence
<220> FEATURE:
<223> OTHER INFORMATION: Synthetic Construct

```
<400> SEQUENCE: 61
cttgacccag cgtgcctttc agc                                           23

<210> SEQ ID NO 62
<211> LENGTH: 22
<212> TYPE: DNA
<213> ORGANISM: Artificial Sequence
<220> FEATURE:
<223> OTHER INFORMATION: Synthetic Construct

<400> SEQUENCE: 62
gtgcaaattc acaactcagc gg                                            22

<210> SEQ ID NO 63
<211> LENGTH: 22
<212> TYPE: DNA
<213> ORGANISM: Artificial Sequence
<220> FEATURE:
<223> OTHER INFORMATION: Synthetic Construct

<400> SEQUENCE: 63
caccaacgta tcgggcattg cc                                            22

<210> SEQ ID NO 64
<211> LENGTH: 24
<212> TYPE: DNA
<213> ORGANISM: Artificial Sequence
<220> FEATURE:
<223> OTHER INFORMATION: Synthetic Construct

<400> SEQUENCE: 64
ggcttaccgt ttacgctttc cagc                                          24

<210> SEQ ID NO 65
<211> LENGTH: 23
<212> TYPE: DNA
<213> ORGANISM: Artificial Sequence
<220> FEATURE:
<223> OTHER INFORMATION: Synthetic Construct

<400> SEQUENCE: 65
ctaatgcaat acgtgtcccg agc                                           23

<210> SEQ ID NO 66
<211> LENGTH: 99
<212> TYPE: DNA
<213> ORGANISM: Artificial Sequence
<220> FEATURE:
<223> OTHER INFORMATION: Synthetic Construct

<400> SEQUENCE: 66
aaaattttca ttctgtgaca gagaaaaagt agccgaagat gacggtttgt cacatggagt   60
tggcaggatg tttgattaca tgggaattag ccatggtcc                          99

<210> SEQ ID NO 67
<211> LENGTH: 100
<212> TYPE: DNA
<213> ORGANISM: Artificial Sequence
<220> FEATURE:
<223> OTHER INFORMATION: Synthetic Construct

<400> SEQUENCE: 67
gaccagccgc gtaacctggc aaaatcggtt acggttgagt aataaatgga tgccctgcgt   60
aagcggggca ttttcttgg tgtaggctgg agctgcttcg                          100
```

<210> SEQ ID NO 68
<211> LENGTH: 144
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 115
<223> OTHER INFORMATION: n = A,T,C or G

<400> SEQUENCE: 68

```
actggaaatt catggaaatc aagtgcactt tgttttaact ggtcatccat tatatacctc    60
ctgctatttg ttagtgaata aaagtggttg aattatttgc tcaggatgtg gcatngtcaa   120
gggcgtgtag gctggagctg cttc                                          144
```

<210> SEQ ID NO 69
<211> LENGTH: 90
<212> TYPE: DNA
<213> ORGANISM: Artificial Sequence
<220> FEATURE:
<223> OTHER INFORMATION: Synthetic Construct

<400> SEQUENCE: 69

```
agagtttgga cttgctcaaa gtctgtagac tccggcaggg taataatgtg cgccacgttg    60
tgggcagggg atgggaatta gccatggtcc                                     90
```

<210> SEQ ID NO 70
<211> LENGTH: 20
<212> TYPE: DNA
<213> ORGANISM: Artificial Sequence
<220> FEATURE:
<223> OTHER INFORMATION: Synthetic Construct

<400> SEQUENCE: 70

```
gtgaactgtt tgatgccgtc                                                20
```

<210> SEQ ID NO 71
<211> LENGTH: 24
<212> TYPE: DNA
<213> ORGANISM: Artificial Sequence
<220> FEATURE:
<223> OTHER INFORMATION: Synthetic Construct

<400> SEQUENCE: 71

```
ggtaagtgaa tcggttcaat tcgg                                           24
```

<210> SEQ ID NO 72
<211> LENGTH: 24
<212> TYPE: DNA
<213> ORGANISM: Artificial Sequence
<220> FEATURE:
<223> OTHER INFORMATION: Synthetic Construct

<400> SEQUENCE: 72

```
cgctcaacac cttcttcacg gatg                                           24
```

<210> SEQ ID NO 73
<211> LENGTH: 24
<212> TYPE: DNA
<213> ORGANISM: Artificial Sequence
<220> FEATURE:
<223> OTHER INFORMATION: Synthetic Construct

<400> SEQUENCE: 73
cctgtatgga cataaggtga atac                                          24

<210> SEQ ID NO 74
<211> LENGTH: 24
<212> TYPE: DNA
<213> ORGANISM: Artificial Sequence
<220> FEATURE:
<223> OTHER INFORMATION: Synthetic Construct

<400> SEQUENCE: 74
cctgtcccat tgaactctcg ccgg                                          24

<210> SEQ ID NO 75
<211> LENGTH: 24
<212> TYPE: DNA
<213> ORGANISM: Artificial Sequence
<220> FEATURE:
<223> OTHER INFORMATION: Synthetic Construct

<400> SEQUENCE: 75
cctgtatgga cataaggtga atac                                          24

<210> SEQ ID NO 76
<211> LENGTH: 24
<212> TYPE: DNA
<213> ORGANISM: Artificial Sequence
<220> FEATURE:
<223> OTHER INFORMATION: Synthetic Construct

<400> SEQUENCE: 76
cctgtcccat tgaactctcg ccgg                                          24

<210> SEQ ID NO 77
<211> LENGTH: 80
<212> TYPE: DNA
<213> ORGANISM: Artificial Sequence
<220> FEATURE:
<223> OTHER INFORMATION: Synthetic Construct

<400> SEQUENCE: 77
agagttcaat gggacaggtt ccagaaaact caacgttatt agatagataa ggaataaccc   60
gtgtaggctg gagctgcttc                                               80

<210> SEQ ID NO 78
<211> LENGTH: 187
<212> TYPE: DNA
<213> ORGANISM: Artificial Sequence
<220> FEATURE:
<223> OTHER INFORMATION: Synthetic Construct

<400> SEQUENCE: 78
cgtcatttgg gaaacgttct gacatgtttt tttacctcct ttgcaccttc atggtggtca   60
gtgcgtcctg ctgatgtgct cagtatcacc gccagtggta tttatgtcaa caccgccaga  120
gataatttat caccgcagat ggttatctgt atgttttta tatgaattca tatgaatatc   180
ctcctta                                                            187

<210> SEQ ID NO 79
<211> LENGTH: 25
<212> TYPE: DNA
<213> ORGANISM: Artificial Sequence
<220> FEATURE:
<223> OTHER INFORMATION: Synthetic Construct

<400> SEQUENCE: 79
atgtcagaac gtttcccaaa tgacg                                  25

<210> SEQ ID NO 80
<211> LENGTH: 77
<212> TYPE: DNA
<213> ORGANISM: Artificial Sequence
<220> FEATURE:
<223> OTHER INFORMATION: Synthetic Construct

<400> SEQUENCE: 80
gcggcgtggt tagccgcttt tttaattgcc ggatgttccg gcaaacgaaa aattacttct    60
tcttcgcttt cgggttc                                           77

<210> SEQ ID NO 81
<211> LENGTH: 18
<212> TYPE: DNA
<213> ORGANISM: Artificial Sequence
<220> FEATURE:
<223> OTHER INFORMATION: Synthetic Construct

<400> SEQUENCE: 81
gaagtggtta aagcacac                                          18

<210> SEQ ID NO 82
<211> LENGTH: 22
<212> TYPE: DNA
<213> ORGANISM: Artificial Sequence
<220> FEATURE:
<223> OTHER INFORMATION: Synthetic Construct

<400> SEQUENCE: 82
ttaatctact ttcagacctt gc                                     22

<210> SEQ ID NO 83
<211> LENGTH: 81
<212> TYPE: DNA
<213> ORGANISM: Artificial Sequence
<220> FEATURE:
<223> OTHER INFORMATION: Synthetic Construct

<400> SEQUENCE: 83
aaagtagccg aagatgacgg tttgtcacat ggagttggca ggatgtttga ttaaaagcaa    60
ttaaccctca ctaaagggcg g                                      81

<210> SEQ ID NO 84
<211> LENGTH: 107
<212> TYPE: DNA
<213> ORGANISM: Artificial Sequence
<220> FEATURE:
<223> OTHER INFORMATION: Synthetic Construct

<400> SEQUENCE: 84
tcctgctgat gtgctcagta tcaccgccag tggtatttaa gtcaacaccg ccagagataa    60
tttatcaccg cagatggtta tcttaatacg actcactata gggctcg          107

<210> SEQ ID NO 85
<211> LENGTH: 118
<212> TYPE: DNA
<213> ORGANISM: Artificial Sequence
<220> FEATURE:
<223> OTHER INFORMATION: Synthetic Construct

```
<400> SEQUENCE: 85
ggcggtgata ctgagcacat cagcaggacg cactgctcta aggattaaag aggagaagat    60
ttcctgatgt atcgatttaa ataaggagga ataacatatg gtatcctgtt ctgcgccg    118

<210> SEQ ID NO 86
<211> LENGTH: 116
<212> TYPE: DNA
<213> ORGANISM: Artificial Sequence
<220> FEATURE:
<223> OTHER INFORMATION: Synthetic Construct

<400> SEQUENCE: 86
ggcggtgata ctgagcacat cagcaggacg cactgctcct aggggcgatt aggggaccta    60
ctacatgtat cgatttaaat aaggaggaat aacatatggt atcctgttct gcgccg    116

<210> SEQ ID NO 87
<211> LENGTH: 115
<212> TYPE: DNA
<213> ORGANISM: Artificial Sequence
<220> FEATURE:
<223> OTHER INFORMATION: Synthetic Construct

<400> SEQUENCE: 87
ggcggtgata ctgagcacat cagcaggacg cactgctcta gagcgcacta aggaggcaac    60
tggatgtatc gatttaaata aggaggaata acatatggta tcctgttctg cgccg    115

<210> SEQ ID NO 88
<211> LENGTH: 107
<212> TYPE: DNA
<213> ORGANISM: Artificial Sequence
<220> FEATURE:
<223> OTHER INFORMATION: Synthetic Construct

<400> SEQUENCE: 88
ggcggtgata ctgagcacat cagcaggacg cactgctgca gcgaggaggt aagggatgta    60
tcgatttaaa taaggaggaa taacatatgg tatcctgttc tgcgccg    107

<210> SEQ ID NO 89
<211> LENGTH: 115
<212> TYPE: DNA
<213> ORGANISM: Artificial Sequence
<220> FEATURE:
<223> OTHER INFORMATION: Synthetic Construct

<400> SEQUENCE: 89
ggcggtgata ctgagcacat cagcaggacg cactgctcct aggggcgatt aggggaccta    60
ctacatgtat cgatttaaat aaggaggaat aacatatgat aacgtgctct gcgcc    115

<210> SEQ ID NO 90
<211> LENGTH: 82
<212> TYPE: DNA
<213> ORGANISM: Artificial Sequence
<220> FEATURE:
<223> OTHER INFORMATION: Synthetic Construct

<400> SEQUENCE: 90
ggctctcaac tctgacatgt ttttttcctc cttaagggtg caggcctatc gcaaattagc    60
ttactgacat tctacgcgaa ca    82

<210> SEQ ID NO 91
<211> LENGTH: 45
```

```
<212> TYPE: DNA
<213> ORGANISM: Artificial Sequence
<220> FEATURE:
<223> OTHER INFORMATION: Synthetic Construct

<400> SEQUENCE: 91
gtttaaactt taactagact ttactgacat tctacgcgaa caccg              45

<210> SEQ ID NO 92
<211> LENGTH: 41
<212> TYPE: DNA
<213> ORGANISM: Artificial Sequence
<220> FEATURE:
<223> OTHER INFORMATION: Synthetic Construct

<400> SEQUENCE: 92
cataaaggag gtaaaaaaac atgataacgt gctctgcgcc g                  41

<210> SEQ ID NO 93
<211> LENGTH: 30
<212> TYPE: DNA
<213> ORGANISM: Artificial Sequence
<220> FEATURE:
<223> OTHER INFORMATION: Synthetic Construct

<400> SEQUENCE: 93
gggtaagatt agtctagtta aagtttaaac                               30

<210> SEQ ID NO 94
<211> LENGTH: 30
<212> TYPE: DNA
<213> ORGANISM: Artificial Sequence
<220> FEATURE:
<223> OTHER INFORMATION: Synthetic Construct

<400> SEQUENCE: 94
taactagact aatcttaccc ggcgcagaac                               30

<210> SEQ ID NO 95
<211> LENGTH: 24
<212> TYPE: DNA
<213> ORGANISM: Artificial Sequence
<220> FEATURE:
<223> OTHER INFORMATION: Synthetic Construct

<400> SEQUENCE: 95
cagcaaatag caggtgtatc cagc                                     24

<210> SEQ ID NO 96
<211> LENGTH: 24
<212> TYPE: DNA
<213> ORGANISM: Artificial Sequence
<220> FEATURE:
<223> OTHER INFORMATION: Synthetic Construct

<400> SEQUENCE: 96
gcaaccgact gttgatagaa caac                                     24

<210> SEQ ID NO 97
<211> LENGTH: 24
<212> TYPE: DNA
<213> ORGANISM: Artificial Sequence
<220> FEATURE:
<223> OTHER INFORMATION: Synthetic Construct

<400> SEQUENCE: 97
```
ggttacaaaa tgattggcgt acgc     24

<210> SEQ ID NO 98
<211> LENGTH: 84
<212> TYPE: DNA
<213> ORGANISM: Artificial Sequence
<220> FEATURE:
<223> OTHER INFORMATION: Synthetic Construct

<400> SEQUENCE: 98
cgggctttgc ttttcgtcag tggttgaatt atttgctcag gatgtggcat cgtcaagggc     60
taatacgact cactataggg ctcg     84

<210> SEQ ID NO 99
<211> LENGTH: 74
<212> TYPE: DNA
<213> ORGANISM: Artificial Sequence
<220> FEATURE:
<223> OTHER INFORMATION: Synthetic Construct

<400> SEQUENCE: 99
gttacttggg gcgattttt aacatttcca taagttacgc ttatttaaag caattaaccc     60
tcactaaagg gcgg     74

<210> SEQ ID NO 100
<211> LENGTH: 25
<212> TYPE: DNA
<213> ORGANISM: Artificial Sequence
<220> FEATURE:
<223> OTHER INFORMATION: Synthetic Construct

<400> SEQUENCE: 100
ggaaacacgg tttatcaagc ccacc     25

<210> SEQ ID NO 101
<211> LENGTH: 24
<212> TYPE: DNA
<213> ORGANISM: Artificial Sequence
<220> FEATURE:
<223> OTHER INFORMATION: Synthetic Construct

<400> SEQUENCE: 101
cgtgaagatt tcgacaactt acgg     24

<210> SEQ ID NO 102
<211> LENGTH: 24
<212> TYPE: DNA
<213> ORGANISM: Artificial Sequence
<220> FEATURE:
<223> OTHER INFORMATION: Synthetic Construct

<400> SEQUENCE: 102
caggtaatgc attacggcca actg     24

<210> SEQ ID NO 103
<211> LENGTH: 23
<212> TYPE: DNA
<213> ORGANISM: Artificial Sequence
<220> FEATURE:
<223> OTHER INFORMATION: Synthetic Construct

<400> SEQUENCE: 103
caggctgtac gctggctgat gac     23

```
<210> SEQ ID NO 104
<211> LENGTH: 26
<212> TYPE: DNA
<213> ORGANISM: Artificial Sequence
<220> FEATURE:
<223> OTHER INFORMATION: Synthetic Construct

<400> SEQUENCE: 104
atgatcccgg aaaagcgaat tatacg                                          26

<210> SEQ ID NO 105
<211> LENGTH: 22
<212> TYPE: DNA
<213> ORGANISM: Artificial Sequence
<220> FEATURE:
<223> OTHER INFORMATION: Synthetic Construct

<400> SEQUENCE: 105
gtgcaaattc acaactcagc gg                                              22

<210> SEQ ID NO 106
<211> LENGTH: 21
<212> TYPE: DNA
<213> ORGANISM: Artificial Sequence
<220> FEATURE:
<223> OTHER INFORMATION: Synthetic Construct

<400> SEQUENCE: 106
caccaacgta tcgggcattg c                                               21

<210> SEQ ID NO 107
<211> LENGTH: 94
<212> TYPE: DNA
<213> ORGANISM: Artificial Sequence
<220> FEATURE:
<223> OTHER INFORMATION: Synthetic Construct

<400> SEQUENCE: 107
gttaactggt tgcagtcacc tggaggcacc aggcaccgca tcaacaaagt tcatttgtaa     60
aaatggagat aattgtgtag gctggagctg cttc                                 94

<210> SEQ ID NO 108
<211> LENGTH: 187
<212> TYPE: DNA
<213> ORGANISM: Artificial Sequence
<220> FEATURE:
<223> OTHER INFORMATION: Synthetic Construct

<400> SEQUENCE: 108
tcgtgtcaat tactatccac ttcatgtttt tttacctcct ttgcaccttc atggtggtca     60
gtgcgtcctg ctgatgtgct cagtatcacc gccagtggta tttatgtcaa caccgccaga   120
gataatttat caccgcagat ggttatctgt atgttttta tatgaattca tatgaatatc    180
ctcctta                                                              187

<210> SEQ ID NO 109
<211> LENGTH: 25
<212> TYPE: DNA
<213> ORGANISM: Artificial Sequence
<220> FEATURE:
<223> OTHER INFORMATION: Synthetic Construct

<400> SEQUENCE: 109
atgaagtgga tagtaattga cacga                                           25
```

<210> SEQ ID NO 110
<211> LENGTH: 100
<212> TYPE: DNA
<213> ORGANISM: Artificial Sequence
<220> FEATURE:
<223> OTHER INFORMATION: Synthetic Construct

<400> SEQUENCE: 110
gcattctttc aatagctttg ctttcttcaa cgtctttttt gcaaaggtgg taagcacatt     60
ttattttctt agtcattact tgagcccata tgggcatatt                         100

<210> SEQ ID NO 111
<211> LENGTH: 132
<212> TYPE: DNA
<213> ORGANISM: Artificial Sequence
<220> FEATURE:
<223> OTHER INFORMATION: Synthetic Construct

<400> SEQUENCE: 111
gcattctttc aatagctttg ctttcttcaa cgtctttttt gcaaaggtgg taagcacatt     60
ttattttctt agtcaagtca aaagcctccg gtcggaggct tttgacttta cttgagccca    120
tatgggcata tt                                                        132

<210> SEQ ID NO 112
<211> LENGTH: 94
<212> TYPE: DNA
<213> ORGANISM: Artificial Sequence
<220> FEATURE:
<223> OTHER INFORMATION: Synthetic Construct

<400> SEQUENCE: 112
gttaactggt tgcagtcacc tggaggcacc aggcaccgca tcaacaaagt tcatttgtaa     60
aaatggagat aattgtgtag gctggagctg cttc                                94

<210> SEQ ID NO 113
<211> LENGTH: 120
<212> TYPE: DNA
<213> ORGANISM: Artificial Sequence
<220> FEATURE:
<223> OTHER INFORMATION: Synthetic Construct

<400> SEQUENCE: 113
tcgtgtcaat tactatccac ttcattttat atacctcctg ctatttgtta gtgaataaaa     60
gtggttgaat tatttgctca ggatgtggca ttgtcaaggg ccatatgaat atcctcctta    120

<210> SEQ ID NO 114
<211> LENGTH: 29
<212> TYPE: DNA
<213> ORGANISM: Artificial Sequence
<220> FEATURE:
<223> OTHER INFORMATION: Synthetic Construct

<400> SEQUENCE: 114
gttcgtgaat ttacaggtgt tagatttac                                      29

<210> SEQ ID NO 115
<211> LENGTH: 29
<212> TYPE: DNA
<213> ORGANISM: Artificial Sequence
<220> FEATURE:
<223> OTHER INFORMATION: Synthetic Construct

<400> SEQUENCE: 115

```
gtgcaatcgt aggatattgc gccaccggc                                       29

<210> SEQ ID NO 116
<211> LENGTH: 20
<212> TYPE: DNA
<213> ORGANISM: Artificial Sequence
<220> FEATURE:
<223> OTHER INFORMATION: Synthetic Construct

<400> SEQUENCE: 116
ccgtaccgtt agagatcacc                                                 20

<210> SEQ ID NO 117
<211> LENGTH: 125
<212> TYPE: DNA
<213> ORGANISM: Artificial Sequence
<220> FEATURE:
<223> OTHER INFORMATION: Synthetic Construct

<400> SEQUENCE: 117
aattcatata aaaacatac agataaccat ctgcggtgat aaattatctc tggcggtgtt      60
gacataaata ccactggcgg tgatactgag cacatcagca ggacgcactg accaccatga    120
aggtg                                                                125
```